United States Patent
Abudayyeh et al.

(10) Patent No.: US 11,827,881 B2
(45) Date of Patent: *Nov. 28, 2023

(54) SYSTEMS, METHODS, AND COMPOSITIONS FOR SITE-SPECIFIC GENETIC ENGINEERING USING PROGRAMMABLE ADDITION VIA SITE-SPECIFIC TARGETING ELEMENTS (PASTE)

(71) Applicant: Massachusetts Institute of Technology, Cambridge, MA (US)

(72) Inventors: Omar Abudayyeh, Cambridge, MA (US); Jonathan Gootenberg, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/066,223

(22) Filed: Dec. 14, 2022

(65) Prior Publication Data

US 2023/0279391 A1 Sep. 7, 2023

Related U.S. Application Data

(63) Continuation of application No. 17/649,308, filed on Jan. 28, 2022, now Pat. No. 11,572,556, which is a continuation of application No. 17/451,734, filed on Oct. 21, 2021, now abandoned.

(60) Provisional application No. 63/222,550, filed on Jul. 16, 2021, provisional application No. 63/094,803, filed on Oct. 21, 2020.

(51) Int. Cl.

| | |
|---|---|
| *C12N 15/11* | (2006.01) |
| *A61K 31/7105* | (2006.01) |
| *C12N 9/12* | (2006.01) |
| *C12N 9/22* | (2006.01) |
| *C12N 15/10* | (2006.01) |
| *C12N 15/85* | (2006.01) |
| *C12N 15/113* | (2010.01) |
| *C12N 15/90* | (2006.01) |

(52) U.S. Cl.
CPC ........ *C12N 15/111* (2013.01); *A61K 31/7105* (2013.01); *C12N 9/1276* (2013.01); *C12N 9/22* (2013.01); *C12N 15/102* (2013.01); *C12N 15/113* (2013.01); *C12N 15/85* (2013.01); *C12N 15/907* (2013.01); *C12N 2310/20* (2017.05); *C12N 2310/3519* (2013.01); *C12Y 207/07049* (2013.01)

(58) Field of Classification Search
None
See application file for complete search history.

(56) References Cited

U.S. PATENT DOCUMENTS

| | | |
|---|---|---|
| 9,023,649 B2 | 5/2015 | Mali et al. |
| 9,914,939 B2 | 3/2018 | Church et al. |
| 10,113,163 B2 | 10/2018 | Liu et al. |
| 10,125,361 B2 | 11/2018 | May et al. |
| 11,193,123 B2 | 12/2021 | Halperin |
| 11,299,731 B1 | 4/2022 | Held |
| 11,352,623 B2 | 6/2022 | Halperin |
| 11,447,770 B1 | 9/2022 | Liu et al. |
| 2011/0059502 A1 | 3/2011 | Chalasani |
| 2014/0186958 A1 | 7/2014 | Zhang et al. |
| 2014/0349400 A1 | 11/2014 | Noah et al. |
| 2015/0071898 A1 | 3/2015 | Liu et al. |
| 2018/0230464 A1 | 8/2018 | Zhong |
| 2019/0055543 A1 | 2/2019 | Tran et al. |
| 2019/0062734 A1 | 2/2019 | Cotta-Ramusino et al. |
| 2019/0330619 A1 | 10/2019 | Smith et al. |
| 2020/0109398 A1 | 4/2020 | Rubens |
| 2022/0119848 A1 | 4/2022 | Doudna |

FOREIGN PATENT DOCUMENTS

| | | |
|---|---|---|
| WO | 2015035139 A2 | 3/2015 |
| WO | 2015195798 A1 | 12/2015 |
| WO | 2016205728 A1 | 12/2016 |
| WO | 2017151719 A1 | 9/2017 |
| WO | 2018049161 A1 | 3/2018 |
| WO | 2018049168 A1 | 3/2018 |
| WO | 20180165629 A1 | 9/2018 |
| WO | 2019051097 A1 | 3/2019 |
| WO | 2019118935 A1 | 6/2019 |
| WO | 2020047124 A1 | 3/2020 |

(Continued)

OTHER PUBLICATIONS

Ata-Abadi (Mol. Biol. Rep, 2015, vol. 42: pp. 1175-1185). (Year: 2015).*
Anzalone, A., et al., "Programmable deletion, replacement, integration and inversion of large DNA sequences with twin prime editing," Nat. Biotechnol., 2022, 40(5):731-740.
Chen, P., et al., "Enhanced prime editing systems by manipulating cellular determinants of editing outcomes," Cell, 2021, 184(22):5635-5652.e29.
Guilinger, J., et al., "Fusion of catalytically inactive Cas9 to FokI nuclease improves the specificity of genome modification," Nat. Biotechnol., 2014, 32(6):577-582.

(Continued)

*Primary Examiner* — Celine X Qian
(74) *Attorney, Agent, or Firm* — Lathrop GPM LLP; Laura A. Labeots

(57) ABSTRACT

This disclosure provides systems, methods, and compositions for site-specific genetic engineering using Programmable Addition via Site-Specific Targeting Elements (PASTE). PASTE comprises the addition of an integration site into a target genome followed by the insertion of one or more genes of interest or one or more nucleic acid sequences of interest at the site. PASTE combines gene editing technologies and integrase technologies to achieve unidirectional incorporation of genes in a genome for the treatment of diseases and diagnosis of disease.

23 Claims, 144 Drawing Sheets

Specification includes a Sequence Listing.

(56) References Cited

FOREIGN PATENT DOCUMENTS

| | | |
|---|---|---|
| WO | 2020191153 A2 | 9/2020 |
| WO | 2020191171 A1 | 9/2020 |
| WO | 2020191233 A1 | 9/2020 |
| WO | 2020191234 A1 | 9/2020 |
| WO | 2020191239 A1 | 9/2020 |
| WO | 2020191242 A1 | 9/2020 |
| WO | 2020191243 A1 | 9/2020 |
| WO | 2020191245 A1 | 9/2020 |
| WO | 2020191246 A1 | 9/2020 |
| WO | 2020191248 A1 | 9/2020 |
| WO | 2020191249 A1 | 9/2020 |
| WO | WO-2020191249 A1 * | 9/2020 |
| WO | 2020247587 A1 | 12/2020 |
| WO | 2021046243 A2 | 3/2021 |
| WO | 2021072328 A1 | 4/2021 |
| WO | 2021138469 A1 | 7/2021 |
| WO | 2021188840 A1 | 9/2021 |
| WO | 2021226558 A1 | 11/2021 |
| WO | 2022067130 A2 | 3/2022 |
| WO | 2022087235 A1 | 4/2022 |
| WO | 2022098885 A1 | 5/2022 |

OTHER PUBLICATIONS

Halperin, S., et al., "CRISPR-guided DNA polymerases enable diversification of all nucleotides in a tunable window," Nature, 2018, 560(7717):248-252. doi: 10.1038/s41586-018-0384-8.

Ioannidi, E., et al., "Drag-and-drop genome insertion without DNA cleavage with CRISPR-directed integrases," bioRxiv, 2021. doi: 10.1101/2021.11.01.466786.

Jiang, T., et al., "Deletion and replacement of long genomic sequences using prime editing," Nat. Biotechnol., 2022, 40(2):227-234.

Krzywkowski, T., et al., "Limited reverse transcriptase activity of phi29 DNA polymerase," Nucleic Acids Res., 2018, 46(7):3625-3632.

Lee, H. K., et al., "Simultaneous targeting of linked loci in mouse embryos using base editing," Sci. Rep., 2019, 9(1):1662.

Lin, Q., et al., "High-efficiency prime editing with optimized, paired pegRNAs in plants," Nat. Biotechnol., 2021, 39(8):923-927.

Marzec, M., et al., "Prime Editing: A New Way for Genome Editing," Trends Cell Biol., 2020, 30(4):257-259.

Mohr, G., et al., "A Reverse Transcriptase-Cas1 Fusion Protein Contains a Cas6 Domain Required for Both CRISPR RNA Biogenesis and RNA Spacer Acquisition," Molecular Cell, 2018, 72(4):700-714, available at https://doi.org/10.1016/j.molcel.2018.09.013.

Nelson, J., et al., "Engineered pegRNAs improve prime editing efficiency," Nat. Biotechnol., 2022, 40(3):402-410. https://doi.org/10.1038/s41587-021-01039-7.

Pallarès-Masmitjà, M., et al., "Find and cut-and-transfer (FiCAT) mammalian genome engineering," Nat. Commun., 2021, 12(1):7071. https://doi.org/10.1038/s41467-021-27183-x.

Ran, F. A., et al., "Double Nicking by RNA-Guided CRISPR Cas9 for Enhanced Genome Editing Specificity," Cell, 2013, 154(6):1380-89.

Sharon, E., et al., "Functional Genetic Variants Revealed by Massively Parallel Precise Genome Editing," Cell, 2018, 175(2):544-557.e16.

Su, Y., et al., "Human DNA polymerase η has reverse transcriptase activity in cellular environments," J. Biol. Chem., 2019, 294(15):6073-6081.

Wang, J., et al., "Efficient targeted insertion of large DNA fragments without DNA donors," Nat. Methods, 2022, 19(3):331-340. https://doi.org/10.1038/s41592-022-01399-1.

Wang, Z., et al., "Optimized paired-sgRNA/Cas9 cloning and expression cassette triggers high-efficiency multiplex genome editing in kiwifruit," Plant Biotechnol. J., 2018, 16(8):1424-1433.

Xu, W., et al., "Multiplex Nucleotide Editing by High-Fidelity Cas9 Variants with Improved Efficiency in Rice," BMC Plant Biol., 2019, 19(1):511.

Yang, L., et al., "One Prime for All Editing," Cell, 2019, 179(7):1448-1450.

Flotte Human Gene Therapy, 2019, vol. 30, No. 2, pp. 1445-1446). (Year: 2019).

Anzalone et al., Nature 2019, vol. 576, 149-157, and methods and supplement. (Year: 2019).

Anzalone et al., Programmable Deletion, Replacement, Integration and Inversion of Large DNA Sequences with Twin Prime Editing, Nature Biotechnology, Dec. 9, 2021.

Innis et al., A Novel Bxb1 Integrase RMCE System for High Fidelity Site-Specific Integration of mAb Expression Cassette in CHO Cells, Biotechnology and BioEngineering, John Wiley, Hoboken, USA, vol. 114, No. 8, Mar. 14, 2017, pp. 1837-1846.

Merrick, et al., Serine Integrases: Advancing Synthetic Biology, ACS Synthetic Biology, vol. 7, No. 2, Jan. 9, 2018, pp. 299-310.

Lee et al., Conditional Targeting of Ispd Using Paired Cas9 Nickase and a Single DNA Template in Mice, FEBS Open Bio, vol. 4, No. 1, Jul. 1, 2014, pp. 637-642.

PCT Application No. PCT/US2021/056006, International Search Report and Written Opinion, dated Feb. 23, 2022, 20 pages.

Maeder et al., Development of a Gene-Editing Approach to Restore Vision Loss in Leber Congenital Amaurosis Type 10, Letters, Nature Medicine, 25, 229-233 (2019).

Anzalone, et al., Genome Editing with CRISPR-Cas Nucleases, Base Editors, Transposases and Prime Editors, Nat. Biotechnol. 38, 824-844 (2020).

Jiang et al., Deletion and Replacement of Long Genomic Sequences Using Prime Editing. Nat. Biotechnol. 1-8 (2021).

Hisu, P. D., Lander, E. S. & Zhang, F. Development and applications of CRISPR-Cas9 for genome engineering. Cell 157, 1262-1278 (2014).

Wright, A. V., Nuñez, J. K. & Doudna, J. A. Biology and Applications of CRISPR Systems: Harnessing Nature's Toolbox for Genome Engineering. Cell 164, 29-44 (2016).

Nami, F. et al. Strategies for In Vivo Genome Editing in Nondividing Cells. Trends Biotechnol. 36, 770-786 (2018).

Suzuki, K. et al. In vivo genome editing via CRISPR/Cas9 mediated homology-independent targeted integration. Nature 540, 144-149 (2016).

Mali, P. et al. RNA-guided human genome engineering via Cas9. Science 339, 823-826 (2013).

Cong, L. et al. Multiplex genome engineering using CRISPR/Cas systems. Science 339, 819-823 (2013).

Rouet, P., Smih, F. & Jasin, M. Introduction of double-strand breaks into the genome of mouse cells by expression of a rare-cutting endonuclease. Mol. Cell. Biol. 14, 8096-8106 (1994).

Rudin, N., Sugarman, E. & Haber, J. E. Genetic and physical analysis of double-strand break repair and recombination in Saccharomyces cerevisiae. Genetics 122, 519-534 (1989).

Chapman, J. R., Taylor, M. R. G. & Boulton, S. J. Playing the end game: DNA double-strand break repair pathway choice. Mol. Cell 47, 497-510 (2012).

Geisinger, J. M. & Stearns, T. CRISPR/Cas9 treatment causes extended TP53-dependent cell cycle arrest in human cells. Nucleic Acids Res. 48, 9067-9081 (2020).

Wang, H. et al. Development of a Self-Restricting CRISPR-Cas9 System to Reduce Off-Target Effects. Mol Ther Methods Clin Dev 18, 390-401 (2020).

Kanca, O. et al. An efficient CRISPR-based strategy to insert small and large fragments of DNA using short homology arms. Elife 8, (2019).

Gaudelli, N. M. et al. Programmable base editing of A•T to G•C in genomic ONA without DNA cleavage. Nature 551, 464-471 (2017).

Komor, A. C., Kim, Y. B., Packer, M. S., Zuris, J. A. & Liu, D. R. Programmable editing of a target base in genomic DNA without double-stranded DNA cleavage. Nature 533, 420-424 (2016).

Rees, H. A. & Liu, D. R. Base editing: precision chemistry on the genome and transcriptome of living cells. Nat. Rev. Genet. 19, 770-788 (2018).

Anzalone, A. V. et al. Search-and-replace genome editing without double-strand breaks or donor DNA. Nature 576, 149-157 (2019).

(56) References Cited

OTHER PUBLICATIONS

Ivics, Z., Hackett, P. B., Plasterk, R. H. & Izsvák, Z. Molecular reconstruction of Sleeping Beauty, a Tc1-like transposon from fish, and its transposition in human cells. Cell 91, 501-510 (1997).
Choi, J. et al. Precise genomic deletions using paired prime editing. Nat. Biotechnol. 1-9 (2021).
Calos, M. P. The C31 Integrase System for Gene Therapy. Curr. Gene Ther. 6, 633-645 (2006).
Mulholland, C. B. et al. A modular open platform for systematic functional studies under physiological conditions. Nucleic Acids Res. 43, e112 (2015).
Burke, W. D. et al., Molecular Biology and Evolution 2003, 20(8), 1260-1270).
Wang et al., 2010, Genome Res. 20, 19-27.
Bannert and Kurth, 2006, Proc. Natl. Acad. USA 101, 14572-14579.
Lander et al., 2001, Nature 409, 860-921; Hua-Van et al., 2011, Biol. Dir. 6, 19.
Graham et al. (1973) Virology, 52: 456.
Anzalone et al., Programmable Large DNA Deletion, Replacement, Integration, and Inversion with Twin Prime Editing and Site-Specific Recombinases, https://doi.org/10.1101/2021.11.01.466790.
Gaj, et al., Genome-Editing Technologies: Principles and Applications, Cold Spring Harbor Perspectives in Biology 2016;8:a023754.
Ehrhardt, A., Engler, J. A., Xu, H., Cherry, A. M. & Kay, M. A. Molecular Analysis of Chromosomal Rearrangements in Mammalian Cells After øC31-Mediated Integration. Hum. Gene Ther. 17, 1077-1094 (2006).
Liu, J., Jeppesen, I., Nielsen, K. & Jensen, T. G. Phi c31 integrase induces chromosomal aberrations in primary human fibroblasts. Gene Ther. 13, 1188-1190 (2006).
Kovac, A. et al. RNA-guided retargeting of Sleeping Beauty transposition in human cells. Elife 9, (2020).
Ma, S. et al. Enhancing site-specific DNA integration by a Cas9 nuclease fused with a DNA donor-binding domain. Nucleic Acids Res. 48, 10590-10601 (2020).
Chen, S. P. & Wang, H. H. An Engineered Cas-Transposon System for Programmable and Site-Directed DNA Transpositions. CRISPR J 2, 376-394 (2019).
Bhatt, S. & Chalmers, R. Targeted DNA transposition using a dCas9-transposase fusion protein. bioRxiv 571653 (2019) doi:10.1101/571653.
Hew, B. E., Sato, R., Mauro, D., Stoytchev, I. & Owens, J. B. RNA-guided piggyBac transposition in human cells. Synth. Biol. 4, ysz018 (2019).
Chaikind, B., Bessen, J. L., Thompson, D. B., Hu, J. H. & Liu, D. R. A programmable Cas9-serine recombinase fusion protein that operates on DNA sequences in mammalian cells. Nucleic Acids Res. 44, 9758-9770 (2016).
Akopian, A., He, J., Boocock, M. R. & Stark, W. M. Chimeric recombinases with designed DNA sequence recognition. Proc. Natl. Acad. Sci. U. S. A. 100, 8688-8691 (2003).
Gordley, R. M., Smith, J. D., Gräslund, T. & Barbas, C. F., 3rd. Evolution of programmable zinc finger-recombinases with activity in human cells. J. Mol. Biol. 367, 802-813 (2007).
Mercer, A. C., Gaj, T., Fuller, R. P. & Barbas, C. F., 3rd. Chimeric TALE recombinases with programmable DNA sequence specificity. Nucleic Acids Res. 40, 11163-11172 (2012).
Gersbach, C. A., Gaj, T., Gordley, R. M., Mercer, A. C. & Barbas, C. F. Targeted plasmid integration into the human genome by an engineered zinc-finger recombinase. Nucleic Acids Res. 39, 7868-7878 (2011).
Prorocic, M. M. et al. Zinc-finger recombinase activities in vitro. Nucleic Acids Res. 39, 9316-9328 (2011).
Zhang, Q., Azarin, S. M. & Sarkar, C. A. Model-guided engineering of DNA sequences with predictable site-specific recombination rates. bioRxiv 2021.08.02.454698 (2021) doi:10.1101/2021.08.02.454698.

Peters, J. E., Makarova, K. S., Shmakov, S. & Koonin, E. V. Recruitment of CRISPR-Cas systems by Tn7-like transposons. Proc. Natl. Acad. Sci. U. S. A. 114, E7358-E7366 (2017).
Strecker, J. et al. RNA-guided DNA insertion with CRISPR-associated transposases. Science (2019) doi:10.1126/science.aax9181.
Klompe, S. E., Vo, P. L. H., Halpin-Healy, T. S. & Sternberg, S. H. Transposon-encoded CRISPR-Cas systems direct RNA-guided DNA integration. Nature 1 (2019).
Xu, Z. et al. Accuracy and efficiency define Bxb1 integrase as the best of fifteen candidate serine recombinases for the integration of DNA into the human genome. BMC Biotechnol. 13, 87 (2013).
Kay, M. A., He, C.-Y. & Chen, Z.-Y. A robust system for production of minicircle DNA vectors. Nat. Biotechnol. 28, 1287-1289 (2010).
Moss, W. N. et al., RNA Biol. 2011, 8(5), 714-718.
Oscorbin, I. P., Wong, P. F., Boyarskikh, U. A., Khrapov, E. A. & Filipenko, M. L. The attachment of a DNA-binding Sso7d-like protein improves processivity and resistance to inhibitors of M-MuLV reverse transcriptase. FEBS Lett. 594, 4338-4356 (2020).
Ghosh, P., Kim, A. I. & Hatfull, G. F. The orientation of mycobacteriophage Bxb1 integration is solely dependent on the central dinucleotide of attP and attB. Mol. Cell 12, 1101-1111 (2003).
Keravala, A. et al. A diversity of serine phage integrases mediate site-specific recombination in mammalian cells. Molecular Genetics and Genomics vol. 276 (2006).
Singh, S., Ghosh, P. & Hatfull, G. F. Attachment site selection and identity in Bxb1 serine integrase-mediated site-specific recombination. PLoS Genet. 9, e1003490 (2013).
Jusiak, B. et al. Comparison of Integrases Identifies Bxb1-GA Mutant as the Most Efficient Site-Specific Integrase System in Mammalian Cells. ACS Synth. Biol. 8, 16-24 (2019).
Schwinn, M. K. et al. CRISPR-Mediated Tagging of Endogenous Proteins with a Luminescent Peptide. ACS Chem. Biol. 13, 467-474 (2018).
Lin, S., Staahl, B. T., Alla, R. K. & Doudna, J. A. Enhanced homology-directed human genome engineering by controlled timing of CRISPR/Cas9 delivery. Elife 3, e04766 (2014).
Schnepp, B. C., Jensen, R. L., Chen, C.-L., Johnson, P. R. & Clark, K. R. Characterization of adeno-associated virus genomes isolated from human tissues. J. Virol. 79, 14793-14803 (2005).
Wold, W. S. M. & Toth, K. Adenovirus vectors for gene therapy, vaccination and cancer gene therapy. Curr. Gene Ther. 13, 421-433 (2013).
Wesselhoeft, R. A., Kowalski, P. S. & Anderson, D. G. Engineering circular RNA for potent and stable translation in eukaryotic cells. Nat. Commun. 9, 2629 (2018).
Azuma, H. et al. Robust expansion of human hepatocytes in Fah-/-/Rag2-/-/Il2rg-/-mice. Nat. Biotechnol. 25, 903-910 (2007).
Bateman, A. et al. UniProt: the universal protein knowledgebase in 2021. Nucleic Acids Res. (2020).
Amberger, J. S., Bocchini, C. A., Schiettecatte, F., Scott, A. F. & Hamosh, A. OMIM.org: Online Mendelian Inheritance in Man (OMIM®), an online catalog of human genes and genetic disorders. Nucleic Acids Res. 43, D789-98 (2015).
Ruan, J. et al. Efficient Gene Editing at Major CFTR Mutation Loci. Mol. Ther. Nucleic Acids 16, 73-81 (2019).
Mackay, D. S. et al. Screening of a large cohort of leber congenital amaurosis and retinitis pigmentosa patients identifies novel LCA5 mutations and new genotype-phenotype correlations. Hum. Mutat. 34, 1537-1546 (2013).
Marson, F. A. L., Bertuzzo, C. S. & Ribeiro, J. D. Classification of CFTR mutation classes. The Lancet. Respiratory medicine vol. 4 e37-e38 (2016).
Eyquem, J. et al. Targeting a CAR to the TRAC locus with CRISPR/Cas9 enhances tumour rejection. Nature 543, 113-117 (2017).
Tareen, A. & Kinney, J. B. Logomaker: beautiful sequence logos in Python. Bioinformatics 36, 2272-2274 (2020).
Su, Q., Sena-Esteves, M. & Gao, G. Purification of the recombinant Adenovirus by cesium chloride gradient centrifugation. Cold Spring Harb. Protoc. 2019, db.prot095547 (2019).

(56) References Cited

OTHER PUBLICATIONS

Brown et al., "Serine recombinases as tools for genome engineering." Methods, 2011; 53(4):372-9.
Hirano et al., "Site-specific recombinases as tools for heterologous gene integration." Appl. Microbiol. Biotechnol. 2011; 92(2):227-39.
Chavez and Calos, "Therapeutic applications of the φC31 integrase system." Curr. Gene Ther. 2011; 11(5):375-81.
Turan and Bode, "Site-specific recombinases: from tag-and-target- to tag-and-exchange-based genomic modifications." FASEB J. 2011; 25(12):4088-107.
Venken and Bellen, "Genome-wide manipulations of *Drosophila melanogaster* with transposons, Flp recombinase, and φC31 integrase." Methods Mol. Biol. 2012; 859:203-28.
Murphy, "Phage recombinases and their applications." Adv. Virus Res. 2012; 83:367-414.
Zhang et al., "Conditional gene manipulation: Creating a new biological era." J. Zhejiang Univ. Sci. B. 2012; 13(7):511-24.
Karpenshif and Bernstein, "From yeast to mammals: recent advances in genetic control of homologous recombination." DNA Repair (Amst). 2012; 1; 11(10):781-8.
Groth et al., "Phage integrases: biology and applications." J. Mol. Biol. 2004; 335, 667-678.
Gordley et al., "Synthesis of programmable integrases." Proc. Natl. Acad. Sci. USA. 2009; 106, 5053-5058.

\* cited by examiner

PASTE literature

ACTB (cytoskeletal)

SUPT16H (nucleus)

PASTE      literature

NOLC1 (fibrillar center)

SRRM2 (nuclear speckles)

PASTE　　　literature

LMNB1 (nuclear membrane)

DEPDC4 (aggresome)

ACTB (cytoskeletal) LMNB1 (nuc. membrane)

SEQUENCE LISTING

```
Sequence total quantity: 431
SEQ ID NO: 1              moltype = DNA    length = 34
FEATURE                   Location/Qualifiers
misc_feature              1..34
                          note = Description of Artificial Sequence: Synthetic
                          oligonucleotide
misc_feature              1..34
                          note = Lox71
source                    1..34
                          mol_type = other DNA
                          organism = synthetic construct
SEQUENCE: 1
ataacttcgt ataatgtatg ctatacgaac ggta                                    34

SEQ ID NO: 2              moltype = DNA    length = 34
FEATURE                   Location/Qualifiers
misc_feature              1..34
                          note = Description of Artificial Sequence: Synthetic
                          oligonucleotide
misc_feature              1..34
                          note = Lox66
source                    1..34
                          mol_type = other DNA
                          organism = synthetic construct
SEQUENCE: 2
taccgttcgt ataatgtatg ctatacgaag ttat                                    34

SEQ ID NO: 3              moltype = DNA    length = 46
FEATURE                   Location/Qualifiers
misc_feature              1..46
                          note = Description of Artificial Sequence: Synthetic
                          oligonucleotide
misc_feature              1..46
                          note = AttB
source                    1..46
                          mol_type = other DNA
                          organism = synthetic construct
SEQUENCE: 3
ggccggcttg tcgacgacgg cggtctccgt cgtcaggatc atccgg                       46

SEQ ID NO: 4              moltype = DNA    length = 46
FEATURE                   Location/Qualifiers
misc_feature              1..46
                          note = Description of Artificial Sequence: Synthetic
                          oligonucleotide
misc_feature              1..46
                          note = AttP
source                    1..46
                          mol_type = other DNA
                          organism = synthetic construct
SEQUENCE: 4
ccggatgatc ctgacgacgg agaccgccgt cgtcgacaag ccggcc                       46

SEQ ID NO: 5              moltype = DNA    length = 38
FEATURE                   Location/Qualifiers
misc_feature              1..38
                          note = Description of Artificial Sequence: Synthetic
                          oligonucleotide
misc_feature              1..38
                          note = AttB-TT
source                    1..38
                          mol_type = other DNA
                          organism = synthetic construct
SEQUENCE: 5
ggcttgtcga cgacggcgtt ctccgtcgtc aggatcat                                38

SEQ ID NO: 6              moltype = DNA    length = 52
FEATURE                   Location/Qualifiers
misc_feature              1..52
                          note = Description of Artificial Sequence: Synthetic
                          oligonucleotide
misc_feature              1..52
                          note = AttP-TT
source                    1..52
                          mol_type = other DNA
                          organism = synthetic construct
SEQUENCE: 6
gtggtttgtc tggtcaacca ccgcgttctc agtggtgtac ggtacaaacc ca                52
```

```
SEQ ID NO: 7              moltype = DNA   length = 38
FEATURE                   Location/Qualifiers
misc_feature              1..38
                          note = Description of Artificial Sequence: Synthetic
                            oligonucleotide
misc_feature              1..38
                          note = AttB-AA
source                    1..38
                          mol_type = other DNA
                          organism = synthetic construct
SEQUENCE: 7
ggcttgtcga cgacggcgaa ctccgtcgtc aggatcat                           38

SEQ ID NO: 8              moltype = DNA   length = 52
FEATURE                   Location/Qualifiers
misc_feature              1..52
                          note = Description of Artificial Sequence: Synthetic
                            oligonucleotide
misc_feature              1..52
                          note = AttP-AA
source                    1..52
                          mol_type = other DNA
                          organism = synthetic construct
SEQUENCE: 8
gtggtttgtc tggtcaacca ccgcgaactc agtggtgtac ggtacaaacc ca           52

SEQ ID NO: 9              moltype = DNA   length = 38
FEATURE                   Location/Qualifiers
misc_feature              1..38
                          note = Description of Artificial Sequence: Synthetic
                            oligonucleotide
misc_feature              1..38
                          note = AttB-CC
source                    1..38
                          mol_type = other DNA
                          organism = synthetic construct
SEQUENCE: 9
ggcttgtcga cgacggcgcc ctccgtcgtc aggatcat                           38

SEQ ID NO: 10             moltype = DNA   length = 52
FEATURE                   Location/Qualifiers
misc_feature              1..52
                          note = Description of Artificial Sequence: Synthetic
                            oligonucleotide
misc_feature              1..52
                          note = AttP-CC
source                    1..52
                          mol_type = other DNA
                          organism = synthetic construct
SEQUENCE: 10
gtggtttgtc tggtcaacca ccgcgccctc agtggtgtac ggtacaaacc ca           52

SEQ ID NO: 11             moltype = DNA   length = 38
FEATURE                   Location/Qualifiers
misc_feature              1..38
                          note = Description of Artificial Sequence: Synthetic
                            oligonucleotide
misc_feature              1..38
                          note = AttB-GG
source                    1..38
                          mol_type = other DNA
                          organism = synthetic construct
SEQUENCE: 11
ggcttgtcga cgacggcggg ctccgtcgtc aggatcat                           38

SEQ ID NO: 12             moltype = DNA   length = 52
FEATURE                   Location/Qualifiers
misc_feature              1..52
                          note = Description of Artificial Sequence: Synthetic
                            oligonucleotide
misc_feature              1..52
                          note = AttP-GG
source                    1..52
                          mol_type = other DNA
                          organism = synthetic construct
SEQUENCE: 12
gtggtttgtc tggtcaacca ccgcgggctc agtggtgtac ggtacaaacc ca           52
```

-continued

```
SEQ ID NO: 13          moltype = DNA   length = 38
FEATURE                Location/Qualifiers
misc_feature           1..38
                       note = Description of Artificial Sequence: Synthetic
                       oligonucleotide
misc_feature           1..38
                       note = AttB-TG
source                 1..38
                       mol_type = other DNA
                       organism = synthetic construct
SEQUENCE: 13
ggcttgtcga cgacggcgtg ctccgtcgtc aggatcat                              38

SEQ ID NO: 14          moltype = DNA   length = 52
FEATURE                Location/Qualifiers
misc_feature           1..52
                       note = Description of Artificial Sequence: Synthetic
                       oligonucleotide
misc_feature           1..52
                       note = AttP-TG
source                 1..52
                       mol_type = other DNA
                       organism = synthetic construct
SEQUENCE: 14
gtggtttgtc tggtcaacca ccgcgtgctc agtggtgtac ggtacaaacc ca             52

SEQ ID NO: 15          moltype = DNA   length = 38
FEATURE                Location/Qualifiers
misc_feature           1..38
                       note = Description of Artificial Sequence: Synthetic
                       oligonucleotide
misc_feature           1..38
                       note = AttB-GT
source                 1..38
                       mol_type = other DNA
                       organism = synthetic construct
SEQUENCE: 15
ggcttgtcga cgacggcggt ctccgtcgtc aggatcat                              38

SEQ ID NO: 16          moltype = DNA   length = 52
FEATURE                Location/Qualifiers
misc_feature           1..52
                       note = Description of Artificial Sequence: Synthetic
                       oligonucleotide
misc_feature           1..52
                       note = AttP-GT
source                 1..52
                       mol_type = other DNA
                       organism = synthetic construct
SEQUENCE: 16
gtggtttgtc tggtcaacca ccgcggtctc agtggtgtac ggtacaaacc ca             52

SEQ ID NO: 17          moltype = DNA   length = 38
FEATURE                Location/Qualifiers
misc_feature           1..38
                       note = Description of Artificial Sequence: Synthetic
                       oligonucleotide
misc_feature           1..38
                       note = AttB-CT
source                 1..38
                       mol_type = other DNA
                       organism = synthetic construct
SEQUENCE: 17
ggcttgtcga cgacggcgct ctccgtcgtc aggatcat                              38

SEQ ID NO: 18          moltype = DNA   length = 52
FEATURE                Location/Qualifiers
misc_feature           1..52
                       note = Description of Artificial Sequence: Synthetic
                       oligonucleotide
misc_feature           1..52
                       note = AttP-CT
source                 1..52
                       mol_type = other DNA
                       organism = synthetic construct
SEQUENCE: 18
gtggtttgtc tggtcaacca ccgcgctctc agtggtgtac ggtacaaacc ca             52
```

```
SEQ ID NO: 19          moltype = DNA   length = 38
FEATURE                Location/Qualifiers
misc_feature           1..38
                       note = Description of Artificial Sequence: Synthetic
                        oligonucleotide
misc_feature           1..38
                       note = AttB-CA
source                 1..38
                       mol_type = other DNA
                       organism = synthetic construct
SEQUENCE: 19
ggcttgtcga cgacggcgca ctccgtcgtc aggatcat                              38

SEQ ID NO: 20          moltype = DNA   length = 52
FEATURE                Location/Qualifiers
misc_feature           1..52
                       note = Description of Artificial Sequence: Synthetic
                        oligonucleotide
misc_feature           1..52
                       note = AttP-CA
source                 1..52
                       mol_type = other DNA
                       organism = synthetic construct
SEQUENCE: 20
gtggtttgtc tggtcaacca ccgcgcactc agtggtgtac ggtacaaacc ca             52

SEQ ID NO: 21          moltype = DNA   length = 38
FEATURE                Location/Qualifiers
misc_feature           1..38
                       note = Description of Artificial Sequence: Synthetic
                        oligonucleotide
misc_feature           1..38
                       note = AttB-TC
source                 1..38
                       mol_type = other DNA
                       organism = synthetic construct
SEQUENCE: 21
ggcttgtcga cgacggcgtc ctccgtcgtc aggatcat                             38

SEQ ID NO: 22          moltype = DNA   length = 52
FEATURE                Location/Qualifiers
misc_feature           1..52
                       note = Description of Artificial Sequence: Synthetic
                        oligonucleotide
misc_feature           1..52
                       note = AttP-TC
source                 1..52
                       mol_type = other DNA
                       organism = synthetic construct
SEQUENCE: 22
gtggtttgtc tggtcaacca ccgcgtcctc agtggtgtac ggtacaaacc ca             52

SEQ ID NO: 23          moltype = DNA   length = 38
FEATURE                Location/Qualifiers
misc_feature           1..38
                       note = Description of Artificial Sequence: Synthetic
                        oligonucleotide
misc_feature           1..38
                       note = AttB-GA
source                 1..38
                       mol_type = other DNA
                       organism = synthetic construct
SEQUENCE: 23
ggcttgtcga cgacggcgga ctccgtcgtc aggatcat                             38

SEQ ID NO: 24          moltype = DNA   length = 52
FEATURE                Location/Qualifiers
misc_feature           1..52
                       note = Description of Artificial Sequence: Synthetic
                        oligonucleotide
misc_feature           1..52
                       note = AttP-GA
source                 1..52
                       mol_type = other DNA
                       organism = synthetic construct
SEQUENCE: 24
gtggtttgtc tggtcaacca ccgcggactc agtggtgtac ggtacaaacc ca             52
```

```
SEQ ID NO: 25          moltype = DNA  length = 38
FEATURE                Location/Qualifiers
misc_feature           1..38
                       note = Description of Artificial Sequence: Synthetic
                       oligonucleotide
misc_feature           1..38
                       note = AttB-AG
source                 1..38
                       mol_type = other DNA
                       organism = synthetic construct
SEQUENCE: 25
ggcttgtcga cgacggcgag ctccgtcgtc aggatcat                              38

SEQ ID NO: 26          moltype = DNA  length = 52
FEATURE                Location/Qualifiers
misc_feature           1..52
                       note = Description of Artificial Sequence: Synthetic
                       oligonucleotide
misc_feature           1..52
                       note = AttP-AG
source                 1..52
                       mol_type = other DNA
                       organism = synthetic construct
SEQUENCE: 26
gtggtttgtc tggtcaacca ccgcgagctc agtggtgtac ggtacaaacc ca              52

SEQ ID NO: 27          moltype = DNA  length = 38
FEATURE                Location/Qualifiers
misc_feature           1..38
                       note = Description of Artificial Sequence: Synthetic
                       oligonucleotide
misc_feature           1..38
                       note = AttB-AC
source                 1..38
                       mol_type = other DNA
                       organism = synthetic construct
SEQUENCE: 27
ggcttgtcga cgacggcgac ctccgtcgtc aggatcat                              38

SEQ ID NO: 28          moltype = DNA  length = 52
FEATURE                Location/Qualifiers
misc_feature           1..52
                       note = Description of Artificial Sequence: Synthetic
                       oligonucleotide
misc_feature           1..52
                       note = AttP-AC
source                 1..52
                       mol_type = other DNA
                       organism = synthetic construct
SEQUENCE: 28
gtggtttgtc tggtcaacca ccgcgacctc agtggtgtac ggtacaaacc ca              52

SEQ ID NO: 29          moltype = DNA  length = 38
FEATURE                Location/Qualifiers
misc_feature           1..38
                       note = Description of Artificial Sequence: Synthetic
                       oligonucleotide
misc_feature           1..38
                       note = AttB-AT
source                 1..38
                       mol_type = other DNA
                       organism = synthetic construct
SEQUENCE: 29
ggcttgtcga cgacggcgat ctccgtcgtc aggatcat                              38

SEQ ID NO: 30          moltype = DNA  length = 52
FEATURE                Location/Qualifiers
misc_feature           1..52
                       note = Description of Artificial Sequence: Synthetic
                       oligonucleotide
misc_feature           1..52
                       note = AttP-AT
source                 1..52
                       mol_type = other DNA
                       organism = synthetic construct
SEQUENCE: 30
gtggtttgtc tggtcaacca ccgcgatctc agtggtgtac ggtacaaacc ca              52
```

```
SEQ ID NO: 31           moltype = DNA  length = 38
FEATURE                 Location/Qualifiers
misc_feature            1..38
                        note = Description of Artificial Sequence: Synthetic
                          oligonucleotide
misc_feature            1..38
                        note = AttB-GC
source                  1..38
                        mol_type = other DNA
                        organism = synthetic construct
SEQUENCE: 31
ggcttgtcga cgacggcggc ctccgtcgtc aggatcat                               38

SEQ ID NO: 32           moltype = DNA  length = 52
FEATURE                 Location/Qualifiers
misc_feature            1..52
                        note = Description of Artificial Sequence: Synthetic
                          oligonucleotide
misc_feature            1..52
                        note = AttP-GC
source                  1..52
                        mol_type = other DNA
                        organism = synthetic construct
SEQUENCE: 32
gtggtttgtc tggtcaacca ccgcggcctc agtggtgtac ggtacaaacc ca              52

SEQ ID NO: 33           moltype = DNA  length = 38
FEATURE                 Location/Qualifiers
misc_feature            1..38
                        note = Description of Artificial Sequence: Synthetic
                          oligonucleotide
misc_feature            1..38
                        note = AttB-CG
source                  1..38
                        mol_type = other DNA
                        organism = synthetic construct
SEQUENCE: 33
ggcttgtcga cgacggcgcg ctccgtcgtc aggatcat                               38

SEQ ID NO: 34           moltype = DNA  length = 52
FEATURE                 Location/Qualifiers
misc_feature            1..52
                        note = Description of Artificial Sequence: Synthetic
                          oligonucleotide
misc_feature            1..52
                        note = AttB-CG
source                  1..52
                        mol_type = other DNA
                        organism = synthetic construct
SEQUENCE: 34
gtggtttgtc tggtcaacca ccgcgcgctc agtggtgtac ggtacaaacc ca              52

SEQ ID NO: 35           moltype = DNA  length = 38
FEATURE                 Location/Qualifiers
misc_feature            1..38
                        note = Description of Artificial Sequence: Synthetic
                          oligonucleotide
misc_feature            1..38
                        note = AttB-TA
source                  1..38
                        mol_type = other DNA
                        organism = synthetic construct
SEQUENCE: 35
ggcttgtcga cgacggcgta ctccgtcgtc aggatcat                               38

SEQ ID NO: 36           moltype = DNA  length = 52
FEATURE                 Location/Qualifiers
misc_feature            1..52
                        note = Description of Artificial Sequence: Synthetic
                          oligonucleotide
misc_feature            1..52
                        note = AttP-TA
source                  1..52
                        mol_type = other DNA
                        organism = synthetic construct
SEQUENCE: 36
gtggtttgtc tggtcaacca ccgcgtactc agtggtgtac ggtacaaacc ca              52
```

```
SEQ ID NO: 37            moltype = DNA   length = 45
FEATURE                  Location/Qualifiers
misc_feature             1..45
                         note = Description of Artificial Sequence: Synthetic
                           oligonucleotide
misc_feature             1..45
                         note = C-31-B
source                   1..45
                         mol_type = other DNA
                         organism = synthetic construct
SEQUENCE: 37
tgcgggtgcc agggcgtgcc cttgggctcc ccgggcgcgt actcc                45

SEQ ID NO: 38            moltype = DNA   length = 42
FEATURE                  Location/Qualifiers
misc_feature             1..42
                         note = Description of Artificial Sequence: Synthetic
                           oligonucleotide
misc_feature             1..42
                         note = C31-P
source                   1..42
                         mol_type = other DNA
                         organism = synthetic construct
SEQUENCE: 38
gtgcccaac tggggtaacc tttgagttct ctcagttggg gg                    42

SEQ ID NO: 39            moltype = DNA   length = 57
FEATURE                  Location/Qualifiers
misc_feature             1..57
                         note = Description of Artificial Sequence: Synthetic
                           oligonucleotide
misc_feature             1..57
                         note = R4-B
source                   1..57
                         mol_type = other DNA
                         organism = synthetic construct
SEQUENCE: 39
gcgcccaagt tgcccatgac catgccgaag cagtggtaga agggcaccgg cagacac    57

SEQ ID NO: 40            moltype = DNA   length = 70
FEATURE                  Location/Qualifiers
misc_feature             1..70
                         note = Description of Artificial Sequence: Synthetic
                           oligonucleotide
misc_feature             1..70
                         note = R4-P
source                   1..70
                         mol_type = other DNA
                         organism = synthetic construct
SEQUENCE: 40
aggcatgttc cccaaagcga taccacttga agcagtggta ctgcttgtgg gtacactctg 60
cgggtgatga                                                        70

SEQ ID NO: 41            moltype = DNA   length = 60
FEATURE                  Location/Qualifiers
misc_feature             1..60
                         note = Description of Artificial Sequence: Synthetic
                           oligonucleotide
misc_feature             1..60
                         note = BT1-B
source                   1..60
                         mol_type = other DNA
                         organism = synthetic construct
SEQUENCE: 41
gtccttgacc aggtttttga cgaaagtgat ccagatgatc cagctccaca ccccgaacgc 60

SEQ ID NO: 42            moltype = DNA   length = 63
FEATURE                  Location/Qualifiers
misc_feature             1..63
                         note = Description of Artificial Sequence: Synthetic
                           oligonucleotide
misc_feature             1..63
                         note = BT1-P
source                   1..63
                         mol_type = other DNA
                         organism = synthetic construct
SEQUENCE: 42
ggtgctgggt tgttgtctct ggacagtgat ccatgggaaa ctactcagca ccaccaatgt 60
tcc                                                               63
```

```
SEQ ID NO: 43            moltype = DNA  length = 50
FEATURE                  Location/Qualifiers
misc_feature             1..50
                         note = Description of Artificial Sequence: Synthetic
                          oligonucleotide
misc_feature             1..50
                         note = Bxb-B
source                   1..50
                         mol_type = other DNA
                         organism = synthetic construct
SEQUENCE: 43
tcggccggct tgtcgacgac ggcggtctcc gtcgtcagga tcatccgggc           50

SEQ ID NO: 44            moltype = DNA  length = 58
FEATURE                  Location/Qualifiers
misc_feature             1..58
                         note = Description of Artificial Sequence: Synthetic
                          oligonucleotide
misc_feature             1..58
                         note = Bxb-P
source                   1..58
                         mol_type = other DNA
                         organism = synthetic construct
SEQUENCE: 44
gtcgtggttt gtctggtcaa ccaccgcggt ctcagtggtg tacggtacaa accccgac  58

SEQ ID NO: 45            moltype = DNA  length = 46
FEATURE                  Location/Qualifiers
misc_feature             1..46
                         note = Description of Artificial Sequence: Synthetic
                          oligonucleotide
misc_feature             1..46
                         note = TG1-B
source                   1..46
                         mol_type = other DNA
                         organism = synthetic construct
SEQUENCE: 45
gatcagctcc gcgggcaaga ccttctcctt cacggggtgg aaggtc               46

SEQ ID NO: 46            moltype = DNA  length = 67
FEATURE                  Location/Qualifiers
misc_feature             1..67
                         note = Description of Artificial Sequence: Synthetic
                          oligonucleotide
misc_feature             1..67
                         note = TG1-P
source                   1..67
                         mol_type = other DNA
                         organism = synthetic construct
SEQUENCE: 46
tcaaccccgt tccagcccaa cagtgttagt ctttgctctt acccagttgg gcgggatagc 60
ctgcccg                                                          67

SEQ ID NO: 47            moltype = DNA  length = 57
FEATURE                  Location/Qualifiers
misc_feature             1..57
                         note = Description of Artificial Sequence: Synthetic
                          oligonucleotide
misc_feature             1..57
                         note = C1-B
source                   1..57
                         mol_type = other DNA
                         organism = synthetic construct
SEQUENCE: 47
aacgattttc aaaggatcac tgaatcaaaa gtattgctca tccacgcgaa attttc    57

SEQ ID NO: 48            moltype = DNA  length = 57
FEATURE                  Location/Qualifiers
misc_feature             1..57
                         note = Description of Artificial Sequence: Synthetic
                          oligonucleotide
misc_feature             1..57
                         note = C1-P
source                   1..57
                         mol_type = other DNA
                         organism = synthetic construct
SEQUENCE: 48
aatatttag gtatatgatt tgtttatta gtgtaaataa cactatgtac ctaaaat     57
```

```
SEQ ID NO: 49          moltype = DNA  length = 53
FEATURE                Location/Qualifiers
misc_feature           1..53
                       note = Description of Artificial Sequence: Synthetic
                       oligonucleotide
misc_feature           1..53
                       note = C370-B
source                 1..53
                       mol_type = other DNA
                       organism = synthetic construct
SEQUENCE: 49
tgtaaaggag actgataatg gcatgtacaa ctatactcgt cggtaaaaag gca             53

SEQ ID NO: 50          moltype = DNA  length = 52
FEATURE                Location/Qualifiers
misc_feature           1..52
                       note = Description of Artificial Sequence: Synthetic
                       oligonucleotide
misc_feature           1..52
                       note = C370-P
source                 1..52
                       mol_type = other DNA
                       organism = synthetic construct
SEQUENCE: 50
taaaaaaata cagcgttttt catgtacaac tatactagtt gtagtgccta aa              52

SEQ ID NO: 51          moltype = DNA  length = 56
FEATURE                Location/Qualifiers
misc_feature           1..56
                       note = Description of Artificial Sequence: Synthetic
                       oligonucleotide
misc_feature           1..56
                       note = K38-B
source                 1..56
                       mol_type = other DNA
                       organism = synthetic construct
SEQUENCE: 51
gagcgccgga tcagggagtg gacggcctgg gagcgctaca cgctgtggct gcggtc          56

SEQ ID NO: 52          moltype = DNA  length = 56
FEATURE                Location/Qualifiers
misc_feature           1..56
                       note = Description of Artificial Sequence: Synthetic
                       oligonucleotide
misc_feature           1..56
                       note = K38-P
source                 1..56
                       mol_type = other DNA
                       organism = synthetic construct
SEQUENCE: 52
ccctaatacg caagtcgata actctcctgg gagcgttgac aacttgcgca ccctga          56

SEQ ID NO: 53          moltype = DNA  length = 68
FEATURE                Location/Qualifiers
misc_feature           1..68
                       note = Description of Artificial Sequence: Synthetic
                       oligonucleotide
misc_feature           1..68
                       note = RB-B
source                 1..68
                       mol_type = other DNA
                       organism = synthetic construct
SEQUENCE: 53
tctcgtggtg gtggaaggtg ttggtgcggg gttggccgtg gtcgaggtgg ggtggtggta      60
gccattcg                                                              68

SEQ ID NO: 54          moltype = DNA  length = 69
FEATURE                Location/Qualifiers
misc_feature           1..69
                       note = Description of Artificial Sequence: Synthetic
                       oligonucleotide
misc_feature           1..69
                       note = RV-P
source                 1..69
                       mol_type = other DNA
                       organism = synthetic construct
```

```
SEQUENCE: 54
gcacaggtgt agtgtatctc acaggtccac ggttggccgt ggactgctga agaacattcc    60
acgccagga                                                            69

SEQ ID NO: 55           moltype = DNA  length = 65
FEATURE                 Location/Qualifiers
misc_feature            1..65
                        note = Description of Artificial Sequence: Synthetic
                        oligonucleotide
misc_feature            1..65
                        note = SPBC-B
source                  1..65
                        mol_type = other DNA
                        organism = synthetic construct
SEQUENCE: 55
agtgcagcat gtcattaata tcagtacaga taaagctgta tctcctgtga acacaatggg    60
tgcca                                                                65

SEQ ID NO: 56           moltype = DNA  length = 55
FEATURE                 Location/Qualifiers
misc_feature            1..55
                        note = Description of Artificial Sequence: Synthetic
                        oligonucleotide
misc_feature            1..55
                        note = SPBC-P
source                  1..55
                        mol_type = other DNA
                        organism = synthetic construct
SEQUENCE: 56
aaagtagtaa gtatcttaaa aaacagataa agctgtatat taagatactt actac         55

SEQ ID NO: 57           moltype = DNA  length = 54
FEATURE                 Location/Qualifiers
misc_feature            1..54
                        note = Description of Artificial Sequence: Synthetic
                        oligonucleotide
misc_feature            1..54
                        note = TP901-B
source                  1..54
                        mol_type = other DNA
                        organism = synthetic construct
SEQUENCE: 57
tgataattgc caacacaatt aacatctcaa tcaaggtaaa tgcttttcg tttt            54

SEQ ID NO: 58           moltype = DNA  length = 54
FEATURE                 Location/Qualifiers
misc_feature            1..54
                        note = Description of Artificial Sequence: Synthetic
                        oligonucleotide
misc_feature            1..54
                        note = TP901-P
source                  1..54
                        mol_type = other DNA
                        organism = synthetic construct
SEQUENCE: 58
aattgcgagt ttttatttcg tttatttcaa ttaaggtaac taaaaaactc cttt           54

SEQ ID NO: 59           moltype = DNA  length = 68
FEATURE                 Location/Qualifiers
misc_feature            1..68
                        note = Description of Artificial Sequence: Synthetic
                        oligonucleotide
misc_feature            1..68
                        note = Wbeta-B
source                  1..68
                        mol_type = other DNA
                        organism = synthetic construct
SEQUENCE: 59
aaggtagcgt caacgatagg tgtaactgtc gtgtttgtaa cggtacttcc aacagctggc    60
gtttcagt                                                             68

SEQ ID NO: 60           moltype = DNA  length = 68
FEATURE                 Location/Qualifiers
misc_feature            1..68
                        note = Description of Artificial Sequence: Synthetic
                        oligonucleotide
misc_feature            1..68
                        note = Wbeta-P
```

```
source                   1..68
                         mol_type = other DNA
                         organism = synthetic construct
SEQUENCE: 60
tagtttaaaa gttggttatt agttactgtg atatttatca cggtacccaa taaccaatga    60
atatttga                                                             68

SEQ ID NO: 61            moltype = DNA  length = 57
FEATURE                  Location/Qualifiers
misc_feature             1..57
                         note = Description of Artificial Sequence: Synthetic
                         oligonucleotide
misc_feature             1..57
                         note = A118-B
source                   1..57
                         mol_type = other DNA
                         organism = synthetic construct
SEQUENCE: 61
tgtaactttt tcggatcaag ctatgaagga cgcaaagagg gaactaaaca cttaatt       57

SEQ ID NO: 62            moltype = DNA  length = 57
FEATURE                  Location/Qualifiers
misc_feature             1..57
                         note = Description of Artificial Sequence: Synthetic
                         oligonucleotide
misc_feature             1..57
                         note = A118-P
source                   1..57
                         mol_type = other DNA
                         organism = synthetic construct
SEQUENCE: 62
ttgtttagtt cctcgttttc tctcgttgga agaagaagaa acgagaaact aaaatta       57

SEQ ID NO: 63            moltype = DNA  length = 63
FEATURE                  Location/Qualifiers
misc_feature             1..63
                         note = Description of Artificial Sequence: Synthetic
                         oligonucleotide
misc_feature             1..63
                         note = BL3-B
source                   1..63
                         mol_type = other DNA
                         organism = synthetic construct
SEQUENCE: 63
caacctgttg acatgtttcc acagacaact cacgtggagg tagtcacggc ttttacgtta    60
gtt                                                                  63

SEQ ID NO: 64            moltype = DNA  length = 61
FEATURE                  Location/Qualifiers
misc_feature             1..61
                         note = Description of Artificial Sequence: Synthetic
                         oligonucleotide
misc_feature             1..61
                         note = BL3-P
source                   1..61
                         mol_type = other DNA
                         organism = synthetic construct
SEQUENCE: 64
gagaatactg ttgaacaatg aaaaactagg catgtagaag ttgtttgtgc actaactta    60
a                                                                    61

SEQ ID NO: 65            moltype = DNA  length = 120
FEATURE                  Location/Qualifiers
misc_feature             1..120
                         note = Description of Artificial Sequence: Synthetic
                         polynucleotide
misc_feature             1..120
                         note = MR11-B
source                   1..120
                         mol_type = other DNA
                         organism = synthetic construct
SEQUENCE: 65
acaggtcaac acatcgcagt tatcgaacaa tcttcgaaaa tgtatggagg cacttgtatc    60
aatataggat gtataccttc gaagacactt gtacatgatg gattagaagg caaatccttt   120
```

```
SEQ ID NO: 66            moltype = DNA  length = 120
FEATURE                  Location/Qualifiers
misc_feature             1..120
                         note = Description of Artificial Sequence: Synthetic
                         polynucleotide
misc_feature             1..120
                         note = MR11-P
source                   1..120
                         mol_type = other DNA
                         organism = synthetic construct
SEQUENCE: 66
caaaataaaa aacattgatt tttattaact tcttttgtgc ggaactacga acagttcatt    60
aatacgaagt gtacaaactt ccatacaaaa ataaccacga caattaagac gtggtttcta   120

SEQ ID NO: 67            moltype = DNA  length = 17
FEATURE                  Location/Qualifiers
misc_feature             1..17
                         note = Description of Artificial Sequence: Synthetic
                         oligonucleotide
misc_feature             1..17
                         note = AttL
source                   1..17
                         mol_type = other DNA
                         organism = synthetic construct
SEQUENCE: 67
attatttctc accctga                                                   17

SEQ ID NO: 68            moltype = DNA  length = 17
FEATURE                  Location/Qualifiers
misc_feature             1..17
                         note = Description of Artificial Sequence: Synthetic
                         oligonucleotide
misc_feature             1..17
                         note = AttR
source                   1..17
                         mol_type = other DNA
                         organism = synthetic construct
SEQUENCE: 68
atcatctccc acccgga                                                   17

SEQ ID NO: 69            moltype = DNA  length = 34
FEATURE                  Location/Qualifiers
misc_feature             1..34
                         note = Description of Artificial Sequence: Synthetic
                         oligonucleotide
misc_feature             1..34
                         note = Vox
source                   1..34
                         mol_type = other DNA
                         organism = synthetic construct
SEQUENCE: 69
aataggtctg agaacgccca ttctcagacg tatt                                34

SEQ ID NO: 70            moltype = DNA  length = 34
FEATURE                  Location/Qualifiers
misc_feature             1..34
                         note = Description of Artificial Sequence: Synthetic
                         oligonucleotide
misc_feature             1..34
                         note = FRT
source                   1..34
                         mol_type = other DNA
                         organism = synthetic construct
SEQUENCE: 70
gaagttccta tactttctag agaataggaa cttc                                34

SEQ ID NO: 71            moltype = DNA  length = 5881
FEATURE                  Location/Qualifiers
misc_feature             1..5881
                         note = Description of Artificial Sequence: Synthetic
                         polynucleotide
misc_feature             1..5881
                         note = Cre Recombinase Expression Plasmid
source                   1..5881
                         mol_type = other DNA
                         organism = synthetic construct
```

```
SEQUENCE: 71
ggtcgacatt gattattgac tagttattaa tagtaatcaa ttacggggtc attagttcat    60
agcccatata tggagttccg cgttacataa cttacggtaa atgggcccgcc tggctgaccg   120
cccaacgacc cccgcccatt gacgtcaata atgacgtatg ttcccatagt aacgccaata   180
gggactttcc attgacgtca atgggtggag tatttacggt aaactgccca cttggcagta   240
catcaagtgt atcatatgcc aagtacgccc cctattgacg tcaatgacgg taaatggccc   300
gcctggcatt atgcccagta catgacctta tgggactttc ctacttggca gtacatctac   360
gtattagtca tcgctattac catggtcgag gtgagcccca cgttctgctt cactctcccc   420
atctccccc cctccccacc cccaattttg tatttattta ttttttaatt attttgtgca    480
gcgatggggg cggggggggg ggggcgcgc gccaggcggg gggggggggg gggggggggca   540
ggggggggg gggcggggggg gggcggcggc agccaatcag agcggcgcgc tccgaaagtt   600
tccttttatg gcgaggcggc ggcggcggcg gccctataaa aagcgaagcg cgcggcgggc   660
gggagtcgct gcgcgctgcc ttcgccccgt gccccgctcc gccgccgcct cgcgccgccc   720
gccccggctc tgactgaccg cgttactccc acaggtgagc gggcgggacg gcccttctcc   780
tccgggctgt aattagcgct tggtttaatg acggcttcgtt tcttttctgt ggctgcgtga   840
aagccttgag gggctccggg agggcccttt gtgcggggggg agcggctcgg ggggtgcgtg   900
cgtgtgtgtg tgcgtgggga gcgccgcgtg cggctccgcg ctgcccggcg gctgtgagcg   960
ctgcgggcgc ggcgcggggc tttgtgcgct ccgcagtgtg cgcgaggggga gcgcggccgg  1020
gggcggtgcc ccgcggtgcg gggggggctg cgaggggaac aaaggctgcg tgcggggtgt  1080
gtgcgtgggg gggtgagcag ggggtgtggg cgcgtcggtc gggctgcaac cccccctgca  1140
cccccctccc cgagttgctg agcacggccc ggcttcgggt gcggggctcc gtacggggcg  1200
tggcgcgggg ctcgccgtgc cggggggggg gtggcggcag gtggggtgc cgggcggggc   1260
ggggccgcct cgggccgggg agggctcggg ggagggggcgc ggcggccccc ggagcgccgg  1320
cggctgtcga ggcgcggcga gccgcagcca ttgccttta tggtaatcgt gcgagagggc   1380
gcagggactt cctttgtccc aaatctgtgc ggagccgaaa tctgggaggc gccgccgcac  1440
cccctctagc gggcgcgggg cgaagcggtg cggcgccggg aggaaggaaa tgggcgggga  1500
gggccttcgt gcgtcgccgc gccgccgtcc ccttctccct ctccagcctc ggggctgtcc  1560
gcgggggggac ggctgccttc ggggggggacg gggcagggcg gggttcggct tctggcgtgt  1620
gaccggcggc tctagagcct ctgctaacca tgttcatgcc ttcttcttt tcctacagct   1680
cctggccgac gtgctggtta ttgtgctgtc tcatcatttt ggcaaagaat tctgagccgc  1740
caccatggcc aatttactga ccgtacacca aaatttgcct gcattaccgg tcgatgcaac  1800
gagtgatgag gttcgcaaga acctgatgga catgttcagg gatcgccagg cgttttctga  1860
gcatacctgg aaaatgcttc tgtccgtttg ccggtcgtgg gcggcatggt gcaagttgaa  1920
taaccggaaa tggtttcccg cagaacctga agatgttcgc gattatcttc tatatcttca  1980
ggcgcgcggt ctggcagtaa aaactatcca gcaacatttg ggccagctaa acatgcttca  2040
tcgtcggtcc gggctgccac gaccaagtga cagcaatgct gtttcactgg ttatgcggcg  2100
gatccgaaaa gaaaacgttg atgccggtga acgtgcaaaa caggctctag cgttcgaacg  2160
cactgatttc gaccaggttc gttcactcat ggaaaatagc gatcgctgcc aggatatacg  2220
taatctgaca ttttctgggga ttgcttataa caccctgtta cgtatagccg aaattgccaa  2280
gatcagggtt aaagatatct cacgtactga cggtgggaga atgttaatcc atattggcag  2340
aacgaaaacg ctggttagca ccgcaggtgt agagaaggca cttagcctgg gggtaactaa  2400
actggtcgag cgatggattt ccgtctctgg tgtagctgat gatccgaata actacctgtt  2460
ttgccgggtc agaaaaaatg gtgttgccgc gccatctgcc accagccagc tatcaactcg  2520
cgccctggaa gggattttttg aagcaactca tcgattgatt tacggcgcta aggatgactc  2580
tggtcagaga tacctggcct ggtctggaca cagtgcccgt gtcggagccg cgcgagatat  2640
ggcccgcgct ggagtttcaa taccgagat catgcaagct ggtggctgga ccaatgtaaa  2700
tattgtcatg aactatatcc gtaacctgga tagtgaaaca tggcaatgg tcgcctgct   2760
ggaagatggc gatggaccgg tggaacaaaa acttatttct gaagaagatc tgtgatagcg  2820
gccgcactcc tcaggtgcag gctgccatc agaaggtggt ggctggtgtg ccaatgccc   2880
tggctcacaa ataccactga gatctttttc cctctgccaa aaattatggg gacatcatga  2940
agccccttga gcatctgact tctggctaat aaaggaaatt tattttcatt gcaatagtgt  3000
gttggaattt tttgtgtctc tcactcggaa ggacatatgg agggcaaat catttaaaac  3060
atcagaatga gtatttggtt tagagtttgg caacatatgc ccatatgctg gctgccatga  3120
acaaaggttg gctataaaga ggtcatcagt atatgaaaca gccccctgct gtccattcct  3180
tattccatag aaaagcctgg acttgaggtt agatttttt tatatttgt tttgtgttat   3240
ttttttcttt aacatcccta aaattttcct tacatgtttt actagccaga tttttcctcc  3300
tctcctgact actcccagtc atagctgtcc ctcttctctt atggagatcc ctcgacctgc  3360
agcccaagct tggcgtaatc atggtcatag ctgtttcctg tgtgaaattg ttatccgctc  3420
acaattccac acaacatacg agccggaagc ataaagtgta aagcctgggg tgcctaatga  3480
gtgagctaac tcacattaat tgcgttgcgc tcactgcccg ctttccagtc gggaaacctg  3540
tcgtgccagc ggatccgcat tcaattagt cagcaaccat agtcccgccc ctaactccgc   3600
ccatcccgcc cctaactccg cccagttccg cccattctcc gccccatggc tgactaattt  3660
ttttttattta tgcagaggcc gaggccgcct cggcctctga gctattccag aagtagtgag  3720
gaggctttt tggaggccta ggcttttgca aaaagctaac ttgtttattg cagcttataa  3780
tggttacaaa taaagcaata gcatcacaaa tttcacaaat aaagcatttt ttcactgca   3840
ttctagttgt ggtttgtcca aactcatcaa tgtatcttat catgtctgga tccgctgcat  3900
taatgaatcg gccaacgcgc ggggagaggc ggtttgcgta ttgggcgctc ttccgcttcc  3960
tcgctcactg actcgctgcg ctcggtcgtt cggctgcggc gagcggtatc agctcactca  4020
aaggcggtaa tacggttatc cacagaatca ggggataacg caggaaagaa catgtgagca  4080
aaaggccagc aaaaggccag gaaccgtaaa aaggccgcgt tgctggcgtt tttccatagg  4140
ctccgccccc ctgacgagca tcacaaaaat cgacgctcaa gtcagaggtg gcgaaacccg  4200
acaggactat aaagatacca ggcgtttccc cctggaagct ccctcgtgcg ctctcctgtt  4260
ccgaccctgc cgcttaccgg atacctgtcc gcctttctcc cttcgggaag cgtggcgctt  4320
tctcatagct cacgctgtag gtatctcagt tcggtgtagg tcgttcgctc caagctgggc  4380
tgtgtgcacg aaccccccgt tcagcccgac cgctgcgcct tatccggtaa ctatcgtctt  4440
gagtccaacc cggtaagaca cgacttatcg ccactggcag cagccactgg taacaggatt  4500
agcagagcga ggtatgtagg cggtgctaca gagttcttga agtggtggcc taactacggc  4560
tacactagaa gaacagtatt tggtatctgc gctctgctga agccagttac cttcggaaaa  4620
agagttggta gctcttgatc cggcaaacaa accaccgctg gtagcggtgg tttttttgtt  4680
```

```
tgcaagcagc agattacgcg cagaaaaaaa ggatctcaag aagatccttt gatcttttct    4740
acggggtctg acgctcagtg gaacgaaaac tcacgttaag ggattttggt catgagatta    4800
tcaaaaagga tcttcaccta gatcctttta aattaaaaat gaagttttaa atcaatctaa    4860
agtatatatg agtaaacttg gtctgacagt taccaatgct taatcagtga ggcacctatc    4920
tcagcgatct gtctatttcg ttcatccata gttgcctgac tccccgtcgt gtagataact    4980
acgatacggg agggcttacc atctggcccc agtgctgcaa tgataccgcg agacccacgc    5040
tcaccggctc cagatttatc agcaataaac cagccagccg gaagggccga gcgcagaagt    5100
ggtcctgcaa ctttatccgc ctccatccag tctattaatt gttgccggga agctagagta    5160
agtagttcgc cagttaatag tttgcgcaac gttgttgcca ttgctacagg catcgtggtg    5220
tcacgctcgt cgtttggtat ggcttcattc agctccggtt cccaacgatc aaggcgagtt    5280
acatgatccc ccatgttgtg caaaaaagcg gttagctcct tcggtcctcc gatcgttgtc    5340
agaagtaagt tggccgcagt gttatcactc atggttatgg cagcactgca taattctctt    5400
actgtcatgc catccgtaag atgcttttct gtgactggtg agtactcaac caagtcattc    5460
tgagaatagt gtatgcggcg accgagttgc tcttgcccgg cgtcaatacg ggataatacc    5520
gcgccacata gcagaacttt aaaagtgctc atcattggaa aacgttcttc ggggcgaaaa    5580
ctctcaagga tcttaccgct gttgagatcc agttcgatgt aacccactcg tgcacccaac    5640
tgatcttcag catcttttac tttcaccagc gtttctgggt gagcaaaaac aggaaggcaa    5700
aatgccgcaa aaaagggaat aagggcgaca cggaaatgtt gaatactcat actcttcctt    5760
tttcaatatt attgaagcat ttatcagggt tattgtctca tgagcggata catatttgaa    5820
tgtatttaga aaaataaaca aataggggtt ccgcgcacat ttccccgaaa agtgccacct    5880
g                                                                    5881

SEQ ID NO: 72           moltype = DNA   length = 4915
FEATURE                 Location/Qualifiers
misc_feature            1..4915
                        note = Description of Artificial Sequence: Synthetic
                         polynucleotide
misc_feature            1..4915
                        note = GFP-Lox66-Cre expression plasmid
source                  1..4915
                        mol_type = other DNA
                        organism = synthetic construct
SEQUENCE: 72
agctctgatc aagagacagg atgaggatcg tttcgcatga ttgaacaaga tggattgcac      60
gcaggttctc cggccgcttg ggtggagagg ctattcggct atgactgggc acaacagaca     120
atcggctgct ctgatgccgc cgtgttccgg ctgtcagcgc aggggcgccc ggttcttttt     180
gtcaagaccg acctgtccgg tgccctgaat gaactgcaag acgaggcagc gcggctatcg     240
tggctggcca cgacgggcgt tccttgcgca gctgtgctcg acgttgtcac tgaagcggga     300
agggactggc tgctattggg cgaagtgccg gggcaggatc tcctgtcat ctacaccttg     360
ctcctgccga gaaagtatcc atcatggctg atgcaatgcg gcggctgcat acgcttgatc     420
cggctacctg cccattcgac caccaagcga aacatcgcat cgagcgagca cgtactcgga     480
tggaagccgg tcttgtcgat caggatgatc tggacgaaga gcatcagggg ctcgcgccag     540
ccgaactgtt cgccaggctc aaggcgagca tgcccgacgg cgaggatctc gtcgtgaccc     600
atggcgatgc ctgcttgccg aatatcatgg tggaaaatgg ccgcttttct ggattcatcg     660
actgtggccg ctgggtgtg gcggaccgct atcaggacat agcgttggct acccgtgata     720
ttgctgaaga gcttggcggc gaatgggctg accgcttcct cgtgctttac ggtatcgccg     780
ctcccgattc gcagcgcatc gccttctatc gccttcttga cgagttcttc tgaattatta     840
actcgagatc cactagagtg tggcggccgc attcttataa tcagcatcat gatgtggtac     900
cacatcatga tgctgattac ccccaactga gagaactcaa aggttacccc agttggggcg     960
ggcccacaaa taaagcaata gcatcacaaa tttcacaaat aaagcatttt ttcactgca    1020
ttctagttgt ggtttgtcca aactcatcga gctcgagatc ttgccaaggc gatggggctc    1080
ttgaaggcgt gctggtactc cacgatgccc agctcggtgt tgctgtgcag ctcctccacg    1140
cggcggaagg cgaacatggg gccccgttc tgcaggatgc tggggtggat ggcgctcttg    1200
aagtgcatgt ggctgtccac cacgaagctg tagtagccgc cgtcgcgcag gctgaaggtg    1260
cgggcgaagc tgcccaccag cacgttatcg cccatggtgc caggtgctc cacggtggcg    1320
ttgctgcgca tgatcttgtc ggtgaagatc acgctgtcct cggggaagcc ggtgcccacc    1380
accttgaagt cgccgatcac gcggccggcc tcgtagcggt agctgaagct cacgtgcagc    1440
acgccgccgt cctcgtactt ctcgatgcgg gtgttggtgt agccgccgtt gttgatggcg    1500
tgcaggaagg ggttctcgta gccgctgggg taggtgcga agtggtagaa gcgctagccc    1560
atcacgtggc tcagcaggta ggggtgaag gtcagggcgc ctttggtgct cttcatcttg    1620
ttggtcatgc ggccctgctc gggggtgccc tctccgccgc ccaccagctc gaactccacg    1680
ccgttcaggg tgccggtgat gcggcactcg atcttcatgg cgggcatggt ggcgaccggt    1740
agcgctagcg gcttcggata acttcgtata gcatacatta tacgaacggt aagcgctacc    1800
gccggcatac ccaagtgaag ttgctcgcag cttatagtcg cgccgggga gcccaaggc    1860
acgccctggc accgcggccg ctgagtctcc accatcatca tcatcatcat tgagtttatc    1920
tgggataaca gggtaatgtc atctagggat aacagggtat gtcatctggg ataacagggt    1980
aatgtatcta gggataacag ggtaatgtca tctgggataa cagggtaatg tcatctaggg    2040
ataacagggt atgtcatctg gataacagg gtaatgtcat tagggataac agggtaatgt    2100
catctgggat aacagggtaa tgtcatctag ggataacagg gtatgtcatc tgggataaca    2160
gggtaatgta tctagggata acagggtaat gtcatctggg ataacagggt aatgtcatct    2220
agggataaca gggtatgtca tctgggataa cagggtaatg tatctaggga taacagggta    2280
atgtcatctg gataacagg gtaatgtcat ctagggataa cagggtatgt catctgggat    2340
aacagggtaa tgtatctagg gataacaggg taatgtcatc tgggataaca gggtaatgtc    2400
atctagggat aacagggtat gtcatctggg ataacagggt aatgtatcta gggataacag    2460
ggtaatgtca tctgggataa cagggtaatg tcatctaggg ataacagggt aaatgtcatc    2520
tagggataac agggtaatgt catctaggga taacagggta atgtcatctg gataacagg    2580
gtaatgtcat ctagggataa cagggtaatg tatcgcagc gtcgcacagc atgtttgctt    2640
gtcgccgtcg cgtctgtcac atcttttccg ccagcagtta gggattagcg tcttaagctg    2700
gcgcgaggac caacgtatca gccaggcgaa gctgcttttg agcaccaccc ggatgccta    2760
```

-continued

```
cgccaccgtc ggtcgcaatg ttggttttga cgatcaactc tatttctcgc gggtatttaa    2820
aaaatgcacc ggggccagcc cgagcgagtt ccgtgccggt tgtgaagaaa aagtgaatga    2880
tgtagccgtc aagttgtcat aattggtaac gaatcagaca attgacggct tgacggagta    2940
gcataggggt tgcagaatcc ctgcttcgtc catttgacag gcacattatg catgccgctt    3000
cgccttcgcg cgcgaattga tctgcttgcct cgcgcgtttc ggtgatgacg gtgaaaacct    3060
ctgacacatg cagctcccgg agacggtcac agcttgtctg taagcggatg ccggggagcag   3120
acaagcccgt cagggcgcgt cagcgggtgt tggcgggtgt cggggcgcag ccatgaccca    3180
gtcacgtagc gatagcggag tgtatactgg cttaactatg cggcatcaga gcagattgta    3240
ctgagagtgc accatatgcg gtgtgaaata ccgcacagat gcgtaaggag aaaataccgc    3300
atcaggcgct cttccgcttc ctcgctcact gactcgctgc gctcggtcgt tcggctgcgg    3360
cgagcggtat cagctcactc aaaggcggta atacggttat ccacagaatc aggggataac    3420
gcaggaaaga acatgtgagc aaaaggccag caaaaggcca ggaaccgtaa aaaggccgcg    3480
ttgctggcgt ttttccatag gctccgcccc cctgacgagc atcacaaaaa tcgacgctca    3540
agtcagaggt ggcgaaaccc gacaggacta taaagatacc aggcgtttcc ccctggaagc    3600
tccctcgtgc gctctcctgt tccgaccctg ccgcttaccg gatacctgtc cgcctttctc    3660
ccttcgggaa gcgtggcgct ttctcatagc tcacgctgta ggtatctcag ttcggtgtag    3720
gtcgttcgct ccaagctggg ctgtgtgcac gaaccccccg ttcagcccga ccgctgcgcc    3780
ttatccggta actatcgtct tgagtccaac ccggtaagac acgacttatc gccactggca    3840
gcagccactg gtaacaggat tagcagagcg aggtatgtag gcggtgctac agagttcttg    3900
aagtggtggc ctaactacgg ctacactaga aggacagtat ttggtatctg cgctctgctg    3960
aagccagtta ccttcggaaa aagagttggt agctcttgat ccggcaaaca aaccaccgct    4020
ggtagcggtg gttttttgt ttgcaagcag cagattacgc gcagaaaaaa aggatctcaa    4080
gaagatcctt tgatctttc tacgggtct gacgctcagt ggaacgaaaa ctcacgttaa     4140
gggattttgg tcatgagcgg atacatattt gaatgtattt agaaaaataa acaaaagagt    4200
ttgtagaaac gcaaaaggc catccgtcag gatggccttc tgcttaattt gatgcctggc    4260
agtttatgc gggcgtcctg cccgccaccc tccgggccgt tgcttcgcaa cgttcaaatc    4320
cgctcccggc ggatttgtcc tactcaggag agcgttcacc gacaaacaac agataaaacg    4380
aaaggcccag tctttcgact gagcctttcg ttttatttga tgcctggcag ttccctactc    4440
tcgcatgggg agaccccaca ctaccatcgg cgctacggcg tttcacttct gagttcggca    4500
tggggtcagg tgggaccacc gcgctactgc cgccaggcaa attctgtttt atcagaccgc    4560
ttctgcgttc tgatttaatc tgtatcaggc tgaaaatctt ctctcatccg ccaaaacagc    4620
caagctggag accgtttggc ccccctcgag cacgtagaaa gccagtccgc agaaacggtg    4680
ctgacccccg gatgaatgtca gctactgggc tatctgaca agggaaaacg caagcgcaaa    4740
gagaaagcag gtagccttgca gtgggcttac atggcgatag ctagactggg cggttttatg    4800
gacagcaagc gaaccggaat tgccagctgg ggcgccctct gtaaggttg ggaagccctg     4860
caaagtaaac tggatggctt tctcgccgcc aaggactga tggcgcaggg gatca          4915
```

| SEQ ID NO: 73 | moltype = DNA length = 10815 |
|---|---|
| FEATURE | Location/Qualifiers |
| misc_feature | 1..10815 |
| | note = Description of Artificial Sequence: Synthetic polynucleotide |
| misc_feature | 1..10815 |
| | note = pCMV-PE2-P2A-Cre |
| source | 1..10815 |
| | mol_type = other DNA |
| | organism = synthetic construct |

SEQUENCE: 73

```
acgcgttgac attgattatt gactagttat taatagtaat caattacggg gtcattagtt    60
catagcccat atatggagtt ccgcgttaca taacttacgg taaatggccc gcctggctga    120
ccgcccaacg accccgccc attgacgtca ataatgacgt atgttcccat agtaacgcca    180
atagggactt tccattgacg tcaatgggtg gagtatttac ggtaaactgc ccacttggca    240
gtacatcaag tgtatcatat gccaagtacg ccccctattg acgtcaatga cggtaaatgg    300
cccgcctggc attatgccca gtacatgacc ttatgggact ttcctacttg gcagtacatc    360
tacgtattag tcatcgctat taccatggtg atgcggtttt ggcagtacat caatgggcgt    420
ggatagcggt ttgactcacg gggatttcca agtctccacc ccattgacgt caatgggagt    480
ttgttttggc accaaaatca acgggacttt ccaaaatgtc gtaacaactc cgccccattg    540
acgcaaatgg gcggtaggcg tgtacggtgg gaggtctata taagcagagc tggtttagtg    600
aaccgtcaga tccgctagag atccgcggcc gctaatacga ctcactatag ggagagccac    660
caccatgaaa cggacagccg acggaagcga gttcgagtca ccaaagaaga agcggaaagt    720
cgacaagaag tacagcatcg gcctggacat cggcaccaac tctgtgggct gggccgtgat    780
caccgacgag tacaaggtgc ccagcaagaa attcaaggtg ctgggcaaca ccgaccggca    840
cagcatcaag aagaacctga tcggagccct gctgttcgac agcggcgaaa cagccgaggc    900
cacccggctg aagagaaccg ccagaagaag atacaccaga cggaagaacc ggatctgtta    960
tctgcaagag atcttcagca acgagatggc caaggtggac gacagcttct tccacagact   1020
ggaagagtcc ttcctggtgg aagaggataa gaagcacgag cggcacccca tcttcggcaa   1080
catcgtggac gaggtggcct accacgagaa gtaccccacc atctaccacc tgagaaagaa   1140
actggtggac agcaccgaca aggccgacct gcggctgatc tatctggccc tggcccacat   1200
gatcaagttc cggggccact tcctgatcga gggcgacctg aaccccgaca acagcgacgt   1260
ggacaagctg ttcatccagc tggtgcagac ctacaaccag ctgttcgagg aaaaccccat   1320
caacgccagc ggcgtggacg ccaaggccat cctgtctgcc agactgagca gagcagacg    1380
gctggaaaat ctgatcgccc agctgcccgg cgagaagaag aatggcctgt tcggaaacct   1440
gattgccctg agcctgggcc tgacccccaa cttcaagagc aacttcgacc tggccgagga   1500
tgccaaactg cagctgagca aggacaccta cgacgacgac ctggacaacc tgctggccca   1560
gatcggcgac cagtacgccg acctgtttct ggccgccaag aacctgtccg acgccatcct   1620
gctgagcgac atcctgagag tgaacaccga gatcaccaag gcccccctga gcgcctctat   1680
gatcaagaga tacgacgagc accaccagga cctgaccctg ctgaaagctc tcgtgcggca   1740
gcagctgcct gagaagtaca aagagatttt cttcgaccag agcaagaacg gctacgccgg   1800
ctacattgac ggcggagcca gccaggaaga gttctacaag ttcatcaagc ccatcctgga   1860
```

```
aaagatggac ggcaccgagg aactgctcgt gaagctgaac agagaggacc tgctgcggaa   1920
gcagcggacc ttcgacaacg gcagcatccc ccaccagatc cacctgggag agctgcacgc   1980
cattctgcgg cggcaggaag atttttaccc attcctgaag gacaaccggg aaaagatcga   2040
gaagatcctg accttccgca tcccctacta cgtgggccct ctggccaggg gaaacagcag   2100
attcgctctgg atgaccagaa agagcgagga aaccatcacc ccctggaact tcgaggaagt   2160
ggtggacaag ggcgcttccg cccagagctt catcgagcgg atgaccaact tcgataagaa   2220
cctgcccaac gagaaggtgc tgcccaagca cagcctgctg tacgagtact tcaccgtgta   2280
taacgagctg accaaagtga aatacgtgac cgagggaatg agaaagcccg ccttcctgag   2340
cggcgagcag aaaaaggcca tcgtggacct gctgttcaag accaaccgga aagtgaccgt   2400
gaagcagctg aaagaggact acttcaagaa aatcgagtgc ttcgactccg tggaaatctc   2460
cggcgtggaa gatcggttca acgcctcccct gggcacatac cacgatctgc tgaaaattat   2520
caaggacaag gacttcctgg acaatgagga aaacgaggac attctggaag atatcgtgct   2580
gacccctgaca ctgtttgagg acagagagat gatcgaggaa cggctgaaaa cctatgccca   2640
cctgttcgac gacaaagtga tgaagcagct gaagcggcgg agatacaccg gctggggcag   2700
gctgagccgg aagctgatca acggcatccg ggacaagcag tccggcaaga caatcctgga   2760
tttcctgaag tccgacggct tcgccaacag aaacttcatg cagctgatcc acgacgacag   2820
cctgaccttt aaagaggaca tccagaaagc ccaggtgtcc ggccagggcg atagcctgca   2880
cgagcacatt gccaatctgg ccggcagccc cgccattaag aagggcatcc tgcagacagt   2940
gaaggtggtg gacgagctcg tgaaagtgat gggccggcac aagcccgaga catcgtgat    3000
cgaaatggcc agagagaacc agaccaccca agggacaa agaacagcc gcgagagaat      3060
gaagcggatc gaagagggca tcaaagagct gggcagccag atcctgaaag aacacccgt    3120
ggaaaacacc cagctgcaga acgagaagct gtacctgtac tacctgcaga atgggcggga   3180
tatgtacgtg gaccaggaac tggacatcaa ccgctgtcc gactacgatg tgggctat     3240
cgtgcctcag agctttctga aggacgactc catcgacaac aaggtgctga ccagaagcga   3300
caagaaccgg gcaagagcg acaacgtgcc ctccgaagag gtcgtgaaga agatgaagaa    3360
ctactgcgcg cagctgctga acgccaagct gattacccac agaaagttcg acaatctgac   3420
caaggccgag agaggcggcc tgagcgaact ggataaggcc ggcttcatca agagacagct   3480
ggtgaaaacc cggcagatca caagcacgt ggcacagatc ctggactccc ggatgaacac    3540
taagtacgac gagaatgaca agctgatccg ggaagtgaaa gtgatcaccc tgaagtccaa   3600
gctggtgtcc gatttccgga aggatttcca gttttacaaa gtgcgcgaga tcaacaacta   3660
ccaccacgcc cacgacgcct acctgaacgc cgtcgtggga accgccctga tcaaaaagta   3720
ccctaagctg gaaagcgagt tcgtgtacgg cgactacaag gtgtacgacg tgcggaagat   3780
gatcgccaag agcgagcagg aaatcggcaa ggctaccgcc aagtactct tctacagcaa    3840
catcatgaac ttttcaaga ccgagattac cctggccaac ggcgagatcc ggaagcgcc    3900
tctgatcgag acaaacggcg aaaccgggga gatcgtgtgg gataagggcc gggattttgc   3960
caccgtgcgg aaagtgctga gcatgccca agtaatatc gtgaaaaaga ccgaggtgca     4020
gacaggcggc ttcagcaaag agtctatcct gcccaagagg aacagcgata gctgatcgc    4080
cagaaagaag gactgggacc ctaagaagta cggcggcttc gacagcccca ccgtggccta   4140
ttctgtgctg gtagtggcca aagtggaaaa gggcaagtcc aagaaactga agagtgtgaa   4200
agagctgctg gggatcacca tcatggaaag aagcagcttc gagaagaatc ccatcgactt   4260
tctgaagcc aagggctaca aagaagtgaa aaaggacctg atcatcaagc tgcctaagta    4320
ctccctgttc gagctggaaa acggccgaa gagaatgctg gcctctgccg gcgaactgca    4380
gaagggaaac gaactggccc tgccctccaa atatgtgaac ttcctgtacc tggccagcca   4440
ctatgagaag ctgaagggct cccccgagga taatgagcag aaacagctgt ttgtggaaca   4500
gcacaagcac tacctggacg agatcatcga gcagatcagc gagttctcca agagagtgat   4560
cctggccgac gctaatctgg acaaagtgct gtccgcctac aacaagcacc gggataagcc   4620
catcagagaa caggccgaga atatcatcca cctgtttacc ctgaccaatc tgggagccc    4680
tgccgccttc aagtactttg acaccaccat cgaccggaag aggtacacca gcaccaaaga   4740
ggtgctggac gccaccctga tccaccagag catcaccggc ctgtacgaga cacggatcga   4800
cctgtctcag ctgggaggtg actctggagg atctagcgga ggatcctctg cagcgagac    4860
accaggaaca agcgagtcag caacaccaga gagcagtggc ggcagcgga gcggcagcag   4920
caccctaaat atagaagatg agtatcggct acatgagacc tcaaagagc cagatgtttc    4980
tctagggtcc acatggctgt ctgatttttcc tcaggcctgg gcggaaaccg ggggcatggg   5040
actggcagtt cgccaagctc ctctgatcat acctctgaaa gcaacctcta cccccgtgtc   5100
cataaaacaa tacccccatgt cacaagaagc cagactgggg atcaagcccc acatacagag   5160
actgttggac cagggaatac tggtaccctg ccagtccccc tggaacacg ccctgctacc     5220
cgttaagaaa ccaggggacta atgattatag gcctgtccag gatctgagag aagtcaacaa   5280
gcgggtggaa gacatccacc ccaccgtgcc caacccttac aacctcttga gcgggctccc    5340
accgtcccac cagtggtaca ctgtgcttga tttaaaggat gcctttttct gcctgagact   5400
ccaccccacc agtcagcctc tcttcgcctt tgagtggaga gatccagaga tgggaatctc    5460
aggacaattg acctggacca gactcccaca gggtttcaaa aacagtccca ccctgttaa    5520
tgaggcactg cacagagacc tagcagactt ccggatccag cacccagact gatcctgct    5580
acagtacgtg gatgacttac tgctggccgc cacttctgag ctagactgcc aacaaggtac   5640
tcgggcctg ttacaaaccc tagggaacct cgggtatccg gcctcggcca gaaagccca     5700
aatttgccag aaaacaggtca gtatctgggg gtatcttcta aaagagggtc agagatggca   5760
gactgaggcc agaaaagaga ctgtgatggg gcagcctact ccgaagaccc ctcgacaact   5820
aagggagttc ctagggaagg caggcttctg tcgcctcttc atccctgggt ttgcagaat    5880
ggcagccccc ctgtaccctc tccaacaaccc ggggactctg tttaattggg gcccagacca   5940
acaaaaggcc tatcaagaaa tcaagcaagc tcttctaact gccccagcc tgggggttgcc   6000
agatttgact aagcccttg aactctttgt cgacgagaag cagggctacg ccaaaggtgt    6060
cctaacgcaa aaactgggac cttggcgtcg gccgtggcc tacctgtcca aaagctaga    6120
cccagtagca gctgggtggc cccttgcct acggatggta gcagccattg ccgtactgac    6180
aaaggatgca ggcaagctaa ccatgggaca gccactagtc attctggccc ccatgcagt    6240
agaggcacta gtcaaacaac cccccgaccg ctggcttttc aacgcccgga tgactacta    6300
tcaggccttg ctttttggaca cggacccggg ccagttcgga ccggtggtag ccctgaaccc   6360
ggctacgctg ctcccactgc tgaggaagg gctgcaacac aactgccttg atatcctgg    6420
cgaagcccac ggaacccgac ccgacctaac ggaccagccg ctcccagacg ccgaccacac   6480
ctggtacacg gatggaagca gtctcttaca agagggacag cgtaaggcgg gagctgcggt   6540
gaccaccgag accgaggtaa tctgggctaa agccctgcca gccgggacat ccgctcagcg   6600
```

```
ggctgaactg atagcactca cccaggccct aaagatggca gaaggtaaga agctaaatgt  6660
ttatactgat agccgttatg cttttgctac tgcccatatc catggagaaa tatacagaag  6720
gcgtgggtgg ctcacatcag aaggcaaaga gatcaaaaat aaagacgaga tcttggccct  6780
actaaaagcc ctctttctgc ccaaaagact tagcataatc cattgtccag gacatcaaaa  6840
gggacacagc gccgaggcta gaggcaaccg gatggctgac caagcggccg gaaaggcagc  6900
catcacagag actccagaca cctctaccct cctcatagaa aattcatcac cctctggccg  6960
ctcaaaaaga accgccgacg gcagcgaatt cgagcccaag aagaaggaga aagtcggaag  7020
cggagctact aacttcagcc tgctgaagca ggctggcgac gtggaggaga accctggacc  7080
taatttactg accgtacacc aaaatttgcc tgcattaccg gtcgatgcaa cgagtgatga  7140
ggttcgcaag aacctgatgg acatgttcag ggatcgccag gcgttttctg agcatacctg  7200
gaaaatgctt ctgtccgttt gccggtcgtg ggcggcatgg tgcaagttga ataaccggaa  7260
atggtttccc gcagaacctg aagatgttcg cgattatctt ctatatcttc aggcgcgcgg  7320
tctggcagta aaaactatcc agcaacattt gggccagcta aactgcttc atcgtcggtc  7380
cgggctgcca cgaccaagtg acagcaatgc tgtttcactg gttatgcggc ggatccgaaa  7440
agaaaacgtt gatgccggtg aacgtgcaaa acaggctcta gcgttcgaac gcactgattt  7500
cgaccaggtt cgttcactca tggaaaatag cgatcgctgc caggatatac gtaatctggc  7560
atttctgggg attgcttata acaccctgtt acgtatagcc gaaattgcca ggatcagggt  7620
taaagatatc tcacgtactg acggtgggag aatgttaatc tatattggca gaacgaaaac  7680
gctggttagc accgcaggtg tagagaaggc acttagcctg ggggtaacta aactggtcga  7740
gcgatggatt tccgtctctg gtgtagctga tgatccgaat aactacctgt tttgccgggt  7800
cagaaaaaat ggtgttgccg cgccatctgc caccagccag ctatcaactc gcgccctgga  7860
agggattttt gaagcaactc atcgattgat ttacggcgct aaggatgact ctggtcagag  7920
ataccctggcc tggtctggac acagtgcccg tgtcggagcc gcgcgagata tggcccgcgc  7980
tggagtttca ataccggaga tcatgcaagc tggtggctgg accaatgtaa atattgtcat  8040
gaactatatc cgtaacctgg atagtgaaac aggggcaatg gtgcgcctgc tggaagatgg  8100
cgattaattt aaacccgctg atcagcctcg actgtgcctt ctagttgcca gccatctgtt  8160
gtttgcccct cccccgtgcc ttccttgacc ctggaaggtg ccactcccac tgtcctttcc  8220
taataaaatg agaaaattgc atcgcattgt ctgagtaggt gtcattctat tctggggggt  8280
ggggtggggc aggacagcaa gggggaggat tgggaagaca atagcaggca tgctggggat  8340
gcggtgggct ctatgcttc tgaggcggaa agaaccagct ggggctcgat accgtcgac  8400
tctagctaga gcttggcgta atcatggtca tagctgtttc ctgtgtgaaa ttgttatccg  8460
ctcacaattc cacacaacat acgagccgga agcataaagt gtaaagccta gggtgcctaa  8520
tgagtgagct aactcacatt aattgcgttg cgctcactgc ccgctttcca gtcgggaaac  8580
ctgtcgtgcc agctgcatta atgaatcggc caacgcgcgg ggagaggcgg tttgcgtatt  8640
gggcgctctt ccgcttcctc gctcactgac tcgctgcgct cggtcgttcg gctgcggcga  8700
gcggtatcag ctcactcaaa ggcggtaata cggttatcca cagaatcagg gataacgca  8760
ggaaagaaca tgtgagcaaa aggccagcaa aaggccagga accgtaaaaa ggccgcgttg  8820
ctggcgtttt tccataggct ccgcccccct gacgagcatc acaaaaatcg acgctcaagt  8880
cagaggtggc gaaacccgac aggactataa agataccagg cgtttccccc tggaagctcc  8940
ctcgtgcgct ctcctgttcc gaccctgccg cttaccggat acctgtccgc ctttctccct  9000
tcgggaagcg tggcgctttc tcatagctca cgctgtaggt atctcagttc ggtgtaggtc  9060
gttcgctcca agctgggctg tgtgcacgaa ccccccgttc agcccgaccg ctgcgcctta  9120
tccggtaact atcgtcttga gtccaacccg gtaagacacg acttatcgcc actggcagca  9180
gccactggta acaggattag cagagcgagg tatgtaggcg gtgctacaga gttcttgaag  9240
tggtggccta actacggcta cactagaaga acagtatttg gtatctgcgc tctgctgaag  9300
ccagttacct tcggaaaaag agttggtagc tcttgatccg gcaaacaaac caccgctggt  9360
agcggtggtt tttttgtttg caagcagcag attacgcgca gaaaaaaagg atctcaagaa  9420
gatcctttga tcttttctac ggggtctgac gctcagtgga acgaaaactc acgttaaggg  9480
attttggtca tgagattatc aaaaaggatc ttcacctaga tccttttaaa ttaaaaatga  9540
agttttaaat caatctaaag tatatatgag taaacttggt ctgacagtta ccaatgctta  9600
atcagtgagg cacctatctc agcgatctgt ctatttcgtt catccatagt tgcctgactc  9660
cccgtcgtgt agataactac gatacgggag ggcttaccat ctggccccag tgctgcaatg  9720
ataccgcgag acccacgctc accggctcca gatttatcag caataaacca gccagccgga  9780
agggccgagc gcagaagtgg tcctgcaact ttatccgcct ccatccagtc tattaattgt  9840
tgccgggaag ctagagtaag tagttcgcca gttaatagtt tgcgcaacgt tgttgccatt  9900
gctacaggca tcgtggtgtc acgctcgtcg tttggtatgg cttcattcag ctccggttcc  9960
caacgatcaa ggcgagttac atgatccccc atgttgtgca aaaaagcggt tagctccttc 10020
ggtcctccga tcgttgtcag aagtaagttg gccgcagtgt tatcactcat ggttatggca 10080
gcactgcata attctcttac tgtcatgcca tccgtaagat gcttttctgt gactggtgag 10140
tactcaacca agtcattctg agaatagtgt atgcggcgac cgagttgctc ttgcccggcg 10200
tcaatacggg ataataccgc gccacatagc agaactttaa aagtgctcat cattggaaaa 10260
cgttcttcgg ggcgaaaact ctcaaggatc ttaccgctgt tgagatccag ttcgatgtaa 10320
cccactcgtg cacccaactg atcttcagca tcttttactt tcaccagcgt ttctgggtga 10380
gcaaaaacag gaaggcaaaa tgccgcaaaa aagggaataa gggcgacacg gaaatgttga 10440
atactcatac tcttcctttt tcaatattat tgaagcattt atcagggtta ttgtctcatg 10500
agcggataca tatttgaatg tatttagaaa aataaacaaa tagggggttcc gcgcacattt 10560
ccccgaaaag tgccacctga cgtcgacgga tcggagatc gatctcccga tccctaggg 10620
tcgactctca gtacaatctg ctctgatgcc gcatagttaa gccagtatct gctccctgct 10680
tgtgtgttgg aggtcgctga gtagtgcgcg agcaaaattt aagctacaac aaggcaaggc 10740
ttgaccgaca attgcatgaa gaatctgctt agggttaggc gttttgcgct gcttcgcgat 10800
gtacgggcca gatat                                                 10815

SEQ ID NO: 74          moltype = DNA  length = 20
FEATURE                Location/Qualifiers
misc_feature           1..20
                       note = Description of Artificial Sequence: Synthetic
                       oligonucleotide
misc_feature           1..20
                       note = +90ngRNA guide sequence
```

```
                         source              1..20
                                             mol_type = other DNA
                                             organism = synthetic construct
SEQUENCE: 74
gtcaaccagt atcccggtgc                                                      20

SEQ ID NO: 75            moltype = DNA  length = 96
FEATURE                  Location/Qualifiers
misc_feature             1..96
                         note = Description of Artificial Sequence: Synthetic
                          oligonucleotide
misc_feature             1..96
                         note = +90ngRNA
source                   1..96
                         mol_type = other DNA
                         organism = synthetic construct
SEQUENCE: 75
gtcaaccagt atcccggtgc gttttagagc tagaaatagc aagttaaaat aaggctagtc   60
cgttatcaac ttgaaaaagt ggcaccgagt cggtgc                             96

SEQ ID NO: 76            moltype = DNA  length = 4968
FEATURE                  Location/Qualifiers
misc_feature             1..4968
                         note = Description of Artificial Sequence: Synthetic
                          polynucleotide
misc_feature             1..4968
                         note = GFP minicircle template (before cleavage)
source                   1..4968
                         mol_type = other DNA
                         organism = synthetic construct
SEQUENCE: 76
tgatccctg cgccatcaga tccttggcgg cgagaaagcc atccagttta ctttgcaggg    60
cttcccaacc ttaccagagg gcgccccagc tggcaattcc ggttcgcttg ctgtccataa  120
aaccgccag tctagctatc gccatgtaag cccactgcaa gctacctgct ttctctttgc  180
gcttgcgttt tccttgtcc agatagccca gtagctgaca ttcatccggg gtcagcaccg  240
tttctgcgga ctggctttct acgtgctcga gggggccaa acggtctcca gcttggctgt   300
tttggcggat gagagaagat tttcagcctg atacagatta aatcagaacg cagaagcggt   360
ctgataaaac agaatttgcc tggcggcagt agcgcggtgg tcccacctga ccccatgccg   420
aactcagaag tgaaacgccg tagcgccgat ggtagtgtgg gtctccccca tgcgagagta   480
gggaactgcc aggcatcaaa taaaacgaaa ggctcagtcg aaagactggg cctttcgttt   540
tatctgttgt ttgtcggtga acgctctcct gagtaggaca aatccgccgg gagcggattt   600
gaacgttgcg aagcaacggc ccggagggtg gcgggcagga cgcccgccat aaactgccag   660
gcatcaaatt aagcagaagg ccatcctgac ggatggcctt tttgcgtttc tacaaactct   720
tttgtttatt tttctaaata cattcaaata tgtatccgct catgaccaaa atcccttaac   780
gtgagttttc gttccactga gcgtcagacc ccgtagaaaa gatcaaagga tcttcttgag   840
atcctttttt tctgcgcgta atctgctgct tgcaaacaaa aaaaccaccg ctaccagcgg   900
tggtttgttt gccggatcaa gagctaccaa ctctttttcc gaaggtaact ggcttcagca   960
gagcgcagat accaaatact gtccttctag tgtagccgta gttaggccac cacttcaaga  1020
actctgtagc accgcctaca tacctcgctc tgctaatcct gttaccagtg gctgctgcca  1080
gtggcgataa gtcgtgtctt accgggttgg actcaagacg atagttaccg gataaggcgc  1140
agcggtcggg ctgaacgggg ggttcgtgca cacagcccag cttggagcga acgacctaca  1200
ccgaactgag atacctacag cgtgagctat gagaaagcgc cacgcttccc gaagggagaa  1260
aggcggacag gtatccggta agcggcaggg tcggaacagg agagcgcacg agggagcttc  1320
cagggggaaa cgcctggtat ctttatagtc ctgtcgggtt tcgccacctc tgacttgagc  1380
gtcgatttt gtgatgctcg tcagggggc ggagcctatg gaaaaacgcc agcaacgcgg   1440
cctttttacg gttcctggcc ttttgctggc cttttgctca catgttcttt cctgcgttat  1500
ccctgattc tgtggataac cgtattaccg cctttgagtg agctgatacc gctcgccgca  1560
gccgaacgac cgagcgcagc gagtcagtga gcgaggaagc ggaagagcgc ctgatgcggt  1620
attttctcct tacgcatctg tgcggtattt cacaccgcat atggtgcact ctcagtacaa  1680
tctgctctga tgccgcatag ttaagccagt atacactccg ctatcgctac gtgactgggt  1740
catggctgcg ccccgacacc cgccaacacc cgctgacgcg ccctgacggg cttgtctgct  1800
cccggcatcc gcttacagac aagctgtgac cgtctccggg agctgcatgt gtcagaggtt  1860
ttcaccgtca tcaccgaaac gcgcgaggca gcagatcaat tcgcgcgcga aggcgaagcg  1920
gcatgcataa tgtgcctgtc aaatggacga agcagggatt ctgcaaaccc tatgctactc  1980
cgtcaagccg tcaattgtct gattcgttac caattatgac aacttgacgg ctacatcatt  2040
cacttttttct tcacaaccgg cacggaactc gctcgggctg gccccggtgc atttttaaa   2100
tacccgcgag aaatagagtt gatcgtcaaa accaacattg cgaccgacgg tggcgatagg  2160
catccggtg gtgctcaaaa gcagcttcgc ctggctgata cgttggtcct cgcgccagct  2220
taagacgcta atccctaact gctggcgaa aagatgtgac agacgcgacg gcgacaagca  2280
aacatgctgt gcgacgctgg cgatacatta ccctgttatc cctagatgac attaccctgt  2340
tatcccagat gacattaccc tgttatccct agatgacatt accctgttat ccctagatga  2400
catttacccct gttatcccta gatgacatta ccctgttatc ccagatgaca ttaccctgtt  2460
atccctagat acattaccct gttatcccag atgacatacc ctgttatccc tagatgacat  2520
taccctgtta tccctagatga cattacctg ttatcccag atacattacc ctgttatccc  2580
agatgacata ccctgttatc cctagatgac attaccctgt tatcccagat gacattaccc  2640
tgttatcccct agatacatta ccctgttatc ccagatgaca taccctgtta tcccctagatg  2700
acattaccct gttatcccag atgacattac cctgttatcc ctagatacat accctgtta   2760
tcccagatga cataccctgt tatccctaga tgacattacc ctgttatccc agatgacatt  2820
accctgttat ccctagatac attaccctgt tatcccctagat gacataccct gttatcccta  2880
```

```
gatgacatta ccctgttatc ccagatgaca ttaccctgtt atccctagat acattaccct    2940
gttatcccag atgacatacc ctgttatccc tagatgacat taccctgtta tcccagataa    3000
actcaatgat gatgatgatg atggtcgaga ctcagcggcc gcggtgccag ggcgtgccct    3060
tgggctcccc gggcgcgact ataagctgcg agcaacttca cttgggtatg ccggcggtag    3120
cgcttaccgt tcgtataatg tatgctatac gaagttcgca gaagccgcta gcggtggttt    3180
gtctggtcaa ccaccgcggt ctcagtggtg tacggtacaa acccagctac cggtcgccac    3240
catgcccgcc atgaagatcg agtgccgcat caccggcacc ctgaacggcg tggagttcga    3300
gctggtgggc ggcggagagg gcaccccccga gcagggccgc atgaccaaca agatgaagag    3360
caccaaaggc gccctgacct tcagccccta cctgctgagc cacgtgatgg gctacggctt    3420
ctaccacttc ggcacctacc ccagcggcta cgagaacccc ttcctgcacg ccatcaacaa    3480
cggcggctac accaacaccc gcatcgagaa gtacgaggac ggcggcgtgc tgcacgtgag    3540
cttcagctac cgctacgagg ccggccgcgt gatcggcgac ttcaaggtgg tgggcaccgg    3600
cttccccgag gacagcgtga tcttcaccga caagatcatc cgcagcaacg ccaccgtgga    3660
gcacctgcac cccatgggcg ataacgtgct ggtgggcagc ttcgcccgca ccttcagcct    3720
gcgcgacggc ggctactaca gcttcgtggt ggacagccac atgcacttca gagcgcat    3780
ccaccccagc atcctgcaga acgggggccc catgttcgcc ttccgccgcg tggaggagct    3840
gcacagcaac accgagctgg gcatcgtgga gtaccagcac gccttcaaga cccccatcgc    3900
cttcgccaga tctcgagctc gatgagtttg gacaaaccac aactagaatg cagtgaaaaa    3960
aatgctttat ttgtgaaatt tgtgatgcta ttgctttatt tgtgggcccg cccaactgg     4020
ggtaacctt t gagttctctc agttgggggt aatcagcatc atgatgtggt accacatcat    4080
gatgctgatt ataagaatgc ggccgccaca ctctagtgga tctcgagtta ataattcaga    4140
agaactcgtc aagaaggcga tagaaggcga tgcgctgcga atcgggagcg gcgataccgt    4200
aaagcacgag gaagcggtca gcccattcgc cgccaagctc ttcagcaata tcacgggtag    4260
ccaacgctat gtcctgatag cggtccgcca cacccagccg ccacagtcg atgaatccag    4320
aaaagcggcc attttccacc atgatattcg gcaagcaggc atcgccatgg gtcacgacga    4380
gatcctgcgc gtcgggcatg ctcgccttga gcctggcgaa cagttcggct ggcgcgagcc    4440
cctgatgctc ttcgtccaga tcatcctgat cgacaagacc ggcttccatc cgagtacgtg    4500
ctcgctcgat gcgatgtttc gcttggtggt cgaatgggca ggtagccgga tcaagcgtat    4560
gcagccgccg cattgcatca gccatgatgg atactttctc ggcaggagca aggtgtagat    4620
gacatggaga tcctgccccg gcacttcgcc caatagcagc cagtccccttc ccgcttcagt    4680
gacaacgtcg agcacagctg cgcaaggaac gcccgtcgtg gccagccacg atagccgcgc    4740
tgcctcgtct tgcagttcat tcagggcacc ggacaggtcg gtcttgacaa aaagaaccgg    4800
gcgcccctgc gctgacagcc ggaacacggc ggcatcagag cagccgattg tctgttgtgc    4860
ccagtcatag ccgaatagcc tctccaccca agcggccgga gaacctgcgt gcaatccatc    4920
ttgttcaatc atgcgaaacg atcctcatcc tgtctcttga tcagagct                 4968

SEQ ID NO: 77           moltype = DNA   length = 4855
FEATURE                 Location/Qualifiers
misc_feature            1..4855
                        note = Description of Artificial Sequence: Synthetic
                        polynucleotide
misc_feature            1..4855
                        note = GLuc minicircle template
source                  1..4855
                        mol_type = other DNA
                        organism = synthetic construct
SEQUENCE: 77
tgatccctg cgccatcaga tccttggcgg cgagaaagcc atccagttta ctttgcaggg     60
cttcccaacc ttaccagagg gcgccccagc tggcaattcc ggttcgcttg ctgtccataa    120
aaccgcccag tctagctatc gccatgtaag cccactgcaa gctacctgct ttctctttgc    180
gcttcgtttt tcccttgtcc agatagccca gtagctgaca ttcatccggg gtcagcaccg    240
tttctgcgga ctggctttct acgtgctcga gggggccaa acggtctcca gcttggctgt    300
tttggcggat gagagaagat tttcagcctg atacagatta aatcagaacg cagaagcggt    360
ctgataaaac agaatttgcc tggcggcagt agcgcggtgg tcccacctga ccccatgccg    420
aactcagaag tgaaacgccg tagcgccgat ggtagtgtgg ggtctcccca tgcgagagta    480
gggaactgcc aggcatcaaa taaaacgaaa ggctcagtcg aaagactggg cctttcgttt    540
tatctgttgt ttgtcggtga acgctctcct gagtaggaca aatccgccgg agcggatttt    600
gaacgttgcg aagcaacggc ccggagggtg cgggcagga cgcccgccat aaactgccag    660
gcatcaaatt aagcagaagg ccatcctgac ggatggcctt tttgcgtttc tacaaactct    720
tttgtttatt tttctaaata cattcaaata tgtatccgct catgaccaaa atcccttaac    780
gtgagttttc gttccactga gcgtcagacc ccgtagaaaa gatcaaagga tcttcttgag    840
atccttttttt tctgcgcgta atctgctgct tgcaaacaaa aaaaccaccg ctaccagcgg    900
tggtttgttt gccggatcaa gagctaccaa ctcttttttcc gaaggtaact ggcttcagca    960
gagcgcagat accaaatact gtccttctag tgtagccgta gttaggccac cacttcaaga    1020
actctgtagc accgcctaca tacctcgctc tgctaatcct gttaccagtg gctgctgcca    1080
gtggcgataa gtcgtgtctt accgggttgg actcaagacg atagttaccg gataagcgc     1140
agcggtcggg ctgaacgggg ggttcgtgca cacagcccag cttggagcga acgacctaca    1200
ccgaactgag atacctacag cgtgagctat gagaaagcgc cacgcttccc gaagggagaa    1260
aggcggacag gtatccggta agcggcaggg tcggaacagg agagcgcacg agggagcttc    1320
cagggggaaa cgcctggtat ctttatagtc ctgtcgggtt tcgccacctc tgacttgagc    1380
gtcgatttt gtgatgctcg tcagggggc ggagcctatg gaaaaacgcc agcaacgcgg    1440
ccttttacg gttcctggcc ttttgctggc cttttgctca catgttcttt cctgcgttat    1500
cccctgattc tgtggataac cgtattaccg cctttgagtg agctgatacc gctcgccgca    1560
gccgaacgac cgagcgcagc gagtcagtga gcgaggaagc ggaagagcgc ctgatgcggt    1620
atttttctcct tacgcatctg tgcggtattt cacaccgcat atggtgcact ctcagtacaa    1680
tctgctctga tgccgcatag ttaagccagt atacactccg ctatcgctac gtgactgggt    1740
catggctgcg ccccgacacc cgccaacacc cgctgacgcg ccctgacggg cttgtctgct    1800
cccggcatcc gcttacagac aagctgtgac cgtctccggg agctgcatgt gtcagaggtt    1860
ttcaccgtca tcaccgaaac gcgcgaggca gcagatcaat tcgcgcgcga aggcgaagcg    1920
```

```
gcatgcataa tgtgcctgtc aaatggacga agcagggatt ctgcaaaccc tatgctactc  1980
cgtcaagccg tcaattgtct gattcgttac caattatgac aacttgacgg ctacatcatt  2040
cacttttttct tcacaaccgg cacggaactc gctcgggctg gccccggtgc attttttaaa  2100
tacccgcgag aaatagagtt gatcgtcaaa accaacattg cgaccgacgg tggcgatagg  2160
catccgggtg gtgctcaaaa gcagcttcgc ctggctgata cgttggtcct cgcgccagct  2220
taagacgcta atccctaact gctggcggaa aagatgtgac agacgcgacg gcgacaagca  2280
aacatgctgt gcgacgctgg cgatacatta ccctgttatc cctagatgac attaccctgt  2340
tatcccagat gacattaccc tgttatccct agatgacatt accctgttat ccctagatga  2400
catttacccct gttatcccta gatgacatta ccctgttatc cagatgaca ttaccctgt   2460
atccctagat acattaccct gttatcccag atgacatacc ctgttatccc tagatgacat  2520
taccctgtta tcccagatga cattaccctg ttatccctag atacattacc ctgttatccc  2580
agatgacata ccctgttatc cctagatgac attaccctgt tatcccagat gacattaccc  2640
tgttatccct agatacatta ccctgttatc ccagatgaca taccctgtta tccctagatg  2700
acattaccct gttatcccag atgacattac cctgttatcc ctagatacat taccctgtta  2760
tcccagatga catccctgt tatccctaga tgacattacc ctgttatccc agatgacatt  2820
accctgttat ccctagatac attaccctgt tatcccagat gacataccct gttatcccta  2880
gatgacatta ccctgttatc ccagatgaca ttaccctgtt atccctagat acattaccct  2940
gttatcccag atgacatacc ctgttatccc tagatgacat taccctgtta tcccagataa  3000
actcaatgat gatgatgatg atggtcgaga ctcagcggcc gcggtgccag ggcgtgccct  3060
tgggctcccc gggcgcgact ataagctgcg agcaacttca cttgggtatg ccggcggtag  3120
cgcttaccgt tcgtataatg tatgctatac gaagttatcc gaagccgcta gcggtggttt  3180
gtctgtcaa ccaccgcggt ctcagtggtg tacggtacaa acccactacc ggtcgccacc  3240
atgggagtca aagttctgtt tgccctgatc tgcatcgctg tggccgaggc caagcccacc  3300
gagaacaacg aagacttcaa catcgtggcc gtggccagca acttcgcgac cacggatctc  3360
gatgctgacc gcgggaagtt gcccggcaag aagctgccgc tggaggtgct caaagagatg  3420
gaagccaatg cccggaaagc tggctgcacc aggggctgtc tgatctgcct gtcccacatc  3480
aagtgcacgc ccaagatgaa gaagttcatc ccaggacgct gccacaccta cgaaggcgac  3540
aaagagtccg cacagggcgg cataggcgag gcgatcgtcg acattcctga gattcctggg  3600
ttcaaggact tggagcccat ggagcagttc atcgcacagg tcgatctgtg tgtggactgc  3660
acaactggct gcctcaaagg gcttgccaac gtgcagtgtt ctgacctgcc caagaagtgg  3720
ctgccgcaac gctgtgcgac cttgccacgc aagatccagg gccaggtgga caagatcaag  3780
ggggccggtg gtgactaagc ggagctcgat gagtttggac aaaccacaac tagaatgcag  3840
tgaaaaaaat gctttatttg tgaaatttgt gatgctattg cttttattgt gggcccgccc  3900
caactgggt aacctttgag ttctctcagt tgggggtaat cagcatcatg atggtgtacc   3960
acatcatgat gctgattata agaatgcggc cgccacactc tagtggatct cgagttaata  4020
attcagaaga actcgtcaag aaggcgatag aaggcgatgc gctgcgaatc gggagcggcg  4080
ataccgtaaa gcacgaggaa gcggtcagcc cattcgccgc caagctcttc agcaatatca  4140
cgggtagcca acgctatgtc ctgatagcgg tccgccacac ccagccggcc acagtcgatg  4200
aatccagaaa agcggccatt ttccaccatg atattcggca agcaggcatc gccatgggtc  4260
acgacgagat cctcgccgtc gggcatgctc gccttgagcc tggcgaacag ttcggctggc  4320
gcgagcccct gatgctcttc gtccagatca tcctgatcga caagaccggc ttccatccga  4380
gtacgtgctc gctcgatgcg atgtttcgct tggtggtcga atgggcaggt agccggatca  4440
agcgtatgca gccgccgcat tgcatcagcc atgatggata tttctcggc aggagcaagg   4500
tgtagatgac atggagatcc tgccccggca cttcgcccaa tagcagccag tcccttcccg  4560
cttcagtgac aacgtcgagc acagctgcgc aaggaacgcc cgtcgtggcc agccacgata  4620
gccgcgctgc ctcgtcttgc agttcattca gggcaccgga caggtcggtc ttgacaaaaa  4680
gaaccgggcg cccctgcgct gacagccgga acacggcggc atcagagcag ccgattgtct  4740
gttgtgccca gtcatagccg aatagcctct cacccaagc ggccggagaa cctgcgtgca   4800
atccatcttg ttcaatcatg cgaaacgatc ctcatcctgt ctcttgatca gagct        4855

SEQ ID NO: 78           moltype = DNA  length = 38
FEATURE                 Location/Qualifiers
misc_feature            1..38
                        note = Description of Artificial Sequence: Synthetic
                          oligonucleotide
misc_feature            1..38
                        note = pseudo-attP
source                  1..38
                        mol_type = other DNA
                        organism = synthetic construct
SEQUENCE: 78
ccccaactgg ggtaaccttt gagttctctc agttggggg                            38

SEQ ID NO: 79           moltype = DNA  length = 194
FEATURE                 Location/Qualifiers
misc_feature            1..194
                        note = Description of Artificial Sequence: Synthetic
                          polynucleotide
misc_feature            1..194
                        note = Albumin-pegRNA-SERPIN
source                  1..194
                        mol_type = other DNA
                        organism = synthetic construct
SEQUENCE: 79
gactgaaact tcacagaata gttttagagc tagaaatagc aagttaaaat aaggctagtc      60
cgttatcaac ttgaaaaagt ggcaccgagt cggtgcttgg gatagttatg aattcaatct     120
tcaaccctat ccgatgatc ctgacgacgg agaccgccgt cgtcgacaag ccggcctctg      180
tgaagtttca gtca                                                       194
```

| SEQ ID NO: 80 | moltype = DNA length = 189 |
|---|---|
| FEATURE | Location/Qualifiers |
| misc_feature | 1..189 |
| | note = Description of Artificial Sequence: Synthetic polynucleotide |
| misc_feature | 1..189 |
| | note = Albumin-pegRNA-CPS1 |
| source | 1..189 |
| | mol_type = other DNA |
| | organism = synthetic construct |

SEQUENCE: 80
```
gactgaaact tcacagaata gttttagagc tagaaatagc aagttaaaat aaggctagtc   60
cgttatcaac ttgaaaaagt ggcaccgagt cggtgcttgg gatagttatg aattcaatct  120
tcaacccat ccggatgatc ctgacgacgg agaccgccgt cgtcgacaag ccggcctctg  180
tgaagtttc                                                          189
```

| SEQ ID NO: 81 | moltype = DNA length = 177 |
|---|---|
| FEATURE | Location/Qualifiers |
| misc_feature | 1..177 |
| | note = Description of Artificial Sequence: Synthetic polynucleotide |
| misc_feature | 1..177 |
| | note = 34bp lox71 pegRNA |
| source | 1..177 |
| | mol_type = other DNA |
| | organism = synthetic construct |

SEQUENCE: 81
```
ggcccagact gagcacgtga gttttagagc tagaaatagc aagttaaaat aaggctagtc   60
cgttatcaac ttgaaaaagt ggcaccgagt cggtgctgga ggaagcaggg cttcctttcc  120
tctgccatca taccgttcgt atagcataca ttatacgaag ttatcgtgct cagtctg     177
```

| SEQ ID NO: 82 | moltype = DNA length = 177 |
|---|---|
| FEATURE | Location/Qualifiers |
| misc_feature | 1..177 |
| | note = Description of Artificial Sequence: Synthetic polynucleotide |
| misc_feature | 1..177 |
| | note = 34bp lox66 pegRNA |
| source | 1..177 |
| | mol_type = other DNA |
| | organism = synthetic construct |

SEQUENCE: 82
```
ggcccagact gagcacgtga gttttagagc tagaaatagc aagttaaaat aaggctagtc   60
cgttatcaac ttgaaaaagt ggcaccgagt cggtgctgga ggaagcaggg cttcctttcc  120
tctgccatca ataacttcgt atagcataca ttatacgaac ggtacgtgct cagtctg     177
```

| SEQ ID NO: 83 | moltype = DNA length = 20 |
|---|---|
| FEATURE | Location/Qualifiers |
| misc_feature | 1..20 |
| | note = Description of Artificial Sequence: Synthetic oligonucleotide |
| misc_feature | 1..20 |
| | note = gRNA2 |
| source | 1..20 |
| | mol_type = other DNA |
| | organism = synthetic construct |

SEQUENCE: 83
```
ggcccagact gagcacgtga                                               20
```

| SEQ ID NO: 84 | moltype = DNA length = 184 |
|---|---|
| FEATURE | Location/Qualifiers |
| misc_feature | 1..184 |
| | note = Description of Artificial Sequence: Synthetic polynucleotide |
| source | 1..184 |
| | mol_type = other DNA |
| | organism = synthetic construct |

SEQUENCE: 84
```
gctattctcg cagctcacca gttttagagc tagaaatagc aagttaaaat aaggctagtc   60
cgttatcaac ttgaaaaagt ggcaccgagt cggtgcgacg agcgcggcga tatcatcatc  120
catggccgga tgatcctgac gacggagacc gccgtcgtcg acaagccggc ctgagctgcg  180
agaa                                                               184
```

| SEQ ID NO: 85 | moltype = DNA length = 179 |
|---|---|
| FEATURE | Location/Qualifiers |
| misc_feature | 1..179 |
| | note = Description of Artificial Sequence: Synthetic polynucleotide |

```
source                  1..179
                        mol_type = other DNA
                        organism = synthetic construct
SEQUENCE: 85
gctattctcg cagctcacca gttttagagc tagaaatagc aagttaaaat aaggctagtc    60
cgttatcaac ttgaaaaagt ggcaccgagt cggtgcgagt cggtgcgacg agcgcggcga   120
tatcatcatc catggcacaa ttaacatctc aatcaaggta aatgcttgag ctgcgagaa    179

SEQ ID NO: 86           moltype = DNA  length = 179
FEATURE                 Location/Qualifiers
misc_feature            1..179
                        note = Description of Artificial Sequence: Synthetic
                        polynucleotide
source                  1..179
                        mol_type = other DNA
                        organism = synthetic construct
SEQUENCE: 86
gctattctcg cagctcacca gttttagagc tagaaatagc aagttaaaat aaggctagtc    60
cgttatcaac ttgaaaaagt ggcaccgagt cggtgcgagt cggtgcgacg agcgcggcga   120
tatcatcatc catggagcat ttaccttgat tgagatgtta attgtgtgag ctgcgagaa    179

SEQ ID NO: 87           moltype = DNA  length = 182
FEATURE                 Location/Qualifiers
misc_feature            1..182
                        note = Description of Artificial Sequence: Synthetic
                        polynucleotide
source                  1..182
                        mol_type = other DNA
                        organism = synthetic construct
SEQUENCE: 87
gctattctcg cagctcacca gttttagagc tagaaatagc aagttaaaat aaggctagtc    60
cgttatcaac ttgaaaaagt ggcaccgagt cggtgcgagt cggtgcgacg agcgcggcga   120
tatcatcatc catggcaggt ttttgacgaa agtgatccag atgatccagt gagctgcgag   180
aa                                                                  182

SEQ ID NO: 88           moltype = DNA  length = 182
FEATURE                 Location/Qualifiers
misc_feature            1..182
                        note = Description of Artificial Sequence: Synthetic
                        polynucleotide
source                  1..182
                        mol_type = other DNA
                        organism = synthetic construct
SEQUENCE: 88
gctattctcg cagctcacca gttttagagc tagaaatagc aagttaaaat aaggctagtc    60
cgttatcaac ttgaaaaagt ggcaccgagt cggtgcgagt cggtgcgacg agcgcggcga   120
tatcatcatc catggctgga tcatctggat cactttcgtc aaaaacctgt gagctgcgag   180
aa                                                                  182

SEQ ID NO: 89           moltype = DNA  length = 96
FEATURE                 Location/Qualifiers
misc_feature            1..96
                        note = Description of Artificial Sequence: Synthetic
                        oligonucleotide
source                  1..96
                        mol_type = other DNA
                        organism = synthetic construct
SEQUENCE: 89
gaagccggcc ttgcacatgc gttttagagc tagaaatagc aagttaaaat aaggctagtc    60
cgttatcaac ttgaaaaagt ggcaccgagt cggtgc                              96

SEQ ID NO: 90           moltype = DNA  length = 164
FEATURE                 Location/Qualifiers
misc_feature            1..164
                        note = Description of Artificial Sequence: Synthetic
                        polynucleotide
source                  1..164
                        mol_type = other DNA
                        organism = synthetic construct
SEQUENCE: 90
gaagccggcc ttgcacatgc gttttagagc tagaaatagc aagttaaaat aaggctagtc    60
cgttatcaac ttgaaaaagt ggcaccgagt cggtgcatat catcatccat ggtaccgttc   120
gtatagcata cattatacga agttattgag ctgcgagaat agcc                    164

SEQ ID NO: 91           moltype = DNA  length = 172
FEATURE                 Location/Qualifiers
misc_feature            1..172
                        note = Description of Artificial Sequence: Synthetic
                        polynucleotide
```

```
source                          1..172
                                mol_type = other DNA
                                organism = synthetic construct
SEQUENCE: 91
gaagccggcc ttgcacatgc gttttagagc tagaaatagc aagttaaaat aaggctagtc    60
cgttatcaac ttgaaaaagt ggcaccgagt cggtgcgacg agcgcggcga tatcatcatc   120
catggtaccg ttcgtatagc atacattata cgaagttatt gagctgcgag aa           172

SEQ ID NO: 92                   moltype = DNA   length = 189
FEATURE                         Location/Qualifiers
misc_feature                    1..189
                                note = Description of Artificial Sequence: Synthetic
                                polynucleotide
source                          1..189
                                mol_type = other DNA
                                organism = synthetic construct
SEQUENCE: 92
gctattctcg cagctcacca gttttagagc tagaaatagc aagttaaaat aaggctagtc    60
cgttatcaac ttgaaaaagt ggcaccgagt cggtgctcga cgacgagcgc ggcgatatca   120
tcatccatgg ccggatgatc ctgacgacgg agaccgccgt cgtcgacaag ccggcctgag   180
ctgcgagaa                                                           189

SEQ ID NO: 93                   moltype = DNA   length = 181
FEATURE                         Location/Qualifiers
misc_feature                    1..181
                                note = Description of Artificial Sequence: Synthetic
                                polynucleotide
source                          1..181
                                mol_type = other DNA
                                organism = synthetic construct
SEQUENCE: 93
gctattctcg cagctcacca gttttagagc tagaaatagc aagttaaaat aaggctagtc    60
cgttatcaac ttgaaaaagt ggcaccgagt cggtgcgagc gcggcgatat catcatccat   120
ggccggatga tcctgacgac ggagaccgcc gtcgtcgaca agccggcctg agctgcgaga   180
a                                                                   181

SEQ ID NO: 94                   moltype = DNA   length = 178
FEATURE                         Location/Qualifiers
misc_feature                    1..178
                                note = Description of Artificial Sequence: Synthetic
                                polynucleotide
source                          1..178
                                mol_type = other DNA
                                organism = synthetic construct
SEQUENCE: 94
gctattctcg cagctcacca gttttagagc tagaaatagc aagttaaaat aaggctagtc    60
cgttatcaac ttgaaaaagt ggcaccgagt cggtgccgcg cgatatcat catccatggc   120
cggatgatcc tgacgacgga gaccgccgtc gtcgacaagc cggcctgagc tgcgagaa    178

SEQ ID NO: 95                   moltype = DNA   length = 175
FEATURE                         Location/Qualifiers
misc_feature                    1..175
                                note = Description of Artificial Sequence: Synthetic
                                polynucleotide
source                          1..175
                                mol_type = other DNA
                                organism = synthetic construct
SEQUENCE: 95
gctattctcg cagctcacca gttttagagc tagaaatagc aagttaaaat aaggctagtc    60
cgttatcaac ttgaaaaagt ggcaccgagt cggtgcggcg atatcatcat ccatggccgg   120
atgatcctga cgacggagac cgccgtcgtc gacaagccgc ctgagctgc gagaa         175

SEQ ID NO: 96                   moltype = DNA   length = 171
FEATURE                         Location/Qualifiers
misc_feature                    1..171
                                note = Description of Artificial Sequence: Synthetic
                                polynucleotide
source                          1..171
                                mol_type = other DNA
                                organism = synthetic construct
SEQUENCE: 96
gctattctcg cagctcacca gttttagagc tagaaatagc aagttaaaat aaggctagtc    60
cgttatcaac ttgaaaaagt ggcaccgagt cggtgcatat catcatccat ggccggatga   120
tcctgacgac ggagaccgcc gtcgtcgaca agccggcctg agctgcgaga a             171
```

```
SEQ ID NO: 97              moltype = DNA  length = 194
FEATURE                    Location/Qualifiers
misc_feature               1..194
                           note = Description of Artificial Sequence: Synthetic
                             polynucleotide
source                     1..194
                           mol_type = other DNA
                           organism = synthetic construct
SEQUENCE: 97
gctattctcg cagctcacca gttttagagc tagaaatagc aagttaaaat aaggctagtc   60
cgttatcaac ttgaaaaagt ggcaccgagt cggtgctcga cgacgagcgc ggcgatatca  120
tcatccatgg ccggatgatc ctgacgacgg agaccgccgt cgtcgacaag ccggcctgag  180
ctgcgagaat agcc                                                    194

SEQ ID NO: 98              moltype = DNA  length = 189
FEATURE                    Location/Qualifiers
misc_feature               1..189
                           note = Description of Artificial Sequence: Synthetic
                             polynucleotide
source                     1..189
                           mol_type = other DNA
                           organism = synthetic construct
SEQUENCE: 98
gctattctcg cagctcacca gttttagagc tagaaatagc aagttaaaat aaggctagtc   60
cgttatcaac ttgaaaaagt ggcaccgagt cggtgcgacg agcgcggcga tatcatcatc  120
catggccgga tgatcctgac gacggagacc gccgtcgtca caagccggc ctgagctgcg  180
agaatagcc                                                          189

SEQ ID NO: 99              moltype = DNA  length = 176
FEATURE                    Location/Qualifiers
misc_feature               1..176
                           note = Description of Artificial Sequence: Synthetic
                             polynucleotide
source                     1..176
                           mol_type = other DNA
                           organism = synthetic construct
SEQUENCE: 99
gctattctcg cagctcacca gttttagagc tagaaatagc aagttaaaat aaggctagtc   60
cgttatcaac ttgaaaaagt ggcaccgagt cggtgcatat catcatccat ggccggatga  120
tcctgacgac ggagaccgcc gtcgtcgaca agccggcctg agctgcgaga atagcc      176

SEQ ID NO: 100             moltype = DNA  length = 194
FEATURE                    Location/Qualifiers
misc_feature               1..194
                           note = Description of Artificial Sequence: Synthetic
                             polynucleotide
source                     1..194
                           mol_type = other DNA
                           organism = synthetic construct
SEQUENCE: 100
gctgtctccg ccgcccgcca gttttagagc tagaaatagc aagttaaaat aaggctagtc   60
cgttatcaac ttgaaaaagt ggcaccgagt cggtgcctgc ccatccgcgg cggcacgggg  120
gtcgcagtcg ccatgccgga tgatcctgac gacggagacc gccgtcgtcg acaagccggc  180
ccgggcggcg gaga                                                    194

SEQ ID NO: 101             moltype = DNA  length = 189
FEATURE                    Location/Qualifiers
misc_feature               1..189
                           note = Description of Artificial Sequence: Synthetic
                             polynucleotide
source                     1..189
                           mol_type = other DNA
                           organism = synthetic construct
SEQUENCE: 101
gctgtctccg ccgcccgcca gttttagagc tagaaatagc aagttaaaat aaggctagtc   60
cgttatcaac ttgaaaaagt ggcaccgagt cggtgccatc cgcggcggca cggggtcgc  120
agtcgccatg ccggatgatc ctgacgacgg agaccgccgt cgtcgacaag ccggcccggg  180
cggcggaga                                                          189

SEQ ID NO: 102             moltype = DNA  length = 184
FEATURE                    Location/Qualifiers
misc_feature               1..184
                           note = Description of Artificial Sequence: Synthetic
                             polynucleotide
source                     1..184
                           mol_type = other DNA
                           organism = synthetic construct
```

-continued

```
SEQUENCE: 102
gctgtctccg ccgcccgcca gttttagagc tagaaatagc aagttaaaat aaggctagtc    60
cgttatcaac ttgaaaaagt ggcaccgagt cggtgcgcgg cggcacgggg gtcgcagtcg   120
ccatgccgga tgatcctgac gacggagacc gccgtcgtcg acaagccggc ccgggcggcg   180
gaga                                                                184

SEQ ID NO: 103          moltype = DNA   length = 179
FEATURE                 Location/Qualifiers
misc_feature            1..179
                        note = Description of Artificial Sequence: Synthetic
                          polynucleotide
source                  1..179
                        mol_type = other DNA
                        organism = synthetic construct
SEQUENCE: 103
gctgtctccg ccgcccgcca gttttagagc tagaaatagc aagttaaaat aaggctagtc    60
cgttatcaac ttgaaaaagt ggcaccgagt cggtgcggca cggggtcgc agtcgccatg   120
ccggatgatc ctgacgacgg agaccgccgt cgtcgacaag ccggcccggg cggcggaga   179

SEQ ID NO: 104          moltype = DNA   length = 174
FEATURE                 Location/Qualifiers
misc_feature            1..174
                        note = Description of Artificial Sequence: Synthetic
                          polynucleotide
source                  1..174
                        mol_type = other DNA
                        organism = synthetic construct
SEQUENCE: 104
gctgtctccg ccgcccgcca gttttagagc tagaaatagc aagttaaaat aaggctagtc    60
cgttatcaac ttgaaaaagt ggcaccgagt cggtgcgggg gtcgcagtcg ccatgccgga   120
tgatcctgac gacggagacc gccgtcgtcg acaagccggc ccgggcggcg gaga         174

SEQ ID NO: 105          moltype = DNA   length = 199
FEATURE                 Location/Qualifiers
misc_feature            1..199
                        note = Description of Artificial Sequence: Synthetic
                          polynucleotide
source                  1..199
                        mol_type = other DNA
                        organism = synthetic construct
SEQUENCE: 105
gctgtctccg ccgcccgcca gttttagagc tagaaatagc aagttaaaat aaggctagtc    60
cgttatcaac ttgaaaaagt ggcaccgagt cggtgcctgc ccatccgcgg cggcacgggg   120
gtcgcagtcg ccatgccgga tgatcctgac gacggagacc gccgtcgtcg acaagccggc   180
ccgggcggcg gagacagcg                                                199

SEQ ID NO: 106          moltype = DNA   length = 194
FEATURE                 Location/Qualifiers
misc_feature            1..194
                        note = Description of Artificial Sequence: Synthetic
                          polynucleotide
source                  1..194
                        mol_type = other DNA
                        organism = synthetic construct
SEQUENCE: 106
gctgtctccg ccgcccgcca gttttagagc tagaaatagc aagttaaaat aaggctagtc    60
cgttatcaac ttgaaaaagt ggcaccgagt cggtgccatc cgcggcggca cggggtcgc    120
agtcgccatg ccggatgatc ctgacgacgg agaccgccgt cgtcgacaag ccggcccggg   180
cggcggagac agcg                                                     194

SEQ ID NO: 107          moltype = DNA   length = 189
FEATURE                 Location/Qualifiers
misc_feature            1..189
                        note = Description of Artificial Sequence: Synthetic
                          polynucleotide
source                  1..189
                        mol_type = other DNA
                        organism = synthetic construct
SEQUENCE: 107
gctgtctccg ccgcccgcca gttttagagc tagaaatagc aagttaaaat aaggctagtc    60
cgttatcaac ttgaaaaagt ggcaccgagt cggtgcgcgg cggcacgggg gtcgcagtcg   120
ccatgccgga tgatcctgac gacggagacc gccgtcgtcg acaagccggc ccgggcggcg   180
gagacagcg                                                           189

SEQ ID NO: 108          moltype = DNA   length = 184
FEATURE                 Location/Qualifiers
misc_feature            1..184
                        note = Description of Artificial Sequence: Synthetic
                          polynucleotide
```

```
source                  1..184
                        mol_type = other DNA
                        organism = synthetic construct
SEQUENCE: 108
gctgtctccg ccgcccgcca gttttagagc tagaaatagc aagttaaaat aaggctagtc    60
cgttatcaac ttgaaaaagt ggcaccgagt cggtgcggca cggggtcgc agtcgccatg    120
ccggatgatc ctgacgacgg agaccgccgt cgtcgacaag ccggcccggg cggcggagac   180
agcg                                                                184

SEQ ID NO: 109          moltype = DNA   length = 179
FEATURE                 Location/Qualifiers
misc_feature            1..179
                        note = Description of Artificial Sequence: Synthetic
                         polynucleotide
source                  1..179
                        mol_type = other DNA
                        organism = synthetic construct
SEQUENCE: 109
gctgtctccg ccgcccgcca gttttagagc tagaaatagc aagttaaaat aaggctagtc    60
cgttatcaac ttgaaaaagt ggcaccgagt cggtgcgggg gtcgcagtcg ccatgccgga   120
tgatcctgac gacggagacc gccgtcgtcg acaagccggc ccgggcggcg gagacagcg    179

SEQ ID NO: 110          moltype = DNA   length = 96
FEATURE                 Location/Qualifiers
misc_feature            1..96
                        note = Description of Artificial Sequence: Synthetic
                         oligonucleotide
source                  1..96
                        mol_type = other DNA
                        organism = synthetic construct
SEQUENCE: 110
gcgtggtggg gccgccagcg gttttagagc tagaaatagc aagttaaaat aaggctagtc    60
cgttatcaac ttgaaaaagt ggcaccgagt cggtgc                              96

SEQ ID NO: 111          moltype = DNA   length = 180
FEATURE                 Location/Qualifiers
misc_feature            1..180
                        note = Description of Artificial Sequence: Synthetic
                         polynucleotide
source                  1..180
                        mol_type = other DNA
                        organism = synthetic construct
SEQUENCE: 111
gctattctcg cagctcacca gttttagagc tagaaatagc aagttaaaat aaggctagtc    60
cgttatcaac ttgaaaaagt ggcaccgagt cggtgcgacg agcgcggcga tatcatcatc   120
catggggatg atcctgacga cggagaccgc cgtcgtcgac aagccggtga gctgcgagaa   180

SEQ ID NO: 112          moltype = DNA   length = 178
FEATURE                 Location/Qualifiers
misc_feature            1..178
                        note = Description of Artificial Sequence: Synthetic
                         polynucleotide
source                  1..178
                        mol_type = other DNA
                        organism = synthetic construct
SEQUENCE: 112
gctattctcg cagctcacca gttttagagc tagaaatagc aagttaaaat aaggctagtc    60
cgttatcaac ttgaaaaagt ggcaccgagt cggtgcgacg agcgcggcga tatcatcatc   120
catgggatga tcctgacgac ggagaccgcc gtcgtcgaca agccgtgagc tgcgagaa     178

SEQ ID NO: 113          moltype = DNA   length = 176
FEATURE                 Location/Qualifiers
misc_feature            1..176
                        note = Description of Artificial Sequence: Synthetic
                         polynucleotide
source                  1..176
                        mol_type = other DNA
                        organism = synthetic construct
SEQUENCE: 113
gctattctcg cagctcacca gttttagagc tagaaatagc aagttaaaat aaggctagtc    60
cgttatcaac ttgaaaaagt ggcaccgagt cggtgcgacg agcgcggcga tatcatcatc   120
catggatgat cctgacgacg gagaccgccg tcgtcgacaa gcctgagctg cgagaa       176

SEQ ID NO: 114          moltype = DNA   length = 174
FEATURE                 Location/Qualifiers
misc_feature            1..174
                        note = Description of Artificial Sequence: Synthetic
                         polynucleotide
```

```
source                  1..174
                        mol_type = other DNA
                        organism = synthetic construct
SEQUENCE: 114
gctattctcg cagctcacca gttttagagc tagaaatagc aagttaaaat aaggctagtc    60
cgttatcaac ttgaaaaagt ggcaccgagt cggtgcgacg agcgcggcga tatcatcatc   120
catggtgatc ctgacgacgg agaccgccgt cgtcgacaag ctgagctgcg agaa         174

SEQ ID NO: 115          moltype = DNA  length = 182
FEATURE                 Location/Qualifiers
misc_feature            1..182
                        note = Description of Artificial Sequence: Synthetic
                         polynucleotide
source                  1..182
                        mol_type = other DNA
                        organism = synthetic construct
SEQUENCE: 115
gctgtctccg ccgcccgcca gttttagagc tagaaatagc aagttaaaat aaggctagtc    60
cgttatcaac ttgaaaaagt ggcaccgagt cggtgcgcgg cggcacgggg gtcgcagtcg   120
ccatgcggat gatcctgacg acggagaccg ccgtcgtcga caagccggcc gggcggcgga   180
ga                                                                  182

SEQ ID NO: 116          moltype = DNA  length = 180
FEATURE                 Location/Qualifiers
misc_feature            1..180
                        note = Description of Artificial Sequence: Synthetic
                         polynucleotide
source                  1..180
                        mol_type = other DNA
                        organism = synthetic construct
SEQUENCE: 116
gctgtctccg ccgcccgcca gttttagagc tagaaatagc aagttaaaat aaggctagtc    60
cgttatcaac ttgaaaaagt ggcaccgagt cggtgcgcgg cggcacgggg gtcgcagtcg   120
ccatgggatg atcctgacga cggagaccgc cgtcgtcgac aagccggcgg gcggcggaga   180

SEQ ID NO: 117          moltype = DNA  length = 178
FEATURE                 Location/Qualifiers
misc_feature            1..178
                        note = Description of Artificial Sequence: Synthetic
                         polynucleotide
source                  1..178
                        mol_type = other DNA
                        organism = synthetic construct
SEQUENCE: 117
gctgtctccg ccgcccgcca gttttagagc tagaaatagc aagttaaaat aaggctagtc    60
cgttatcaac ttgaaaaagt ggcaccgagt cggtgcgcgg cggcacgggg gtcgcagtcg   120
ccatggatga tcctgacgac ggagaccgcc gtcgtcgaca agccgcgggc ggcggaga     178

SEQ ID NO: 118          moltype = DNA  length = 176
FEATURE                 Location/Qualifiers
misc_feature            1..176
                        note = Description of Artificial Sequence: Synthetic
                         polynucleotide
source                  1..176
                        mol_type = other DNA
                        organism = synthetic construct
SEQUENCE: 118
gctgtctccg ccgcccgcca gttttagagc tagaaatagc aagttaaaat aaggctagtc    60
cgttatcaac ttgaaaaagt ggcaccgagt cggtgcgcgg cggcacgggg gtcgcagtcg   120
ccatgatgat cctgacgacg gagaccgccg tcgtcgacaa gcccgggcgg cggaga       176

SEQ ID NO: 119          moltype = DNA  length = 189
FEATURE                 Location/Qualifiers
misc_feature            1..189
                        note = Description of Artificial Sequence: Synthetic
                         polynucleotide
source                  1..189
                        mol_type = other DNA
                        organism = synthetic construct
SEQUENCE: 119
gcgtattgcc tggaggatgg gttttagagc tagaaatagc aagttaaaat aaggctagtc    60
cgttatcaac ttgaaaaagt ggcaccgagt cggtgcgaac cacgcggcga atgccggcgt   120
ccgcccgga tgatcctgac gacggagacc gccgtcgtcg acaagccggc ctcctccagg   180
caatacgcg                                                           189
```

```
SEQ ID NO: 120           moltype = DNA   length = 184
FEATURE                  Location/Qualifiers
misc_feature             1..184
                         note = Description of Artificial Sequence: Synthetic
                          polynucleotide
source                   1..184
                         mol_type = other DNA
                         organism = synthetic construct
SEQUENCE: 120
gcgtattgcc tggaggatgg gttttagagc tagaaatagc aagttaaaat aaggctagtc    60
cgttatcaac ttgaaaaagt ggcaccgagt cggtgcgaac cacgcggcga atgccggcgt   120
ccgccccgga tgatcctgac gacggagacc gccgtcgtcg acaagccggc ctcctccagg   180
caat                                                                184

SEQ ID NO: 121           moltype = DNA   length = 182
FEATURE                  Location/Qualifiers
misc_feature             1..182
                         note = Description of Artificial Sequence: Synthetic
                          polynucleotide
source                   1..182
                         mol_type = other DNA
                         organism = synthetic construct
SEQUENCE: 121
gcgtattgcc tggaggatgg gttttagagc tagaaatagc aagttaaaat aaggctagtc    60
cgttatcaac ttgaaaaagt ggcaccgagt cggtgcgaac cacgcggcga atgccggcgt   120
ccgcccggat gatcctgacg acggagaccg ccgtcgtcga caagccggct cctccaggca   180
at                                                                  182

SEQ ID NO: 122           moltype = DNA   length = 180
FEATURE                  Location/Qualifiers
misc_feature             1..180
                         note = Description of Artificial Sequence: Synthetic
                          polynucleotide
source                   1..180
                         mol_type = other DNA
                         organism = synthetic construct
SEQUENCE: 122
gcgtattgcc tggaggatgg gttttagagc tagaaatagc aagttaaaat aaggctagtc    60
cgttatcaac ttgaaaaagt ggcaccgagt cggtgcgaac cacgcggcga atgccggcgt   120
ccgccggatg atcctgacga cggagaccgc cgtcgtcgac aagccggtcc tccaggcaat   180

SEQ ID NO: 123           moltype = DNA   length = 178
FEATURE                  Location/Qualifiers
misc_feature             1..178
                         note = Description of Artificial Sequence: Synthetic
                          polynucleotide
source                   1..178
                         mol_type = other DNA
                         organism = synthetic construct
SEQUENCE: 123
gcgtattgcc tggaggatgg gttttagagc tagaaatagc aagttaaaat aaggctagtc    60
cgttatcaac ttgaaaaagt ggcaccgagt cggtgcgaac cacgcggcga atgccggcgt   120
ccgccgatga tcctgacgac ggagaccgcc gtcgtcgaca gccgtcctc caggcaat     178

SEQ ID NO: 124           moltype = DNA   length = 176
FEATURE                  Location/Qualifiers
misc_feature             1..176
                         note = Description of Artificial Sequence: Synthetic
                          polynucleotide
source                   1..176
                         mol_type = other DNA
                         organism = synthetic construct
SEQUENCE: 124
gcgtattgcc tggaggatgg gttttagagc tagaaatagc aagttaaaat aaggctagtc    60
cgttatcaac ttgaaaaagt ggcaccgagt cggtgcgaac cacgcggcga atgccggcgt   120
ccgccatgat cctgacgacg gagaccgccg tcgtcgacaa gcctcctcca ggcaat      176

SEQ ID NO: 125           moltype = DNA   length = 97
FEATURE                  Location/Qualifiers
misc_feature             1..97
                         note = Description of Artificial Sequence: Synthetic
                          oligonucleotide
source                   1..97
                         mol_type = other DNA
                         organism = synthetic construct
SEQUENCE: 125
gagccgagca cgaggggata cgtttagag ctagaaatag caagttaaaa taaggctagt     60
ccgttatcaa cttgaaaaag tggcaccgag tcggtgc                            97
```

```
SEQ ID NO: 126          moltype = DNA  length = 167
FEATURE                 Location/Qualifiers
misc_feature            1..167
                        note = Description of Artificial Sequence: Synthetic
                         polynucleotide
source                  1..167
                        mol_type = other DNA
                        organism = synthetic construct
SEQUENCE: 126
gctattctcg cagctcacca gttttagagc tagaaatagc aagttaaaat aaggctagtc   60
cgttatcaac ttgaaaaagt ggcaccgagt cggtgcggcg atatcatcat ccatggatga  120
tcctgacgac ggagaccgcc gtcgtcgaca agcctgagct gcgagaa               167

SEQ ID NO: 127          moltype = DNA  length = 162
FEATURE                 Location/Qualifiers
misc_feature            1..162
                        note = Description of Artificial Sequence: Synthetic
                         polynucleotide
source                  1..162
                        mol_type = other DNA
                        organism = synthetic construct
SEQUENCE: 127
gctattctcg cagctcacca gttttagagc tagaaatagc aagttaaaat aaggctagtc   60
cgttatcaac ttgaaaaagt ggcaccgagt cggtgctatc atcatccatg gatgatcctg  120
acgacggaga ccgccgtcgt cgacaagcct gagctgcgag aa                    162

SEQ ID NO: 128          moltype = DNA  length = 157
FEATURE                 Location/Qualifiers
misc_feature            1..157
                        note = Description of Artificial Sequence: Synthetic
                         polynucleotide
source                  1..157
                        mol_type = other DNA
                        organism = synthetic construct
SEQUENCE: 128
gctattctcg cagctcacca gttttagagc tagaaatagc aagttaaaat aaggctagtc   60
cgttatcaac ttgaaaaagt ggcaccgagt cggtgctcat ccatggatga tcctgacgac  120
ggagaccgcc gtcgtcgaca agcctgagct gcgagaa                          157

SEQ ID NO: 129          moltype = DNA  length = 163
FEATURE                 Location/Qualifiers
misc_feature            1..163
                        note = Description of Artificial Sequence: Synthetic
                         polynucleotide
source                  1..163
                        mol_type = other DNA
                        organism = synthetic construct
SEQUENCE: 129
gctattctcg cagctcacca gttttagagc tagaaatagc aagttaaaat aaggctagtc   60
cgttatcaac ttgaaaaagt ggcaccgagt cggtgcggcg atatcatcat ccatggatga  120
tcctgacgac ggagaccgcc gtcgtcgaca agcctgagct gcg                   163

SEQ ID NO: 130          moltype = DNA  length = 158
FEATURE                 Location/Qualifiers
misc_feature            1..158
                        note = Description of Artificial Sequence: Synthetic
                         polynucleotide
source                  1..158
                        mol_type = other DNA
                        organism = synthetic construct
SEQUENCE: 130
gctattctcg cagctcacca gttttagagc tagaaatagc aagttaaaat aaggctagtc   60
cgttatcaac ttgaaaaagt ggcaccgagt cggtgctatc atcatccatg gatgatcctg  120
acgacggaga ccgccgtcgt cgacaagcct gagctgcg                         158

SEQ ID NO: 131          moltype = DNA  length = 153
FEATURE                 Location/Qualifiers
misc_feature            1..153
                        note = Description of Artificial Sequence: Synthetic
                         polynucleotide
source                  1..153
                        mol_type = other DNA
                        organism = synthetic construct
SEQUENCE: 131
gctattctcg cagctcacca gttttagagc tagaaatagc aagttaaaat aaggctagtc   60
cgttatcaac ttgaaaaagt ggcaccgagt cggtgctcat ccatggatga tcctgacgac  120
ggagaccgcc gtcgtcgaca agcctgagct gcg                              153
```

| | | |
|---|---|---|
| SEQ ID NO: 132 | moltype = DNA length = 167 | |
| FEATURE | Location/Qualifiers | |
| misc_feature | 1..167 | |
| | note = Description of Artificial Sequence: Synthetic polynucleotide | |
| source | 1..167 | |
| | mol_type = other DNA | |
| | organism = synthetic construct | |

SEQUENCE: 132
```
gctgtctccg ccgcccgcca gttttagagc tagaaatagc aagttaaaat aaggctagtc   60
cgttatcaac ttgaaaaagt ggcaccgagt cggtgccggg ggtcgcagtc gccatgatga  120
tcctgacgac ggagaccgcc gtcgtcgaca agcccgggcg gcggaga              167
```

| | | |
|---|---|---|
| SEQ ID NO: 133 | moltype = DNA length = 162 | |
| FEATURE | Location/Qualifiers | |
| misc_feature | 1..162 | |
| | note = Description of Artificial Sequence: Synthetic polynucleotide | |
| source | 1..162 | |
| | mol_type = other DNA | |
| | organism = synthetic construct | |

SEQUENCE: 133
```
gctgtctccg ccgcccgcca gttttagagc tagaaatagc aagttaaaat aaggctagtc   60
cgttatcaac ttgaaaaagt ggcaccgagt cggtgcgtcg cagtcgccat gatgatcctg  120
acgacggaga ccgccgtcgt cgacaagccc gggcggcgga ga                   162
```

| | | |
|---|---|---|
| SEQ ID NO: 134 | moltype = DNA length = 157 | |
| FEATURE | Location/Qualifiers | |
| misc_feature | 1..157 | |
| | note = Description of Artificial Sequence: Synthetic polynucleotide | |
| source | 1..157 | |
| | mol_type = other DNA | |
| | organism = synthetic construct | |

SEQUENCE: 134
```
gctgtctccg ccgcccgcca gttttagagc tagaaatagc aagttaaaat aaggctagtc   60
cgttatcaac ttgaaaaagt ggcaccgagt cggtgcagtc gccatgatga tcctgacgac  120
ggagaccgcc gtcgtcgaca agcccgggcg gcggaga                         157
```

| | | |
|---|---|---|
| SEQ ID NO: 135 | moltype = DNA length = 163 | |
| FEATURE | Location/Qualifiers | |
| misc_feature | 1..163 | |
| | note = Description of Artificial Sequence: Synthetic polynucleotide | |
| source | 1..163 | |
| | mol_type = other DNA | |
| | organism = synthetic construct | |

SEQUENCE: 135
```
gctgtctccg ccgcccgcca gttttagagc tagaaatagc aagttaaaat aaggctagtc   60
cgttatcaac ttgaaaaagt ggcaccgagt cggtgccggg ggtcgcagtc gccatgatga  120
tcctgacgac ggagaccgcc gtcgtcgaca agcccgggcg gcg                  163
```

| | | |
|---|---|---|
| SEQ ID NO: 136 | moltype = DNA length = 158 | |
| FEATURE | Location/Qualifiers | |
| misc_feature | 1..158 | |
| | note = Description of Artificial Sequence: Synthetic polynucleotide | |
| source | 1..158 | |
| | mol_type = other DNA | |
| | organism = synthetic construct | |

SEQUENCE: 136
```
gctgtctccg ccgcccgcca gttttagagc tagaaatagc aagttaaaat aaggctagtc   60
cgttatcaac ttgaaaaagt ggcaccgagt cggtgcgtcg cagtcgccat gatgatcctg  120
acgacggaga ccgccgtcgt cgacaagccc gggcggcg                        158
```

| | | |
|---|---|---|
| SEQ ID NO: 137 | moltype = DNA length = 153 | |
| FEATURE | Location/Qualifiers | |
| misc_feature | 1..153 | |
| | note = Description of Artificial Sequence: Synthetic polynucleotide | |
| source | 1..153 | |
| | mol_type = other DNA | |
| | organism = synthetic construct | |

SEQUENCE: 137
```
gctgtctccg ccgcccgcca gttttagagc tagaaatagc aagttaaaat aaggctagtc   60
cgttatcaac ttgaaaaagt ggcaccgagt cggtgcagtc gccatgatga tcctgacgac  120
ggagaccgcc gtcgtcgaca agcccgggcg gcg                             153
```

```
SEQ ID NO: 138           moltype = DNA  length = 180
FEATURE                  Location/Qualifiers
misc_feature             1..180
                         note = Description of Artificial Sequence: Synthetic
                         polynucleotide
source                   1..180
                         mol_type = other DNA
                         organism = synthetic construct
SEQUENCE: 138
gagaagcggc gtccggggct agttttagag ctagaaatag caagttaaaa taaggctagt   60
ccgttatcaa cttgaaaaag tggcaccgag tcggtgctct ttgtccagag tcacagccat  120
accggatgat cctgacgacg gagaccgccg tcgtcgacaa gccggccccc cggacgccgc  180

SEQ ID NO: 139           moltype = DNA  length = 179
FEATURE                  Location/Qualifiers
misc_feature             1..179
                         note = Description of Artificial Sequence: Synthetic
                         polynucleotide
source                   1..179
                         mol_type = other DNA
                         organism = synthetic construct
SEQUENCE: 139
gggcacgggg ccatgtacaa gttttagagc tagaaatagc aagttaaaat aaggctagtc   60
cgttatcaac ttgaaaaagt ggcaccgagt cggtgcggcg tcggcagccc gatcccgttg  120
ccggatgatc ctgacgacgg agaccgccgt cgtcgacaag ccggcctaca tggcccgt   179

SEQ ID NO: 140           moltype = DNA  length = 185
FEATURE                  Location/Qualifiers
misc_feature             1..185
                         note = Description of Artificial Sequence: Synthetic
                         polynucleotide
source                   1..185
                         mol_type = other DNA
                         organism = synthetic construct
SEQUENCE: 140
gtgtcaggtg gggcggggct agttttagag ctagaaatag caagttaaaa taaggctagt   60
ccgttatcaa cttgaaaaag tggcaccgag tcggtgcgct ggctcctccc ctggcaccat  120
accggatgat cctgacgacg gagaccgccg tcgtcgacaa gccggccccc cgccccacct  180
gacac                                                              185

SEQ ID NO: 141           moltype = DNA  length = 184
FEATURE                  Location/Qualifiers
misc_feature             1..184
                         note = Description of Artificial Sequence: Synthetic
                         polynucleotide
source                   1..184
                         mol_type = other DNA
                         organism = synthetic construct
SEQUENCE: 141
gagtgggtca gacgagcagg agttttagag ctagaaatag caagttaaaa taaggctagt   60
ccgttatcaa cttgaaaaag tggcaccgag tcggtgcgat ggagggctgc atggggagg   120
agtcgccgga tgatcctgac gacggagacc gccgtcgtcg acaagccggc ctgctcgtct  180
gacc                                                               184

SEQ ID NO: 142           moltype = DNA  length = 97
FEATURE                  Location/Qualifiers
misc_feature             1..97
                         note = Description of Artificial Sequence: Synthetic
                         oligonucleotide
source                   1..97
                         mol_type = other DNA
                         organism = synthetic construct
SEQUENCE: 142
gcagccaccc gctctcggcc cgttttagag ctagaaatag caagttaaaa taaggctagt   60
ccgttatcaa cttgaaaaag tggcaccgag tcggtgc                            97

SEQ ID NO: 143           moltype = DNA  length = 97
FEATURE                  Location/Qualifiers
misc_feature             1..97
                         note = Description of Artificial Sequence: Synthetic
                         oligonucleotide
source                   1..97
                         mol_type = other DNA
                         organism = synthetic construct
SEQUENCE: 143
gtgtagtcag gccgctcacc cgttttagag ctagaaatag caagttaaaa taaggctagt   60
ccgttatcaa cttgaaaaag tggcaccgag tcggtgc                            97
```

| | |
|---|---|
| SEQ ID NO: 144 | moltype = DNA length = 97 |
| FEATURE | Location/Qualifiers |
| misc_feature | 1..97<br>note = Description of Artificial Sequence: Synthetic oligonucleotide |
| source | 1..97<br>mol_type = other DNA<br>organism = synthetic construct |

SEQUENCE: 144
gctgacaagt ctacggaacc tgttttagag ctagaaatag caagttaaaa taaggctagt   60
ccgttatcaa cttgaaaaag tggcaccgag tcggtgc                            97

| | |
|---|---|
| SEQ ID NO: 145 | moltype = DNA length = 96 |
| FEATURE | Location/Qualifiers |
| misc_feature | 1..96<br>note = Description of Artificial Sequence: Synthetic oligonucleotide |
| source | 1..96<br>mol_type = other DNA<br>organism = synthetic construct |

SEQUENCE: 145
gctcctccag cgccttgacc gttttagagc tagaaatagc aagttaaaat aaggctagtc   60
cgttatcaac ttgaaaaagt ggcaccgagt cggtgc                             96

| | |
|---|---|
| SEQ ID NO: 146 | moltype = DNA length = 20 |
| FEATURE | Location/Qualifiers |
| misc_feature | 1..20<br>note = Description of Artificial Sequence: Synthetic oligonucleotide |
| source | 1..20<br>mol_type = other DNA<br>organism = synthetic construct |

SEQUENCE: 146
gctattctcg cagctcacca                                               20

| | |
|---|---|
| SEQ ID NO: 147 | moltype = DNA length = 20 |
| FEATURE | Location/Qualifiers |
| misc_feature | 1..20<br>note = Description of Artificial Sequence: Synthetic oligonucleotide |
| source | 1..20<br>mol_type = other DNA<br>organism = synthetic construct |

SEQUENCE: 147
agaagcggcg tccggggcta                                               20

| | |
|---|---|
| SEQ ID NO: 148 | moltype = DNA length = 20 |
| FEATURE | Location/Qualifiers |
| misc_feature | 1..20<br>note = Description of Artificial Sequence: Synthetic oligonucleotide |
| source | 1..20<br>mol_type = other DNA<br>organism = synthetic construct |

SEQUENCE: 148
gggcacgggg ccatgtacaa                                               20

| | |
|---|---|
| SEQ ID NO: 149 | moltype = DNA length = 20 |
| FEATURE | Location/Qualifiers |
| misc_feature | 1..20<br>note = Description of Artificial Sequence: Synthetic oligonucleotide |
| source | 1..20<br>mol_type = other DNA<br>organism = synthetic construct |

SEQUENCE: 149
gcgtattgcc tggaggatgg                                               20

| | |
|---|---|
| SEQ ID NO: 150 | moltype = DNA length = 20 |
| FEATURE | Location/Qualifiers |
| misc_feature | 1..20<br>note = Description of Artificial Sequence: Synthetic oligonucleotide |
| source | 1..20<br>mol_type = other DNA<br>organism = synthetic construct |

SEQUENCE: 150
tgtcaggtgg ggcggggcta                                               20

```
SEQ ID NO: 151           moltype = DNA  length = 20
FEATURE                  Location/Qualifiers
misc_feature             1..20
                         note = Description of Artificial Sequence: Synthetic
                         oligonucleotide
source                   1..20
                         mol_type = other DNA
                         organism = synthetic construct
SEQUENCE: 151
agtgggtcag acgagcagga                                                     20

SEQ ID NO: 152           moltype = DNA  length = 20
FEATURE                  Location/Qualifiers
misc_feature             1..20
                         note = Description of Artificial Sequence: Synthetic
                         oligonucleotide
source                   1..20
                         mol_type = other DNA
                         organism = synthetic construct
SEQUENCE: 152
gctgtctccg ccgcccgcca                                                     20

SEQ ID NO: 153           moltype = DNA  length = 96
FEATURE                  Location/Qualifiers
misc_feature             1..96
                         note = Description of Artificial Sequence: Synthetic
                         oligonucleotide
source                   1..96
                         mol_type = other DNA
                         organism = synthetic construct
SEQUENCE: 153
gctattctcg cagctcacca gttttagagc tagaaatagc aagttaaaat aaggctagtc         60
cgttatcaac ttgaaaaagt ggcaccgagt cggtgc                                   96

SEQ ID NO: 154           moltype = DNA  length = 184
FEATURE                  Location/Qualifiers
misc_feature             1..184
                         note = Description of Artificial Sequence: Synthetic
                         polynucleotide
misc_difference          148..149
                         note = CG, GC, AT, TA, GG, TT, GA, AG, CC, TC, CT, AA, TG,
                         GT, CA, or AC
source                   1..184
                         mol_type = other DNA
                         organism = synthetic construct
SEQUENCE: 154
gctattctcg cagctcacca gttttagagc tagaaatagc aagttaaaat aaggctagtc         60
cgttatcaac ttgaaaaagt ggcaccgagt cggtgcgacg agcgcggcga tatcatcatc        120
catggccgga tgatcctgac gacggagnnc gccgtcgtcg acaagccggc ctgagctgcg        180
agaa                                                                    184

SEQ ID NO: 155           moltype = DNA  length = 183
FEATURE                  Location/Qualifiers
misc_feature             1..183
                         note = Description of Artificial Sequence: Synthetic
                         polynucleotide
source                   1..183
                         mol_type = other DNA
                         organism = synthetic construct
SEQUENCE: 155
gctattctcg cagctcacca gttttagagc tagaaatagc aagttaaaat aaggctagtc         60
cgttatcaac ttgaaaaagt ggcaccgagt cggtgcgacg agcgcggcga tatcatcatc        120
catgccggat gatcctgacg acggagaccg ccgtcgtcga caagccggcc tgagctgcga        180
gaa                                                                     183

SEQ ID NO: 156           moltype = DNA  length = 183
FEATURE                  Location/Qualifiers
misc_feature             1..183
                         note = Description of Artificial Sequence: Synthetic
                         polynucleotide
source                   1..183
                         mol_type = other DNA
                         organism = synthetic construct
SEQUENCE: 156
gctattctcg cagctcacca gttttagagc tagaaatagc aagttaaaat aaggctagtc         60
cgttatcaac ttgaaaaagt ggcaccgagt cggtgcgacg agcgcggcga tatcatcatc        120
catgccggat gatcctgacg acggagagcg ccgtcgtcga caagccggcc tgagctgcga        180
gaa                                                                     183
```

```
SEQ ID NO: 157          moltype = DNA   length = 189
FEATURE                 Location/Qualifiers
misc_feature            1..189
                        note = Description of Artificial Sequence: Synthetic
                         polynucleotide
source                  1..189
                        mol_type = other DNA
                        organism = synthetic construct
SEQUENCE: 157
gcgtattgcc tggaggatgg gttttagagc tagaaatagc aagttaaaat aaggctagtc   60
cgttatcaac ttgaaaaagt ggcaccgagt cggtgcgaac cacgcggcga atgccggcgt  120
ccgccccgga tgatcctgac gacggagtcc gccgtcgtcg acaagccggc ctcctccagg  180
caatacgcg                                                          189

SEQ ID NO: 158          moltype = DNA   length = 189
FEATURE                 Location/Qualifiers
misc_feature            1..189
                        note = Description of Artificial Sequence: Synthetic
                         polynucleotide
source                  1..189
                        mol_type = other DNA
                        organism = synthetic construct
SEQUENCE: 158
gctgtctccg ccgcccgcca gttttagagc tagaaatagc aagttaaaat aaggctagtc   60
cgttatcaac ttgaaaaagt ggcaccgagt cggtgcgcgg cggcacgggg gtcgcagtcg  120
ccatgccgga tgatcctgac gacggagctc gccgtcgtcg acaagccggc ccgggcggcg  180
gagacagcg                                                          189

SEQ ID NO: 159          moltype = DNA   length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 159
gtcacctcca atgactaggg                                               20

SEQ ID NO: 160          moltype = DNA   length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 160
gggcaaccac aaacccacga                                               20

SEQ ID NO: 161          moltype = DNA   length = 194
FEATURE                 Location/Qualifiers
misc_feature            1..194
                        note = Description of Artificial Sequence: Synthetic
                         polynucleotide
source                  1..194
                        mol_type = other DNA
                        organism = synthetic construct
SEQUENCE: 161
gctattctcg cagctcacca gttttagagc tagaaatagc aagttaaaat aaggctagtc   60
cgttatcaac ttgaaaaagt ggcaccgagt cggtgcgacg agcgcggcga tatcatcatc  120
catggctatg ccggatgatc ctgacgacgg agtccgccgt cgtcgacaag ccggccctag  180
ctgagctgcg agaa                                                    194

SEQ ID NO: 162          moltype = DNA   length = 189
FEATURE                 Location/Qualifiers
misc_feature            1..189
                        note = Description of Artificial Sequence: Synthetic
                         polynucleotide
source                  1..189
                        mol_type = other DNA
                        organism = synthetic construct
SEQUENCE: 162
gctattctcg cagctcacca gttttagagc tagaaatagc aagttaaaat aaggctagtc   60
cgttatcaac ttgaaaaagt ggcaccgagt cggtgcgacg agcgcggcga tatcatcatc  120
catggtgccg gatgatcctg acgacggagt ccgccgtcgt cgacaagccg gccctatgag  180
ctgcgagaa                                                          189
```

```
SEQ ID NO: 163          moltype = DNA  length = 184
FEATURE                 Location/Qualifiers
misc_feature            1..184
                        note = Description of Artificial Sequence: Synthetic
                         polynucleotide
source                  1..184
                        mol_type = other DNA
                        organism = synthetic construct
SEQUENCE: 163
gctattctcg cagctcacca gttttagagc tagaaatagc aagttaaaat aaggctagtc   60
cgttatcaac ttgaaaaagt ggcaccgagt cggtgcgacg agcgcggcga tatcatcatc  120
catggccgga tgatcctgac gacggagtcc gccgtcgtcg acaagccggc ctgagctgcg  180
agaa                                                               184

SEQ ID NO: 164          moltype = DNA  length = 179
FEATURE                 Location/Qualifiers
misc_feature            1..179
                        note = Description of Artificial Sequence: Synthetic
                         polynucleotide
source                  1..179
                        mol_type = other DNA
                        organism = synthetic construct
SEQUENCE: 164
gctattctcg cagctcacca gttttagagc tagaaatagc aagttaaaat aaggctagtc   60
cgttatcaac ttgaaaaagt ggcaccgagt cggtgcgacg agcgcggcga tatcatcatc  120
catggggatg atcctgacga cggagtccgc cgtcgtcgaa aagccgtgag ctgcgagaa   179

SEQ ID NO: 165          moltype = DNA  length = 174
FEATURE                 Location/Qualifiers
misc_feature            1..174
                        note = Description of Artificial Sequence: Synthetic
                         polynucleotide
source                  1..174
                        mol_type = other DNA
                        organism = synthetic construct
SEQUENCE: 165
gctattctcg cagctcacca gttttagagc tagaaatagc aagttaaaat aaggctagtc   60
cgttatcaac ttgaaaaagt ggcaccgagt cggtgcgacg agcgcggcga tatcatcatc  120
catggtgatc ctgacgacgg agtccgccgt cgtcgacaag ctgagctgcg agaa        174

SEQ ID NO: 166          moltype = DNA  length = 169
FEATURE                 Location/Qualifiers
misc_feature            1..169
                        note = Description of Artificial Sequence: Synthetic
                         polynucleotide
source                  1..169
                        mol_type = other DNA
                        organism = synthetic construct
SEQUENCE: 166
gctattctcg cagctcacca gttttagagc tagaaatagc aagttaaaat aaggctagtc   60
cgttatcaac ttgaaaaagt ggcaccgagt cggtgcgacg agcgcggcga tatcatcatc  120
catggatcct gacgacggag tccgccgtcg tcgacatgag ctgcgagaa              169

SEQ ID NO: 167          moltype = DNA  length = 164
FEATURE                 Location/Qualifiers
misc_feature            1..164
                        note = Description of Artificial Sequence: Synthetic
                         polynucleotide
source                  1..164
                        mol_type = other DNA
                        organism = synthetic construct
SEQUENCE: 167
gctattctcg cagctcacca gttttagagc tagaaatagc aagttaaaat aaggctagtc   60
cgttatcaac ttgaaaaagt ggcaccgagt cggtgcgacg agcgcggcga tatcatcatc  120
catggcctga cgacggagtc cgccgtcgtc gtgagctgcg agaa                   164

SEQ ID NO: 168          moltype = DNA  length = 159
FEATURE                 Location/Qualifiers
misc_feature            1..159
                        note = Description of Artificial Sequence: Synthetic
                         polynucleotide
source                  1..159
                        mol_type = other DNA
                        organism = synthetic construct
SEQUENCE: 168
gctattctcg cagctcacca gttttagagc tagaaatagc aagttaaaat aaggctagtc   60
cgttatcaac ttgaaaaagt ggcaccgagt cggtgcgacg agcgcggcga tatcatcatc  120
catggtgacg acggagtccg ccgtcgtgag ctgcgagaa                         159
```

```
SEQ ID NO: 169         moltype = DNA   length = 154
FEATURE                Location/Qualifiers
misc_feature           1..154
                       note = Description of Artificial Sequence: Synthetic
                        polynucleotide
source                 1..154
                       mol_type = other DNA
                       organism = synthetic construct
SEQUENCE: 169
gctattctcg cagctcacca gttttagagc tagaaatagc aagttaaaat aaggctagtc    60
cgttatcaac ttgaaaaagt ggcaccgagt cggtgcgacg agcgcggcga tatcatcatc   120
catggacgac ggagtccgcc gtgagctgcg agaa                               154

SEQ ID NO: 170         moltype = DNA   length = 149
FEATURE                Location/Qualifiers
misc_feature           1..149
                       note = Description of Artificial Sequence: Synthetic
                        polynucleotide
source                 1..149
                       mol_type = other DNA
                       organism = synthetic construct
SEQUENCE: 170
gctattctcg cagctcacca gttttagagc tagaaatagc aagttaaaat aaggctagtc    60
cgttatcaac ttgaaaaagt ggcaccgagt cggtgcgacg agcgcggcga tatcatcatc   120
catgggacgg agtccgtgag ctgcgagaa                                     149

SEQ ID NO: 171         moltype = DNA   length = 144
FEATURE                Location/Qualifiers
misc_feature           1..144
                       note = Description of Artificial Sequence: Synthetic
                        polynucleotide
source                 1..144
                       mol_type = other DNA
                       organism = synthetic construct
SEQUENCE: 171
gctattctcg cagctcacca gttttagagc tagaaatagc aagttaaaat aaggctagtc    60
cgttatcaac ttgaaaaagt ggcaccgagt cggtgcgacg agcgcggcga tatcatcatc   120
catggcggag ttgagctgcg agaa                                          144

SEQ ID NO: 172         moltype = DNA   length = 182
FEATURE                Location/Qualifiers
misc_feature           1..182
                       note = Description of Artificial Sequence: Synthetic
                        polynucleotide
source                 1..182
                       mol_type = other DNA
                       organism = synthetic construct
SEQUENCE: 172
gaagccggcc ttgcacatgc gttttagagc tagaaatagc aagttaaaat aaggctagtc    60
cgttatcaac ttgaaaaagt ggcaccgagt cggtgctcga cgacgagcgc ggcgatatca   120
tcatccatgg taccgttcgt atagcataca ttatacgaag ttattgagct gcgagaatag   180
cc                                                                  182

SEQ ID NO: 173         moltype = DNA   length = 177
FEATURE                Location/Qualifiers
misc_feature           1..177
                       note = Description of Artificial Sequence: Synthetic
                        polynucleotide
source                 1..177
                       mol_type = other DNA
                       organism = synthetic construct
SEQUENCE: 173
gaagccggcc ttgcacatgc gttttagagc tagaaatagc aagttaaaat aaggctagtc    60
cgttatcaac ttgaaaaagt ggcaccgagt cggtgcgacg agcgcggcga tatcatcatc   120
catggtaccg ttcgtatagc atacattata cgaagttatt gagctgcgag aatagcc      177

SEQ ID NO: 174         moltype = DNA   length = 177
FEATURE                Location/Qualifiers
misc_feature           1..177
                       note = Description of Artificial Sequence: Synthetic
                        polynucleotide
source                 1..177
                       mol_type = other DNA
                       organism = synthetic construct
SEQUENCE: 174
gaagccggcc ttgcacatgc gttttagagc tagaaatagc aagttaaaat aaggctagtc    60
cgttatcaac ttgaaaaagt ggcaccgagt cggtgctcga cgacgagcgc ggcgatatca   120
tcatccatgg taccgttcgt atagcataca ttatacgaag ttattgagct gcgagaa      177
```

```
SEQ ID NO: 175          moltype = DNA  length = 159
FEATURE                 Location/Qualifiers
misc_feature            1..159
                        note = Description of Artificial Sequence: Synthetic
                         polynucleotide
source                  1..159
                        mol_type = other DNA
                        organism = synthetic construct
SEQUENCE: 175
gaagccggcc ttgcacatgc gttttagagc tagaaatagc aagttaaaat aaggctagtc    60
cgttatcaac ttgaaaaagt ggcaccgagt cggtgcatat catcatccat ggtaccgttc   120
gtatagcata cattatacga agttattgag ctgcgagaa                          159

SEQ ID NO: 176          moltype = DNA  length = 96
FEATURE                 Location/Qualifiers
misc_feature            1..96
                        note = Description of Artificial Sequence: Synthetic
                         oligonucleotide
source                  1..96
                        mol_type = other DNA
                        organism = synthetic construct
SEQUENCE: 176
ccccacgatg gagggaaga gttttagagc tagaaatagc aagttaaaat aaggctagtc     60
cgttatcaac ttgaaaaagt ggcaccgagt cggtgc                              96

SEQ ID NO: 177          moltype = DNA  length = 96
FEATURE                 Location/Qualifiers
misc_feature            1..96
                        note = Description of Artificial Sequence: Synthetic
                         oligonucleotide
source                  1..96
                        mol_type = other DNA
                        organism = synthetic construct
SEQUENCE: 177
ccttctcctg gagccgcgac gttttagagc tagaaatagc aagttaaaat aaggctagtc    60
cgttatcaac ttgaaaaagt ggcaccgagt cggtgc                              96

SEQ ID NO: 178          moltype = DNA  length = 52
FEATURE                 Location/Qualifiers
misc_feature            1..52
                        note = Description of Artificial Sequence: Synthetic
                         oligonucleotide
source                  1..52
                        mol_type = other DNA
                        organism = synthetic construct
SEQUENCE: 178
gtggtttgtc tggtcaacca ccgcggtctc agtggtgtac ggtacaaacc ca            52

SEQ ID NO: 179          moltype = DNA  length = 52
FEATURE                 Location/Qualifiers
misc_feature            1..52
                        note = Description of Artificial Sequence: Synthetic
                         oligonucleotide
source                  1..52
                        mol_type = other DNA
                        organism = synthetic construct
SEQUENCE: 179
tgggtttgta ccgtacacca ctgagaccgc ggtggttgac cagacaaacc ac            52

SEQ ID NO: 180          moltype = DNA  length = 52
FEATURE                 Location/Qualifiers
misc_feature            1..52
                        note = Description of Artificial Sequence: Synthetic
                         oligonucleotide
source                  1..52
                        mol_type = other DNA
                        organism = synthetic construct
SEQUENCE: 180
gtggtttgtc tggtcaacca ccgcgcgctc agtggtgtac ggtacaaacc ca            52

SEQ ID NO: 181          moltype = DNA  length = 52
FEATURE                 Location/Qualifiers
misc_feature            1..52
                        note = Description of Artificial Sequence: Synthetic
                         oligonucleotide
source                  1..52
                        mol_type = other DNA
                        organism = synthetic construct
```

```
SEQUENCE: 181
tgggtttgta ccgtacacca ctgagcgcgc ggtggttgac cagacaaacc ac                52

SEQ ID NO: 182           moltype = DNA  length = 52
FEATURE                  Location/Qualifiers
misc_feature             1..52
                         note = Description of Artificial Sequence: Synthetic
                         oligonucleotide
source                   1..52
                         mol_type = other DNA
                         organism = synthetic construct
SEQUENCE: 182
gtggtttgtc tggtcaacca ccgcggcctc agtggtgtac ggtacaaacc ca                52

SEQ ID NO: 183           moltype = DNA  length = 52
FEATURE                  Location/Qualifiers
misc_feature             1..52
                         note = Description of Artificial Sequence: Synthetic
                         oligonucleotide
source                   1..52
                         mol_type = other DNA
                         organism = synthetic construct
SEQUENCE: 183
tgggtttgta ccgtacacca ctgaggccgc ggtggttgac cagacaaacc ac                52

SEQ ID NO: 184           moltype = DNA  length = 52
FEATURE                  Location/Qualifiers
misc_feature             1..52
                         note = Description of Artificial Sequence: Synthetic
                         oligonucleotide
source                   1..52
                         mol_type = other DNA
                         organism = synthetic construct
SEQUENCE: 184
gtggtttgtc tggtcaacca ccgcgatctc agtggtgtac ggtacaaacc ca                52

SEQ ID NO: 185           moltype = DNA  length = 52
FEATURE                  Location/Qualifiers
misc_feature             1..52
                         note = Description of Artificial Sequence: Synthetic
                         oligonucleotide
source                   1..52
                         mol_type = other DNA
                         organism = synthetic construct
SEQUENCE: 185
tgggtttgta ccgtacacca ctgagatcgc ggtggttgac cagacaaacc ac                52

SEQ ID NO: 186           moltype = DNA  length = 52
FEATURE                  Location/Qualifiers
misc_feature             1..52
                         note = Description of Artificial Sequence: Synthetic
                         oligonucleotide
source                   1..52
                         mol_type = other DNA
                         organism = synthetic construct
SEQUENCE: 186
gtggtttgtc tggtcaacca ccgcgtactc agtggtgtac ggtacaaacc ca                52

SEQ ID NO: 187           moltype = DNA  length = 52
FEATURE                  Location/Qualifiers
misc_feature             1..52
                         note = Description of Artificial Sequence: Synthetic
                         oligonucleotide
source                   1..52
                         mol_type = other DNA
                         organism = synthetic construct
SEQUENCE: 187
tgggtttgta ccgtacacca ctgagtacgc ggtggttgac cagacaaacc ac                52

SEQ ID NO: 188           moltype = DNA  length = 52
FEATURE                  Location/Qualifiers
misc_feature             1..52
                         note = Description of Artificial Sequence: Synthetic
                         oligonucleotide
source                   1..52
                         mol_type = other DNA
                         organism = synthetic construct
SEQUENCE: 188
gtggtttgtc tggtcaacca ccgcgggctc agtggtgtac ggtacaaacc ca                52
```

```
SEQ ID NO: 189         moltype = DNA  length = 52
FEATURE                Location/Qualifiers
misc_feature           1..52
                       note = Description of Artificial Sequence: Synthetic
                       oligonucleotide
source                 1..52
                       mol_type = other DNA
                       organism = synthetic construct
SEQUENCE: 189
tgggtttgta ccgtacacca ctgagcccgc ggtggttgac cagacaaacc ac         52

SEQ ID NO: 190         moltype = DNA  length = 52
FEATURE                Location/Qualifiers
misc_feature           1..52
                       note = Description of Artificial Sequence: Synthetic
                       oligonucleotide
source                 1..52
                       mol_type = other DNA
                       organism = synthetic construct
SEQUENCE: 190
gtggtttgtc tggtcaacca ccgcgttctc agtggtgtac ggtacaaacc ca         52

SEQ ID NO: 191         moltype = DNA  length = 52
FEATURE                Location/Qualifiers
misc_feature           1..52
                       note = Description of Artificial Sequence: Synthetic
                       oligonucleotide
source                 1..52
                       mol_type = other DNA
                       organism = synthetic construct
SEQUENCE: 191
tgggtttgta ccgtacacca ctgagaacgc ggtggttgac cagacaaacc ac         52

SEQ ID NO: 192         moltype = DNA  length = 52
FEATURE                Location/Qualifiers
misc_feature           1..52
                       note = Description of Artificial Sequence: Synthetic
                       oligonucleotide
source                 1..52
                       mol_type = other DNA
                       organism = synthetic construct
SEQUENCE: 192
gtggtttgtc tggtcaacca ccgcggactc agtggtgtac ggtacaaacc ca         52

SEQ ID NO: 193         moltype = DNA  length = 52
FEATURE                Location/Qualifiers
misc_feature           1..52
                       note = Description of Artificial Sequence: Synthetic
                       oligonucleotide
source                 1..52
                       mol_type = other DNA
                       organism = synthetic construct
SEQUENCE: 193
tgggtttgta ccgtacacca ctgagtccgc ggtggttgac cagacaaacc ac         52

SEQ ID NO: 194         moltype = DNA  length = 52
FEATURE                Location/Qualifiers
misc_feature           1..52
                       note = Description of Artificial Sequence: Synthetic
                       oligonucleotide
source                 1..52
                       mol_type = other DNA
                       organism = synthetic construct
SEQUENCE: 194
gtggtttgtc tggtcaacca ccgcgagctc agtggtgtac ggtacaaacc ca         52

SEQ ID NO: 195         moltype = DNA  length = 52
FEATURE                Location/Qualifiers
misc_feature           1..52
                       note = Description of Artificial Sequence: Synthetic
                       oligonucleotide
source                 1..52
                       mol_type = other DNA
                       organism = synthetic construct
SEQUENCE: 195
tgggtttgta ccgtacacca ctgagctcgc ggtggttgac cagacaaacc ac         52
```

```
SEQ ID NO: 196         moltype = DNA   length = 52
FEATURE                Location/Qualifiers
misc_feature           1..52
                       note = Description of Artificial Sequence: Synthetic
                         oligonucleotide
source                 1..52
                       mol_type = other DNA
                       organism = synthetic construct
SEQUENCE: 196
gtggtttgtc tggtcaacca ccgcgccctc agtggtgtac ggtacaaacc ca           52

SEQ ID NO: 197         moltype = DNA   length = 52
FEATURE                Location/Qualifiers
misc_feature           1..52
                       note = Description of Artificial Sequence: Synthetic
                         oligonucleotide
source                 1..52
                       mol_type = other DNA
                       organism = synthetic construct
SEQUENCE: 197
tgggtttgta ccgtacacca ctgagggcgc ggtggttgac cagacaaacc ac           52

SEQ ID NO: 198         moltype = DNA   length = 52
FEATURE                Location/Qualifiers
misc_feature           1..52
                       note = Description of Artificial Sequence: Synthetic
                         oligonucleotide
source                 1..52
                       mol_type = other DNA
                       organism = synthetic construct
SEQUENCE: 198
gtggtttgtc tggtcaacca ccgcgtcctc agtggtgtac ggtacaaacc ca           52

SEQ ID NO: 199         moltype = DNA   length = 52
FEATURE                Location/Qualifiers
misc_feature           1..52
                       note = Description of Artificial Sequence: Synthetic
                         oligonucleotide
source                 1..52
                       mol_type = other DNA
                       organism = synthetic construct
SEQUENCE: 199
tgggtttgta ccgtacacca ctgaggacgc ggtggttgac cagacaaacc ac           52

SEQ ID NO: 200         moltype = DNA   length = 52
FEATURE                Location/Qualifiers
misc_feature           1..52
                       note = Description of Artificial Sequence: Synthetic
                         oligonucleotide
source                 1..52
                       mol_type = other DNA
                       organism = synthetic construct
SEQUENCE: 200
gtggtttgtc tggtcaacca ccgcgctctc agtggtgtac ggtacaaacc ca           52

SEQ ID NO: 201         moltype = DNA   length = 52
FEATURE                Location/Qualifiers
misc_feature           1..52
                       note = Description of Artificial Sequence: Synthetic
                         oligonucleotide
source                 1..52
                       mol_type = other DNA
                       organism = synthetic construct
SEQUENCE: 201
tgggtttgta ccgtacacca ctgagagcgc ggtggttgac cagacaaacc ac           52

SEQ ID NO: 202         moltype = DNA   length = 52
FEATURE                Location/Qualifiers
misc_feature           1..52
                       note = Description of Artificial Sequence: Synthetic
                         oligonucleotide
source                 1..52
                       mol_type = other DNA
                       organism = synthetic construct
SEQUENCE: 202
gtggtttgtc tggtcaacca ccgcgaactc agtggtgtac ggtacaaacc ca           52
```

```
SEQ ID NO: 203          moltype = DNA  length = 52
FEATURE                 Location/Qualifiers
misc_feature            1..52
                        note = Description of Artificial Sequence: Synthetic
                          oligonucleotide
source                  1..52
                        mol_type = other DNA
                        organism = synthetic construct
SEQUENCE: 203
tgggtttgta ccgtacacca ctgagttcgc ggtggttgac cagacaaacc ac          52

SEQ ID NO: 204          moltype = DNA  length = 52
FEATURE                 Location/Qualifiers
misc_feature            1..52
                        note = Description of Artificial Sequence: Synthetic
                          oligonucleotide
source                  1..52
                        mol_type = other DNA
                        organism = synthetic construct
SEQUENCE: 204
gtggtttgtc tggtcaacca ccgcgcactc agtggtgtac ggtacaaacc ca          52

SEQ ID NO: 205          moltype = DNA  length = 52
FEATURE                 Location/Qualifiers
misc_feature            1..52
                        note = Description of Artificial Sequence: Synthetic
                          oligonucleotide
source                  1..52
                        mol_type = other DNA
                        organism = synthetic construct
SEQUENCE: 205
tgggtttgta ccgtacacca ctgagtgcgc ggtggttgac cagacaaacc ac          52

SEQ ID NO: 206          moltype = DNA  length = 52
FEATURE                 Location/Qualifiers
misc_feature            1..52
                        note = Description of Artificial Sequence: Synthetic
                          oligonucleotide
source                  1..52
                        mol_type = other DNA
                        organism = synthetic construct
SEQUENCE: 206
gtggtttgtc tggtcaacca ccgcgacctc agtggtgtac ggtacaaacc ca          52

SEQ ID NO: 207          moltype = DNA  length = 52
FEATURE                 Location/Qualifiers
misc_feature            1..52
                        note = Description of Artificial Sequence: Synthetic
                          oligonucleotide
source                  1..52
                        mol_type = other DNA
                        organism = synthetic construct
SEQUENCE: 207
tgggtttgta ccgtacacca ctgaggtcgc ggtggttgac cagacaaacc ac          52

SEQ ID NO: 208          moltype = DNA  length = 52
FEATURE                 Location/Qualifiers
misc_feature            1..52
                        note = Description of Artificial Sequence: Synthetic
                          oligonucleotide
source                  1..52
                        mol_type = other DNA
                        organism = synthetic construct
SEQUENCE: 208
gtggtttgtc tggtcaacca ccgcgtgctc agtggtgtac ggtacaaacc ca          52

SEQ ID NO: 209          moltype = DNA  length = 52
FEATURE                 Location/Qualifiers
misc_feature            1..52
                        note = Description of Artificial Sequence: Synthetic
                          oligonucleotide
source                  1..52
                        mol_type = other DNA
                        organism = synthetic construct
SEQUENCE: 209
tgggtttgta ccgtacacca ctgagcacgc ggtggttgac cagacaaacc ac          52
```

```
SEQ ID NO: 210            moltype = DNA  length = 46
FEATURE                   Location/Qualifiers
misc_feature              1..46
                          note = Description of Artificial Sequence: Synthetic
                          oligonucleotide
source                    1..46
                          mol_type = other DNA
                          organism = synthetic construct
SEQUENCE: 210
ggccggcttg tcgacgacgg cggtctccgt cgtcaggatc atccgg            46

SEQ ID NO: 211            moltype = DNA  length = 46
FEATURE                   Location/Qualifiers
misc_feature              1..46
                          note = Description of Artificial Sequence: Synthetic
                          oligonucleotide
source                    1..46
                          mol_type = other DNA
                          organism = synthetic construct
SEQUENCE: 211
ccggatgatc ctgacgacgg agaccgccgt cgtcgacaag ccggcc            46

SEQ ID NO: 212            moltype = DNA  length = 46
FEATURE                   Location/Qualifiers
misc_feature              1..46
                          note = Description of Artificial Sequence: Synthetic
                          oligonucleotide
source                    1..46
                          mol_type = other DNA
                          organism = synthetic construct
SEQUENCE: 212
ggccggcttg tcgacgacgg cgaactccgt cgtcaggatc atccgg            46

SEQ ID NO: 213            moltype = DNA  length = 46
FEATURE                   Location/Qualifiers
misc_feature              1..46
                          note = Description of Artificial Sequence: Synthetic
                          oligonucleotide
source                    1..46
                          mol_type = other DNA
                          organism = synthetic construct
SEQUENCE: 213
ccggatgatc ctgacgacgg agttcgccgt cgtcgacaag ccggcc            46

SEQ ID NO: 214            moltype = DNA  length = 46
FEATURE                   Location/Qualifiers
misc_feature              1..46
                          note = Description of Artificial Sequence: Synthetic
                          oligonucleotide
source                    1..46
                          mol_type = other DNA
                          organism = synthetic construct
SEQUENCE: 214
ggccggcttg tcgacgacgg cggactccgt cgtcaggatc atccgg            46

SEQ ID NO: 215            moltype = DNA  length = 46
FEATURE                   Location/Qualifiers
misc_feature              1..46
                          note = Description of Artificial Sequence: Synthetic
                          oligonucleotide
source                    1..46
                          mol_type = other DNA
                          organism = synthetic construct
SEQUENCE: 215
ccggatgatc ctgacgacgg agtccgccgt cgtcgacaag ccggcc            46

SEQ ID NO: 216            moltype = DNA  length = 46
FEATURE                   Location/Qualifiers
misc_feature              1..46
                          note = Description of Artificial Sequence: Synthetic
                          oligonucleotide
source                    1..46
                          mol_type = other DNA
                          organism = synthetic construct
SEQUENCE: 216
ggccggcttg tcgacgacgg cgcactccgt cgtcaggatc atccgg            46
```

```
SEQ ID NO: 217         moltype = DNA   length = 46
FEATURE                Location/Qualifiers
misc_feature           1..46
                       note = Description of Artificial Sequence: Synthetic
                         oligonucleotide
source                 1..46
                       mol_type = other DNA
                       organism = synthetic construct
SEQUENCE: 217
ccggatgatc ctgacgacgg agtgcgccgt cgtcgacaag ccggcc            46

SEQ ID NO: 218         moltype = DNA   length = 46
FEATURE                Location/Qualifiers
misc_feature           1..46
                       note = Description of Artificial Sequence: Synthetic
                         oligonucleotide
source                 1..46
                       mol_type = other DNA
                       organism = synthetic construct
SEQUENCE: 218
ggccggcttg tcgacgacgg cgtactccgt cgtcaggatc atccgg            46

SEQ ID NO: 219         moltype = DNA   length = 46
FEATURE                Location/Qualifiers
misc_feature           1..46
                       note = Description of Artificial Sequence: Synthetic
                         oligonucleotide
source                 1..46
                       mol_type = other DNA
                       organism = synthetic construct
SEQUENCE: 219
ccggatgatc ctgacgacgg agtacgccgt cgtcgacaag ccggcc            46

SEQ ID NO: 220         moltype = DNA   length = 46
FEATURE                Location/Qualifiers
misc_feature           1..46
                       note = Description of Artificial Sequence: Synthetic
                         oligonucleotide
source                 1..46
                       mol_type = other DNA
                       organism = synthetic construct
SEQUENCE: 220
ggccggcttg tcgacgacgg cgagctccgt cgtcaggatc atccgg            46

SEQ ID NO: 221         moltype = DNA   length = 46
FEATURE                Location/Qualifiers
misc_feature           1..46
                       note = Description of Artificial Sequence: Synthetic
                         oligonucleotide
source                 1..46
                       mol_type = other DNA
                       organism = synthetic construct
SEQUENCE: 221
ccggatgatc ctgacgacgg agctcgccgt cgtcgacaag ccggcc            46

SEQ ID NO: 222         moltype = DNA   length = 46
FEATURE                Location/Qualifiers
misc_feature           1..46
                       note = Description of Artificial Sequence: Synthetic
                         oligonucleotide
source                 1..46
                       mol_type = other DNA
                       organism = synthetic construct
SEQUENCE: 222
ggccggcttg tcgacgacgg cgggctccgt cgtcaggatc atccgg            46

SEQ ID NO: 223         moltype = DNA   length = 46
FEATURE                Location/Qualifiers
misc_feature           1..46
                       note = Description of Artificial Sequence: Synthetic
                         oligonucleotide
source                 1..46
                       mol_type = other DNA
                       organism = synthetic construct
SEQUENCE: 223
ccggatgatc ctgacgacgg agcccgccgt cgtcgacaag ccggcc            46
```

```
SEQ ID NO: 224          moltype = DNA   length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 224
ggccggcttg tcgacgacgg cgcgctccgt cgtcaggatc atccgg              46

SEQ ID NO: 225          moltype = DNA   length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 225
ccggatgatc ctgacgacgg agcgcgccgt cgtcgacaag ccggcc              46

SEQ ID NO: 226          moltype = DNA   length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 226
ggccggcttg tcgacgacgg cgtgctccgt cgtcaggatc atccgg              46

SEQ ID NO: 227          moltype = DNA   length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 227
ccggatgatc ctgacgacgg agcacgccgt cgtcgacaag ccggcc              46

SEQ ID NO: 228          moltype = DNA   length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 228
ggccggcttg tcgacgacgg cgacctccgt cgtcaggatc atccgg              46

SEQ ID NO: 229          moltype = DNA   length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 229
ccggatgatc ctgacgacgg aggtcgccgt cgtcgacaag ccggcc              46

SEQ ID NO: 230          moltype = DNA   length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 230
ggccggcttg tcgacgacgg cggcctccgt cgtcaggatc atccgg              46
```

```
SEQ ID NO: 231          moltype = DNA  length = 46
FEATURE                 Location/Qualifiers
misc_feature            1..46
                        note = Description of Artificial Sequence: Synthetic
                         oligonucleotide
source                  1..46
                        mol_type = other DNA
                        organism = synthetic construct
SEQUENCE: 231
ccggatgatc ctgacgacgg aggccgccgt cgtcgacaag ccggcc                          46

SEQ ID NO: 232          moltype = DNA  length = 46
FEATURE                 Location/Qualifiers
misc_feature            1..46
                        note = Description of Artificial Sequence: Synthetic
                         oligonucleotide
source                  1..46
                        mol_type = other DNA
                        organism = synthetic construct
SEQUENCE: 232
ggccggcttg tcgacgacgg cgccctccgt cgtcaggatc atccgg                          46

SEQ ID NO: 233          moltype = DNA  length = 46
FEATURE                 Location/Qualifiers
misc_feature            1..46
                        note = Description of Artificial Sequence: Synthetic
                         oligonucleotide
source                  1..46
                        mol_type = other DNA
                        organism = synthetic construct
SEQUENCE: 233
ccggatgatc ctgacgacgg agggcgccgt cgtcgacaag ccggcc                          46

SEQ ID NO: 234          moltype = DNA  length = 46
FEATURE                 Location/Qualifiers
misc_feature            1..46
                        note = Description of Artificial Sequence: Synthetic
                         oligonucleotide
source                  1..46
                        mol_type = other DNA
                        organism = synthetic construct
SEQUENCE: 234
ggccggcttg tcgacgacgg cgtcctccgt cgtcaggatc atccgg                          46

SEQ ID NO: 235          moltype = DNA  length = 46
FEATURE                 Location/Qualifiers
misc_feature            1..46
                        note = Description of Artificial Sequence: Synthetic
                         oligonucleotide
source                  1..46
                        mol_type = other DNA
                        organism = synthetic construct
SEQUENCE: 235
ccggatgatc ctgacgacgg aggacgccgt cgtcgacaag ccggcc                          46

SEQ ID NO: 236          moltype = DNA  length = 46
FEATURE                 Location/Qualifiers
misc_feature            1..46
                        note = Description of Artificial Sequence: Synthetic
                         oligonucleotide
source                  1..46
                        mol_type = other DNA
                        organism = synthetic construct
SEQUENCE: 236
ggccggcttg tcgacgacgg cgatctccgt cgtcaggatc atccgg                          46

SEQ ID NO: 237          moltype = DNA  length = 46
FEATURE                 Location/Qualifiers
misc_feature            1..46
                        note = Description of Artificial Sequence: Synthetic
                         oligonucleotide
source                  1..46
                        mol_type = other DNA
                        organism = synthetic construct
SEQUENCE: 237
ccggatgatc ctgacgacgg agatcgccgt cgtcgacaag ccggcc                          46
```

```
SEQ ID NO: 238         moltype = DNA  length = 46
FEATURE                Location/Qualifiers
misc_feature           1..46
                       note = Description of Artificial Sequence: Synthetic
                       oligonucleotide
source                 1..46
                       mol_type = other DNA
                       organism = synthetic construct
SEQUENCE: 238
ggccggcttg tcgacgacgg cgctctccgt cgtcaggatc atccgg                46

SEQ ID NO: 239         moltype = DNA  length = 46
FEATURE                Location/Qualifiers
misc_feature           1..46
                       note = Description of Artificial Sequence: Synthetic
                       oligonucleotide
source                 1..46
                       mol_type = other DNA
                       organism = synthetic construct
SEQUENCE: 239
ccggatgatc ctgacgacgg agagcgccgt cgtcgacaag ccggcc                46

SEQ ID NO: 240         moltype = DNA  length = 46
FEATURE                Location/Qualifiers
misc_feature           1..46
                       note = Description of Artificial Sequence: Synthetic
                       oligonucleotide
source                 1..46
                       mol_type = other DNA
                       organism = synthetic construct
SEQUENCE: 240
ggccggcttg tcgacgacgg cgttctccgt cgtcaggatc atccgg                46

SEQ ID NO: 241         moltype = DNA  length = 46
FEATURE                Location/Qualifiers
misc_feature           1..46
                       note = Description of Artificial Sequence: Synthetic
                       oligonucleotide
source                 1..46
                       mol_type = other DNA
                       organism = synthetic construct
SEQUENCE: 241
ccggatgatc ctgacgacgg agaacgccgt cgtcgacaag ccggcc                46

SEQ ID NO: 242         moltype = DNA  length = 38
FEATURE                Location/Qualifiers
misc_feature           1..38
                       note = Description of Artificial Sequence: Synthetic
                       oligonucleotide
source                 1..38
                       mol_type = other DNA
                       organism = synthetic construct
SEQUENCE: 242
ggcttgtcga cgacggcggt ctccgtcgtc aggatcat                         38

SEQ ID NO: 243         moltype = DNA  length = 38
FEATURE                Location/Qualifiers
misc_feature           1..38
                       note = Description of Artificial Sequence: Synthetic
                       oligonucleotide
source                 1..38
                       mol_type = other DNA
                       organism = synthetic construct
SEQUENCE: 243
atgatcctga cgacggagac cgccgtcgtc gacaagcc                         38

SEQ ID NO: 244         moltype = DNA  length = 38
FEATURE                Location/Qualifiers
misc_feature           1..38
                       note = Description of Artificial Sequence: Synthetic
                       oligonucleotide
source                 1..38
                       mol_type = other DNA
                       organism = synthetic construct
SEQUENCE: 244
ggcttgtcga cgacggcgaa ctccgtcgtc aggatcat                         38

SEQ ID NO: 245         moltype = DNA  length = 38
```

```
FEATURE                 Location/Qualifiers
misc_feature            1..38
                        note = Description of Artificial Sequence: Synthetic
                         oligonucleotide
source                  1..38
                        mol_type = other DNA
                        organism = synthetic construct
SEQUENCE: 245
atgatcctga cgacggagtt cgccgtcgtc gacaagcc                                 38

SEQ ID NO: 246          moltype = DNA  length = 38
FEATURE                 Location/Qualifiers
misc_feature            1..38
                        note = Description of Artificial Sequence: Synthetic
                         oligonucleotide
source                  1..38
                        mol_type = other DNA
                        organism = synthetic construct
SEQUENCE: 246
ggcttgtcga cgacggcgga ctccgtcgtc aggatcat                                 38

SEQ ID NO: 247          moltype = DNA  length = 38
FEATURE                 Location/Qualifiers
misc_feature            1..38
                        note = Description of Artificial Sequence: Synthetic
                         oligonucleotide
source                  1..38
                        mol_type = other DNA
                        organism = synthetic construct
SEQUENCE: 247
atgatcctga cgacggagtc cgccgtcgtc gacaagcc                                 38

SEQ ID NO: 248          moltype = DNA  length = 38
FEATURE                 Location/Qualifiers
misc_feature            1..38
                        note = Description of Artificial Sequence: Synthetic
                         oligonucleotide
source                  1..38
                        mol_type = other DNA
                        organism = synthetic construct
SEQUENCE: 248
ggcttgtcga cgacggcgca ctccgtcgtc aggatcat                                 38

SEQ ID NO: 249          moltype = DNA  length = 38
FEATURE                 Location/Qualifiers
misc_feature            1..38
                        note = Description of Artificial Sequence: Synthetic
                         oligonucleotide
source                  1..38
                        mol_type = other DNA
                        organism = synthetic construct
SEQUENCE: 249
atgatcctga cgacggagtg cgccgtcgtc gacaagcc                                 38

SEQ ID NO: 250          moltype = DNA  length = 38
FEATURE                 Location/Qualifiers
misc_feature            1..38
                        note = Description of Artificial Sequence: Synthetic
                         oligonucleotide
source                  1..38
                        mol_type = other DNA
                        organism = synthetic construct
SEQUENCE: 250
ggcttgtcga cgacggcgta ctccgtcgtc aggatcat                                 38

SEQ ID NO: 251          moltype = DNA  length = 38
FEATURE                 Location/Qualifiers
misc_feature            1..38
                        note = Description of Artificial Sequence: Synthetic
                         oligonucleotide
source                  1..38
                        mol_type = other DNA
                        organism = synthetic construct
SEQUENCE: 251
atgatcctga cgacggagta cgccgtcgtc gacaagcc                                 38

SEQ ID NO: 252          moltype = DNA  length = 38
FEATURE                 Location/Qualifiers
misc_feature            1..38
```

```
                    note = Description of Artificial Sequence: Synthetic
                          oligonucleotide
source              1..38
                    mol_type = other DNA
                    organism = synthetic construct
SEQUENCE: 252
ggcttgtcga cgacggcgag ctccgtcgtc aggatcat                              38

SEQ ID NO: 253      moltype = DNA  length = 38
FEATURE             Location/Qualifiers
misc_feature        1..38
                    note = Description of Artificial Sequence: Synthetic
                          oligonucleotide
source              1..38
                    mol_type = other DNA
                    organism = synthetic construct
SEQUENCE: 253
atgatcctga cgacggagct cgccgtcgtc gacaagcc                              38

SEQ ID NO: 254      moltype = DNA  length = 38
FEATURE             Location/Qualifiers
misc_feature        1..38
                    note = Description of Artificial Sequence: Synthetic
                          oligonucleotide
source              1..38
                    mol_type = other DNA
                    organism = synthetic construct
SEQUENCE: 254
ggcttgtcga cgacggcggg ctccgtcgtc aggatcat                              38

SEQ ID NO: 255      moltype = DNA  length = 38
FEATURE             Location/Qualifiers
misc_feature        1..38
                    note = Description of Artificial Sequence: Synthetic
                          oligonucleotide
source              1..38
                    mol_type = other DNA
                    organism = synthetic construct
SEQUENCE: 255
atgatcctga cgacggagcc cgccgtcgtc gacaagcc                              38

SEQ ID NO: 256      moltype = DNA  length = 38
FEATURE             Location/Qualifiers
misc_feature        1..38
                    note = Description of Artificial Sequence: Synthetic
                          oligonucleotide
source              1..38
                    mol_type = other DNA
                    organism = synthetic construct
SEQUENCE: 256
ggcttgtcga cgacggcgcg ctccgtcgtc aggatcat                              38

SEQ ID NO: 257      moltype = DNA  length = 38
FEATURE             Location/Qualifiers
misc_feature        1..38
                    note = Description of Artificial Sequence: Synthetic
                          oligonucleotide
source              1..38
                    mol_type = other DNA
                    organism = synthetic construct
SEQUENCE: 257
atgatcctga cgacggagcg cgccgtcgtc gacaagcc                              38

SEQ ID NO: 258      moltype = DNA  length = 38
FEATURE             Location/Qualifiers
misc_feature        1..38
                    note = Description of Artificial Sequence: Synthetic
                          oligonucleotide
source              1..38
                    mol_type = other DNA
                    organism = synthetic construct
SEQUENCE: 258
ggcttgtcga cgacggcgtg ctccgtcgtc aggatcat                              38

SEQ ID NO: 259      moltype = DNA  length = 38
FEATURE             Location/Qualifiers
misc_feature        1..38
                    note = Description of Artificial Sequence: Synthetic
                          oligonucleotide
```

```
source              1..38
                    mol_type = other DNA
                    organism = synthetic construct
SEQUENCE: 259
atgatcctga cgacggagca cgccgtcgtc gacaagcc                              38

SEQ ID NO: 260      moltype = DNA   length = 38
FEATURE             Location/Qualifiers
misc_feature        1..38
                    note = Description of Artificial Sequence: Synthetic
                    oligonucleotide
source              1..38
                    mol_type = other DNA
                    organism = synthetic construct
SEQUENCE: 260
ggcttgtcga cgacggcgac ctccgtcgtc aggatcat                              38

SEQ ID NO: 261      moltype = DNA   length = 38
FEATURE             Location/Qualifiers
misc_feature        1..38
                    note = Description of Artificial Sequence: Synthetic
                    oligonucleotide
source              1..38
                    mol_type = other DNA
                    organism = synthetic construct
SEQUENCE: 261
atgatcctga cgacggaggt cgccgtcgtc gacaagcc                              38

SEQ ID NO: 262      moltype = DNA   length = 38
FEATURE             Location/Qualifiers
misc_feature        1..38
                    note = Description of Artificial Sequence: Synthetic
                    oligonucleotide
source              1..38
                    mol_type = other DNA
                    organism = synthetic construct
SEQUENCE: 262
ggcttgtcga cgacggcggc ctccgtcgtc aggatcat                              38

SEQ ID NO: 263      moltype = DNA   length = 38
FEATURE             Location/Qualifiers
misc_feature        1..38
                    note = Description of Artificial Sequence: Synthetic
                    oligonucleotide
source              1..38
                    mol_type = other DNA
                    organism = synthetic construct
SEQUENCE: 263
atgatcctga cgacggaggc cgccgtcgtc gacaagcc                              38

SEQ ID NO: 264      moltype = DNA   length = 38
FEATURE             Location/Qualifiers
misc_feature        1..38
                    note = Description of Artificial Sequence: Synthetic
                    oligonucleotide
source              1..38
                    mol_type = other DNA
                    organism = synthetic construct
SEQUENCE: 264
ggcttgtcga cgacggcgcc ctccgtcgtc aggatcat                              38

SEQ ID NO: 265      moltype = DNA   length = 38
FEATURE             Location/Qualifiers
misc_feature        1..38
                    note = Description of Artificial Sequence: Synthetic
                    oligonucleotide
source              1..38
                    mol_type = other DNA
                    organism = synthetic construct
SEQUENCE: 265
atgatcctga cgacggaggg cgccgtcgtc gacaagcc                              38

SEQ ID NO: 266      moltype = DNA   length = 38
FEATURE             Location/Qualifiers
misc_feature        1..38
                    note = Description of Artificial Sequence: Synthetic
                    oligonucleotide
```

```
source                  1..38
                        mol_type = other DNA
                        organism = synthetic construct
SEQUENCE: 266
ggcttgtcga cgacggcgtc ctccgtcgtc aggatcat                              38

SEQ ID NO: 267          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 267
atgatcctga cgacggagga cgccgtcgtc gacaagcc                              38

SEQ ID NO: 268          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 268
ggcttgtcga cgacggcgat ctccgtcgtc aggatcat                              38

SEQ ID NO: 269          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 269
atgatcctga cgacggagat cgccgtcgtc gacaagcc                              38

SEQ ID NO: 270          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 270
ggcttgtcga cgacggcgct ctccgtcgtc aggatcat                              38

SEQ ID NO: 271          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 271
atgatcctga cgacggagag cgccgtcgtc gacaagcc                              38

SEQ ID NO: 272          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 272
ggcttgtcga cgacggcgtt ctccgtcgtc aggatcat                              38

SEQ ID NO: 273          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
```

```
                        organism = synthetic construct
SEQUENCE: 273
atgatcctga cgacggagaa cgccgtcgtc gacaagcc                          38

SEQ ID NO: 274          moltype = DNA   length = 34
FEATURE                 Location/Qualifiers
misc_feature            1..34
                        note = Description of Artificial Sequence: Synthetic
                        oligonucleotide
source                  1..34
                        mol_type = other DNA
                        organism = synthetic construct
SEQUENCE: 274
taccgttcgt ataatgtatg ctatacgaag ttat                              34

SEQ ID NO: 275          moltype = DNA   length = 34
FEATURE                 Location/Qualifiers
misc_feature            1..34
                        note = Description of Artificial Sequence: Synthetic
                        oligonucleotide
source                  1..34
                        mol_type = other DNA
                        organism = synthetic construct
SEQUENCE: 275
ataacttcgt atagcataca ttatacgaac ggta                              34

SEQ ID NO: 276          moltype = DNA   length = 34
FEATURE                 Location/Qualifiers
misc_feature            1..34
                        note = Description of Artificial Sequence: Synthetic
                        oligonucleotide
source                  1..34
                        mol_type = other DNA
                        organism = synthetic construct
SEQUENCE: 276
ataacttcgt ataatgtatg ctatacgaac ggta                              34

SEQ ID NO: 277          moltype = DNA   length = 34
FEATURE                 Location/Qualifiers
misc_feature            1..34
                        note = Description of Artificial Sequence: Synthetic
                        oligonucleotide
source                  1..34
                        mol_type = other DNA
                        organism = synthetic construct
SEQUENCE: 277
taccgttcgt atagcataca ttatacgaag ttat                              34

SEQ ID NO: 278          moltype = DNA   length = 27
FEATURE                 Location/Qualifiers
misc_feature            1..27
                        note = Description of Artificial Sequence: Synthetic
                        oligonucleotide
source                  1..27
                        mol_type = other DNA
                        organism = synthetic construct
SEQUENCE: 278
tttaccttga ttgagatgtt aattgtg                                      27

SEQ ID NO: 279          moltype = DNA   length = 27
FEATURE                 Location/Qualifiers
misc_feature            1..27
                        note = Description of Artificial Sequence: Synthetic
                        oligonucleotide
source                  1..27
                        mol_type = other DNA
                        organism = synthetic construct
SEQUENCE: 279
cacaattaac atctcaatca aggtaaa                                      27

SEQ ID NO: 280          moltype = DNA   length = 50
FEATURE                 Location/Qualifiers
misc_feature            1..50
                        note = Description of Artificial Sequence: Synthetic
                        oligonucleotide
source                  1..50
                        mol_type = other DNA
                        organism = synthetic construct
```

```
SEQUENCE: 280
gcgagttttt atttcgttta tttcaattaa ggtaactaaa aaactccttt           50

SEQ ID NO: 281          moltype = DNA   length = 50
FEATURE                 Location/Qualifiers
misc_feature            1..50
                        note = Description of Artificial Sequence: Synthetic
                        oligonucleotide
source                  1..50
                        mol_type = other DNA
                        organism = synthetic construct
SEQUENCE: 281
aaaggagttt tttagttacc ttaattgaaa taaacgaaat aaaaactcgc           50

SEQ ID NO: 282          moltype = DNA   length = 34
FEATURE                 Location/Qualifiers
misc_feature            1..34
                        note = Description of Artificial Sequence: Synthetic
                        oligonucleotide
source                  1..34
                        mol_type = other DNA
                        organism = synthetic construct
SEQUENCE: 282
ctggatcatc tggatcactt tcgtcaaaaa cctg                            34

SEQ ID NO: 283          moltype = DNA   length = 34
FEATURE                 Location/Qualifiers
misc_feature            1..34
                        note = Description of Artificial Sequence: Synthetic
                        oligonucleotide
source                  1..34
                        mol_type = other DNA
                        organism = synthetic construct
SEQUENCE: 283
caggtttttg acgaaagtga tccagatgat ccag                            34

SEQ ID NO: 284          moltype = DNA   length = 57
FEATURE                 Location/Qualifiers
misc_feature            1..57
                        note = Description of Artificial Sequence: Synthetic
                        oligonucleotide
source                  1..57
                        mol_type = other DNA
                        organism = synthetic construct
SEQUENCE: 284
ttcgggtgct gggttgttgt ctctggacag tgatccatgg gaaactactc agcacca   57

SEQ ID NO: 285          moltype = DNA   length = 57
FEATURE                 Location/Qualifiers
misc_feature            1..57
                        note = Description of Artificial Sequence: Synthetic
                        oligonucleotide
source                  1..57
                        mol_type = other DNA
                        organism = synthetic construct
SEQUENCE: 285
tggtgctgag tagtttccca tggatcactg tccagagaca caacccagc acccgaa    57

SEQ ID NO: 286          moltype = DNA   length = 24
FEATURE                 Location/Qualifiers
misc_feature            1..24
                        note = Description of Artificial Sequence: Synthetic
                        oligonucleotide
source                  1..24
                        mol_type = other DNA
                        organism = synthetic construct
SEQUENCE: 286
aaaagtgtgg gctgcaggat ctga                                       24

SEQ ID NO: 287          moltype = DNA   length = 22
FEATURE                 Location/Qualifiers
misc_feature            1..22
                        note = Description of Artificial Sequence: Synthetic
                        oligonucleotide
source                  1..22
                        mol_type = other DNA
                        organism = synthetic construct
SEQUENCE: 287
ggagctggca gctgtcaatg cc                                         22
```

| | |
|---|---|
| SEQ ID NO: 288 | moltype = DNA  length = 21 |
| FEATURE | Location/Qualifiers |
| misc_feature | 1..21 |
| | note = Description of Artificial Sequence: Synthetic oligonucleotide |
| source | 1..21 |
| | mol_type = other DNA |
| | organism = synthetic construct |
| SEQUENCE: 288 | |
| agtcaatgcc gctctcgtgg a | 21 |
| | |
| SEQ ID NO: 289 | moltype = DNA  length = 21 |
| FEATURE | Location/Qualifiers |
| misc_feature | 1..21 |
| | note = Description of Artificial Sequence: Synthetic oligonucleotide |
| source | 1..21 |
| | mol_type = other DNA |
| | organism = synthetic construct |
| SEQUENCE: 289 | |
| cagcgggctc agctgatagc a | 21 |
| | |
| SEQ ID NO: 290 | moltype = DNA  length = 21 |
| FEATURE | Location/Qualifiers |
| misc_feature | 1..21 |
| | note = Description of Artificial Sequence: Synthetic oligonucleotide |
| source | 1..21 |
| | mol_type = other DNA |
| | organism = synthetic construct |
| SEQUENCE: 290 | |
| cggatggcta accaagcggc c | 21 |
| | |
| SEQ ID NO: 291 | moltype = DNA  length = 17 |
| FEATURE | Location/Qualifiers |
| misc_feature | 1..17 |
| | note = Description of Artificial Sequence: Synthetic primer |
| source | 1..17 |
| | mol_type = other DNA |
| | organism = synthetic construct |
| SEQUENCE: 291 | |
| cccggcttcc tttgtcc | 17 |
| | |
| SEQ ID NO: 292 | moltype = DNA  length = 17 |
| FEATURE | Location/Qualifiers |
| misc_feature | 1..17 |
| | note = Description of Artificial Sequence: Synthetic primer |
| source | 1..17 |
| | mol_type = other DNA |
| | organism = synthetic construct |
| SEQUENCE: 292 | |
| gaactccacg ccgttca | 17 |
| | |
| SEQ ID NO: 293 | moltype = DNA  length = 17 |
| FEATURE | Location/Qualifiers |
| misc_feature | 1..17 |
| | note = Description of Artificial Sequence: Synthetic primer |
| source | 1..17 |
| | mol_type = other DNA |
| | organism = synthetic construct |
| SEQUENCE: 293 | |
| cccggcttcc tttgtcc | 17 |
| | |
| SEQ ID NO: 294 | moltype = DNA  length = 22 |
| FEATURE | Location/Qualifiers |
| misc_feature | 1..22 |
| | note = Description of Artificial Sequence: Synthetic primer |
| source | 1..22 |
| | mol_type = other DNA |
| | organism = synthetic construct |
| SEQUENCE: 294 | |
| aaccacaact agaatgcagt ga | 22 |
| | |
| SEQ ID NO: 295 | moltype = DNA  length = 17 |
| FEATURE | Location/Qualifiers |
| misc_feature | 1..17 |
| | note = Description of Artificial Sequence: Synthetic primer |

```
source                  1..17
                        mol_type = other DNA
                        organism = synthetic construct
SEQUENCE: 295
cccggcttcc tttgtcc                                                          17

SEQ ID NO: 296          moltype = DNA  length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 296
gaactccacg ccgttca                                                          17

SEQ ID NO: 297          moltype = DNA  length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 297
cccggcttcc tttgtcc                                                          17

SEQ ID NO: 298          moltype = DNA  length = 22
FEATURE                 Location/Qualifiers
misc_feature            1..22
                        note = Description of Artificial Sequence: Synthetic primer
source                  1..22
                        mol_type = other DNA
                        organism = synthetic construct
SEQUENCE: 298
aaccacaact agaatgcagt ga                                                    22

SEQ ID NO: 299          moltype = DNA  length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 299
cccggcttcc tttgtcc                                                          17

SEQ ID NO: 300          moltype = DNA  length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 300
gaactccacg ccgttca                                                          17

SEQ ID NO: 301          moltype = DNA  length = 21
FEATURE                 Location/Qualifiers
misc_feature            1..21
                        note = Description of Artificial Sequence: Synthetic primer
source                  1..21
                        mol_type = other DNA
                        organism = synthetic construct
SEQUENCE: 301
tccttatcac ggtcccgctc g                                                     21

SEQ ID NO: 302          moltype = DNA  length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 302
gaactccacg ccgttca                                                          17
```

```
SEQ ID NO: 303            moltype = DNA   length = 17
FEATURE                   Location/Qualifiers
misc_feature              1..17
                          note = Description of Artificial Sequence: Synthetic primer
source                    1..17
                          mol_type = other DNA
                          organism = synthetic construct
SEQUENCE: 303
cgtcgacaac ggtagtg                                                          17

SEQ ID NO: 304            moltype = DNA   length = 17
FEATURE                   Location/Qualifiers
misc_feature              1..17
                          note = Description of Artificial Sequence: Synthetic primer
source                    1..17
                          mol_type = other DNA
                          organism = synthetic construct
SEQUENCE: 304
gaactccacg ccgttca                                                          17

SEQ ID NO: 305            moltype = DNA   length = 18
FEATURE                   Location/Qualifiers
misc_feature              1..18
                          note = Description of Artificial Sequence: Synthetic primer
source                    1..18
                          mol_type = other DNA
                          organism = synthetic construct
SEQUENCE: 305
tcgcgtgatt ctcggaac                                                         18

SEQ ID NO: 306            moltype = DNA   length = 17
FEATURE                   Location/Qualifiers
misc_feature              1..17
                          note = Description of Artificial Sequence: Synthetic primer
source                    1..17
                          mol_type = other DNA
                          organism = synthetic construct
SEQUENCE: 306
gaactccacg ccgttca                                                          17

SEQ ID NO: 307            moltype = DNA   length = 20
FEATURE                   Location/Qualifiers
misc_feature              1..20
                          note = Description of Artificial Sequence: Synthetic primer
source                    1..20
                          mol_type = other DNA
                          organism = synthetic construct
SEQUENCE: 307
gggcggtaag tggttagttt                                                       20

SEQ ID NO: 308            moltype = DNA   length = 17
FEATURE                   Location/Qualifiers
misc_feature              1..17
                          note = Description of Artificial Sequence: Synthetic primer
source                    1..17
                          mol_type = other DNA
                          organism = synthetic construct
SEQUENCE: 308
gaactccacg ccgttca                                                          17

SEQ ID NO: 309            moltype = DNA   length = 17
FEATURE                   Location/Qualifiers
misc_feature              1..17
                          note = Description of Artificial Sequence: Synthetic primer
source                    1..17
                          mol_type = other DNA
                          organism = synthetic construct
SEQUENCE: 309
aagaggcgga gccagta                                                          17

SEQ ID NO: 310            moltype = DNA   length = 17
FEATURE                   Location/Qualifiers
misc_feature              1..17
                          note = Description of Artificial Sequence: Synthetic primer
source                    1..17
                          mol_type = other DNA
```

```
                        organism = synthetic construct
SEQUENCE: 310
gaactccacg ccgttca                                                  17

SEQ ID NO: 311          moltype = DNA   length = 19
FEATURE                 Location/Qualifiers
misc_feature            1..19
                        note = Description of Artificial Sequence: Synthetic primer
source                  1..19
                        mol_type = other DNA
                        organism = synthetic construct
SEQUENCE: 311
ctcccttctc ccggtgccc                                                19

SEQ ID NO: 312          moltype = DNA   length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 312
gaactccacg ccgttca                                                  17

SEQ ID NO: 313          moltype = DNA   length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 313
cccggcttcc tttgtcc                                                  17

SEQ ID NO: 314          moltype = DNA   length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 314
gaactccacg ccgttca                                                  17

SEQ ID NO: 315          moltype = DNA   length = 20
FEATURE                 Location/Qualifiers
misc_feature            1..20
                        note = Description of Artificial Sequence: Synthetic primer
source                  1..20
                        mol_type = other DNA
                        organism = synthetic construct
SEQUENCE: 315
gggcggtaag tggttagttt                                               20

SEQ ID NO: 316          moltype = DNA   length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 316
gaactccacg ccgttca                                                  17

SEQ ID NO: 317          moltype = DNA   length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 317
cgtcgacaac ggtagtg                                                  17

SEQ ID NO: 318          moltype = DNA   length = 17
FEATURE                 Location/Qualifiers
misc_feature            1..17
                        note = Description of Artificial Sequence: Synthetic primer
```

```
source                  1..17
                        mol_type = other DNA
                        organism = synthetic construct
SEQUENCE: 318
gaactccacg ccgttca                                                 17

SEQ ID NO: 319          moltype = DNA  length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 319
aagaggcgga gccagta                                                 17

SEQ ID NO: 320          moltype = DNA  length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 320
gaactccacg ccgttca                                                 17

SEQ ID NO: 321          moltype = DNA  length = 19
FEATURE                 Location/Qualifiers
misc_feature            1..19
                        note = Description of Artificial Sequence: Synthetic primer
source                  1..19
                        mol_type = other DNA
                        organism = synthetic construct
SEQUENCE: 321
ctcccttctc ccggtgccc                                               19

SEQ ID NO: 322          moltype = DNA  length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 322
gaactccacg ccgttca                                                 17

SEQ ID NO: 323          moltype = DNA  length = 21
FEATURE                 Location/Qualifiers
misc_feature            1..21
                        note = Description of Artificial Sequence: Synthetic primer
source                  1..21
                        mol_type = other DNA
                        organism = synthetic construct
SEQUENCE: 323
tccttatcac ggtcccgctc g                                            21

SEQ ID NO: 324          moltype = DNA  length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 324
gaactccacg ccgttca                                                 17

SEQ ID NO: 325          moltype = DNA  length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 325
cccggcttcc tttgtcc                                                 17
```

```
SEQ ID NO: 326          moltype = DNA   length = 18
FEATURE                 Location/Qualifiers
misc_feature            1..18
                        note = Description of Artificial Sequence: Synthetic primer
source                  1..18
                        mol_type = other DNA
                        organism = synthetic construct
SEQUENCE: 326
ggcctgccag caggagga                                                       18

SEQ ID NO: 327          moltype = DNA   length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 327
cccggcttcc tttgtcc                                                        17

SEQ ID NO: 328          moltype = DNA   length = 25
FEATURE                 Location/Qualifiers
misc_feature            1..25
                        note = Description of Artificial Sequence: Synthetic primer
source                  1..25
                        mol_type = other DNA
                        organism = synthetic construct
SEQUENCE: 328
ggtgtgcagt cacattggta aagcc                                               25

SEQ ID NO: 329          moltype = DNA   length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 329
cccggcttcc tttgtcc                                                        17

SEQ ID NO: 330          moltype = DNA   length = 22
FEATURE                 Location/Qualifiers
misc_feature            1..22
                        note = Description of Artificial Sequence: Synthetic primer
source                  1..22
                        mol_type = other DNA
                        organism = synthetic construct
SEQUENCE: 330
gatgggtcta gtccagctaa ag                                                  22

SEQ ID NO: 331          moltype = DNA   length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 331
cccggcttcc tttgtcc                                                        17

SEQ ID NO: 332          moltype = DNA   length = 18
FEATURE                 Location/Qualifiers
misc_feature            1..18
                        note = Description of Artificial Sequence: Synthetic primer
source                  1..18
                        mol_type = other DNA
                        organism = synthetic construct
SEQUENCE: 332
gagagacaag gctgcaca                                                       18

SEQ ID NO: 333          moltype = DNA   length = 26
FEATURE                 Location/Qualifiers
misc_feature            1..26
                        note = Description of Artificial Sequence: Synthetic primer
source                  1..26
                        mol_type = other DNA
                        organism = synthetic construct
```

| | | |
|---|---|---|
| SEQUENCE: 333 ccaggtgaga gtcagggtag tgttca | | 26 |
| SEQ ID NO: 334 FEATURE misc_feature source | moltype = DNA length = 17 Location/Qualifiers 1..17 note = Description of Artificial Sequence: Synthetic primer 1..17 mol_type = other DNA organism = synthetic construct | |
| SEQUENCE: 334 gaactccacg ccgttca | | 17 |
| SEQ ID NO: 335 FEATURE misc_feature source | moltype = DNA length = 23 Location/Qualifiers 1..23 note = Description of Artificial Sequence: Synthetic primer 1..23 mol_type = other DNA organism = synthetic construct | |
| SEQUENCE: 335 agggaccttt gcctgtgtga gtc | | 23 |
| SEQ ID NO: 336 FEATURE misc_feature source | moltype = DNA length = 17 Location/Qualifiers 1..17 note = Description of Artificial Sequence: Synthetic primer 1..17 mol_type = other DNA organism = synthetic construct | |
| SEQUENCE: 336 gaactccacg ccgttca | | 17 |
| SEQ ID NO: 337 FEATURE misc_feature source | moltype = DNA length = 21 Location/Qualifiers 1..21 note = Description of Artificial Sequence: Synthetic primer 1..21 mol_type = other DNA organism = synthetic construct | |
| SEQUENCE: 337 tcagctctgt gctgaggcga a | | 21 |
| SEQ ID NO: 338 FEATURE misc_feature source | moltype = DNA length = 17 Location/Qualifiers 1..17 note = Description of Artificial Sequence: Synthetic primer 1..17 mol_type = other DNA organism = synthetic construct | |
| SEQUENCE: 338 gaactccacg ccgttca | | 17 |
| SEQ ID NO: 339 FEATURE misc_feature source | moltype = DNA length = 32 Location/Qualifiers 1..32 note = Description of Artificial Sequence: Synthetic primer 1..32 mol_type = other DNA organism = synthetic construct | |
| SEQUENCE: 339 aagccatctc ccagaatatc tgcttagaaa tg | | 32 |
| SEQ ID NO: 340 FEATURE misc_feature source | moltype = DNA length = 17 Location/Qualifiers 1..17 note = Description of Artificial Sequence: Synthetic primer 1..17 mol_type = other DNA organism = synthetic construct | |
| SEQUENCE: 340 gaactccacg ccgttca | | 17 |
| SEQ ID NO: 341 FEATURE misc_feature | moltype = DNA length = 25 Location/Qualifiers 1..25 note = Description of Artificial Sequence: Synthetic primer | |

```
source                  1..25
                        mol_type = other DNA
                        organism = synthetic construct
SEQUENCE: 341
gagaggagca acagtgagca tgatg                                              25

SEQ ID NO: 342          moltype = DNA   length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 342
gaactccacg ccgttca                                                       17

SEQ ID NO: 343          moltype = DNA   length = 32
FEATURE                 Location/Qualifiers
misc_feature            1..32
                        note = Description of Artificial Sequence: Synthetic primer
source                  1..32
                        mol_type = other DNA
                        organism = synthetic construct
SEQUENCE: 343
aagccatctc ccagaatatc tgcttagaaa tg                                      32

SEQ ID NO: 344          moltype = DNA   length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 344
gaactccacg ccgttca                                                       17

SEQ ID NO: 345          moltype = DNA   length = 25
FEATURE                 Location/Qualifiers
misc_feature            1..25
                        note = Description of Artificial Sequence: Synthetic primer
source                  1..25
                        mol_type = other DNA
                        organism = synthetic construct
SEQUENCE: 345
gagaggagca acagtgagca tgatg                                              25

SEQ ID NO: 346          moltype = DNA   length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 346
gaactccacg ccgttca                                                       17

SEQ ID NO: 347          moltype = DNA   length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 347
cccggcttcc tttgtcc                                                       17

SEQ ID NO: 348          moltype = DNA   length = 22
FEATURE                 Location/Qualifiers
misc_feature            1..22
                        note = Description of Artificial Sequence: Synthetic primer
source                  1..22
                        mol_type = other DNA
                        organism = synthetic construct
SEQUENCE: 348
ggctatgaac taatgacccc gt                                                 22
```

-continued

```
SEQ ID NO: 349          moltype = DNA   length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 349
cccggcttcc tttgtcc                                                              17

SEQ ID NO: 350          moltype = DNA   length = 18
FEATURE                 Location/Qualifiers
misc_feature            1..18
                        note = Description of Artificial Sequence: Synthetic primer
source                  1..18
                        mol_type = other DNA
                        organism = synthetic construct
SEQUENCE: 350
ggcctgccag caggagga                                                             18

SEQ ID NO: 351          moltype = DNA   length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 351
cccggcttcc tttgtcc                                                              17

SEQ ID NO: 352          moltype = DNA   length = 25
FEATURE                 Location/Qualifiers
misc_feature            1..25
                        note = Description of Artificial Sequence: Synthetic primer
source                  1..25
                        mol_type = other DNA
                        organism = synthetic construct
SEQUENCE: 352
ggtgtgcagt cacattggta aagcc                                                     25

SEQ ID NO: 353          moltype = DNA   length = 52
FEATURE                 Location/Qualifiers
misc_feature            1..52
                        note = Description of Artificial Sequence: Synthetic
                        oligonucleotide
source                  1..52
                        mol_type = other DNA
                        organism = synthetic construct
SEQUENCE: 353
acactctttc cctacacgac gctcttccga tctccgacct cggctcacag cg                       52

SEQ ID NO: 354          moltype = DNA   length = 53
FEATURE                 Location/Qualifiers
misc_feature            1..53
                        note = Description of Artificial Sequence: Synthetic
                        oligonucleotide
source                  1..53
                        mol_type = other DNA
                        organism = synthetic construct
SEQUENCE: 354
acactctttc cctacacgac gctcttccga tctaccgacc tcggctcaca gcg                      53

SEQ ID NO: 355          moltype = DNA   length = 54
FEATURE                 Location/Qualifiers
misc_feature            1..54
                        note = Description of Artificial Sequence: Synthetic
                        oligonucleotide
source                  1..54
                        mol_type = other DNA
                        organism = synthetic construct
SEQUENCE: 355
acactctttc cctacacgac gctcttccga tctgaccgac ctcggctcac agcg                     54

SEQ ID NO: 356          moltype = DNA   length = 55
FEATURE                 Location/Qualifiers
misc_feature            1..55
                        note = Description of Artificial Sequence: Synthetic
                        oligonucleotide
```

```
source                  1..55
                        mol_type = other DNA
                        organism = synthetic construct
SEQUENCE: 356
acactctttc cctacacgac gctcttccga tcttgaccga cctcggctca cagcg          55

SEQ ID NO: 357          moltype = DNA   length = 56
FEATURE                 Location/Qualifiers
misc_feature            1..56
                        note = Description of Artificial Sequence: Synthetic
                          oligonucleotide
source                  1..56
                        mol_type = other DNA
                        organism = synthetic construct
SEQUENCE: 357
acactctttc cctacacgac gctcttccga tctctgaccg acctcggctc acagcg         56

SEQ ID NO: 358          moltype = DNA   length = 57
FEATURE                 Location/Qualifiers
misc_feature            1..57
                        note = Description of Artificial Sequence: Synthetic
                          oligonucleotide
source                  1..57
                        mol_type = other DNA
                        organism = synthetic construct
SEQUENCE: 358
acactctttc cctacacgac gctcttccga tctactgacc gacctcggct cacagcg        57

SEQ ID NO: 359          moltype = DNA   length = 58
FEATURE                 Location/Qualifiers
misc_feature            1..58
                        note = Description of Artificial Sequence: Synthetic
                          oligonucleotide
source                  1..58
                        mol_type = other DNA
                        organism = synthetic construct
SEQUENCE: 359
acactctttc cctacacgac gctcttccga tcttactgac cgacctcggc tcacagcg       58

SEQ ID NO: 360          moltype = DNA   length = 59
FEATURE                 Location/Qualifiers
misc_feature            1..59
                        note = Description of Artificial Sequence: Synthetic
                          oligonucleotide
source                  1..59
                        mol_type = other DNA
                        organism = synthetic construct
SEQUENCE: 360
acactctttc cctacacgac gctcttccga tctgtactga ccgacctcgg ctcacagcg      59

SEQ ID NO: 361          moltype = DNA   length = 51
FEATURE                 Location/Qualifiers
misc_feature            1..51
                        note = Description of Artificial Sequence: Synthetic
                          oligonucleotide
source                  1..51
                        mol_type = other DNA
                        organism = synthetic construct
SEQUENCE: 361
gtgactggag ttcagacgtg tgctcttccg atctccaccc agccagctcc c              51

SEQ ID NO: 362          moltype = DNA   length = 51
FEATURE                 Location/Qualifiers
misc_feature            1..51
                        note = Description of Artificial Sequence: Synthetic
                          oligonucleotide
source                  1..51
                        mol_type = other DNA
                        organism = synthetic construct
SEQUENCE: 362
acactctttc cctacacgac gctcttccga tctccggtgg cgcattgcca c              51

SEQ ID NO: 363          moltype = DNA   length = 52
FEATURE                 Location/Qualifiers
misc_feature            1..52
                        note = Description of Artificial Sequence: Synthetic
                          oligonucleotide
source                  1..52
                        mol_type = other DNA
```

```
                        organism = synthetic construct
SEQUENCE: 363
acactctttc cctacacgac gctcttccga tctaccggtg gcgcattgcc ac          52

SEQ ID NO: 364          moltype = DNA  length = 53
FEATURE                 Location/Qualifiers
misc_feature            1..53
                        note = Description of Artificial Sequence: Synthetic
                        oligonucleotide
source                  1..53
                        mol_type = other DNA
                        organism = synthetic construct
SEQUENCE: 364
acactctttc cctacacgac gctcttccga tctgaccggt ggcgcattgc cac         53

SEQ ID NO: 365          moltype = DNA  length = 54
FEATURE                 Location/Qualifiers
misc_feature            1..54
                        note = Description of Artificial Sequence: Synthetic
                        oligonucleotide
source                  1..54
                        mol_type = other DNA
                        organism = synthetic construct
SEQUENCE: 365
acactctttc cctacacgac gctcttccga tcttgaccgg tggcgcattg ccac        54

SEQ ID NO: 366          moltype = DNA  length = 55
FEATURE                 Location/Qualifiers
misc_feature            1..55
                        note = Description of Artificial Sequence: Synthetic
                        oligonucleotide
source                  1..55
                        mol_type = other DNA
                        organism = synthetic construct
SEQUENCE: 366
acactctttc cctacacgac gctcttccga tctctgaccg gtggcgcatt gccac       55

SEQ ID NO: 367          moltype = DNA  length = 56
FEATURE                 Location/Qualifiers
misc_feature            1..56
                        note = Description of Artificial Sequence: Synthetic
                        oligonucleotide
source                  1..56
                        mol_type = other DNA
                        organism = synthetic construct
SEQUENCE: 367
acactctttc cctacacgac gctcttccga tctactgacc ggtggcgcat tgccac      56

SEQ ID NO: 368          moltype = DNA  length = 57
FEATURE                 Location/Qualifiers
misc_feature            1..57
                        note = Description of Artificial Sequence: Synthetic
                        oligonucleotide
source                  1..57
                        mol_type = other DNA
                        organism = synthetic construct
SEQUENCE: 368
acactctttc cctacacgac gctcttccga tcttactgac cggtggcgca ttgccac     57

SEQ ID NO: 369          moltype = DNA  length = 58
FEATURE                 Location/Qualifiers
misc_feature            1..58
                        note = Description of Artificial Sequence: Synthetic
                        oligonucleotide
source                  1..58
                        mol_type = other DNA
                        organism = synthetic construct
SEQUENCE: 369
acactctttc cctacacgac gctcttccga tctgtactga ccggtggcgc attgccac    58

SEQ ID NO: 370          moltype = DNA  length = 54
FEATURE                 Location/Qualifiers
misc_feature            1..54
                        note = Description of Artificial Sequence: Synthetic
                        oligonucleotide
source                  1..54
                        mol_type = other DNA
                        organism = synthetic construct
```

| | | |
|---|---|---|
| SEQUENCE: 370 | | |
| gtgactggag ttcagacgtg tgctcttccg atctcagagt ccagcttggg ccca | | 54 |

SEQ ID NO: 371          moltype = DNA   length = 20
FEATURE                 Location/Qualifiers
misc_feature           1..20
                         note = Description of Artificial Sequence: Synthetic
                         oligonucleotide
source                   1..20
                         mol_type = other DNA
                         organism = synthetic construct
SEQUENCE: 371
gatattttcc cagctcacca                                   20

SEQ ID NO: 372          moltype = DNA   length = 20
FEATURE                 Location/Qualifiers
misc_feature           1..20
                         note = Description of Artificial Sequence: Synthetic
                         oligonucleotide
source                   1..20
                         mol_type = other DNA
                         organism = synthetic construct
SEQUENCE: 372
tctattctcc cagctcccca                                   20

SEQ ID NO: 373          moltype = DNA   length = 40
FEATURE                 Location/Qualifiers
misc_feature           1..40
                         note = Description of Artificial Sequence: Synthetic
                         oligonucleotide
source                   1..40
                         mol_type = other DNA
                         organism = synthetic construct
SEQUENCE: 373
agcggcttct gtctctgtga gtgagctggc ggtctccgtc                    40

SEQ ID NO: 374          moltype = DNA   length = 43
FEATURE                 Location/Qualifiers
misc_feature           1..43
                         note = Description of Artificial Sequence: Synthetic
                         oligonucleotide
source                   1..43
                         mol_type = other DNA
                         organism = synthetic construct
SEQUENCE: 374
gactagccca cgctccggtt ctgagccgcg acggcggtct ccg                 43

SEQ ID NO: 375          moltype = DNA   length = 41
FEATURE                 Location/Qualifiers
misc_feature           1..41
                         note = Description of Artificial Sequence: Synthetic
                         oligonucleotide
source                   1..41
                         mol_type = other DNA
                         organism = synthetic construct
SEQUENCE: 375
cccagggtcc catgcgctcc ccggccctga cggcggtctc c                  41

SEQ ID NO: 376          moltype = AA   length = 2560
FEATURE                 Location/Qualifiers
REGION                   1..2560
                         note = Description of Artificial Sequence: Synthetic
                         polypeptide
source                   1..2560
                         mol_type = protein
                         organism = synthetic construct
SEQUENCE: 376
MKRTADGSEF ESPKKKRKVD KKYSIGLDIG TNSVGWAVIT DEYKVPSKKF KVLGNTDRHS   60
IKKNLIGALL FDSGETAEAT RLKRTARRRY TRRKNRICYL QEIFSNEMAK VDDSFFHRLE   120
ESFLVEEDKK HERHPIFGNI VDEVAYHEKY PTIYHLRKKL VDSTDKADLR LIYLALAHMI   180
KFRGHFLIEG DLNPDNSDVD KLFIQLVQTY NQLFEENPIN ASGVDAKAIL SARLSKSRRL   240
ENLIAQLPGE KKNGLFGNLI ALSLGLTPNF KSNFDLAEDA KLQLSKDTYD DDLDNLLAQI   300
GDQYADLFLA AKNLSDAILL SDILRVNTEI TKAPLSASMI KRYDEHHQDL TLLKALVRQQ   360
LPEKYKEIFF DQSKNGYAGY IDGGASQEEF YKFIKPILEK MDGTEELLVK LNREDLLRKQ   420
RTFDNGSIPH QIHLGELHAI LRRQEDFYPF LKDNREKIEK ILTFRIPYYV GPLARGNSRF   480
AWMTRKSEET ITPWNFEEVV DKGASAQSFI ERMTNFDKNL PNEKVLPKHS LLYEYFTVYN   540
ELTKVKYVTE GMRKPAFLSG EQKKAIVDLL FKTNRKVTVK QLKEDYFKKI ECFDSVEISG   600
VEDRFNASLG TYHDLLKIIK DKDFLDNEEN EDILEDIVLT LTLFEDREMI EERLKTYAHL   660
FDDKVMKQLK RRRYTGWGRL SRKLINGIRD KQSGKTILDF LKSDGFANRN FMQLIHDDSL   720

```
TFKEDIQKAQ VSGQGDSLHE HIANLAGSPA IKKGILQTVK VVDELVKVMG RHKPENIVIE    780
MARENQTTQK GQKNSRERMK RIEEGIKELG SQILKEHPVE NTQLQNEKLY LYYLQNGRDM    840
YVDQELDINR LSDYDVDAIV PQSFLKDDSI DNKVLTRSDK NRGKSDNVPS EEVVKKMKNY    900
WRQLLNAKLI TQRKFDNLTK AERGGLSELD KAGFIKRQLV ETRQITKHVA QILDSRMNTK    960
YDENDKLIRE VKVITLKSKL VSDFRKDFQF YKVREINNYH HAHDAYLNAV VGTALIKKYP   1020
KLESEFVYGD YKVYDVRKMI AKSEQEIGKA TAKYFFYSNI MNFFKTEITL ANGEIRKRPL   1080
IETNGETGEI VWDKGRDFAT VRKVLSMPQV NIVKKTEVQT GGFSKESILP KRNSDKLIAR   1140
KKDWDPKKYG GFDSPTVAYS VLVVAKVEKG KSKKLKSVKE LLGITIMERS SFEKNPIDFL   1200
EAKGYKEVKK DLIIKLPKYS LFELENGRKR MLASAGELQK GNELALPSKY VNFLYLASHY   1260
EKLKGSPEDN EQKQLFVEQH KHYLDEIIEQ ISEFSKRVIL ADANLDKVLS AYNKHRDKPI   1320
REQAENIIHL FTLTNLGAPA AFKYFDTTID RKRYTSTKEV LDATLIHQSI TGLYETRIDL   1380
SQLGGDSGGS SGGSSGSETP GTSESATPES SGSETPGTSE SATPESSGSE TPGTSESATP   1440
ESSGGSSGGS STLNIEDEYR LHETSKEPDV SLGSTWLSDF PQAWAETGGM GLAVRQAPLI   1500
IPLKATSTPV SIKQYPMSQE ARLGIKPHIQ RLLDQGILVP CQSPWNTPLL PVKKPGTNDY   1560
RPVQDLREVN KRVEDIHPTV PNPYNLLSGP PPSHQWYTVL DLKDAFFCLR LHPTSQPLFA   1620
FEWRDPEMGI SGQLTWTRLP QGFKNSPTLF NEALHRDLAD FRIQHPDLIL LQYVDDLLLA   1680
ATSELDCQQG TRALLQTLGN LGYRASAKKA QICQKQVKYL GYLLKEGQRW LTEARKETVM   1740
GQPTPKTPRQ LREFLGKAGF CRLFIPGFAE MAAPLYPLTK PGTLFNWGPD QQKAYQEIKQ   1800
ALLTAPALGL PDLTKPFELF VDEKQGYAKG VLTQKLGPWR RPVAYLSKKL DPVAAGWPPC   1860
LRMVAAIAVL TKDAGKLTMG QPLVILAPHA VEALVKQPPD RWLSNARMTH YQALLLDTDR   1920
VQFGPVVALN PATLLPLPEE GLQHNCLDGT GGGGVTVKFK YKGEELEVDI SKIKKVWRVG   1980
KMISFTYDDN GKTGRGAVSE KDAPKELLQM LEKSGKKSGG SKRTADGSEF EPKKKRKVGG   2040
GGSPKKKRKV YPYDVPDYAG SRALVVIRLS RVTDATTSPE RQLESCQQLC AQRGWDVVGV   2100
AEDLDVSGAV DPFDRKRRPN LARWLAFEEQ PFDVIVAYRV DRLTRSIRHL QQLVHWAEDH   2160
KKLVVSATEA HFDTTTPFAA VVIALMGTVA QMELEAIKER NRSAAHFNIR AGKYRGSLPP   2220
WGYLPTRVDG EWRLVPDPVQ RERILEVYHR VVDNHEPLHL VAHDLNRRGV LSPKDYFAQL   2280
QGREPQGREW SATALKRSMI SEAMLGYATL NGKTVRDDDG APLVRAEPIL TREQLEALRA   2340
ELVKTSRAKP AVSTPSLLLR VLFCAVCGEP AYKFAGGGRK HPRYRCRSMG FPKHCGNGTV   2400
AMAEWDAFCE EQVLDLLGDA ERLEKVWVAG SDSAVELAEV NAELVDLTSL IGSPAYRAGS   2460
PQREALDARI AALAARQEEL EGLEARPSGW EWRETGQRFG DWWREQDTAA KNTWLRSMNV   2520
RLTFDVRGGL TRTIDFGDLQ EYEQHLRLGS VVERLHTGMS                         2560

SEQ ID NO: 377          moltype = DNA   length = 7680
FEATURE                 Location/Qualifiers
misc_feature            1..7680
                        note = Description of Artificial Sequence: Synthetic
                        polynucleotide
source                  1..7680
                        mol_type = other DNA
                        organism = synthetic construct
SEQUENCE: 377
atgaaacgga cagccgacgg aagcgagttc gagtcaccaa agaagaagcg gaaagtcgac     60
aagaagtaca gcatcggcct ggacatcggc accaactctg tgggctggcc cgtgatcacc    120
gacgagtaca aggtgcccag caagaaattc aaggtgctgg gcaacaccga ccggcacagc    180
atcaagaaga acctgatcgg agccctgctg ttcgacagcg gcgaaacagc cgaggccacc    240
cggctgaaga gaaccgccag aagaagatac accagacgga gaaccggat  ctgctatctg    300
caagagatct tcagcaacga gatggccaag gtggacgaca gcttcttcca cagactggaa    360
gagtccttcc tggtggaaga ggataagaag cacgagcggc accccatcttc ggcaacatc    420
gtggacgagg tggcctacca cgagaagtac cccaccatct accacctgag aaagaaactg    480
gtggacagca ccgacaaggc cgacctgcgc ctgatctatc tggccctggc ccacatgatc    540
aagttccggg gccacttcct gatcgagggc gacctgaacc cggacaactg cgacgtggac    600
aagctgttca tccagctggt gcagacctac aaccagctgt tcgaggaaaa ccccatcaac    660
gccagcggcg tggacgccaa ggccatcctg tctgccagac tgagcaagag cagacggctg    720
gaaaatctga tcgcccagct gcccggcgag aagaagaatg gcctgttcgg aaacctgatt    780
gccctgagcc tgggcctgac ccccaacttc aagagcaatt tcgacctggc cgaggatgcc    840
aaactgcagc tgagcaagga cacctacgac gacgacctgg acaacctgct ggcccagatc    900
ggcgaccagt acgccgacct gtttctggcc gccaagaacc tgtccgacgc catcctgctg    960
agcgacatcc tgagagtgaa caccgagatc accaaggccc ccctgagcgc ctctatgatc   1020
aagagatacg acgagcacca ccaggacctg accctgctga aagctctcgt gcggcagcag   1080
ctgcctgaga agtacaaaga gattttcttc gaccagagca agaacggcta cgccggctac   1140
attgacggcg gagccagcca ggaagagttc tacaagttca tcaagcccat cctggaaaag   1200
atggacggca ccgaggaact gctcgtgaag ctgaacagag aggacctgct gcggaagcag   1260
cggaccttcg acaacggcag catcccccac cagatccacc tgggagagct gcacgccatt   1320
ctgcggcggc aggaagattt tacccattcc tgaaggaca accgggaaaa gatcgagaag   1380
atcctgacct tccgcatccc ctactacgtg ggccctctgg caggggaaa  cagcagattc   1440
gcctggatga ccagaagag  cgaggaaacc atcacccct  ggaacttcga ggaagtggtg   1500
gacaaggggc cttccgccca gagcttcatc gagcggatga ccaacttcga taagaacctg   1560
cccaacgaga aggtgctgcc caagcacagc ctgctgtacg agtactttac cgtgtataac   1620
gagctgacca aagtgaaata cgtgaccgag ggaatgaaa  agcccgccct  cctgagcggc   1680
gagcagaaaa aggccatcgt ggacctgctg ttcaagacca accggaaagt gaccgtgaag   1740
cagctgaaag gactacttca agaaaatc  gagtgcttcg actccgtgga aatctccggc   1800
gtggaagatc ggttcaacgc ctccctgggc acataccacg atctgctgaa  attatcaag   1860
gacaaggact tcctggacaa tgaggaaaac gaggacattc tggaagatat cgtgctgacc   1920
ctgacactgt ttgaggacag agagatgatc gaggaacggc tgaaaaccta tgcccacctg   1980
ttcgacgaca aagtgatgaa gcagctgaag cggcggagat acaccggctg  ggcaggctg   2040
agccggaagc tgatcaacgg catccgggac aagcagtccg gcaagacaat  cctggatttc   2100
ctgaagtccg acggcttcgc caacagaaac ttcatgcagc tgatccacga cgacagcctg   2160
acctttaaag aggacatcca gaaagcccag gtgtccggcc agggcgatag cctgcacgag   2220
cacattgcca atctggccgg cagccccgcc attaagaagg gcatcctgca gacagtgaag   2280
```

```
gtggtggacg agctcgtgaa agtgatgggc cggcacaagc ccgagaacat cgtgatcgaa    2340
atggccagag agaaccagac cacccagaag ggacagaaga acagccgcga gagaatgaag    2400
cggatcgaag agggcatcaa agagctgggc agccagatcc tgaaagaaca ccccgtggaa    2460
aacacccagc tgcagaacga gaagctgtac ctgtactacc tgcagaatgg gcgggatatg    2520
tacgtggacc aggaactgga catcaaccgg ctgtccgact acgatgtgga cgctatcgtg    2580
cctcagagct ttctgaagga cgactccatc gacaacaagg tgctgaccag aagcgacaag    2640
aaccggggca gagcgacaa cgtgccctcc gaagaggtcg tgaagaagat gaagaactac     2700
tggcggcagc tgctgaacgc caagctgatt acccagagaa agttcgacaa tctgaccaag    2760
gccgagagag gcggcctgag cgaactggat aaggccggct tcatcaagag acagctggtg    2820
gaaacccggc agatcacaaa gcacgtggca cagatcctgg actcccggat gaacactaag    2880
tacgacgaga atgacaagct gatccggaaa gtgaaagtga tcaccctgaa gtccaagctg    2940
gtgtccgatt ccggaaggga tttccagttt tacaaagtgc gcgagatcaa caactaccac    3000
cacgcccacg acgcctacct gaacgccgtc gtgggaaccg ccctgatcaa aaagtaccct    3060
aagctggaaa gcgagttcgt gtacggcgac tacaaggtgt acgacgtgcg gaagatgatc    3120
gccaagagcg agcaggaaat cggcaaggct accgccaagt acttcttcta cagcaacatc    3180
atgaactttt tcaagaccga gattaccctg ccaacggcg agatccggaa gcggcctctg    3240
atcgagacaa acggcgaaac cggggagatc gtgtgggata agggccggga ttttgccacc    3300
gtgcggaaag tgctgagcat gccccaagtg aatatcgtga aaaagaccga ggtgcagaca    3360
ggcggcttca gcaaagagtc tatcctgccc aagaggaaca gcgataagct gatcgccaga    3420
aagaaggact gggaccctaa gaagtacggc ggcttcgaca gccccaccgt ggcctattct    3480
gtgctggtgg tggccaaagt ggaaaagggc aagtccaaga aactgaagag tgtgaaagag    3540
ctgctgggga tcaccatcat ggaaagaagc agcttcgaga gaatcccat cgactttctg    3600
gaagccaagg gctacaaaga agtgaaaaag gacctgatca tcaagctgcc taagtactcc    3660
ctgttcgagc tggaaaacgg ccggaagaga atgctggcct ctgccggcga actgcagaag    3720
ggaaacgaac tggccctgcc ctccaaatat gtgaacttcc tgtacctggc cagccactat    3780
gagaagctga aggctccc cgaggataat gagcagaaac agctgtttgt ggaacagcac    3840
aagcactacc tggacgagag catcgagcag atcagcgagt tctccaagag agtgatcctg    3900
gccgacgcta atctggacaa agtgctgtcc gcctacaaca gcaccggga taagcccatc    3960
agagagcagg ccgagaatat catccacctg tttacccctga ccaatctggg agcccctgcc    4020
gccttcaagt actttgacac caccatcgac cggaagaggt acacccagcac caagagggtg    4080
ctggacgcca ccctgatcca ccagagcatc accggcctgt acgagacacg gatcgacctg    4140
tctcagctgg gaggtgactc tggaggatct agcggaggat cctctggcag cgagacacca    4200
ggaacaagcg agtcagcaac accagagagc tctggtagcg agacacccgg taccagtgaa    4260
agcgccacgc cagaaagcag tgggagtgag actccgggta catctgaatc agcgacaccg    4320
gaatcaagtg gcgcagcag cggcggcagc agcaccctaa atatagaaga tgagtatcgt    4380
ctacatgaga cctcaaaaga gccagatgtt tctctagggt ccacatggct gtctgatttt    4440
cctcaggcct gggcggaaac cggggcatg ggactgcag ttcgccaagc tcctctgatc     4500
atacctctga aagcaacctc taccccgtg tccataaaac aataccccat gtcacaagaa     4560
gccagactgg ggatcaagcc ccacatacag agactgttgg atccaggaa actggtaccc     4620
tgccagtccc cctggaacac gcccctgcta cccgttaaga aaccaggac taatgattat    4680
aggcctgtcc aggatctgag agaagtcaac aagcgggtgg aagacatcca cccaccgtg    4740
cccaacccctt acaacctctt gagcgggccc ccaccgtccc accagtggta cactgtgctt    4800
gatttaaagg atgccttttt ctgcctgaga ctccaccccca cagtcagcc tctcttcgcc    4860
tttgagtgga gagatccaga gatgggaatc tcaggacaat tgacctggac cagactccca    4920
cagggtttca aaaacagtcc caccctgttt aatgaggcac tgcacagaga cctagcagac    4980
ttccggatcc agcacccaga cttgatcctg ctacagtacg tggatgactt actgctggcc    5040
gccacttctg agctagactg ccaacaaggt actcgggcc tgttacaaac cctagggaac    5100
ctcgggtatc gggcctcggc caagaaagcc caaatttgcc agaaacaggt caagtatctg    5160
gggtatcttc taaaagaggg tcagagatgg ctgactgagg ccagaaaaga gactgtgatg    5220
gggcagccta ctccgaagac ccctcgacaa ctaagggagt tcctaggaa ggcaggcttc    5280
tgtcgcctct tcatccctgg gttttgcaaa atggcagccc ccctgtacc tctcaccaaa    5340
ccggggactc tgtttaattg gggcccagac caacaaaagg cctatcaaga aatcaagcaa    5400
gctcttctaa ctgccccagc cctggggttg ccagatttga ctaagccctt tgaactcttt    5460
gtcgacgaga agcagggcta cgccaaaggt gtcctaacgc aaaaactggg accttggcgt    5520
cggccggtgg cctacctgtc caaaaagcta gaccccagtag cagctgggtg gccccccttgc    5580
ctacggatgg tagcagccat tgccgtactg acaaaggatg caggcaagct aaccatgggg    5640
cagccactag tcattctggc cccccatgca gtagaggcac tagtcaaaca acccccgac    5700
cgctggcttt ccaacgcccg gatgactcac tatcaggcct tgcttttgga cacggaccggg    5760
gtccagttcg gaccggtggt agccctgaac ccggctacgc tgctccact gcctgaggaa    5820
gggctgcaac acaactgcct tgatggaca ggtggcggtg gtgtcaccgt caagttcaag    5880
tacaaggtg aggaacttga agttgatatt agcaaaatca agaaggtttg gcgcgttggt    5940
aaaatgatat ctttttactta tgacgacaac ggcaagacag gtagagggc agtgtctgag    6000
aaagacgccc ccaaggagct gttgcaaatg ttggaaaagt ctgggaaaaa gtctggcggc    6060
tcaaaaagaa ccgccgacgg cagcgaattc gagcccagaa agaagaggaa agtcggagc    6120
ggcgggagcc caaaaagaa aagaaaagtg tatcccctatg atgtcccga ttatgccggt    6180
tcaagagccc tggtcgtgat tagactgagc cgagtgacag acgccaccac aagtcccgag    6240
agacagctgg aatcatgcca gcagctctgt gctcagcggg gttgggatgt ggtcggcgtg    6300
gcagaggatc tggacgtgag cggggccgtc gatcattcg acagaaagag gaggcccaac    6360
ctggcaagat ggctcgcttt cgaggaacag ccctttgatg tgatcctgc ctacagatg    6420
gaccggctga cccgctcaat tcgacatctc cagcagctgg tgcattggc tgaggaccac    6480
aagaaactgg tggtcagcgc aacagaagcc cacttcgata ctaccacacc ttttgccgct    6540
gtggtcatcg cactgatggg cactgtgcc cagatgagc tcgaagctat caaggagcga    6600
aacaggagcg cagcccattt caatattagg gccggtaaat acagaggctc cctgcccct    6660
tgggatatc tccctaccag ggtggatggg taggccaaa ccccgtccag                 6720
agagagcgga ttctgaagt gtaccacaga gtgtccgata accacgaacc actccatctg    6780
gtggcacacg acctgaatag acgcggcgtg ctctctccaa aggattattt tgctcagctg    6840
cagggaagag agccacaggg aagagaatgg agtgctactg cactgaagag atctatgatc    6900
agtgaggcta tgctgggtta cgcaacactc aatggcaaaa ctgtccggga cgatgacgga    6960
gcccctctgg tgagggctga gcctattctc accagagagc agctcgaagc tctgcgggca    7020
```

```
gaactggtca agactagtcg cgccaaacct gccgtgagca ccccaagcct gctcctgagg 7080
gtgctgttct gcgccgtctg tggagagcca gcatacaagt ttgccggcgg agggcgcaaa 7140
catcccgct atcgatgcag gagcatgggg ttccctaagc actgtggaaa cgggacagtg 7200
gccatggctg agtgggacgc cttttgcgag gaacaggtgc tggatctcct gggtgacgct 7260
gagcggctgg aaaaagtgtg ggtggcagga tctgactccg ctgtggagct ggcagaagtc 7320
aatgccgagc tcgtggatct gacttccctc atcggatctc ctgcatatag agctgggtcc 7380
ccacagagag aagtctggga cgcacgaatt gctgcactcg ctgctagaca ggaggaactg 7440
gagggcctgg aggccaggcc ctctggatgg gagtggcgag aaaccggaca gaggtttggg 7500
gattggtgga gggagcagga caccgcagcc aagaacacat ggctgagatc catgaatgtc 7560
cggctcacat tcgacgtgcg cggtggcctg actcgaacca tcgattttgg cgaccgtcag 7620
gagtatgaac agcacctgag actggggtcc gtggtcgaaa gactgcacac tgggatgtcc 7680
```

```
SEQ ID NO: 378          moltype = AA   length = 1367
FEATURE                 Location/Qualifiers
REGION                  1..1367
                        note = Description of Artificial Sequence: Synthetic
                          polypeptide
source                  1..1367
                        mol_type = protein
                        organism = synthetic construct
SEQUENCE: 378
DKKYSIGLDI GTNSVGWAVI TDEYKVPSKK FKVLGNTDRH SIKKNLIGAL LFDSGETAEA    60
TRLKRTARRR YTRRKNRICY LQEIFSNEMA KVDDSFFHRL EESFLVEEDK KHERHPIFGN   120
IVDEVAYHEK YPTIYHLRKK LVDSTDKADL RLIYLALAHM IKFRGHFLIE GDLNPDNSDV   180
DKLFIQLVQT YNQLFEENPI NASGVDAKAI LSARLSKSRR LENLIAQLPG EKKNGLFGNL   240
IALSLGLTPN FKSNFDLAED AKLQLSKDTY DDDLDNLLAQ IGDQYADLFL AAKNLSDAIL   300
LSDILRVNTE ITKAPLSASM IKRYDEHHQD LTLLKALVRQ QLPEKYKEIF FDQSKNGYAG   360
YIDGGASQEE FYKFIKPILE KMDGTEELLV KLNREDLLRK QRTFDNGSIP HQIHLGELHA   420
ILRRQEDFYP FLKDNREKIE KILTFRIPYY VGPLARGNSR FAWMTRKSEE TITPWNFEEV   480
VDKGASAQSF IERMTNFDKN LPNEKVLPKH SLLYEYFTVY NELTKVKYVT EGMRKPAFLS   540
GEQKKAIVDL LFKTNRKVTV KQLKEDYFKK IECFDSVEIS GVEDRFNASL GTYHDLLKII   600
KDKDFLDNEE NEDILEDIVL TLTLFEDREM IEERLKTYAH LFDDKVMKQL KRRRYTGWGR   660
LSRKLINGIR DKQSGKTILD FLKSDGFANR NFMQLIHDDS LTFKEDIQKA QVSGQGDSLH   720
EHIANLAGSP AIKKGILQTV KVVDELVKVM GRHKPENIVI EMARENQTTQ KGQKNSRERM   780
KRIEEGIKEL GSQILKEHPV ENTQLQNEKL YLYYLQNGRD MYVDQELDIN RLSDYDVDAI   840
VPQSFLKDDS IDNKVLTRSD KNRGKSDNVP SEEVVKKMKN YWRQLLNAKL ITQRKFDNLT   900
KAERGGLSEL DKAGFIKRQL VETRQITKHV AQILDSRMNT KYDENDKLIR EVKVITLKSK   960
LVSDFRKDFQ FYKVREINNY HHAHDAYLNA VVGTALIKKY PKLESEFVYG DYKVYDVRKM  1020
IAKSEQEIGK ATAKYFFYSN IMNFFKTEIT LANGEIRKRP LIETNGETGE IVWDKGRDFA  1080
TVRKVLSMPQ VNIVKKTEVQ TGGFSKESIL PKRNSDKLIA RKKDWDPKKY GGFDSPTVAY  1140
SVLVVAKVEK GKSKKLKSVK ELLGITIMER SSFEKNPIDF LEAKGYKEVK KDLIIKLPKY  1200
SLFELENGRK RMLASAGELQ KGNELALPSK YVNFLYLASH YEKLKGSPED NEQKQLFVEQ  1260
HKHYLDEIIE QISEFSKRVI LADANLDKVL SAYNKHRDKP IREQAENIIH LFTLTNLGAP  1320
AAFKYFDTTI DRKRYTSTKE VLDATLIHQS ITGLYETRID LSQLGGD                1367

SEQ ID NO: 379          moltype = AA   length = 576
FEATURE                 Location/Qualifiers
REGION                  1..576
                        note = Description of Artificial Sequence: Synthetic
                          polypeptide
source                  1..576
                        mol_type = protein
                        organism = synthetic construct
SEQUENCE: 379
LNIEDEYRLH ETSKEPDVSL GSTWLSDFPQ AWAETGGMGL AVRQAPLIIP LKATSTPVSI    60
KQYPMSQEAR LGIKPHIQRL LDQGILVPCQ SPWNTPLLPV KKPGTNDYRP VQDLREVNKR   120
VEDIHPTVPN PYNLLSGPPP SHQWYTVLDL KDAFFCLRLH PTSQPLFAFE WRDPEMGISG   180
QLTWTRLPQG FKNSPTLFNE ALHRDLADFR IQHPDLILLQ YVDDLLLAAT SELDCQQGTR   240
ALLQTLGNLG YRASAKKAQI CQKQVKYLGY LLKEGQRWLT EARKETVMGQ PTPKTPRQLR   300
EFLGKAGFCR LFIPGFAEMA APLYPLTKPG TLFNWGPDQQ KAYQEIKQAL LTAPALGLPD   360
LTKPFELFVD EKQGYAKGVL TQKLGPWRRP VAYLSKKLDP VAAGWPPCLR MVAAIAVLTK   420
DAGKLTMGQP LVILAPHAVE ALVKQPPDRW LSNARMTHYQ ALLLDTDRVQ FGPVVALNPA   480
TLLPLPEEGL QHNCLDGTGG GGVTVKFKYK GEELEVDISK IKKVWRVGKM ISFTYDDNGK   540
TGRGAVSEKD APKELLQMLE KSGKKSGGSK RTADGS                            576

SEQ ID NO: 380          moltype = AA   length = 500
FEATURE                 Location/Qualifiers
REGION                  1..500
                        note = Description of Artificial Sequence: Synthetic
                          polypeptide
source                  1..500
                        mol_type = protein
                        organism = synthetic construct
SEQUENCE: 380
SRALVVIRLS RVTDATTSPE RQLESCQQLC AQRGWDVVGV AEDLDVSGAV DPFDRKRRPN    60
LARWLAFEEQ PFDVIVAYRV DRLTRSIRHL QQLVHWAEDH KKLVVSATEA HFDTTTPFAA   120
VVIALMGTVA QMELEAIKER NRSAAHFNIR AGKYRGSLPP WGYLPTRVDG EWRLVPDPVQ   180
RERILEVYHR VVDNHEPLHL VAHDLNRRGV LSPKDYFAQL QGREPQGREW SATALKRSMI   240
SEAMLGYATL NGKTVRDDDG APLVRAEPIL TREQLEALRA ELVKTSRAKP AVSTPSLLLR   300
```

```
VLFCAVCGEP AYKFAGGGRK HPRYRCRSMG FPKHCGNGTV AMAEWDAFCE EQVLDLLGDA    360
ERLEKVWVAG SDSAVELAEV NAELVDLTSL IGSPAYRAGS PQREALDARI AALAARQEEL    420
EGLEARPSGW EWRETGQRFG DWWREQDTAA KNTWLRSMNV RLTFDVRGGL TRTIDFGDLQ    480
EYEQHLRLGS VVERLHTGMS                                                500

SEQ ID NO: 381          moltype = DNA   length = 11344
FEATURE                 Location/Qualifiers
misc_feature            1..11344
                        note = Description of Artificial Sequence: Synthetic
                         polynucleotide
source                  1..11344
                        mol_type = other DNA
                        organism = synthetic construct
SEQUENCE: 381
ccgaaaagtg ccacctgacg tcgacggatc gggagatcga tctcccgatc ccctagggtc     60
gactctcagt acaatctgct ctgatgccgc atagttaagc cagtatctgc tccctgcttg    120
tgtgttggag gtcgctgagt agtgcgcgag caaaatttaa gctacaacaa ggcaaggctt    180
gaccgacaat tgcatgaaga atctgcttag ggttaggcgt tttgcgctgc ttcgcgatgt    240
acgggccaga tatacgcgtt gacattgatt attgactagt tattaatagt aatcaattac    300
ggggtcatta gttcatagcc catatatgga gttccgcgtt acataactta cggtaaatgg    360
cccgcctggc tgaccgccca cgaccccccg cccattgacg tcaataatga cgtatgttcc    420
catagtaacg ccaataggga cttttccatt acgtcaatgg gtggagtatt tacggtaaac    480
tgcccacttg gcagtacatc aagtgtatca tatgccaagt acgccccta ttgacgtcaa     540
tgacggtaaa tggcccgcct ggcattatgc ccagtacatg accttatggg actttcctac    600
ttggcagtac atctacgtat tagtcatcgc tattaccatg gtgatgcggt tttggcagta    660
catcaatgtg cgtggatagc ggtttgactc acggggattt ccaagtctcc accccattga    720
cgtcaatggg agtttgtttt ggcaccaaaa tcaacgggac tttccaaaat gtcgtaacaa    780
ctccgcccca ttgacgcaaa tgggcggtag gcgtgtacgg tgggaggtct atataagcag    840
agctggttta gtgaaccgtc agatccgcta gagatccgcg ccgctaata cgactcacta    900
tagggagagc cgccaccatg aaacggacag ccgagttcga tcaccaaaga    960
agaagcggaa agtcgacaag aagtacagca tcggcctgga catcggcacc aactctgtgt   1020
gctgggccgt gatcaccgac gagtacaagg tgcccagcaa gaaattcaag gtgctgggca   1080
acaccgaccg gcacagcatc aagaagaacc tgatcggagc cctgctgttc gacagcggca   1140
aaacagccga ggccaccagg ctgaagagaa ccgccagaag aagatacacc agacggaaga   1200
accggatctg ctatctgcaa gagatcttca gcaacgagat ggccaaggtg gacgacagct   1260
tcttccacag actggaagag tccttcctgg tggaagagga taagaagcac gagcggcacc   1320
ccatcttcgg caacatcgtg gacgaggtgg cctaccacga gaagtacccc accatctacc   1380
acctgagaaa gaaactggtg gacagcaccg acaaggcga cctgcggctg atctatctgg   1440
ccctggccca catgatcaag ttccggggcc acttcctgat cgagggcgac ctgaacccgc   1500
acaacgcga cgtggacaag ctgttcatcc agctggtgca gacctacaac agctgttcg    1560
aggaaaaccc catcaacgcc agcggcgtgg acgccaaggc catcctgtct gcagactga    1620
gcaagagcag acggctggaa aatctgatcg cccagctgcc cggcgagaag aagaatggcc   1680
tgttcggaaa cctgattgcc ctgagcctgg gcctgaccc caacttcaag agcaacttcg   1740
acctggccga ggatgccaaa ctgcagctga gcaaggacac ctacgacgac gacctggaca   1800
acctgctggc ccagatcggc gaccagtacg ccgacctgtt tctggccgcc aagaacctgt   1860
ccgacgccat cctgctgagc gacatcctga gagtgaacac cgagatcacc aaggcccccc   1920
tgagcgcctc tatgatcaag agatacgacg agcaccacca ggacctgacc ctgctgaaag   1980
ctctcgtgcg gcagcagctg cctgagaagt acaaagagat tttcttcgac cagagcaaga   2040
acggctacgc cggctacatt gacggcgag ccagccagga agttctac aagttcatca     2100
agcccatcct ggaaaagatg gacggcaccg aggaactgct cgtgaagctg aacagagagg   2160
acctgctgcg gaagcagcgg accttcgaca cggcagcat ccccaccag atccacctgg    2220
gagagctgca cgccattctg cggcggcagg aagattttta cccattcctg aaggacaacc   2280
gggaaaagat cgaaaagatc ctgaccttcc gcatccccta ctacgtgggc cctctggcca   2340
ggggaaacag cagattcgcc tggatgacca gaaagagcga ggaaaccatc accccctgga   2400
acttcgagga agtggtggac aagggcgctt ccgcccagag cttcatcgag cggatgacca   2460
acttcgataa gaacctgccc aacgagaagg tgctgcccaa gcacagcctg ctgtacgagt   2520
acttcaccgt gtataacgag ctgaccaaag tgaaatacgt gaccgaggga atgagaaagc   2580
ccgccttcct gagcggcgag cagaaaaagg ccatcgtgga cctgctgttc aagaccaacc   2640
ggaaagtgac cgtgaagcag ctgaaagagg actacttcaa gaaaatcgag tgcttcgaca   2700
gcgtggaaat ctccggcgtg gaagatcggt tcaacgcctc cctgggcaca taccacgatc   2760
tgctgaaaat tatcaaggac aaggacttcc tggacaatga ggaaaacgag gacattctgg   2820
aagatatcgt gctgaccctg acactgtttg aggacagaga gatgatcgag gaacggctga   2880
aaacctatgc ccacctgttc gacgacaaag tgatgaagca gctgaagcgg cggagataca   2940
ccggctgggg caggctgagc cggaagctga tcaacggcat ccgggacaag cagtccgga    3000
agacaatcct ggatttcctg aagtccgacg gcttcgccaa cagaaacttc atgcagctga   3060
tccacgacga cagcctgacc tttaaagagg catccagaa agcccaggtg tccggccagg   3120
gcgatagcct gcacgagcac attgccaatc tggccggcag cccgccatt aagaagggca   3180
tcctgcagac agtgaaggtg gtggacgagc tcgtgaaagt gatgggccgg cacaagccg    3240
agaacatcgt gatcgaaatg gccagagaga accagaccac ccagaaggga cagaagaaca   3300
gccgcgagag aatgaagcgg atcgaagagg gcatcaaaga gctgggcagc cagatcctga   3360
aagaacaccc cgtggaaaac acccagctgc agaacgagaa gctgtacctg tactacctgc   3420
agaatgggcg ggatatgtac gtggaccagg aactggacat caaccggctg tccgactacg   3480
atgtggacgc tatcgtgcct cagagctttc tgaaggacga ctccatcgac aacaaggtgc   3540
tgaccagaag cgacaagaac cggggcaaga gcgacaacgt gcccctccga gaggtcgtga   3600
agaagatgaa gaactactgg cggcagctgc tgaacgccaa gctgattacc cagagaaagt   3660
tcgacaatct gaccaaggcc gagagaggcg gcctgagcga actggataag gccgcttca    3720
tcaagagaca gctggtggaa acccggcaga tcacaaagca cgtggcacag atcctggact   3780
cccgatgaa cactaagtac gacgagatg acaagctgat ccgggaagtg aaagtgatca    3840
ccctgaagtc caagctggtg tccgattcc ggaaggattt ccagttttac aaagtgcgcg   3900
```

```
agatcaacaa ctaccaccac gcccacgacg cctacctgaa cgccgtcgtg ggaaccgccc   3960
tgatcaaaaa gtaccctaag ctggaaagcg agttcgtgta cggcgactac aaggtgtacg   4020
acgtgcggaa gatgatcgcc aagagcgagc aggaaatcgg caaggctacc gccaagtact   4080
tcttctacag caacatcatg aacttttca agaccgagat taccctggcc aacggcgaga   4140
tccggaagcg gcctctgatc gagacaaacg gcgaaaccgg ggagatcgtg tgggataagg   4200
gccgggattt tgccaccgtg cggaaagtgc tgagcatgcc ccaagtgaat atcgtgaaaa   4260
agaccgaggt gcagacaggc ggcttcagca aagagtctat cctgcccaag aggaacagcg   4320
ataagctgat cgccagaaag aaggactggg accctaagaa gtacggcggc ttcgacagcc   4380
ccaccgtggc ctattctgtg ctggtggtgg ccaaagtgga aaagggcaag tccaagaaac   4440
tgaagagtgt gaaagagctg ctggggatca ccatcatgga aagaagcagc ttcgagaaga   4500
atcccatcga ctttctggaa gccaagggct acaaagaagt gaaaaaggac ctgatcatca   4560
agctgcctaa gtactccctg ttcgagctgg aaaacggccg gaagagaatg ctggcctctg   4620
ccggcgaact gcagaaggga aacgaactgg ccctgccccc caaatatgtg aacttcctgt   4680
acctggccag ccactatgag aagctgaagg gctcccccga ggataatgag cagaaacagc   4740
tgtttgtgga acagcacaag cactacctgg acgagatcat cgagcagatc agcgagttct   4800
ccaagagagt gatcctggcc gacgctaatc tggacaaagt gctgtccgcc tacaacaagc   4860
accgggataa gcccatcaga gagcaggccg agaatatcat ccacctgttt accctgacca   4920
atctgggagc ccctgccgcc ttcaagtact ttgacaccac catcgaccgg aagaggtaca   4980
ccagcaccaa agaggtgctg gacgccaccc tgatccacca gagcatcacc ggcctgtacg   5040
agacacggat cgacctgtct cagctgggag gtgactctgg aggatctagc ggaggatcct   5100
ctggcagcga gacaccagga acaagcgagt cagcaacacc agagagcagt ggcggcagca   5160
gcggcggcag cagcaccta aatatagaag atgagtatcg gctacatgag acctcaaaag   5220
agccagatgt ttctctaggg tccacatggc tgtctgattt tcctcaggcc tgggcggaaa   5280
ccgggggcat gggactggca gttcgccaag ctcctctgat catacctctg aaagcaacct   5340
ctaccccgt gtccataaaa caatacccca tgtcacaaga agccagactg gggatcaagc   5400
cccacataca gagactgttg gaccagggaa tactggtacc ctgccagtcc ccctggaaca   5460
cgccctgct acccgttaag aaaccaggga ctaatgatta taggcctgtc caggatctga   5520
gagaagtcaa caagcgggtg gaagacatcc accccaccgt gcccaaccct acaacctct   5580
tgagcgggct cccaccgtcc caccagtggt acactgtgct tgatttaaag gatgccttt   5640
tctgcctgag actccacccc accagtcagc ctctcttcgc ctttgagtgg agagatccag   5700
agatgggaat ctcaggacaa ttgacctgga ccagactccc acaggggttc aaaaacagtc   5760
ccaccctgtt taatgaggca ctgcacagag acctagcaga cttccggatc cagcacccag   5820
acttgatcct gctacagtac gtggatgact tactgctggc cgccacttct gagctagact   5880
gccaacaagg tactcgggcc ctgttacaaa ccctagggaa cccggggtat cgggcctcgg   5940
ccaagaaagc ccaaatttgc cagaaacagg tcaagtatct ggggtatctt ctaaaagagg   6000
gtcagagatg gctgactgag gccagaaaag agactgtgat ggggcagcct actccgaaga   6060
cccctcgaca actaagggag ttcctaggga aggcaggctt ctgtcgcctc ttcatccctg   6120
ggtttgcaga aatggcagcc ccctgtacc ctctcaccaa accggggact ctgtttaatt   6180
ggggcccaga ccaacaaaag gcctatcaag aaatcaagca agctcttcta actgccccag   6240
ccctgggtt gccagatttg actaagccct ttgaactctt tgtcgacgag aagcagggct   6300
acgccaaagg tgtcctaacg caaaaactgg gaccttggcg tcgccggtg gcctacctgt   6360
ccaaaaagct agacccagta gcagctgggt ggccccttg cctacggatg gtagcagcca   6420
ttgcctact gacaaaggat gcaggcaagc taacctggg acagccacta gtcattctgg   6480
cccccatgc agtagaggca ctagtcaaac aaccccccga ccgctggctt tccaacgccc   6540
ggatgactca ctatcaggcc ttgcttttgg acacggaccg ggtccagttc ggaccggtgg   6600
tagccctgaa cccggctacg ctgctccac tgcctgagga agggctgcaa cacaactgcc   6660
ttgatatcct ggccgaagcc cacggaaccc gaccgacct aacggaccag ccgctcccag   6720
acgccgacca cacctggtac acggatggaa gcagtctctt acaagaggga cagcgtaagg   6780
cgggagctgc ggtgaccacc gagaccgagg taatctgggc taaagccctg ccagccggga   6840
catccgctca gcgggctgaa ctgatagcac tcacccaggc cctaaagatg gcagaaggta   6900
agaagctaaa tgtttatact gatagccgtt atgcttttgc tactgcccat atccatggag   6960
aaatatacag aaggcgtggg tggctcacat cagaaggcaa agagatcaaa aataaagacg   7020
agatcttggc cctactaaaa gccctctttc tgcccaaaag acttagcata atccattgtc   7080
caggacatca aaagggacac agcgccgagg ctagaggcaa ccggatgcta gaccaagcgg   7140
cccgaaaggc agccatcaca gagactccag cacctctac cctcctcata gaaaattcat   7200
caccctctgg cggctcaaaa agaaccgccg acgcagcga attcgagccc aagaagaaga   7260
ggaaagtcgg aagcggagct actaacttca gcctgctgaa gcaggctggc gacgtggagg   7320
agaaccctgg acctccaaaa aagaaagaa agtgtatcc ctatgatgtc cccgattatg   7380
ccggttcaag agccctggtc gtgattagac tgagccgagt gagccactgt accacaagtc   7440
ccgagagaca gctggaatca tgccagcagc tctgtgctca gcggggttgg gatgtggtcg   7500
gcgtggcaga ggatcggac gtgagcgggg ccgtcgatcc attcgacaga aagaggaggc   7560
ccaacctggc aagatggctc gctttcgagg aacagccctt tgatgtgatc gtcgcctaca   7620
gagtggaccg gctgacccgc tcaattcgac atctccagca gctggtgcat gggctgagg   7680
accacaagaa actggtggtc agcgcaacag aagccactt cgatactacc acacctttg   7740
ccgctgtggt catcgcactg atgggcactg tggcccagat ggagctcgaa gctatcaagg   7800
agcgaaacag gagcgcagcc catttcaata ttagggccgg taaatacaga ggctccctgc   7860
cccttgggg atatctccct accagggtgg atggggagtg gagactggtg ccagaccccg   7920
tccagagaga gcggattctg gaagtgtacc acagagtggt cgataaccac gaaccactcc   7980
atctgagaca acacgacctg atagacgcg gcgtgctctc tccaaaggat tattttgctc   8040
agctgcaggg aagagagcca cagggaagag aatggagtgc tactgcactg aagagatcta   8100
tgatcagtga ggctatgctg ggttacgcaa cactcaatgg caaaactgtc cggacgatg   8160
acggagcccc tctggtgagg gctgagccta ttctcaccag agagcagctc gaagctctgc   8220
gggcagaact ggtcaagact agtcgcgcca aacctgccgt gagcacccca agcctgctcc   8280
tgaaggtgt gttctgcgcc gtctgtggga gccagcata caagtttttg gccggagggc   8340
gcaaacatcc ccgctatcga tgcaggagca tgggttccc taagcactgt gaaaacggaa   8400
cagtggccat ggctgagtgg gacgcctttt gcgaggaaca ggtgctggat ctcctgggtg   8460
acgctgagcg gctggaaaaa gtgtgggtgg caggatctga ctcgctgtg gagctggcag   8520
aagtcaatgc cgagctcgtg gatctgactt ccctcatcgg atctcctgca tatagagctg   8580
ggtccccaca gagagaagct ctggacgcac gaattgctgc actcgctgct agacaggagg   8640
```

```
aactggaggg cctggaggcc aggccctctg gatgggagtg gcgagaaacc ggacagaggt 8700
ttggggattg gtggagggag caggacaccg cagccaagaa cacatggctg agatccatga 8760
atgtccggct cacattcgac gtgcgcggtg gcctgactcg aaccatcgat tttggcgacc 8820
tgcaggagta tgaacagcac ctgagactgg ggtccgtggt cgaaagactg cacactggga 8880
tgtcctaggt ttaaacccgc tgatcagcct cgactgtgcc ttctagttgc cagccatctg 8940
ttgtttgccc ctccccgtg ccttccttga ccctgaagg tgccactccc actgtccttt 9000
cctaataaaa tgagaaaatt gcatcgcatt gtctgagtag gtgtcattct attctgggg 9060
gtggggtggg gcaggacagc aaggggagg attgggaaga caatagcagg catgctgggg 9120
atgcggtggg ctctatgct tctgaggcgg aaagaaccag ctggggctcg ataccgtcga 9180
cctctagcta gagcttggcg taatcatggt catagctgtt tcctgtgtga aattgttatc 9240
cgctcacaat tccacacaac atcgagccg gaagcataaa gtgtaaagcc tagggtgcct 9300
aatgagtgag ctaactcaca ttaattgcgt tgcgctcact gcccgctttc cagtcgggaa 9360
acctgtcgtg ccagctgcat taatgaatcg gccaacgcgc ggggagaggc ggtttgcgta 9420
ttgggcgctc ttccgcttcc tcgctcactg actcgctgcg ctcggtcgtt cggctgcggc 9480
gagcggtatc agctcactca aaggcggtaa tacggttatc cacagaatca ggggataacg 9540
caggaaagaa catgtgagca aaaggccagc aaaaggccag gaaccgtaaa aaggccgcgt 9600
tgctggcgtt tttccatagg ctccgccccc ctgacgagca tcacaaaaat cgacgctcaa 9660
gtcagaggtg gcgaaacccg acaggactat aaagataccag gcgtttccc cctggaagct 9720
ccctcgtgcg ctctcctgtt ccgaccctgc cgcttaccgg atacctgtcc gcctttctcc 9780
cttcgggaag cgtggcgctt tctcatagct cacgctgtag gtatctcagt tcggtgtagg 9840
tcgttcgctc caagctgggc tgtgtgcacg aaccccccgt tcagcccgac cgctgcgcct 9900
tatccggtaa ctatcgtctt gagtccaacc cggtaagaca cgacttatcg ccactggcag 9960
cagccactgg taacaggatt agcagagcga ggtatgtagg cggtgctaca gagttcttga 10020
agtggtggcc taactacggc tacactagaa gaacagtatt tggtatctgc gctctgctga 10080
agccagttac cttcggaaaa agagttggta gctcttgatc cggcaaacaa accaccgctg 10140
gtagcggtgg tttttttgtt tgcaagcagc agattacgcg cagaaaaaaa ggatctcaag 10200
aagatccttt gatcttttct acggggtctg acgctcagtg gaacgaaaac tcacgttaag 10260
ggatttggt catgagatta tcaaaaagga tcttcaccta gatcctttta aattaaaaat 10320
gaagttttaa atcaatctaa agtatatatg agtaaacttg gtctgacagt taccaatgct 10380
taatcagtga ggcacctatc tcagcgatct gtctatttcg ttcatccata gttgcctgac 10440
tccccgtcgt gtagataact acgatacggg agggcttacc atctggcccc agtgctgcaa 10500
tgataccgcg agacccacgc tcaccggctc cagatttatc agcaataaac cagccagccg 10560
gaagggccga gcgcagaagt ggtcctgcaa ctttatccgc ctccatccag tctattaatt 10620
gttgccggga agctagagta agtagttcgc cagttaatag tttgcgcaac gttgttgcca 10680
ttgctacagg catcgtggtg tcacgctcgt cgtttggtat ggcttcattc agctccggtt 10740
cccaacgatc aaggcgagtt acatgatccc ccatgttgtg caaaaaagcg gttagctcct 10800
tcggtcctcc gatcgttgtc agaagtaagt tggccgcagt gttatcactc atggttatgg 10860
cagcactgca taattctctt actgtcatgc catccgtaag atgcttttct gtgactggtg 10920
agtactcaac caagtcattc tgagaatagt gtatgcggcg accgagttgc tcttgcccgg 10980
cgtcaatacg ggataatacc gcgccacata gcagaacttt aaaagtgctc atcattggaa 11040
aacgttcttc ggggcgaaaa ctctcaagga tcttaccgct gttgagatcc agttcgatgt 11100
aacccactcg tgcacccaac tgatcttcag catcttttac tttcaccagc gtttctgggt 11160
gagcaaaaac aggaaggcaa aatgccgcaa aaaagggaat aagggcgaca cggaaatgtt 11220
gaatactcat actcttcctt tttcaatatt attgaagcat ttatcagggt tattgtctca 11280
tgagcggata catatttgaa tgtatttaga aaaataaaca ataggggtt ccgcgcacat 11340
ttcc                                                                11344
```

| SEQ ID NO: 382 | moltype = DNA length = 9753 |
|---|---|
| FEATURE | Location/Qualifiers |
| misc_feature | 1..9753 |
| | note = Description of Artificial Sequence: Synthetic polynucleotide |
| source | 1..9753 |
| | mol_type = other DNA |
| | organism = synthetic construct |

SEQUENCE: 382

```
ccgaaaagtg ccacctgacg tcgacggatc gggagatcga tctcccgatc ccctagggtc 60
gactctcagt acaatctgct ctgatgccgc atagttaagc cagtatctgc tccctgcttg 120
tgtgttggag gtcgctgagt agtgcgcgag caaaatttaa gctacaacaa ggcaaggctt 180
gaccgacaat tgcatgaaga atctgcttag ggttaggcgt tttgcgctgc ttcgcgatgt 240
acgggccaga tatacgcgtt gacattgatt ttgactagt tattaatagt aatcaattac 300
ggggtcatta gttcatagcc catatatgga gttccgcgtt acataactta cggtaaatgg 360
cccgcctggc tgaccgccca acgaccccg cccattgacg tcaataatga cgtatgttcc 420
catagtaacg ccaataggga cttttccattg acgtcaatgg gtggagtatt tacggtaaac 480
tgcccacttg gcagtacatc aagtgtatca tatgccaagt acgccccta ttgacgtcaa 540
tgacggtaaa tggcccgcct ggcattatgc ccagtacatg accttatggg actttcctac 600
ttggcagtac atctacgtat tagtcatcgc tattaccatg gtgatgcggt tttggcagta 660
catcaatggg cgtggatagc ggtttgactc acggggattt ccaagtctcc accccattga 720
cgtcaatggg agtttgtttt ggcaccaaaa tcaacgggac tttccaaaat gtcgtaacaa 780
ctccgcccca ttgacgcaaa tgggcggtag gcgtgtacgg tgggaggtct atataagcag 840
agctggttta gtgaaccgtc agatccgcta gagatccgcg gccgctaata cgactcacta 900
tagggagagc cgccaccatg aaacggacag ccgacggaag cgagttcgag tcaccaaaga 960
agaagcgaa agtcgacaag agtacagca tcggcctgga catcggcacc aactctgtgg 1020
gctgggcggt gatcagcgac gagtcaaagg tgcccagaa gaaattcaaa gtgctgggca 1080
acaccgaccg gcacagcatc aagaagaacc tgatcggagc cctgctgttc gacagcggcg 1140
aaacagccga ggccacccgg ctgaagagaa ccgccagaag aagataccc agacggaaga 1200
accggatctg ctatctgcaa gagatcttca gcaacgagat ggccaaggtg gacgacagct 1260
tcttccacag actggaagag tccttcctgg tggaagagga taagaagcac gagcggcacc 1320
ccatcttccg caacatcgtg gacgaggtgg cctaccacga gaagtacccc accatctacc 1380
```

```
acctgagaaa gaaactggtg gacagcaccg acaaggccga cctgcggctg atctatctgg   1440
ccctggccca catgatcaag ttccggggcc acttcctgat cgagggcgac ctgaaccccg   1500
acaacagcga cgtggacaag ctgttcatcc agctggtgca gacctacaac cagctgttcg   1560
aggaaaaccc catcaacgcc agcggcgtgg acgccaaggc catcctgtct gccagactga   1620
gcaagacag acggctggaa aatctgatcg cccagctgcc cggcgagaag aagaatggcc   1680
tgttcggaaa cctgattgcc ctgagcctgg gcctgacccc caacttcaag agcaacttcg   1740
acctggccga ggatgccaaa ctgcagctga gcaaggacac ctacgacgac gacctggaca   1800
acctgctggc ccagatcggc gaccagtacg ccgacctgtt tctggccgcc aagaacctgt   1860
ccgacgccat cctgctgagc gacatcctga gagtgaaccac cgagatcacc aaggcccccc   1920
tgagcgcctc tatgatcaag agatacgacg agcaccacca ggacctgacc ctgctgaaag   1980
ctctcgtgcg gcagcagctg cctgagaagt acaaagagat tttcttcgac cagagcaaga   2040
acggctacgc cggctacatt gacggcgag ccagccagga gagttctac aagttcatca   2100
agcccatcct ggaaaagatg gacggcaccg aggaactgct cgtgaagctg aacagagagg   2160
acctgctgcg gaagcagcgg accttcgaca acggcagcat ccccaccag atccacctgg   2220
gagagctgca cgccattctg cggcggcagg aagattttta cccattcctg aaggacaacc   2280
gggaaaagat cgaccttcc gcatccccta ctacgtgggc cctctggcca   2340
ggggaaacag cagattcgcc tggatgacca gaaagagcga ggaaaccatc accccctgga   2400
acttcgagga agtggtggac aagggcgctt ccgcccagag cttcatcgag cggatgacca   2460
acttcgataa gaacctgccc aacgagaagg tgctgcccaa gcacagcctg ctgtacgagt   2520
acttcaccgt gtataacgag ctgaccaaag tgaaatacgt gaccgaggga atgagaaagc   2580
ccgccttcct gagcggcgag cagaaaaagg ccatcgtgga cctgctgttc aagaccaacc   2640
ggaaagtgac cgtgaagcag ctgaaagagg actacttcaa gaaaatcgaa tgcttcgact   2700
ccgtggaaat ctccggcgtg gaagatcggt tcaacgcctc cctgggcaca taccacgatc   2760
tgctgaaaat tatcaaggac aaggacttcc tggacaatga ggaaaacgag acattctgg   2820
aagatatcgt gctgaccctg acactgtttg aggacagaga gatgatcgag aacggctga   2880
aaacctatgc ccacctgttc gacgacaaag tgatgaagca gctgaagcgg cggagataca   2940
ccggctgggg caggctgagc cggaagctga tcaacggcat ccgggacaag cagtccggca   3000
agacaatcct ggatttcctg aagtccgacg gcttcgccaa cagaaacttc atgcagctga   3060
tccacgacga cagcctgacc tttaaagagg acatccagaa agcccaggtg tccggccagg   3120
gcgatagcct gcacgagcac attgccaatc tggccggcag ccccgccatt aagaagggca   3180
tcctgcagac agtgaaggtg gtggacgagc tcgtgaaagt gatgggccgg cacaagcccg   3240
agaacatcgt gatcgaaatg gccagagaga accagaccac ccagaaggga cagaagaaca   3300
gccgcgagaa aatgaagcgg atcgagagg gcatcaaaga gctgggcagc cagatcctga   3360
aagaacaccc cgtggaaaac acccagctgc agaacgagaa gctgtacctg tactacctgc   3420
agaatgggcg ggatatgtac gtggaccagg aactggacat caaccggctg tccgactacg   3480
atgtggacgc tatcgtgcct cagagctttc tgaaggacga ctccatcgac aacaaggtgc   3540
tgaccagaag cgacaagaac cggggcaaga gcgacaacgt gcccctccgaa gaggtcgtga   3600
agaagatgaa gaactactgg cggcagctgc tgaacgccaa gctgattacc cagagaaagt   3660
tcgacaatct gaccaaggcc gagagaggcg gcctgagcga actggataag gccggcttca   3720
tcaagagaca gctggtggaa accggcagca tcacaaagca cgtggcacag atcctggact   3780
cccggatgaa cactaagtac gacgagaatg acaagctgat ccgggaagtg aaagtgatca   3840
ccctgaagtc caagctggtg tccgatttcc ggaaggattt ccagtttac aaagtgcgcg   3900
agatcaacaa ctaccaccac gcccacgacg cctacctgaa cgccgtcgtg ggaaccgcca   3960
tgatcaaaaa gtaccctaag ctggaaagcg agttcgtgta cggcgactac aaggtgtacg   4020
acgtgcggaa gatgatcgcc aagagcgagc aggaaatcgg caaggctacc gccaagtact   4080
tcttctacag caacatcatg aactttttca agaccgagat taccctggcc aacggcgaga   4140
tccggaagcg gcctctgatc gagacaaacg gcgaaaccgg ggatcgtg tgggataagg   4200
gccgggattt tgccaccgtg cggaaagtgc tgagcatgcc ccaagtgaat atcgtgaaaa   4260
agaccgaggt gcagacaggc ggcttcagca aagagtctat cctgcccaag aggaacagcg   4320
ataagctgat cgccagaaag aaggactggg accctaagaa gtacggcggc ttcgacagcc   4380
ccaccgtggc ctattctgtg ctggtggtgg ccaaagtgga aaagggcaag tccaagaaac   4440
tgaagagtgt gaaagagctg ctggggatca ccatcatgga aagaagcagc ttcgagaaga   4500
atcccatcga ctttctggaa gccaagggct acaaagaagt gaaaaaggac ctgatcatca   4560
agctgcctaa gtactccctg ttcgagctgg aaaacggccg gaagagaatg ctggcctctg   4620
ccggcgaact gcagaaggga aacgaactgg ccctgccctc caaatatgtg aacttcctgt   4680
acctggccag ccactatgag aagctgaagg gctcccccga ggataatgag cagaaacagc   4740
tgttgtgga acagcacaag cactacctgg acgagatcat cgagcagatc agcgagttct   4800
ccaagagagt gatcctggcc gacgctaatc tggacaaagt gctgtccgcc tacaacaagc   4860
accgggataa gcccatcaga gagcaggccg agaatatcat ccacctgttt accctgacca   4920
atctgggagc ccctgccgcc ttcaagtact ttgacaccac catcgaccgg aagaggtaca   4980
ccagcaccaa agaggtgctg gacgccaccc tgatccacca gagcatcacc ggcctgtacg   5040
agacacggat cgacctgtct cagctgggag gtgactctgg aggatctagc ggaggatcct   5100
ctggcagcga gacaccagga acaagcgagt cagcaacacc agagagcagt ggcggcagca   5160
gcggcggcag cagcaccccta aatatagaag atgagtatcg gctacatgag acctcaaaag   5220
agccagatgt ttctctaggg tccacatggc tgtctgattt tcctcaggcc tgggcggaaa   5280
ccgggggcat gggactggca gttcgccaag ctcctctgat catacctctg aaagcaacct   5340
ctaccccgt gtccataaaa caatacccca tgtcacaaga agccagactg gggatcaagc   5400
cccacataca gagactgttg gaccaggaa tactggtacc ctgccagtcc ccctggaaca   5460
cgccctgct acccgttaag aaaccaggga ctaatgatta taggcctgtc caggatctga   5520
gagaagtcaa caagcgggtg gaagacatcc accccaccgt gcccaaccct tacaacctct   5580
tgagcgggct cccaccgtcc caccagtggt acactgtgct tgatttaaag gatgcctttt   5640
tctgcctgag actccacccc accagtcagc ctctcttcgc ctttgagtgg agagatccag   5700
agatgggaat ctcaggacaa ttgacctgga ccagactccc acagggtttc aaaaacagtc   5760
ccaccctgtt taatgaggca ctcacagag acctagcaga cttccgggatc ctgagcaccag   5820
acttgatcct gctacagtac gtggatgact tactgctgca cgccacttct gagctagact   5880
gccaacaagg tactcgggcc ctgttacaaa ccctagggaa cctcgggtat cgggcctcgg   5940
ccaagaaagc ccaaatttgc cagaaacagg tcaagtatct ggggtatctt ctaaaagagg   6000
gtcagagatg gctgactgag gccagaaaag agactgtgat ggggcagcct actccgaaga   6060
cccctcgaca actaagggag ttcctaggga aggcaggctt ctgtcgcctc ttcatccctg   6120
```

```
ggtttgcaga aatggcagcc ccctgtacc ctctcaccaa accgggact ctgtttaatt   6180
ggggcccaga ccaacaaaag gcctatcaag aaatcaagca agctcttcta actgccccag   6240
ccctgggtt gccagatttg actaagccct ttgaactctt tgtcgacgag aagcagggct   6300
acgccaaagg tgtcctaacg caaaaactgg daccttggcg tcggccggtg gcctacctgt   6360
ccaaaaagct agacccagta gcagctgggt ggccccttg cctacggatg gtagcagcca   6420
ttgccgtact gacaaaggat gcaggcaagc taaccatggg acagccacta gtcattctgg   6480
ccccccatgc agtagaggca ctagtcaaac aaccccccga ccgctggctt tccaacgccc   6540
ggatgactca ctatcaggcc ttgcttttgg acacggaccg gtccagttc ggaccggtgg   6600
tagccctgaa cccggctacg ctgctcccac tgcctgagga agggctgcaa cacaactgtc   6660
ttgatatcct ggccgaagcc cacggaaccc gacccgacct aacggaccag ccgctcccag   6720
acgccgacca cacctggtac acggatggaa gcagtctctt acaagaggga cagcgtaagg   6780
cgggagctgc ggtgaccacc gagaccgagg taatctgggc taaagccctg ccagccggga   6840
catccgctca gcgggctgaa ctgatagcac tcacccaggc cctaaagatg gcagaaggta   6900
agaagctaaa tgtttatact gatagccgtt atgcttttgc tactgcccat atccatggag   6960
aaatatacag aaggcgtggg tggctcacat cagaaggcaa agagatcaaa aataaagacg   7020
agatcttggc cctactaaaa gccctctttc tgcccaaaag acttagcata atccattgtc   7080
caggacatca aaagggacac agcgccgagg ctagaggcaa ccggatggct gaccaagcgg   7140
cccgaaaggc agccatcaca gagactccag acacctctac cctcctcata gaaaattcat   7200
caccctctgg cggctcaaaa agaaccgccg acggcagcga attcgagccc aagaagaaga   7260
ggaaagtcta accggtcatc atcaccatca ccattgagtt taaacccgct gatcagcctc   7320
gactgtgcct tctagttgcc agccatctgt tgtttgcccc tcccccgtgc cttccttgac   7380
cctgaaaggt gccatcccca ctgtcctttc ctaataagat gagaaaattg catcgcattg   7440
tctgagtagg tgtcattcta ttctgggggg tgggtgggg caggacagca aggggagga   7500
ttgggaagac aatagcaggc atgctgggga tgcggtgggc tctatggctt ctgaggcgga   7560
aagaaccagc tggggctcga taccgtcgac ctctagctag agcttggcgt aatcatggtc   7620
atagctgttt cctgtgtgaa attgttatcc gctcacaatt ccacacaaca tacgagccgg   7680
aagcataaag tgtaaagcct agggtgccta atgagtgagc taactcacat taattgcgtt   7740
gcgctcactg cccgctttcc agtcgggaaa cctgtcgtgc cagctgcatt aatgaatcgg   7800
ccaacgcgcg gggagaggcg gtttgcgtat gggcgctct ccgcttcct cgctcactga   7860
ctcgctgcgc tcggtcgttc ggctgcggcg agcggtatca gctcactcaa aggcggtaat   7920
acggttatcc acagaatcag gggataacgc aggaaagaac atgtgagcaa aaggccagca   7980
aaaggccagg aaccgtaaaa aggccgcgtt gctggcgttt ttccataggc tccgccccc   8040
tgacgagcat cacaaaaatc gacgctcaag tcagaggtgg cgaaacccga caggactata   8100
aagataccag gcgtttcccc ctggaagctc cctcgtgcgc tctcctgttc cgaccctgcc   8160
gcttaccgga tacctgtccg cctttctccc ttcgggaagc gtggcgcttt ctcatagctc   8220
acgctgtagg tatctcagtt cggtgtaggt cgttcgctcc aagctgggct gtgtgcacga   8280
accccccgtt cagcccgacc gctgcgcctt atccggtaac tatcgtcttg agtccaaccc   8340
ggtaagacac gacttatcgc cactggcagc agccactggt aacaggatta gcagagcgag   8400
gtatgtaggc ggtgctacag agttcttgaa gtggtggcct aactacggct acactagaag   8460
aacagtattt ggtatctgcg ctctgctgaa gccagttacc ttcggaaaaa gagttggtag   8520
ctcttgatcc ggcaaacaaa ccaccgctgg tagcggtggt ttttttgttt gcaagcagca   8580
gattacgcgc agaaaaaaag gatctcaaga agatcctttg atcttttcta cggggtctga   8640
cgctcagtgg aacgaaaact cacgttaagg gattttggtc atgagattat caaaaaggat   8700
cttcacctag atccttttaa attaaaaatg aagttttaaa tcaatctaaa gtatatatga   8760
gtaaacttgg tctgacagtt accaatgctt aatcagtgag gcacctatct cagcgatctg   8820
tctatttcgt tcatccatag ttgcctgact ccccgtcgtg tagataacta cgatacggga   8880
gggcttacca tctggcccca gtgctgcaat gataccgcga gacccacgct caccggctcc   8940
agatttatca gcaataaacc agccagccgg aagggccgag cgcagaagtg gtcctgcaac   9000
tttatccgcc tccatccagt ctattaattg ttgccgggaa gctagagtaa gtagttcgcc   9060
agttaatagt ttgcgcaacg ttgttgccat tgctacaggc atcgtggtgt cacgctcgtc   9120
gtttggtatg gcttcattca gctccggttc caaacgatca aggcgagtta catgatcccc   9180
catgttgtgc aaaaaagcgg ttagctcctt cggtcctccg atcgttgtca gaagtaagtt   9240
ggccgcagtg ttatcactca tggttatggc agcactgcat aattctctta ctgtcatgcc   9300
atccgtaaga tgcttttctg tgactggtga gtactcaacc aagtcattct gagaatagtg   9360
tatgcggcga ccgagttgct cttgcccggc gtcaatacgg gataataccg cgccacatag   9420
cagaacttta aaagtgctca tcattggaaa acgttcttcg gggcgaaaac tctcaaggat   9480
cttaccgctg ttgagatcca gttcgatgta acccactcgt gcacccaact gatcttcagc   9540
atcttttact ttcaccagcg tttctgggtg agcaaaaaca ggaaggcaaa atgccgcaaa   9600
aaagggaata agggcgacac ggaaatgttg aatactcata ctcttccttt ttcaatatta   9660
ttgaagcatt tatcagggtt attgtctcat gagcggatac atatttgaat gtatttagaa   9720
aaataaacaa ataggggttc cgcgcacatt tcc                                9753
```

SEQ ID NO: 383        moltype = DNA  length = 11433
FEATURE              Location/Qualifiers
misc_feature         1..11433
                     note = Description of Artificial Sequence: Synthetic
                     polynucleotide
source               1..11433
                     mol_type = other DNA
                     organism = synthetic construct
SEQUENCE: 383

```
ccgaaaagtg ccacctgacg tcgacggatc gggagatcga tctcccgatc ccctagggtc    60
gactctcagt acaatctgct ctgatgccgc atagttaagc cagtatctgc tccctgcttg   120
tgtgttggag gtcgctgagt agtgcgcgag caaaatttaa gctacaacaa ggcaaggctt   180
gaccgacaat tgcatgaaga atctgcttag ggttaggcgt tttgcgctgc ttcgcgatgt   240
acgggccaga tatacgcgtt gacattgatt attgactagt tattaatagt aatcaattac   300
ggggtcatta gttcatagcc catatatgga gttccgcgtt acataactta cggtaaatgg   360
cccgcctggc tgaccgccca acgaccccg cccattgacg tcaataatga cgtatgttcc   420
catagtaacg ccaataggga cttttccattg acgtcaatgg gtggagtatt tacggtaaac   480
```

```
tgcccacttg gcagtacatc aagtgtatca tatgccaagt acgccccta ttgacgtcaa   540
tgacggtaaa tggcccgcct ggcattatgc ccagtacatg accttatggg actttcctac   600
ttggcagtac atctacgtat tagtcatcgc tattaccatg gtgatgcggt tttggcagta   660
catcaatggg cgtggatagc ggtttgactc acggggattt ccaagtctcc accccattga   720
cgtcaatggg agtttgtttt ggcaccaaaa tcaacgggac tttccaaaat gtcgtaacaa   780
ctccgcccca ttgacgcaaa tgggcggtag gcgtgtacgg tgggaggtct atataagcag   840
agctggttta gtgaaccgtc agatccgcta gagatccgcg gccgctaata cgactcacta   900
tagggagagc cgccaccatg cccgcggcta agagggtgaa gcttgacggt ggaaaacgga   960
cagccgacgg aagcgagttc gagtcaccaa agaagaagcg gaaagtcgac aagaagtaca  1020
gcatcggcct ggacatcggc accaactctg tgggctgggc cgtgatcacc gacgagtaca  1080
aggtgcccag caagaaattc aaggtgctgg gcaacaccga ccggcacagc atcaagaaga  1140
acctgatcgg agccctgctg ttcgacagcg gcgaaacagc cgaggccacc cggctgaaga  1200
gaaccgccaa gaagaagatac accagacgga gaaccggat ctgctatctg caagagatct  1260
tcagcaacga gatggccaag gtggacgaca gcttcttcca cagactggaa gagtccttcc  1320
tggtggaaga ggataagaag cacgagcggc accccatctt cggcaacatc gtggacgagg  1380
tggcctacca cgagaagtac cccaccatct accacctgag aaagaaactg gtggacagca  1440
ccgacaaggc cgacctgcgg ctgatctatc tggccctggc ccacatgatc aagttccggg  1500
gccacttcct gatcgagggc gacctgaacc ccgacaacag cgacgtggac aagctgttca  1560
tccagctggt gcagacctac aaccagcgt tcgaggaaaa ccccatcaac gccagcggcg  1620
tggacgccaa ggccatcctg tctgccgagac tgagcaagag cagacggctg gaaaatctga  1680
tcgcccagct gcccggcgag aagaagaatg gcctgttcgg aaacctgatt gccctgagcc  1740
tgggcctgac ccccaacttc aagagcaact tcgacctggc agaggatgcc aaactgcagc  1800
tgagcaagga cacctacgac gacgacctgg acaacctgct ggcccagatc ggcgaccagt  1860
acgccgacct gttctggcc gccaagaacc tgtccgacgc catcctgctg agcgacatcc  1920
tgagagtgaa caccgagatc accaaggccc cctgagcgc ctctatgatc aagagatacg  1980
acgagcacca ccaggacctg accctgctga agctctccgt gcggcagcag ctgcctgaga  2040
gtacaaaga gatttttcttc gaccagagca gaacggcta cgccggctac attgacggca  2100
gagccagcca ggaagagttc tacaagttca tcaagcccat cctggaaaag atggacggca  2160
ccgaggaact gctcgtgaag ctgaacagag aggacctgct gcggaagcag cggaccttcg  2220
acaacggcag catccccac cagatccacc tgggagagct gcacgccatt ctgcggcggc  2280
aggaagattt ttacccattc ctgaaggaca accgggaaaa gatcgagaag atcctgacct  2340
tccgcatccc ctactacgtg ggccctctgg ccaggggaaa cagcagattc gcctggatga  2400
ccagaaagag cgaggaaacc atcacccct ggaacttcga ggaagtggtg acaagggcg  2460
cttccgcgga gagcttcatc gagcggatga ccaacttcga taagaacctg cccaacgaga  2520
aggtgctgcc caagcacagc ctgctgtacg agtacttcac cgtgtataac gagctgacca  2580
aagtgaaata cgtgaccgag ggaatgagaa agcccgcctt cctgagcggc gagcagaaaa  2640
aggccatcgt ggacctgctg ttcaagacca accggaaagt gaccgtgaag cagctgaaag  2700
aggactactt caagaaaatc gagtgcttcg actccgtgga aatctccggc gtggaagatc  2760
ggttcaacgc ctccctgggc acataccacg atctgctgaa aattatcaag gacaaggact  2820
tcctggacaa tgaggaaaac gaggacattc tggaagatat cgtgctgacc ctgacactgt  2880
ttgaggacag agagatgatc gaggaacggc tgaaaaccta tgcccacctg ttcgacgaca  2940
aagtgatgaa gcagctgaag cggcgagat acaccggctg gggcaggctg agccggaagc  3000
tgatcaacgg catccgggac aagcagtccg caagacaat cctggatttc ctgaagtcgc  3060
acggcttcgc caacagaaac ttcatgcagc tgatccacga cgacagcctg acctttaaag  3120
aggacatcca gaaagcccag gtgtccggcc agggcgatag cctgcacgag cacattgcca  3180
atctggccgg cagccccgcc attaagaagg gcatcctgca gacagtgaag gtggtggacg  3240
agctcgtgaa agtgatgggc cggcacaagc ccgagaacat cgtgatcgaa atggccagag  3300
agaaccagac cacccagaag ggacagaaga cagccgcga gaatgaag cggatcgaag  3360
agggcatcaa agagctgggc agccagatcc tgaaagaaca ccccgtggaa aacacccagc  3420
tgcagaacga gaagctgtac ctgtactacc tgcagaatgg gcgggatatg tacgtggacc  3480
aggaactgga catcaaccgg ctgtccgact acgatgtgga cgctatcgtg cctcagagct  3540
ttctgaagga cgactccatc gacaacaagg tgctgaccag aagcgacaag aaccggggca  3600
agagcgacaa cgtgccctcc gaagaggcg tgaagaagat gaagaactac tggcggcagc  3660
tgctgaacgc caagctgatt acccagagaa agttcgacaa tctgaccaag gccgagagag  3720
gcggcctgag cgaactggat aaggccgct tcatcaagag acagctgtg gaaaccctgc  3780
agatcacaaa gcacgtggca cagatcctgg actcccggat gaacactaag tacgacgaga  3840
atgacaagct gatccgggaa gtgaaagtga tcacctgaa gtccaagctg gtgtccgatt  3900
tccgaagga tttccagttt tacaaagtgc gcgagatcaa caactaccac cacgcccacg  3960
acgcctacct gaacgccgtc gtgggaaccg ccctgatcaa aaagtaccct aagctggaaa  4020
gcgagttcgt gtacggcgac tacaaggtgt acgacgtgcg gaagatgatc gccagagcg  4080
agcaggaaat cggcaaggct accgccaagt acttcttcta cagcaacatc atgaactttt  4140
tcaagaccga gattaccctg gccaacgcg agatccggaa gcggcctctg atcgagacaa  4200
acggcgaaac cggggagatc gtgtgggata gggcccggga ttttgccacc gtgcggaaag  4260
tgctgagcat gccccaagtg aatatcgtga aaaagaccga ggtgcagaca ggcgttca  4320
gcaaagagtc tatcctgccc aagaggaaca gcgataagct gatcgccaga aagaaggact  4380
gggacccta agagtacggc ggcttcgaca gccccaccgt ggctattct gtgctggtgg  4440
tggccaaagt ggaaaaggc aagtccaaga aactgaagag tgtgaaagag ctgctgggga  4500
tcaccatcat ggaaagaagc agcttcgaga agaatcccat cgactttctg gaagccaagg  4560
gctacaaaga agtgaaaaag gacctgatca tcaagctgcc taagtactcc ctgttcgagc  4620
tggaaaacgg ccggaagaga atgctggcct ctgccggcga actgcagaag ggaaacgaac  4680
tggccctgcc ctccaaatat gtgaacttcc tgtacctggc cagccactat gagaagctga  4740
agggctcccc cgaggataat gagcagaaac agctgtttgt ggaacagcac aagcactacc  4800
tggacgagat catcgagcag atcagcgagt ctccaagag agtgatcctg gccgacgcta  4860
atctggacaa agtgctgtcc gcctacaaca agcaccggga taagcccatc agagagcagg  4920
ccgagaatat catccacctg tttaccctga ccaatctggg agcccctgcc gccttcaagt  4980
actttgacac caccatcgac cggaagagg acaccagcac caagaggtg ctggacgcca  5040
ccctgatcca ccagagcatc accggcctgt acgagacacg gatcgacctg tctcagctgg  5100
gaggtgactc tggaggatct agcggaggat cctctgcag cgagacacca ggaacaagcg  5160
agtcagcaac accagagagc agtggcggca gcagcggcgg cagcagcacc ctaaatatag  5220
```

```
aagatgagta tcggctacat gagacctcaa aagagccaga tgtttctcta gggtccacat   5280
ggctgtctga ttttcctcag gcctgggcgg aaaccggggg catgggactg gcagttcgcc   5340
aagctcctct gatcatacct ctgaaagcaa cctctacccc cgtgtccata aaacaatacc   5400
ccatgtcaca agaagccaga ctggggatca agccccacat acagagactg ttggaccagg   5460
gaatatggta ccctgccagt cccccctgga cacgcccctg ctacccgtta agaaaccagg   5520
gactaatgat tataggcctg tccaggatct gagagaagtc aacaagcggg tggaagacat   5580
ccacccacc gtgcccaacc cttacaacct cttgagcggg ctccaccgt cccaccagtg    5640
gtacactgtg cttgatttaa aggatgcctt tttctgcctg agactccacc ccaccagtca   5700
gcctctcttc gcctttgagt ggagagatcc agagatggga atctcaggac aattgacctg   5760
gaccagactc ccacagggtt tcaaaaacag tcccaccctg tttaatgagg cactgcacag   5820
agacctagca gacttccgga tccagcaccc agacttgatc ctgctacagt acgtggatga   5880
cttactgctg gccgccactt ctgagctaga ctgccaacaa ggtactcggg ccctgttaca   5940
aaccctaggg aacctcgggt atcgggcctc ggccaagaaa gcccaaattt gccagaaaca   6000
ggtcaagtat ctgagggtatc ttctaaaaga gggtcagaaa tggctgactg aggccagaaa   6060
agagactgtg atggggcagc ctactccgaa gaccccctcga caactaaggg agttcctagg   6120
gaaggcaggc ttctgtcgcc tcttcatccc tgggtttgca gaaatggcag ccccccctgta  6180
ccctctcacc aaaccgggga ctctgtttaa ttggggccca gaccaacaaa aggcctatca   6240
agaaatcaag caagctcttc taactgcccc agccctgggg ttgccagatt tgactaagcc   6300
cttttgaactc tttgtcgacg agaagcaggg ctacgccaaa ggtgtcctaa cgcaaaaact   6360
gggaccttgg cgtcggccgg tggcctacct gtccaaaaag ctagcccag tagcagctgg   6420
gtggcccct tgcctacgga tggtagcagc cattgccgta ctgacaaagg atgcaggcaa   6480
gctaaccatg ggacagccac tagtcattct ggcccccccat gcagtagagg cactagtcaa   6540
acaaccccc gaccgctggc tttcaacgc ccgatgact cactatcagg ccttgctttt    6600
ggacacggac cgggtccagt tcggaccggt ggtagccctg aacccggcta cgctgctccc   6660
actgcctgag gaagggctgc aacacaactg ccttgatatc ctggccgaag cccacggaac   6720
ccgacccgac ctaacggacc agccgctccc agacgccgac cacacctggt acacggatgg   6780
aagcagtctc ttacaagagg gacacgtaa ggcgggagct gcggtgacca ccgagaccga   6840
ggtaatctgg gctaaagccc tgccagccgg gacatccgct cagcgggctg aactgatagc   6900
actcacccag gccctaaaga tggcagaagg taagaagcta aatgtttata ctgatagccg   6960
ttatgctttt gctactgccc atatccatgg agaaatatac agaaggcgtg ggtggctcac   7020
atcagaaggc aaaagatca aaataaaga cgagatcttg gccctactaa aagccctctt   7080
tctgcccaaa agacttagca taatccattg tccaggacat caaaagggac acagcgccga   7140
ggctagaggc aaccggatgg ctgaccaagc ggcccgaaag gcagccatca cagagactcc   7200
agacacctct accctcctca tagaaaattc atcaccctct ggcggctcaa aaagaaccgc   7260
cgacggcagc gaaaaaagaa ccgctgactc tcaacattcc acacctccaa aaaccaagcg   7320
aaaagtggaa ttcgagccca agaagaagag gaaagtcgga agcggagcta ctaacttcag   7380
cctgctgaag caggctggcg acgtggagga gaaccctgga cctccaaaaa agaaaagaaa   7440
agtgtatccc tatgatgtcc ccgattatgc cggttcaaga gccctggtcg tgattagact   7500
gagccgagtg acagacgcca ccacaagtcc cgagagacag ctggaatcat gccagcagct   7560
ctgtgctcag cggggttggg atgtggtcgg cgtggcagag gatctggacg tgagcggggc   7620
cgtcgatcca ttcgacagaa agaggaggcc caacctggca agatggctcg ctttcgagga   7680
acagcccttt gatgtgatcg tcgcctacag agtggaccctg ctgacccgct caattcgaca   7740
tctccagcag ctggtgcatt gggctgagga ccacaagaaa ctggtggtca gcgcaacaga   7800
agcccacttc gatactacca caccttttgc cgctgtggtc atcgcactga tgggcactgt   7860
ggcccagatg gagctcgaag ctatcaagga gcgaaacagg agcgcagccc atttcaatat   7920
tagggccggt aaatacagag gctccctgcc cccttgggga tatctcccta ccagggtgga   7980
tggggatgg agactggtgc cagacccccgt ccagagagag cggattctgg aagtgtacca   8040
cagagtggtc gataaccacg aaccactcca tctggtggca cacgacctga atagacgcgg   8100
cgtgctctct ccaaaggatt attttgctca gctgcaggga agagagccac agggaagaga   8160
atggagtgct actgcactga agagatctat gatcagtgag ctatgctgg gttacgcaac    8220
actcaatgcc aaaactgtcc gggacgatga cggagcccct ctggtgaggg ctgagcctat   8280
tctcaccaga gagcagctcg aagctctgcg ggcagaactg gtcaagacta gtcgcgccaa   8340
acctgccgtg agcacccca gcctgctcct gagggtgctg ttctgcgccg tctgtggaga   8400
gccagcatac aagtttgccg gcggagggcg caaacatccc cgctatcgat gcaggagcat   8460
gggttccct aagcactgtg gaaacggac agtggccatg gctgagtggg acgccttttg   8520
cgaggaacag gtgctggatc tcctgggtga cgctgagcgg ctggaaaaag tgtgggtggc   8580
aggatctgac tccgctgtgg agctggcaga agtcaatgcc gagctcgtgg atctgacttc   8640
cctcatcgga tctcctgcat atagagctgg gtccccacag agagaagctc tggacgcacg   8700
aattgctgca ctcgctgcta gacaggagga actggagggc ctggaggcca ggccctctgg   8760
atgggagtgg cgagaaaccg gacagaggtt tggggattgg tggagggagc aggacaccgc   8820
agccaagaac acatgggctga gatccatgaa tgtccggctc acattcgacg tgcgcggtgg   8880
cctgactcga accatcgatt ttggcgacct gcaggagtat gaacagcacc tgagactggg   8940
gtccgtggtc gaaagactgc acactgggat gtcctaggtt taaacccgct gatcagcctc   9000
gactgtgcct tctagttgcc agccatctgt tgtttgcccc tcccccgtgc cttccttgac   9060
cctggaaggt gccactccca ctgtcctttc ctaataaaat gagaaaattg catcgcattg   9120
tctgagtagg tgtcattcta ttctgggggg tggggtgggg caggacagca agggggagga   9180
ttgggaagac aatagcaggc atgctgggga tcggtgggc tctatggctt ctgaggcgga   9240
aagaaccagc tggggctcga taccgtcgac ctctagctag agcttggcgt aatcatggtc   9300
atagctgttt cctgtgtgaa attgttatcc gctcacaatt ccacacaaca tacgagccgg   9360
aagcataaag tgtaaagcct agggtgccta atgagtgagc taactcacat taattgcgtt   9420
gcgctcactg cccgctttcc agtcgggaaa cctgtcgtgc cagctgcatt aatgaatcgg   9480
ccaacgcgcg gggagaggcg gtttgcgtat gggcgctct ccgcttcct cgctcactga    9540
ctcgctgcgc tcggtcgttc ggctgcggcg agcggtatca gctcactcaa aggcggtaat   9600
acggttatcc acagaatcag gggataacgc aggaaagaac atgtgagcaa aaggccagca   9660
aaaggccagg aaccgtaaaa aggccgcgtt gctggcgttt ttccataggc tccgcccccc   9720
tgacgagcat cacaaaaatc gacgctcaag tcagaggtgg cgaaacccga caggactata   9780
aagataccag gcgtttcccc ctggaagctc cctcgtgcgc tctcctgttc cgaccctgcc   9840
gcttaccgga tacctgtccg cctttctccc ttcgggaagc gtggcgcttt ctcatagctc   9900
acgctgtagg tatctcagtt cggtgtaggt cgttcgctcc aagctgggct gtgtgcacga   9960
```

```
acccccgtt cagcccgacc gctgcgcctt atccggtaac tatcgtcttg agtccaaccc    10020
ggtaagacac gacttatcgc cactggcagc agccactggt aacaggatta gcagagcgag    10080
gtatgtaggc ggtgctacag agttcttgaa gtggtggcct aactacggct acactagaag    10140
aacagtattt ggtatctgcg ctctgctgaa gccagttacc ttcggaaaaa gagttggtag    10200
ctcttgatcc ggcaaacaaa ccaccgctgg tagcggtggt ttttttgttt gcaagcagca    10260
gattacgcgc agaaaaaaag gatctcaaga agatcctttg atcttttcta cggggtctga    10320
cgctcagtgg aacgaaaact cacgttaagg gattttggtc atgagattat caaaaaggat    10380
cttcacctag atccttttaa attaaaaatg aagttttaaa tcaatctaaa gtatatatga    10440
gtaaacttgg tctgacagtt accaatgctt aatcagtgag gcacctatct cagcgatctg    10500
tctatttcgt tcatccatag ttgcctgact cccgtcgtg tagataacta cgatacggga    10560
gggcttacca tctggcccca gtgctgcaat gataccgcga gacccacgct caccggctcc    10620
agatttatca gcaataaacc agccagccgg aagggccgag cgcagaagtg gtcctgcaac    10680
tttatccgcc tccatccagt ctattaattg ttgccgggaa gctagagtaa gtagttcgcc    10740
agttaatagt ttgcgcaacg ttgttgccat tgctacagge atcgtggtgt cacgctcgtc    10800
gtttggtatg gcttcattca gctccggttc ccaacgatca aggcgagtta catgatcccc    10860
catgttgtgc aaaaaagcgg ttagctcctt cggtcctccg atcgttgtca gaagtaagtt    10920
ggccgcagtg ttatcactca tggttatggc agcactgcat aattctctta ctgtcatgcc    10980
atccgtaaga tgcttttctg tgactggtga gtactcaacc aagtcattct gagaatagtg    11040
tatgcggcga ccgagttgct cttgcccggc gtcaatacgg gataataccg cgccacatag    11100
cagaacttta aaagtgctca tcattggaaa acgttcttcg gggcgaaaac tctcaaggat    11160
cttaccgctg ttgagatcca gttcgatgta acccactcgt gcacccaact gatcttcagc    11220
atcttttact ttcaccagcg tttctgggtg agcaaaaaca ggaaggcaaa atgccgcaaa    11280
aaagggaata agggcgacac ggaaatgttg aatactcata ctcttccttt ttcaatatta    11340
ttgaagcatt tatcagggtt attgtctcat gagcggatac atatttgaat gtatttagaa    11400
aaataaacaa atagggggttc cgcgcacatt tcc                                11433

SEQ ID NO: 384         moltype = DNA  length = 11056
FEATURE                Location/Qualifiers
misc_feature           1..11056
                       note = Description of Artificial Sequence: Synthetic
                        polynucleotide
source                 1..11056
                       mol_type = other DNA
                       organism = synthetic construct
SEQUENCE: 384
ccgaaaagtg ccacctgacg tcgacggatc gggagatcga tctcccgatc ccctagggtc      60
gactctcagt acaatctgct ctgatgccgc atagttaagc cagtatctgc tccctgcttg     120
tgtgttggag gtcgctgagt agtgcgcgag caaaatttaa gctacaacaa ggcaaggctt     180
gaccgacaat tgcatgaaga atctgcttag ggttaggcgt tttgcgctgc ttcgcgatgt     240
acgggccaga tatacgcgtt gacattgatt attgactagt tattaatagt aatcaattac     300
ggggtcatta gttcatagcc catatatgga gttccgcgtt acataactta cggtaaatgg     360
cccgcctggc tgaccgccca acgacccccg cccattgacg tcaataatga cgtatgttcc     420
catagtaacg ccaataggga cttttccattg acgtcaatgg gtggagtatt tacggtaaac     480
tgcccacttg gcagtacatc aagtgtatca tatgccaagt acgccccta ttgacgtcaa     540
tgacggtaaa tggcccgcct ggcattatgc ccagtacatg accttatggg acttcctac     600
ttggcagtac atctacgtat tagtcatcgc tattaccatg gtgatgcggt tttggcagta     660
catcaatggg cgtggatagc ggtttgactc acggggattt ccaagtctcc accccattga     720
cgtcaatggg agtttgtttt ggcaccaaaa tcaacgggac tttccaaaat gtcgtaacaa     780
ctccgcccca ttgacgcaaa tgggcggtag gcgtgtacgg tgggaggtct atataagcag     840
agctggttta gtgaaccgtc agatccgcta gagatccgcg ccgctaata cgactcacta     900
tagggagagc cgccaccatg aaacggacag cgacggcag cgagttcgag tcaccaaaga     960
agaagcggaa agtcgacaag aagtacagca tcggcctgga catcggcacc aactctgtgg    1020
gctgggccgt gatcaccgac gagtacaagg tgcccagcaa gaaattcaag gtgctgggca    1080
acaccgaccg gcacagcatc aagaagaacc tgatcggagc cctgctgttc gacagcggcg    1140
aaacagccga ggccaccccg gctgaaagaa ccgccagaag agatacacc agacggaaga    1200
accggatctg ctatctgcaa gagatcttca gcaacgagat ggccaaggtg gacgacagct    1260
tcttccacag actggaagag tccttcctgg tggaagagga taagaagcac gagcggcacc    1320
ccatcttcgg caacatcgtg gacgaggtgg cctaccacga gaagtacccc accatctacc    1380
acctgagaaa gaaactggtg gacagcaccg acaaggcga cctccggctg atctatctgg    1440
ccctggccca catgatcaag ttccggggcc acttcctgat cgagggcgac ctgaaccccg    1500
acaacagcga cgtggacaag ctgttcatcc agctggtgca gacctacaac cagctgttcg    1560
aggaaaaccc catcaacgcc agcggcgtgg acgccaaggc catcctgtct gccagactga    1620
gcaagagcag acggctggaa aatctgatcg cccagctgcc cggcgagaag aagaatggcc    1680
tgttcggaaa cctgattgcc ctgagcctgg gcctgaccc caacttcaag agcaacttcg    1740
acctggccga ggatgccaaa ctgcagctga gcaaggacac ctacgacgac gacctggaca    1800
acctgctggc ccagatcggc gaccagtacg ccgacctgtt tctggccgcc aagaacctgt    1860
ccgacgccat cctgctgagc gacatcctga gtgaacac cgagatcacc aaggccccc    1920
tgagcgcctc tatgatcaag agatacgacg agccaccca ggacctgacc ctgctgaaag    1980
ctctcgtgcg gcagcagctg cctgagaagt acaaagaggt tttcttcgac cagagcaaga    2040
acggctacgc cggctacatt gacggcgaga ccagccagga agagttctac aagttcatca    2100
agcccatcct ggaaaagatg gacggcaccg aggaactgct cgtgaagctg aacagagagg    2160
acctgctgcg gaagcagcgg accttcgaca acggcagcat ccccaccag atccacctgg    2220
gagagctgca cgccattctg cggcggcagg aagattttta cccattcctg aaggacaacc    2280
gggaaaagat cgagaagatc ctgaccttcc gcatccccta ctacgtggga ccctgctgga    2340
ggggaaacag cagattcgcc tggatgacca gaaagagcga ggaaaccatc accccctgga    2400
acttcgagga agtggtggac aagggcgctt ccgcccagag cttcatcgag cggatgacca    2460
acttcgataa gaacctgccc aacgagaagg tgctgcccaa gcacagcctg ctgtacgagt    2520
acttcaccgt gtataacgag ctgaccaaag tgaaatacgt gaccgaggga atgagaaagc    2580
ccgccttcct gagcggcgag cagaaaaagg ccatcgtgga cctgctgttc aagaccaacc    2640
```

```
ggaaagtgac cgtgaagcag ctgaaagagg actacttcaa gaaaatcgag tgcttcgact   2700
ccgtggaaat ctccggcgtg gaagatcggt tcaacgcctc cctgggcaca taccacgatc   2760
tgctgaaaat tatcaaggac aaggacttcc tggacaatga ggaaaacgag gacattctgg   2820
aagatatcgt gctgaccctg acactgtttg aggacagaga gatgatcgag gaacggctga   2880
aaacctatgc ccacctgttc gacgacaaag tgatgaagca gctgaagcgg cggagataca   2940
ccggctgggg caggctgagc cggaagctga tcaacggcat ccgggacaag cagtccggca   3000
agacaatcct ggatttcctg aagtccgacg gcttcgccaa cagaaacttc atgcagctga   3060
tccacgacga cagcctgacc tttaaagagg acatccagaa agcccaggtg tccggccagg   3120
gcgatagcct gcacgagcac attgccaatc tggccggcag ccccgccatt aagaagggca   3180
tcctgcagac agtgaaggtg gtggacgagc tcgtgaaagt gatgggccgg cacaagcccg   3240
agaacatcgt gatcgaaatg gccagagaga accagaccac ccagaaggga cagaagaaca   3300
gccgcgagaa aatgaagcgg atcgaagagg gcatcaaaga gctgggcagc cagatcctga   3360
aagaacaccc cgtggaaaac acccagctgc agaacgagaa gctgtacctg tactacctgc   3420
agaatgggcg ggatatgtac gtggaccagg aactggacat caaccggctg tccgactacg   3480
atgtggacgc tatcgtgcct cagagctttc tgaaggacga ctccatcgac aacaaggtgc   3540
tgaccagaag cgacaagaac cggggcaaga gcgacaacgt gccctccgaa gaggtcgtga   3600
agaagatgaa gaactactgg cggcagctgc tgaacgccaa gctgattacc cagagaaagt   3660
tcgacaatct gaccaaggcc gagagaggcg gcctgagcga actggataag gccgcttca   3720
tcaagagaca gctggtggaa acccggcaga tcacaaagca cgtggcacag atcctggact   3780
cccgatgaa cactaagtac gacgagaatg acaagctgat ccgggaagtg aaagtgatca   3840
ccctgaagtc caagctggtg tccgatttcc ggaaggattt ccagttttac aaagtgcgcg   3900
agatcaacaa ctaccaccac gcccacgacg cctacctgaa cgctgtccgg ggaaccgccc   3960
tgatcaaaaa gtaccctaag ctggaaagcg agttcgtgta cggcgactac aaggtgtacg   4020
acgtgcggaa gatgatcgcc aagagcgagc aggaaatcgg caaggctacc gccaagtact   4080
tcttctacag caacatcatg aacttttca agaccgagat taccctggcc aacggcgaga   4140
tccggaagcg gcctctgatc gagacaaacg gcgaaacggg ggagatcgtg tgggataagg   4200
gccgggattt tgccaccgtg cggaaagtgc tgagcatgcc ccaagtgaat atcgtgaaaa   4260
agaccgaggt gcagacaggc ggcttcagca aagagtctat cctgcccaag aggaacagcg   4320
ataagctgat cgccagaaag aaggactggg accctaagaa gtacggcggc ttcgacagcc   4380
ccaccgtggc ctattctgtg ctggtggtgg ccaaagtgga aaagggcaag tccaagaaac   4440
tgaagagtgt gaaagagctg ctggggatca ccatcatgga aagaagcagc ttcgagaaga   4500
atcccatcga ctttctggaa gccaagggct acaagaagt gaaaaaggac ctgatcatca   4560
agctgcctaa gtactccctg ttcgagctgg aaaacggccg gaagagaatg ctggcctctg   4620
ccggcgaact gcagaaggga aacgaactgg ccctgccctc caaatatgtg aacttcctgt   4680
acctggccag ccactatgag aagctgaagg gctcccccga ggataatgga cagaaacagc   4740
tgtttgtgga acagcacaag cactacctgg acgagatcat cgagcagatc agcgagttct   4800
ccaagagagt gatcctggcc gacgctaatc tggacaaagt gctgtccgcc tacaacaagc   4860
accgggataa gcccatcaga gagcaggccg agaatatcat ccacctgttt accctgacca   4920
atctgggagc ccctgccgcc ttcaagtact tgacaccac catcgaccgg aagaggtaca   4980
ccagcaccaa agaggtgctg gacgccaccc tgatccacca gagcatcacc ggcctgtacg   5040
agacacggat cgacctgtct cagctgggag gtgactctgg aggatctagc ggaggatcct   5100
ctggcagcga gacaccagga acaagcgagt cagcaacacc agagagctct ggtagcgaga   5160
cacccggtac cagtgaaagc gccacgccag aaagcgagtg gagtgagact ccgggtacat   5220
ctgaatcagc gacaccggaa tcaagtggcg gcagcagcgg cggcagcagc acctaaata   5280
tagaagatga gtatcggcta catgagacct caaaagagcc agatgtttct ctagggtcca   5340
catggctgtc tgattttcct caggcctggg cggaaaccgg gggcatggga ctggcagttc   5400
gccaagctcc tctgatcata cctctgaaag caacctctac ccccgtgtcc ataaaacaat   5460
accccatgtc acaagaagcc agactgggga tcaagcccca catacagaga ctgttggacc   5520
agggaatact ggtaccctgc cagtcccct ggaacacgcc cctgctaccc gttaagaaac   5580
cagggactaa tgattatagg cctgtccagg atctgagaga agtcaacaag cgggtggaag   5640
acatccaccc caccgtgccc aacccttaca acctcttgag cgggcccca ccgtcccacc   5700
agtggtacac tgtgcttgat ttaaaggatg ccttttctg cctgagactc caccccacca   5760
gtcagcctct cttcgccttt gagtggagag atccagagat gggaatctca ggacaattga   5820
cctgaccag actcccacag ggtttcaaaa acagtcccac cctgtttaat gaggcactga   5880
acagagacct agcagacttc cggatccagc acccagactt gatcctgcta cagtacgtgg   5940
atgacttact gctggccgcc acttctgagc tagactgcca acaaggtact cgggccctgt   6000
tacaaacct aggggaacctc gggtatcggg cctcggccaa gaaagcccaa atttgccaga   6060
aacaggtcaa gtatctgggg tatcttctaa agagggtca gagatggctg actgaggcca   6120
gaaagagac tgtgatgggg cagcctactc cgaagacccc tcgacaacta agggagttcc   6180
tagggaaggc aggcttctgt cgcctcttca tccctgggtt tgcagaaatg gcagccccc   6240
tgtaccctct caccaaaccg gggactctgt ttaattgggg cccagaccaa caaaaggcct   6300
atcaagaaat caagcaagct cttctaactg ccccagccct ggggttgcca gatttgacta   6360
agcccttga actctttgtc gacgagaagc agggctacgc caaggtgtc ctaacgcaaa   6420
aactgggacc ttggcgtcgg ccggtggcct acctgtccaa aaagctagc ccagtagcag   6480
ctggtggcc cccttgccta cggatggtag cagccattgc cgtactgaca aaggatgcag   6540
gcaagctaac catgggacag ccactagtca ttctggcccc ccatgcagta gaggcactag   6600
tcaaacaacc ccccgaccgc tggctttcca acgcccggat gactcactat caggccttgc   6660
ttttggacac ggaccgggtc cagttcggac cggtggtagc cctgaacccg gctacgtgc   6720
tccccactgcc tgaggagggg ctgcaacaca actgccttga tgggtggtta   6780
tcaccgtcaa gttcaagtac aagggtgagg aacttgaagt tgatattagc aaaatcaaga   6840
aggtttggcg cgttggtaaa atgatatctt ttacttatga cgacaacggc aagacaggta   6900
gaggggcagt gtctgagaaa gacgccccca aggagctgtt gcaaatgttg aaaagtctg   6960
ggaaaaagtc tggcggctca aaaagaaccg ccgacggcag cgaattcgag cccaagaaga   7020
agaggaaagt ggaggtggc gggagcccaa aaaagaaaag aaaagtgat ccctatgatg   7080
tccccgatta tgccggttca agagccctgg tcgtgattag actgagccga gtgacagacg   7140
ccaccacaag tcccgagaga cagctggaat catgccagca gctctgtgct cagcggggtt   7200
gggatgtgt cggcgtggca gaggatcgg acgtgagcgg ggccgtcgat ccattcgaca   7260
gaaagaggag gcccaacctg gcaagatggc tgctttcga ggaacagccc tttgatgtga   7320
tcgtcgccta cagagtggac cggctgaccc gtcaattcg acatctccag cagctggtgc   7380
```

```
attgggctga ggaccacaag aaactggtgg tcagcgcaac agaagcccac ttcgatacta   7440
ccacaccttt tgccgctgtg gtcatcgcac tgatgggcac tgtggcccag atggagctcg   7500
aagctatcaa ggagcgaaac aggagcgcag cccatttcaa tattagggcc ggtaaataca   7560
gaggctccct gccccttgg ggatatctcc ctaccagggt ggatgggag tggagactga     7620
tgccagacc cgtccagaga gagcggattc tggaagtgta ccacagagtg gtcgataacc    7680
acgaaccact ccatctggtg gcacacgacc tgaatagacg cggcgtgctc tctccaaagg   7740
attattttgc tcagctgcag ggaagagagc cacaggaag agaatggagt gctactgcac    7800
tgaagagatc tatgatcagt gaggctatgc tgggttacgc aacactcaat ggcaaaactg   7860
tccgggacga tgacggagcc cctctggtga gggctgagc tattctcacc agagagcagc    7920
tcgaagctct gcgggcagaa ctggtcaaga ctagtcgcgc caaacctgcc gtgagcaccc   7980
caagcctgct cctgagggtg ctgttctgcg ccgtctgtgg agagcagca tacaagtttg     8040
ccggcggagg gcgcaaacat ccccgctatc gatgcaggag catggggttc cctaagcact   8100
gtggaaacgg gacagtggcc atggctgagt gggacgcctt tgcgaggaa caggtgctgg    8160
atctcctggg tgacgctgag cggctggaaa aagtgtgggt ggcaggatct gactccgctc   8220
tggagctggc agaagtcaat gccgagctcg tggatctgac ttccctcatc ggatctcctg   8280
catatagagc tgggtcccca cagagagaag ctctggacgc acgaattgct gcactcgctg   8340
ctagacagga ggaactggag ggcctggagg ccaggccctc tggatgggag tggcgagaaa   8400
ccggacagag gtttgggat tggtggaggg agcaggacac cgcagccaag aacacatggc     8460
tgagatccat gaatgtccgg ctcacattcg acgtgcgcgg tggcctgact cgaaccatcg   8520
attttggcga cctgcaggag tatgaacagc acctgagact ggggtccgtg gtcgaaagac    8580
tgcacactgg gatgtcctag gtttaaaccc gctgatcagc ctcgactgtg ccttctagtt   8640
gccagccatc tgttgtttgc ccctcccccg tgccttcctt gacccctggaa ggtgccactc   8700
ccactgtcct ttcctaataa aatgagaaaa ttgcatccgca ttgtctgagt aggtgtcatt   8760
ctattctggg gggtggggtg gggcaggaca gcaaggggga ggattgggaa gacaatagca   8820
ggcatgctgg ggatgcggtg ggctctatgg cttctgaggc ggaaagaacc agctgggcgt   8880
cgataccgtc gacctctagc tagagcttgg cgtaatcatg gtcatagctg tttcctgtgt   8940
gaaattgtta tccgctcaca attccacaca acatacgagc cggaagcata agtgtaaag    9000
cctagggtgc ctaatgagtg agctaactca cattaattgc gttgcgctca ctgcccgctt   9060
tccagtcggg aaacctgtcg tgccagctgc attaatgaat cggccaacgc gcggggagag   9120
gcggtttgcg tattgggcgc tcttccgctt cctcgctcac tgactcgctg cgctcggtcg   9180
ttcggctgcg gcgagcggta tcagctcact caaaggcggt aatacggtta tccacagaat   9240
caggggataa cgcaggaaag aacatgtgag caaaaggcca gcaaaaggcc aggaaccgta   9300
aaaaggccgc gttgctggcg tttttccata ggctccgccc cctgacgag catcacaaaa     9360
atcgacgctc aagtcagagg tggcgaaacc cgacaggact ataaagatac caggcgtttc   9420
ccctggaag ctccctcgtg cgctctcctg ttccgaccct gccgcttacc ggatacctgt     9480
ccgcctttct cccttcggga agcgtggcgc tttctcatag ctcacgctgt aggtatctca   9540
gttcggtgta ggtcgttcgc tccaagctgg gctgtgtgca cgaacccccc gttcagcccg   9600
accgctgcgc cttatccggt aactatcgtc ttgagtccaa cccggtaaga cacgacttat   9660
cgccactggc agcagccact ggtaacagga ttagcagagc gaggtatgta ggcggtgcta   9720
cagagttctt gaagtggtgg cctaactacg gctacactag aagaacagta tttggtatct   9780
gcgctctgct gaagccagtt accttcggaa aaagagttgg tagctcttga tccggcaaac   9840
aaaccaccgc tggtagcggt ggtttttttg tttgcaagca gcagattacg cgcagaaaaa   9900
aaggatctca agaagatcct ttgatctttt ctacggggtc tgacgctcag tggaacgaaa   9960
actcacgtta agggattttg gtcatgagat tatcaaaaag gatcttcacc tagatccttt   10020
taaattaaaa atgaagtttt aaatcaatct aaagtatata tgagtaaact tggtctgaca   10080
gttaccaatg cttaatcagt gaggcaccta tctcagcgat ctgtctattt cgttcatcca   10140
tagttgcctg actccccgtc gtgtagataa ctacgatacg ggagggctta ccatctggcc   10200
ccagtgctgc aatgataccg cgagacccac gctcaccggc tccagattta tcagcaataa   10260
accagccagc cggaagggcc gagcgcagaa gtggtcctgc aactttatcc gcctccatcc   10320
agtctattaa ttgttgccgg gaagctagag taagtagttc gccagttaat agtttgcgca   10380
acgttgttgc cattgctaca ggcatcgtgg tgtcacgctc gtcgtttggt atggcttcat   10440
tcagctccgg ttcccaacga tcaaggcgag ttacatgatc ccccatgttg tgcaaaaaag   10500
cggttagctc cttcggtcct ccgatcgttg tcagaagtaa gttggccgca gtgttatcac   10560
tcatggttat ggcagcactg cataattctc ttactgtcat gccatccgta agatgctttt   10620
ctgtgactgg tgagtactca accaagtcat tctgagaata gtgtatgcgg cgaccgagtt   10680
gctcttgccc ggcgtcaata cgggataata ccgcgccaca tagcagaact ttaaaagtgc   10740
tcatcattgg aaaacgttct tcggggcgaa aactctcaag gatcttaccg ctgttgagat   10800
ccagttcgat gtaacccact cgtgcaccca actgatcttc agcatctttt actttcacca   10860
gcgtttctgg gtgagcaaaa acaggaaggc aaaatgccgc aaaaaaggga ataagggcga   10920
cacggaaatg ttgaatactc atactcttcc ttttcaata ttattgaagc atttatcagg    10980
gttattgtct catgagcgga tacatatttg aatgtattta gaaaaataaa caatagggg     11040
ttccgcgcac atttcc                                                    11056

SEQ ID NO: 385           moltype = DNA   length = 2367
FEATURE                  Location/Qualifiers
misc_feature             1..2367
                         note = Description of Artificial Sequence: Synthetic
                         polynucleotide
source                   1..2367
                         mol_type = other DNA
                         organism = synthetic construct
SEQUENCE: 385
tgttgagatc cagttcgatg taacccactc gtgcacccaa ctgatcttca gcatctttta     60
cttcaccag cgtttctggg tgagcaaaaa caggaaggca aaatgccgca aaaaagggaa     120
taagggcgac acggaaatgt tgaatactca tactcttcct ttttcaatat tattgaagca   180
tttatcaggg ttattgtctc atgagcggat acatatttga atgtatttag aaaaataaac   240
aaataggggt tccgcgcaca tttccccgaa aagtgccacc tgacgtcgct agctgtacaa   300
aaaagcaggc tttaaaggaa ccaattcagt cgactggatc cggtaccaag gtcgggcagg   360
aagagggcct atttcccatg attccttcat atttgcatat acgatacaag gctgttagag   420
```

```
agataattag aattaatttg actgtaaaca caaagatatt agtacaaaat acgtgacgta    480
gaaagtaata atttcttggg tagtttgcag ttttaaaatt atgttttaaa atggactatc    540
atatgcttac cgtaacttga aagtatttcg atttcttggc tttatatatc ttgtggaaag    600
gacgaaacac cgctattctc gcagctcacc agttttagag ctagaaatag caagttaaaa    660
taaggctagt ccgttatcaa cttgaaaaag tggcaccgag tcggtgcgac gagcgcggcg    720
atatcatcat ccatggccgg atgatcctga cgacggagac cgccgtcgtc gacaagccgg    780
cctgagctgc gagaattttt ttaagcttgg gccgctcgag gtacctctct acatatgaca    840
tgtgagcaaa aggccagcaa aaggccagga accgtaaaaa ggccgcgttg ctggcgtttt    900
tccataggct ccgcccccct gacgagcatc acaaaaatcg acgctcaagt cagaggtggc    960
gaaacccgac aggactataa agataccagg cgtttccccc tggaagctcc ctcgtgcgct   1020
ctcctgttcc gaccctgccg cttaccggat acctgtccgc ctttctccct tcgggaagcg   1080
tggcgctttc tcatagctca cgctgtaggt atctcagttc ggtgtaggtc gttcgctcca   1140
agctgggctg tgtgcacgaa ccccccgttc agcccgaccg ctgcgcctta tccggtaact   1200
atcgtcttga gtccaacccg gtaagacacg acttatcgcc actggcagca gccactggta   1260
acaggattag cagagcgagg tatgtaggcg gtgctacaga gttcttgaag tggtggccta   1320
actacggcta cactagaaga acagtatttg gtatctgcgc tctgctgaag ccagttacct   1380
tcggaaaaag agttggtagc tcttgatccg gcaaacaaac caccgctggt agcggtggtt   1440
tttttgtttg caagcagcag attacgcgca gaaaaaaagg atctcaagaa gatccttga    1500
tcttttctac ggggtctgac gctcagtgga acgaaaactc acgttaaggg attttggtca   1560
tgagattatc aaaaaggatc ttcacctaga tccttttaaa ttaaaaatga gttttaaat    1620
caatctaaag tatatatgag taaacttggt ctgacagtta ccaatgctta atcagtgagg   1680
cacctatctc agcgatctgt ctatttcgtt catccatagt tgcctgactc ccgtcgtgt    1740
agataaactac gatacgggag ggcttaccat ctggccccag tgctgcaatg ataccgcgag   1800
atccacgctc accggctcca gatttatcag caataaacca gccagccgga agggccgagc   1860
gcagaagtgg tcctgcaact tatccgcctc catccagtc tattaattgt tgccgggaag    1920
ctagagtaag tagttcgcca gttaatagtt tgcgcaacgt tgttgccatt gctacaggca   1980
tcgtggtgtc acgctcgtcg tttggtatgg cttcattcag ctccggttcc caacgatcaa   2040
ggcgagttac atgatccccc atgttgtgca aaaaagcggt tagctccttc ggtcctccga   2100
tcgttgtcag aagtaagttg gccgcagtgt tatcactcat ggttatggca gcactgcata   2160
attctcttac tgtcatgcca tccgtaagat gcttttctgt gactggtgag tactcaacca   2220
agtcattctg agaatagtgt atgcggcgac cgagttgctc ttgcccggcg tcaatacggg   2280
ataataccgc gccacatagc agaactttaa aagtgctcat cattggaaaa cgttcttcgg   2340
ggcgaaaact ctcaaggatc ttaccgc                                       2367
```

| | | |
|---|---|---|
| SEQ ID NO: 386 | | moltype = DNA   length = 2280 |
| FEATURE | | Location/Qualifiers |
| misc_feature | | 1..2280 |
| | | note = Description of Artificial Sequence: Synthetic polynucleotide |
| source | | 1..2280 |
| | | mol_type = other DNA |
| | | organism = synthetic construct |

SEQUENCE: 386
```
ctccatccag tctattaatt gttgccggga agctagagta agtagttcgc cagttaatag     60
tttgcgcaac gttgttgcca ttgctacagg catcgtggtg tcacgctcgt cgtttggtat    120
ggcttcattc agctccggtt cccaacgatc aaggcgagtt acatgatccc catgttgtg    180
caaaaagcg gttagctcct tcggtcctcc gatcgttgtc agaagtaagt tggccgcagt    240
gttatcactc atggttatgg cagcactgca taattctctt actgtcatgc catccgtaag    300
atgcttttct gtgactggtg agtactcaac caagtcattc tgagaatagt gtatgcggcg    360
accgagttgc tcttgcccgg cgtcaatacg ggataatacc gcgccacata gcagaacttt    420
aaaagtgctc atcattggaa aacgttcttc ggggcgaaac tctcaaggga tcttaccgct    480
gttgagatcc agttcgatgt aacccactcg tgcacccaac tgatcttcag catcttttac    540
tttcaccagc gtttctgggt gagcaaaaac aggaaggcaa aatgccgcaa aaagggaat    600
aagggcgaca cggaaatgtt gaatactcat actcttcctt tttcaatatt attgaagcat    660
ttatcagggt tattgtctca tgagcggata catatttgaa tgtatttaga aaaataaaca    720
aataggggtt ccgcgcacat ttccccgaaa agtgccacct gacgtcgcta gctgtacaaa    780
aaagcaggct ttaaaggaac caattcagtc gactggatcc ggtaccaagg tcgggcagga    840
agagggccta tttcccatga ttccttcata tttgcatata cgatacaagg ctgttagaga    900
gataattaga attaattgga ctgtaaacac aaagatatta gtacaaaata cgtgacgtag    960
aaagtaataa tttcttgggt agtttgcagt tttaaaatta tgttttaaaa tggactatca   1020
tatgcttacc gtaacttgaa agtatttcga tttcttggct ttatatatct tgtggaaagg   1080
acgaaacacc gaagccggcc ttgcacatgc gtttagagc tagaaatagc aagttaaaat   1140
aaggctagtc cgttatcaac ttgaaaaagt ggcaccgagt cggtgcgttt tttaagctt    1200
gggccgctcg aggtacctct ctacatatga catgtgcacg aaccccagcc aaaaggccag   1260
gaaccgtaaa aaggccgcgt tgctggcgtt tttccatagg ctccgccccc ctgacgagca   1320
tcacaaaaat cgacgctcaa gtcagaggtg gcgaaacccg acaggactat aaagatacca   1380
ggcgtttccc cctggaagct ccctcgtgcg ctctcctgtt ccgaccctgc cgcttaccgg   1440
atacctgtcc gcctttctcc cttcgggaag cgtggcgctt tctcatagct cacgctgtag   1500
gtatctcagt tcggtgtagg tcgttcgctc caagctgggc tgtgtgcacg aaccccccgt   1560
tcagcccgac cgctgcgcct tatccggtaa ctatcgtctt gagtccaacc cggtaagaca   1620
cgacttatcg ccactggcag cagccactgg taacaggatt agcagagcga ggtatgtagg   1680
cggtgctaca gagttcttga agtggtggcc taactacggc tacactagaa gaacagtatt   1740
tggtatctgc gctctgctga agccagttac cttcggaaaa agagttggta gctcttgatc   1800
cggcaaacaa accaccgctg gtagcggtgg tttttttgtt tgcaagcagc agattacgcg   1860
cagaaaaaaa ggatctcaag aagatccttt gatcttttct acggggtctg acgctcagtg   1920
gaacgaaaac tcacgttaag ggattttggt catgagatta tcaaaaagga tcttcaccta   1980
gatcctttta aattaaaaat gaagtttaa atcaatctaa agtatatatg agtaaacttg    2040
gtctgacagt taccaatgct taatcagtga ggcacctatc tcagcgatct gtctatttcg   2100
ttcatccata gttgcctgac tccccgtcgt gtagataact acgatacggg agggcttacc   2160
```

```
atctggcccc agtgctgcaa tgataccgcg agatccacgc tcaccggctc cagatttatc   2220
agcaataaac cagccagccg gaagggccga gcgcagaagt ggtcctgcaa ctttatccgc   2280

SEQ ID NO: 387        moltype = DNA  length = 6386
FEATURE               Location/Qualifiers
misc_feature          1..6386
                      note = Description of Artificial Sequence: Synthetic
                      polynucleotide
source                1..6386
                      mol_type = other DNA
                      organism = synthetic construct
SEQUENCE: 387
tgagcgcaac gcaattaatg tgagttagct cactcattag gcaccccagg ctttacactt     60
tatgcttccg gctcgtatgt tgtgtggaat tgtgagcgga taacaatttc acacaggaaa    120
cagctatgac catgaggcgc gccggattcg acattgatta ttgactagtt attaatagta    180
atcaattacg gggtcattag ttcatagccc atatatggag ttccgcgtta cataacttac    240
ggtaaatggc ccgcctggct gaccgcccaa cgacccccgc ccattgacgt caataatgac    300
gtatgttccc atagtaacgc caataggac tttccattga cgtcaatggg tggagtattt    360
acggtaaact gcccacttgg cagtacatca agtgtatcat atgccaagta cgccccctat    420
tgacgtcaat gacggtaaat ggcccgcctg gcattatgcc cagtacatga ccttatggga    480
ctttcctact tggcagtaca tctacgtatt agtcatcgct attaccatgg tcgaggtgag    540
ccccacgttc tgcttcactc tccccatctc ccccccctcc ccacccccaa ttttgtattt    600
atttattttt taattatttt gtgcagcgat gggggcgggg ggggggggg ggcgcgcgcc    660
rggsggggsg gggsgggsg rgggsgggg sgggsgagg cggagaggtg cggcggcagc    720
caatcagagc ggcgcgctcc gaaagtttcc ttttatggcg aggcggcggc ggcggcggcc    780
ctataaaaag cgaagcgcgc ggcgggcggg agtcgctgcg cgctgccttc gccccgtgcc    840
ccgctccgcc gccgcctcgc gccgcccgcc ccggctctga ctgaccgcgt tactcccaca    900
ggtgagcggg cgggacggcc cttctcctcc gggctgtaat tagcgcttgg tttaatgacg    960
gcttgtttct tttctgtggc tgcgtgaaag ccttgagggg ctccgggagg gccctttgtg   1020
cggggggagc ggctcggggg gtgcgtgcgt gtgtgtgtgc ggtgggagcg ccgcgtgcgg   1080
ctccgcgctg cccggcggct gtgagcgctg cgggcgcggc gcggggcttt gtgcgctccg   1140
cagtgtgcgc gaggggagcg cggccggggg cggtgccccg cggtgcgggg ggggctgcga   1200
ggggaacaaa ggctgcgtgc ggggtgtgtg cgtgggggg tgagcagggg gtgtgggcgc   1260
gtcggtcggg ctgcaacccc ccctgcaccc ccctcccccga gttgctgagc acggcccggc   1320
ttcgggtgcg gggtccgta cggggcgtgg cgcggggctc gccgtgccgg gccgcggggt   1380
gcggcaggtg ggggtgccgg gcggggcggg gccgcctcgg gccggggagg gctcggggga   1440
ggggcgcggc ggccccgga gcgccggcgg ctgtcgaggc gcggcgagcc gcagccattg   1500
cctttatgg taatcgtgcg agagggcgca gggacttcct ttgtcccaaa tctgtgcgga   1560
gccgaaatct gggaggcgcc gccgcacccc tctagcgggc gcgggggcga agcggtgcgg   1620
cgccggcagg aaggaaatgg gcgggggaggg ccttcgtgcg tcgccgcgcc gccgtccct   1680
tctccctctc cagcctcggg gctgtccgcg gggggacggc tgccttcggg ggggacgggg   1740
cagggcgggg ttcggcttct ggcgtgtgac cggcggctct agagcctctg ctaaccatgt   1800
tcatgcctc ttcttttcc tacagatcct taattaataa tacgactcac tatagggggt   1860
cgacccgcca ccatgccaaa aaagaaaaga aaagtgtatc cctatgatgt ccccgattat   1920
gccggttcaa gagccctggt cgtgattaga ctgagccgag tgacagacgc caccacaagt   1980
cccgagagac agctggaatc atgccagcag ctctgtgctc agcggggttg ggatgtggtc   2040
ggcgtggcag aggatctgga cgtgagcggg gccgtcgatc cattcgacag aaagaggagg   2100
cccaacctgg caagatggct cgctttcgag aacagccct ttgatgtgat cgtcgcctac   2160
agagtggacc ggctgacccg ctcaattcga catctccagc agctggtgca ttgggctgag   2220
gaccacaaga aactggtggt cagcgcaaca gaagcccact tcgatactac cacaccttt    2280
gccgctgtgg tcatcgcact gatgggcact gtggcccaga tggagctcga agctatcaag   2340
gagcgaaaca ggagcgcagc ccatttcaat attagggccg gtaaatacag aggctccctg   2400
cccccttggg gatatctccc tacccagggtg gatgggggagt ggagactggt gccagacccc   2460
gtccagagag agcggattct ggaagtgtac cacagagtgg tcgataacca cgaaccactc   2520
catctggtgg cacacgacct gaatagacgc ggctgtctct ctccaaagga ttattttgct   2580
cagctgcagg gaaagagcc acagggaaga gaatgagtg ctactgcact gaagagatct   2640
atgatcagtg aggctatgct gggttacgca acactcaatg gcaaaactgt ccgggacgat   2700
gacggagccc ctctggtgag ggctgagcct attctcacca gagagcagct cgaagctctg   2760
cgggcagaac tggtcaagac tagtcgcgcc aaacctgccg tgacaccc aagcctgctc   2820
ctgagggtgc tgttctgcgc cgtctgtgga gagccagcat acaagtttgc cggcggaggg   2880
cgcaaacatc ccgctatcg atgcaggagc atgggttcc ctaagcactg tggaaacggg   2940
acagtggcca tggctgagtg ggacgccttt tgcgaggaac aggtgctgga tctcctgggt   3000
gacgctgagc ggctggaaaa agtgtgggtg gcaggatctg actccgctgt ggagctggca   3060
gaagtcaatg ccgagctcgt ggatctgact ccctcatcg atatagagct   3120
gggtccccac agagagaagc tctggacgca cgaattgctg cactcgctgc tagacaggag   3180
gaactggagg gcctgaggc cagggcctct ggatggggagt ggcagaaaac cggacagagg   3240
tttgggggat tggtggaggga gcaggacacc gcagccaaga acacatggct gagatccatg   3300
aatgtccggc tcacattcga cgtgcgcggt ggcctgactc gaaccatcga ttttggcgac   3360
ctgcaggagt atgaacagca cctgagactg ggtcggtga tcgaaagact gcacactgga   3420
atgtcctagg tcagagctcg ctgatcagcc tcgactgtgc cttctagttg ccagccatct   3480
gttgtttgcc cctccccgt gccttccttg accctggaag gtgccactcc cactgtcctt   3540
tcctaataaa atgaggaaat tgcatcgcat tgtctgagta ggtgtcattc tattctgggg   3600
ggtgggtgg ggcaggacag caaggggag gattgggaag acaatagcag gcatgctggg   3660
gatgcgtggg gtctctatgg ttctgaggcg gaaagaacca gctgggcctc gagatccact   3720
agttctagcc tcgaggctag agcggccgcc actggccgtc gttttacaac gtcgtgactg   3780
ggaaaaccct ggcgttaccc aacttaatcg ccttgcagca catcccctt tcgccagctg   3840
gcgtaatagc gaagaggccc gcaccgatcg cccttcccaa cagttgcgca gcctgaatgg   3900
cgaatgggac gcgccctgta gcggcgcatt aagcgcggcg ggtgtggtgg ttacgcgcag   3960
cgtgaccgct acacttgcca gcgccctagc gcccgctcct ttcgctttct tcccttcctt   4020
```

```
tctcgccacg ttcgccggct ttccccgtca agctctaaat cggggggctcc ctttagggtt  4080
ccgatttagt gctttacggc acctcgaccc caaaaaactt gattaggtgt gatggttcacg  4140
tagtgggcca tcgccctgat agacggtttt tcgcccttg acgttggagt ccacgttctt  4200
taatagtgga ctcttgttcc aaactggaac aacactcaac cctatctcgg tctattcttt  4260
tgatttataa gggattttgc cgatttcggc ctattggtta aaaaatgagc tgatttaaca  4320
aaaatttaac gcgaattta acaaaatatt aacgcttacr mktymsrtks smcwttymgg  4380
sgaaatgtgc gcggaacccc tatttgttta tttttctaaa tacattcaaa tatgtatccg  4440
ctcatgagac aataaccctg ataaatgctt caataatatt gaaaaggaa gagtatgagt  4500
attcaacatt tccgtgtcgc ccttattccc tttttgcgg catttttgcct tcctgttttt  4560
gctcacccag aaacgctggt gaaagtaaaa gatgctgaag atcagttggg tgcacgagtg  4620
ggttacatcg aactggatct caacagcggt aagatccttg agagttttcg ccccgaagaa  4680
cgttttccaa tgatgagcac ttttaaagtt ctgctatgtg gcgcggtatt atcccgtatt  4740
gacgccggc aagagcaact cggtcgccgc atacactatt ctcagaatga cttggttgag  4800
tactcaccag tcacagaaaa gcatcttacg gatggcatga cagtaagaga attatgcagt  4860
gctgccataa ccatgagtga taacactgcg gccaacttac ttctgacaac gatcggagga  4920
ccgaaggagc taaccgcttt tttgcacaac atggggatc atgtaactcg ccttgatcgt  4980
tgggaaccgg agctgaatga agccatacca aacgacgagc gtgacaccac gatgcctgta  5040
gcaatggcaa caacgttgcg caaactatta actggcgaac tacttactct agcttcccgg  5100
caacaattaa tagactggat ggaggcggat aaagttgcag gaccacttct gcgctcggcc  5160
cttccggctg gctggtttat tgctgataaa tctggagccg gtgagcgtgg gtctcgcggt  5220
atcattgcag cactggggcc agatggtaag ccctcccgta tcgtagttat ctacacgacg  5280
gggagtcagg caactatgga tgaacgaaat agacagatcg ctgccctactg  5340
attaagcatt ggtaactgtc agaccaagtt tactcatata tactttagat tgatttaaaa  5400
cttcatttt aatttaaaag gatctaggtg aagatccttt ttgataatct catgaccaaa  5460
atcccttaac gtgagttttc gttccactga gcgtcagacc ccgtagaaaa gatcaaagga  5520
tcttcttgag atcctttttt tctgcgcgta atctgctgct tgcaaacaaa aaaaccaccg  5580
ctaccagcgg tggtttgttt gccggatcaa gagctaccaa ctctttttcc gaaggtaact  5640
ggcttcagca gagcgcagat accaaatact gttcttctag tgtagccgta gttaggccac  5700
cacttcaaga actctgtagc accgcctaca tacctcgctc tgctaatcct gttaccagtg  5760
gctgctgcca gtggcgataa gtcgtgtctt accgggttgg actcaagacg atagttaccg  5820
gataaggcgc agcggtcggg ctgaacgggg ggttcgtgca cacagcccag cttggagcga  5880
acgacctaca ccgaactgag atacctacag cgtgagctat gagaaagcgc cacgcttccc  5940
gaagggagaa aggcggacag gtatccgta agcggcaggg tcggaacagg agagcgcacg  6000
agggagcttc caggggggaaa cgcctggtat ctttatagtc ctgtcgggtt tcgccacctc  6060
tgacttgagc gtcgattttt gtgatgctcg tcagggggc ggagcctatg gaaaaacgcc  6120
agcaacgcgg cctttttacg gttcctggcc ttttgctggc cttttgctca catgttcttt  6180
cctgcgttat cccctgattc tgtggataac cgtattaccg cctttgagtg agctgatacc  6240
gctcgccgca gccgaacgac cgagcgcagc gagtcagtga gcgaggaagc ggaagagcgc  6300
ccaatacgca aaccgcctct ccccgcgcgt tggccgattc attaatgcag ctggcacgac  6360
aggtttcccg actggaaagc gggcag                                      6386
SEQ ID NO: 388       moltype = DNA  length = 6317
FEATURE              Location/Qualifiers
misc_feature         1..6317
                     note = Description of Artificial Sequence: Synthetic
                     polynucleotide
source               1..6317
                     mol_type = other DNA
                     organism = synthetic construct
SEQUENCE: 388
gattcgacat tgattattga ctagttatta atagtaatca attacggggt cattagttca  60
tagcccatat atggagttcc gcgttacata acttacggta aatggcccgc ctggctgacc  120
gcccaacgac ccccgcccat tgacgtcaat aatgacgtat gttcccatag taacgccaat  180
agggactttc cattgacgtc aatgggtgga gtatttacgg taaactgccc acttggcagt  240
acatcaagtg tatcatatgc caagtacgcc ccctattgac gtcaatgacg gtaaatggcc  300
cgcctggcat tatgcccagt acatgacctt atgggacttt cctacttggc agtacatcta  360
cgtattagtc atcgctatta ccatggtcga ggtgagcccc acgttctgct tcactctccc  420
catctccccc cctccccac cccaatttt gtatttattt attttttaat tattttgtgc  480
agcgatgggg gcgggggggg ggggggggcg cgcgccrggs ggggsggggs gggsgrggg  540
gsgggggggg gsgaggcgga gaggtgcggc ggcagccaat cagagcgggc cgctccgaaa  600
gtttcctttt atggcgaggc ggcggcggcg gcggccctat aaaaagcgaa gcgcgcggcg  660
ggcgggagtc gctgcgcgct gccttcgccc cgtgccccgc tccgccgccg cctcgcgccg  720
cccgccccgg ctctgactga ccgcgttact cccacaggtg agcgggcggg acggcccttc  780
tcctccgggc tgtaattagc gcttggttta atgacggctt gtttcttttc tgtggctgcg  840
tgaaagcctt gaggggctcc ggggggccc tttgtgcggg ggagcggct cgggggggtgc  900
gtgcgtgtgt gtgtgcgtgg ggagcgccgc gtgcggctcc gcgctgcccg gcggctgtga  960
gcgctgcggg cgcggcgcgg ggctttgtgc gctccgcagt gtgcgcgagg ggagcgcggc 1020
cggggggcggt gcccgcgcgt gcggggggg ctgcgagggg aacaaaggct gcgtgcgggg 1080
tgtgtgcgtg gggggtgag caggggtgt ggggtctgc aaccccccgc 1140
gcaccccct ccccgagttg ctgagcacgg cccggcttcg ggtgcgggc tccgtacggg 1200
gcgtggcgcg ggctcgccg tgccggcgg gggtgcgg caggtggggg tgccgtcgg 1260
ggcggggccg cctcggccg gggagggctc ggggaggg cgcggcggcc cccggagcgc 1320
cggcggctgt cgaggcgcgg cgagccgcag ccattgcctt ttatggtaat cgtgcgagag 1380
ggcgcagga cttcctttgt cccaaatctg tgcggagccg aaatctgggg ggcgccgcg 1440
caccccctct agcggggcg gggcgaagcg tgcggcgcc ggcaggaagg aaatgggcgg 1500
ggagggcctt cgtgcgtcgc cgcgccgccg tcccttctc cctctccagc ctcggggctg 1560
tccgcggggg gacggctgcc ttcggggggg acgggcagg gcggggttcg gcttctggcg 1620
tgtgaccggc ggctctagag cctctgctaa ccatgttcat gccttcttct ttttcctaca 1680
gatccttaat taataataacg actcactata ggggggtcgac ccgccaccat gacagcgcca 1740
```

```
aagaaaaaga ggaaggtcat gaccaagaaa gtggccatct atactagagt gagcacaacg 1800
aatcaggccg aggaggggtt ctctattgac gagcaaatcg atcgtctgac caagtacgcg 1860
gaagcaatgg gctggcaagt cagcgacact tacaccgatg ctgggttctc cggcgccaaa 1920
ctggaaaggc ctgccatgca gcggctgatt aacgacattg agaacaaggc ctttgataca 1980
gtgctcgtat acaagctcga caggctcagc cgatctgtgc gggacacgct ttacctcgta 2040
aaggatgttt tcactaagaa taaaatcgac ttcattagcc tgaacgaatc cattgacacc 2100
agctcagcta tgggctctct gttcctgacc atcctgagcg ctatcaatga gtttgagagg 2160
gagaatataa aggagcgcat gacaatggga aagctgggta gagcgaagtc cgggaaatct 2220
atgatgtgga ccaagaccgc ttttggatac taccacaata ggaagacggg cattctggag 2280
atcgtgccct tgcaggcaac catcgttgag cagatcttca ccgactacct gagcggaata 2340
tctctcacga agttgcgaga taagctgaat gagagcggac acattggcaa ggatattcct 2400
tggtcatata gaaccctccg ccaaactctg gataatccgg tgtactgcgg ttacatcaag 2460
ttcaaagaca gcctcttcga gggaatgcat aaacctatca ttccatacga gacatacctg 2520
aaagtccaaa aggaactcga agagcgccag caacagatct acgaacggaa taataatccc 2580
aggcctttcc aggccaaata tatgctgtcc ggcatggcaa gatgcggata ctgcggggca 2640
ccactcaaga ttgtgcttgg ccataaacgg aaggatggaa gcagaaccat gaaatatcac 2700
tgcgcaaacc gctttccaag gaaaacgaag gggattaccg tgtacaatga caacaaaaaa 2760
tgtgatagcg gaacctacga tctgtccaac ttggaaaaca ccgtcattga caatttaatt 2820
ggatttcagg aaaataatga cagccttctg aagattatca acgggaacaa tcagccgatt 2880
ctggacactt catctttcaa aaaacagatc tctcagattg ataagaaaat tcagaaaaat 2940
tccgatttat acctcaatga tttcataacg atggatgagc tgaaggaccg gaccgacagt 3000
ttgcaggccg agaagaaact gctgaaagca aagatctccg aacaagttt caatgacagt 3060
accgatgtct tcgagttggt gaagacccag ctgggtagta tcccaatcaa cgagttgagc 3120
tatgacaata agaagaagat tgttaataac ctggtgagca aagtggacgt gaccgctgat 3180
aacgtggata ttatcttcaa gttccagctg gcctgagtca gagctcgctg atcagcctcg 3240
actgtccctt ctagttgcca gccatctgtt gtttgccct cccccgtgcc ttccttgacc 3300
ctggaaggtg ccactcccac tgtccttttcc taataaaatg aggaaattgc atcgcattgt 3360
ctgagtaggt gtcattctat tctggggggt ggggtgggc aggacagcaa ggggaggat 3420
tgggaagaca atagcaggca tgctgggat gcggtgggct ctatggcttc tgaggcggaa 3480
agaaccagct ggggctcgag atccactagt tctagcctcg aggctagagc ggccgccact 3540
ggccgtcgtt ttacaacgtc gtgactggga aaaccctggc gttacccaac ttaatcgcct 3600
tgcagcacat ccccctttcg ccagctggcg taatagcgaa gaggcccgca ccgatcgccc 3660
ttcccaacag ttgcgcagcc tgaatggcga atgggacgcg ccctgtagcg cgcattaag 3720
cgcggcgggt gtggtggtta cgcgcagcgt gaccgctaca cttgccagcg ccctagcgcc 3780
cgctcctttc gctttcttcc cttcctttct cgccacgttc gccggctttc cccgtcaagc 3840
tctaaatcgg gggctccctt tagggttccg atttagtgct ttacggcacc tcgaccccaa 3900
aaaacttgat tagggtgatg gttcacgtag tgggccatcg ccctgataga cggttttttcg 3960
cccttttgacg ttggagtcca cgttctttaa tagtggactc ttgttccaaa ctggaacaac 4020
actcaaccct atctcggtct attcttttga tttataaggg attttgccga tttcggccta 4080
ttggttaaaa aatgagctga tttaacaaaa atttaacgcg aattttaaca aaatattaac 4140
gcttacrmkt ymsrtkssmc wttymggsga aatgtgcggg gaaccccctat ttgtttattt 4200
ttctaaaatac attcaaatat gtatccgctc atgagacaat aaccctgata aatgcttcaa 4260
taatattgaa aaaggaagag tatgagtatt caacatttcc gtgtcgccct tattcccttt 4320
tttgcggcat tttgccttcc tgtttttgct cacccagaaa cgctggtgaa agtaaaagat 4380
gctgaagatc agttgggtgc acgagtgggt tacatcgaac tggatctcaa cagcggtaag 4440
atccttgaga gttttcgccc cgaagaacgt ttttccaatga tgagcacttt taaagttctg 4500
ctatgtggcg cggtattatc ccgtattgac gccgggcaag agcaactcgg tcgccgcata 4560
cactattctc agaatgactt ggttgagtac tcaccagtca cagaaaagca tcttacggat 4620
ggcatgacag taagagaatt atgcagtgct gccataacca tgagtgataa cactgcggcc 4680
aacttacttc tgacaacgat cggaggaccg aaggagctaa ccgcttttttt gcacaacatg 4740
gggatcatg taactcgcct tgatcgttgg gaaccggagc tgaatgaagc cataccaaac 4800
gacgagcgtg acaccacgat gcctgtagca atggcaacaa cgttgcgcaa actattaact 4860
ggcgaactac ttactctagc ttcccggcaa caattaatag actggatgga ggcggataaa 4920
gttgcaggac cacttctgcg ctcggccctt ccggctggct ggtttattgc tgataaatct 4980
ggagccggtg agcgtgggtc tcgcggtatc attgcagcac tggggccaga tggtaagccc 5040
tcccgtatcg tagttatcta cacgacgggg agtcaggcaa ctatggatga acgaaataga 5100
cagatcgctg agataggtgc ctcactgatt aagcattggt aactgtcaga ccaagtttac 5160
tcatatatac tttagattga tttaaaactt catttttaat ttaaaaggat ctaggtgaag 5220
atcctttttg ataatctcat gaccaaaatc ccttaacgtg agttttcgtt ccactgagcg 5280
tcagacccg tagaaaagat caaggatct tcttgagatc ctttttttct gcgcgtaatc 5340
tgctgcttgc aaacaaaaaa accaccgcta ccagcggtgg tttgtttgcc ggatcaagag 5400
ctaccaactc tttttccgaa ggtaactggc ttcagcagag cgcagatacc aaatactgtt 5460
cttctagtgt agccgtagtt aggccaccac ttcaagaact ctgtagcacc gcctacatac 5520
ctcgctctgc taatcctgtt accagtggct gctgccagtg gcgataagtc gtgtcttacc 5580
gggttggact caagacgata gttaccggat aaggcgcagc ggtcgggctg aacggggggt 5640
tcgtgcacac agcccagctt ggagcgaacg acctacaccg aactgagata cctacagcgt 5700
gagctatgag aaagcgccac gcttcccgaa gggagaaagg cggacaggta tccggtaagc 5760
ggcagggtcg aacaggaga gcgcacgagg gagcttccag ggggaaacgc ctggtatctt 5820
tatagtcctg tcgggtttcg ccacctctga cttgagcgtc gatttttgtg atgctcgtca 5880
ggggggcgga gcctatggaa aaacgccagc aacgcggcct ttttacggtt cctgccttt 5940
tgctggcctt ttgctcacat gttctttcct gcgttatccc ctgattctgt ggataaccgt 6000
attaccgcctt ttgagtgagc tgataccgct cgccgcagcc gaacgaccga gcgcagcgag 6060
tcagtgagcg aggaagcgga agagcgccca atacgcaaac cgcctctccc cgcgcgttgg 6120
ccgattcatt aatgcagctg gcacgacagg tttcccgact ggaaagcggg cagtgagcgc 6180
aacgcaatta atgtgagtta gctcactcat taggcacccc aggctttaca ctttatgctt 6240
ccggctcgta tgttgtgtgg aattgtgagc ggataacaat ttcacacagg aaacagctat 6300
gaccatgagg cgcgccg                                                 6317
```

SEQ ID NO: 389          moltype = DNA   length = 6638
FEATURE                 Location/Qualifiers
misc_feature            1..6638
                        note = Description of Artificial Sequence: Synthetic
                        polynucleotide
source                  1..6638
                        mol_type = other DNA
                        organism = synthetic construct
SEQUENCE: 389
gattcgacat tgattattga ctagttatta atagtaatca attacggggt cattagttca   60
tagcccatat atggagttcc gcgttacata acttacggta aatggcccgc ctggctgacc  120
gcccaacgac ccccgcccat tgacgtcaat aatgacgtat gttcccatag taacgccaat  180
agggactttc cattgacgtc aatgggtgga gtatttacgg taaactgccc acttggcagt  240
acatcaagtg tatcatatgc caagtacgcc ccctattgac gtcaatgacg gtaaatggcc  300
cgcctggcat tatgcccagt acatgacctt atgggacttt cctacttggc agtacatcta  360
cgtattagtc atcgctatta ccatggtcga ggtgagcccc acgttctgct tcactctccc  420
catctccccc ccctccccac ccccaatttt gtatttattt attttttaat tattttgtgc  480
agcgatgggg gcggggggg ggggggcg cgcgccrggs ggggsgggs gggsgrggg       540
gsggggsggg gsgaggcgga gaggtgcggg ggcagccaat cagagcggcg cgctccgaaa  600
gtttcctttt atggcgaggc ggcggcgcg cggccctat aaaaagcgaa gcgcgcggcg    660
ggcgggagtc gctgcgcgct gccttcgccc cgtgccccgc tccgccgccg cctcgcgccg  720
cccgcccgg ctctgactga ccgcgttact cccacaggtg agcgggcggg acggcccttc   780
tcctccggc tgtaattagc gcttggttta atgacggctt gtttcttttc tgtgctgcg    840
tgaaagcctt gaggggctcc gggagggccc tttgtgcggg gggagcggct cgggggtgc   900
gtgcgtgtgt gtgtgcgtgg ggagcgccgc gtgcggctcc gcgctgcccg gcggctgtga  960
gcgctgcgcg cgcggcgcgg ggctttgtgc gctccgcagt gtgcgcgagg ggagccgcgg 1020
cgggggcggt gccccgcggt gcgggggggg ctgcgagggg aacaaaggct gcgtgcgggg 1080
tgtgtgcgtg ggggggtgag caggggtgt gggcgcgtcg gtcgggctgc aaccccccct  1140
gcaccccct ccccgagttg ctgagcacgg cccgccttcg ggtgcgggc tccgtacggg    1200
gcgtggcgcg ggctcgccg tgccgggcgg ggggtggcgg caggtggggg tgccgggcgg   1260
ggcgggggcg cctcggggcg gggagggctc ggggagggg cgcggcggcc ccggagcgc    1320
cggcggctgt cgaggcgcgg cgagccgcag ccattgccctt ttatggtaat cgtgcgagag 1380
ggcgcaggga cttcctttgt cccaaatctg tgcggagccg aaatctggga ggcgccgccg 1440
caccccctct agcgggcgcg gggcgaagcg gtgcggcgac ggcaggaagg aaatgggcgg 1500
ggagggcctt cgtgcgtcgc cgcgccgcg tccccttctc cctctccagc ctcggggctg   1560
tccgcggggg gacggctgcc ttcggggggg acggggcagg gcggggttcg gcttctggcg 1620
tgtgaccggc ggctctagag cctctgctaa ccatgttcat gccttcttct tttcctacta  1680
gatccttaat taataatacg actcactata ggggtcgac ccgccaccat gcccaagaag  1740
aaacggaaag tgatgagccc ctttatcgcc ccggacgtgc ccgagcacct cctgacact   1800
gtgcgcgtct ttctgtacgc ccgtcagagt aaaggacggt cagatggatc tgacgtgtcc 1860
accgaagcac agctcgctgc cggacgggcc cttgttgcct caagaaacgc caagggggga 1920
gctagatgga tggtggcggg cgaattcgtg gatgtgggca gatcagggtg ggaccgaat  1980
gtgacacgcg ccgacttcga aagaatgatg ggcgaggtgc gcgccggtga gggagacgta  2040
gtggtggtta atgaactgag tcgccttacg aggaagggcg cccacgacgc tctgagatc   2100
gataacgaac tcaaaaaaca cggtgtgcgg ttcatgagcg tgctgaacc attcctggat  2160
accagcaccc caatcggtgt cgcgatcttt gccctgattg ccgcgctcgc taaacaggat 2220
tcagaccttta aagctgagcg gctgaagggg gctaaagatg agatcgctgc cttgggggt  2280
gtgcacagct catctgcgcc attcggcatg agggcggtca gaaagaaagt ggataacctg 2340
gtcatatctg ttctggagcc tgatgaggac aacccggacc acgttgagct tgtggaacgg 2400
atggctaaga tgtcttttga aggcgtcagc gataacgcaa ttgccacaac atttgagaag 2460
gagaaaatcc cctctccggg gatgctgagg acgagcca cggagaagag gcttgcttct  2520
attaaggcac ggaggctcaa tggcgccgaa aagccgatca tgtggcgggc gcagacagtt 2580
agatggattc ttaaccatcc cgcgattggt ggattcgcat tcgagcgggt gaaacacgga 2640
aaagcccaca tcaacgtgat acgaagagat cccggccgga aaccccttac ccctcacact 2700
ggtatcctgt ctggatccaa gtggttgaa ctccaggaga agagaagcgg gaaaaatctc  2760
tccgaccgca aaccaggtgc cgaagtgaa cctacgctgc tttccgggtg gagatttctg 2820
ggatgtcgga tatgcggtgg gtcaatgggc cagtcccaag ggggcgtaa gaggaatggg  2880
gacttggctg agggggcaatta catgtgtgca aacccaaagg ggcacggcgg tctgagcgtc 2940
aagaggtctg gcttgatga attcgtggca tcaaaagtct gggcaggtt gcgcacggct  3000
gacatggagg atgaacatga ccaagcatgg attgcagctg cagctgaacg gtttgctttg 3060
cagcacgacc tggcgggggt agctgacgag cgacgggagc aacaagctca cctgataac   3120
gttcggagat caataaaaga tctccaggcg gataggaagg caggtctcta cgtgggacgc 3180
gaagaactgg agacctggcg cagtaccgtc ctgcaatata ggctgactgt             3240
actactaggt tggctgagct ggatgaaaaa atgaatggat ccaccgggt gccttcagaa   3300
tggtttagcg gcgaggaccc aaccgcgaa ggaggcatat gggcgagctg gatgtctat    3360
gagcgccggg agtttctcag cttttttttg gactccgtaa tggttgacag gggcagacat  3420
cctgaaacca agaatatat accattgaaa gaccgggtga ccttaaagtg gcggagctg    3480
ttaaaggaag aggatgaagc aagcgaggcc acagaacggg agctggcagc tctttaggtc  3540
agagctcgct gatcagcctc gactgtgcct tctagttgcc agccatctgt tgtttgcccc  3600
tcccccgtgc cttccttgac cctggaaggt gccactccca ctgtcctttc ctaataaaat 3660
gaggaaattg catcgcattg tctgagtagg tgtcattcta ttctgggggg tggggtggg   3720
caggacagca agggggagga ttgggaagac aatagcaggc atgctgggga tcggtgggc   3780
tctatgcttc ctgaggcgaa aagaaccagc tggggctcga gatccactag ttctagccct 3840
gaggctagag cggccgccac tggccgtcgt tttacaacgt cgtgactggg aaaaccctgg 3900
cgttacccaa cttaatcgcc ttgcagcaca tccccctttc gccagctggg gtaatagcga 3960
agaggcccgc accgatcgcc cttcccaaca gttgcgcagc ctgaatggcg aatgggacgc 4020
gccctgtagc ggcgcattaa gcggcgggg tgtggtggtt acgcgcagcg tgaccgctac 4080
acttgccagc gccctagcgc ccgctccttt cgctttcttc ccttcctttc tcgccacgtt 4140

```
cgccggcttt cccgtcaag ctctaaatcg ggggctccct ttaggttcc gatttagtgc   4200
tttacggcac ctcgacccca aaaaacttga ttagggtgat ggttcacgta gtgggccatc   4260
gccctgatag acggttttc gcccttgac gttggagtcc acgttcttta atagtggact   4320
cttgttccaa actggaacaa cactcaaccc tatctcggtc tattcttttg atttataagg   4380
gattttgccg atttcggcct attggttaaa aaatgagctg atttaacaaa aattaacgc   4440
gaattttaac aaaatattaa cgcttacrmk tymsrtkssm cwttymggsg aaatgtgcgc   4500
ggaaccccta tttgtttatt tttctaaata cattcaaata tgtatccgct catgagacaa   4560
taaccctgat aaatgcttca ataatattga aaaggaaga gtatgagtat tcaacatttc   4620
cgtgtcgccc ttattccctt ttttgcggca ttttgccttc ctgtttttgc tcacccagaa   4680
acgctggtga agtaaaaga tgctgaagat cagttgggtg cacgagtggg ttacatcgaa   4740
ctggatctca acagcggtaa gatccttgag agttttcgcc ccgaagaacg ttttccaatg   4800
atgagcactt ttaaagttct gctatgtggc gcggtattat cccgtattga cgccgggcaa   4860
gagcaactcg gtcgccgcat acactattct cagaatgact tggttgagta ctcaccagtc   4920
acagaaaagc atcttacgga tggcatgaca gtaagagaat tatgcagtgc tgccataacc   4980
atgagtgata acactgcggc caacttactt ctgacaacga tcggaggacc gaaggagcta   5040
accgcttttt tgcacaacat ggggatcat gtaactcgcc ttgatcgttg ggaaccggag   5100
ctgaatgaag ccataccaaa cgacgagcgt gacaccacga tgcctgtagc aatggcaaca   5160
acgttgcgca aactattaac tggcgaacta cttactctag cttcccggca acaattaata   5220
gactggatgg aggcggataa agttgcagga ccacttctgc gctcggccct tccggctggc   5280
tggtttattg ctgataaatc tggagccggt gagcgtgggt ctcgcggtat cattgcagca   5340
ctggggccag atggtaagcc ctcccgtatc gtagttatct acacgacggg gagtcaggca   5400
actatggatg aacgaaatag acagatcgct gagataggtg cctcactgat taagcattgg   5460
taactgtcag accaagttta ctcatatata ctttagattg atttaaaact tcattttta   5520
tttaaaagga tctaggtgaa gatcctttt gataatctca tgaccaaaat cccttaacgt   5580
gagttttcgt tccactgagc gtcagacccc gtagaaaaga tcaaaggatc ttcttgagat   5640
cctttttttc tgcgcgtaat ctgctgcttg caaacaaaaa aaccaccgct accagcggtg   5700
gtttgtttgc cggatcaaga gctaccaact cttttccga aggtaactgg cttcagcaga   5760
gcgcagatac caaatactgt tcttctagtg tagccgtagt taggccacca cttcaagaac   5820
tctgtagcac cgcctacata cctcgctctg ctaatcctgt taccagtggc tgctgccagt   5880
ggcgataagt cgtgtcttac cgggttggac tcaagacgat agttaccgga taaggcgcag   5940
cggtcgggct gaacggggggg ttcgtgcaca cagcccagct tggagcgaac gacctacacc   6000
gaactgagat acctacagcg tgagctatga gaaagcgcca cgcttcccga agggagaaag   6060
gcggacaggt atccggtaag cggcagggtc ggaacaggag agcgcacgag ggagcttcca   6120
gggggaaacg cctggtatct ttatagtcct gtcgggtttc gccacctctg acttgagcgt   6180
cgattttgt gatgctcgtc agggggggcgg agcctatgga aaaacgccag caacgcggcc   6240
tttttacggt tcctggcctt ttgctggcct tttgctcaca tgttctttcc tgcgttatcc   6300
cctgattctg tggataaccg tattaccgcc tttgagtgag ctgataccgc tcgccgcagc   6360
cgaacgaccg agcgcagcga gtcagtgagc gaggaagcgg aagagcgccc aatacgcaaa   6420
ccgcctctcc ccgcgcgttg gccgattcat taatgcagct ggcacgacag gtttcccgac   6480
tggaaagcgg gcagtgagcg caacgcaatt aatgtgagtt agctcactca ttaggcaccc   6540
caggctttac actttatgct tccggctcgt atgttgtgtg gaattgtgag cggataacaa   6600
tttcacacag gaaacagcta tgaccatgag gcgcgccg                          6638

SEQ ID NO: 390        moltype = DNA   length = 9530
FEATURE               Location/Qualifiers
misc_feature          1..9530
                      note = Description of Artificial Sequence: Synthetic
                      polynucleotide
source                1..9530
                      mol_type = other DNA
                      organism = synthetic construct
SEQUENCE: 390
taatcagcat catgatgtgg taccacatca tgatgctgat tataagaatg cggccgccac     60
actctagtgg atctcgagtt aataattcag aagaactcgt caagaaggcg atagaaggcg    120
atgcgctgcg aatcgggagc ggcgataccg taaagcggta ggaagcggtc agcccattcg    180
ccgccaagct cttcagcaat atcacgggta gccaacgcta tgtcctgata gcggtccgcc    240
acacccagcc ggccacagtc gatgaatcca gaaaagcggc catttccac catgatattc    300
ggcaagcagg catcgccatg ggtcacgacg agatcctcgc cgtcgggcat gctcgccttg    360
agcctggcga acagttcggc tggcgcgagc ccctgatgct cttcgtccag atcatcctga    420
tcgacaagac cggcttccat ccgagtacgt gtcgctcgca tgcgatgttt cgcttggtgg    480
tcgaatgggc aggtagccgg atcaagcgta tgcagccgcc gcattgcatc agccatgatg    540
gatactttct cggcaggagc aaggtgtaga tgacatggag atcctgcccc ggcacttcgc    600
ccaatagcag ccagtccctt cccgcttcag tgacaacgtc gagcacagct gcgcaaggaa    660
cgcccgtcgt ggccagccac gatagccgcg ctgcctcgtc ttgcagttca ttcagggcac    720
cggacaggtc ggtcttgaca aaaagaaccg ggcgcccctg cgctgacagc cggaacacgg    780
cggcatcaga gcagccgatt gtctgttgtg cccagtcata gccgaatagc ctctccaccc    840
aagcggccgg agaacctgcg tgcaatccat cttgttcaat catgcgaaac gatcctcatc    900
ctgtctcttg atcagagctt gatccctgc gccatcagat ccttggcgg gagaaagcca    960
tccagtttac tttgcaggc ttcccaacct taccagaggg cgccccagct ggcaattccg   1020
gttcgcttgc tgtccataaa accgcccagt ctagctatcg ccatgtaagc ccactgcaag   1080
ctacctgctt tctctttgcg cttgcgtttt cccttgtcca gatagcccag tagctgacat   1140
tcatccgggg tcagcaccgt ttctgcggac tggctttcta cgtgctcgag gggggccaaa   1200
cggtctccag cttggctgtt ttggcggatg agagaagatt ttcagcctga tacagattaa   1260
atcagaacgc agaagcggtc tgataaaaca gaatttgcct ggcggcagta gcgcggtggt   1320
cccacctgac cccatgccga actcagaagt gaaacgccgt agcgccgatg gtagtgtggg   1380
gtctccccat gcgagagtag ggaactgcca ggcatcaaat aaaacgaaag gctcagtcga   1440
aagactgggc ctttcgtttt atctgttgtt tgtcggtgaa cgctctcctg agtaggacaa   1500
atccgccggg agcggatttg aacgttgcga agcaacggcc cggagggtgg cgggcaggac   1560
gcccgccata aactgccagg catcaaatta agcagaaggc catcctgacg gatggccttt   1620
```

```
ttgcgtttct acaaactctt ttgtttattt ttctaaatac attcaaatat gtatccgctc 1680
atgaccaaaa tcccttaacg tgagttttcg ttccactgag cgtcagaccc cgtagaaaag 1740
atcaaaggat cttcttgaga tccttttttt ctgcgcgtaa tctgctgctt gcaaacaaaa 1800
aaaccaccgc taccagcggt ggtttgtttg ccggatcaag agctaccaac tcttttttccg 1860
aaggtaactg gcttcagcag agcgcagata ccaaatactg tccttctagt gtagccgtag 1920
ttaggccacc acttcaagaa ctctgtagca ccgcctacat acctcgctct gctaatcctg 1980
ttaccagtgg ctgctgccag tggcgataag tcgtgtctta ccgggttgga ctcaagacga 2040
tagttaccgg ataaggcgca gcggtcgggc tgaacggggg gttcgtgcac acagcccagc 2100
ttggagcgaa cgacctacac cgaactgaga tacctacagc gtgagctatg agaaagcgcc 2160
acgcttcccg aagggagaaa ggcggacagg tatccggtaa gcggcagggt cggaacagga 2220
gagcgcacga gggagcttcc agggggaaac gcctggtatc tttatagtcc tgtcgggttt 2280
cgccacctct gacttgagcg tcgatttttg tgatgctcgt caggggggcg agcctatgg 2340
aaaaacgcca gcaacgcggc cttttacgg ttcctggcct tttgctggcc ttttgctcac 2400
atgttctttc ctgcgttatc ccctgattct gtggataacc gtattaccgc ctttgagtga 2460
gctgataccg ctcgccgcag ccgaacgacc gagcgcagcg agtcagtgag cgaggaagcg 2520
gaagagcgcc tgatgcggta ttttctcctt acgcatctgt gcggtatttc acaccgcata 2580
tggtgcactc tcagtacaat ctgctctgat gccgcatagt taagccagta tacactccgc 2640
tatcgctacg tgactgggtc atggctgcgc cccgacaccc gccaacaccc gctgacgcgc 2700
cctgacgggc ttgtctgctc ccggcatccg cttacagaca agctgtgacc gtctccggga 2760
gctgcatgtg tcagaggttt tcaccgtcat caccgaaacg cgcgaggcag cagatcaatt 2820
cgcgcgcgaa ggcgaagcgg catgcataat gtgcctgtca aatggacgaa gcagggattc 2880
tgcaaaccct atgctactcc gtcaagccgt caattgtctg attcgttacc aaattatgaca 2940
acttgacggc tacatcattc acttttttctt cacaaccggc acggaactcg ctcgggctgg 3000
ccccggtgca tttttttaaat acccgcgaga aatagagttg atcgtcaaaa ccaacattgc 3060
gaccgacggt ggcgataggc atccgggtgg tgctcaaaag cagcttcgcc tggctgatac 3120
gttggtcctc gcgccagctt aagacgctaa tccctaactg ctggcggaaa agatgtgaca 3180
gacgcgacgg cgacaagcaa acatgctgtg cgacgctggc gatacattac cctgttatcc 3240
ctagatgaca ttaccctgtt atcccagatg acattaccct gttatcccta gatgacatta 3300
ccctgttatc cctagatgac atttaccctg ttatccctag atgacattac cctgttatcc 3360
cagatgacat taccctgtta tccctagata cattaccct ttatcccaga tgacatacc 3420
tgttatccct agatgacatt accctgttat cccagatgac attaccctgt tatccctaga 3480
tacattaccc tgttatccca gatgacatac cctgttatcc ctagatgaca ttaccctgtt 3540
atcccagatg acattaccct gttatcccta gatacattac cctgttatcc cagatgacat 3600
accctgttat ccctagatga cattaccctg ttatcccaga tgacattacc ctgttatccc 3660
tagatacatt accctgttat cccagatgac ataccctgtt atccctagat gacattaccc 3720
tgttatccca gatgacatta ccctgttatc cctagataca ttaccctgtt atcccagatg 3780
acataccctg ttatccctag atgacattac cctgttatcc cagatgacat accctgtta 3840
tccctagata cattaccctg ttatcccaga tgacatacc tgttatccct agatgacatt 3900
accctgttat cccagataaa ctcaatgatg atgatgatga tggtcgagac tcagcggccg 3960
cggtgccagg gcgtgccctt gggctccccg ggcgcgacta taagctgcga gcaacttcac 4020
ttgggtatgc cggcggtagc gctgagggcc tatttcccat gattccttca tatttgcata 4080
tacgatacaa ggctgttaga gagataattg gaattaattt gactgtaaac acaaagatat 4140
tagtacaaaa tacgtgacgt agaaagtaat aatttcttgg gtagtttgca gttttaaaat 4200
tatgttttaa aatggactat catatgctta ccgtaacttg aaagtatttc gatttcttgg 4260
ctttatatat cttgtggaaa ggacgaaaca ccgggtcttc gagaagacct gttttagagc 4320
tagaaatcgt ggttcgcacc gactcggtgc cacagcaagt taaaataagg ctagtccgtt 4380
atcaacttga aaaagtggca ccgagtcggt gctttttttga attcgctagc taggtcttga 4440
aaggagtggg aattggctcc ggtgcccgtc agtgggcaga gcgcacatcg cccacagtcc 4500
ccgagaagtt ggggggaggg tcggcaatt gatccggtgc ctagaaagg tggcgcgggg 4560
taaactggga aagtgatgtc gtgtactggc tccgccttt tcccgagggt ggggagaac 4620
cgtatataag tgcagtagtc gccgtgaacg ttctttttcg caacgggttt gccgccaaa 4680
cacaggaccg gttctagagc gctgccacca tggacaagaa gtacagcatc ggcctggaca 4740
tcggcaccaa ctctgtgggc tgggccgtga tcaccgacga gtacaaggtg cccagcaaga 4800
aattcaaggt gctgggcaac accgaccggc acagcatcaa gaagaacctg atcggagccc 4860
tgctgttcga cagcggcgaa acagccgagg ccacccgcct gaagagaacc gcagaagaa 4920
gatacaccag acggaagaac cggatctgct atctgcaaga gatcttcagc aacgagatgg 4980
ccaaggtgga cgacagcttc ttccacagac tggaagagtc cttcctggtg gaagaggata 5040
agaagcacga gcggcacccc atcttcggca acatcgtgga cgaggtggcc taccacgaga 5100
agtacccac catctaccac ctgagaaaga aactggtgga cagcaccgac aaggccgacc 5160
tgcggctgat ctatctggcc ctggcccaca tgatcaagtt ccggggccac ttcctgatcg 5220
agggcgacct gaaccccgac aacagcgacg tggacaagct gttcatccag ctggtgcaga 5280
cctacaacca gctgttcgag gaaaacccca tcaacgccag cggcgtggac gccaaggcca 5340
tcctgtctgc cagactgagc aagagcagac ggctggaaaa tctgatcgcc cagctgcccg 5400
gcgagaagaa gaatggcctg ttcggaaacc tgattgcctg tgacccccca 5460
acttcaagag caacttcgac ctggccgagg atgccaaact gcagctgagc aaggacacct 5520
acgacgacga cctggacaac ctgctggccc agatcggcga ccagtacgcc gacctgtttc 5580
tggccgccaa gaacctgtcc gacgccatcc tgctgagcga catcctgaga gtgaacaccg 5640
agatcaccaa ggcccccctg agcgcctcta tgatcaagag atacgacgag caccaccagg 5700
acctgaccct gctgaaagct ctcgtgcggc agcagctgcc tgagaagtac aaagagattt 5760
tcttcgacca gagcaagaac ggctacgccg ctacattga cggcggagcc agccaggaag 5820
agttctacaa gttcatcaag cccatcctgg aaaagatgga cggcaccgag gaactgctcg 5880
tgaagctgaa cagagaggac ctgctgcgga agcagcggac cttcgacaac ggcagcatcc 5940
cccaccagat ccacctggga gagctgcacg ccattctgcg gcgccaggaa gatttttacc 6000
cattctggaa ggacaaccgg gaaaagatcg agaagatcct gaccttccgc atcccctact 6060
acgtgggccc tctggccagg ggaaacagca gattcgcctg gatgaccaga aagagcgagg 6120
aaaccatcac cccctggaac ttcgaggaag tggtggacaa gggcgcttcc gcccagagct 6180
tcatcgagcg gatgaccaac ttcgataaga acctgcccaa cgagaaggtg ctgcccaagc 6240
acagcctgct gtacgagtac ttcaccgtgt ataacgagct gaccaaagtg aaatacgtga 6300
ccgagggaat gagaaagccc gccttcctga gcggcgagca gaaaaaggcc atcgtggacc 6360
```

```
tgctgttcaa gaccaaccgg aaagtgaccg tgaagcagct gaaagaggac tacttcaaga    6420
aaatcgagtg cttcgactcc gtggaaatct ccgcgtgga agatcggttc aacgcctccc     6480
tgggcacata ccacgatctg ctgaaaatta tcaaggacaa ggacttcctg gacaatgagg    6540
aaaacgagga cattctggaa gatatcgtgc tgacccctga actgtttgag gacagagaga    6600
tgatcgagga acggctgaaa acctatgccc acctgttcga cgacaaagtg atgaagcagc    6660
tgaagcggcg gagatacacc ggctgggca ggctgagccg gaagctgatc aacggcatcc     6720
gggacaagca gtccggcaag acaatcctgg atttcctgaa gtccgacggc ttcgccaaca    6780
gaaacttcat gcagctgatc cacgacgaca gcctgacctt taaagaggac atccagaaag    6840
cccaggtgtc cggccagggc gatagcctgc acgagcacat tgccaatctg gccggcagcc    6900
ccgccattaa gaagggcatc ctgcagacag tgaaggtggt ggacgagctc gtgaaagtga    6960
tgggccggca caagcccgag aacatcgtga tcgaaatggc cagagagaac cagaccaccc    7020
agaagggaca gaagaacagc cgcgagagaa tgaagcggat cgaagagggc atcaaagagc    7080
tgggcagcca gatcctgaaa gaacaccccg tggaaaacac ccagctgcag aacgagaagc    7140
tgtacctgta ctacctgcag aatgggcggg atatgtacgt ggaccaggaa ctggacatca    7200
accggctgtc cgactacgat gtggaccata tcgtgcctca gagctttctg aaggacgact    7260
ccatcgacaa caaggtgctg accagaagcg acaagaaccg gggcaagagc gacaacgtgc    7320
cctccgaaga ggtcgtgaag aagatgaaga actactggcg gcagctgctg aacgccaagc    7380
tgattaccca gagaaagttc gacaatctga caaggccga gagggccgc ctgagcgaac     7440
tggataaggc cggcttcatc aagagacagc tggtggaaac ccggcagatc acaaagcacg    7500
tggcacagat cctggactcc cggatgaaca ctaagtacga cgagaatgac aagctgatcc    7560
gggaagtgaa agtgatcacc ctgaagtcca agctggtgtc cgatttccgg aaggatttcc    7620
agttttacaa agtgcgcgag atcaacaact accaccacgc ccacgacgcc tacctgaacg    7680
ccgtcgtggg aaccgccctg atcaaaaagt accctaagct ggaaagcgag ttcgtgtacg    7740
gcgactacaa ggtgtacgac gtgcggaaga tgatcgccaa gagcgagcag gaaatcggca    7800
aggctaccgc caagtacttc ttctacagca acatcatgaa ctttttcaag accgagatta    7860
ccctggccaa cggcgagatc cggaagcggc ctctgatcga gacaaacggc gaaacgggaa    7920
agatcgtgtg ggataagggc cgggattttg ccaccgtgcg gaaagtgctg agcatgcccc    7980
aagtgaatat cgtgaaaaag accgaggtgc agacaggcgg cttcagcaaa gagtctatcc    8040
tgcccaagag gaacagcgat aagctgatcg ccagaaagaa ggactgggac cctaagaagt    8100
acggcggctt cgacagcccc accgtggcct attctgtgct ggtggtggcc aaagtggaaa    8160
agggcaagtc caagaaactg aagagtgtga aagagctgct ggggatcacc atcatggaaa    8220
gaagcagctt cgagaagaat cccatcgact ttctggaagc caagggctac aaagaagtga    8280
aaaaggacct gatcatcaag ctgcctaagt actccctgtt cgagctggaa aacggccgga    8340
agagaatgct ggcctctgcc ggcgaactgc agaagggaaa cgaactggcc ctgccctcca    8400
aatatgtgaa cttcctgtac ctggccagcc actatgagaa gctgaagggc tcccccgagg    8460
ataatgagca gaaacagctg tttgtggaac agcacaagca ctaccttggac gagatcatcg    8520
agcagatcag cgagttctcc aagagagtga tcctggccga cgctaatctg gacaaagtgc    8580
tgtccgccta caacaagcac cgggataagc ccatcagaga gcaggccgag aatatcatcc    8640
acctgttac cctgaccaat ctgggagccc tgcggcctt caagtacttt gacaccacca    8700
tcgaccggaa gaggtacacc agcaccaaaa gggtgctgga cgccaccctg atccaccaga    8760
gcatcaccgg cctgtacgag acacggatcg acctgtctca gctgggaggc gacaagcgac    8820
ctgccgccac aaagaaggct ggacaggcta agaagaagaa agattacaaa gacgatgacg    8880
ataagtaact agagctcgct gatcagcctc gactgtgcct tctagttgcc agccatctgt    8940
tgtttgcccc tcccccgtgc cttccttgac cctggaaggt gccactccca ctgtcctttc    9000
ctaataaaat gaggaaattg catcgcattg tctgagtagg tgtcattcta ttctggggg     9060
tggggtgggg caggacagca aggggagga ttgggaagag aatagcaggc atgctgggga     9120
ctgaggcgga aagaaccagc tgtggaatgt gtgtcagtta gggtgtggaa agtccccagg    9180
ctccccagca ggcagaagta tgcaaagcat gcatctcaat tagtcagcaa ccaggtgtgg    9240
aaagtcccca ggctcccag caggcagaag tatgcaaagc atgcatctca attagtcagc      9300
aaccatagtc cgcccctaa ctccgcccat cccgcccta actccgccca gttccgccca      9360
ttctccgcc catggctgac taattttttt tatttatgca gaggccgagg ccgcctcggc     9420
ctctgagcta ttccagaagt agtgaggagg cttttttgga ggcctaggct tttgcaaaaa    9480
gcttgggccc gccccaactg gggtaacctt tgagttctct cagttgggg                9530
```

```
SEQ ID NO: 391        moltype = DNA    length = 5722
FEATURE               Location/Qualifiers
misc_feature          1..5722
                      note = Description of Artificial Sequence: Synthetic
                      polynucleotide
source                1..5722
                      mol_type = other DNA
                      organism = synthetic construct
SEQUENCE: 391
tgatcccctg cgccatcaga tccttggcgg cgagaaagcc atccagttta ctttgcaggg     60
cttcccaacc ttaccagagg gcgccccagc tggcaattcc ggttcgcttg ctgtccataa    120
aaccgcccag tctagctatc gccatgtaag cccactgcaa gctacctgct ttctctttgc    180
gcttgcgttt tcccttgtcc agatagccca gtagctgaca ttcatccggg gtcagcaccg    240
tttctgcgga ctggctttct acgtgctcga ggggggccaa acggtctcca gcttggctgt    300
tttggcggat gagagaagat tttcagcctg atacagatta aatcagaacg cagaagcggt    360
ctgataaaac agaatttgcc tggcggcagt agcgcggtgg tcccacctga ccccatgccg    420
aactcagaag tgaaacgccg tagcgccgat ggtagtgtgg ggtctcccca tgcgagagta    480
gggaactgcc aggcatcaaa taaaacgaaa ggctcagtcg aaagactggg cctttcgttt    540
tatctgttgt ttgtcggtga acgctctcct gagtaggaca atccgccgg gagcggattt     600
gaacgttgcg aagcaacggc ccggagggtg cgggcaggca tccgccat aaactgccag      660
gcatcaaatt aagcagaagg ccatcctgac ggatggcctt tttgcgttc tacaaactct     720
tttgtttatt tttctaaata cattcaaata tgtatccgct catgaccaaa atcccttaac    780
gtgagttttc gttccactga gcgtcagacc ccgtagaaaa gatcaaagga tcttcttgag    840
atccttttt tctgcgcgta atctgctgct tgcaaacaaa aaaaccaccg ctaccagcgg     900
tggtttgttt gccggatcaa gagctaccaa ctctttttcc gaaggtaact ggcttcagca    960
```

```
gagcgcagat accaaatact gtccttctag tgtagccgta gttaggccac cacttcaaga  1020
actctgtagc accgcctaca tacctcgctc tgctaatcct gttaccagtg gctgctgcca  1080
gtggcgataa gtcgtgtctt accgggttgg actcaagacg atagttaccg gataaggcgc  1140
agcggtcggc tgaacggggg ggttcgtgca cacagcccag cttggagcga acgacctaca  1200
ccgaactgag atacctacag cgtgactat gagaaagcgc cacgcttccc gaagggagaa  1260
aggcggacag gtatccggta agcggcaggg tcggaacagg agagcgcacg agggagcttc  1320
caggggggaaa cgcctggtat ctttatagtc ctgtcgggtt tcgccacctc tgacttgagc  1380
gtcgattttt gtgatgctcg tcagggggc ggagcctatg gaaaaacgcc agcaacgcgg  1440
cctttttacg gttcctggcc ttttgctggc cttttgctca catgttcttt cctgcgttat  1500
cccctgattc tgtggataac cgtattaccg cctttgagtg agctgatacc gctcgccgca  1560
gccgaacgac cgagcgcagc gagtcagtga gcgaggaagc ggaagagcgc ctgatgcggt  1620
attttctcct tacgcatctg tgcggtattt cacaccgcat atggtgcact ctcagtacaa  1680
tctgctctga tgccgcatag ttaagccagt atacactccg ctatcgctac gtgactgggt  1740
catggctgcg ccccgacacc cgccaacacc cgctgacgcg ccctgacggg cttgtctgct  1800
cccggcatcc gcttacagac aagctgtgac cgtctccggg agctgcatgt gtcagaggtt  1860
ttcaccgtca tcaccgaaac gcgcgaggca gcagatcaat tcgcgcgcga aggcgaagcg  1920
gcatgcataa tgtgcctgtc aaatggacga agcagggatt ctgcaaaccc tatgctactc  1980
cgtcaagccg tcaattgtct gattcgttac caattatgac aacttgacgg ctacatcatt  2040
cactttttct tcacaaccgg cacgaactc gctcggctg ccccggtgc atttttttaaa  2100
tacccgcgag aaatagagtt gatcgtcaaa accaacattg cgaccgacgg tggcgatagg  2160
catccggtg gtgctcaaaa gcagcttcgc ctggctgata cgttggtcct cgcgccagct  2220
taagacgcta atccctaact gctggcgaa aagatgtgac agacgcgacg gcgacaagca  2280
aacatgctgt gcgacgctgg cgatacatta ccctgttatc cctagatgac attacccctgt  2340
tatcccagat gacattaccc tgttatccct agatgacatt accctgttat ccctagatga  2400
catttaccct gttatcccta gatgacatta ccctgttatc ccagatgaca ttaccctgtt  2460
atccctagat acattaccc gttatcccag atgacatact ccgttatcccc tagatgacat  2520
taccctgtta tcccagatga cattaccctg ttatccctag atacattacc ctgttatccc  2580
agatgacata ccctgttatc cctagatgac attaccctgt tatcccagat gacattaccc  2640
tgttatccct agatacatta ccctgttatc ccagatgaca taccctgtta tccctagatg  2700
acattaccct gttatcccag atgacattac ctgttatccc tagatacatt accctgtta  2760
tcccagatga cataccctgt tatccctaga tgacattacc ctgttatccc agatgacatt  2820
accctgttat cctagatac attaccctgt tatcccagat gacataccct gttatcccta  2880
gatgacatta ccctgttatc ccagatgaca ttaccctgtt atccctagat acattaccct  2940
gttatcccag atgacatacc ctgttatccc tagatgacat accctgtta tcccagataa  3000
actcaatgat gatgatgatg atggtcgaga ctcagcggac gcggtgccag gcgtgccct  3060
tgggctcccc gggcgcggtc ctttgggcgc taactcgtg cgcgctggga attggcgcta  3120
attgcgcgtg cgcgctggga ctcaaggcgc taactcgcg tgcgttctgg ggcccggggt  3180
gccgcggcct gggctgggc gaaggcgggc tcggccggaa ggggtgggt cgccgcggct  3240
cccgggcgct tgcgcgcact tcctgcccga gccgctggcc gccgagggt gtggccgctg  3300
cgtgcgcgcg cgccgacccg gcgctgtttg aaccgggcgg aggcggggct ggcgcccggt  3360
tggggcctg ttggggcctg gcttcctgcc gcgcgccggg gacgcgcctc cgaccagtgat  3420
ttgccttta tggtaataac gcggccggcc cggcttcctt tgtccccaat ctgggcgcgc  3480
gccggcgccc cctggcggcc taaggactcg gcgcgccgga agtggccagg gcgggggcga  3540
cctcggctca cagcgcgccc ggctattctc gcagctcgcc accatgcccg ccatgaagat  3600
cgagtgccgc atcaccggca ccctgaacgg cgtggagttc gagctggtgg cgcggcggaga  3660
gggcacccc gagcagggcc gcatgaccaa caagatgaag agcaccaaag gcgccctgac  3720
cttcagcccc tacctgctga gccacgtgat gggctacggc ttctaccact tcggcaccta  3780
ccccagcggc tacgagaacc ccttcctgca cgccatcaac aacggcggct acaccaacac  3840
ccgcatcgag aagtacgagg acggcggcgt gctgcacgtg agcttcagct accgctacga  3900
ggccggccgc gtgatcggcg acttcaaggt ggtgggcacc ggcttcccc g aggacagcgt  3960
gatcttcacc gacaagatca tccgcagcaa cgccacctgc gagcacctgc acccatggg  4020
cgataacgtg ctggtgggca gcttcgcccg caccttcagc ctgcgcgacg gcggctacta  4080
cagcttcgtg gtggacagcc acatgcactt caagagcgcc atccaccca gcatcctgca  4140
gaacgggggc cccatgttcg ccttccgccg cgtggaggag ctgcacagca caccgagct  4200
gggcatcgtg gagtaccagc acgccttcaa gacccccatc gccttcgcca gatctcgagc  4260
tcgaaccatg gatgatgata tcgtcgacg aacggctccg ccgatgtgca a  4320
ggccggcttc gcgggcgacg atgcccccg ggccgtcttc ccctccatcg tgggcgccc  4380
caggcaccag gtaggggagc tggctgggtg gggcagcccc gggagcgggc gggaggcaag  4440
ggcgctttct ctgcacagga gcctcccggt tccgggggtg gggctgcgc ccgtgctcag  4500
ggcttctgt cctttccttc caggcgtg atggtggga tgggtcagaa ggattcctat  4560
gtgggcgacg aggcccagag caagagaggc atcctcaccc tgaagtaccc catcgagcac  4620
ggcatcgtca ccaactggga cgacatgag aaaatctggc accacaccttc ctacaatgag  4680
ctgcgtgtgg ctcccgagga gcaccccgtg ctgctgaccg aggcccccct gaacccaag  4740
gccaaccgcg agaagatgac ccagcccaa ctggggtaac ctttgagttc tctcagttgg  4800
gggtaatcag catcatgatg tggtaccaca tcatgatgct gattataaga atgcggccgc  4860
cacactctag tggatctcga gttaataatt cagaagaact cgtcaagaag gcgatagaag  4920
gcgatgcgct gcgaatcggg agcggcgata ccgtaaagca cgaggaagcg gtcagcccat  4980
tcgccgccaa gctcttcagc aatatcacgg gtagccaacg ctatgtcctg atagcggtcc  5040
gccacaccca gccggccaca gtcgatgaat ccagaaaagc ggccattttc caccatgata  5100
ttcggcaagc aggcatcgcc atgggtcacg acgagatcct cgccgtcggg catgctcgcc  5160
ttgagcctgg cgaacagttc ggctggcgcg agccctgat gctcttcgtc cagatcatcc  5220
tgatcgacaa gaccggcttc catccgagta tgcttcttgg  5280
tggtcgaatg ggcaggtagc cggatcaagc gtatgcagcc gccgcattgc atcagccatg  5340
atggatactt tctcggcagg agcaaggtgt agatgacatg gagatcctgc cccggcactt  5400
cgcccaatag cagccagtcc cttccgcgtt cagtgacaac gtcgagcaca gctgcgcaag  5460
gaacgcccgt cgtggccagc cacgatagcc gcgctgcctc gtcttgcagt tcattcaggg  5520
caccggacag gtcggtcttg acaaaaagaa ccgggcgccc ctgcgctgac agccggaaca  5580
```

```
cggcggcatc agagcagccg attgtctgtt gtgcccagtc atagccgaat agcctctcca    5640
cccaagcggc cggagaacct gcgtgcaatc catcttgttc aatcatgcga aacgatcctc    5700
atcctgtctc ttgatcagag ct                                            5722

SEQ ID NO: 392         moltype = DNA  length = 15424
FEATURE                Location/Qualifiers
misc_feature           1..15424
                       note = Description of Artificial Sequence: Synthetic
                       polynucleotide
source                 1..15424
                       mol_type = other DNA
                       organism = synthetic construct
SEQUENCE: 392
tcgacggtat cgataagctt gatatcgaat tcctgcagcc cggggatcc actagttcta     60
gagcggccgc caccgcggtg gagctccagc ttttgttccc tttagtgagg gttaatttcg    120
agcttggcgt aatcatggtc atagctgttt cctgtgtgaa attgttatcc gctcacaatt    180
ccacacaaca tacgagccgg aagcataaag tgtaaagcct ggggtgccta atgagtgagc    240
taactcacat taattgcgtt gcgctcactg cccgctttcc agtcgggaaa cctgtcgtgc    300
cagctgcatt aatgaatcgg ccaacgcgcg gggagaggcg gtttgcgtat gggcgctct    360
tccgcttcct cgctcactga ctcgctgcgc tcggtcgttc ggctgcggcg agcggtatca    420
gctcactcaa aggcggtaat acggttatcc acagaatcag gggataacgc aggaaagaac    480
atgtgagcaa aaggccagca aaaggccagg aaccgtaaaa aggccgcgtt gctggcgttt    540
ttccataggc tccgcccccc tgacgagcat cacaaaaatc gacgctcaag tcagaggtgg    600
cgaaacccga caggactata aagataccag gcgtttcccc ctggaagctc cctcgtgcgc    660
tctcctgttc cgaccctgcc gcttaccgga tacctgtccg cctttctccc ttcgggaagc    720
gtggcgcttt ctcatagctc acgctgtagg tatctcagtt cggtgtaggt cgttcgctcc    780
aagctgggct gtgtgcacga accccccgtt cagcccgacc gctgcgcctt atccggtaac    840
tatcgtcttg agtccaaccc ggtaagacac gacttatcgc cactggcagc agccactggt    900
aacaggatta gcagagcgag gtatgtaggc ggtgctacag agttcttgaa gtggtggcct    960
aactacggct acactagaag gacagtattt ggtatctgcg ctctgctgaa gccagttacc    1020
ttcggaaaaa gagttggtag ctcttgatcc ggcaaacaaa ccaccgctgg tagcggtggt    1080
ttttttgttt gcaagcagca gattacgcgc agaaaaaaag gatctcaaga agatcctttg    1140
atcttttcta cggggtctga cgctcagtgg aacgaaaact cacgttaagg gattttggtc    1200
atgagattat caaaaaggat cttcacctag atcctttta attaaaaatg aagttttaaa    1260
tcaatctaaa gtatatatga gtaaacttgg tctgacagtt accaatgctt aatcagtgag    1320
gcacctatct cagcgatctg tctatttcgt tcatccatag ttgcctgact ccccgtcgtg    1380
tagataacta cgatacggga gggcttacca tctggcccca gtgctgcaat gataccgcga    1440
gacccacgct caccggctcc agatttatca gcaataaacc agccagccgg aagggccgag    1500
cgcagaagtg gtcctgcaac tttatccgcc tccatccagt ctattaattg ttgccgggaa    1560
gctagagtaa gtagttcgcc agttaatagt ttgcgcaacg ttgttgccat tgctacaggc    1620
atcgtggtgt cacgctcgtc gtttggtatg gcttcattca gctccggttc caacgatca    1680
aggcgagtta catgatcccc catgttgtgc aaaaaagcgg ttagctcctt cggtcctccg    1740
atcgttgtca gaagtaagtt ggccgcagtg ttatcactca tggttatggc agcactgcat    1800
aattctctta ctgtcatgcc atccgtaaga tgcttttctg tgactggtga gtactcaacc    1860
aagtcattct gagaatagtg tatgcggcga ccgagttgct cttgcccggc gtcaatacgg    1920
gataataccg cgccacatag cagaacttta aaagtgctca tcattggaaa acgttcttcg    1980
gggcgaaaac tctcaaggat cttaccgctg ttgagatcca gttcgatgta acccactcgt    2040
gcacccaact gatcttcagc atcttttact ttcaccagcg tttctgggtg agcaaaaaca    2100
ggaaggcaaa atgccgcaaa aaagggaata agggcgacac ggaaatgttg aatactcata    2160
ctcttccttt ttcaatatta ttgaagcatt tatcagggtt attgtctcat gagcggatac    2220
atatttgaat gtatttagaa aaataaacaa taggggttc cgcgcacatt tccccgaaaa    2280
gtgccacctg acgtctaaga aaccattatt atcatgacat taacctataa aaataggcgt    2340
atcacgaggc cctttcgtct tcaagaattc tcatgtttga cagcttatca tcgataagct    2400
ttaatgcggt agtttatcac agttaaattg ctaacgcagt caggcaccgt gtatgaaatc    2460
taacaatgcg ctcatcgtca tcctcggcac cgtcaccctg gatgctgtag gcataggctt    2520
ggttatgccg gtactgccgg gcctcttgcg ggatatcgtc cattccgaca gcatcgccag    2580
tcactatggc gtgctgctag cgctatatgc gttgatgcaa tttctatgcg cacccgttct    2640
cggagcactg tccgaccgct ttggccgccg cccagtcctg ctcgcttcgc tacttggagc    2700
cactatcgac tacgcgatca tggcgaccac acccgtcctg tggatccggc gcacaccaaa    2760
aacgtcactt tgccacatc cgtcgcttac atgtgttccg ccacacttgc aacatcacac    2820
ttccgccaca ctactacgtc acccgccccg ttcccacgcc ccgcgccacg tcacaaactc    2880
cacccccctca ttatcatatt ggcttcaatc caaaataaat catcaataat ataccttatt    2940
ttggattgaa gccaatatga taatgagggg gtggagtttg tgacgtggcg cggggcgtgg    3000
gaacgggcgg ggtgacgtag gttttagggc ggagtaactt gtatgtgttg ggaattgtag    3060
ttttcttaaa atgggaagtt acgtaacgtg gaaaacgga agtgacgatt tgaggaagtt    3120
gtgggttttt tggctttcgt ttctgggcgt aggttcgcgt gcggtttctt gggtgttttt    3180
tgtgacttt aaccgttacg tcatttttta gtcctatata tactcgctct gcacttggcc    3240
cttttttaca ctgtgactga ttgagctggt gccgtgtcga gtggtgtttt tttaataggt    3300
tttcttttt actggtaagg ctgactgtta ggctgccgct ggaagcgct gtagttgttt    3360
ctggagcggg aggtgctat tttgcctagg caggagggtt tttcaggtgt ttatgtgttt    3420
ttctctccta ttaattttgt tatacctcct atggggggctc taatgttgtc tctacgcctg    3480
cgggtatgta ttccccgggg ctattccggt cgcttttag cactgaccga tgaatcaacc    3540
tgatgtgttt accgagtctt acattatgac tccggacatg accgaggagc tgtcggtggt    3600
gcttttaat caggttgacc agtttttta cggtcacgcc ggcatgccg tagtccgtct    3660
tatgcttata aggggtgttt ttcctgttgt aagacaggct tctaatgttt aaatgttttt    3720
ttgttatttt atttttgtgtt tatgcagaaa cccgcagaca tgtttgagag aaaaatggtg    3780
tcttttttctg tggtggttcc ggagcttacc tgcctttatc tgcatgagca tgactacgat    3840
gtgctttctt ttttgcgcga ggctttgcct gattttttga gcagcacctt gcattttata    3900
tcgccgccca tgcaacaaag cttacatcgg ggctacgctg gttagcatag ctccgagtat    3960
```

```
gcgtgtcata atcagtgtgg gttcttttgt caaggttcct ggcggggaag tggccgcgct   4020
ggtccgtgca gacctgcacg attatgttca gctggccctg cgaagggacc tacgggatcg   4080
cggtatttt  gttaatgttc cgcttttgaa tcttatacag gtctgtgagg aacctgaatt   4140
tttgcaatca tgattcgctg cttgaggctg aaggtggagg gcgctctgga gcagatttt   4200
acaatggccg gacttaatat tcgggatttg cttagagata tattgagaag gtggcgagat   4260
gagaattatt tgggcatggt tgaaggtgct ggaatgttta tagaggagat tcaccctgaa   4320
gggtttagcc tttacgtcca cttggacgtg agggccgttt gccttttgga agccattgtg   4380
caacatctta caaatgccat tatctgttct ttggctgtag agtttgacca cgccaccgga   4440
ggggagcgcg ttcacttaat agatcttcat tttgaggttt tggataatct tttgaaataa   4500
aaaaaaaaac atggttcttc cagctcttcc cgctcctccc gtgtgtgact cgcagaacga   4560
atgtgtaggt tggctgggtg tggcttattc tgccgtggtg gatgttatca gggcagcggc   4620
gcatgaagga gtttacatag aacccgaagc caggggcgc  ctggatgctt tgagagagtg   4680
gatatactac aactactaca cagagcgatc taagcggcga gaccggagac gcagatctgt   4740
ttgtcacgcc cgcaccttgg tttgcttcag gaaatatgac tacgtccggc gttccattg   4800
gcatgacact acgaccaaca cgatctcggt tgtctcggcg cactccgtac agtagggatc   4860
gtctacctcc ttttgagaca gaaacccgcg ctaccatact ggaggatcat ccgctgctgc   4920
ccgaatgtaa cactttgaca atgcacaacg tgagttacgt gcgaggtctt ccctgcagtg   4980
tgggatttac gctgattcag gaatgggttg ttccctggga tatggttcta acgcgggagg   5040
agcttgtaat cctgaggaag tgtatgcacg tgtgcctgtg ttgtgccaac attgatatca   5100
tgacgagcat gatgatccat ggttacgagt cctgggctct ccactgtcat tgttccagtc   5160
ccggttcct  gcagtgtata gccggcgggc aggttttggc cagctggttt aggatggtgg   5220
tggatggcgc catgtttaat cagaggttta tatggtaccg ggaggtggtg aattacaaca   5280
tgccaaaaga ggtaatgttt atgtccagcg tgtttatgag gggtcgccac ttaatctacc   5340
tgcgcttgtg gtatgatggc cacgtgggtt ctgtggtccc cgccatgagc tttggataca   5400
gcgccttgca ctgtgggatt ttgaacaata ttgtggtgct gtgctgcagt tactgtgctg   5460
atttaagtga gatcagggtg cgctgctgtg cccggagtga aggcgcctt  atgctgcgag   5520
cggtgcgaat catcgctgag gagaccactg ccatgttgta ttcctgcagg acggagcggc   5580
ggcggcagca gtttattcgc gcgctgctgc agcaccaccg ccctatcctg atgcacgatt   5640
atgactctac ccccatgtag gcgtggactt ctccttcgcc gcccgttaag caaccgcaag   5700
ttggcacgca gcctgtgct  cagcagctgg acagcgacat gaacttaagt gagctgcccg   5760
gggagtttat taatatcact gatgagcgtt tggctcgaca ggaaaccgtg tggaatataa   5820
cacctaagaa tatgtctgtt acccatgata tgatgctttt taaggccagc cggggagaaa   5880
ggactgtgta ctctgtgtgt tgggaggag  gtggcaggtt gaatactagg gttctgtgag   5940
tttgattaag gtacggtgat ctgtataagc tatgtggtgg tggggctata ctactgaatg   6000
aaaaatgact tgaaattttc tgcaattgaa aaataaacac gttgaaacat aacacaaacg   6060
attctttatt cttgggcaat gtatgaaaaa gtgtaagagg atgtggcaaa tatttcatta   6120
atgtagttgt ggccagacca gtcccatgaa aatgacatag agtatgcact tggagttgtg   6180
tctcctgttt cctgtgtacc gtttagtgta atggttagtg ttacaggttt agttttgtct   6240
ccgtttaagt aaacttgact gacaatgtta cttttgacg  ttttaccgtg agattttgga   6300
taagctgata ggttaggcat aaatccaaca gcgtttgtat aggctgtgcc ttcagtaaga   6360
tctccatttc taaagttcca atattctggg tccaggaagg aattgtttag tagcactcca   6420
ttttcgtcaa atcttataat aagatgagca ctttgaactg ttccagatat tggagccaaa   6480
ctgcctttaa cagccaaaac tgaaactgca gcaagtattt gactgccaca ttttgttaag   6540
accaaagtga gtttagcatc tttctctgca tttagtctac agtaggagat ggagctggt   6600
gtggtccaca aagttagctt atcattattt ttgtttccta ctgtaatggc acctgtgctg   6660
tcaaaactaa ggccagttcc tagtttagga accatagcct tgtttgaatc aaattctagg   6720
ccatgccaa  tttttgtttt gagggggattt gtgtttggtg cattaggtga accaaattca   6780
agcccatctc ctgcattaat ggctatggct gtagcgtcaa acatcaaccc cttggcagtg   6840
cttaggttaa cctcaagctt tttggaattg tttgaagctg taaacaagta aaggcctttg   6900
ttgtagttaa tatccaagtt gtgggctgag tttataaaaa gagggccctg tcctagtctt   6960
agatttagtt ggttttgagc atcaaacgga taactaacat caagtataag gcgtctgttt   7020
tgagaatcaa tccttagtcc tcctgctaca ttaagttgca tattgccttg tgaatcaaaa   7080
cccaaggctc cagtaacttt agtttgcaag gaagtattat taatagtcac acctggacca   7140
gttgctacgg tcaaagtgtt taggtcgtct gttacatgca aaggagcccc gtactttagt   7200
cctagtttc  cattttgtgt ataaatgggc tctttcaagt caatgcccaa gctaccagtg   7260
gcagtagtta gagggggtga ggcagtgata gtaagggtac tgctatcggt ggtggtgagg   7320
gggcctgatg tttgcagggc tagctttcct tctgacactg tgaggggtcc ttgggtggca   7380
atgctaagtt tggagtcgtg cacggttagc ggggcctgtg attgcatggt gagtgtgttg   7440
cccgcgacca ttagaggtgc ggcggcagcc acagttaggg cttctgaggt aactgtgagg   7500
ggtgcagata tttccaggtt tatgtttgac ttggtttttt tgagaggtgg gctcacagtg   7560
gttacatttt gggaggtaag gttgccggcc tcgtccagag agaggccgtt gcccattttg   7620
agcgcaagca tgccattgga ggtaactaga ggttcggata ggcgcaaaga gagtacccca   7680
gggggactct cttgaaaccc attgggggat acaaaggggag gagtaagaaa aggcacagtt   7740
ggaggacggg tttccgtgtc atatggatac acggggttga aggtatcttc agacggtctt   7800
gcgcgcttca tctgcaacaa catgaagata gtgggtgcgg atggacagga acaggaggaa   7860
actgacattc catttagatt gtggagaaag tttcagcca  ggaggaagct gcaataccag   7920
agctgggagg agggcaagga ggtgctgctg aataaactgg acagaaattt gctaactgat   7980
tttaagtaag tgatgcttta ttattttttt ttattagtta aaggggaataa gatccccggg   8040
tactctagtt aattaactag aggatcttga tgtaatccaa ggttaggaca gttgcaaatc   8100
acagtgagaa cacagggtcc cctgtcccgc tcaactagca gggggcgctg ggtaaactcc   8160
cgaatcaggc tacgggcaag ctccctctgg gcggtaagcc ggacgccgtg cgccgggccc   8220
tcgatatgat cctcgggcaa ttcaaagtag caaaactcac cggagtcgcg ggcaaagcac   8280
ttgtggcgga gacagtggac caggtgtttc aggcgcagtt gctctgcctc tccacttaac   8340
attcagtcgc agccgtccgc cgagtccttt accgcgtcca agttaggaat aaattgatcc   8400
ggatagtggc cggagggtcc cgagaagggg ttaaagtaga ccgatggcac aaactcctca   8460
ataaattgca gagttccaat gcctccagag cgcggctcag aggacgaggt ctgcagagtt   8520
aggattgcct gacgaggcgt gaatgaagga cggccggcgc cgccgatctg aaatgtcccg   8580
tccggacgga gaccaagcga ggagctcacc gactcgtcgt tgagctgaat acctcgccct   8640
ctgattgtca ggtgagttat accctgcccg ggcgaccgca ccctgtgacg aaagccgccc   8700
```

```
gcaagctgcg cccctgagtt agtcatctga acttcggcct gggcgtctct gggaagtacc   8760
acagtggtgg gagcgggact ttcctggtac accagggcag cgggccaact acggggatta   8820
aggttattac gaggtgtggt ggtaatagcc gcctgttcca agagaattcg gtttcgtgg    8880
gcgcggattc cgttgacccg ggatatcatg tggggtcccg cgctcatgta gtttattcgg   8940
gttgagtagt cttgggcagc tccagccgca agtcccattt gtggctggta actccacatg   9000
tagggcgtgg gaattccctt gctcataatg gcgctgacga caggtgctgg cgccgggtgt   9060
ggccgctgga gatgacgtag ttttcgcgct taaatttgag aaaggggcgcg aaactagtcc   9120
ttaagagtca gcgcgcagta tttactgaag agagcctccg cgtcttccag cgtgcgccga   9180
agctgatctt cgcttttgtg atacaggcag ctgcgggtga gggatcgcag agacctgttt   9240
tttattttca gctcttgttc ttggcccctg ctctgttgaa atatagcata cagagtggga   9300
aaaatcctgt ttctaagctc gcgggtcgat acgggttcgt tgggcgccag acgcagcgct   9360
cctcctcctg ctgctgccgc cgctgtggat ttcttgggct ttgtcagagt cttgctatcc   9420
ggtcgccttt gcttctgtgt ggccgctgct gttgctgccg ctgccgctgc cgccggtgca   9480
gtatgggctg tagagatgac ggtagtaatg caggatgtta cgggggaagg ccacgccgtg   9540
atggtagaga agaaagcggc gggcgaagga gatgttgccc ccacagtctt gcaagcaagc   9600
aactatggcg ttcttgtgcc cgcgccatga gcggtagcct tggcgctgtt gttgctcttg   9660
ggctaacggg ggcggctgct tggacttacc ggccctggtt ccagtggtgt cccatctacg   9720
gttgggtcgg cgaacgggca gtgccggcgg cgcctgagga gcggaggttg tagccatgct   9780
ggaaccggtt gccgatttct ggggcgccgg cgaggggaat gcgaccgagg gtgacggtgt   9840
ttcgtctgac acctcttcga cctcggaagc ttcctcgtct aggctctccc agtcttccat   9900
catgtcctcc tcctcctcgt ccaaaacctc tctgcctga ctgtcccagt attcctcctc     9960
gtccgtgggt ggcggcggca gctgcagctt cttttttggt gccatcctgg gaagcaaggg   10020
cccgcggctg ctgctgatag ggctgcggcg gcggggggat tgggttgagc tcctcgccgg   10080
actgggggtc caagtaaacc cccgtccct ttcgtagcag aaactcttgg cgggctttgt    10140
tgatggcttg caattggcca agaatgtggc cctgggtaat gacgcaggcg gtaagctccg   10200
catttggcgg gcgggattgg tcttcgtaga acctaatctc gtgggcgttg tagtcctcag   10260
gtacaaattt gcgaaggtaa ccgacgtcc acagccccgg agtgagtttc aaccccggag    10320
ccgcggactt ttcgtcaggc gagggaccct gcagctcaaa ggtaccgata atttgacttt   10380
cgttaagcag ctgcgaattg caaaccaggg agcggtgcgg ggtgcatagg ttgcagcgac   10440
agtgacactc cagtagaccg tcaccgctca cgtcttccat tatgtcagag tggtaggcaa   10500
ggtagttggc tagctgcaga aggtagcagt ggccccaaag cggcggaggg cattcgcggt   10560
acttaatggg cacaaagtcg ctaggaagtg cacagcaggt ggcgggcaag attcctgagc   10620
gctctaggat aaagttccta aagttctgca acatgctttg actggtgaag tctggcagac   10680
cctgttgcag ggttttaagc aggcgttcgg ggaaaatgat gtccgccagg tgcgcggcca   10740
cggagcgctc gttgaaggcc gtccataggt ccttcaagtt ttgctttagc agttctgca    10800
gctccttgag gttgcactcc tccaagcact gctgccaaac gcccatggcc gtctgccagg   10860
tgtagcatag aaataagtaa acgcagtcgc ggacgtagtc gcggcgcgcc tcgcccttga   10920
gcgtggaatg aagcacgttt tgcccaaggc ggttttcgtg caaaattcca aggtaggaga   10980
ccaggttgca gagctccacg ttggagatct tgcaggccg gcgtacgtag ccctgtcgaa    11040
aggtgtagtg caatgtttcc tctagcttgc gctgcatctc cgggtcagca agaaccgct    11100
gcatgcactc aagctccacg gtaacgagca ctgcggccat cattagtttg cgtcgctcct   11160
ccaagtcggc aggctcgcgc gtttgaagcc agcgcgctag ctgctcgtcg ccaactgcgg   11220
gtaggccctc ctctgtttgt tcttgcaaat ttgcatccct ctccagggc tgcgcacggc    11280
gcacgatcag ctcactcatg actgtgctca tgaccttggg gggtaggtta agtgccgggt   11340
aggcaaagtg ggtgacctcg atgctgcgtt ttagtacggc taggcgcgcg ttgtcaccct   11400
cgagttccac caacactcca gagtgacttt cattttcgct gttttcctgt tgcagagcgt   11460
ttgccgccgg cttctcgtcg cgtccaagac cctcaaagat ttttggcact tcgttgagcg   11520
aggcgatatc aggtatgaca gcgccctgcc gcaaggccag ctgcttgtcc gctcggctgc   11580
ggttggcacg gcaggatagg ggtatcttgc agttttggaa aaagatgtga taggtggcaa   11640
gcacctctgg cacggcaaat acggggtaga agttgaggcg cgggttgggc tcgcatgtgc   11700
cgttttcttg gcgttttggg ggtacgcgcg gtgagaatag gtgccgttcg taggcaaggc   11760
tgacatccgc tatggcgagg ggcacatcgc tgcgctcttg caacgcgtcg cagataatgg   11820
cgcactggcg ctgcagatgc ttcaacagca cgtcgtctcc cacatctagg tagtcgccat   11880
gccttttcgtc ccccgcccg acttgttcct cgtttgcctc tgcgttgtcc tggtcttgct   11940
ttttatcctc tgttggtact gagcggtcct cgtcgtcttc gcttacaaaa cctgggtcct   12000
gctcgataat cacttcctcc tcctcaagcg ggggtgcctc gacggggaag gtggtaggcg   12060
cgttggcggc atcggtggag gcggtggtgg cgaactcaga gggggcggtt aggctgtcct   12120
tcttctcgac tgactccatg atctttttct gcctatagga gaaggaaatg gccagtcggg   12180
aagaggagca gcgcgaaacc accccgagc gcggacgcgg tgcggcgcga cgtccccaa     12240
ccatggagca cgtgtcgtcc ccgtcccgt cgccgccgcc tcccccggcg ccccaaaaa     12300
agcggatgag gcggcgtatc gagtccgagg acgaggaaga ctcatcacaa gacgcgctgg   12360
tgccgcgcac acccagcccg cggccatcga cctcggcggc ggatttggcc attgcgccca   12420
agaagaaaaa gaagcgccct tctcccaagc ccgagcgccc gccatcacca gaggtaatcg   12480
tggacagcga ggaagaaaga gaagatgtgg cgctacaaat ggtgggtttc agcaacccac   12540
cggtgctaat caagcatggc aaaggaggta agcgcacagt gcgcggctg aatgaagacg    12600
acccagtggc gcgtggtatg cggacgcaag aggaagagga agcgcccagc gaagcggaaa   12660
gtgaaattac ggtgatgaac ccgctgagtg tgccgatcgt gtctgcgtgg gagaagggca   12720
tggaggctgc gcgcgcgctg atggacaagt accacgtgga taacgatcta aaggcgaact   12780
tcaaactact gcctgaccaa gtggaagctc tggcggccgt atgcaagacc tggctgaacg   12840
aggagcaccg cggggttcag ctgaccttca ccagcaacaa gacctttgtg acgatgatgg   12900
ggcgattcct gcaggcgtac ctgcagtcgt ttgcagaggt gacctacaag catcacgagc   12960
ccacgggctg cgcgttgtgg ctgcaccgct gcgctgagat cgaaggcgag cttaagtgtc   13020
tacacgaag cattatgata aataaggagc acgtgattga aatggatgtg acgagcgaaa   13080
acgggcggcg cgcgtgaag gagcagtcta gcaaggccaa gatcgtgaag aaccgtggtg     13140
gccgaaatgt ggtgcagatc tccaacaccg acgcaaggtg ctgcgtgcac gacgcggcct   13200
gtccggccaa tcagttttcc ggcaagtctt cggcatgtt cttctctgaa ggcgcaaagg    13260
ctcaggtggc ttttaagcag atcaaggctt ttatgcaggc gctgtatcct aacgcccaga   13320
ccgggcacgg tcacctttg atgccactac ggtgcgagtg caactcaaag cctgggcacg    13380
cgccctttt gggaaggcag ctaccaaagt tgactccgtt cgccctgagc aacgcggagg   13440
```

```
acctggacgc ggatctgatc tccgacaaga gcgtgctggc cagcgtgcac cacccgcgc    13500
tgatagtgtt ccagtgctgc aaccctgtgt atcgcaactc gcgcgcgcag ggcggaggcc   13560
ccaactgcga cttcaagata tcggcgcccg acctgctaaa cgcgttggtg atggtgcgca   13620
gcctgtggag tgaaaacttc accgagctgc cgcggatggt tgtgcctgag tttaagtgga   13680
gcactaaaca ccagtatcgc aacgtgtccc tgccagtggc gcatagcggt gcgcggcaga   13740
accccttga ttttaaacg gcgcagacgg caagggtggg ggtaaataat cacccgagag     13800
tgtacaaata aaagcatttg cctttattga aagtgtctct agtacattat ttttacatgt   13860
ttttcaagtg acaaaaagaa gtggcgctcc taatctgcgc actgtggctg cggaagtagg   13920
gcgagtggcg ctccaggaag ctgtagagct gttcctggtt gcgacgcagg gtgggctgta   13980
cctggggact gttgagcatg gagttgggta ccccggtaat aaggttcatg gtggggttgt   14040
gatccatggg agtttgggc cagttggcaa aggcgtggag aaacatgcag cagaatagtc    14100
cacaggcggc cgagttgggc ccctgtacgc tttgggtgga cttttccagc gttatacagc   14160
ggtcggggga agaagcaatg gcgctacggc gcaggagtga ctcgtactca aactggtaaa   14220
cctgcttgag tcgctggtca gaaaagcaaa agggctcaaa gaggtagcat gttttttgagt  14280
gcggttcca ggcaaaggcc atccagtgta cgcccccagt ctcggtccga gactcgaacc    14340
ggggtcccg cgactcaacc cttggaaaat aaccctccgg ctacagggag cgagccactt    14400
aatgctttcg ctttccagcc taaccgctta cgctgcgcgc ggccagtggc caaaaaagct   14460
agcgcagcag ccgccgcgcc tggaaggaag ccaaaaggag cactccccccg ttgtctgacg  14520
tcgcacacct gggttcgaca cgcgggcggt aaccgcatgg atcacggcgg acggccggat   14580
acggggctcg aacccggtc gtccgccatg atacccttgc gaatttatcc accagaccac    14640
ggaagagtgc ccgcttacag gctctccttt tgcacgtag agcgtcaacg attgcgcgcg    14700
cctgaccggc cagagcgtcc cgaccatgga gcacttttg ccgctgcgca acatctggaa    14760
ccgcgtccgc gactttccgc gcgcctccac caccgccgcc ggcatcacct ggatgtccga   14820
gtacatctac ggatatcatc gccttatgtt ggaagatctc gccccggag ccccggccac    14880
cctacgctgg ccccctctacc gccagccgcc gccgcacttt ttggtgggat accagtacct  14940
ggtgcggact tgcaacgact acgtatttga ctcgagggct tactcgcgtc tcaggtacac   15000
cgagctctcg cagccgggtc accagaccgt taactggtcc gttatgccca actgcactta   15060
caccatcaac acgggcgcat accaccgctt tgtggacatg gatgacttcc agtctaccct   15120
cacgcaggtg cagcaggcca tattagccga gcgcgttgtc gccgacctag ccctgcttca   15180
gccgatgagg ggcttcgggg tcacacgcat gggaggaaga gggcgccacc tacggccaaa   15240
ctccgccgcc gccgcagcga tagatgcaag agatgcagga caagaggaag gagaagaaga   15300
agtgccggta gaaaggctca tgcaagacta ctacaaagac ctgcgccgat gtcaaaacga   15360
agcctggggc atggccgacc gcctgcgcat tcagcaggcc ggacccaagg acatggtgct   15420
tctg                                                                15424

SEQ ID NO: 393         moltype = DNA   length = 3849
FEATURE                Location/Qualifiers
misc_feature           1..3849
                       note = Description of Artificial Sequence: Synthetic
                       polynucleotide
source                 1..3849
                       mol_type = other DNA
                       organism = synthetic construct
SEQUENCE: 393
cggcgtcaat acgggataat accgcgccac atagcagaac tttaaaagtg ctcatcattg      60
gaaaacgttc tcggggcga aaactctcaa ggatcttacc gctgttgaga tccagttcga     120
tgtaacccac tcgtgcaccc aactgatctt cagcatcttt tactttccac agcgtttctg    180
ggtgagcaaa aacaggaagg caaaatgccg caaaaaaggg aataagggcg cacggaaat    240
gttgaatact catactcttc cttttcaat attattgaag catttatcag ggttattgtc    300
tcatgagcgg atacatattt gaatgtattt agaaaaataa acaaatagg gttccgcgca    360
catttccccg aaaagtgcca cctaaattgt aagcgttaat attttgttaa aattcgcgtt    420
aaatttttgt taaatcagct catttttaa ccaataggcc gaaatcggca aaatccctta    480
taaatcaaaa gaatagaccg atagggtt gagtgttgtt ccagtttgga acaagagtcc    540
actattaaag aacgtggact ccaacgtcaa agggcgaaaa accgtctatc agggcgatgg    600
cccactacgt gaaccatcac cctaatcaag ttttttgggg tcgaggtgcc gtaaagcact    660
aaatcggaac cctaaaggga gccccccgatt tagagcttga cggggaaagc cggcgaacgt    720
ggcgagaaag gaaggaaga aagcgaaagg agcgggcgct agggcgctgg caagtgtagc    780
ggtcacgctg cgcgtaacca ccacacccgc cgcgcttaat gcgccgctac agggcgcgtc    840
ccattcgcca ttcaggctgc gcaactgttg ggaagggcga tcggtgcggg cctcttcgct    900
attacgccag ctgcgcgctc gtcgctcac tgaggccgcc caagcaaagc ccggcgtcg    960
ggcgaccttt ggtcgcccgg cctcagtgag cgagcgagcg cgcagagagg gagtggccaa   1020
ctccatcact agggggttcct tgtagttaat gattaacccg ccatgctact tatctacgta   1080
gccatgctct aggaagagta ccattgacgt caataatgac gtatgttccc atagtaacgc   1140
caatagggac tttccattga cgtcaatggg tggagtattt acggtaaact gcccacttgg   1200
cagtacatca agtgtatcag tggtttgtct ggtcaaccac cgcggtctca gtggtgtacg   1260
gtacaaaccc agctaccggt cgccaccatg cccgccatga agatcgagtg ccgcatcacc   1320
ggcacccctga acgcgtgga gttcgagctg gtgggcggcg agagggcac cccgagcag    1380
ggccgcatga ccaacaagat gaagagcacc aaaggcgcc tgacctcag ccctctacctg    1440
ctgagccacg tgatgggcta cggcttctac cacttcgga cctaccccag cggctacgag    1500
aacccctcc tgcacgccat caacaacggc ggctacacca caccgcat cgagaagtac     1560
gaggacggcg gcgtgctgca cgtgagcttc agctaccgct acgaggccgg ccgcgtgatc    1620
ggcgacttca aggtggtggg caccggcttc cccgaggaca gcgtgatctt caccgacaag    1680
atcatccgca gcaacgccac cgtggagcac ctgcacccca tgggcgataa cgtgctggtg    1740
ggcagcttcgc ccgcaccctt cagcctgcgc gacggccgc actacagctt cgtggtgtca   1800
agccacatga cttcaagag cgccatccac cccagcatcc tgcagaacgg gggcccatg    1860
ttcgccttcc gccgcgtgga ggagctgcac agcaacaccg agctgggcat cgtggagtac   1920
cagcacgcct tcaagacccc catcgccttc gccagatctc gagctcgatg agtttggaca   1980
aaccacaact agaatgcagt gaaaaaaatg ctttatttgt gaaatttgtg atgctattgc    2040
tttatttgtg ggccccgggat cttcctagag catggctacg tagataagta gcatggcggg   2100
```

-continued

```
ttaatcatta actacaagga accoctagtg atggagttgg ccactccctc tctgcgcgct    2160
cgctcgctca ctgaggccgg gcgaccaaag gtcgcccgac gcccgggctt tgcccgggcg    2220
gcctcagtga gcgagcgagc gcgcagctgc attaatgaat cggccaacgc gcggggagag    2280
gcggtttgcg tattgggcgc tcttccgctt cctcgctcac tgactcgctg cgctcggtcg    2340
ttcggctgcg gcgagcggta tcagctcact caaaggcggt aatacggtta tccacagaat    2400
caggggataa cgcaggaaag aacatgtgag caaaaggcca gcaaaaggcc aggaaccgta    2460
aaaaggccgc gttgctggcg ttttccata ggctccgccc ccctgacgag catcacaaaa     2520
atcgacgctc aagtcagagg tggcgaaacc cgacaggact ataaagatac caggcgtttc    2580
ccctggaag ctccctcgtg cgctctcctg ttccgaccct gccgcttacc ggatacctgt     2640
ccgcctttct cccttcggga agcgtggcgc tttctcatag ctcacgctgt aggtatctca    2700
gttcggtgta ggtcgttcgc tccaagctgg gctgtgtgca cgaaccccc gttcagcccg     2760
accgctgcgc cttatccggt aactatcgtc ttgagtccaa cccggtaaga cacgacttat    2820
cgccactggc agcagccact ggtaacagga ttagcagagc gaggtatgta ggcggtgcta    2880
cagagttctt gaagtggtgg cctaactacg gctacactag aagaacagta tttggtatct    2940
gcgctctgct gaagccagtt accttcggaa aaagagttgg tagctcttga tccggcaaac    3000
aaaccaccgc tggtagcggt ggttttttg tttgcaagca gcagattacg cgcagaaaaa    3060
aaggatctca agaagatcct ttgatctttt ctacggggtc tgacgctcag tggaacgaaa    3120
actcacgtta agggattttg gtcatgagat tatcaaaaag gatcttcacc tagatctttt    3180
taaattaaaa atgaagtttt aaatcaatct aaagtatata tgagtaaact tggtctgaca    3240
gttaccaatg cttaatcagt gaggcaccta tctcagcgat ctgtctattt cgttcatcca    3300
tagttgcctg actccccgtc gtgtagataa ctacgatacg ggagggctta ccatctggcc    3360
ccagtgctgc aatgataccg cgagacccac gctcaccggc tccagattta tcagcaataa    3420
accagccagc cggaagggcc gagcgcagaa gtggtcctgc aactttatcc gcctccatcc    3480
agtctattaa ttgttgccgg gaagctagag taagtagttc gccagttaat agtttgcgca    3540
acgttgttgc cattgctaca ggcatcgtgg tgtcacgctc gtcgtttggt atggcttcat    3600
tcagctcggt tcccaacga tcaaggcgag ttacatgatc ccccatgttg tgcaaaaaag    3660
cggttagctc cttcggtcct ccgatcgttg tcagaagtaa gttggccgca gtgttatcac    3720
tcatggttat ggcagcactg cataattctc ttactgtcat gccatccgta agatgctttt    3780
ctgtgactgg tgagtactca accaagtcat tctgagaata gtgtatgcgg cgaccgagtt    3840
gctcttgcc                                                            3849
```

| | | |
|---|---|---|
| SEQ ID NO: 394 | moltype = DNA length = 7336 | |
| FEATURE | Location/Qualifiers | |
| misc_feature | 1..7336 | |
| | note = Description of Artificial Sequence: Synthetic polynucleotide | |
| source | 1..7336 | |
| | mol_type = other DNA | |
| | organism = synthetic construct | |

SEQUENCE: 394

```
atgccggggt tttacgagat tgtgattaag gtccccagcg accttgacga gcatctgccc     60
ggcatttctg acagctttgt gaactgggtg gccgagaagg aatgggagtt gccgccagat    120
tctgacatgg atctgaatct gattgagcag gcaccccgta ccgtggccga gaagctgcag    180
cgcgactttc tgacggaatg gcgccgtgtg agtaaggccc cggaggctct ttttctttgtg    240
caatttgaga agggagagag ctactccac atgcacgtgc tcgtgaaaac caccggggtg    300
aaatccatgg ttttgggacg tttcctgagt cagattcgcg aaaaactgat tcagagaatt    360
taccgcggga tcgagccgac tttgccaaac tggttccggg tcacaaagac cagaaatgcc    420
gccggaggcg ggaacaaggt ggtgatgag tgctacatcc ccaattactt gctccccaaa    480
acccagcctg agctccagtg ggcgtggact aatatgaac agtatttaag cgcctgtttg     540
aatctcacg agcgtaaacg gttggtggcg cagcatctga cgcacgtgtc gcagacgcag    600
gagcagaaca aagagaatca gaatcccaat tctgatgccgc cggtgatcag atcaaaaact    660
tcagccaggt acatggagct ggtcgggtgg ctcgtggaca aggggattac ctcggagaag    720
cagtggatcc aggaggacca ggcctcatac atctcctca atgcggcctc caactcgcgg    780
tcccaaatca aggctgcctt ggacaatgcg ggaaagatta tgagcctgac taaaaccgcc    840
cccgactacc tggtgggcca gcagcccgtg gaggacattt ccagcaatcg gatttataaa    900
attttggaac taaacgggta cgatccccaa tatgcggctt ccgtctttct gggatgggcc    960
acgaaaaagt tcggcaagag gaacaccatc tggctgtttg gcctgcaac taccggggaag   1020
accaacatcg cggaggccat agcccacact gtgcccttct acgggtcgt aaactggacc    1080
aatgagaact ttcccttcaa cgactgtgtc gacaagatgg tgatctggtg ggagagggg    1140
aagatgaccg ccaaggtcgt ggagtcgcc aaagccattc tcggaggaag caaggtgcgc   1200
gtggaccaga aatgcaagtc ctcggcccag atagacccga ctcccgtgat cgtcacctcc    1260
aacaccaaca tgtgcgccgt gattgacggg aactcaacga ccttcgaaca ccagcagccg    1320
ttgcaagacc ggatgttcaa atttgaactc acccgccgtc tggatcatga ctttgggaag    1380
gtcaccaagc aggaagtcaa agacttttttc cggtgggcaa aggatcacgt ggttgaggtg    1440
gagcatgaat tctacgtcaa aaagggtgga gccaagaaaa gaccccgccc cagtgacgca    1500
gatataagtg agcccaaacg gtgcgcgag tcagttgcgc agccatcgac gtcagacgcg    1560
gaagcttcga tcaactacgc agacaggtac caaaacaaat gttctcgtca cgtgggcatg    1620
aatctgatgc tgtttccctg cagacaatgc gagagaatga atcagaattc aaatatctgc    1680
ttcactcacg gacagaagag ctgtttagag tgctttccg tgtcagaatc tcaaccgtt     1740
tctgtcgtca aaaaggcgta tcagaaactg tgctacattc atcatatcat gggaaaggtg    1800
ccagacgctt gcactgcctg cgatctgtc aatgtggatt tggatgactg catctttgaa    1860
caataaatga tttaaatcag gtatggctgc cgatggttat cttccagatt ggctcgagga    1920
caacctctct gagggcattc gcgagtggtg ggcgctgaaa cctggagccc cgaagcccaa    1980
agccaaccag caaaagcagg acgacgcgcg ggtctggtta cttcctggct acaagtacct    2040
cggaccttcc aacggactcg acaaggggga gccgtcaac gcgcggacg cagcggccct    2100
cgagcacgac aaggcctacg accagcagct cgaggcggt gacaatccgt acctgcggta    2160
taaccacgcc gacgccgagt ttcaggacgc tctgcaagaa gatacgtctt ttggggcaa    2220
cctcgggcga gcagtcttcc aggccaagaa gcgggttctc gaacctctcg gtctggttga    2280
ggaaggcgct aagacggctc ctggaaagaa gagaccggta gagccatcac cccagcgttc    2340
```

```
tccagactcc tctacgggca tcggcaagaa aggccaacag cccgccagaa aaagactcaa 2400
ttttggtcag actggcgact cagagtcagt tccagaccct caacctctcg gagaacctcc 2460
agcagcgccc tctggtgtgg gacctaatac aatggctgca ggcggtggcg caccaatggc 2520
agacaataac gaaggcgccg acggagtggg tagttcctcg ggaaattggc attgcgattc 2580
cacatggctg ggcgacagag tcatcaccac cagcacccga acctgggccc tgcccaccta 2640
caacaaccac ctctacaagc aaatctccaa cgggacatcg ggaggagcca ccaacgacaa 2700
cacctacttc ggctacagca cccccctggg gtatttgac tttaacagat tccactgcca 2760
cttttcacca cgtgactggc agcgactcat caacaacaac tggggattcc ggcccaagag 2820
actcagcttc aagctcttca acatccaggt caaggaggtc acgcagaatg aaggcaccaa 2880
gaccatcgcc aataacctca ccagcaccat ccaggtgttt acggactcgg agtaccagct 2940
gccgtacgtt ctcggctctg cccaccaggg ctgcctgcct ccgttcccgg cggacgtgtt 3000
catgattccc cagtacggct acctaacact caacaacggt agtcaggccg tgggacgctc 3060
ctccttctac tgcctggaat actttccttc gcagatgctg agaaccggca acaacttcca 3120
gtttacttac accttcgagg acgtgccttt ccacagcagc tacgcccaca gccagagctt 3180
ggaccggctg atgaatcctc tgattgacca gtacctgtac tacttgtctc ggactcaaac 3240
aacaggaggc acggcaaata cgcagactct gggcttcagc caaggtgggc ctaatacaat 3300
ggccaatcag gcaaagaact ggctgccagg accctgttac cgccaacaac gcgtctcaac 3360
gacaaccggg caaaacaaca atagcaactt tgcctggact gctgggacca aataccatct 3420
gaatggaaga aattcattgg ctaatcctgg catcgctatg gcaacacaca aagacgacga 3480
ggagcgtttt tttcccagta acgggatcct gattttggc aaacaaaatg ctgccagaga 3540
caatgcggat tacagcgatg tcatgctcac cagcgaggaa gaaatcaaaa ccactaaccc 3600
tgtggctaca gaggaatacg gtatcgtggc agataacttg cagcagcagaa acacggctgc 3660
tcaaattgga actgtcaaca gccaggggc cttaccggt atggtctggc agaaccggga 3720
cgtgtacctg caggggtccca tctgggccaa gattcctcac acggacggca acttccaccc 3780
gtctccgctg atgggcggct ttggcctgaa acatcctccg cctcagatcc tgatcaagaa 3840
cacgcctgta cctgccggatc ctccgaccac ctttcaaccag tcaaagctga actctttcat 3900
cacgcaatac agcaccggac aggtcagcgt ggaaattgga tgggagctgc agaaggaaaa 3960
cagcaagcgc tggaacccg agatccagta cacctccaac tactacaaat ctacaagtgt 4020
ggactttgct gttaatacag aaggcgtgta ctctgaaccc cgcccattg gcacccgtta 4080
cctcacccgt aatctgtaat tgcctgttaa tcaataaacc ggttgattcg tttcagttga 4140
actttggtct ctgcgaaggg cgaattcgtt taaacctgca ggactagagg tcctgtatta 4200
gaggtcacgt gagtgttttg cgacatttt cgacaccatg tggtcacgct gggtatttaa 4260
gcccgagtga gcacgcaggg tctccatttt gaagcgggag gtttgaacgc gcagccgcca 4320
agccgaattc tgcagatatc catcacactg gcggccgctc gactagagcg gccgccaccg 4380
cggtggagct ccagcttttg ttcccttag tgagggttaa ttgcgcgctt ggcgtaatca 4440
tggtcatagc tgtttcctgt gtgaaattgt tatccgctca caattccaca acatacga 4500
gccgaagca taaagtgtaa agcctgggt gcctaatgag tgagctaact cacattaatt 4560
gcgttgcgct cactgcccgc tttccagtcg ggaaacctgt cgtgccagct gcattaatga 4620
atcggccaac gcgcggggag aggcggttg cgtattgggc gctcttccgc ttcctcgctc 4680
actgactcgc tgcgctcggt cgttcggctg cggcgagcgg tatcagctca ctcaaaggcg 4740
gtaatacggt tatccacaga atcagggat aacgcaggaa agaacatgtg agcaaaaggc 4800
cagcaaaagg ccaggaaccg taaaaaggcc gcgttgctgg cgtttttcca taggctccgc 4860
cccctgacg agcatcacaa aaatcgacgc tcaagtcaga ggtggcgaaa cccgacagga 4920
ctataaagat accaggcgtt tcccctgga agctccctcg tgcgctctcc tgttccgacc 4980
ctgccgctta ccggatacct gtccgccttt ctcccttcgg gaagcgtggc gctttctcat 5040
agctcacgct gtaggtatct cagttcggtg taggtcgttc gctccaagct gggctgtgtg 5100
cacgaacccc ccgttcagcc cgaccgctgc gccttatccg gtaactatcg tcttgagtcc 5160
aacccggtaa gacacgactt atcgccactg gcagcagcca ctggtaacag gattagcaga 5220
gcgaggtatg taggcggtgc tacagagttc ttgaagtggt ggcctaacta cggctacact 5280
agaagaacag tatttggtat ctgcgctctg ctgaagccag ttaccttcgg aaaaagagtt 5340
ggtagctctt gatccggcaa acaaaccacc gctggtagcg gtggtttttt tgtttgcaag 5400
cagcagatta cgcgcagaaa aaaaggatct caagaagatc ctttgatctt ttctacgggg 5460
tctgacgctc agtggaacga aaactcacgt taagggattt tggtcatgag attatcaaaa 5520
aggatcttca cctagatcct tttaaattaa aaatgaagtt ttaaatcaat ctaaagtata 5580
tatgagtaaa cttggtctga cagttaccaa tgcttaatca gtgaggcacc tatctcagcg 5640
atctgtctat ttcgttcatc catagttgcc tgactcccg tcgtgtagat aactacgata 5700
cgggagggct taccatctgg ccccagtgct gcaatgatac gcgagaccc acgctcaccg 5760
gctccagatt tatcagcaat aaaccagcca gccgaaggg ccgagcgcag aagtggtcct 5820
gcaactttat ccgcctccat ccagtctatt aattgttgcc gggaagctag agtaagtagt 5880
tcgccagtta atagtttgcg caacgttgtt gccattgcta caggcatcgt ggtgtcacgc 5940
tcgtcgtttg gtatggcttc attcagctcc ggttcccaac gatcaaggcg agttacatga 6000
tcccccatgt tgtgcaaaaa agcggttagc tccttcggtc ctccgatcgt tgtcagaagt 6060
aagttggccg cagtgttatc actcatggtt atggcagcac tgcataattc tcttactgtc 6120
atgccatccg taagatgctt ttctgtgact ggtgagtact caaccaagtc attctgagaa 6180
tagtgtatgc ggcgaccgag ttgctcttgc ccggcgtcaa tacgggataa taccgcgcca 6240
catagcagaa ctttaaaagt gctcatcatt ggaaaacgtt cttcggggcg aaaactctca 6300
aggatcttac cgctgttgag atccagttcg atgtaaccca ctcgtgcacc caactgatct 6360
tcagcatctt ttactttcac cagcgtttct gggtgagcaa aaacaggaag gcaaaatgcc 6420
gcaaaaaagg gaataagggc gacacggaaa tgttgaatac tcatactctt cctttttcaa 6480
tattattgaa gcatttatca gggttattgt ctcatgagcg gatacatatt tgaatgtatt 6540
tagaaaaata aacaaatagg ggttccgcgc acatttcccc gaaaagtgcc acctaaattg 6600
taagcgttaa tattttgtta aaattcgcgt taaattttg ttaaatcagc tcatttttta 6660
accaataggc cgaaatcggc aaaatccctt ataaatcaaa agaatagacc gagataggt 6720
tgagtgttgt tccagtttgg aacaagagtc cactattaaa gaacgtggac tccaacgtca 6780
aagggcgaaa aaccgtctat cagggcgatg gcccactacg tgaaccatca ccctaatcaa 6840
gttttttggg gtcgaggtgc cgtaaagcac taaatcggaa ccctaaaggg agcccccgat 6900
ttagagcttg acgggaaag ccggcgaacg tggcgagaaa ggaagggaag aaagcgaaag 6960
gagcgggcgc tagggcgctg gcaagtgtag cggtcacgct gcgcgtaacc accacacccg 7020
ccgcgcttaa tgcgccgcta cagggcgcgt cccattcgcc attcaggctg cgcaactgtt 7080
```

```
gggaagggcg atcggtgcgg gcctcttcgc tattacgcca gctggcgaaa gggggatgtg    7140
ctgcaaggcg attaagttgg gtaacgccag ggttttccca gtcacgacgt tgtaaaacga    7200
cggccagtga gcgcgcgtaa tacgactcac tataggcga attgggtacc gggcccccc      7260
tcgatcgagg tcgacggtat cgggggagct cgcagggtct ccattttgaa gcgggaggtt    7320
tgaacgcgca gccgcc                                                    7336

SEQ ID NO: 395          moltype = DNA   length = 969
FEATURE                 Location/Qualifiers
misc_feature            1..969
                        note = Description of Artificial Sequence: Synthetic
                        polynucleotide
source                  1..969
                        mol_type = other DNA
                        organism = synthetic construct
SEQUENCE: 395
ccccaactgg ggtaaccttt gggctccccg ggcgcgacta taagctgcga gcaacttcac    60
ttgggtatgc cggcggtagc gcttaccgtt cgtataatgt atgctatacg aagttatccg    120
aagccgctag cggtggtttg tctggtcaac caccgcggtc tcagtggtgt acggtacaaa    180
cccagctacc ggtcgccacc atgcccgcca tgaagatcga gtgccgcatc accggcaccc    240
tgaacggcgt ggagttcgag ctggtgggcg gcggagaggg caccccgag cagggccgca    300
tgaccaacaa gatgaagagc accaaggcg ccctgacctt cagcccctac ctgctgagcc    360
acgtgatggg ctacggcttc taccacttcg gcacctaccc cagcggctac gagaacccct    420
tcctgcacgc catcaacaac ggcggctaca ccaacacccg catcgagaag tacgaggacg    480
gcggcgtgct gcacgtgagc ttcagctacc gctacgaggc cggccgcgtg atcggcgact    540
tcaaggtggt gggcaccggc ttccccgagg acagcgtgat cttcaccgac aagatcatcc    600
gcagcaacgc caccgtggag cacctgcacc ccatgggcga taacgtgctg gtgggcagct    660
tcgcccgcac cttcagcctg cgcgacggcg gctactacga cttcgtggtg gacagccaca    720
tgcacttcaa gagcgccatc caccccagca tcctgcagaa cggggccccc atgttcgcct    780
tccgccgcgt ggaggagctg cacagcaaca ccgagctggg catcgtggag taccagcacg    840
ccttcaagac ccccatcgcc ttcgccagat tcgagctcg atgagtttgg acaaaccaca    900
actagaatgc agtgaaaaaa atgctttatt tgtgaaattt gtgatgctat tgctttattt    960
gtgggcccg                                                            969

SEQ ID NO: 396          moltype = DNA   length = 4769
FEATURE                 Location/Qualifiers
misc_feature            1..4769
                        note = Description of Artificial Sequence: Synthetic
                        polynucleotide
source                  1..4769
                        mol_type = other DNA
                        organism = synthetic construct
SEQUENCE: 396
tgatcccctg cgccatcaga tccttggcgg cgagaaagcc atccagttta ctttgcaggg    60
cttcccaacc ttaccagagg gcgccccagc tggcaattcc ggttcgcttg ctgtccataa    120
aaccgcccag tctagctatc gccatgtaag cccactgcaa gctacctgct ttctctttgc    180
gcttgcgttt tcccttgtcc agatagccca gtagctgaca ttcatccggg gtcagcaccg    240
tttctgcgga ctggctttct acgtgctcga gggggccaa acggtctcca gcttggctgt    300
tttggcggat gagagaagat tttcagcctg atacagatta aatcagaacg cagaagcggt    360
ctgataaaac agaatttgcc tggcggcagt agcgcggtgg tcccacctga ccccatgccg    420
aactcagaag tgaaacgccg tagcgccgat ggtagtgtgg ggtctcccca tgcgagagta    480
gggaactgcc aggcatcaaa taaaacgaaa ggctcagtcg aaagactggg cctttcgttt    540
tatctgttgt ttgtcggtga acgctctcct gagtaggaca aatccgccgg gagcggattt    600
gaacgttgcg aagcaacggc ccggagggtg gcgggcagga cgcccgccat aaactgccag    660
gcatcaaatt aagcagaagg ccatcctgac ggatggcctt tttgcgtttc tacaaactct    720
tttgtttatt tttctaaata cattcaaata tgtatccgct catgaccaaa atccccttaac   780
gtgagttttc gttccactga gcgtcagacc ccgtagaaaa gatcaaagga tcttcttgag    840
atccttttt tctgcgcgta atctgctgct tgcaaacaaa aaaaccaccg ctaccagcgg    900
tggtttgttt gccggatcaa gagctaccaa ctcttttcc gaaggtaact ggcttcagca    960
gagcgcagat accaaatact gtccttctag tgtagccgta gttaggccac cacttcaaga    1020
actctgtagc accgcctaca tacctcgctc tgctaatcct gttaccagtg gctgctgcca    1080
gtggcgataa gtcgtgtctt accgggttgg actcaagacg atagttaccg gataaggcgc    1140
agcggtcggg ctgaacgggg ggttcgtgca cacagcccag cttggagcga acgacctaca    1200
ccgaactgag atacctacag cgtgagctat gagaaagcgc cacgcttccc gaagggagaa    1260
aggcggacag gtatccggta agcggcaggg tcggaacagg agagcgcacg agggagcttc    1320
caggggggaaa cgcctggtat ctttatagtc ctgtcgggtt tcgccacctc tgacttgagc    1380
gtcgatttt tgtgatgctcg tcagggggc ggagcctatg gaaaaacgcc agcaacgcgg    1440
ccttttacg gttcctggcc ttttgctggc cttttgctca catgttcttt cctgcgttat    1500
ccctgattc tgtggataac cgtattaccg cctttgagtg agctgatacc gctcgccgca    1560
gccgaacgac cgagcgcagc gagtcagtga gcgaggaagc ggaagagcgc ctgatgcggt    1620
attttctcct tacgcatctg tgcggtattt cacaccgcat atggtgcact ctcagtacaa    1680
tctgctctga tgccgcatag ttaagccagt atacactccg ctatcgctac gtgactgggt    1740
catggctgcg ccccgacacc cgccaacacc cgctgacgcg ccctgacggg cttgtctgct    1800
cccggcatcc gcttacagac aagctgtgac cgtctccgga agctgcatgt gtcagaggtt    1860
ttcaccgtca tcaccgaaac gcgcgaggca gcagatcaat ctgcaaaccc tatgctactc    1920
gcatgcataa tgtgcctgtc aaatggacga agcaggatt ctgcaaaccc tatgctactc    1980
cgtcaagccg tcaattgtct gattcgttac caattatgac aacttgacgg ctacatcatt    2040
cactttttct tcacaaccgg cacggaactc gctcggctg ccccggtgc attttttaaa    2100
tacccgcgag aaatagagtt gatcgtcaaa accaacattg cgaccgacgg tggcgatagg    2160
catccggggtg gtgctcaaaa gcagcttcgc ctggctgata cgttggtcct cgcgccagct    2220
```

```
taagacgcta atccctaact gctggcggaa aagatgtgac agacgcgacg gcgacaagca   2280
aacatgctgt gcgacgctgg cgatacatta ccctgttatc cctagatgac attaccctgt   2340
tatcccagat gacattaccc tgttatccct agatgacatt accctgttat ccctagatga   2400
catttaccct gttatcccta gatgacatta ccctgttatc cagatgaca ttaccctgtt    2460
atccctagat acattaccct gttatcccag atgacatacc ctgttatccc tagatgacat   2520
taccctgtta tcccagatga cattaccctg ttatccctag atacattacc ctgttatccc   2580
agatgacata ccctgttatc cctagatgac attaccctgt tatcccagat gacattaccc   2640
tgttatccct agatacatta ccctgttatc cagatgaca tacccctgtta tcccctagatg   2700
acattaccct gttatcccag atgacattac cctgttatcc ctagatacat taccctgtta   2760
tcccagatga catacccctgt tatcccctaga tgacattacc ctgttatccc agatgacatt   2820
accctgttat ccctagatac attaccctgt tatcccagat gacatacct gttatccta     2880
gatgacatta ccctgttatc cagatgaca ttaccctgtt atccctagat acattaccct     2940
gttatcccag atgacatacc ctgttatccc tagatgacat accctgtta tcccagataa    3000
actcaatgat gatgatgatg atggtcgaga ctcagcggcc gcggtgcag gggcgccct      3060
tgggctcccc gggcgcgatg cccgccatga agatcgagtg ccgcatcacc ggcaccctga    3120
acggcgtgga gttcgagctg gtgggcgcgg agagggcac cccgagcag gccgcatga      3180
ccaacaagat gaagagcacc aaaggcgccc tgaccttcag cccctacctg ctgagccacg    3240
tgatggcgta cggcttctac cacttcggca cctaccccag cggctacagg aacccctcc    3300
tgcacgccat caacaacggc ggctacacca cacccgcat cgagaagtac gaggacggcg    3360
gcgtgctgca cgtgagcttc agctaccgct acgaggccgg ccgcgtgatc ggcgacttca   3420
aggtggtggg caccggcttc cccgaggaca gcgtgatctt caccgacaag atcatccgca   3480
gcaacgccac cgtggagcac ctgaacccca tgggcgataa cgtgctggtg ggcagcttcg   3540
cccgcaccttt cagcctgcgc gacggcggct actacagctt cgtggtggac agccacatgc   3600
acttcaagag cgccatccac cccagcatcc tgcagaacgg ggggcccatg ttcgccttcc    3660
gccgcgtgga ggagctgcac agcaacaccg agctgggcat cgtggagtac cagcacgcct   3720
tcaagacccc catcgccttc gccagatctc gagctcgagg tggtttgtct ggtcaaccac    3780
cgcggtctca gtggtgtacg gtacaaaccc accccaactg gggtaacctt tgagttctct   3840
cagttgggggg taatcagcat catgatgtgg taccacatca tgatgctgat tataagaatg   3900
cggccgccac actctagtgg atctcgagtt aataattcag aagaactcgt caagaaggcg   3960
ataagaagcg atgcgctgcg aatcgggagc ggcgataccg taaagcacga ggggaagcggtc   4020
agccccattg ccgccaagct cttcagcaat atcacggta gccacgcta tgtcctgata     4080
gcggtccgcc acacccagcc ggccacagtc gatgaatcca gaaaagcgg catttccac     4140
catgatattc ggcaagcagg catcgccatg ggtcacgacg atcctcgc cgtcgggcat      4200
gctcgccttg agcctggcga acagttcggc tggcgcgagc cctgatgct cttcgtccag    4260
atcatcctga tcgacaagac cggcttccat ccgagtacgt gctcgctcga tgcgatgttt   4320
cgcttggtgg tcgaatgggc aggtagccgg atcaagcgta tgcagccgcc gcattgcatc   4380
agccatgatg gatactttct cggcaggagc aaggtgtaga tgacatggag atcctgcccc   4440
ggcacttcgc ccaatagcag ccagtccctt cccgcttcag tgacaacgtc gagcacagct   4500
gcgcaaggaa cgcccgtcgt ggccaggcac gatgccgc ctgcctgtc ttgcagttca     4560
ttcagggcac cggacaggtc ggtcttgaca aaagaaccg gcgcccctg cgctgacagc    4620
cggaacacgg cggcatcaga gcagccgatt gtctgttgtg cccagtcata gccgaatagc    4680
ctctccaccc aagcggccgg agaacctgcg tgcaatccat cttgttcaat catgcgaaac    4740
gatcctcatc ctgtctcttg atcagagct                                      4769

SEQ ID NO: 397           moltype = DNA   length = 797
FEATURE                  Location/Qualifiers
misc_feature             1..797
                         note = Description of Artificial Sequence: Synthetic
                         polynucleotide
source                   1..797
                         mol_type = other DNA
                         organism = synthetic construct
SEQUENCE: 397
ccccaactgg ggtaaccttt gggctccccg ggcgcgatgg tgagcaaggg cgaggaggat     60
aacatggcca tcatcaagga gttcatgcgc ttcaaggtgc acatggaggg ctccgtgaac   120
ggccacgagt tcgagatcga gggcgagggc gagggccgcc cctacgaggg cacccagacc   180
gccaagctga aggtgaccaa gggtggcccc ctgcccttcg cctgggacat cctgtcccct   240
cagttcatgt acggctccaa ggcctacgtg aagcaccccg ccgacatccc cgactacttg   300
aagctgtcct tccccgaggg cttcaagtgg gagcgcgtga tgaacttcga ggacggcggc    360
gtggtgaccg tgacccagga ctcctccctg caggacggcg agttcatcta caaggtgaag    420
ctgcgcggca ccaacttccc ctccgacggc cccgtaatgc agaagaagac catgggctgg    480
gaggcctcct ccgagcggat gtaccccgag gacggcgccc tgaagggcga gatcaagcag    540
aggctgaagc tgaaggacgg cggccactac gacgctgagg tcaagaccac ctacaaggcc    600
aagaagcccg tgcagctgcc cggcgcctac aacgtcaaca tcaagttgga catcacctcc    660
cacaacgagg actacaccat cgtggaacag tacgaacgcg ccgagggccg ccactccacc    720
ggcggcatgg acgagctgta caaggtggt ttgtctggtc aaccaccgcg agctcagtgg    780
tgtacggtac aaaccca                                                   797

SEQ ID NO: 398           moltype = DNA   length = 815
FEATURE                  Location/Qualifiers
misc_feature             1..815
                         note = Description of Artificial Sequence: Synthetic
                         polynucleotide
source                   1..815
                         mol_type = other DNA
                         organism = synthetic construct
SEQUENCE: 398
ccccaactgg ggtaaccttt gggctccccg ggcgcggccg ccaccatggt gtccaagggt     60
gaggaacttt ttaccggagt ggtgccgata ctggtagagc tggatggcga cgtaaacggg   120
```

```
cacaagttca gtgtacgggg agagggcgag ggcgacgcta cgaatgggaa attgactttg    180
aaatttattt gcaccacggg caaattgccg gtcccgtggc caactttggt tacgaccttg    240
acctatggcg ttcagtgttt ctcacggtac ccagaccaca tgaaacagca tgactttttt    300
aagtcagcga tgccggaggg atatgtgcaa gaacggacta tctcatttaa agatgatggc    360
acatataaga caagagcgga agtcaaattc gaagggaca ccctcgtcaa tcgaatagaa    420
ctcaagggaa tagacttcaa agaagatggt aatatactgg ggcacaaact cgaatacaat    480
ttcaacagtc ataacgtcta catcactgcc gacaaacaaa aaaatgggat caaagcgaac    540
ttcaaaatcc gacataatgt cgaggatggg agcgtccaac tggcagacca ttaccagcaa    600
aatactccaa taggtgatgg tccagtgctt ttgccagata atcattatct tagctatcag    660
agcaagttga gtaaggatcc gaatgaaaag cgagatccaa tggtcttgct ggagtttgtt    720
acggcggctg gtatcacact tggtatggat gaattgtaca agggtggttt gtctggtcaa    780
ccaccgcgga ctcagtggtg tacggtacaa accca                              815

SEQ ID NO: 399         moltype = DNA   length = 1660
FEATURE                Location/Qualifiers
misc_feature           1..1660
                       note = Description of Artificial Sequence: Synthetic
                       polynucleotide
source                 1..1660
                       mol_type = other DNA
                       organism = synthetic construct
SEQUENCE: 399
ccccaactgg ggtaaccttt gggctccccg ggcgcggcca ccatgaaatg ggttactttc    60
atatctctgt tgtttttgtt ttcctctagt tccaggggca tgccgtcttc tgtctcgtgg    120
ggcatcctcc tgctggcagg cctgtgctgc ctggtcctg tctccctggc tgaggatccc    180
cagggagatg ctgcccagaa gacagataca tcccaccatg atcaggatca cccaaccttc    240
aacaagatca ccccccaacct ggctgagttc gccttcagcc tataccgcca gctggcacac    300
cagtccaaca gcaccaatat cttcttctcc ccagtgagca tcgctacagc ctttgcaatg    360
ctctccctgg ggaccaaggc tgacactcac gatgaaatcc tggagggcct gaatttcaac    420
ctcacggaca ttccggaggc tcagatccat gaaggcttcc aggaactcc ccgtaccctc    480
aaccagccag acagccagct ccagctgacc accggcaatg gcctgttcct cagcgagggc    540
ctgaagctag tggataagtt tttggaggat gttaaaaagt tgtaccactc agaagccttc    600
actgtcaact tcgggacac cgaagaggcc aagaaacaga tcaacgatta cgtggagaag    660
ggtactcaag ggaaaattgt ggatttggtc aaggagctga acagacac agttttttgt    720
ctggtgaatt acatcttctt taaggcaaa tgggagagac cctttgaagt caaggacacc    780
gaggaagagg acttccacgt ggaccaggtg accaccgtga aggtgcctat gatgaagcgt    840
ttaggcatgt ttaacatcca gcactgtaag aagctgtcca gctgggtgct gctgatgaaa    900
tacctgggca atgccaccgc catcttcttc ctgcctgatg aggggaaact acagcacctg    960
gaaaatgaac tcacccacga tatcatcacc aagttcctga aaaatgaaga cagaaggtct   1020
gccagcttac atttacccaa actgtccatt actggaacct atgatctgaa gagcgtcctg   1080
ggtcaactgg gcatcactaa ggtcttcagc aatgggggctg acctccggg ggtcacagag   1140
gaggcacccc tgaagctctc caaggccgtg cataaggctg tgctgaccat cgacgagaaa   1200
gggactgaag ctgctgggc catgtttta gaggccatac ccatgtctat ccccccccgag   1260
gtcaagttca acaaaccctt tgtcttctta atgattgaac aaaataccaa gtctcccctc   1320
ttcatgggaa agtggtgaaa tcccacccaa aaataagaat tctaactaga gctcgctgat   1380
cagcctcgac tgtgccttct agttgccagc catctgttgt ttgccccctcc ccgtgcctt   1440
ccttgaccct ggaaggtgcc actcccactg tcctttccta ataaaatgag gaaattgcat   1500
cgcattgtct gagtaggtgt cattctattc tggggggtgg ggtggggcag gacagcaagg   1560
gggaggattg ggaagagaat agcaggcatg ctggggagcg agctcgaggt ggtttgtctg   1620
gtcaaccacc gcggtctcag tggtgtacgg tacaaaccca                         1660

SEQ ID NO: 400         moltype = DNA   length = 4906
FEATURE                Location/Qualifiers
misc_feature           1..4906
                       note = Description of Artificial Sequence: Synthetic
                       polynucleotide
source                 1..4906
                       mol_type = other DNA
                       organism = synthetic construct
SEQUENCE: 400
ccccaactgg ggtaaccttt gggctccccg ggcgcggcca ccatgaaatg ggttactttc    60
atatctctgt tgtttttgtt ttcctctagt tccaggggca tgacgaggat tttgacagct    120
ttcaaagtgt tgaggacact gaagactggt tttggcttta ccaatgtgac tgcacaccaa    180
aaatggaaat tttcaagacc tggcatcagg ctccttctg caggcaca gacagcacac    240
attgtcctgg aagatggaac taagatgaaa ggttactcct ttggccatcc atcctctgtt    300
gctggtgaag tggttttaa tactggcctg ggagggtacc cagaagctat tactgaccct    360
gcctacaaag gacagattct cacaatggcc aacccctatt tgggaatgg tggagctcct    420
gatactactg ctctggatga actgggactt agcaaatatt tggagtctaa tggaatcaag    480
gtttcaggtt tgctggtgct ggattatagt aaagactaca ccactgctgc tgtaccaag    540
agtttagggc aatggctaca ggaagaaaag gttcctgcaa tttatggagt ggacacaaga    600
atgctgacta aaataattcg ggataagggt accatgcttg gaagattga atttgaaggt    660
cagcctgtga attttgtgga tccaaataaa cagaatttga ttgctgaggt ttcaaccaag    720
gatgtcaaag tgtacggcaa aggaaacccc acaaagtgg tagctgtaga ctgtgggatt    780
aaaaacaatg taatccgcct gctagtaaag cgaggagctg aagtcactt agtccctga    840
aaccatgatt tcaccaagat ggagtatgat gggatttga tcgcgggag accggggaac    900
ccagctcttg cagaaccact aattcagaat gtcagaaaga ttttggagag tgatcgcaag    960
gagccattgt ttgaatcag tacaggaaac ttaataacag gattggctgc tggtgccaaa   1020
acctacaaga tgtccatggc caacagaggg cagaatcagc ctgttttgaa tatcacaaac   1080
aaacaggctt tcattactgc tcagaatcat ggctatgcct tggacaacac cctccctgct   1140
```

```
ggctggaaac cacttttgt gaatgtcaac gatcaaacaa atgagggat tatgcatgag   1200
agcaaaccct tcttcgctgt gcagttccac ccagaggtca ccccgggggcc aatagacact  1260
gagtacctgt ttgattcctt tttctcactg ataaagaaag gaaaagctac caccattaca   1320
tcagtcttac cgaagccagc actagttgca tctcggttg aggtttccaa agtccttatt    1380
ctaggatcag gaggtctgtc cattggtcag gctggagaat ttgattactc aggatctcaa   1440
gctgtaaaag ccatgaagga agaaaatgtc aaaactgttc tgatgaaccc aaacattgca   1500
tcagtccaga ccaatgaggt gggcttaaag caagcggata ctgtctactt tcttcccatc   1560
acccctcagt ttgtcacaga ggtcatcaag gcagaacagc cagatgggtt aattctgggc   1620
atgggtggcc agacagctct gaactgtgga gtggaactat tcaagagagg tgtgctcaag   1680
gaatatggtg tgaaagtcct gggaacttca gttgagtcca ttatggctac ggaagacagg   1740
cagctgtttt cagataaact aaatgagatc aatgaaaaga ttgctccaag ttttgcagtg   1800
gaatcgattg aggatgcact gaaggcagca gacaccattg ctacccagt gatgatccgt    1860
tccgcctatg cactgggtgg gttaggctca ggcatctgtc ccaacagaga gactttgatg   1920
gacctcagca caaaggcctt tgctatgacc aaccaaattc tggtggagaa gtcagtgaca   1980
ggttggaaag aaatagaata tgaagtggtt cgagatgctg atgacaattg tgtcactgtc   2040
tgtaacatgg aaaatgttga tgccatgggt gttcacacag gtgactcagt tgttgtggct   2100
cctgcccaga cactctccaa tgccgagttt cagatgttga gacgtacttc aatcaatgtt   2160
gttcgccact tgggcattgt gggtgaatgc aacattcagt ttgcccttca tcctacctca   2220
atggaatact gcatcattga agtgaatgcc agactgtccc gaagctctgc tctggcctca   2280
aaagccactg gctacccatt ggcattcatt gctgcaaaga ttccctagg aatcccactt    2340
ccagaaatta agaacgtcgt atccgggaag acatcagcct gttttgaacc tagcctggat   2400
tacatggtca ccaagattcc ccgctgggat cttgaccgtt ttcatggaac atctagccga   2460
attggtagct ctatgaaaag tgtaggagag gtcatggcta ttggtcgtac ctttgaggag   2520
agtttccaga aagctttacg gatgtgccac ccatctatag aaggtttcac tcccccgtctc  2580
ccaatgaaca aagaatggcc atctaattta gatcttagaa aagagttgtc tgaaccaagc   2640
agcacgcgta tctatgccat tgccaaggcc attgatgaca acatgtccct tgatgagatt   2700
gagaagctca catacattga caagtggttt ttgtataaga tgcgtgatat tttaaacatg   2760
gaaaagacac tgaaaggcct caacagtgag tccatgacag aagaaccct gaaaagggca    2820
aaggagattg ggttctcaga taagcagatt tcaaaatgcc ttgggctcac tgaggcccag   2880
acaaggggac tgaggttaaa gaaaaacatc caccctttggg ttaaacagat tgatacactg  2940
gctgcagaat acccatcagt aacaaactat ctctatgtta cctacaatgg tcaggagcat   3000
gatgtcaatt ttgatgacca tggaatgatg gtgctaggct gtggtccata tcacattggc   3060
agcagtgtgg aatttgattg gtgtgctgtc tctagtatcc gcacactgcg tcaacttggc   3120
aagaagacgg tggtggtgaa ttgcaatcct gagactgtga gcacagactt tgatgagtgt   3180
gacaaactgt actttgaaga gttgtccttg gagagaatcc tagacatcta ccatcaggag   3240
gcatgtggtg gctgcatcat atcagttgga ggccagattc caaacaacct ggcagttcct   3300
ctatacaaga atggtgtcaa gatcatgggc acaagccccc tgcagatcga cagggctgag   3360
gatcgctcca tcttctcagc tgtcttggat gagctgaagg tggctcaggc accttggaaa   3420
gctgttaata ctttgaatga agcactgaa tttgcaaagt ctgtggacta ccctgcttg    3480
ttgaggcctt cctatgtttt gagtgggtct gctatgaatg tggtattctc tgaggatgag   3540
atgaaaaaat tcctagaaga ggcgactaga gtttctcagg agcacccagt ggtgctgaca   3600
aaatttgttg aaggggcccg agaagtagaa atggacgctg ttggcaaaga tggaagggtt   3660
atctctccatg ccatctctga acatgttgaa gatgcaggtg tccactcggg agatgccact   3720
ctgatgctgc ccacacaaac catcagccaa ggggccattg aaaagtgaa ggatgctacc    3780
cggaagattg caaaggcttt tgccatctct ggtccattca acgtccaatt tcttgtcaaa   3840
ggaaatgatg tcttggtgat tgagtgtaac ttgagagctt ctcgatcctt cccctttgtt   3900
tccaagactc ttggggttga cttcattgat gtggccaaca agtgatgat tggagagaat    3960
gttgatgaga aacatcttcc aacattggac catcccataa ttcctgctga ctatgttgca   4020
attaaggctc ccatgttttc ctggccccgg ttgagggatg ctgaccccat tctgagatgt   4080
gagatggctt ccactggaga ggtggcttgc tttggtgaag gtatttatac agccttccta   4140
aaggcaatgc tttccacagg atttaagata ccccagaaag gcatcctgat aggcatccag   4200
caatcattcc ggccaagatt ccttggtgtg gctgaacaat tacacaatga aggttttcaag  4260
ctgtttgcca cggaagccac atcagactgg ctcaacgcca acaatgtccc tgccaccca    4320
gtggcatggc cgtctcaaga aggacagaat cccagcctct cttccatcag aaaattgatt   4380
agagatggca gcattgacct agtgattaac cttcccaaca acaactaa atttgtccat     4440
gataattatg tgattcggag gacagctgtt gatagtggaa tccctctcct cactaatttt   4500
caggtgacca aacttttgc tgaagctgtg cagaaatctc gcaaggtgga ctccaagagt    4560
cttttccact acaggcagta cagtgctgga aaagcagcat aggaattcta actagagctc   4620
gctgatcagc ctcgactgtg cctttctagtt gccagccatc tgttgtttgc cctcccccg   4680
tgccttcctt gaccctggaa ggtgccactc ccactgtcct tcctaataaa aatgaggaaa   4740
ttgcatcgca ttgtctgagt aggtgtcatt ctattctggg gggtggggtg gggcaggaca   4800
gcaagggga ggattgggaa gagaatagca ggcatgctgg ggagcgagct cgaggtggtt    4860
tgtctggtca accaccgcgg tctcagtggt gtacggtaca aaccca                  4906
```

SEQ ID NO: 401        moltype = DNA  length = 4882
FEATURE              Location/Qualifiers
misc_feature       1..4882
                      note = Description of Artificial Sequence: Synthetic
                      polynucleotide
source               1..4882
                      mol_type = other DNA
                      organism = synthetic construct
SEQUENCE: 401

```
ccccaactgg ggtaaccttt gggctccccg ggcgcgacta aagctgcga gcaacttcac     60
ttgggtatgc cggcggtagc gcttaccgtt cgtataatgt atgctatacg aagttatccg   120
aagccgctag cggtggtttg tctggtcaac caccgcggtc tcagtggtgt acggtacaaa   180
cccacccgag agaccatgca gaggtcgcct ctggaaaagg ccagcgttgt ctccaaactt   240
ttctttagct ggactagacc catccttcgt aaaggataca gacagcgcct ggaattgtca   300
gacatatacc aaatcccttc tgttgattct gctgacaatc tatctgaaaa attggaaaga   360
```

```
gaatgggata gagagctggc ttcaaagaaa aatcctaaac tcattaatgc ccttcggcga   420
tgttttttct ggagatttat gttctatgga atctttttat atttagggga agtcaccaaa   480
gcagtacagc ctctcttact gggaagaatc atagcttcct atgacccgga taacaaggag   540
gaacgctcta tcgcgattta tctaggcata ggcttatgcc ttctctttat tgtgaggaca   600
ctgctcctac acccagccat ttttggcctt catcacattg gaatgcagat gagaatagct   660
atgtttagtt tgatttataa gaagacttta aagctgtcaa gccgtgttct agataaaata   720
agtattggac aacttgttag tctcctttcc aacaacctga acaaatttga tgaaggactt   780
gcattggcac atttcgtgtg gatcgctcct ttgcaagtgg cactcctcat ggggctaatc   840
tgggagttgt tacaggcgtc tgccttctgt ggacttggtt tcctgatagt ccttgccctt   900
tttcaggctg ggctagggag aatgatgatg aagtacagag atcagagagc tgggaagatc   960
agtgaaagac ttgtgattac ctcagaaatg attgaaaata tccaatctgt taaggcatac  1020
tgctgggaag aagcaatgga aaaaatgatt gaaaacttaa gacaaacaga actgaaactg  1080
actcggaagg cagcctatgt gagatacttc aatagctcag ccttcttctt ctcagggttc  1140
tttgtggtgt ttttatctgt gcttccctat gcactaatca aaggaatcat cctccggaaa  1200
atattcacca ccatctcatt ctgcattgtt ctgcgcatgg cggtcactcg gcaatttccc  1260
tgggctgtac aaacatggta tgactctctt ggagcaataa acaaaataca ggatttctta  1320
caaaagcaag aatataagac attggaatat aacttaacga ctacagaagt agtgatggag  1380
aatgtaacag ccttctggga ggagggattt ggggaattat ttgagaaagc aaaacaaaac  1440
aataacaata gaaaaacttc taatgatgat gacagcctct tcttcagtaa tttctcactt  1500
cttggtactc ctgtcctgaa agatattaat ttcaagatag aaagaggaca gttgttggcg  1560
gttgctggat ccactggagc aggcaagact tcacttctaa tggtgattat gggagaactg  1620
gagccttcag agggtaaaat taagcacagt ggaagaattt cattctgttc tcagtttttcc  1680
tggattatgc ctggcaccat taagaaaaat atcatctttg tgtttccta tgatgaatat  1740
agatacagaa gcgtcatcaa agcatgccaa ctagaagagg acatctccaa gtttgcagag  1800
aaagacaata tagttcttgg agaaggtgga atcacactgt gtggaggtca acgagcaaga  1860
atttctttag caagagcagt atacaaagat gctgatttgt atttattaga ctctcctttt  1920
ggatacctag acgtattgac tgagaaggag atcttcgagt cctgcgtttg caagcttatg  1980
gccaataaga caagaatcct ggttacaagt aagatggagc acctgaagaa ggccgataag  2040
attctgatcc tgcacgaggg atcttccatc ttctacgacc ttttcagcga gcttcagaac  2100
ttgcaacctg atttctctag caagcttatg ggctgcgact cctttgatca gttctctgcc  2160
gagcgtcgca actccattct gaccgaaaca ctgcataggt tttccctcga gggcgacgca  2220
ccagtgtctt ggactgagac taagaagcag agcttcaagc aaaccggcga attcggtgag  2280
aagagaaaga acagtatcct gaaccccatt aattcaattc ggaagttcag tatcgttcag  2340
aaaacgcctc ttcagatgaa cggattgag gaagactcag acgaaccgct tgaaaggcga  2400
ctctcattgg ttcctgacag tgaacaaggg gaagctattc tcccccggat ttcagtaatt  2460
tccacaggtc cgactctgca agcccggaga agacaatccg tgttgaatct tatgacccat  2520
tccgtgaatc aggggcaaaa tatccataga aagactactg cctctacgag gaaggtatcc  2580
cttgcacccc aagccaatct gacggagctc gacatctact ctcgccgcct gtcccaggag  2640
acaggactgg agattagcga ggagatcaat gaagaggatc tgaaagaatg tttcttcgac  2700
gacatggaat ccatccctgc cgtcacgacg tggaatacct atttgcgtta catcacgtga  2760
cataaaagtc tgatattcgt cctgatctgg tgtcttgtga tcttcctcgc tgaagtcgca  2820
gccagcctgg tcgttctttg gctgctcggg aatacccct tgcaggataa gggaaactcc  2880
acccactctc ggaacaatag ttacgccgtc atcattactt ccacttcctc atactacgta  2940
ttctatatat atgtcgggt cgctgataca ctgctggcca tgggcttctt tcgcggcctg  3000
ccgctcgtcc acacgctgat aactgtctcc aagatcttgc atcataagat gctgcactca  3060
gtgctgcagg ctccaatgag tacactgaat actcttaagg ctggcggcat cctgaaccgc  3120
tttagtaagg acatcgccat acttgacgat ctccttgcccc tgacaatctt cgatttttatt  3180
caactccttt tgatcgttat cggggcgatc gctgtggttg ctgtgttgca gccatatata  3240
ttcgtagcta ctgttccgt catcgtgcg ttcatcatgc tccgtgccta ctttctgcag  3300
acgtcccaac agctgaagca gctcgagagc gagggacggt cccccatatt tacgcacttg  3360
gtaactagtc tgaaggggct gtggactctg agagcatttg tcgacaaacc atatttcgag  3420
accctctttc ataaggccct caacctgcac accgcgaatt ggtttctgta tttgagtacg  3480
ttgcggtggt ttcagatgcg catcgagatg atattcgtga tatctttat cgcagtcaca  3540
tttatcagca tcctgactac gggcgaggga gaggtcgcg tggcatcat actcacgctc  3600
gctataacaa ttatgagcac cctgcaatgg gccgtgaata gctctatcga cgttgacagt  3660
cttatgcgat ctgtgagccg agtctttaag ttcattgaca tgccaacaga aggtaaacct  3720
accaagtcaa ccaaaccata caagaatggc caactctcga aagttatgat tattgagaat  3780
tcacacgtga agaagatga catctggccc tcagggggcc aaatgactgt caaagatctc  3840
acagcaaaat acacagaagg tggaaatgcc atattagaga catttccttt ctcaataagt  3900
cctggccaga gggtgggcct cttgggaaga actggatcag ggaagagtac tttgttatca  3960
gcttttttga gactactgaa cactgaagga gaaatccaga tcgatggtgt gtcttgggat  4020
tcaataactt tgcaacagtg gaggaaagcc tttggagtga taccacagaa agtatttatt  4080
ttttctggaa catttagaaa aaacttggat ccctatgaac agtggagtga tcaagaaata  4140
tggaaagttg cagatgaggt tgggctcaga tctgtgatag aacagttcc tgggaagctt  4200
gactttgtcc ttgtggatgg gggctgtgtc ctaagccatg gccacaagca gttgatgtgc  4260
ttggctagat ctgttctcag taaggcgaag atcttgctg ttgatgaacc cagtgctcat  4320
ttggatccag taacatacca aataattaga agaactctaa aacaagcatt tgctgattgc  4380
acagtaattc tctgtgaaca caggatagaa gcaatgctgg aatgccaaca ttttttggtc  4440
atagaagaga caaagtgcg gcagtacgat tccatccaga aactgctgaa cgagaggagc  4500
ctcttccggc aagccatcag ccctccgac agggtgaagc tctttcccca ccggaactca  4560
agcaagtgca agtctaagcc ccagattgct gctctgaaga aggagacaga agaagaggtg  4620
caagatacaa ggctttagac ccgctgatca gcctcgactg tgcctctag ttgcagcca  4680
tctgttgttt gcccctcccc cgtgccttcc ttgaccctgg aaggtgccac tcccactgtc  4740
cttttcctaat aaaatgagaa aattgcatcg cattgtctga gtaggtgtca ttctattctg  4800
gggggtgggg tggggcagga cagcaagggg gaggattggg aagacaatag caggcatgct  4860
ggggatgcgg tgggctctat gg                                            4882
```

SEQ ID NO: 402           moltype = DNA   length = 1594
FEATURE                  Location/Qualifiers
misc_feature             1..1594
                         note = Description of Artificial Sequence: Synthetic
                         polynucleotide
source                   1..1594
                         mol_type = other DNA
                         organism = synthetic construct
SEQUENCE: 402
ccccaactgg ggtaaccttt gggctccccg ggcgcggttc cggatccgga gagggcaggg    60
gatctctcct tacttgtggc gacgtggagg agaacccgg ccccatgagc atcggcctcc    120
tgtgctgtgc agccttgtct ctcctgtggg caggtccagt gaatgctggt gtcactcaga    180
ccccaaaatt ccaggtcctg aagacaggac agagcatgac actgcagtgt gcccaggata    240
tgaaccatga atacatgtcc tggtatcgac aagacccagg catggggctg aggctgattc    300
attactcagt tggtgctggt atcactgacc aaggagaagt cccccaatggc tacaatgtct    360
ccagatcaac cacagaggat ttcccgctca ggctgctgtc ggctgctccc tcccagacat    420
ctgtgtactt ctgtgccagc agttacgtcg ggaacaccgg ggagctgttt tttggagaag    480
gctctaggct gaccgtactg gaggacctga aaaacgtgtt cccacccgag gtcgctgtgt    540
ttgagccatc agaagcagag atctcccaca cccaaaaggc cacactggta tgcctggcca    600
caggcttcta ccccgaccac gtggagctga gctggtgggt gaatgggaag gaggtgcaca    660
gtggggtcag cacagacccg cagcccctca aggagcagcc cgccctcaat gactccagat    720
actgcctgag cagccgcctg agggtctcgg ccaccttctg gcagaacccc cgcaaccact    780
tccgctgtca agtccagttc tacgggctct cggagaatga cgagtggacc caggataggg    840
ccaaacccgt cacccagatc gtcagcgccg aggcctgggg tagagcagac tgtggcttca    900
cctccgagtc ttaccagcaa ggggtcctgt ctgccaccat cctctatgag atcttgctag    960
gaaaggccac cttgtatgcc gtgctggtca gtgccctcgt gctgatggct atggtcaaga    1020
gaaaggattc cagaggccgg gccaagcggt ccggatccgg agccaccaac ttcagcctgc    1080
tgaagcaggc cggcgacgtg gaggagaacc ccggccccat ggagaccctc ttgggcctgc    1140
ttatcctttg gctgcagctg caatgggtga gcagcaaaca ggaggtgacg cagattcctg    1200
cagctctgag tgtcccagaa ggagaaaact tggttctcaa ctgcagtttc actgatagcg    1260
ctatttacaa cctccagtgg tttaggcagg accctgggaa aggtctcaca tctctgttgc    1320
ttattcagtc aagtcagaga gagcaaacaa gtggaaagat taatgcctcg ctggataaat    1380
catcaggacg tagtactttta tacattgcag cttctcagcc tggtgactca gccacctacc    1440
tctgtgctgt gaggccctg tacggaggaa gctacatacc tacatttgga agaggaacca    1500
gccttattgt tcatccgtat atccagaacc ctgaccctgc gggtggtttg tctggtcaac    1560
caccgcggtc tcagtggtgt acggtacaaa ccca                                1594

SEQ ID NO: 403           moltype = DNA   length = 19
FEATURE                  Location/Qualifiers
misc_feature             1..19
                         note = Description of Artificial Sequence: Synthetic
                         oligonucleotide
source                   1..19
                         mol_type = other DNA
                         organism = synthetic construct
SEQUENCE: 403
ttgagcgggc ccccaccgt                                                  19

SEQ ID NO: 404           moltype = DNA   length = 393
FEATURE                  Location/Qualifiers
misc_feature             1..393
                         note = Description of Artificial Sequence: Synthetic
                         polynucleotide
source                   1..393
                         mol_type = other DNA
                         organism = synthetic construct
SEQUENCE: 404
atgactcact atcaggcctt gcttttggac acgaccgggt ccagttcgg accggtggta    60
gccctgaacc cggctacgct gctcccactg cctgaggaag ggctgcaaca caactgcctt    120
gatgggacag gtggcggtgg tgtcaccgtc aagttcaagt acaagggtga ggaacttgaa    180
gttgatatta gcaaaatcaa gaaggttttgg cgcgttggta aaatgatatc ttttacttat    240
gacgacaacg caagacagg tagagggca gtgtctgaga aagacgcccc caaggagctg    300
ttgcaaatgt tggaaaagtc tgggaaaaag tctggcggct caaaagaac cgccgacggc    360
agcgaattcg agcccaagaa gaagaggaaa gtc                                 393

SEQ ID NO: 405           moltype = DNA   length = 11
FEATURE                  Location/Qualifiers
misc_feature             1..11
                         note = Description of Artificial Sequence: Synthetic probe
source                   1..11
                         mol_type = other DNA
                         organism = synthetic construct
SEQUENCE: 405
cgacgacggc g                                                          11

```
SEQ ID NO: 406           moltype = DNA  length = 16
FEATURE                  Location/Qualifiers
misc_feature             1..16
                         note = Description of Artificial Sequence: Synthetic probe
source                   1..16
                         mol_type = other DNA
                         organism = synthetic construct
SEQUENCE: 406
tttatttgtg ggcccg                                                           16

SEQ ID NO: 407           moltype = DNA  length = 15
FEATURE                  Location/Qualifiers
misc_feature             1..15
                         note = Description of Artificial Sequence: Synthetic probe
source                   1..15
                         mol_type = other DNA
                         organism = synthetic construct
SEQUENCE: 407
tcgagtgccg catca                                                            15

SEQ ID NO: 408           moltype = DNA  length = 17
FEATURE                  Location/Qualifiers
misc_feature             1..17
                         note = Description of Artificial Sequence: Synthetic probe
source                   1..17
                         mol_type = other DNA
                         organism = synthetic construct
SEQUENCE: 408
aaagtggtga ggacact                                                          17

SEQ ID NO: 409           moltype = DNA  length = 15
FEATURE                  Location/Qualifiers
misc_feature             1..15
                         note = Description of Artificial Sequence: Synthetic probe
source                   1..15
                         mol_type = other DNA
                         organism = synthetic construct
SEQUENCE: 409
aacccacccg agaga                                                            15

SEQ ID NO: 410           moltype = DNA  length = 66
FEATURE                  Location/Qualifiers
misc_feature             1..66
                         note = Description of Artificial Sequence: Synthetic
                         oligonucleotide
source                   1..66
                         mol_type = other DNA
                         organism = synthetic construct
SEQUENCE: 410
ggaagcggag ctactaactt cagcctgctg aagcaggctg gcgacgtgga ggagaaccct           60
ggacct                                                                      66

SEQ ID NO: 411           moltype = DNA  length = 45
FEATURE                  Location/Qualifiers
misc_feature             1..45
                         note = Description of Artificial Sequence: Synthetic
                         oligonucleotide
source                   1..45
                         mol_type = other DNA
                         organism = synthetic construct
SEQUENCE: 411
gggggaggag gttctggagg cggaggctcc ggaggcggag ggtca                           45

SEQ ID NO: 412           moltype = DNA  length = 15
FEATURE                  Location/Qualifiers
misc_feature             1..15
                         note = Description of Artificial Sequence: Synthetic
                         oligonucleotide
source                   1..15
                         mol_type = other DNA
                         organism = synthetic construct
SEQUENCE: 412
ggaggtggcg ggagc                                                            15
```

```
SEQ ID NO: 413          moltype = DNA  length = 15
FEATURE                 Location/Qualifiers
misc_feature            1..15
                        note = Description of Artificial Sequence: Synthetic
                         oligonucleotide
source                  1..15
                        mol_type = other DNA
                        organism = synthetic construct
SEQUENCE: 413
cccgcaccag cgcct                                                           15

SEQ ID NO: 414          moltype = DNA  length = 45
FEATURE                 Location/Qualifiers
misc_feature            1..45
                        note = Description of Artificial Sequence: Synthetic
                         oligonucleotide
source                  1..45
                        mol_type = other DNA
                        organism = synthetic construct
SEQUENCE: 414
gaggcagctg ccaaggaagc cgctgccaag gaggcggccg caaag                          45

SEQ ID NO: 415          moltype = DNA  length = 48
FEATURE                 Location/Qualifiers
misc_feature            1..48
                        note = Description of Artificial Sequence: Synthetic
                         oligonucleotide
source                  1..48
                        mol_type = other DNA
                        organism = synthetic construct
SEQUENCE: 415
agtgggagcg agacccctgg gactagcgag tcagctacac ccgaaagc                       48

SEQ ID NO: 416          moltype = DNA  length = 54
FEATURE                 Location/Qualifiers
misc_feature            1..54
                        note = Description of Artificial Sequence: Synthetic
                         oligonucleotide
source                  1..54
                        mol_type = other DNA
                        organism = synthetic construct
SEQUENCE: 416
gggggtcag gtggatccgg cggaagtggc ggatccggtg gatctggcgg cagt                 54

SEQ ID NO: 417          moltype = DNA  length = 15
FEATURE                 Location/Qualifiers
misc_feature            1..15
                        note = Description of Artificial Sequence: Synthetic
                         oligonucleotide
source                  1..15
                        mol_type = other DNA
                        organism = synthetic construct
SEQUENCE: 417
gaagctgctg ctaag                                                           15

SEQ ID NO: 418          moltype = AA  length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 418
GSGATNFSLL KQAGDVEENP GP                                                   22

SEQ ID NO: 419          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 419
GGGGSGGGGS GGGGS                                                           15
```

```
SEQ ID NO: 420           moltype = AA   length = 5
FEATURE                  Location/Qualifiers
REGION                   1..5
                         note = Description of Artificial Sequence: Synthetic peptide
source                   1..5
                         mol_type = protein
                         organism = synthetic construct
SEQUENCE: 420
GGGGS                                                                     5

SEQ ID NO: 421           moltype = AA   length = 5
FEATURE                  Location/Qualifiers
REGION                   1..5
                         note = Description of Artificial Sequence: Synthetic peptide
source                   1..5
                         mol_type = protein
                         organism = synthetic construct
SEQUENCE: 421
PAPAP                                                                     5

SEQ ID NO: 422           moltype = AA   length = 15
FEATURE                  Location/Qualifiers
REGION                   1..15
                         note = Description of Artificial Sequence: Synthetic peptide
source                   1..15
                         mol_type = protein
                         organism = synthetic construct
SEQUENCE: 422
EAAAKEAAAK EAAAK                                                         15

SEQ ID NO: 423           moltype = AA   length = 16
FEATURE                  Location/Qualifiers
REGION                   1..16
                         note = Description of Artificial Sequence: Synthetic peptide
source                   1..16
                         mol_type = protein
                         organism = synthetic construct
SEQUENCE: 423
SGSETPGTSE SATPES                                                        16

SEQ ID NO: 424           moltype = AA   length = 18
FEATURE                  Location/Qualifiers
REGION                   1..18
                         note = Description of Artificial Sequence: Synthetic peptide
source                   1..18
                         mol_type = protein
                         organism = synthetic construct
SEQUENCE: 424
GGSGGSGGSG GSGGSGGS                                                      18

SEQ ID NO: 425           moltype = AA   length = 5
FEATURE                  Location/Qualifiers
REGION                   1..5
                         note = Description of Artificial Sequence: Synthetic peptide
source                   1..5
                         mol_type = protein
                         organism = synthetic construct
SEQUENCE: 425
EAAAK                                                                     5

SEQ ID NO: 426           moltype = AA   length = 16
FEATURE                  Location/Qualifiers
REGION                   1..16
                         note = Description of Artificial Sequence: Synthetic peptide
source                   1..16
                         mol_type = protein
                         organism = synthetic construct
SEQUENCE: 426
GLSGQPPRSP SSGSSG                                                        16

SEQ ID NO: 427           moltype = AA   length = 17
FEATURE                  Location/Qualifiers
REGION                   1..17
                         note = Description of Artificial Sequence: Synthetic peptide
source                   1..17
                         mol_type = protein
                         organism = synthetic construct
```

```
SEQUENCE: 427
GGLSGQPPRS PSSGSSG                                                          17

SEQ ID NO: 428        moltype = RNA  length = 88
FEATURE               Location/Qualifiers
misc_feature          1..88
                      note = Description of Artificial Sequence: Synthetic
                       oligonucleotide
source                1..88
                      mol_type = other RNA
                      organism = synthetic construct
SEQUENCE: 428
gacgagcgcg gcgatatcat catccatggc cggatgatcc tgacgacgga gaccgccgtc   60
gtcgacaagc cggcctgagc tgcgagaa                                      88

SEQ ID NO: 429        moltype = RNA  length = 20
FEATURE               Location/Qualifiers
misc_feature          1..20
                      note = Description of Artificial Sequence: Synthetic
                       oligonucleotide
source                1..20
                      mol_type = other RNA
                      organism = synthetic construct
SEQUENCE: 429
gaagccggcc ttgcacatgc                                               20

SEQ ID NO: 430        moltype = DNA  length = 95
FEATURE               Location/Qualifiers
source                1..95
                      mol_type = unassigned DNA
                      organism = Homo sapiens
SEQUENCE: 430
gcgcgcccgg ctattctcgc agctcaccat ggatgatgat atcgccgcgc tcgtcgtcga   60
caacggctcc ggcatgtgca aggccggctt cgcgg                              95

SEQ ID NO: 431        moltype = RNA  length = 20
FEATURE               Location/Qualifiers
misc_feature          1..20
                      note = Description of Artificial Sequence: Synthetic
                       oligonucleotide
source                1..20
                      mol_type = other RNA
                      organism = synthetic construct
SEQUENCE: 431
accactcgac gctcttatcg                                               20
```

SYSTEMS, METHODS, AND COMPOSITIONS FOR SITE-SPECIFIC GENETIC ENGINEERING USING PROGRAMMABLE ADDITION VIA SITE-SPECIFIC TARGETING ELEMENTS (PASTE)

CROSS REFERENCE TO RELATED APPLICATIONS

This application is a continuation of U.S. application Ser. No. 17/649,308, filed Jan. 28, 2022, which is a continuation of U.S. application Ser. No. 17/451,734, filed Oct. 21, 2021, which claims the benefit of U.S. Provisional Patent Application Ser. No. 63/222,550, filed Jul. 16, 2021 and U.S. Provisional Patent Application Ser. No. 63/094,803, filed Oct. 21, 2020. The entire contents of the above-referenced patent applications are incorporated by reference in their entirety herein.

SEQUENCE LISTING

The instant application contains a Sequence Listing which has been submitted electronically in XML format and is hereby incorporated by reference in its entirety. Said XML file, created on Dec. 14, 2022, is named 737592_083474_016CON3_SL_st26v2.xml.txt and is 775 kilobytes in size.

FIELD OF DISCLOSURE

The subject matter disclosed herein is generally directed to systems, methods, and compositions for site-specific genetic engineering using Programmable Addition via Site-Specific Targeting Elements (PASTE) for the treatment of diseases and diagnostics.

BACKGROUND

Editing genomes using the RNA-guided DNA targeting principle of CRISPR-Cas (Clustered Regularly Interspaced Short Palindromic Repeats-CRISPR associated proteins) immunity has been widely exploited and has become a powerful genome editing means for a wide variety of applications. The main advantage of CRISPR-Cas system lies in the minimal requirement for programmable DNA interference: an endonuclease, such as a Cas9, Cas12, or any programmable nucleases, guided by a customizable dual-RNA structure. Cas9 is a multi-domain enzyme that uses an HNH nuclease domain to cleave the target strand. The CRISPR/Cas9 protein-RNA complex is localized on the target by a guide RNA (guide RNA), then cleaved to generate a DNA double strand break (dsDNA break, DSB). After cleavage, DNA repair mechanisms are activated to repair the cleaved strand. Repair mechanisms are generally from one of two types: non-homologous end joining (NHEJ) or homologous recombination (HR). In general, NHEJ dominates the repair, and, being error prone, generates random indels (insertions or deletions) causing frame shift mutations, among others. In contrast, HR has a more precise repairing capability and is potentially capable of incorporating the exact substitution or insertion. To enhance HR, several techniques have been tried, for example: combination of fusion proteins of Cas9 nuclease with homology-directed repair (HDR) effectors to enforce their localization at DSBs, introducing an overlapping homology arm, or suppression of NHEJ. Most of these techniques rely on the host DNA repair systems.

Recently, new guided editors have been developed, such as guided prime editors (PE) PE1, PE2, and PE3, e.g., Liu, D. et al., Nature 2019, 576, 149-157. These PEs are reverse transcriptase (RT) fused with Cas 9 H 840A nickase (Cas9n (H840A)), and the genome editing is achieved using a prime-editing guide RNA (pegRNA). Despite these developments, programmable gene integration is still generally dependent on cellular pathways or repair processes.

Therefore, there is a need for more effective tools for gene editing and delivery.

SUMMARY

The present disclosure provides a method of site-specific integration of a nucleic acid into a cell genome. The method comprises incorporating an integration site at a desired location in the cell genome by introducing into the cell a DNA binding nuclease linked to a reverse transcriptase domain, wherein the DNA binding nuclease comprises a nickase activity; and a guide RNA (gRNA) comprising a primer binding sequence linked to an integration sequence, wherein the gRNA interacts with the DNA binding nuclease and targets the desired location in the cell genome, wherein the DNA binding nuclease nicks a strand of the cell genome and the reverse transcriptase domain incorporates the integration sequence of the gRNA into the nicked site, thereby providing the integration site at the desired location of the cell genome. The method further comprises integrating the nucleic acid into the cell genome by introducing into the cell a DNA or RNA strand comprising the nucleic acid linked to a sequence that is complementary or associated to the integration site, and an integration enzyme, wherein the integration enzyme incorporates the nucleic acid into the cell genome at the integration site by integration, recombination, or reverse transcription of the sequence that is complementary or associated to the integration site, thereby introducing the nucleic acid into the desired location of the cell genome of the cell.

In some embodiments, the gRNA can be hybridized to a complementary strand of the cell genome to the genomic strand that is nicked by the DNA binding nuclease.

In some embodiments, the integration enzyme can be introduced as a peptide or a nucleic acid encoding the same.

In some embodiments, the DNA binding nuclease can be introduced as a peptide or a nucleic acid encoding the same.

In some embodiments, the DNA or RNA strand comprising the nucleic acid can be introduced into the cell as a minicircle, a plasmid, mRNA or a linear DNA.

In some embodiments, the DNA or RNA strand comprising the nucleic acid can be between 1000 bp and 10,000 bp.

In some embodiments, the DNA or RNA strand comprising the nucleic acid can be more than 10,000 bp.

In some embodiments, the DNA or RNA strand comprising the nucleic acid can be less than 1000 bp.

In some embodiments, the DNA comprising the nucleic acid can be introduced into the cell as a minicircle.

In some embodiment, the minicircle cannot comprise sequences of a bacterial origin.

In some embodiments, the DNA binding nuclease can be linked to a reverse transcriptase domain and the integration enzyme can be linked via a linker. The linker can be cleavable. The linker can be non-cleavable. The linker can be replaced by two associating binding domains of the DNA binding nuclease linked to a reverse transcriptase.

In some embodiments, the integration enzyme can be selected from the group consisting of Cre, Dre, Vika, Bxb1, φC31, RDF, FLP, φBT1, R1, R2, R3, R4, R5, TP901-1, A118, φFC1, φC1, MR11, TG1, φ370.1, Wβ, BL3, SPBc, K38, Peaches, Veracruz, Rebeuca, Theia, Benedict, KSSJEB, PattyP, Doom, Scowl, Lockley, Switzer, Bob3, Troube, Abrogate, Anglerfish, Sarfire, SkiPole, ConceptII, Museum, Severus, Airmid, Benedict, Hinder, ICleared, Sheen, Mundrea, BxZ2, φRV, retrotransposases encoded by R2, L1, Tol2 Tc1, Tc3, Mariner (Himar 1), Mariner (mos 1), and Minos, and any mutants thereof.

In some embodiments, the integration enzyme can be Bxb1 or a mutant thereof.

In some embodiments, the integration site can be selected from an attB site, an attP site, an attL site, an attR site, a lox71 site a Vox site, or a FRT site.

In some embodiments, the DNA binding nuclease comprising a nickase activity can be selected from Cas9-D10A, Cas9-H840A, and Cas12a/b nickase.

In some embodiments, the reverse transcriptase domain can be selected from the group consisting of Moloney Murine Leukemia Virus (M-MLV) reverse transcriptase domain, transcription xenopolymerase (RTX), avian myeloblastosis virus reverse transcriptase (AMV-RT), and *Eubacterium* rectale maturase RT (MarathonRT).

In some embodiments, the reverse transcriptase domain can comprise a mutation relative to the wild-type sequence.

In some embodiments, the M-MLV reverse transcriptase domain can comprise one or more mutations selected from the group consisting of D200N, T306K, W313F, T330P and L603W.

In some embodiments, the method can further comprise introducing a second nicking guide RNA (ngRNA). The ngRNA can direct nicking at 90 bases downstream of the gRNA nick on a complementary strand.

In some embodiments, the gRNA, the nucleic acid encoding the DNA binding nuclease, the reverse transcriptase, the DNA comprising nucleic acid linked to a complementary integration site, the integration enzyme, and optionally the ngRNA can be introduced into a cell in a single reaction.

In some embodiments, the gRNA, the nucleic acid encoding the DNA binding nuclease, the reverse transcriptase, the DNA comprising nucleic acid linked to a complementary integration site, the integration enzyme, and optionally the ngRNA can be introduced using a virus, a RNP, an mRNA, a lipid, or a polymeric nanoparticle.

In some embodiments, the nucleic acid can be a reporter gene. The reporter gene can be a fluorescent protein.

In some embodiments, the cell can be a dividing cell.

In some embodiments, the cell can be a non-dividing cell.

In some embodiments, the desired location in the cell genome can be the locus of a mutated gene.

In some embodiments, the nucleic acid can be a degradation tag for programmable knockdown of proteins in the presence of small molecules.

In some embodiments, the cell can be a mammalian cell, a bacterial cell or a plant cell.

In some embodiments, nucleic acid can be a T-cell receptor (TCR), a chimeric antigen receptor (CAR), an interleukin, a cytokine, or an immune checkpoint gene for integration into a T-cell or natural killer (NK) cell. The TCR, the CAR, the interleukin, the cytokine, or the immune checkpoint gene can be incorporated into the target site of the T-cell or NK cell genome using a minicircle DNA.

In some embodiments, the nucleic acid can be a beta hemoglobin (HBB) gene and the cell can be a hematopoietic stem cell (HSC). The HBB gene can be incorporated into the target site in the HSC genome using a minicircle DNA. The nucleic acid can be a gene responsible for beta thalassemia or sickle cell anemia.

In some embodiments, the nucleic acid can be a metabolic gene. The metabolic gene can be involved in alpha-1 antitrypsin deficiency or ornithine transcarbamylase (OTC) deficiency. The metabolic gene can be a gene involved in inherited diseases.

In some embodiments, the nucleic acid can be a gene involved in an inherited disease or an inherited syndrome. The inherited disease can be cystic fibrosis, familial hypercholesterolemia, adenosine deaminase (ADA) deficiency, X-linked SCID (X-SCID), Wiskott-Aldrich syndrome (WAS), hemochromatosis, Tay-Sachs, fragile X syndrome, Huntington's disease, Marfan syndrome, phenylketonuria, or muscular dystrophy.

The present disclosure provides a vector comprising a nucleic acid encoding a DNA binding nuclease comprising a nickase activity C-terminally linked to a reverse transcriptase linked to an integration enzyme via a linker.

In some embodiments, the linker can be cleavable.

In some embodiments, the linker can be non-cleavable.

In some embodiments, the linker can comprise two associating binding domains of the DNA binding nuclease linked to a reverse transcriptase.

In some embodiments, the integration enzyme can comprise a conditional activation domain or conditional expression domain.

In some embodiments, the integration enzyme can be fused to an estrogen receptor.

In some embodiments, the DNA binding nuclease comprising a nickase activity can be selected from the group consisting of Cas9-D10A, Cas9-H840A, and Cas12a/b.

In some embodiments, the reverse transcriptase can be a M-MLV reverse transcriptase, a AMV-RT, MarathonRT, or a RTX. The reverse transcriptase can be a modified M-MLV reverse transcriptase relative to the wildtype M-MLV reverse transcriptase. The M-MLV reverse transcriptase domain can comprise one or more of the mutations selected from the group consisting of D200N, T306K, W313F, T330P and L603W.

In some embodiments, the integration enzyme can be selected from the group consisting of Cre, Dre, Vika, Bxb1, φC31, RDF, FLP, φBT1, R1, R2, R3, R4, R5, TP901-1, A118, φFC1, φC1, MR11, TG1, φ370.1, Wβ, BL3, SPBc, K38, Peaches, Veracruz, Rebeuca, Theia, KSSJEB, PattyP, Doom, Scowl, Lockley, Switzer, Bob3, Troube, Abrogate, Anglerfish, Sarfire, SkiPole, ConceptII, Museum, Severus, Airmid, Benedict, Hinder, ICleared, Sheen, Mundrea, BxZ2, φRV, retrotransposases encoded by R2, L1, Tol2 Tc1, Tc3, Mariner (Himar 1), Mariner (mos 1), and Minos, and any mutants thereof.

In some embodiments, the recombinase or integrase can be Bxb1 or a mutant thereof.

The present disclosure provides a cell comprising a vector comprising a nucleic acid encoding a DNA binding nuclease comprising a nickase activity C-terminally linked to a reverse transcriptase linked to an integration enzyme via a linker. The cell further comprises a gRNA comprising a primer binding sequence, an integration sequence, and a guide sequence, wherein the gRNA can interact with the encoded nuclease comprising a nickase activity. The cell further comprising a DNA minicircle comprising a nucleic acid and a sequence recognized by the encoded integrase, recombinase, or reverse transcriptase. The cell further comprising a nicking guide RNA (ngRNA) capable of binding the encoded nuclease comprising a nickase activity, and wherein the ngRNA targets a sequence away from the gRNA.

In some embodiments, the minicircle cannot comprise a sequence of bacterial origin.

In some embodiments, the integration enzyme can be selected from the group consisting of Cre, Dre, Vika, Bxb1, φC31, RDF, FLP, φBT1, R1, R2, R3, R4, R5, TP901-1, A118, φFC1, φC1, MR11, TG1, φ370.1, Wβ, BL3, SPBc, K38, Peaches, Veracruz, Rebeuca, Theia, KSSJEB, PattyP, Doom, Scowl, Lockley, Switzer, Bob3, Troube, Abrogate, Anglerfish, Sarfire, SkiPole, ConceptII, Museum, Severus, Airmid, Benedict, Hinder, ICleared, Sheen, Mundrea, BxZ2, φRV, retrotransposases encoded by R2, L1, Tol2 Tc1, Tc3, Mariner (Himar 1), Mariner (mos 1), and Minos, and any mutants thereof.

In some embodiments, the integration enzyme can be Bxb1 or a mutant thereof.

In some embodiments, the DNA binding nuclease comprising a nickase activity can be selected from the group consisting of Cas9-D10A, Cas9-H840A and Cas12a.

In some embodiments, the reverse transcriptase can be a M-MLV reverse transcriptase. The reverse transcriptase can be a modified M-MLV reverse transcriptase. The amino acid sequence of the M-MLV reverse transcriptase can comprise one or more mutations selected from the group consisting of D200N, T306K, W313F, T330P, and L603W.

In some embodiments, the cell can further comprise introducing ngRNA to the cell. The ngRNA can be a +90 ngRNA. The +90 ngRNA can direct nicking at 90 bases downstream of the gRNA nick on a complementary strand.

The present disclosure provides a polypeptide comprising a DNA binding nuclease comprising a nickase activity C-terminally linked to a reverse transcriptase linked to an integration enzyme via a linker.

In some embodiments, the linker can be cleavable.

In some embodiments, the linker can be non-cleavable.

In some embodiments, the integration enzyme can be fused to an estrogen receptor.

In some embodiments, the DNA binding nuclease comprising a nickase activity can be selected from the group consisting of Cas9-D10A, Cas9-H840A, and Cas12a/b.

In some embodiments, the reverse transcriptase can be a M-MLV reverse transcriptase, a AMV-RT, a MarathonRT, or a XRT. The reverse transcriptase can be a modified M-MLV relative to a wild-type M-MLV reverse transcriptase. The M-MLV reverse transcriptase domain can comprise one or more of mutations selected from the group consisting of D200N, T306K, W313F, T330P, and L603W.

In some embodiments, the integration enzyme can be selected from group consisting of Cre, Dre, Vika, Bxb1, φC31, RDF, FLP, φBT1, R1, R2, R3, R4, R5, TP901-1, A118, φFC1, φC1, MR11, TG1, φ370.1, Wβ, BL3, SPBc, K38, Peaches, Veracruz, Rebeuca, Theia, KSSJEB, PattyP, Doom, Scowl, Lockley, Switzer, Bob3, Troube, Abrogate, Anglerfish, Sarfire, SkiPole, ConceptII, Museum, Severus, Airmid, Benedict, Hinder, ICleared, Sheen, Mundrea, BxZ2, φRV, retrotransposases encoded by R2, L1, Tol2 Tc1, Tc3, Mariner (Himar 1), Mariner (mos 1), and Minos, and any mutants thereof.

In some embodiments, the integration enzyme can be Bxb1 or a mutant thereof.

The present disclosure provides a gRNA that specifically binds to a DNA binding nuclease comprising nickase activity, the gRNA comprising a primer binding site, which hybridizes to a nicked DNA strand, a recognition site for an integration enzyme, and a target recognition sequence recognizing a target site in a cell genome and hybridizing to a genomic strand complementary to the strand that is nicked by the DNA binding nuclease.

In some embodiments, the DNA binding nuclease comprising a nickase activity can be selected from the group consisting of Cas9-D10A, Cas9-H840A, and Cas12a/b.

In some embodiments, the primer binding site can hybridize to the 3' end of the nicked DNA strand.

In some embodiments, the recognition site for the integration enzyme can be selected from an attB site, an attP site, an attL site, an attR site, a lox71 site, and a FRT site.

In some embodiments, the recognition site for the integration enzyme can be a Bxb1 site.

The present disclosure provides a method of site-specific integration of two or more nucleic acids into a cell genome. The method comprises incorporating two integration sites at desired locations in the cell genome by introducing into the cell a DNA binding nuclease linked to a reverse transcriptase domain, wherein the DNA binding nuclease comprises a nickase activity, and two guide RNAs (gRNAs), each comprising, a primer binding sequence, linked to a unique integration sequence, wherein the gRNA interacts with the DNA binding nuclease and targets the desired locations in the cell genome, wherein the DNA binding nuclease nicks a strand of the cell genome and the reverse transcriptase domain incorporates each of the integration sequence of the gRNA into the nicked site, thereby providing the integration site at the desired locations of the cell genome. The method further comprises integrating the nucleic acid by introducing into the cell two or more DNA or RNA comprising the nucleic acids, wherein each DNA is flanked by orthogonal integration sites, and an integration enzyme, wherein the integration enzyme incorporates the nucleic acids into the cell genome at the integration sites by integrase, recombinase, or reverse transcriptase of the sequence that is complementary or associated to the integration site, thereby introducing the nucleic acids into the desired locations of the cell genome of the cell.

In some embodiments, each of the two different integration sites inserted into the cell genome can be attB sequences comprising different palindromic or non-palindromic central dinucleotide.

In some embodiments, each of the two different integration sites inserted into the cell genome can be attP sequences comprising different palindromic or non-palindromic central dinucleotide.

In some embodiments, the integration enzyme can enable each of the two or more DNA or RNA comprising the nucleic acids to directionally enable integration of the nucleic acids into a genome via recombination of a pair of orthogonal attB site sequence and an attP site sequence.

In some embodiments, the integration enzyme can be selected from the group consisting of Cre, Dre, Vika, Bxb1, φC31, RDF, FLP, φBT1, TP901-1, A118, φFC1, φC1, MR11, TG1, φ370.1, Wβ, BL3, SPBc, K38, Peaches, Veracruz, Rebeuca, Theia, KSSJEB, PattyP, Doom, Scowl, Lockley, Switzer, Bob3, Troube, Abrogate, Anglerfish, Sarfire, SkiPole, ConceptII, Museum, Severus, Airmid, Benedict, Hinder, ICleared, Sheen, Mundrea, BxZ2, φRV, retrotransposases encoded by R1, R2, R3, R4, R5, L1, Tol2 Tc1, Tc3, Mariner (Himar 1), Mariner (mos 1), and Minos, and any mutants thereof.

In some embodiments, the integration enzyme can be Bxb1 or a mutant thereof.

In some embodiments, the DNA comprising genes can be genes involved in a cell maintenance pathway, cell-division, or a signal transduction pathway.

In some embodiments, the reverse transcriptase domain can comprise Moloney Murine Leukemia Virus (M-MLV) reverse transcriptase domain, transcription xenopolymerase (RTX), avian myeloblastosis virus reverse transcriptase (AMV-RT), or *Eubacterium* rectale maturase RT (MarathonRT).

In some embodiments, the DNA binding nuclease comprising a nickase activity can be selected from the group consisting of Cas9-D10A, Cas9-H840A, and Cas12a/b.

In some embodiments, the pair of an attB site sequence and an attP site sequence can be selected from the group consisting of SEQ ID NO: 5 and SEQ ID NO: 6, SEQ ID NO: 7 and SEQ ID NO: 8, SEQ ID NO: 9 and SEQ ID NO: 10, SEQ ID NO: 11 and SEQ ID NO: 12, SEQ ID NO: 13 and SEQ ID NO: 14, SEQ ID NO: 15 and SEQ ID NO: 16, SEQ ID NO: 17 and SEQ ID NO: 18, SEQ ID NO: 19 and SEQ ID NO: 20, SEQ ID NO: 21 and SEQ ID NO: 22, SEQ ID NO: 23 and SEQ ID NO: 24, SEQ ID NO: 25 and SEQ ID NO: 26, SEQ ID NO: 27 and SEQ ID NO: 28, SEQ ID NO: 29 and SEQ ID NO: 30, SEQ ID NO: 31 and SEQ ID NO: 32, SEQ ID NO: 33 and SEQ ID NO: 34 and SEQ ID NO: 35 and SEQ ID NO: 36.

The present disclosure provides a cell comprising a vector comprising a nucleic acid encoding a DNA binding nuclease comprising a nickase activity, wherein the DNA binding nuclease is C-terminally linked to a reverse transcriptase, wherein the reverse transcriptase is linked to a recombinase or integrase via a linker. The cell further comprises two guide RNAs (gRNAs) comprising a primer binding sequence, an integration sequence and a guide sequence, wherein the gRNA can interact with the encoded DNA binding nuclease comprising a nickase activity. The cell further comprises two or more DNA or RNA strands comprising a nucleic acid and a pair of flanking attB site sequence and an attP site sequence recognized by the encoded integrase or recombinase. The cell optionally further comprises a nicking guide RNA (ngRNA) capable of binding the encoded nuclease comprising a nickase activity, and wherein the ngRNA targets a sequence away from the gRNA.

The present disclosure provides a cell comprising a modified genome, wherein the modification comprises incorporation of two orthogonal integration sites within the cell genome by introducing into the cell a: vector comprising a nucleic acid encoding a DNA binding nuclease comprising a nickase activity, wherein the DNA binding nuclease is C-terminally linked to a reverse transcriptase; two guide RNAs (gRNAs), each comprising a primer binding sequence, a genomic integration sequence, and a guide sequence, wherein the gRNA can interact with the encoded nuclease comprising a nickase activity; and optionally a nicking guide RNA (ngRNA) capable of binding the encoded nuclease comprising a nickase activity, and wherein the ngRNA targets a sequence away from the gRNA.

The present disclosure provides a method of integrating two or more nucleic acids into the cell genome of cell of claim 90, the method comprising introducing into the cell: two or more DNA, each comprising a nucleic acid and a pair of flanking orthogonal integration site sequences; an integration enzyme that can recognize the integration site sequence enabling directional linking of the two or more DNA comprising nucleic acid; and enabling incorporation of the nucleic acids into the cell genome by integrating the 5' orthogonal integration sequence of the first DNA with the first genomic integration sequence and 3' orthogonal integration sequence of the last DNA with the last genomic integration sequence, thereby incorporating the two or more nucleic acids into the cell genome.

The present disclosure provides a cell comprising a modified genome, wherein the modification comprises incorporation of two orthogonal integration sites within the cell genome by introducing into the cell: a vector comprising a nucleic acid encoding a DNA binding nuclease comprising a nickase activity, wherein the DNA binding nuclease is C-terminally linked to a reverse transcriptase; two guide RNAs (gRNAs), each comprising a primer binding sequence, a genomic integration sequence, and a guide sequence, wherein the gRNA can interact with the encoded nuclease comprising a nickase activity; and optionally a nicking guide RNA (ngRNA) capable of binding the encoded nuclease comprising a nickase activity, and wherein the ngRNA targets a sequence away from the gRNA; two or more DNA or RNA comprising the nucleic acids, wherein each DNA is flanked by orthogonal integration sites; and an integration enzyme, wherein the integration enzyme incorporates the nucleic acids into the cell genome at the integration sites.

BRIEF DESCRIPTION OF THE DRAWINGS

Aspects, features, benefits and advantages of the embodiments described herein will be apparent with regard to the following description, appended claims, and accompanying drawings where:

FIG. 29E discloses SEQ ID NOS 428-431, respectively, in order of appearance;

FIG. 40C shows the validation of ddPCR assays for detecting editing at predicted PASTE ACTB Cas9 guide off-target sites using synthetic amplicons according to embodiments of the present teachings;

FIG. 40D shows the validation of ddPCR assays for detecting editing at predicted HITI ACTB Cas9 guide off-target sites using synthetic amplicons according to embodiments of the present teachings;

FIG. 41A shows a number of significant differentially regulated genes in HEK293FT cells expressing Bxb1 integrase, PASTE targeting ACTB integration of EGFP, or Prime editing targeting ACTB for EGFP insertion without Bxb1 expression according to embodiments of the present teachings;

Figure 41A:
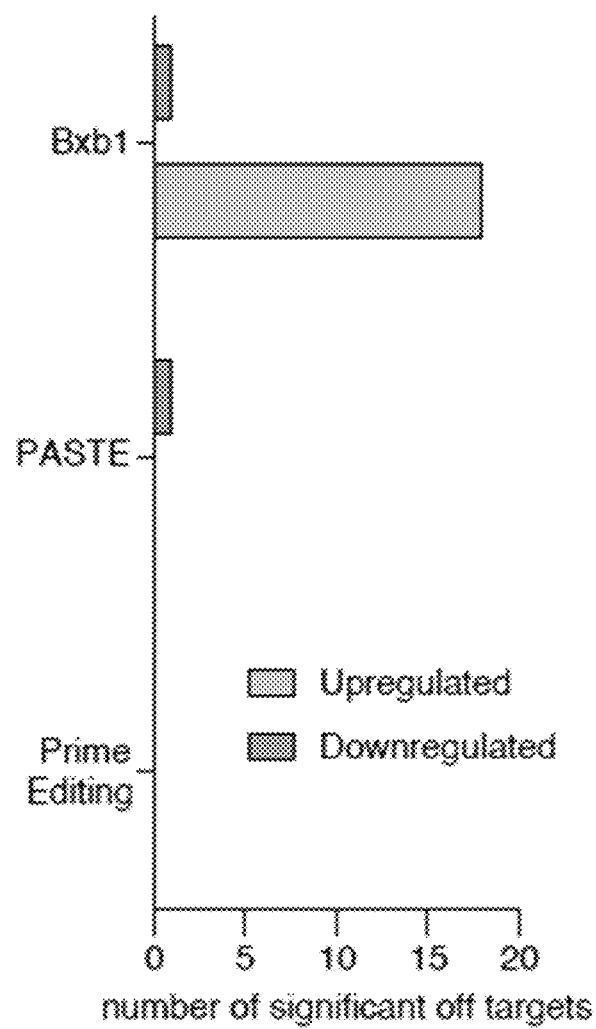
Figure 41B:
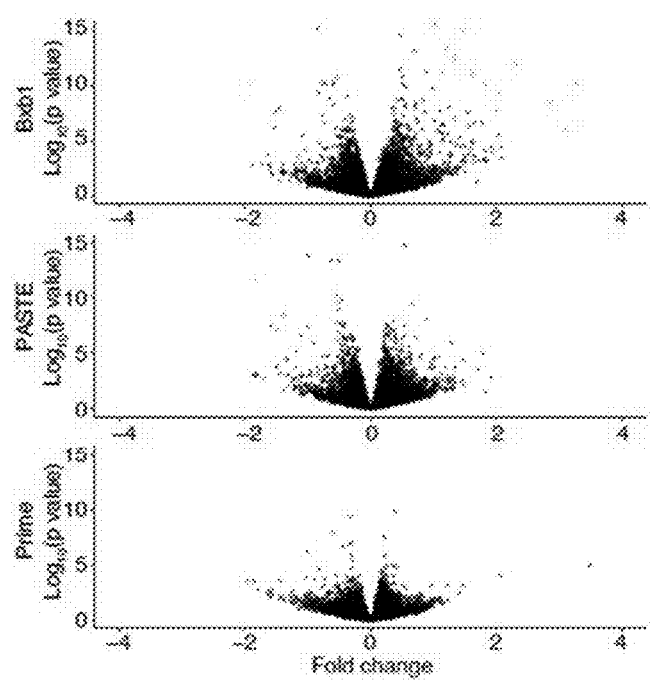
Figure 41C:
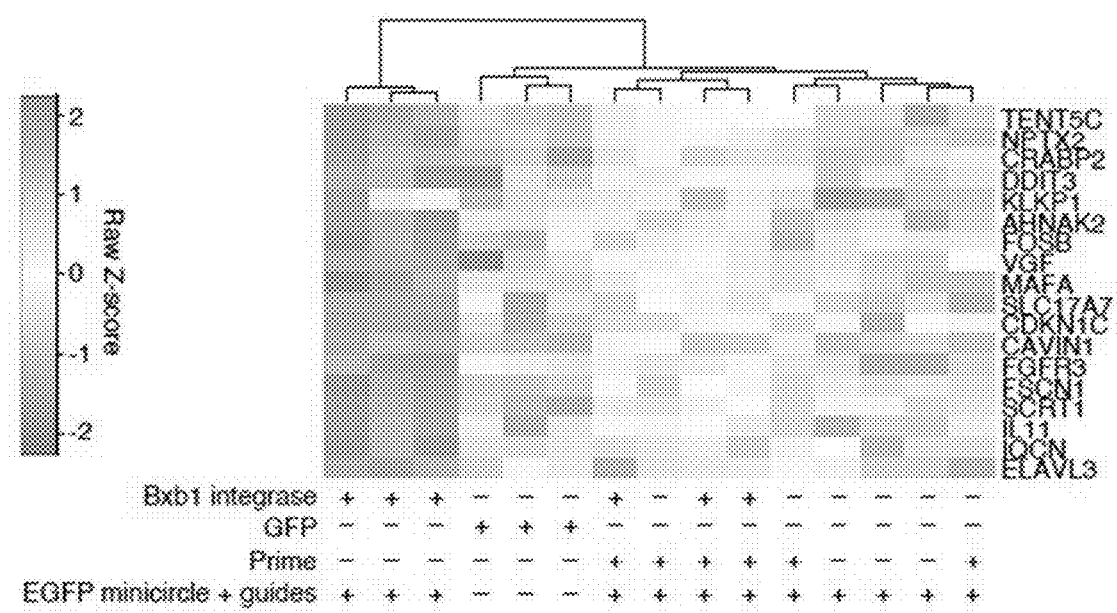
Figure 42A:
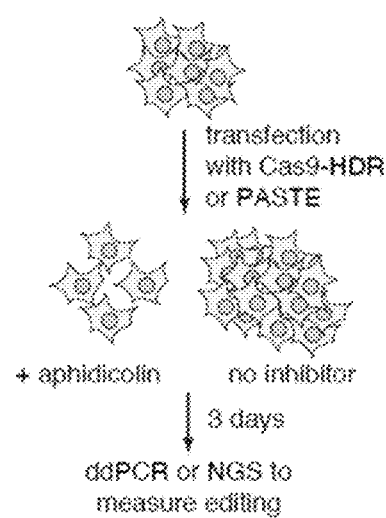
Figure 42B:
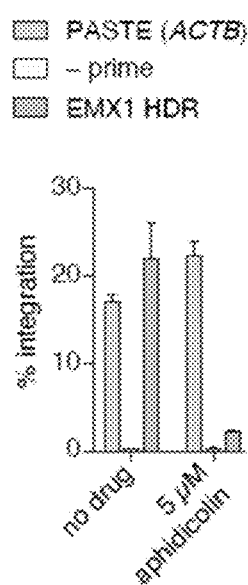
Figure 42C:
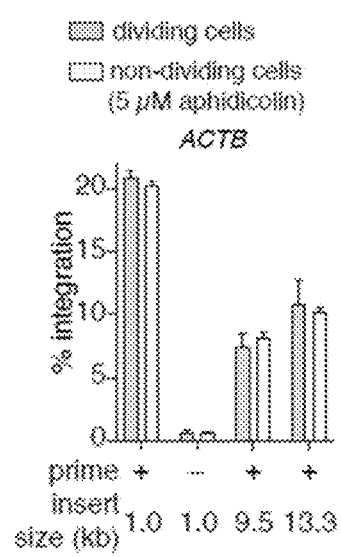
Figure 42D:
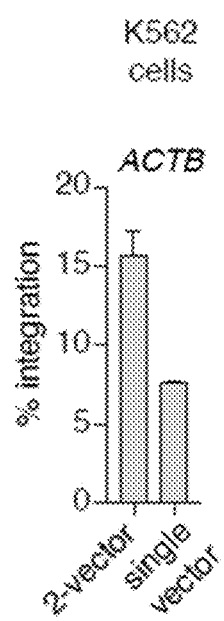
Figure 42E:
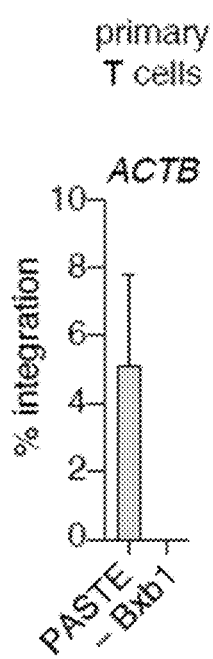
Figure 42F:
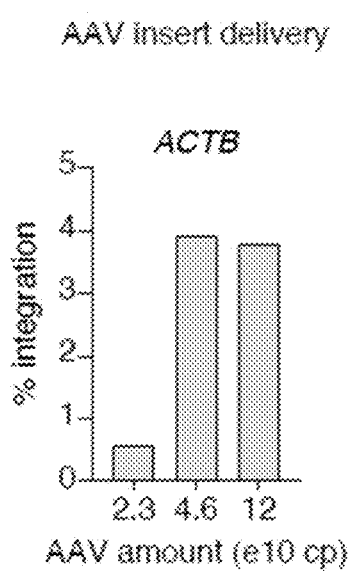
Figure 42G:
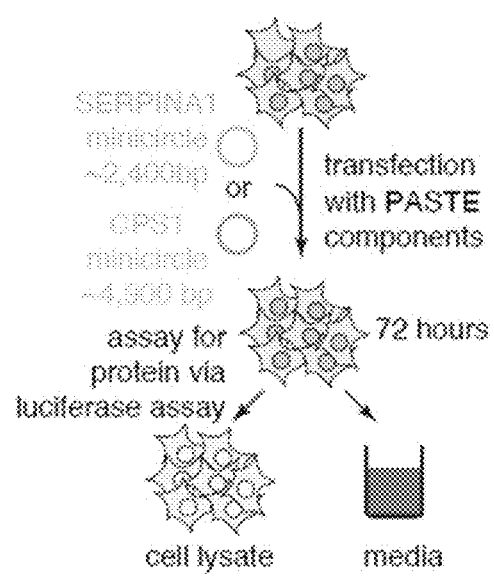
Figure 42H:
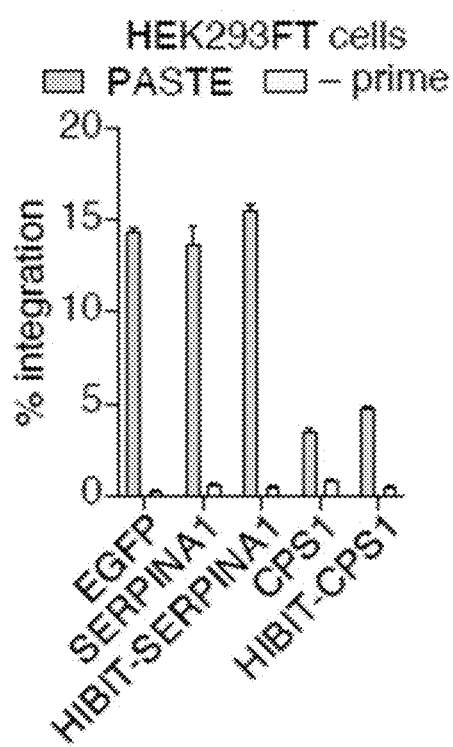
Figure 42I:
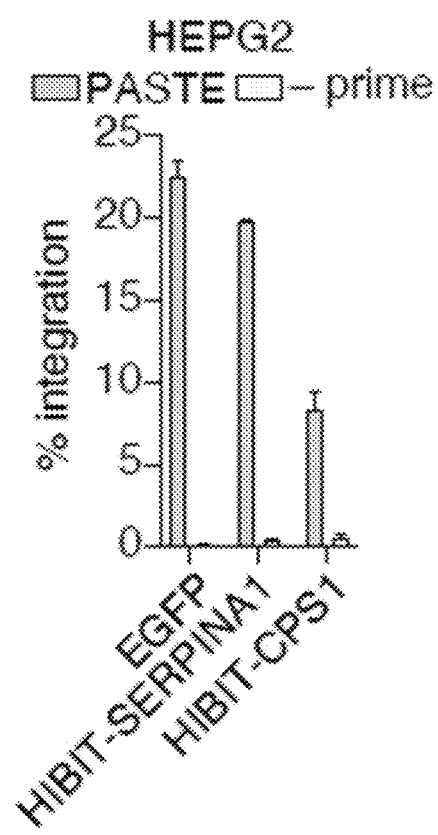
Figure 42J:
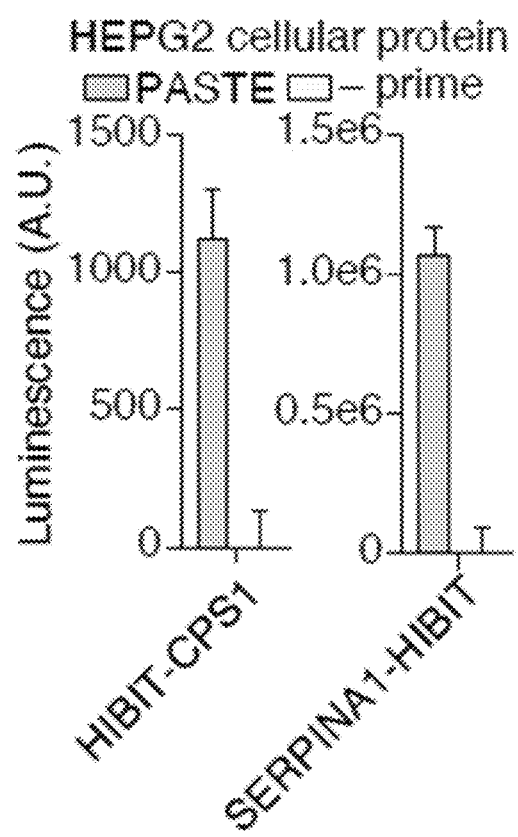
Figure 42K:
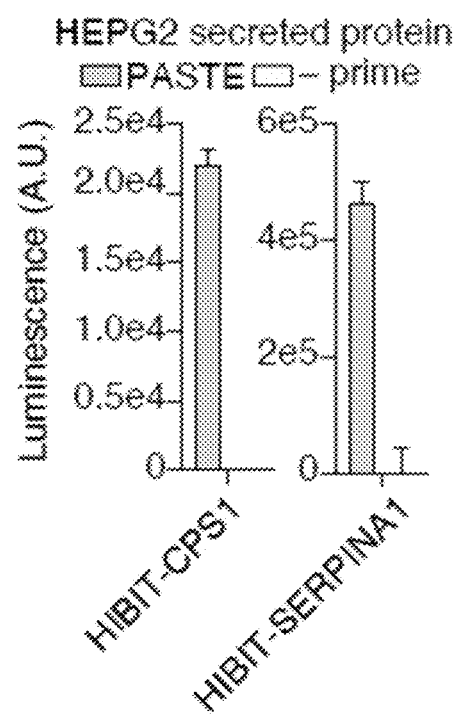
Figure 43A:
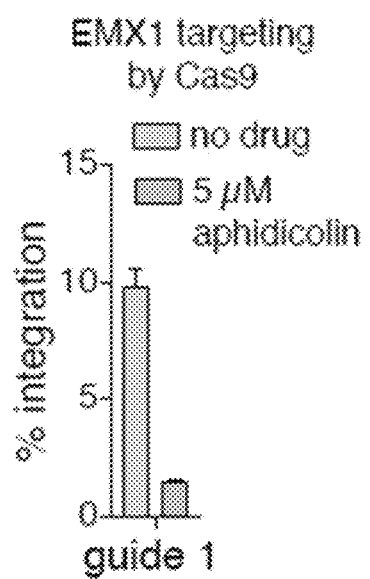
Figure 43B:
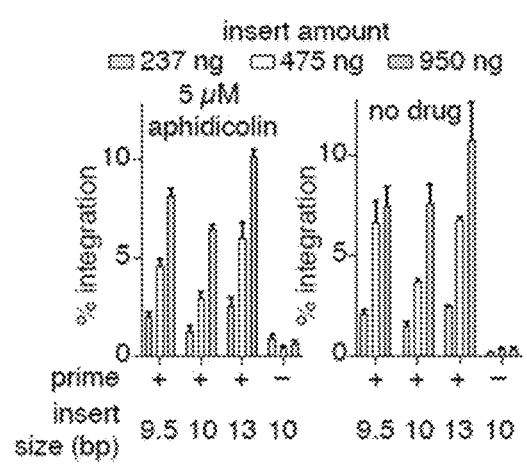
Figure 43C:
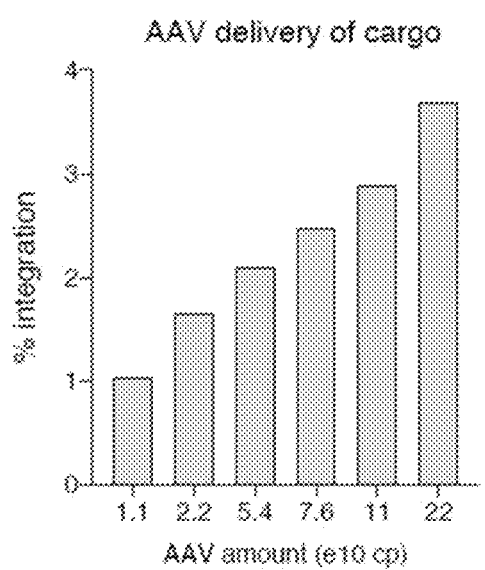
Figure 44A:
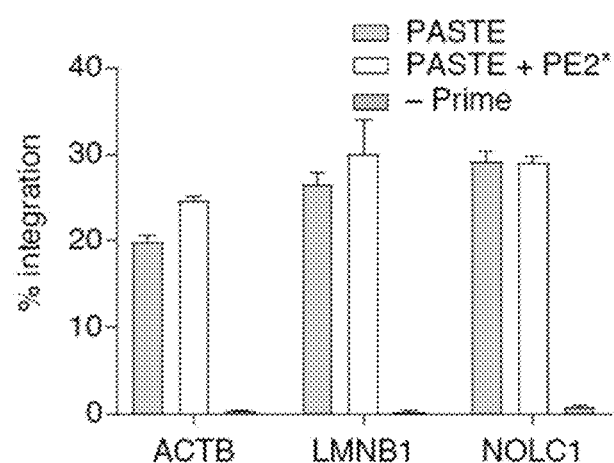
Figure 44B:
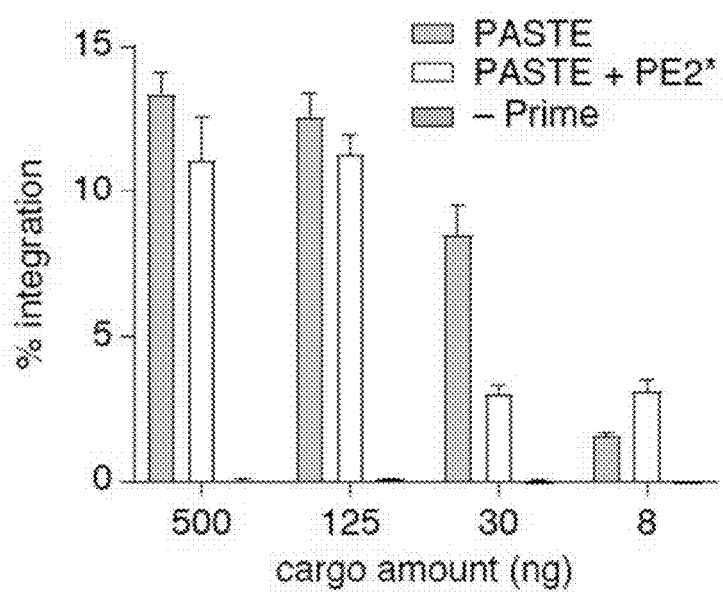
Figure 45:
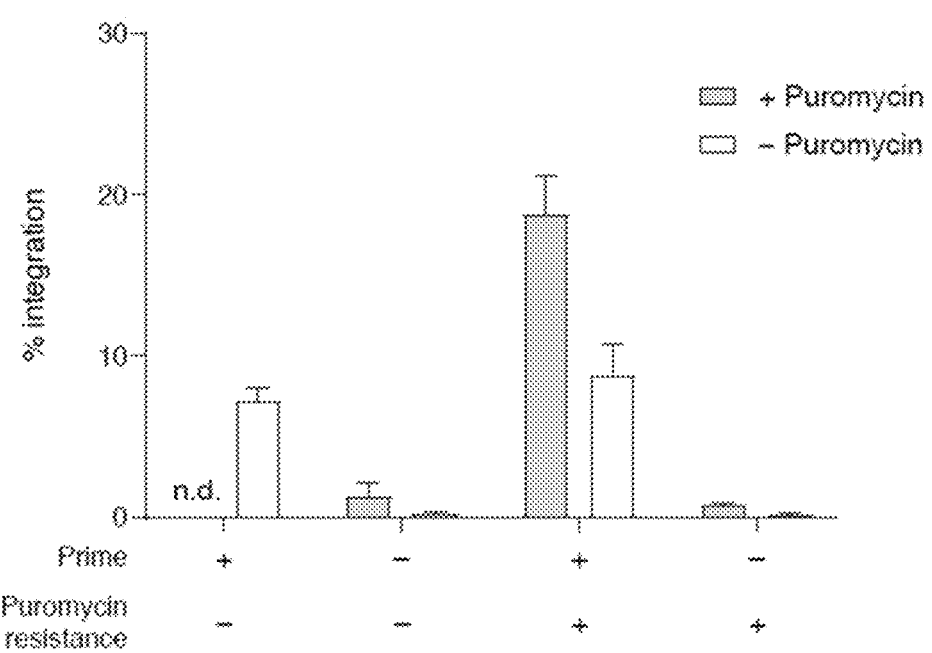
Figure 46A:
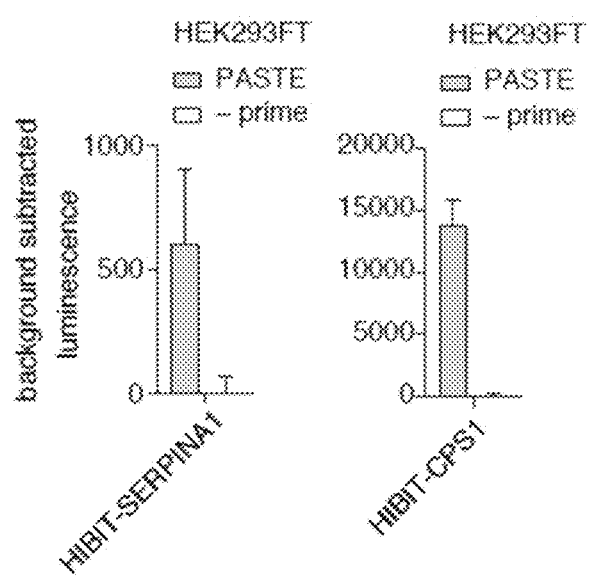
Figure 46B:
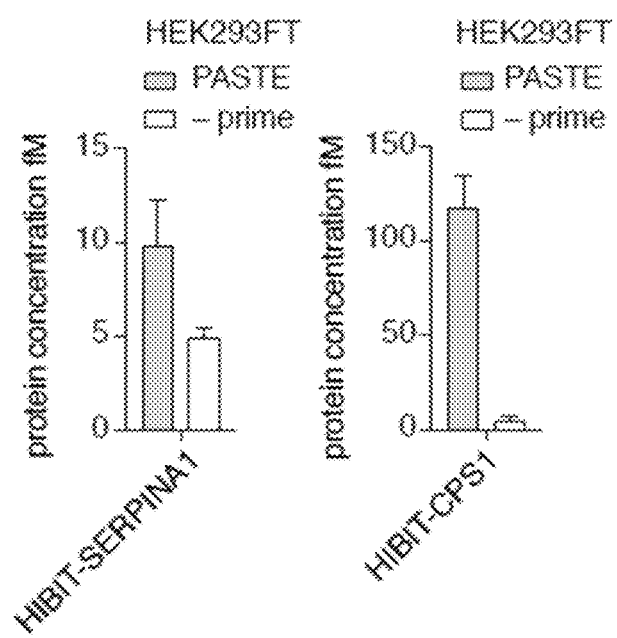
Figure 47A:
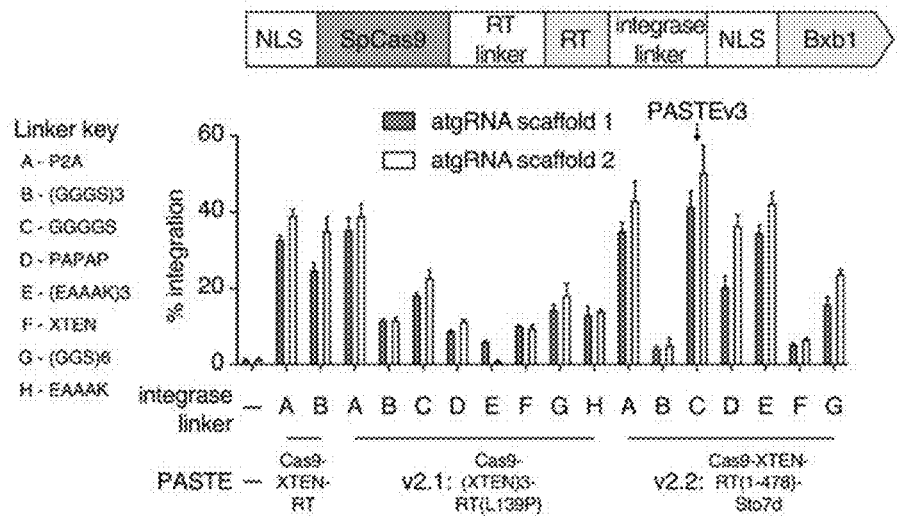
Figure 47B:
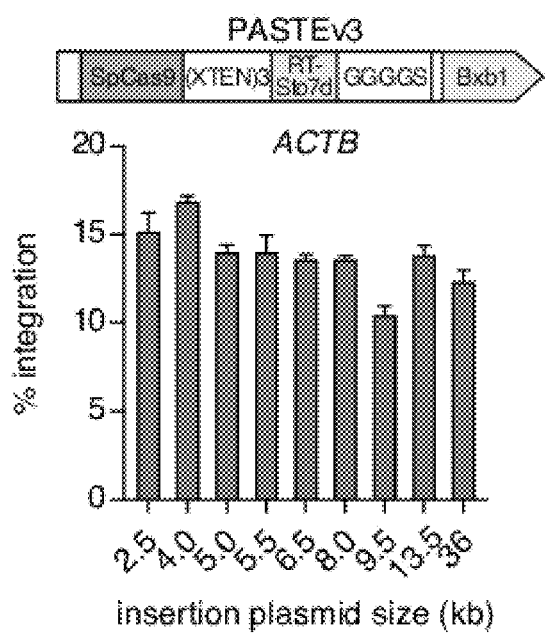
Figure 48A:
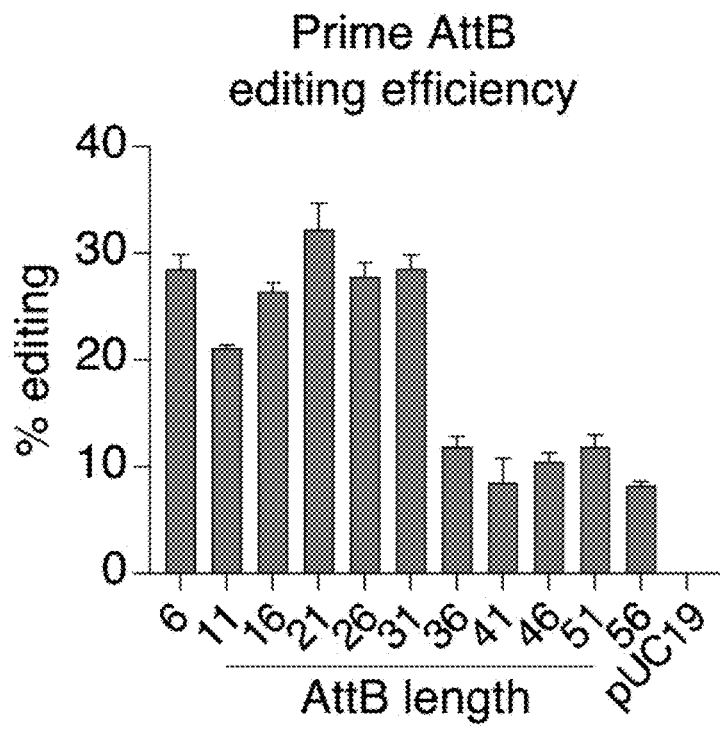
Figure 48B:
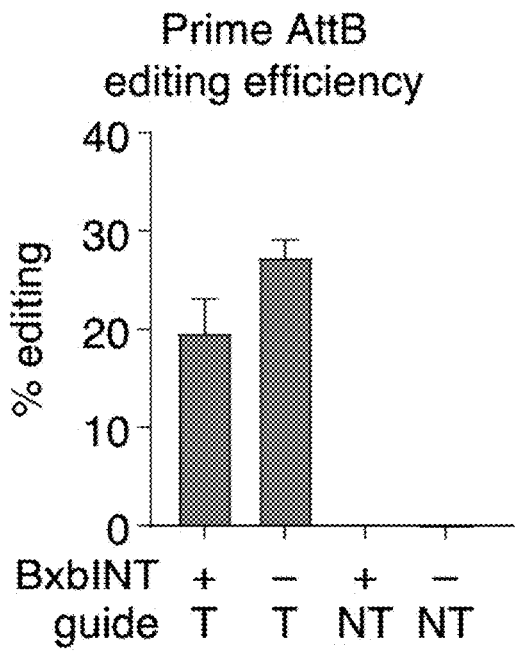
Figure 48C:
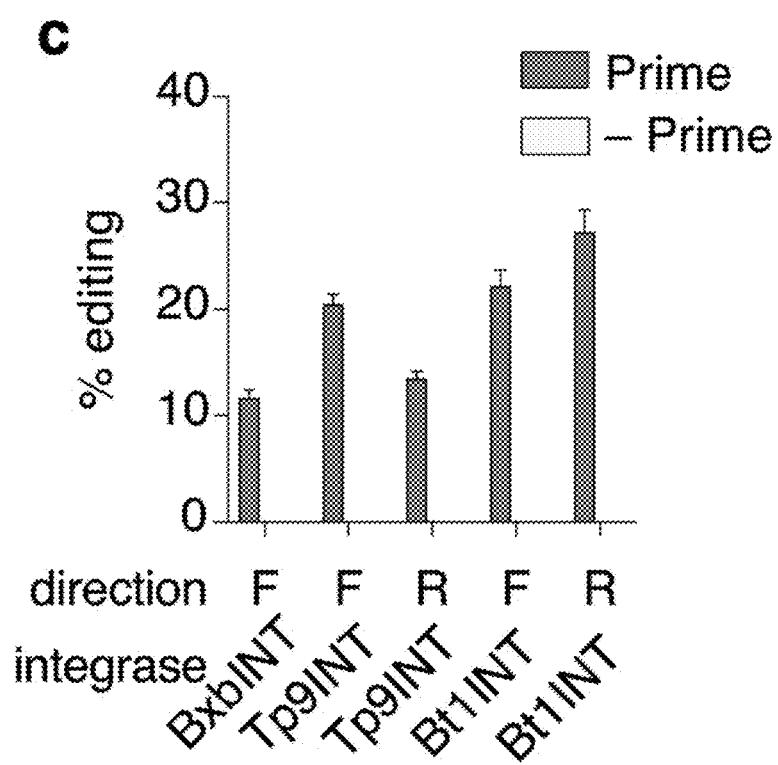
Figure 48D:
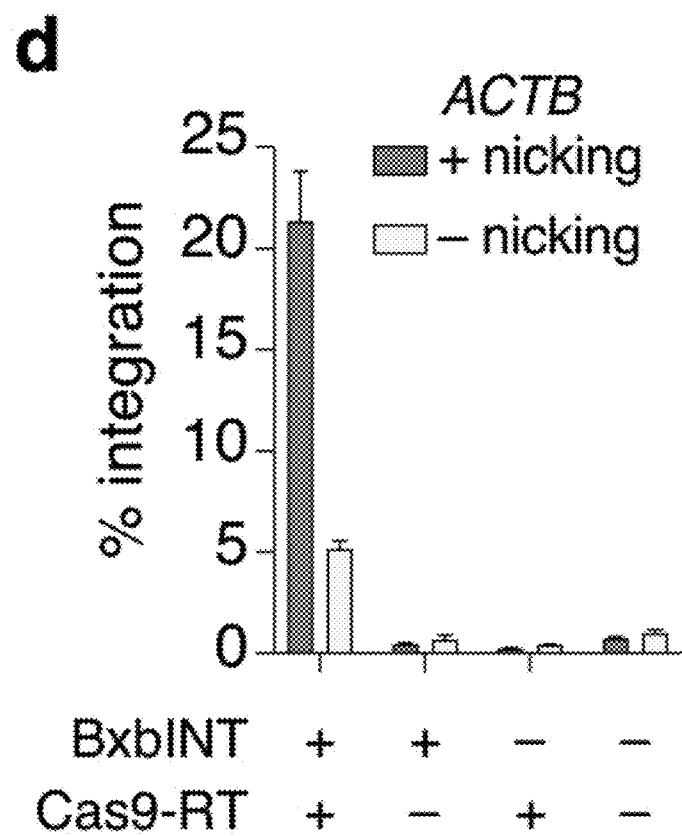
Figures 49A, 49B, 49C, 49D, 49E, 49F:
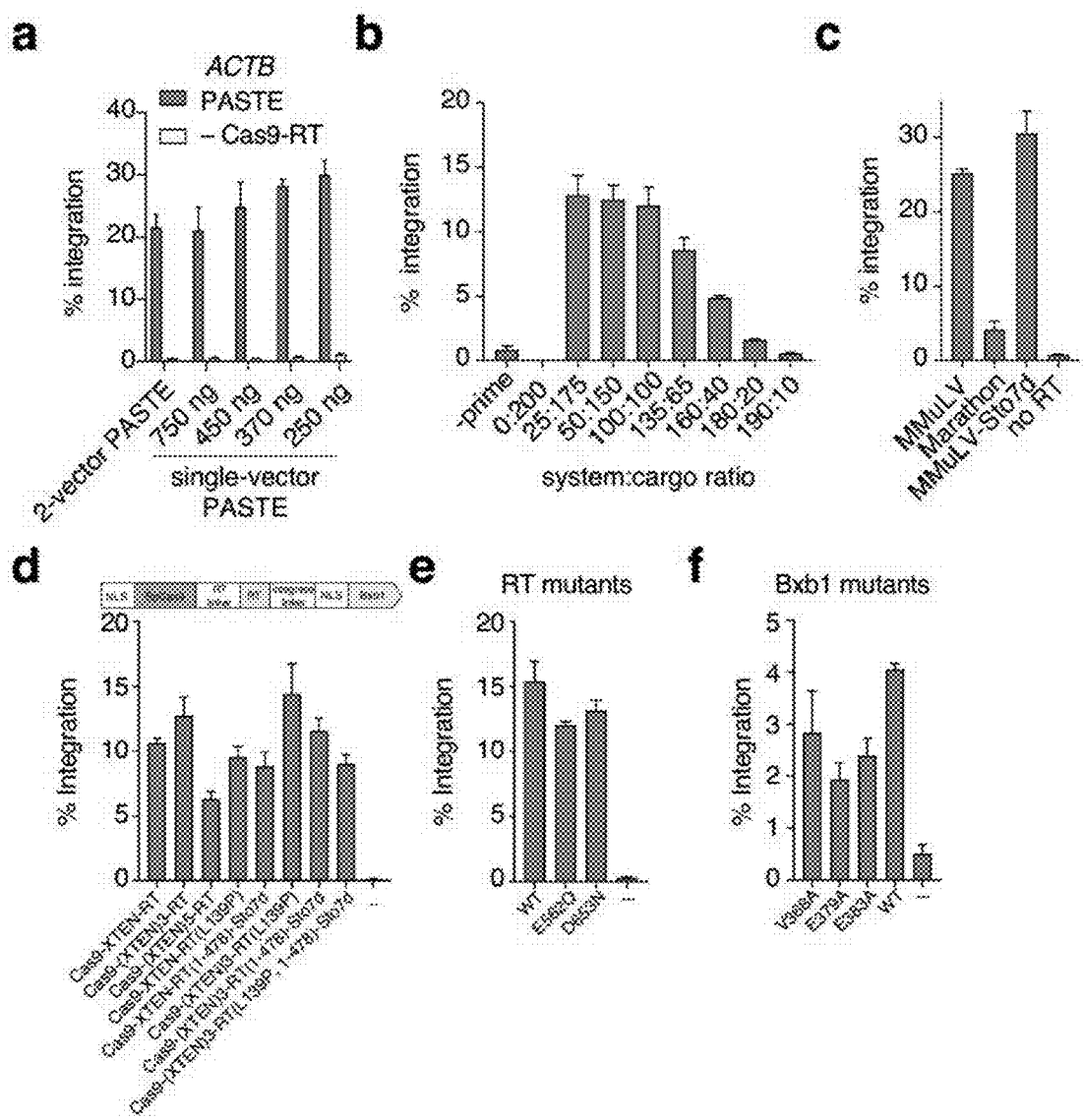

FIG. 41B shows Volcano plots depicting the fold expression change of sequenced mRNAs versus significance (p-value), wherein each dot represents a unique mRNA transcript and significant transcripts are shaded according to either upregulation (red) or downregulation (blue), and wherein fold expression change is measured against ACTB-targeting guide-only expression (including cargo) according to embodiments of the present teachings;

FIG. 41C shows top significantly upregulated and downregulated genes for Bxb1-only conditions, wherein genes are shown with their corresponding Z-scores of counts per million (cpm) for Bxb1 only expression, GFP-only expression, PASTE targeting ACTB for EGFP insertion, Prime targeting ACTB for EGFP expression without Bxb1, and guide/cargo only according to embodiments of the present teachings;

FIG. 42A shows a schematic of PASTE performance in the presence of cell cycle inhibition, wherein cells are transfected with plasmids for insertion with PASTE or Cas9-induced HDR and treated with aphidicolin to arrest cell division, and wherein the efficiency of PASTE and HDR are read out with ddPCR or amplicon sequencing respectively according to embodiments of the present teachings;

FIG. 42B shows the editing efficiency of single mutations by HDR at EMX1 locus with two Cas9 guides in the presence or absence of cell division read out with amplicon sequencing according to embodiments of the present teachings;

FIG. 42C shows the integration efficiency of various sized GFP inserts up to 13.3 kb at the ACTB locus with PASTE in the presence or absence of cell division according to embodiments of the present teachings;

FIG. 42D shows the PASTE editing efficiency with two vector (PE2 and Bxb1) and single vector (PE2-P2A-Bxb1) designs in K562 cells according to embodiments of the present teachings;

FIG. 42E shows the PASTE editing efficiency with single vector (PE2-P2A-Bxb1) designs in primary human T cells according to embodiments of the present teachings;

FIG. 42F shows the integration efficiency of therapeutically relevant genes at the ACTB locus according to embodiments of the present teachings;

FIG. 42G shows a schematic of protein production assay for PASTE-integrated transgene, wherein SERPINA1 and CPS1 transgenes are tagged with HIBIT luciferase for readout with both ddPCR and luminescence according to embodiments of the present teachings;

FIG. 42H shows the integration efficiency of SERPINA1 and CPS1 transgenes in HEK293FT cells at the ACTB locus according to embodiments of the present teachings;

FIG. 42I shows the integration efficiency of SERPINA1 and CPS1 transgenes in HepG2 cells at the ACTB locus according to embodiments of the present teachings;

FIG. 42J shows the intracellular levels of SERPINA1-HIBIT and CPS1-HIBIT in HepG2 cells according to embodiments of the present teachings;

FIG. 42K shows the secreted levels of SERPINA1-HIBIT and CPS1-HIBIT in HepG2 cells according to embodiments of the present teachings;

FIG. 43A shows the HDR mediated editing of the EMX1 locus that is significantly diminished in non-dividing HEK293FT cells blocked by 5 µM aphidicolin treatment according to embodiments of the present teachings;

FIG. 43B shows the effect of insert minicircle DNA amount on PASTE-mediated insertion at the ACTB locus in dividing and nondividing HEK293FT cells blocked by 5 µM aphidicolin treatment according to embodiments of the present teachings;

FIG. 43C shows the PASTE integration of GFP at the ACTB locus with the GFP template delivered via AAV, showing dose dependence of integration efficiency according to embodiments of the present teachings;

FIG. 44A shows the PASTE integration activity at three endogenous loci comparing the normal PASTE SV40 NLS to a c-Myc NLS/variable bi-partite SV40 NLS design according to embodiments of the present teachings;

FIG. 44B shows the PASTE integration activity at the ACTB locus with different GFP minicircle template amounts comparing the normal PASTE SV40 NLS to a c-Myc NLS/variable bi-partite SV40 NLS design according to embodiments of the present teachings;

FIG. 45 shows the improvement of the PASTE editing activity using a puromycin growth selection marker according to embodiments of the present teachings;

FIG. 46A shows the integration of SERPINA1 and CPS1 genes that are HIBIT tagged as measured by a protein expression luciferase assay according to embodiments of the present teachings;

FIG. 46B shows the integration of SERPINA1 and CPS1 genes that are HIBIT tagged as measured by a protein expression luciferase assay normalized to a standardized HIBIT ladder, enabling accurate quantification of protein levels according to embodiments of the present teachings;

FIG. 47A shows optimization of PASTE constructs with a panel of linkers and reverse transcriptase (RT) modifications for EGFP integration at the ACTB locus, according to embodiments of the present teachings;

FIG. 47B shows the effect of cargo size on PASTE insertion efficiency at the endogenous ACTB target. Cargos were transfected with fixed molar amounts, according to embodiments of the present teachings;

FIG. 48A shows prime editing efficiency for the insertion of different length BxbINT AttB sites at ACTB, according to embodiments of the present teachings;

FIG. 48B shows prime editing efficiency for the insertion of a BxbINT AttB site at ACTB with targeting and non-targeting guides, according to embodiments of the present teachings;

FIG. 48C shows prime editing efficiency for the insertion of different integrases' (Bxb1, Tp9, and Bt1) AttB sites at ACTB. Both orientations of landing sites are profiled (F, forward; R, reverse), according to embodiments of the present teachings;

FIG. 48D shows PASTE editing efficiency for the insertion of EGFP at ACTB with and without a nicking guide, according to embodiments of the present teachings; and FIG. 49A shows optimization of PASTE editing by dosage titration and protein optimization. PASTE integration efficiency of EGFP at ACTB measured with different doses of a single-vector delivery of components.

FIG. 49B PASTE integration efficiency of EGFP at ACTB measured with different ratios of a single-vector delivery of components to the EGFP template vector.

FIG. 49C PASTE integration efficiency of EGFP at ACTB with different RT domain fusions.

FIG. 49D PASTE integration efficiency of EGFP at ACTB with different RT domain fusions and linkers.

FIG. 49E PASTE integration efficiency of EGFP at ACTB with mutant RT domains.

FIG. 49F PASTE integration efficiency of EGFP at ACTB with mutated BxbINT domains.

Figures 50A, 50B, 50C, 50D, 50E, 50F, 50G, 50H, 50I:
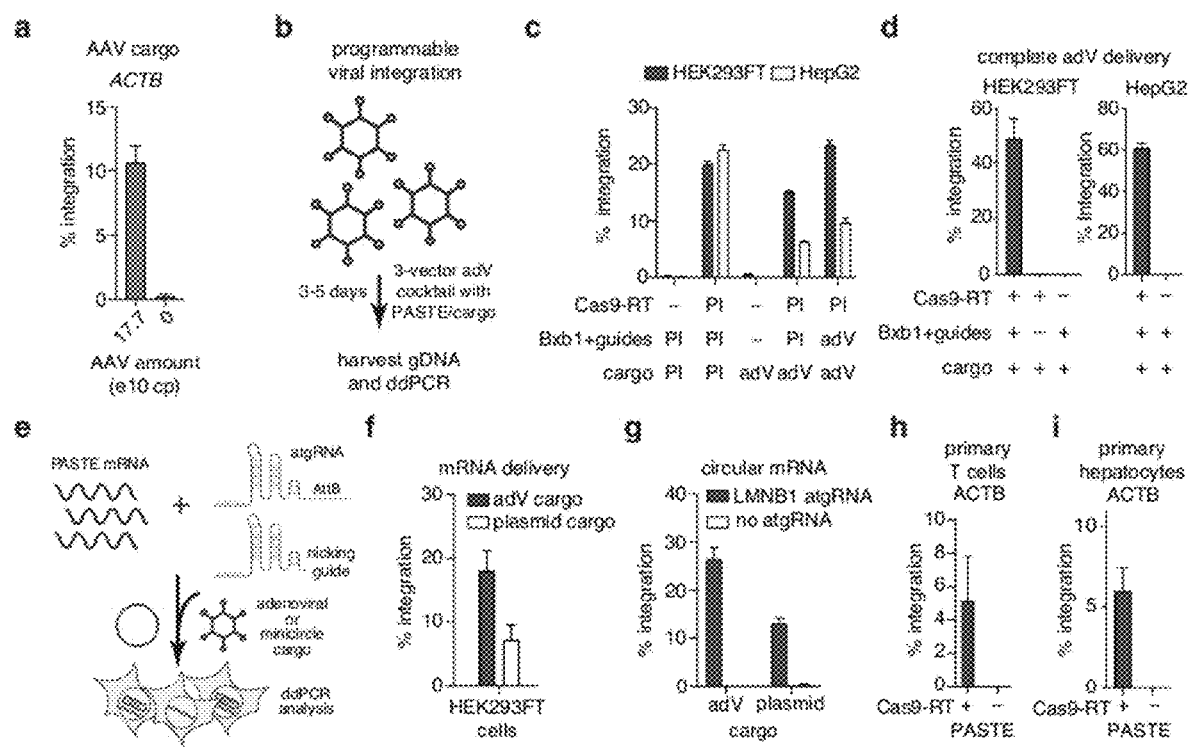

FIG. 50A Insertion templates delivered via AAV transduction. PASTE editing machinery was delivered via transfection, and templates were co-delivered via AAV dosing at levels indicated.

FIG. 50B Schematic of AdV delivery of the complete PASTE system with three viral vectors.

FIG. 50C Integration efficiency of AdV delivery of integrase, guides, and cargo in HEK293FT and HepG2 cells. BxbINT and guide RNAs or cargo were delivered either via plasmid transfection (P1), AdV transduction (AdV), or omitted (−). SpCas9-RT was only delivered as plasmid or omitted.

FIG. 50D AdV delivery of all PASTE components in HEK293FT and HepG2 cells.

FIG. 50E Schematic of mRNA and synthetic guide delivery of PASTE components.

FIG. 50F Delivery of PASTE system components with mRNA and synthetic guides, paired with either AdV or plasmid cargo.

FIG. 50G Delivery of circular mRNA with synthetic guides and either AdV or plasmid cargo.

FIG. 50H PASTE editing efficiency with single vector designs in primary human T cells.

FIG. 50I PASTE editing efficiency with single vector designs in primary human hepatocytes.

Figure 51A:
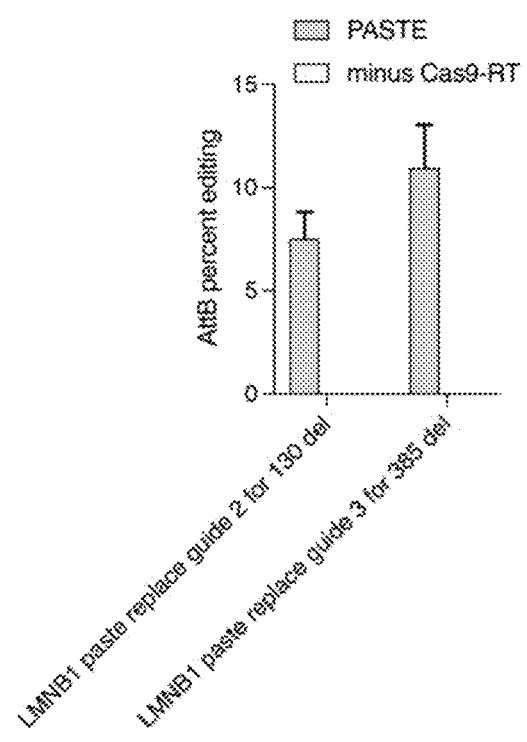

FIG. 51A PASTE editing efficiency at the LMNB1 locus with 130 bp and 385 bp deletions of the first exon of LMNB1 with combined insertion of an attB sequence.

Figure 51B:
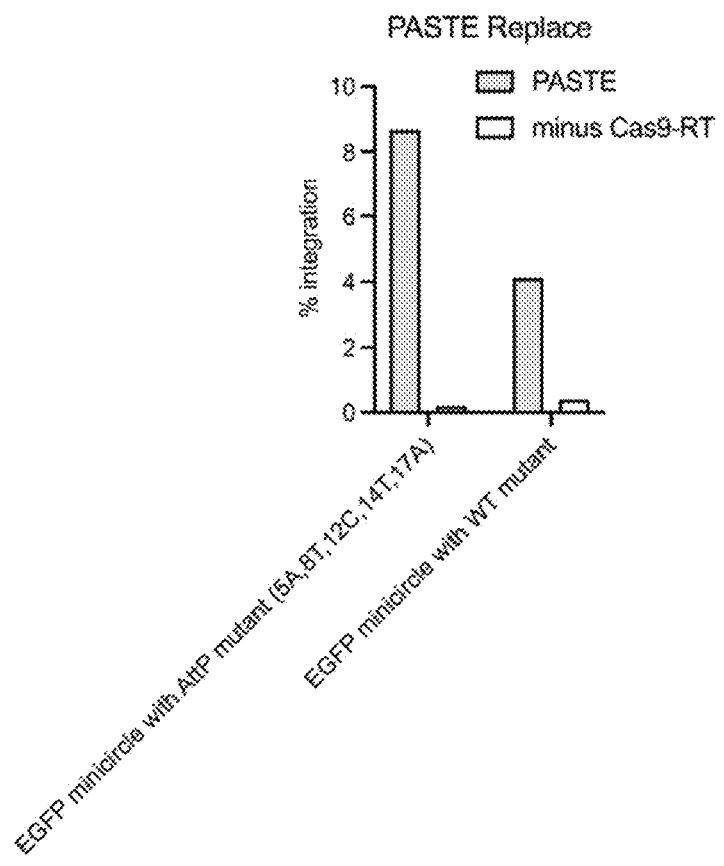

FIG. 51B PASTE editing efficiency with a 130 bp deletion of the first exon of LMNB1 with a combined insertion of a 967 bp cargo using the PASTE system.

DETAILED DESCRIPTION

It will be appreciated that for clarity, the following discussion will describe various aspects of embodiments of the applicant's teachings. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present disclosure. Thus, appearances of the phrases "in one embodiment," "in an embodiment," or "an example embodiment" in various places throughout this specification are not necessarily all referring to the same embodiment, but may. Furthermore, the particular feature, structures or characteristics may be combined in any suitable manner, as would be apparent to a person skilled in the art from this disclosure, in one or more embodiments.

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, 2nd edition (1989) (Sambrook, Fritsch, and Maniatis); Molecular Cloning: A Laboratory Manual, 4th edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, 2nd edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, 2nd edition (2011).

As used herein, the singular forms "a", "an," and "the" include both singular and plural referents unless the context clearly dictates otherwise. Thus, for example, reference to "a cell" includes a plurality of such cells.

As used herein, the term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

As used herein, the term "about" or "approximately" refers to a measurable value such as a parameter, an amount, a temporal duration, and the like, are meant to encompass variations of and from the specified value, such as variations of +/−10% or less, +/−5% or less, +/−1% or less, +/−0.5% or less, and +/−0.1% or less of and from the specified value, insofar such variations are appropriate to perform in the disclosure. It is to be understood that the value to which the modifier "about" or "approximately" refers is itself also specifically, and preferably, disclosed.

It is noted that all publications and references cited herein are expressly incorporated herein by reference in their entirety. The publications discussed herein are provided solely for their disclosure prior to the filing date of the present application. Nothing herein is to be construed as an admission that the present disclosure is not entitled to antedate such publication. Further, the dates of publication provided may be different from the actual publication dates which may need to be independently confirmed.

Overview

Figure 1:
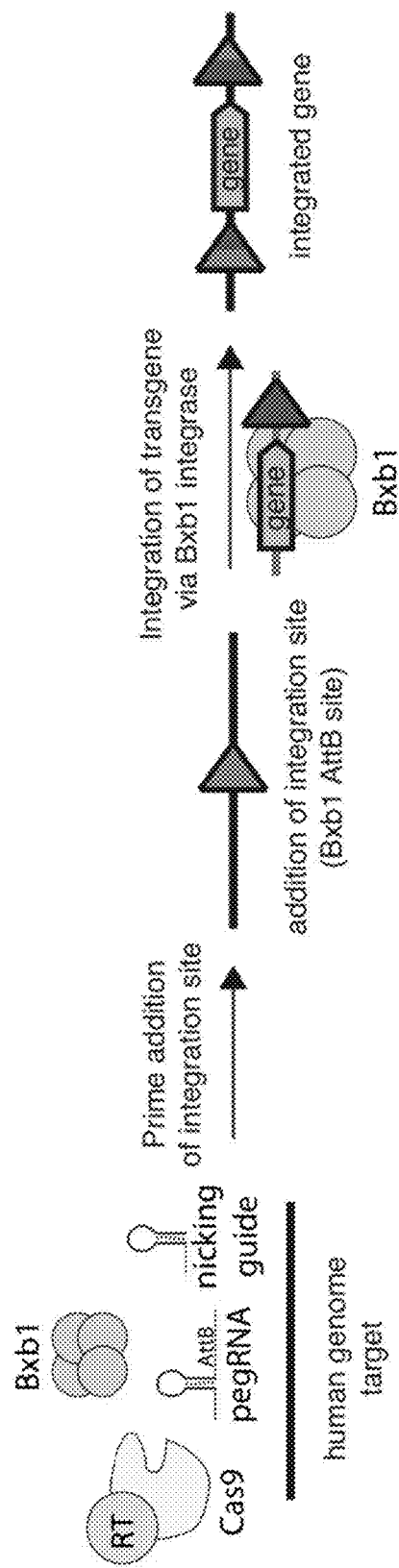
FIG. 1 shows a schematic diagram of a concept of Programmable Addition via Site-Specific Targeting Elements (PASTE) according to embodiments of the present teachings.

The embodiments disclosed herein provide non-naturally occurring or engineered systems, methods, and compositions for site-specific genetic engineering using Programmable Addition via Site-Specific Targeting Elements (PASTE). A schematic diagram illustrating the concept of PASTE is shown in FIG. 1. As discussed in more details below, PASTE comprises the addition of an integration site into a target genome followed by the insertion of one or more genes of interest or one or more nucleic acid sequences of interest at the site. This process can be done as one or more reactions in a cell. The addition of the integration site into the target genome is done using gene editing technologies that include for example, without limitation, prime editing, recombinant adeno-associated virus (rAAV)-mediated nucleic acid integration, transcription activator-like effector nucleases (TALENS), and zinc finger nucleases (ZFNs). The integration of the transgene at the integration site is done using integrase technologies that include for example, without limitation, integrases, recombinases and reverse transcriptases. The necessary components for the site-specific genetic engineering disclosed herein comprise at least one or more nucleases, one or more gRNA, one or more integration enzymes, and one or more sequences that are complementary or associated to the integration site and linked to the one or more genes of interest or one or more nucleic acid sequences of interest to be inserted into the cell genome.

An advantage of the non-naturally occurring or engineered systems, methods, and compositions for site-specific genetic engineering disclosed herein is programmable insertion of large elements without reliance on DNA damage responses.

Another advantage of the non-naturally occurring or engineered systems, methods, and compositions for site-specific genetic engineering disclosed herein is facile multiplexing, enabling programmable insertion at multiple sites.

Another advantage of the non-naturally occurring or engineered systems, methods, and compositions for site-specific genetic engineering disclosed herein is scalable production and delivery through minicircle templates.

Prime Editing

The present disclosure provides non-naturally occurring or engineered systems, methods, and compositions for site-specific genetic engineering using gene editing technologies, such as prime editing, to add an integration site into a target genome. Prime editing will be discussed in more details below.

Figure 2:
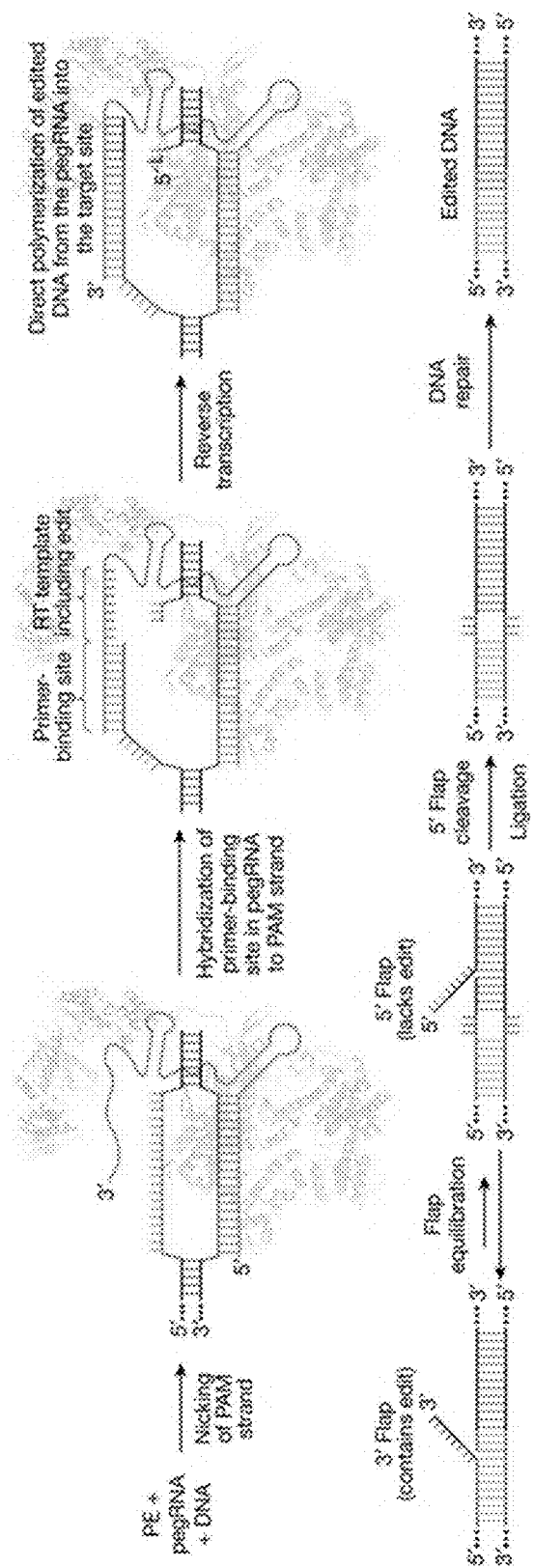
FIG. 2 shows a schematic diagram of a prime editing process according to embodiments of the present teachings.

Prime editing is a versatile and precise genome editing method that directly writes new genetic information into a specified DNA site. A schematic diagram illustrating the concept of prime editing is shown in FIG. 2. See, Anzalone, A. V., et al. "Search-and-replace genome editing without double-strand breaks or donor DNA," Nature 576, 149-157 (2019). Prime editing uses a catalytically-impaired Cas9 endonuclease that is fused to an engineered reverse transcriptase (RT) and programmed with a prime-editing guide RNA (pegRNA). The skilled person in the art would appreciate that the pegRNA both specifies the target site and encodes the desired edit. The catalytically-impaired Cas9 endonuclease also comprises a Cas9 nickase that is fused to the reverse transcriptase. During genetic editing, the Cas9 nickase part of the protein is guided to the DNA target site by the pegRNA. The reverse transcriptase domain then uses the pegRNA to template reverse transcription of the desired edit, directly polymerizing DNA onto the nicked target DNA strand. The edited DNA strand replaces the original DNA strand, creating a heteroduplex containing one edited strand and one unedited strand. Afterward, the prime editor (PE) guides resolution of the heteroduplex to favor copying the edit onto the unedited strand, completing the process.

The prime editors refer to a Moloney Murine Leukemia Virus (M-MLV) reverse transcriptase (RT) fused to a Cas9 H840A nickase. Fusing the RT to the C-terminus of the Cas9 nickase may result in higher editing efficiency. Such a complex is called PE1. The Cas9(H840A) can also be linked to a non-M-MLV reverse transcriptase such as a AMV-RT or XRT (Cas9(H840A)-AMV-RT or XRT). In some embodiments, Cas 9(H840A) can be replaced with Cas12a/b or Cas9(D10A). A Cas9 (wild type), Cas9(H840A), Cas9 (D10A) or Cas 12a/b nickase fused to a pentamutant of M-MLV RT (D200N/L603W/T330P/T306K/W313F), having up to about 45-fold higher efficiency is called PE2. In some embodiments, the M-MLV RT comprise one or more of the mutations: Y8H, P51L, S56A, S67R, E69K, V129P, L139P, T197A, H204R, V223H, T246E, N249D, E286R, Q291I, E302K, E302R, F309N, M320L, P330E, L435G, L435R, N454K, D524A, D524G, D524N, E562Q, D583N, H594Q, E607K, D653N, and L671P. In some embodiments, the reverse transcriptase can also be a wild-type or modified transcription xenopolymerase (RTX), avian myeloblastosis virus reverse transcriptase (AMV-RT), Feline Immunodeficiency Virus reverse transcriptase (FIV-RT), FeLV-RT (Feline leukemia virus reverse transcriptase), HIV-RT (Human Immunodeficiency Virus reverse transcriptase), or Eubacterium rectale maturase RT (MarathonRT). PE3 involves nicking the non-edited strand, potentially causing the cell to remake that strand using the edited strand as the template to induce HR. The nicking of the non-edited strand can involve the use of a nicking guide RNA (ngRNA).

Nicking the non-edited strand can increase editing efficiency. For example, nicking the non-edited strand can increase editing efficiency by about 1.1 fold, about 1.3 fold, about 1.5 fold, about 1.7 fold, about 1.9 fold, about 2.1 fold, about 2.3 fold, about 2.5 fold, about 2.7 fold, about 2.9 fold, about 3.1 fold, about 3.3 fold, about 3.5 fold, about 3.7 fold, about 3.9 fold, 4.1 fold, about 4.3 fold, about 4.5 fold, about 4.7 fold, about 4.9 fold, or any range that is formed from any two of those values as endpoints.

Although the optimal nicking position varies depending on the genomic site, nicks positioned 3' of the edit about 40-90 bp from the pegRNA-induced nick can generally increase editing efficiency without excess indel formation. The prime editing practice allows starting with non-edited strand nicks about 50 bp from the pegRNA-mediated nick, and testing alternative nick locations if indel frequencies exceed acceptable levels.

As used herein, the term "guide RNA" (gRNA) and the like refer to a RNA that guide the insertion or deletion of one or more genes of interest or one or more nucleic acid sequences of interest into a target genome. The gRNA can also refer to a prime editing guide RNA (pegRNA), a nicking guide RNA (ngRNA), and a single guide RNA (sgRNA). In some embodiments, the term "gRNA molecule" refers to a nucleic acid encoding a gRNA. In some embodiments, the gRNA molecule is naturally occurring. In some embodiments, a gRNA molecule is non-naturally occurring. In some embodiments, a gRNA molecule is a synthetic gRNA molecule. A gRNA can target a nuclease or a nickase such as Cas9, Cas 12a/b, Cas9 (H840A) or Cas9 (D10A) molecule to a target nucleic acid or sequence in a genome. In some embodiments, the gRNA can bind to a DNA nickase bound to a reverse transcriptase domain. A "modified gRNA," as used herein, refers to a gRNA molecule that has an improved half-life after being introduced into a cell as compared to a non-modified gRNA molecule after being introduced into a cell. In some embodiments, the guide RNA can facilitate the addition of the insertion site sequence for recognition by integrases, transposases, or recombinases.

Figures 24A, 24B:
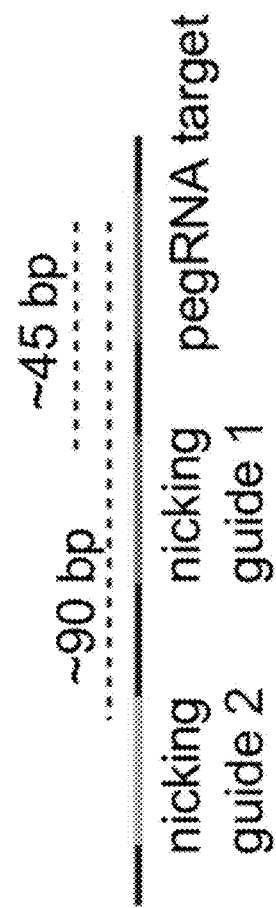
FIG. 24A shows a schematic of the design parameters for the pegRNA according to embodiments of the present teachings.
FIG. 24B shows a schematic of the design parameters for nicking guide RNA according to embodiments of the present teachings.

As used herein, the term "prime-editing guide RNA" (pegRNA) and the like refer to an extended single guide RNA (sgRNA) comprising a primer binding site (PBS), a reverse transcriptase (RT) template sequence, and an integration site sequence that can be recognized by recombinases, integrases, or transposases. Exemplary design parameters for pegRNA are shown in FIG. 24A. For example, the PBS can have a length of at least about 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, 30 nt, or more nt. For example, the PBS can have a length of about 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, 30 nt, or any range that is formed from any two of those values as endpoints. For example, the RT template sequence can have a length of at least about 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, 30 nt, 31 nt, 32 nt, 33 nt, 34 nt, 35 nt, 36 nt, 37 nt, 38 nt, 39 nt, 40 nt, 41 nt, 42 nt, 43 nt, 44 nt, 45 nt, 46 nt, 47 nt, 48 nt, 49 nt, 50 nt, or more nt. For example, the RT template sequence can have a length of about 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, 30 nt, 31 nt, 32 nt, 33 nt, 34 nt, 35 nt, 36 nt, 37 nt, 38 nt, 39 nt, 40 nt, 41 nt, 42 nt, 43 nt, 44 nt, 45 nt, 46 nt, 47 nt, 48 nt, 49 nt, 50 nt, or any range that is formed from any two of those values as endpoints.

During genome editing, the primer binding site allows the 3' end of the nicked DNA strand to hybridize to the pegRNA, while the RT template serves as a template for the synthesis of edited genetic information. The pegRNA is capable for instance, without limitation, of (i) identifying the target nucleotide sequence to be edited and (ii) encoding new genetic information that replaces the targeted sequence. In some embodiments, the pegRNA is capable of (i) identifying the target nucleotide sequence to be edited and (ii) encoding an integration site that replaces the targeted sequence.

As used herein, the term "nicking guide RNA" (ngRNA) and the like refer to an RNA sequence that can nick a strand such as an edited strand and a non-edited strand. Exemplary design parameters for ngRNA are shown in FIG. 24B. The ngRNA can induce nicks at about 1 or more nt away from the site of the gRNA-induced nick. For example, the ngRNA can nick at least at about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, or more nt away from the site of the gRNA induced nick. In some embodiments, the ngRNA comprises SEQ ID NO: 75 with guide sequence SEQ ID NO: 74. As used herein, the terms "reverse transcriptase" and "reverse transcriptase domain" refer to an enzyme or an enzymatically active domain that can reverse a RNA transcribe into a complementary DNA. The reverse transcriptase or reverse transcriptase domain is a RNA dependent DNA polymerase. Such reverse transcriptase domains encompass, but are not limited, to a M-MLV reverse transcriptase, or a modified reverse transcriptase such as, without limitation, Superscript® reverse transcriptase (Invitrogen; Carlsbad, California), Superscript® VILO™ cDNA synthesis (Invitrogen; Carlsbad, California), RTX, AMV-RT, and Quantiscript Reverse Transcriptase (Qiagen, Hilden, Germany).

The pegRNA-PE complex disclosed herein recognizes the target site in the genome and the Cas9 for example nicks a protospacer adjacent motif (PAM) strand. The primer binding site (PBS) in the pegRNA hybridizes to the PAM strand. The RT template operably linked to the PBS, containing the edit sequence, directs the reverse transcription of the RT template to DNA into the target site. Equilibration between the edited 3' flap and the unedited 5' flap, cellular 5' flap cleavage and ligation, and DNA repair results in stably edited DNA. To optimize base editing, a Cas9 nickase can be used to nick the non-edited strand, thereby directing DNA repair to that strand, using the edited strand as a template.

Integrase Technologies

The present disclosure provides non-naturally occurring or engineered systems, methods, and compositions for site-specific genetic engineering using integrase technologies. Integrase technologies will be discussed in more details below.

The integrase technologies used herein comprise proteins or nucleic acids encoding the proteins that direct integration of a gene of interest or nucleic acid sequence of interest into an integration site via a nuclease such as a prime editing nuclease. The protein directing the integration can be an enzyme such as integration enzyme. The integration enzyme can be an integrase that incorporates the genome or nucleic acid of interest into the cell genome at the integration site by integration. The integration enzyme can be a recombinase that incorporates the genome or nucleic acid of interest into the cell genome at the integration site by recombination. The integration enzyme can be a reverse transcriptase that incorporates the genome or nucleic acid of interest into the cell genome at the integration site by reverse transcription. The integration enzyme can be a retrotransposase that incorporates the genome or nucleic acid of interest into the cell genome at the integration site by retrotransposition.

As used herein, the term "integration enzyme" refers to an enzyme or protein used to integrate a gene of interest or nucleic acid sequence of interest into a desired location or at the integration site, in the genome of a cell, in a single reaction or multiple reactions. Example of integration enzymes include for example, without limitation, Cre, Dre, Vika, Bxb1, φC31, RDF, FLP, φBT1, R1, R2, R3, R4, R5, TP901-1, A118, φFC1, φC1, MR11, TG1, φ370.1, Wβ, BL3, SPBc, K38, Peaches, Veracruz, Rebeuca, Theia, Benedict, KSSJEB, PattyP, Doom, Scowl, Lockley, Switzer, Bob3, Troube, Abrogate, Anglerfish, Sarfire, SkiPole, ConceptII, Museum, Severus, Airmid, Benedict, Hinder, ICleared, Sheen, Mundrea, BxZ2, φRV, and retrotransposases encoded by R2, L1, Tol2 Tc1, Tc3, Mariner (Himar 1), Mariner (mos 1), and Minos. In some embodiments, the term "integration enzyme" refers to a nucleic acid (DNA or RNA) encoding the above-mentioned enzymes. In some embodiments, the Cre recombinase is expressed from a Cre recombinase expression plasmid (SEQ ID NO: 71).

Mammalian expression plasmids can be found in Table 1 below.

TABLE 1

| Name | Full Description | SEQ ID NOS: |
|---|---|---|
| PE2-Bxb1 Single Vector | pCMV-PE2-P2A-Bxb1 | (SEQ ID NO: 381) |
| PE2 prime editor | pCMV-PE2/ Addgene #132775 | (SEQ ID NO: 382) |
| PE2*-Bxb1 Single Vector | New NLS pCMV-PE2-P2A-Bxb1 | (SEQ ID NO: 383) |
| PASTEv3 | pCMV-SpCas9-XTEN-RT(1-478)-Sto7d-GGGGS-BxbINT | (SEQ ID NO: 384) |
| ACTB pegRNA | ACTB N-term PBS 13 RT 29 attB 46 pegRNA | (SEQ ID NO: 385) |

TABLE 1-continued

| Name | Full Description | SEQ ID NOS: |
|---|---|---|
| ACTB Nicking +48 | ACTB N-term Nicking guide 1 +48 guide | (SEQ ID NO: 386) |
| Bxb1 integrase | pCAG-NLS-HA-Bxb1integrase/ Addgene #51271 | (SEQ ID NO: 387) |
| TP901-1 Integrase | TP901-1 Integrase | (SEQ ID NO: 388) |
| PhiBT Integrase | PhiBT Integrase | (SEQ ID NO: 389) |
| HDR sgRNA guide | Minicircle U6-sgRNA EFS-SpCas9 | (SEQ ID NO: 390) |
| HDR EGFP cargo | Cas9 HDR template site with EGFP | (SEQ ID NO: 391) |
| AAV helper plasmid | PDF6 AAV helper plasmid | (SEQ ID NO: 392) |
| AAV EGFP donor | GFP AAV donor plasmid | (SEQ ID NO: 393) |
| AAV2/8 | AAV2/8 capsid protein | (SEQ ID NO: 394) |

Minicircle cargo gene maps can be found in Table 2 below.

TABLE 2

| Name | Full Description | SEQ ID NOS: |
|---|---|---|
| Cargo EGFP | Parent minicircle plasmid - Cargo EGFP with attP Bxb1 site | (SEQ ID NO: 76) |
| Cargo EGFP post cleavage | Cargo EGFP with attP Bxb1 site - post minicircle cleavage | (SEQ ID NO: 395) |
| Cargo EGFP for fusion | Parent minicircle plasmid - Cargo EGFP with attP Bxb1 site for fusion | (SEQ ID NO: 396) |
| mCherry Cargo post cleavage | Cargo mCherry with attP Bxb1 site - post minicircle cleavage | (SEQ ID NO: 397) |
| YFP Cargo post cleavage | Cargo YFP with attP Bxb1 site - post minicircle cleavage | (SEQ ID NO: 398) |
| SERPINA1 Cargo post cleavage | Cargo SERPINA1 with attP Bxb1 site - post minicircle cleavage | (SEQ ID NO: 399) |
| CPS1 Cargo post cleavage | Cargo CPS1 with attP Bxb1 site - post minicircle cleavage | (SEQ ID NO: 400) |
| CFTR Cargo | Parent minicircle plasmid - Cargo CFTR with attP Bxb1 site | (SEQ ID NO: 401) |
| NYESO TCR Cargo post cleavage | Cargo NYESO TCR with attP Bxb1 site - post minicircle cleavage | (SEQ ID NO: 402) |

In some embodiments, the serine integrase φC31 from φC31 phage is use as integration enzyme. The integrase φC31 in combination with a pegRNA can be used to insert the pseudo attP integration site (SEQ ID NO: 78). A DNA minicircle containing a gene or nucleic acid of interest and attB (SEQ ID NO: 3) site can be used to integrate the gene or nucleic acid of interest into the genome of a cell. This integration can be aided by a co-transfection of an expression vector having the φC31 integrase.

As used herein, the term "integrase" refers to a bacteriophage derived integrase, including wild-type integrase and any of a variety of mutant or modified integrases. As used herein, the term "integrase complex" may refer to a complex comprising integrase and integration host factor (IF). As used herein, the term "integrase complex" and the like may also refer to a complex comprising an integrase, an integration host factor, and a bacteriophage λ-derived excisionase (Xis).

As used herein, the term "recombinase" and the like refer to a site-specific enzyme that mediates the recombination of DNA between recombinase recognition sequences, which results in the excision, integration, inversion, or exchange (e.g., translocation) of DNA fragments between the recombinase recognition sequences. Recombinases can be classified into two distinct families: serine recombinases (e.g., resolvases and invertases) and tyrosine recombinases (e.g., integrases). Examples of serine recombinases include, without limitation, Hin, Gin, Tn3, β-six, CinH, ParA, γδ, Bxb1, φC31, TP901, TG1, φBT1, R1, R2, R3, R4, R5, φRV1, φFC1, MR11, A118, U153, and gp29. Examples of serine recombinases also include, without limitation, recombinases Peaches, Veracruz, Rebeuca, Theia, Benedict, KSSJEB, PattyP, Doom, Scowl, Lockley, Switzer, Bob3, Troube, Abrogate, Anglerfish, Sarfire, SkiPole, ConceptII, Museum, Severus, Airmid, Benedict, Hinder, ICleared, Sheen, Mundrea, and BxZ2 from Mycobacterial phages. Examples of tyrosine recombinases include, without limitation, Cre, FLP, R, Lambda, HK101, HK022, and pSAM2. The serine and tyrosine recombinase names stem from the conserved nucleophilic amino acid residue that the recombinase uses to attack the DNA and which becomes covalently linked to the DNA during strand exchange.

Recombinases have numerous applications, including the creation of gene knockouts/knock-ins and gene therapy applications. See, e.g., Brown et al., "Serine recombinases as tools for genome engineering."*Methods,* 2011; 53(4):372-9; Hirano et al., "Site-specific recombinases as tools for heterologous gene integration." Appl. Microbiol. Biotechnol. 2011; 92(2):227-39; Chavez and Calos, "Therapeutic applications of the ΦC31 integrase system." *Curr. Gene Ther.* 2011; 11(5):375-81; Turan and Bode, "Site-specific recombinases: from tag-and-target- to tag-and-exchange-based genomic modifications." *FASEB J.* 2011; 25(12): 4088-107; Venken and Bellen, "Genome-wide manipulations of *Drosophila melanogaster* with transposons, Flp recombinase, and ΦC31 integrase."*Methods Mol. Biol.* 2012; 859:203-28; Murphy, "Phage recombinases and their applications."*Adv. Virus Res.* 2012; 83:367-414; Zhang et al., "Conditional gene manipulation: Creating a new biological era." J. Zhejiang Univ. Sci. B. 2012; 13(7):511-24; Karpenshif and Bernstein, "From yeast to mammals: recent advances in genetic control of homologous recombination." DNA Repair (Amst). 2012; 1; 11(10):781-8; the entire contents of each are hereby incorporated by reference in their entirety.

The recombinases provided herein are not meant to be exclusive examples of recombinases that can be used in embodiments of the disclosure. The methods and compositions of the disclosure can be expanded by mining databases for new orthogonal recombinases or designing synthetic recombinases with defined DNA specificities (See, e.g., Groth et al., "Phage integrases: biology and applications." *J. Mol. Biol.* 2004; 335, 667-678; Gordley et al., "Synthesis of programmable integrases." *Proc. Natl. Acad. Sci. USA.* 2009; 106, 5053-5058; the entire contents of each are hereby incorporated by reference in their entirety).

Other examples of recombinases that are useful in the systems, methods, and compositions described herein are known to those of skill in the art, and any new recombinase that is discovered or generated is expected to be able to be used in the different embodiments of the disclosure.

As used herein, the term "retrotransposase" and the like refer to an enzyme, or combination of one or more enzymes, wherein at least one enzyme has a reverse transcriptase domain. Retrotransposases are capable of inserting long sequences (e.g., over 3000 nucleotides) of heterologous nucleic acid into a genome. Examples of retrotransposases include for example, without limitation, retrotransposases encoded by elements such as R2, L1, Tol2 Tc1, Tc3, Mariner (Himar 1), Mariner (mos 1), Minos, and any mutants thereof.

In some embodiments, the one or more genes of interest or one or more nucleic acid sequences of interest are inserted into a desired location in a genome using a RNA fragment, such as a retrotransposon, encoding the nucleic acid linked to a complementary or associated integration site. The insertion of the nucleic acid of interest into a location in the desired location in the genome using a retrotransposon is aided by a retrotransposase.

The gene and nucleic acid sequence of interest disclosed herein can be any gene and nucleic acid sequence that are known in the art. The gene and nucleic acid sequence of interest can be for therapeutic and/or diagnostic uses. Examples of genes of interest include, without limitation, GBA, BTK, ADA, CNGB3, CNGA3, ATF6, GNAT2, ABCA1, ABCA7, APOE, CETP, LIPC, MMP9, PLTP, VTN, ABCA4, MFSD8, TLR3, TLR4, ERCC6, HMCN1, HTRA1, MCDR4, MCDR5, ARMS2, C2, C3, CFB, CFH, JAG1, NOTCH2, CACNA1F, SERPINA1, TTR, GSN, B2M, APOA2, APOA1, OSMR, ELP4, PAX6, ARG, ASL, PITX2, FOXC1, BBS1, BBS10, BBS2, BBS9, MKKS, MKS1, BBS4, BBS7, TTC8, ARL6, BBS5, BBS12, TRIM32, CEP290, ADIPOR1, BBIP1, CEP19, IFT27, LZTFL1, DMD, BEST1, HBB, CYP4V2, AMACR, CYP7B1, HSD3B7, AKR1D1, OPN1SW, NR2F1, RLBP1, RGS9, RGS9BP, PROM1, PRPH2, GUCY2D, CACD, CHM, ALAD, ASS1, SLC25A13, OTC, ACADVL, ETFDH, TMEM67, CC2D2A, RPGRIP1L, KCNV2, CRX, GUCA1A, CERKL, CDHR1, PDE6C, TTLL5, RPGR, CEP78, C21orf2, C8ORF37, RPGRIP1, ADAM9, POC1B, PITPNM3, RAB28, CACNA2D4, AIPL1, UNC119, PDE6H, OPN1LW, RIMS1, CNNM4, IFT81, RAX2, RDH5, SEMA4A, CORD17, PDE6B, GRK1, SAG, RHO, CABP4, GNB3, SLC24A1, GNAT1, GRM6, TRPM1, LRIT3, TGFBI, TACSTD2, KRT12, OVOL2, CPS1, UGT1A1, UGT1A9, UGT1A8, UGT1A7, UGT1A6, UGT1A5, UGT1A4, CFTR, DLD, EFEMP1, ABCC2, ZNF408, LRP5, FZD4, TSPAN12, EVR3, APOB, SLC2A2, LOC106627981, GBA1, NR2E3, OAT, SLC40A1, F8, F9, UROD, CPOX, HFE, JH, LDLR, EPHX1, TJP2, BAAT, NBAS, LARS1, HAMP, HJV, RS1, ADAMTS18, LRAT, RPE65, LCA5, MERTK, GDF6, RD3, CCT2, CLUAP1, DTHD1, NMNAT1, SPATA7, IFT140, IMPDH1, OTX2, RDH12, TULP1, CRB1, MT-ND4, MT-ND1, MT-ND6, BCKDHA, BCKDHB, DBT, MMAB, ARSB, GUSB, NAGS, NPC1, NPC2, NDP, OPA1, OPA3, OPA4, OPA5, RTN4IP1, TMEM126A, OPA6, OPA8, ACO2, PAH, PRKCSH, SEC63, GAA, UROS, PPDX, HPX, HMOX1, HMBS, MIR223, CYP1B1, LTBP2, AGXT, ATP8B1, ABCB11, ABCB4, FECH, ALAS2, PRPF31, RP1, EYS, TOPORS, USH2A, CNGA1, C2ORF71, RP2, KLHL7, ORF1, RP6, RP24, RP34, ROM1, ADGRA3, AGBL5, AHR, ARHGEF18, CA4, CLCC1, DHDDS, EMC1, FAM161A, HGSNAT, HK1, IDH3B, KIAA1549, KIZ, MAK, NEUROD1, NRL, PDE6A, PDE6G, PRCD, PRPF3, PRPF4, PRPF6, PRPF8, RBP3, REEP6, SAMD11, SLC7A14, SNRNP200, SPP2, ZNF513, NEK2, NEK4, NXNL1, OFD1, RP1L1, RP22, RP29, RP32, RP63, RP9, RGR, POMGNT1, DHX38, ARL3, COL2A1, SLCO1B1, SLCO1B3, KCNJ13, TIMP3, ELOVL4, TFR2, FAH, HPD, MYO7A, CDH23, PCDH15, DFNB31, GPR98, USH1C, USH1G, CIB2, CLRN1, HARS, ABHD12, ADGRV1, ARSG, CEP250, IMPG1, IMPG2, VCAN, G6PC1, ATP7B and any derivatives thereof.

As used here, the terms "retrotransposons," "jumping genes," "jumping nucleic acids," and the like refer to cellular movable genetic elements dependent on reverse transcription. The retrotransposons are of non-replication competent cellular origin, and are capable of carrying a foreign nucleic acid sequence. The retrotransposons can act as parasites of retroviruses, retaining certain classical hallmarks, such as long terminal repeats (LTR), retroviral primer binding sites, and the like. However, the naturally occurring retrotransposons usually do not contain functional retroviral structure genes, which would normally be capable of recombining to yield replication competent viruses. Some retrotransposons are examples of so-called "selfish DNA", or genetic information, which encodes nothing except the ability to replicate itself. The retrotransposon may do so by utilizing the occasional presence of a retrovirus or a retrotransposase within the host cell, efficiently packaging itself within the viral particle, which transports it to the new host genome, where it is expressed again as RNA. The information encoded within that RNA is potentially transported with the jumping gene. A retrotransposon can be a DNA transposon or a retrotransposon, including a LTR retrotransposon or a non-LTR retrotransposon.

Non-long terminal repeat (LTR) retrotransposons are a type of mobile genetic elements that are widespread in eukaryotic genomes. They include two classes: the apurinic/apyrimidinic endonuclease (APE)-type and the restriction enzyme-like endonuclease (RLE)-type. The APE class retrotransposons are comprised of two functional domains: an endonuclease/DNA binding domain, and a reverse transcriptase domain. The RLE class are comprised of three functional domains: a DNA binding domain, a reverse transcription domain, and an endonuclease domain. The reverse transcriptase domain of non-LTR retrotransposon functions by binding an RNA sequence template and reverse transcribing it into the host genome's target DNA. The RNA sequence template has a 3' untranslated region which is specifically bound to the transposase, and a variable 5' region generally having Open Reading Frame(s) ("ORF") encoding transposase proteins. The RNA sequence template may also comprise a 5' untranslated region which specifically binds the retrotransposase. In some embodiments, a non-LTR transposons can include a LINE retrotransposon, such as L1, and a SINE retrotransposon, such as an Alu sequence. Other examples include for example, without limitation, R1, R2, R3, R4, and R5 retro-transposons (Moss, W. N. et al., *RNA Biol.* 2011, 8(5), 714-718; and Burke, W. D. et al., *Molecular Biology and Evolution* 2003, 20(8), 1260-1270). The transposon can be autonomous or non-autonomous.

LTR retrotransposons, which include retroviruses, make up a significant fraction of the typical mammalian genome, comprising about 8% of the human genome and 10% of the mouse genome. Lander et al., 2001, *Nature* 409, 860-921; Waterson et al., 2002, *Nature* 420, 520-562. LTR elements include retrotransposons, endogenous retroviruses (ERVs), and repeat elements with HERV origins, such as SINE-R. LTR retrotransposons include two LTR sequences that flank a region encoding two enzymes: integrase and retrotransposase.

ERVs include human endogenous retroviruses (HERVs), the remnants of ancient germ-cell infections. While most HERV proviruses have undergone extensive deletions and mutations, some have retained ORFS coding for functional proteins, including the glycosylated env protein. The env gene confers the potential for LTR elements to spread between cells and individuals. Indeed, all three open reading frames (pol, gag, and env) have been identified in humans, and evidence suggests that ERVs are active in the germline. See, e.g., Wang et al., 2010, *Genome Res.* 20, 19-27. Moreover, a few families, including the HERV-K (HML-2) group, have been shown to form viral particles, and an apparently intact provirus has recently been discovered in a small fraction of the human population. See, e.g., Bannert and Kurth, 2006, Proc. Natl. Acad. USA 101, 14572-14579.

LTR retrotransposons insert into new sites in the genome using the same steps of DNA cleavage and DNA strand-transfer observed in DNA transposons. In contrast to DNA transposons, however, recombination of LTR retrotransposons involves an RNA intermediate. LTR retrotransposons make up about 8% of the human genome. See, e.g., Lander et al., 2001, *Nature* 409, 860-921; Hua-Van et al., 2011, Biol. Dir. 6, 19.

Integration Site

The present disclosure provides non-naturally occurring or engineered systems, methods, and compositions for site-specific genetic engineering via the addition of an integration site into a target genome. The integration site will be discussed in more details below.

As used herein, the term "integration site" refers to the site within the target genome where one or more genes of interest or one or more nucleic acid sequences of interest are inserted. Examples of integration sites include for example, without limitation, a lox71 site (SEQ ID NO: 1), attB sites (SEQ ID NO: 3 and SEQ ID NO: 43), attP sites (SEQ ID NO: 4 and SEQ ID NO: 44), an attL site (SEQ ID NO: 67), an attR site (SEQ ID NO: 68), a Vox site (SEQ ID NO: 69), a FRT site (SEQ ID NO: 70), or a pseudo attP site (SEQ ID NO: 78). The integration site can be inserted into the genome or a fragment thereof of a cell using a nuclease, a gRNA, and/or an integration enzyme. The integration site can be inserted into the genome of a cell using a prime editor such as, without limitation, PE1, PE2, and PE3, wherein the integration site is carried on a pegRNA. The pegRNA can target any site that is known in the art. Examples of cites targeted by the pegRNA include, without limitation, ACTB, SUPT16H, SRRM2, NOLC1, DEPDC4, NES, LMNB1, AAVS1 locus, CC10, CFTR, SERPINA1, ABCA4, and any derivatives thereof. The complementary integration site may be operably linked to a gene of interest or nucleic acid sequence of interest in an exogenous DNA or RNA. In some embodiments, one integration site is added to a target genome. In some embodiments, more than one integration sites are added to a target genome.

To insert multiple genes or nucleic acids of interest, two or more integration sites are added to a desired location. Multiple DNA comprising nucleic acid sequences of interest are flanked orthogonal to the integration sequences, such as, without limitation, attB and attP. An integration site is "orthogonal" when it does not significantly recognize the recognition site or nucleotide sequence of a recombinase. Thus, one attB site of a recombinase can be orthogonal to an attB site of a different recombinase. In addition, one pair of attB and attP sites of a recombinase can be orthogonal to another pair of attB and attP sites recognized by the same recombinase. A pair of recombinases are considered orthogonal to each other, as defined herein, when there is recognition of each other's attB or attP site sequences.

The lack of recognition of integration sites or pairs of sites by the same recombinase or a different recombinase can be less than about 30%. In some embodiments, the lack of recognition of integration sites or pairs of sites by the same recombinase or a different recombinase can be less than about 30%, less than about 28%, less than about 26%, less than about 24%, less than about 22%, less than about 20%, less than about 18%, less than about 16%, less than about 14%, less than about 12%, less than about 10%, less than about 8%, less than about 6%, less than about 4%, less than about 2%, about 1%, or any range that is formed from any two of those values as endpoints. The crosstalk can be less than about 30%. In some embodiments, the crosstalk is less than about 30%, less than about 28%, less than about 26%, less than about 24%, less than about 22%, less than about 20%, less than about 18%, less than about 16%, less than about 14%, less than about 12%, less than about 10%, less than about 8%, less than about 6%, less than about 4%, less than about 2%, less than about 1%, or any range that is formed from any two of those values as endpoints.

In some embodiments, the attB and/or attP site sequences comprise a central dinucleotide sequence. It has been shown that, for example, the central dinucleotide can be changed to GA from GT and that only GA containing attB/attP sites interact and will not cross react with GT containing sequences. In some embodiments, the central dinucleotide is selected from the group consisting of AG, AC, TG, TC, CA, CT, GA, AA, TT, CC, GG, AT, TA, GC, CG and GT.

As used herein, the term "pair of an attB and attP site sequences" and the like refer to attB and attP site sequences that share the same central dinucleotide and can recombine. This means that in the presence of one serine integrase as many as six pairs of these orthogonal att sites can recombine (attPTT will specifically recombine with attBTT, attPTC will specifically recombine with attBTC, and so on).

In some embodiments, the central dinucleotide is nonpalindromic. In some embodiments, the central dinucleotide is palindromic. In some embodiments, a pair of an attB site sequence and an attP site sequence are used in different DNA encoding genes of interest or nucleic acid sequences of interest for inducing directional integration of two or more different nucleic acids.

The Table 3 below shows examples of pairs of attB site sequence and attP site sequence with different central dinucleotide (CD).

TABLE 3

| Pair | attB | attP | CD |
|---|---|---|---|
| 1 | SEQ ID NO: 5 | SEQ ID NO: 6 | TT |
| 2 | SEQ ID NO: 7 | SEQ ID NO: 8 | AA |
| 3 | SEQ ID NO: 9 | SEQ ID NO: 10 | CC |
| 4 | SEQ ID NO: 11 | SEQ ID NO: 12 | GG |
| 5 | SEQ ID NO: 13 | SEQ ID NO: 14 | TG |
| 6 | SEQ ID NO: 15 | SEQ ID NO: 16 | GT |
| 7 | SEQ ID NO: 17 | SEQ ID NO: 18 | CT |
| 8 | SEQ ID NO: 19 | SEQ ID NO: 20 | CA |
| 9 | SEQ ID NO: 21 | SEQ ID NO: 22 | TC |
| 10 | SEQ ID NO: 23 | SEQ ID NO: 24 | GA |
| 11 | SEQ ID NO: 25 | SEQ ID NO: 26 | AG |
| 12 | SEQ ID NO: 27 | SEQ ID NO: 28 | AC |
| 13 | SEQ ID NO: 29 | SEQ ID NO: 30 | AT |
| 14 | SEQ ID NO: 31 | SEQ ID NO: 32 | GC |
| 15 | SEQ ID NO: 33 | SEQ ID NO: 34 | CG |
| 16 | SEQ ID NO: 35 | SEQ ID NO: 36 | TA |

Paste

The present disclosure provides non-naturally occurring or engineered systems, methods, and compositions for site-specific genetic engineering using PASTE. PASTE will be discussed in more details below.

The site-specific genetic engineering disclosed herein is for the insertion of one or more genes of interest or one or more nucleic acid sequences of interest into a genome of a cell. In some embodiments, the gene of interest is a mutated gene implicated in a genetic disease such as, without limitation, a metabolic disease, cystic fibrosis, muscular dystrophy, hemochromatosis, Tay-Sachs, Huntington disease, Congenital Deafness, Sickle cell anemia, Familial hypercholesterolemia, adenosine deaminase (ADA) deficiency, X-linked SCID (X-SCID), and Wiskott-Aldrich syndrome (WAS). In some embodiments, the gene of interest or nucleic acid sequence of interest can be a reporter gene upstream or downstream of a gene for genetic analyses such as, without limitation, for determining the expression of a gene. In some embodiments, the reporter gene is a GFP template (SEQ ID NO: 76) or a *Gaussia* Luciferase (G-Luciferase) template (SEQ ID NO: 77) In some embodiments, the gene of interest or nucleic acid sequence of interest can be used in plant genetics to insert genes to enhance drought tolerance, weather hardiness, and increased yield and herbicide resistance in plants. In some embodiments, the gene of interest or nucleic acid sequence of interest can be used for site-specific insertion of a protein (e.g., a lysosomal enzyme), a blood factor (e.g., Factor I, II, V, VII, X, XI, XII or XIII), a membrane protein, an exon, an intracellular protein (e.g., a cytoplasmic protein, a nuclear protein, an organellar protein such as a mitochondrial protein or lysosomal protein), an extracellular protein, a structural protein, a signaling protein, a regulatory protein, a transport protein, a sensory protein, a motor protein, a defense protein, or a storage protein, an anti-inflammatory signaling molecules into cells for treatment of immune diseases, including but not limited to arthritis, psoriasis, lupus, coeliac disease, glomerulonephritis, hepatitis, and inflammatory bowel disease.

The size of the inserted gene or nucleic acid can vary from about 1 bp to about 50,000 bp. In some embodiments, the size of the inserted gene or nucleic acid can be about 1 bp, 10 bp, 50 bp, 100 bp, 150 bp, 200 bp, 250 bp, 300 bp, 350 bp, 400 bp, 600 bp, 800 bp, 1000 bp, 1200 bp, 1400 bp, 1600 bp, 1800 bp, 2000 bp, 2200 bp, 2400 bp, 2600 bp, 2800 bp, 3000 bp, 3200 bp, 3400 bp, 3600 bp, 3800 bp, 4000 bp, 4200 bp, 4400 bp, 4600 bp, 4800 bp, 5000 bp, 5200 bp, 5400 bp, 5600 bp, 5800 bp, 6000 bp, 6200 bp, 6400 bp, 6600 bp, 6800 bp, 7000 bp, 7200 bp, 7400 bp, 7600 bp, 7800 bp, 8000 bp, 8200 bp, 8400 bp, 8600 bp, 8800 bp, 9000 bp, 9200 bp, 9400 bp, 9600 bp, 9800 bp, 10,000 bp, 10,200 bp, 10,400 bp, 10,600 bp, 10,800 bp, 11,000 bp, 11,200 bp, 11,400 bp, 11,600 bp, 11,800 bp, 12,000 bp, 14,000 bp, 16,000 bp, 18,000 bp, 20,000 bp, 30,000 bp, 40,000 bp, 50,000 bp, or any range that is formed from any two of those values as endpoints.

In some embodiments, the site-specific engineering using the gene of interest or nucleic acid sequence of interest disclosed herein is for the engineering of T cells and NKs for tumor targeting or allogeneic generation. These can involve the use of receptor or CAR for tumor specificity, anti-PD1 antibody, cytokines like IFN-gamma, TNF-alpha, IL-15, IL-12, IL-18, IL-21, and IL-10, and immune escape genes.

In the present disclosure, the site-specific insertion of the gene of interest or nucleic acid of interest is performed through Programmable Addition via Site-Specific Targeting Elements (PASTE). Components for inserting a gene of interest or a nucleic acid of interest using PASTE are for example, without limitation, a nuclease, a gRNA adding the integration site, a DNA or RNA strand comprising the gene or nucleic acid linked to a sequence that is complementary or associated to the integration site, and an integration enzyme. Components for inserting a gene of interest or a nucleic acid of interest using PASTE are for example, without limitation, a prime editor expression, pegRNA adding the integration site, nicking guide RNA, integration enzyme (Cre or serine recombinase), transgene vector comprising the gene of interest or nucleic acid sequence of interest with gene and integration signal. The nuclease and prime editor integrate the integration site into the genome. The integration enzyme integrates the gene of interest into the integration site. In some embodiments, the transgene vector comprising the gene or nucleic acid sequence of interest with gene and integration signal is a DNA minicircle devoid of bacterial DNA sequences. In some embodiments, the transgenic vector is a eukaryotic or prokaryotic vector.

As used herein, the term "vector" or "transgene vector" refers to a recombinant DNA molecule containing a desired coding sequence and appropriate nucleic acid sequences necessary for the expression of the operably linked coding sequence in a host organism. Nucleic acid sequences necessary for expression in prokaryotes usually include for example, without limitation, a promoter, an operator (optional), a ribosome binding site, and/or other sequences. Eukaryotic cells are generally known to utilize promoters (constitutive, inducible or tissue specific), enhancers, and termination and polyadenylation signals, although some elements may be deleted and other elements added without sacrificing the necessary expression. The transgenic vector may encode the PE and the integration enzyme, linked to each other via a linker. The linker can be a cleavable linker. For example, transgenic vector encoding the PE and the integration enzyme, linked to each other via a linker is pCMV PE2 P2A Cre comprises SEQ ID NO: 73. In some embodiments, the linker can be a non-cleavable linker. In some embodiments the nuclease, prime editor, and/or integration enzyme can be encoded in different vectors.

Figure 12:
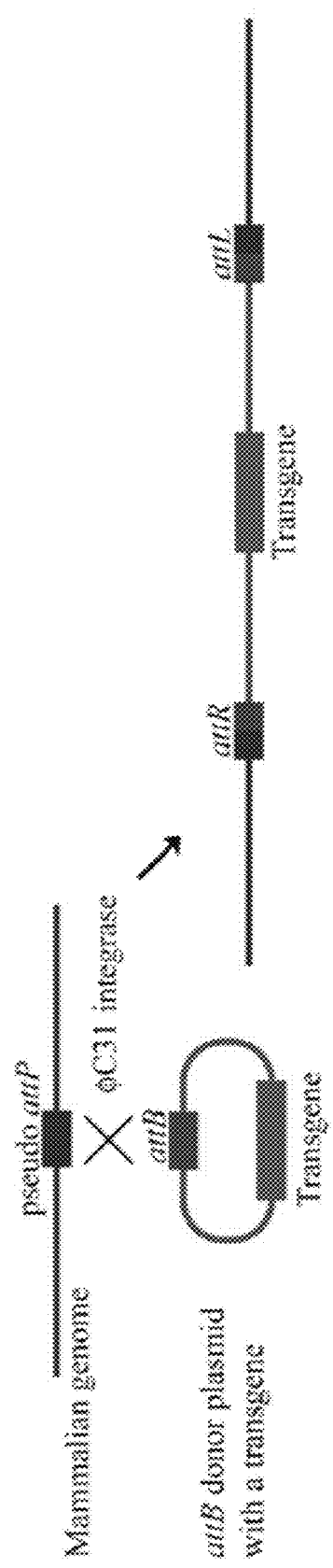
FIG. 12 shows a schematic diagram of the using φC31 as the integration enzyme, according to embodiments of the present teachings.
Figure 13:
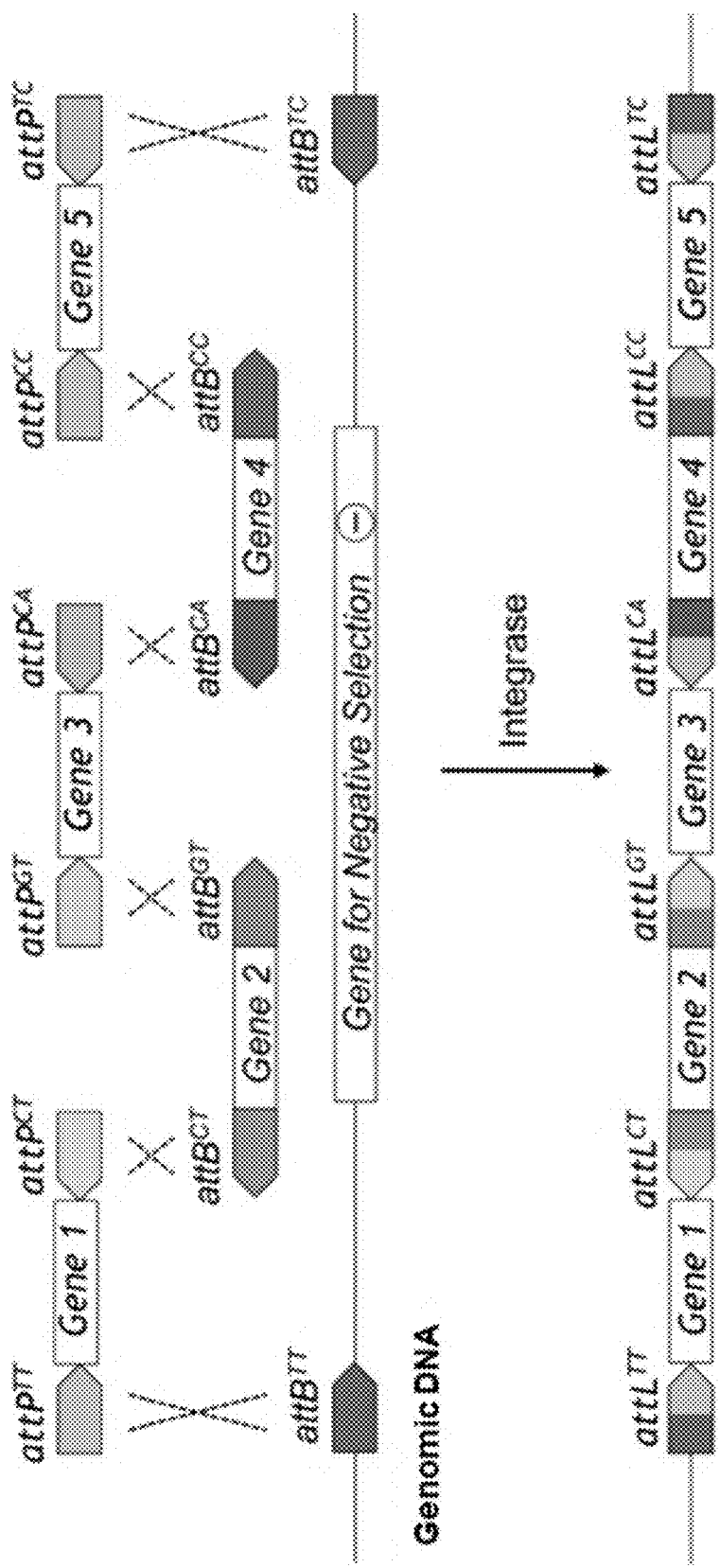
FIG. 13 shows a schematic diagram of multiplexing involving inserting multiple genes of interest in multiple loci using unique guide RNAs that incorporated exterior flanking attB sites according to embodiments of the present teachings.

A method of inserting multiple genes or nucleic acid sequences of interest into a single site according to embodiments of the present disclosure is illustrated in FIG. 12. In some embodiments, multiplexing involves inserting multiple genes of interest in multiple loci using unique pegRNA as illustrated in FIG. 13 (Merrick, C. A. et al., ACS Synth. Biol. 2018, 7, 299-310). The insertion of multiple genes of interest or nucleic acids of interest into a cell genome, referred herein as "multiplexing," is facilitated by incorporation of the complementary 5' integration site to the 5' end of the DNA or RNA comprising the first nucleic acid and 3' integration site to the 3' end of the DNA or RNA comprising the last nucleic acid. In some embodiments, the number of genome of interest or amino acid sequences of interest that are inserted into a cell genome using multiplexing can be about 1, 2, 3, 4, 5, 6, 7, 8, 9 10, 11, 12, 13, 14, 15, 16, 17, 18, 19, 20, 21, 22, 23, 24, 25, or any range that is formed from any two of those values as endpoints.

In some embodiments, multiplexing allows integration of for example, signaling cascade, over-expression of a protein of interest with its cofactor, insertion of multiple genes mutated in a neoplastic condition, or insertion of multiple CARs for treatment of cancer.

In some embodiments, the integration sites may be inserted into the genome using non-prime editing methods such as rAAV mediated nucleic acid integration, TALENS and ZFNs. A number of unique properties make AAV a promising vector for human gene therapy (Muzyczka, CURRENT TOPICS IN MICROBIOLOGY AND IMMUNOLOGY, 158:97-129 (1992)). Unlike other viral vectors, AAVs have not been shown to be associated with any known human disease and are generally not considered pathogenic. Wild type AAV is capable of integrating into host chromosomes in a site-specific manner M. Kotin et al., PROC. NATL. ACAD. SCI, USA, 87:2211-2215 (1990); R. J. Samulski, EMBO 10(12):3941-3950 (1991)). Instead of creating a double-stranded DNA break, AAV stimulates endogenous homologous recombination to achieve the DNA modification. Further, transcription activator-like effector nucleases (TALENs) and Zinc-finger nucleases (ZFNs) for genome editing and introducing targeted DSBs. The specificity of TALENs arises from two polymorphic amino acids, the so-called repeat variable diresidues (RVDs) located at positions 12 and 13 of a repeated unit. TALENS are linked to FokI nucleases, which cleaves the DNA at the desired locations. ZFNs are artificial restriction enzymes for custom site-specific genome editing. Zinc fingers themselves are transcription factors, where each finger recognizes 3-4 bases. By mixing and matching these finger modules, researchers can customize which sequence to target.

As used herein, the terms "administration," "introducing," or "delivery" into a cell, a tissue, or an organ of a plasmid, nucleic acids, or proteins for modification of the host genome refers to the transport for such administration, introduction, or delivery that can occur in vivo, in vitro, or ex vivo. Plasmids, DNA, or RNA for genetic modification can be introduced into cells by transfection, which is typically accomplished by chemical means (e.g., calcium phosphate transfection, polyethyleneimine (PEI) Or lipofection), physical means (electroporation or microinjection), infection (this typically means the introduction of an infectious agent such as a virus (e.g., a baculovirus expressing the AAV Rep gene)), transduction (in microbiology, this refers to the stable infection of cells by viruses, or the transfer of genetic material from one microorganism to another by viral factors (e.g., bacteriophages)). Vectors for the expression of a recombinant polypeptide, protein or oligonucleotide may be obtained by physical means (e.g., calcium phosphate transfection, electroporation, microinjection, or lipofection) in a cell, a tissue, an organ or a subject. The vector can be delivered by preparing the vector in a pharmaceutically acceptable carrier for the in vitro, ex vivo, or in vivo delivery to the carrier.

As used herein, the term "transfection" refers to the uptake of an exogenous nucleic acid molecule by a cell. A cell is "transfected" when an exogenous nucleic acid has been introduced into the cell membrane. The transfection can be a single transfection, co-transfection, or multiple transfection. Numerous transfection techniques are generally known in the art. See, for example, Graham et al. (1973) Virology, 52: 456. Such techniques can be used to introduce one or more exogenous nucleic acid molecules into a suitable host cell.

In some embodiments, the exogenous nucleic acid molecule and/or other components for gene editing are combined and delivered in a single transfection. In other embodiments, the exogenous nucleic acid molecule and/or other components for gene editing are not combined and delivered in a single transfection. In some embodiments, exogenous nucleic acid molecule and/or other components for gene editing are combined and delivered in a single transfection to comprise for example, without limitation, a prime editing vector, a landing site such as a landing site containing pegRNA, a nicking guide such as a nicking guide for stimulating prime editing, an expression vector such as an expression vector for a corresponding integrase or recombinase, a minicircle DNA cargo such as a minicircle DNA cargo encoding for green fluorescent protein (GFP), any derivatives thereof, and any combinations thereof. In some embodiments, the gene of interest or amino acid sequence of interest can be introduced using liposomes. In some embodiments, the gene of interest or amino acid sequence of interest can be delivered using suitable vectors for instance, without limitation, plasmids and viral vectors. Examples of viral vectors include, without limitation, adeno-associated viruses (AAV), lentiviruses, adenoviruses, other viral vectors, derivatives thereof, or combinations thereof. The proteins and one or more guide RNAs can be packaged into one or more vectors, e.g., plasmids or viral vectors. In some embodiments, the delivery is via nanoparticles or exosomes. For example, exosomes can be particularly useful in delivery RNA.

In some embodiments, the prime editing inserts the landing site with efficiencies of at least about 1%, at least about 5%, at least about 10%, at least about 15%, at least about, at least about 20%, at least about 25%, at least about 30%, at least about 35%, at least about 40%, at least about 45%, or at least about 50%. In some embodiments, the prime editing inserts the landing site(s) with efficiencies of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, or any range that is formed from any two of those values as endpoints.

Sequences

Sequences of enzymes, guides, integration sites, and plasmids can be found in Table 4 below.

TABLE 4

| SEQ ID NO/ DESCRIPTION/ SOURCE | SEQUENCE |
|---|---|
| SEQ ID NO: 1<br>Lox71<br>(Artificial sequence) | ATAACTTCGTATAATGTATGCTATACGAACGGTA |
| SEQ ID NO: 2<br>Lox66<br>(Artificial sequence) | TACCGTTCGTATAATGTATGCTATACGAAGTTAT |
| SEQ ID NO: 3<br>attB<br>(Artificial sequence) | GGCCGGCTTGTCGACGACGGCGGTCTCCGTCGTCAGGATCATCCGG |
| SEQ ID NO: 4<br>attP<br>(Artificial Sequence) | CCGGATGATCCTGACGACGGAGACCGCCGTCGTCGACAAGCCGGCC |
| SEQ ID NO: 5<br>attB-TT<br>(Artificial Sequence) | GGCTTGTCGACGACGGCGTTCTCCGTCGTCAGGATCAT |
| SEQ ID NO: 6<br>attP-TT<br>(Artificial Sequence) | GTGGTTTGTCTGGTCAACCACCGCGTTCTCAGTGGTGTACGGTACAAACCCA |
| SEQ ID NO: 7<br>attB-AA<br>(Artificial Sequence) | GGCTTGTCGACGACGGCGAACTCCGTCGTCAGGATCAT |
| SEQ ID NO: 8<br>attP-AA<br>(Artificial Sequence) | GTGGTTTGTCTGGTCAACCACCGCGAACTCAGTGGTGTACGGTACAAACCCA |
| SEQ ID NO: 9<br>attB-CC<br>(Artificial Sequence) | GGCTTGTCGACGACGGCGCCCTCCGTCGTCAGGATCAT |
| SEQ ID NO: 10<br>attP-CC<br>(Artificial Sequence) | GTGGTTTGTCTGGTCAACCACCGCGCCCTCAGTGGTGTACGGTACAAACCCA |
| SEQ ID NO: 11<br>attB-GG<br>(Artificial Sequence) | GGCTTGTCGACGACGGCGGGCTCCGTCGTCAGGATCAT |
| SEQ ID NO: 12<br>attP-GG<br>(Artificial Sequence) | GTGGTTTGTCTGGTCAACCACCGCGGGCTCAGTGGTGTACGGTACAAACCCA |
| SEQ ID NO: 13<br>attB-TG<br>(Artificial Sequence) | GGCTTGTCGACGACGGCGTGCTCCGTCGTCAGGATCAT |
| SEQ ID NO: 14<br>attP-TG<br>(Artificial Sequence) | GTGGTTTGTCTGGTCAACCACCGCGTGCTCAGTGGTGTACGGTACAAACCCA |
| SEQ ID NO: 15<br>attB-GT<br>(Artificial Sequence) | GGCTTGTCGACGACGGCGGTCTCCGTCGTCAGGATCAT |
| SEQ ID NO: 16<br>attP-GT<br>(Artificial Sequence) | GTGGTTTGTCTGGTCAACCACCGCGGTCTCAGTGGTGTACGGTACAAACCCA |
| SEQ ID NO: 17<br>attB-CT<br>(Artificial Sequence) | GGCTTGTCGACGACGGCGCTCTCCGTCGTCAGGATCAT |
| SEQ ID NO: 18<br>attP-CT<br>(Artificial Sequence) | GTGGTTTGTCTGGTCAACCACCGCGCTCTCAGTGGTGTACGGTACAAACCCA |

TABLE 4-continued

| SEQ ID NO/<br>DESCRIPTION/<br>SOURCE | SEQUENCE |
| --- | --- |
| SEQ ID NO: 19<br>attB-CA<br>(Artificial Sequence) | GGCTTGTCGACGACGGCGCACTCCGTCGTCAGGATCAT |
| SEQ ID NO: 20<br>attP-CA<br>(Artificial Sequence) | GTGGTTTGTCTGGTCAACCACCGCGCACTCAGTGGTGTACGGTACA<br>AACCCA |
| SEQ ID NO: 21<br>attB-TC<br>(Artificial Sequence) | GGCTTGTCGACGACGGCGTCCTCCGTCGTCAGGATCAT |
| SEQ ID NO: 22<br>attP-TC<br>(Artificial Sequence) | GTGGTTTGTCTGGTCAACCACCGCGTCCTCAGTGGTGTACGGTACA<br>AACCCA |
| SEQ ID NO: 23<br>attB-GA<br>(Artificial Sequence) | GGCTTGTCGACGACGGCGGACTCCGTCGTCAGGATCAT |
| SEQ ID NO: 24<br>attP-GA<br>(Artificial Sequence) | GTGGTTTGTCTGGTCAACCACCGCGGACTCAGTGGTGTACGGTAC<br>AAACCCA |
| SEQ ID NO: 25<br>attB-AG<br>(Artificial Sequence) | GGCTTGTCGACGACGGCGAGCTCCGTCGTCAGGATCAT |
| SEQ ID NO: 26<br>attP-AG<br>(Artificial Sequence) | GTGGTTTGTCTGGTCAACCACCGCGAGCTCAGTGGTGTACGGTAC<br>AAACCCA |
| SEQ ID NO: 27<br>attB-AC<br>(Artificial Sequence) | GGCTTGTCGACGACGGCGACCTCCGTCGTCAGGATCAT |
| SEQ ID NO: 28<br>attP-AC<br>(Artificial Sequence) | GTGGTTTGTCTGGTCAACCACCGCGACCTCAGTGGTGTACGGTACA<br>AACCCA |
| SEQ ID NO: 29<br>attB-AT<br>(Artificial Sequence) | GGCTTGTCGACGACGGCGATCTCCGTCGTCAGGATCAT |
| SEQ ID NO: 30<br>attP-AT<br>(Artificial Sequence) | GTGGTTTGTCTGGTCAACCACCGCGATCTCAGTGGTGTACGGTACA<br>AACCCA |
| SEQ ID NO: 31<br>attB-GC<br>(Artificial Sequence | GGCTTGTCGACGACGGCGGCCTCCGTCGTCAGGATCAT |
| SEQ ID NO: 32<br>attP-GC<br>(Artificial Sequence) | GTGGTTTGTCTGGTCAACCACCGCGGCCTCAGTGGTGTACGGTACA<br>AACCCA |
| SEQ ID NO: 33<br>attB-CG<br>(Artificial Sequence) | GGCTTGTCGACGACGGCGCGCTCCGTCGTCAGGATCAT |
| SEQ ID NO: 34<br>attP-CG<br>(Artificial Sequence) | GTGGTTTGTCTGGTCAACCACCGCGCGCTCAGTGGTGTACGGTACA<br>AACCCA |
| SEQ ID NO: 35<br>attB-TA<br>(Artificial Sequence) | GGCTTGTCGACGACGGCGTACTCCGTCGTCAGGATCAT |
| SEQ ID NO: 36<br>attP-TA<br>(Artificial Sequence) | GTGGTTTGTCTGGTCAACCACCGCGTACTCAGTGGTGTACGGTACA<br>AACCCA |
| SEQ ID NO: 37<br>C31-attB<br>(Artificial Sequence) | TGCGGGTGCCAGGGCGTGCCCTTGGGCTCCCCGGGCGCGTACTCC |

TABLE 4-continued

| SEQ ID NO/<br>DESCRIPTION/<br>SOURCE | SEQUENCE |
|---|---|
| SEQ ID NO: 38<br>C31-attP<br>(Artificial Sequence) | GTGCCCCAACTGGGGTAACCTTTGAGTTCTCTCAGTTGGGGG |
| SEQ ID NO: 39<br>R4-attB<br>(Artificial Sequence) | GCGCCCAAGTTGCCCATGACCATGCCGAAGCAGTGGTAGAAGGGC<br>ACCGGCAGACAC |
| SEQ ID NO: 40<br>R4-attP<br>(Artificial Sequence) | AGGCATGTTCCCCAAAGCGATACCACTTGAAGCAGTGGTACTGCT<br>TGTGGGTACACTCTGCGGGTGATGA |
| SEQ ID NO: 41<br>BT1-attB<br>(Artificial Sequence) | GTCCTTGACCAGGTTTTTGACGAAAGTGATCCAGATGATCCAGCTC<br>CACACCCCGAACGC |
| SEQ ID NO: 42<br>BT1-attP<br>(Artificial Sequence) | GGTGCTGGGTTGTTGTCTCTGGACAGTGATCCATGGGAAACTACTC<br>AGCACCACCAATGTTCC |
| SEQ ID NO: 43<br>Bxb-attB<br>(Artificial Sequence) | TCGGCCGGCTTGTCGACGACGGCGGTCTCCGTCGTCAGGATCATCC<br>GGGC |
| SEQ ID NO: 44<br>Bxb-attP<br>(Artificial Sequence) | GTCGTGGTTTGTCTGGTCAACCACCGCGGTCTCAGTGGTGTACGGT<br>ACAAACCCCGAC |
| SEQ ID NO: 45<br>TG1-attB<br>(Artificial Sequence) | GATCAGCTCCGCGGGCAAGACCTTCTCCTTCACGGGGTGGAAGGT<br>C |
| SEQ ID NO: 46<br>TG1-attP<br>(Artificial Sequence) | TCAACCCCGTTCCAGCCCAACAGTGTTAGTCTTTGCTCTTACCCAG<br>TTGGGCGGGATAGCCTGCCCG |
| SEQ ID NO: 47<br>C1-attB<br>(Artificial Sequence) | AACGATTTTCAAAGGATCACTGAATCAAAAGTATTGCTCATCCAC<br>GCGAAATTTTTC |
| SEQ ID NO: 48<br>C1-attP<br>(Artificial Sequence) | AATATTTTAGGTATATGATTTTGTTTATTAGTGTAAATAACACTAT<br>GTACCTAAAAT |
| SEQ ID NO: 49<br>C370-attB<br>(Artificial Sequence) | TGTAAAGGAGACTGATAATGGCATGTACAACTATACTCGTCGGTA<br>AAAAGGCA |
| SEQ ID NO: 50<br>C370-attP<br>(Artificial Sequence) | TAAAAAAATACAGCGTTTTTCATGTACAACTATACTAGTTGTAGTG<br>CCTAAA |
| SEQ ID NO: 51<br>K38-attB<br>(Artificial Sequence) | GAGCGCCGGATCAGGGAGTGGACGGCCTGGGAGCGCTACACGCT<br>GTGGCTGCGGTC |
| SEQ ID NO: 52<br>K38-attP<br>(Artificial Sequence) | CCCTAATACGCAAGTCGATAACTCTCCTGGGAGCGTTGACAACTT<br>GCGCACCCTGA |
| SEQ ID NO: 53<br>RB-attB<br>(Artificial Sequence) | TCTCGTGGTGGTGGAAGGTGTTGGTGCGGGGTTGGCCGTGGTCGA<br>GGTGGGGTGGTGGTAGCCATTCG |
| SEQ ID NO: 54<br>RV-attP<br>(Artificial Sequence) | GCACAGGTGTAGTGTATCTCACAGGTCCACGGTTGGCCGTGGACT<br>GCTGAAGAACATTCCACGCCAGGA |
| SEQ ID NO: 55<br>SPBC-attB<br>(Artificial Sequence) | AGTGCAGCATGTCATTAATATCAGTACAGATAAAGCTGTATCTCCT<br>GTGAACACAATGGGTGCCA |
| SEQ ID NO: 56<br>SPBC-attP<br>(Artificial Sequence) | AAAGTAGTAAGTATCTTAAAAAACAGATAAAGCTGTATATTAAGA<br>TACTTACTAC |

TABLE 4-continued

| SEQ ID NO/<br>DESCRIPTION/<br>SOURCE | SEQUENCE |
|---|---|
| SEQ ID NO: 57<br>TP901-attB<br>(Artificial Sequence) | TGATAATTGCCAACACAATTAACATCTCAATCAAGGTAAATGCTTT<br>TTCGTTTT |
| SEQ ID NO: 58<br>TP901-attP<br>(Artificial Sequence) | AATTGCGAGTTTTTATTTCGTTTATTTCAATTAAGGTAACTAAAAA<br>ACTCCTTT |
| SEQ ID NO: 59<br>Wβ-attB<br>(Artificial Sequence) | AAGGTAGCGTCAACGATAGGTGTAACTGTCGTGTTTGTAACGGTA<br>CTTCCAACAGCTGGCGTTTCAGT |
| SEQ ID NO: 60<br>Wβ-attP<br>(Artificial Sequence) | TAGTTTTAAAGTTGGTTATTAGTTACTGTGATATTTATCACGGTAC<br>CCAATAACCAATGAATATTTGA |
| SEQ ID NO: 61<br>A118-attB<br>(Artificial Sequence) | TGTAACTTTTTCGGATCAAGCTATGAAGGACGCAAAGAGGGAACT<br>AAACACTTAATT |
| SEQ ID NO: 62<br>A118-attP<br>(Artificial Sequence) | TTGTTTAGTTCCTCGTTTTCTCTCGTTGGAAGAAGAAGAAACGAGA<br>AACTAAAATTA |
| SEQ ID NO: 63<br>BL3-attB<br>(Artificial Sequence) | CAACCTGTTGACATGTTTCCACAGACAACTCACGTGGAGGTAGTC<br>ACGGCTTTTACGTTAGTT |
| SEQ ID NO: 64<br>BL3-attP<br>(Artificial Sequence) | GAGAATACTGTTGAACAATGAAAAACTAGGCATGTAGAAGTTGTT<br>TGTGCACTAACTTTAA |
| SEQ ID NO: 65<br>MR11-attB<br>(Artificial Sequence) | ACAGGTCAACACATCGCAGTTATCGAACAATCTTCGAAAATGTAT<br>GGAGGCACTTGTATCAATATAGGATGTATACCTTCGAAGACACTT<br>GTACATGATGGATTAGAAGGCAAATCCTTT |
| SEQ ID NO: 66<br>MR11-attP<br>(Artificial Sequence) | CAAAATAAAAAACATTGATTTTTATTAACTTCTTTTGTGCGGAACT<br>ACGAACAGTTCATTAATACGAAGTGTACAAACTTCCATACAAAAA<br>TAACCACGACAATTAAGACGTGGTTTCTA |
| SEQ ID NO: 67<br>attL<br>(Artificial Sequence) | ATTATTTCTCACCCTGA |
| SEQ ID NO: 68<br>attR<br>(Artificial Sequence) | ATCATCTCCCACCCGGA |
| SEQ ID NO: 69<br>Vox<br>(Artificial Sequence) | AATAGGTCTG AGAACGCCCA TTCTCAGACG TATT |
| SEQ ID NO: 70<br>FRT<br>(Artificial Sequence) | GAAGTTCCTATAC TTTCTAGA GAATAGGAACTTC |
| SEQ ID NO: 71<br>Cre recombinase<br>expression plasmid<br>(Artificial Sequence) | GGTCGACATTGATTATTGACTAGTTATTAATAGTAATCAATTACGG<br>GGTCATTAGTTCATAGCCCATATATGGAGTTCCGCGTTACATAACT<br>TACGGTAAATGGCCCGCCTGGCTGACCGCCCAACGACCCCCGCCC<br>ATTGACGTCAATAATGACGTATGTTCCCATAGTAACGCCAATAGG<br>GACTTTCCATTGACGTCAATGGGTGGAGTATTTACGGTAAACTGCC<br>CACTTGGCAGTACATCAAGTGTATCATATGCCAAGTACGCCCCCTA<br>TTGACGTCAATGACGGTAAATGGCCCGCCTGGCATTATGCCCAGT<br>ACATGACCTTATGGGACTTTCCTACTTGGCAGTACATCTACGTATT<br>AGTCATCGCTATTACCATGGTCGAGGTGAGCCCCACGTTCTGCTTC<br>ACTCTCCCCATCTCCCCCCCCTCCCCACCCCCAATTTTGTATTTATT<br>TATTTTTTAATTATTTTGTGCAGCGATGGGGGCGGGGGGGGGGG<br>GGCGCGCGCCAGGCGGGGGGGGGGGGGGGGGGGGGGGGGG<br>GGGGGGGCGGGGGGGGCGGCGGCAGCCAATCAGAGCGGCGCGC<br>TCCGAAAGTTTCCTTTTATGGCGAGGCGGCGGCGGCGGCGGCCCT<br>ATAAAAAGCGAAGCGCGCGGCGGGCGGGAGTCGCTGCGCGCTGC<br>CTTCGCCCCGTGCCCCGCTCCGCCGCCGCCTCGCGCCGCCCGCCCC<br>GGCTCTGACTGACCGCGTTACTCCCACAGGTGAGCGGGCGGGACG<br>GCCCTTCCTCCGGGCTGTAATTAGCGCTTGGTTTAATGACGGCT<br>TGTTTCTTTTCTGTGGCTGCGTGAAAGCCTTGAGGGGCTCCGGGAG |

TABLE 4-continued

| SEQ ID NO/ DESCRIPTION/ SOURCE | SEQUENCE |
| --- | --- |
| | GGCCCTTTGTGCGGGGGAGCGGCTCGGGGGGTGCGTGCGTGTGT |
| | GTGTGCGTGGGGAGCGCCGCGTGCGGCTCCGCGCTGCCCGGCGGC |
| | TGTGAGCGCTGCGGGCGCGGCGCGGGGCTTTGTGCGCTCCGCAGT |
| | GTGCGCGAGGGGAGCGCGGCCGGGGGCGGTGCCCCGCGGTGCGG |
| | GGGGGGCTGCGAGGGGAACAAAGGCTGCGTGCGGGGTGTGTGCG |
| | TGGGGGGGTGAGCAGGGGGTGTGGGCGCGTCGGTCGGGCTGCAA |
| | CCCCCCCTGCACCCCCCTCCCCGAGTTGCTGAGCACGGCCCGGCTT |
| | CGGGTGCGGGGCTCCGTACGGGGCGTGGCGCGGGGCTCGCCGTGC |
| | CGGGCGGGGGTGGCGGCAGGTGGGGGTGCCGGGCGGGGCGGGG |
| | CCGCCTCGGGCCGGGGAGGGCTCGGGGGAGGGGCGCGGCGGCCC |
| | CCGGAGCGCCGGCGGCTGTCGAGGCGCGGCGAGCCGCAGCCATTG |
| | CCTTTTATGGTAATCGTGCGAGAGGGCGCAGGGACTTCCTTTGTCC |
| | CAAATCTGTGCGGAGCCGAAATCTGGGAGGCGCCGCCGCACCCCC |
| | TCTAGCGGGCGCGGGGCGAAGCGGTGCGGCGCCGGCAGGAAGGA |
| | AATGGGCGGGGAGGGCCTTCGTGCGTCGCCGCGCCGCCGTCCCCT |
| | TCTCCCTCTCCAGCCTCGGGGCTGTCCGCGGGGGGACGGCTGCCTT |
| | CGGGGGGGACGGGGCAGGGCGGGGTTCGGCTTCTGGCGTGTGACC |
| | GGCGGCTCTAGAGCCTCTGCTAACCATGTTCATGCCTTCTTCTTTTT |
| | CCTACAGCTCCTGGGCAACGTGCTGGTTATTGTGCTGTCTCATCAT |
| | TTTGGCAAAGAATTCTGAGCCGCCACCATGGCCAATTTACTGACC |
| | GTACACCAAAATTTGCCTGCATTACCGGTCGATGCAACGAGTGAT |
| | GAGGTTCGCAAGAACCTGATGGACATGTTCAGGGATCGCCAGGCG |
| | TTTTCTGAGCATACCTGGAAAATGCTTCTGTCCGTTTGCCGGTCGT |
| | GGGCGGCATGGTGCAAGTTGAATAACCGGAAATGGTTTCCCGCAG |
| | AACCTGAAGATGTTCGCGATTATCTTCTATATCTTCAGGCGCGCGG |
| | TCTGGCAGTAAAAACTATCCAGCAACATTTGGGCCAGCTAAACAT |
| | GCTTCATCGTCGGTCCGGGCTGCCACGACCAAGTGACAGCAATGC |
| | TGTTTCACTGGTTATGCGGCGGATCCGAAAAGAAAACGTTGATGC |
| | CGGTGAACGTGCAAAACAGGCTCTAGCGTTCGAACGCACTGATTT |
| | CGACCAGGTTCGTTCACTCATGGAAAATAGCGATCGCTGCCAGGA |
| | TATACGTAATCTGGCATTTCTGGGGATTGCTTATAACACCCTGTTA |
| | CGTATAGCCGAAATTGCCAGGATCAGGGTTAAAGATATCTCACGT |
| | ACTGACGGTGGGAGAATGTTAATCCATATTGGCAGAACGAAAACG |
| | CTGGTTAGCACCGCAGGTGTAGAGAAGGCACTTAGCCTGGGGGTA |
| | ACTAAACTGGTCGAGCGATGGATTTCCGTCTCTGGTGTAGCTGATG |
| | ATCCGAATAACTACCTGTTTTGCCGGGTCAGAAAAAATGGTGTTG |
| | CCGCGCCATCTGCCACCAGCCAGCTATCAACTCGCGCCCTGGAAG |
| | GGATTTTTGAAGCAACTCATCGATTGATTTACGGCGCTAAGGATG |
| | ACTCTGGTCAGAGATACCTGGCCTGGTCTGGACACAGTGCCCGTG |
| | TCGGAGCCGCGCGAGATATGGCCCGCGCTGGAGTTTCAATACCGG |
| | AGATCATGCAAGCTGGTGGCTGGACCAATGTAAATATTGTCATGA |
| | ACTATATCCGTAACCTGGATAGTGAAACAGGGGCAATGGTGCGCC |
| | TGCTGGAAGATGGCGATGGACCGGTGGAACAAAAACTTATTTCTG |
| | AAGAAGATCTGTGATAGCGGCCGCACTCCTCAGGTGCAGGCTGCC |
| | TATCAGAAGGTGGTGGCTGGTGTGGCCAATGCCCTGGCTCACAAA |
| | TACCACTGAGATCTTTTTCCCTCTGCCAAAAATTATGGGGACATCA |
| | TGAAGCCCCTTGAGCATCTGACTTCTGGCTAATAAAGGAAATTTAT |
| | TTTCATTGCAATAGTGTGTTGGAATTTTTTGTGTCTCTCACTCGGAA |
| | GGACATATGGGAGGGCAAATCATTTAAAACATCAGAATGAGTATT |
| | TGGTTTAGAGTTTGGCAACATATGCCCATATGCTGGCTGCCATGAA |
| | CAAAGGTTGGCTATAAAGAGGTCATCAGTATATGAAACAGCCCCC |
| | TGCTGTCCATTCCTTATTCCATAGAAAAGCCTTGACTTGAGGTTAG |
| | ATTTTTTTTATATTTTGTTTTGTGTTATTTTTTTCTTTAACATCCCTA |
| | AAATTTTCCTTACATGTTTTACTAGCCAGATTTTTCCTCCTCCTG |
| | ACTACTCCCAGTCATAGCTGTCCCTCTTCTCTTATGGAGATCCCTC |
| | GACCTGCAGCCCAAGCTTGGCGTAATCATGGTCATAGCTGTTTCCT |
| | GTGTGAAATTGTTATCCGCTCACAATTCCACACAACATACGAGCC |
| | GGAAGCATAAAGTGTAAAGCCTGGGGTGCCTAATGAGTGAGCTAA |
| | CTCACATTAATTGCGTTGCGCTCACTGCCCGCTTTCCAGTCGGGAA |
| | ACCTGTCGTGCCAGCGGATCCGCATCTCAATTAGTCAGCAACCAT |
| | AGTCCCGCCCCTAACTCCGCCCATCCCGCCCCTAACTCCGCCCAGT |
| | TCCGCCCATTCTCCGCCCCATGGCTGACTAATTTTTTTTATTTATGC |
| | AGAGGCCGAGGCCGCCTCGGCCTCTGAGCTATTCCAGAAGTAGTG |
| | AGGAGGCTTTTTTGGAGGCCTAGGCTTTTGCAAAAAGCTAACTTGT |
| | TTATTGCAGCTTATAATGGTTACAAATAAAGCAATAGCATCACAA |
| | ATTTCACAAATAAAGCATTTTTTTCACTGCATTCTAGTTGTGGTTTG |
| | TCCAAACTCATCAATGTATCTTATCATGTCTGGATCCGCTGCATTA |
| | ATGAATCGGCCAACGCGCGGGGAGAGGCGGTTTGCGTATTGGGCG |
| | CTCTTCCGCTTCCTCGCTCACTGACTCGCTGCGCTCGGTCGTTCGG |
| | CTGCGGCGAGCGGTATCAGCTCACTCAAAGGCGGTAATACGGTTA |
| | TCCACAGAATCAGGGGATAACGCAGGAAAGAACATGTGAGCAAA |
| | AGGCCAGCAAAAGGCCAGGAACCGTAAAAAGGCCGCGTTGCTGG |
| | CGTTTTTCCATAGGCTCCGCCCCCCTGACGAGCATCACAAAAATCG |
| | ACGCTCAAGTCAGAGGTGGCGAAACCCGACAGGACTATAAAGAT |
| | ACCAGGCGTTTCCCCCTGGAAGCTCCCTCGTGCGCTCTCCTGTTCC |
| | GACCCTGCCGCTTACCGGATACCTGTCCGCCTTTCTCCCTTCGGGA |

TABLE 4-continued

| SEQ ID NO/<br>DESCRIPTION/<br>SOURCE | SEQUENCE |
|---|---|
| | AGCGTGGCGCTTTCTCATAGCTCACGCTGTAGGTATCTCAGTTCGG<br>TGTAGGTCGTTCGCTCCAAGCTGGGCTGTGTGCACGAACCCCCCGT<br>TCAGCCCGACCGCTGCGCCTTATCCGGTAACTATCGTCTTGAGTCC<br>AACCCGGTAAGACACGACTTATCGCCACTGGCAGCAGCCACTGGT<br>AACAGGATTAGCAGAGCGAGGTATGTAGGCGGTGCTACAGAGTTC<br>TTGAAGTGGTGGCCTAACTACGGCTACACTAGAAGAACAGTATTT<br>GGTATCTGCGCTCTGCTGAAGCCAGTTACCTTCGGAAAAAGAGTT<br>GGTAGCTCTTGATCCGGCAAACAAACCACCGCTGGTAGCGGTGGT<br>TTTTTTGTTTGCAAGCAGCAGATTACGCGCAGAAAAAAAGGATCT<br>CAAGAAGATCCTTTGATCTTTTCTACGGGGTCTGACGCTCAGTGGA<br>ACGAAAACTCACGTTAAGGGATTTTGGTCATGAGATTATCAAAAA<br>GGATCTTCACCTAGATCCTTTTAAATTAAAAATGAAGTTTTAAATC<br>AATCTAAAGTATATATGAGTAAACTTGGTCTGACAGTTACCAATG<br>CTTAATCAGTGAGGCACCTATCTCAGCGATCTGTCTATTTCGTTCA<br>TCCATAGTTGCCTGACTCCCCGTCGTGTAGATAACTACGATACGGG<br>AGGGCTTACCATCTGGCCCCAGTGCTGCAATGATACCGCGAGACC<br>CACGCTCACCGGCTCCAGATTTATCAGCAATAAACCAGCCAGCCG<br>GAAGGGCCGAGCGCAGAAGTGGTCCTGCAACTTTATCCGCCTCCA<br>TCCAGTCTATTAATTGTTGCCGGGAAGCTAGAGTAAGTAGTTCGCC<br>AGTTAATAGTTTGCGCAACGTTGTTGCCATTGCTACAGGCATCGTG<br>GTGTCACGCTCGTCGTTTGGTATGGCTTCATTCAGCTCCGGTTCCC<br>AACGATCAAGGCGAGTTACATGATCCCCCATGTTGTGCAAAAAAG<br>CGGTTAGCTCCTTCGGTCCTCCGATCGTTGTCAGAAGTAAGTTGGC<br>CGCAGTGTTATCACTCATGGTTATGGCAGCACTGCATAATTCTCTT<br>ACTGTCATGCCATCCGTAAGATGCTTTTCTGTGACTGGTGAGTACT<br>CAACCAAGTCATTCTGAGAATAGTGTATGCGGCGACCGAGTTGCT<br>CTTGCCCGGCGTCAATACGGGATAATACCGCGCCACATAGCAGAA<br>CTTTAAAAGTGCTCATCATTGGAAAACGTTCTTCGGGGCGAAAAC<br>TCTCAAGGATCTTACCGCTGTTGAGATCCAGTTCGATGTAACCCAC<br>TCGTGCACCCAACTGATCTTCAGCATCTTTTACTTTCACCAGCGTTT<br>CTGGGTGAGCAAAAACAGGAAGGCAAAATGCCGCAAAAAAGGGA<br>ATAAGGGCGACACGGAAATGTTGAATACTCATACTCTTCCTTTTTC<br>AATATTATTGAAGCATTTATCAGGGTTATTGTCTCATGAGCGGATA<br>CATATTTGAATGTATTTAGAAAAATAAACAAATAGGGGTTCCGCG<br>CACATTTCCCCGAAAAGTGCCACCTG |
| SEQ ID NO: 72<br>GFP-Lox66 Cre<br>expression plasmid<br>(Artificial Sequence) | AGCTCTGATCAAGAGACAGGATGAGGATCGTTTCGCATGATTGAA<br>CAAGATGGATTGCACGCAGGTTCTCCGGCCGCTTGGGTGGAGAGG<br>CTATTCGGCTATGACTGGGCACAACAGACAATCGGCTGCTCTGAT<br>GCCGCCGTGTTCCGGCTGTCAGCGCAGGGGCGCCCGGTTCTTTTTG<br>TCAAGACCGACCTGTCCGGTGCCCTGAATGAACTGCAAGACGAGG<br>CAGCGCGGCTATCGTGGCTGGCCACGACGGGCGTTCCTTGCGCAG<br>CTGTGCTCGACGTTGTCACTGAAGCGGGAAGGGACTGGCTGCTAT<br>TGGGCGAAGTGCCGGGGCAGGATCTCCATGTCATCTACACCTTGC<br>TCCTGCCGAGAAAGTATCCATCATGGCTGATGCAATGCGGCGGCT<br>GCATACGCTTGATCCGGCTACCTGCCCATTCGACCACCAAGCGAA<br>ACATCGCATCGAGCGAGCACGTACTCGGATGGAAGCCGGTCTTGT<br>CGATCAGGATGATCTGGACGAAGAGCATCAGGGGCTCGCGCCAGC<br>CGAACTGTTCGCCAGGCTCAAGGCGAGCATGCCCGACGGCGAGGA<br>TCTCGTCGTGACCCATGGCGATGCCTGCTTGCCGAATATCATGGTG<br>GAAAATGGCCGCTTTTCTGGATTCATCGACTGTGGCCGGCTGGGTG<br>TGGCGGACCGCTATCAGGACATAGCGTTGGCTACCCGTGATATTG<br>CTGAAGAGCTTGGCGGCGAATGGGCTGACCGCTTCCTCGTGCTTTA<br>CGGTATCGCCGCTCCCGATTCGCAGCGCATCGCCTTCTATCGCCTT<br>CTTGACGAGTTCTTCTGAATTATTAACTCGAGATCCACTAGAGTGT<br>GGCGGCCGCATTCTTATAATCAGCATCATGATGTGGTACCACATCA<br>TGATGCTGATTACCCCCAACTGAGAGAACTCAAAGGTTACCCCAG<br>TTGGGGCGGGCCCACAAATAAAGCAATAGCATCACAAATTTCACA<br>AATAAAGCATTTTTTTCACTGCATTCTAGTTGTGGTTTGTCCAAAC<br>TCATCGAGCTCGAGATCTGGCGAAGGCGATGGGGGTCTTGAAGGC<br>GTGCTGGTACTCCACGATGCCCAGCTCGGTGTTGCTGTGCAGCTCC<br>TCCACGCGGCGGAAGGCGAACATGGGGCCCCCGTTCTGCAGGATG<br>CTGGGGTGGATGCGCTCTTGAAGTGCATGTGGCTGTCCACCACG<br>AAGCTGTAGTAGCCGCCGTCGCGCAGGCTGAAGGTGCGGGCGAAG<br>CTGCCCACCAGCACGTTATCGCCCATGGGTGCAGGTGCTCCACG<br>GTGGCGTTGCTGCGGATGATCTTGTCGGTGAAGATCACGCTGTCCT<br>CGGGGAAGCCGGTGCCCACCACCTTGAAGTCGCCGATCACGCGGC<br>CGGCCTCGTAGCGGTAGCTGAAGCTCACGTGCAGCACGCCGCCGT<br>CCTCGTACTTCTCGATGCGGGTGTTGGTGTAGCCGCCGTTGTTGAT<br>GGCGTGCAGGAAGGGGTTCTCGTAGCCGCTGGGGTAGGTGCCGAA<br>GTGGTAGAAGCCGTAGCCCATCACGTGGCTCAGCAGGTAGGGGCT<br>GAAGGTCAGGGCGCCTTTGGTGCTCTTCATCTTGTTGGTCATGCGG<br>CCCTGCTCGGGGGTGCCCTCTCCGCCGCCCACCAGCTCGAACTCCA<br>CGCCGTTCAGGGTGCCGGTGATGCGGCACTCGATCTTCATGGCGG<br>GCATGGTGGCGACCGGTAGCGCTAGCGGCTTCGGATAACTTCGTA<br>TAGCATACATTATACGAACGGTAAGCGCTACCGCCGGCATACCCA |

TABLE 4-continued

| SEQ ID NO/<br>DESCRIPTION/<br>SOURCE | SEQUENCE |
|---|---|
| | AGTGAAGTTGCTCGCAGCTTATAGTCGCGCCCGGGGAGCCCAAGG<br>GCACGCCCTGGCACCGCGGCCGCTGAGTCTCGACCATCATCATCA<br>TCATCATTGAGTTTATCTGGGATAACAGGGTAATGTCATCTAGGGA<br>TAACAGGGTATGTCATCTGGGATAACAGGGTAATGTATCTAGGGA<br>TAACAGGGTAATGTCATCTGGGATAACAGGGTAATGTCATCTAGG<br>GATAACAGGGTATGTCATCTGGGATAACAGGGTAATGTATCTAGG<br>GATAACAGGGTAATGTCATCTGGGATAACAGGGTAATGTCATCTA<br>GGGATAACAGGGTATGTCATCTGGGATAACAGGGTAATGTATCTA<br>GGGATAACAGGGTAATGTCATCTGGGATAACAGGGTAATGTCATC<br>TAGGGATAACAGGGTATGTCATCTGGGATAACAGGGTAATGTATC<br>TAGGGATAACAGGGTAATGTCATCTGGGATAACAGGGTAATGTCA<br>TCTAGGGATAACAGGGTATGTCATCTGGGATAACAGGGTAATGTA<br>TCTAGGGATAACAGGGTAATGTCATCTGGGATAACAGGGTAATGT<br>CATCTAGGGATAACAGGGTATGTCATCTGGGATAACAGGGTAATG<br>TATCTAGGGATAACAGGGTAATGTCATCTGGGATAACAGGGTAAT<br>GTCATCTAGGGATAACAGGGTAAATGTCATCTAGGGATAACAGGG<br>TAATGTCATCTAGGGATAACAGGGTAATGTCATCTGGGATAACAG<br>GGTAATGTCATCTAGGGATAACAGGGTAATGTATCGCCAGCGTCG<br>CACAGCATGTTTGCTTGTCGCCGTCGCGTCTGTCACATCTTTTCCG<br>CCAGCAGTTAGGGATTAGCGTCTTAAGCTGGCGCGAGGACCAACG<br>TATCAGCCAGGCGAAGCTGCTTTTGAGCACCACCCGGATGCCTAT<br>CGCCACCGTCGGTCGCAATGTTGGTTTTGACGATCAACTCTATTTC<br>TCGCGGGTATTTAAAAAATGCACCGGGGCCAGCCCGAGCGAGTTC<br>CGTGCCGGTTGTGAAGAAAAAGTGAATGATGTAGCCGTCAAGTTG<br>TCATAATTGGTAACGAATCAGACAATTGACGGCTTGACGGAGTAG<br>CATAGGGTTTGCAGAATCCCTGCTTCGTCCATTTGACAGGCACATT<br>ATGCATGCCGCTTCGCCTTCGCGCGCGAATTGATCTGCTGCCTCGC<br>GCGTTTCGGTGATGACGGTGAAAACCTCTGACACATGCAGCTCCC<br>GGAGACGGTCACAGCTTGTCTGTAAGCGGATGCCGGGAGCAGACA<br>AGCCCGTCAGGGCGCGTCAGCGGGTGTTGGCGGGTGTCGGGGCGC<br>AGCCATGACCCAGTCACGTAGCGATAGCGGAGTGTATACTGGCTT<br>AACTATGCGGCATCAGAGCAGATTGTACTGAGAGTGCACCATATG<br>CGGTGTGAAATACCGCACAGATGCGTAAGGAGAAAATACCGCATC<br>AGGCGCTCTTCCGCTTCCTCGCTCACTGACTCGCTGCGCTCGGTCG<br>TTCGGCTGCGGCGAGCGGTATCAGCTCACTCAAAGGCGGTAATAC<br>GGTTATCCACAGAATCAGGGGATAACGCAGGAAAGAACATGTGA<br>GCAAAAGGCCAGCAAAAGGCCAGGAACCGTAAAAAGGCCGCGTT<br>GCTGGCGTTTTTCCATAGGCTCCGCCCCCCTGACGAGCATCACAAA<br>AATCGACGCTCAAGTCAGAGGTGGCGAAACCCGACAGGACTATAA<br>AGATACCAGGCGTTTCCCCCTGGAAGCTCCCTCGTGCGCTCTCCTG<br>TTCCGACCCTGCCGCTTACCGGATACCTGTCCGCCTTTCTCCCTTCG<br>GGAAGCGTGGCGCTTTCTCATAGCTCACGCTGTAGGTATCTCAGTT<br>CGGTGTAGGTCGTTCGCTCCAAGCTGGGCTGTGTGCACGAACCCC<br>CCGTTCAGCCCGACCGCTGCGCCTTATCCGGTAACTATCGTCTTGA<br>GTCCAACCCGGTAAGACACGACTTATCGCCACTGGCAGCAGCCAC<br>TGGTAACAGGATTAGCAGAGCGAGGTATGTAGGCGGTGCTACAGA<br>GTTCTTGAAGTGGTGGCCTAACTACGGCTACACTAGAAGGACAGT<br>ATTTGGTATCTGCGCTCTGCTGAAGCCAGTTACCTTCGGAAAAAGA<br>GTTGGTAGCTCTTGATCCGGCAAACAAACCACCGCTGGTAGCGGT<br>GGTTTTTTTGTTTGCAAGCAGCAGATTACGCGCAGAAAAAAAGGA<br>TCTCAAGAAGATCCTTTGATCTTTTCTACGGGGTCTGACGCTCAGT<br>GGAACGAAAACTCACGTTAAGGGATTTTGGTCATGAGCGGATACA<br>TATTTGAATGTATTTAGAAAAATAAACAAAAGAGTTTGTAGAAAC<br>GCAAAAAGGCCATCCGTCAGGATGGCCTTCTGCTTAATTTGATGCC<br>TGGCAGTTTATGGCGGGCGTCCTGCCCGCCACCCTCCGGGCCGTTG<br>CTTCGCAACGTTCAAATCCGCTCCCGGCGGATTTGTCCTACTCAGG<br>AGAGCGTTCACCGACAAACAACAGATAAAACGAAAGGCCCAGTC<br>TTTCGACTGAGCCTTTCGTTTTATTTGATGCCTGGCAGTTCCCTACT<br>CTCGCATGGGGAGACCCCACACTACCATCGGCGCTACGGCGTTTC<br>ACTTCTGAGTTCGGCATGGGGTCAGGTGGGACCACCGCGCTACTG<br>CCGCCAGGCAAATTCTGTTTTATCAGACCGCTTCTGCGTTCTGATT<br>TAATCTGTATCAGGCTGAAAATCTTCTCTCATCCGCCAAAACAGCC<br>AAGCTGGAGACCGTTTGGCCCCCCTCGAGCACGTAGAAAGCCAGT<br>CCGCAGAAACGGTGCTGACCCCGGATGAATGTCAGCTACTGGGCT<br>ATCTGGACAAGGGAAAACGCAAGCGCAAAGAGAAAGCAGGTAGC<br>TTGCAGTGGGCTTACATGGCGATAGCTAGACTGGGCGGTTTTATG<br>GACAGCAAGCGAACCGGAATTGCCAGCTGGGGCGCCCTCTGGTAA<br>GGTTGGGAAGCCCTGCAAAGTAAACTGGATGGCTTTCTCGCCGCC<br>AAGGATCTGATGGCGCAGGGGATCA |
| SEQ ID NO: 73<br>pCMV PE2 P2A Cre<br>plasmid<br>(Artificial Sequence) | ACGCGTTGACATTGATTATTGACTAGTTATTAATAGTAATCAATTA<br>CGGGGTCATTAGTTCATAGCCCATATATGGAGTTCCGCGTTACATA<br>ACTTACGGTAAATGGCCCGCCTGGCTGACCGCCCAACGACCCCCG<br>CCCATTGACGTCAATAATGACGTATGTTCCCATAGTAACGCCAATA<br>GGGACTTTCCATTGACGTCAATGGGTGGAGTATTTACGGTAAACT<br>GCCCACTTGGCAGTACATCAAGTGTATCATATGCCAAGTACGCCC |

TABLE 4-continued

| SEQ ID NO/<br>DESCRIPTION/<br>SOURCE | SEQUENCE |
|---|---|
| | CCTATTGACGTCAATGACGGTAAATGGCCCGCCTGGCATTATGCCC<br>AGTACATGACCTTATGGGACTTTCCTACTTGGCAGTACATCTACGT<br>ATTAGTCATCGCTATTACCATGGTGATGCGGTTTTGGCAGTACATC<br>AATGGGCGTGGATAGCGGTTTGACTCACGGGGATTTCCAAGTCTC<br>CACCCCATTGACGTCAATGGGAGTTTGTTTTGGCACCAAAATCAAC<br>GGGACTTTCCAAAATGTCGTAACAACTCCGCCCCATTGACGCAAA<br>TGGGCGGTAGGCGTGTACGGTGGGAGGTCTATATAAGCAGAGCTG<br>GTTTAGTGAACCGTCAGATCCGCTAGAGATCCGCGGCCGCTAATA<br>CGACTCACTATAGGGAGAGCCGCCACCATGAAACGGACAGCCGAC<br>GGAAGCGAGTTCGAGTCACCAAAGAAGAAGCGGAAAGTCGACAA<br>GAAGTACAGCATCGGCCTGGACATCGGCACCAACTCTGTGGGCTG<br>GGCCGTGATCACCGACGAGTACAAGGTGCCCAGCAAGAAATTCAA<br>GGTGCTGGGCAACACCGACCGGCACAGCATCAAGAAGAACCTGAT<br>CGGAGCCCTGCTGTTCGACAGCGGCGAAACAGCCGAGGCCACCCG<br>GCTGAAGAGAACCGCCAGAAGAAGATACACCAGACGGAAGAACC<br>GGATCTGCTATCTGCAAGAGATCTTCAGCAACGAGATGGCCAAGG<br>TGGACGACAGCTTCTTCCACAGACTGGAAGAGTCCTTCCTGGTGG<br>AAGAGGATAAGAAGCACGAGCGGCACCCCATCTTCGGCAACATCG<br>TGGACGAGGTGGCCTACCACGAGAAGTACCCCACCATCTACCACC<br>TGAGAAAGAAACTGGTGGACAGCACCGACAAGGCCGACCTGCGG<br>CTGATCTATCTGGCCCTGGCCCACATGATCAAGTTCCGGGGCCACT<br>TCCTGATCGAGGGCGACCTGAACCCCGACAACAGCGACGTGGACA<br>AGCTGTTCATCCAGCTGGTGCAGACCTACAACCAGCTGTTCGAGG<br>AAAACCCCATCAACGCCAGCGGCGTGGACGCCAAGGCCATCCTGT<br>CTGCCAGACTGAGCAAGAGCAGACGGCTGGAAAATCTGATCGCCC<br>AGCTGCCCGGCGAGAAGAAGAATGGCCTGTTCGGAAACCTGATTG<br>CCCTGAGCCTGGGCCTGACCCCCAACTTCAAGAGCAACTTCGACC<br>TGGCCGAGGATGCCAAACTGCAGCTGAGCAAGGACACCTACGACG<br>ACGACCTGGACAACCTGCTGGCCCAGATCGGCGACCAGTACGCCG<br>ACCTGTTTCTGGCCGCCAAGAACCTGTCCGACGCCATCCTGCTGAG<br>CGACATCCTGAGAGTGAACACCGAGATCACCAAGGCCCCCCTGAG<br>CGCCTCTATGATCAAGAGATACGACGAGCACCACCAGGACCTGAC<br>CCTGCTGAAAGCTCTCGTGCGGCAGCAGCTGCCTGAGAAGTACAA<br>AGAGATTTTCTTCGACCAGAGCAAGAACGGCTACGCCGGCTACAT<br>TGACGGCGGAGCCAGCCAGGAAGAGTTCTACAAGTTCATCAAGCC<br>CATCCTGGAAAAGATGGACGGCACCGAGGAACTGCTCGTGAAGCT<br>GAACAGAGAGGACCTGCTGCGGAAGCAGCGGACCTTCGACAACG<br>GCAGCATCCCCCACCAGATCCACCTGGGAGAGCTGCACGCCATTC<br>TGCGGCGGCAGGAAGATTTTTACCCATTCCTGAAGGACAACCGGG<br>AAAAGATCGAGAAGATCCTGACCTTCCGCATCCCCTACTACGTGG<br>GCCCTCTGGCCAGGGGAAACAGCAGATTCGCCTGGATGACCAGAA<br>AGAGCGAGGAAACCATCACCCCCTGGAACTTCGAGGAAGTGGTGG<br>ACAAGGGCGCTTCCGCCCAGAGCTTCATCGAGCGGATGACCAACT<br>TCGATAAGAACCTGCCCAACGAGAAGGTGCTGCCCAAGCACAGCC<br>TGCTGTACGAGTACTTCACCGTGTATAACGAGCTGACCAAAGTGA<br>AATACGTGACCGAGGGAATGAGAAAGCCCGCCTTCCTGAGCGGCG<br>AGCAGAAAAAGGCCATCGTGGACCTGCTGTTCAAGACCAACCGGA<br>AAGTGACCGTGAAGCAGCTGAAAGAGGACTACTTCAAGAAAATC<br>GAGTGCTTCGACTCCGTGGAAATCTCCGGCGTGGAAGATCGGTTC<br>AACGCCTCCCTGGGCACATACCACGATCTGCTGAAAATTATCAAG<br>GACAAGGACTTCCTGGACAATGAGGAAAACGAGGACATTCTGGA<br>AGATATCGTGCTGACCCTGACACTGTTTGAGGACAGAGAGATGAT<br>CGAGGAACGGCTGAAAACCTATGCCCACCTGTTCGACGACAAAGT<br>GATGAAGCAGCTGAAGCGGCGGAGATACACCGGCTGGGGCAGGC<br>TGAGCCGGAAGCTGATCAACGGCATCCGGGACAAGCAGTCCGGCA<br>AGACAATCCTGGATTTCCTGAAGTCCGACGGCTTCGCCAACAGAA<br>ACTTCATGCAGCTGATCCACGACGACAGCCTGACCTTTAAAGAGG<br>ACATCCAGAAAGCCCAGGTGTCCGGCCAGGGCGATAGCCTGCACG<br>AGCACATTGCCAATCTGGCCGGCAGCCCCGCCATTAAGAAGGGCA<br>TCCTGCAGACAGTGAAGGTGGTGGACGAGCTCGTGAAAGTGATGG<br>GCCGGCACAAGCCCGAGAACATCGTGATCGAAATGGCCAGAGAG<br>AACCAGACCACCCAGAAGGGACAGAAGAACAGCCGCGAGAGAAT<br>GAAGCGGATCGAAGAGGGCATCAAAGAGCTGGGCAGCCAGATCC<br>TGAAAGAACACCCCGTGGAAAACACCCAGCTGCAGAACGAGAAG<br>CTGTACCTGTACTACCTGCAGAATGGGCGGGATATGTACGTGGAC<br>CAGGAACTGGACATCAACCGGCTGTCCGACTACGATGTGGACGCT<br>ATCGTGCCTCAGAGCTTTCTGAAGGACGACTCCATCGACAACAAG<br>GTGCTGACCAGAAGCGACAAGAACCGGGGCAAGAGCGACAACGT<br>GCCCTCCGAAGAGGTCGTGAAGAAGATGAAGAACTACTGGCGGC<br>AGCTGCTGAACGCCAAGCTGATTACCCAGAGAAAGTTCGACAATC<br>TGACCAAGGCCGAGAGAGGCGGCCTGAGCGAACTGGATAAGGCC<br>GGCTTCATCAAGAGACAGCTGGTGGAAACCCGGCAGATCACAAAG<br>CACGTGGCACAGATCCTGGACTCCGGATGAACACTAAGTACGAC<br>GAGAATGACAAGCTGATCCGGGAAGTGAAAGTGATCACCCTGAA<br>GTCCAAGCTGGTGTCCGATTTCCGGAAGGATTTCCAGTTTTACAAA<br>GTGCGCGAGATCAACAACTACCACCACGCCCACGACGCCTACCTG |

TABLE 4-continued

| SEQ ID NO/<br>DESCRIPTION/<br>SOURCE | SEQUENCE |
|---|---|
| | AACGCCGTCGTGGGAACCGCCCTGATCAAAAAGTACCCTAAGCTG<br>GAAAGCGAGTTCGTGTACGGCGACTACAAGGTGTACGACGTGCGG<br>AAGATGATCGCCAAGAGCGAGCAGGAAATCGGCAAGGCTACCGC<br>CAAGTACTTCTTCTACAGCAACATCATGAACTTTTTCAAGACCGAG<br>ATTACCCTGGCCAACGGCGAGATCCGGAAGCGGCCTCTGATCGAG<br>ACAAACGGCGAAACCGGGGAGATCGTGTGGGATAAGGGCCGGGA<br>TTTTGCCACCGTGCGGAAAGTGCTGAGCATGCCCCAAGTGAATAT<br>CGTGAAAAAGACCGAGGTGCAGACAGGCGGCTTCAGCAAAGAGT<br>CTATCCTGCCCAAGAGGAACAGCGATAAGCTGATCGCCAGAAAGA<br>AGGACTGGGACCCTAAGAAGTACGGCGGCTTCGACAGCCCCACCG<br>TGGCCTATTCTGTGCTGGTGGTGGCCAAAGTGGAAAAGGGCAAGT<br>CCAAGAAACTGAAGAGTGTGAAAGAGCTGCTGGGGATCACCATCA<br>TGGAAAGAAGCAGCTTCGAGAAGAATCCCATCGACTTTCTGGAAG<br>CCAAGGGCTACAAAGAAGTGAAAAAGGACCTGATCATCAAGCTG<br>CCTAAGTACTCCCTGTTCGAGCTGGAAAACGGCCGGAAGAGAATG<br>CTGGCCTCTGCCGGCGAACTGCAGAAGGGAAACGAACTGGCCCTG<br>CCCTCCAAATATGTGAACTTCCTGTACCTGGCCAGCCACTATGAGA<br>AGCTGAAGGGCTCCCCCGAGGATAATGAGCAGAAACAGCTGTTTG<br>TGGAACAGCACAAGCACTACCTGGACGAGATCATCGAGCAGATCA<br>GCGAGTTCTCCAAGAGAGTGATCCTGGCCGACGCTAATCTGGACA<br>AAGTGCTGTCCGCCTACAACAAGCACCGGGATAAGCCCATCGAG<br>AGCAGGCCGAGAATATCATCCACCTGTTTACCCTGACCAATCTGG<br>GAGCCCCTGCCGCCTTCAAGTACTTTGACACCACCATCGACCGGA<br>AGAGGTACACCAGCACCAAAGAGGTGCTGGACGCCACCCTGATCC<br>ACCAGAGCATCACCGGCCTGTACGAGACACGGATCGACCTGTCTC<br>AGCTGGGAGGTGACTCTGGAGGATCTAGCGGAGGATCCTCTGGCA<br>GCGAGACACCAGGAACAAGCGAGTCAGCAACACCAGAGAGCAGT<br>GGCGGCAGCAGCGGCGGCAGCAGCACCCTAAATATAGAAGATGA<br>GTATCGGCTACATGAGACCTCAAAAGAGCCAGATGTTTCTCTAGG<br>GTCCACATGGCTGTCTGATTTTCCTCAGGCCTGGGCGGAAACCGG<br>GGGCATGGGACTGGCAGTTCGCCAAGCTCCTCTGATCATACCTCTG<br>AAAGCAACCTCTACCCCCGTGTCCATAAAACAATACCCCATGTCA<br>CAAGAAGCCAGACTGGGGATCAAGCCCCACATACAGAGACTGTTG<br>GACCAGGGAATACTGGTACCCTGCCAGTCCCCCTGGAACACGCCC<br>CTGCTACCCGTTAAGAAACCAGGGACTAATGATTATAGGCCTGTC<br>CAGGATCTGAGAGAAGTCAACAAGCGGGTGGAAGACATCCACCC<br>CACCGTGCCCAACCCTTACAACCTCTTGAGCGGGCTCCCACCGTCC<br>CACCAGTGGTACACTGTGCTTGATTTAAAGGATGCCTTTTTCTGCC<br>TGAGACTCCACCCCACCAGTCAGCCTCTCTTCGCCTTTGAGTGGAG<br>AGATCCAGAGATGGGAATCTCAGGACAATTGACCTGGACCAGACT<br>CCCCACAGGGTTTCAAAAACAGTCCCCACCCTGTTTAATGAGGCACT<br>GCACAGAGACCTAGCAGACTTCCGGATCCAGCACCCAGACTTGAT<br>CCTGCTACAGTACGTGGATGACTTACTGCTGGCCGCCACTTCTGAG<br>CTAGACTGCCAACAAGGTACTCGGGCCCTGTTACAAACCCTAGGG<br>AACCTCGGGTATCGoGCCTCGGCCAAGAAAGCCCAAATTTGCCAG<br>AAACAGGTCAAGTATCTGGGGTATCTTCTAAAAGAGGGTCAGAGA<br>TGGCTGACTGAGGCCAGAAAAGAGACTGTGATGGGGCAGCCTACT<br>CCGAAGACCCCTCGACAACTAAGGGAGTTCCTAGGGAAGGCAGGC<br>TTCTGTCGCCTCTTCATCCCTGGGTTTGCAGAAATGGCAGCCCCCC<br>TGTACCCTCTCACCAAACCGGGGACTCTGTTTAATTGGGGCCCAGA<br>CCAACAAAAGGCCTATCAAGAAATCAAGCAAGCTCTTCTAACTGC<br>CCCAGCCCTGGGGTTGCCAGATTTGACTAAGCCCTTTGAACTCTTT<br>GTCGACGAGAAGCAGGGCTACGCCAAAGGTGTCCTAACGCAAAA<br>ACTGGGACCTTGGCGTCGGCCGGTGGCCTACCTGTCCAAAAAGCT<br>AGACCCAGTAGCAGCTGGGTGGCCCCCTTGCCTACGGATGGTAGC<br>AGCCATTGCCGTACTGACAAAGGATGCAGGCAAGCTAACCATGGG<br>ACAGCCACTAGTCATTCTGGCCCCCCATGCAGTAGAGGCACTAGT<br>CAAACAACCCCCGACCGCTGGCTTTCAACGCCCGGATGACTCA<br>CTATCAGGCCTTGCTTTTGGACACGGACCGGGTCCAGTTCGGACCG<br>GTGGTAGCCCTGAACCCGGCTACGCTGCTCCCACTGCCTGAGGAA<br>GGGCTGCAACACAACTGCCTTGATATCCTGGCCGAAGCCCACGGA<br>ACCCGACCCGACCTAACGGACCAGCCGCTCCCAGACGCCGACCAC<br>ACCTGGTACACGGATGAAGCAGTCTCTTACAAGAGGGACAGCGT<br>AAGGCGGGAGCTGCGGTGACCACCGAGACCGAGGTAATCTGGGCT<br>AAAAGCCCTGCCAGCCGGGACATCCGCTCAGCGGGCTGAACTGATA<br>GCACTCACCCAGGCCCTAAAGATGGCAGAAGGTAAGAAGCTAAAT<br>GTTTATACTGATAGCCGTTATGCTTTTGCTACTGCCCATATCCATG<br>GAGAAATATACAGAAGGCGTGGGTGGCTCACATCAGAAGGCAAA<br>GAGATCAAAAATAAAGACGAGATCTTGGCCCTACTAAAAGCCCTC<br>TTTTCTGCCCAAAAGACTTAGCATAATCCATTGTCCAGGACATCAAA<br>AGGGACACAGCGCCGAGGCTAGAGGCAACCGGATGGCTGACCAA<br>GCGGCCCGAAAGGCAGCCATCACAGAGACTCCAGACACCTCTACC<br>CTCCTCATAGAAAATTCATCACCCTCTGGCGGCTCAAAAAGAACC<br>GCCGACGGCAGCGAATTCGAGCCCAAGAAGAAGAGGAAAGTCGG<br>AAGCGGAGCTACTAACTTCAGCCTGCTGAAGCAGGCTGGCGACGT<br>GGAGGAGAACCCTGGACCTAATTTACTGACCGTACACCAAAATTT |

TABLE 4-continued

| SEQ ID NO/<br>DESCRIPTION/<br>SOURCE | SEQUENCE |
|---|---|
| | GCCTGCATTACCGGTCGATGCAACGAGTGATGAGGTTCGCAAGAA<br>CCTGATGGACATGTTCAGGGATCGCCAGGCGTTTTCTGAGCATACC<br>TGGAAAATGCTTCTGTCCGTTTGCCGGTCGTGGGCGGCATGGTGCA<br>AGTTGAATAACCGGAAATGGTTTCCCGCAGAACCTGAAGATGTTC<br>GCGATTATCTTCTATATCTTCAGGCGCGCGGTCTGGCAGTAAAAAC<br>TATCCAGCAACATTTGGGCCAGCTAAACATGCTTCATCGTCGGTCC<br>GGGCTGCCACGACCAAGTGACAGCAATGCTGTTTCACTGGTTATG<br>CGGCGGATCCGAAAAGAAAACGTTGATGCCGGTGAACGTGCAAA<br>ACAGGCTCTAGCGTTCGAACGCACTGATTTCGACCAGGTTCGTTCA<br>CTCATGGAAAATAGCGATCGCTGCCAGGATATACGTAATCTGGCA<br>TTTCTGGGGATTGCTTATAACACCCTGTTACGTATAGCCGAAATTG<br>CCAGGATCAGGGTTAAAGATATCTCACGTACTGACGGTGGGAGAA<br>TGTTAATCCATATTGGCAGAACGAAAACGCTGGTTAGCACCGCAG<br>GTGTAGAGAAGGCACTTAGCCTGGGGGTAACTAAACTGGTCGAGC<br>GATGGATTTCCGTCTCTGGTGTAGCTGATGATCCGAATAACTACCT<br>GTTTTGCCGGGTCAGAAAAATGGTGTTGCCGCGCCATCTGCCAC<br>CAGCCAGCTATCAACTCGCGCCCTGGAAGGGATTTTTGAAGCAAC<br>TCATCGATTGATTTACGGCGCTAAGGATGACTCTGGTCAGAGATA<br>CCTGGCCTGGTCTGGACACAGTGCCCGTGTCGGAGCCGCGCGAGA<br>TATGGCCCGCGCTGGAGTTTCAATACCGGAGATCATGCAAGCTGG<br>TGGCTGGACCAATGTAAATATTGTCATGAACTATATCCGTAACCTG<br>GATAGTGAAACAGGGGCAATGGTGCGCCTGCTGGAAGATGGCGAT<br>TAATTTAAACCCGCTGATCAGCCTCGACTGTGCCTTCTAGTTGCCA<br>GCCATCTGTTGTTTGCCCCTCCCCCGTGCCTTCCTTGACCCTGGAA<br>GGTGCCACTCCCACTGTCCTTTCCTAATAAAATGAGAAAATTGCAT<br>CGCATTGTCTGAGTAGGTGTCATTCTATTCTGGGGGGTGGGGTGGG<br>GCAGGACAGCAAGGGGGAGGATTGGGAAGACAATAGCAGGCATG<br>CTGGGGATGCGGTGGGCTCTATGGCTTCTGAGGCGGAAAGAACCA<br>GCTGGGGCTCGATACCGTCGACCTCTAGCTAGAGCTTGGCGTAAT<br>CATGGTCATAGCTGTTTCCTGTGTGAAATTGTTATCCGCTCACAAT<br>TCCACACAACATACGAGCCGGAAGCATAAAGTGTAAAGCCTAGGG<br>TGCCTAATGAGTGAGCTAACTCACATTAATTGCGTTGCGCTCACTG<br>CCCGCTTTCCAGTCGGGAAACCTGTCGTGCCAGCTGCATTAATGAA<br>tcggccaacgcgcgggagaggcggtttgcgtattgggcgctctt<br>CCGCTTCCTCGCTCACTGACTCGCTGCGCTCGGTCGTTCGGCTGCG<br>GCGAGCGGTATCAGCTCACTCAAAGGCGGTAATACGGTTATCCAC<br>AGAATCAGGGGATAACGCAGGAAAGAACATGTGAGCAAAAGGCC<br>AGCAAAAGGCCAGGAACCGTAAAAAGGCCGCGTTGCTGGCGTTTT<br>TCCATAGGCTCCGCCCCCCTGACGAGCATCACAAAAATCGACGCT<br>CAAGTCAGAGGTGGCGAAACCCGACAGGACTATAAAGATACCAG<br>GCGTTTCCCCCTGGAAGCTCCCTCGTGCGCTCTCCTGTTCCGACCC<br>TGCCGCTTACCGGATACCTGTCCGCCTTTCTCCCTTCGGGAAGCGT<br>GGCGCTTTCTCATAGCTCACGCTGTAGGTATCTCAGTTCGGTGTAG<br>GTCGTTCGCTCCAAGCTGGGCTGTGTGCACGAACCCCCCGTTCAGC<br>CCGACCGCTGCGCCTTATCCGGTAACTATCGTCTTGAGTCCAACCC<br>GGTAAGACACGACTTATCGCCACTGGCAGCAGCCACTGGTAACAG<br>GATTAGCAGAGCGAGGTATGTAGGCGGTGCTACAGAGTTCTTGAA<br>GTGGTGGCCTAACTACGGCTACACTAGAAGAACAGTATTTGGTAT<br>CTGCGCTCTGCTGAAGCCAGTTACCTTCGGAAAAAGAGTTGGTAG<br>CTCTTGATCCGGCAAACAAACCACCGCTGGTAGCGGTGGTTTTTTT<br>GTTTGCAAGCAGCAGATTACGCGCAGAAAAAAAGGATCTCAAGA<br>AGATCCTTTGATCTTTTCTACGGGGTCTGACGCTCAGTGGAACGAA<br>AACTCACGTTAAGGGATTTTGGTCATGAGATTATCAAAAAGGATC<br>TTCACCTAGATCCTTTTAAATTAAAAATGAAGTTTTAAATCAATCT<br>AAAGTATATATGAGTAAACTTGGTCTGACAGTTACCAATGCTTAAT<br>CAGTGAGGCACCTATCTCAGCGATCTGTCTATTTCGTTCATCCATA<br>GTTGCCTGACTCCCCGTCGTGTAGATAACTACGATACGGGAGGGC<br>TTACCATCTGGCCCCAGTGCTGCAATGATACCGCGAGACCCACGC<br>TCACCGGCTCCAGATTTATCAGCAATAAACCAGCCAGCCGGAAGG<br>GCCGAGCGCAGAAGTGGTCCTGCAACTTTATCGCCTCCATCCAGT<br>CTATTAATTGTTGCCGGGAAGCTAGAGTAAGTAGTTCGCCAGTTA<br>ATAGTTTGCGCAACGTTGTTGCCATTGCTACAGGCATCGTGGTGTC<br>ACGCTCGTCGTTTGGTATGGCTTCATTCAGCTCCGGTTCCCAACGA<br>TCAAGGCGAGTTACATGATCCCCCATGTTGTGCAAAAAAGCGGTT<br>AGCTCCTTCGGTCCTCCGATCGTTGTCAGAAGTAAGTTGGCCGCAG<br>TGTTATCACTCATGGTTATGGCAGCACTGCATAATTCTCTTACTGT<br>CATGCCATCCGTAAGATGCTTTTCTGTGACTGGTGAGTACTCAACC<br>AAGTCATTCTGAGAATAGTGTATGCGGCGACCGAGTTGCTCTTGCC<br>CGGCGTCAATACGGGATAATACCGCGCCACATAGCAGAACTTTAA<br>AAGTGCTCATCATTGGAAAACGTTCTTCGGGGCGAAAACTCTCAA<br>GGATCTTACCGCTGTTGAGATCCAGTTCGATGTAACCCACTCGTGC<br>ACCCAACTGATCTTCAGCATCTTTTACTTTCACCAGCGTTTCTGGG<br>TGAGCAAAAACAGGAAGGCAAATGCCGCAAAAAAGGGAATAAG<br>GGCGACACGGAAATGTTGAATACTCATACTCTTCCTTTTTCAATAT<br>TATTGAAGCATTTATCAGGGTTATTGTCTCATGAGCGGATACATAT<br>TTGAATGTATTTAGAAAAATAAACAAATAGGGGTTCCGCGCACAT |

TABLE 4-continued

| SEQ ID NO/<br>DESCRIPTION/<br>SOURCE | SEQUENCE |
|---|---|
| | TTCCCCGAAAAGTGCCACCTGACGTCGACGGATCGGGAGATCGAT<br>CTCCCGATCCCCTAGGGTCGACTCTCAGTACAATCTGCTCTGATGC<br>CGCATAGTTAAGCCAGTATCTGCTCCCTGCTTGTGTGTTGGAGGTC<br>GCTGAGTAGTGCGCGAGCAAAATTTAAGCTACAACAAGGCAAGGC<br>TTGACCGACAATTGCATGAAGAATCTGCTTAGGGTTAGGCGTTTTG<br>CGCTGCTTCGCGATGTACGGGCCAGATAT |
| SEQ ID NO: 74<br>+90 ngRNA guide<br>sequence<br>(Artificial Sequence) | GTCAACCAGTATCCCGGTGC |
| SEQ ID NO: 75<br>+90 ngRNA<br>(Artificial Sequence) | GTCAACCAGTATCCCGGTGCGTTTTAGAGCTAGAAATAGCAAGTT<br>AAAATAAGGCTAGTCCGTTATCAACTTGAAAAAGTGGCACCGAGT<br>CGGTGC |
| SEQ ID NO: 76<br>GFP minicircle<br>template (before<br>cleavage into a<br>minicircle)<br>(Artificial Sequence) | TGATCCCCTGCGCCATCAGATCCTTGGCGGCGAGAAAGCCATCCA<br>GTTTACTTTGCAGGGCTTCCCAACCTTACCAGAGGGCGCCCCAGCT<br>GGCAATTCCGGTTCGCTTGCTGTCCATAAAACCGCCCAGTCTAGCT<br>ATCGCCATGTAAGCCCACTGCAAGCTACCTGCTTTCTCTTTGCGCT<br>TGCGTTTTCCCTTGTCCAGATAGCCCAGTAGCTGACATTCATCCGG<br>GGTCAGCACCGTTTCTGCGGACTGGCTTTCTACGTGCTCGAGGGGG<br>GCCAAACGGTCTCCAGCTTGGCTGTTTTGGCGGATGAGAGAAGAT<br>TTTCAGCCTGATACAGATTAAATCAGAACGCAGAAGCGGTCTGAT<br>AAAACAGAATTTGCCTGGCGGCAGTAGCGCGGTGGTCCCACCTGA<br>CCCCATGCCGAACTCAGAAGTGAAACGCCGTAGCGCCGATGGTAG<br>TGTGGGGTCTCCCCATGCGAGAGTAGGGAACTGCCAGGCATCAAA<br>TAAAACGAAAGGCTCAGTCGAAAGACTGGGCCTTTCGTTTTATCT<br>GTTGTTTGTCGGTGAACGCTCTCCTGAGTAGGACAAATCCGCCGG<br>GAGCGGATTTGAACGTTGCGAAGCAACGGCCCGGAGGGTGGCGG<br>GCAGGACGCCCGCCATAAACTGCCAGGCATCAAATTAAGCAGAAG<br>GCCATCCTGACGGATGGCCTTTTTGCGTTTCTACAAACTCTTTTGTT<br>TATTTTTCTAAATACATTCAAATATGTATCCGCTCATGACCAAAAT<br>CCCTTAACGTGAGTTTTCGTTCCACTGAGCGTCAGACCCCGTAGAA<br>AAGATCAAAGGATCTTCTTGAGATCCTTTTTTTCTGCGCGTAATCT<br>GCTGCTTGCAAACAAAAAAACCACCGCTACCAGCGGTGGTTTGTT<br>TGCCGGATCAAGAGCTACCAACTCTTTTTCCGAAGGTAACTGGCTT<br>CAGCAGAGCGCAGATACCAAATACTGTCCTTCTAGTGTAGCCGTA<br>GTTAGGCCACCACTTCAAGAACTCTGTAGCACCGCCTACATACCTC<br>GCTCTGCTAATCCTGTTACCAGTGGCTGCTGCCAGTGGCGATAAGT<br>CGTGTCTTACCGGGTTGGACTCAAGACGATAGTTACCGGATAAGG<br>CGCAGCGGTCGGGCTGAACGGGGGGTTCGTGCACACAGCCCAGCT<br>TGGAGCGAACGACCTACACCGAACTGAGATACCTACAGCGTGAGC<br>TATGAGAAAGCGCCACGCTTCCCGAAGGGAGAAAGGCGGACAGG<br>TATCCGGTAAGCGGCAGGGTCGGAACAGGAGAGCGCACGAGGGA<br>GCTTCCAGGGGGAAACGCCTGGTATCTTTATAGTCCTGTCGGGTTT<br>CGCCACCTCTGACTTGAGCGTCGATTTTTGTGATGCTCGTCAGGGG<br>GGCGGAGCCTATGGAAAAACGCCAGCAACGCGGCCTTTTTACGGT<br>TCCTGGCCTTTTGCTGGCCTTTTGCTCACATGTTCTTTCCTGCGTTA<br>TCCCCTGATTCTGTGGATAACCGTATTACCGCCTTTGAGTGAGCTG<br>ATACCGCTCGCCGCAGCCGAACGACCGAGCGCAGCGAGTCAGTGA<br>GCGAGGAAGCGGAAGAGCGCCTGATGCGGTATTTTCTCCTTACGC<br>ATCTGTGCGGTATTTCACACCGCATATGGTGCACTCTCAGTACAAT<br>CTGCTCTGATGCCGCATAGTTAAGCCAGTATACACTCCGCTATCGC<br>TACGTGACTGGGTCATGGCTGCGCCCCGACACCCGCCAACACCCG<br>CTGACGCGCCCTGACGGGCTTGTCTGCTCCCGGCATCCGCTTACAG<br>ACAAGCTGTGACCGTCTCCGGGAGCTGCATGTGTCAGAGGTTTTC<br>ACCGTCATCACCGAAACGCGCGAGGCAGCAGATCAATTCGCGCGC<br>GAAGGCGAAGCGGCATGCATAATGTGCCTGTCAAATGGACGAAGC<br>AGGGATTCTGCAAACCCTATGCTACTCCGTCAAGCCGTCAATTGTC<br>TGATTCGTTACCAATTATGACAACTTGACGGCTACATCATTCACTT<br>TTTCTTCACAACCGGCACGGAACTCGCTCGGGCTGGCCCCGGTGC<br>ATTTTTTAAATACCCGCGAGAAATAGAGTTGATCGTCAAAACCAA<br>CATTGCGACCGACGGTGGCGATAGGCATCCGGGTGGTGCTCAAAA<br>GCAGCTTCGCCTGGCTGATACGTTGGTCCTCGCGCCAGCTTAAGAC<br>GCTAATCCCTAACTGCTGGCGGAAAAGATGTGACAGACGCGACGG<br>CGACAAGCAAACATGCTGTGCGACGCTGGCGATACATTACCCTGT<br>TATCCCTAGATGACATTACCCTGTTATCCCAGATGACATTACCCTG<br>TTATCCCTAGATGACATTACCCTGTTATCCCTAGATGACATTTACC<br>CTGTTATCCCTAGATGACATTACCCTGTTATCCCAGATGACATTAC<br>CCTGTTATCCCTAGATACATTACCCTGTTATCCCAGATGACATTACC<br>CTGTTATCCCTAGATGACATTACCCTGTTATCCCAGATGACATTAC<br>CCTGTTATCCCTAGATACATTACCCTGTTATCCCAGATGACATTAC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATGACATTAC |

TABLE 4-continued

| SEQ ID NO/<br>DESCRIPTION/<br>SOURCE | SEQUENCE |
| --- | --- |
| | CCTGTTATCCCTAGATACATTACCCTGTTATCCCAGATGACATACC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATAAACTCAA<br>TGATGATGATGATGATGGTCGAGACTCAGCGGCCGCGGTGCCAGG<br>GCGTGCCCTTGGGCTCCCCGGGCGCGACTATAAGCTGCGAGCAAC<br>TTCACTTGGGTATGCCGGCGGTAGCGCTTACCGTTCGTATAATGTA<br>TGCTATACGAAGTTATCCGAAGCCGCTAGCGGTGGTTTGTCTGGTC<br>AACCACCGCGGTCTCAGTGGTGTACGGTACAAACCCAGCTACCGG<br>TCGCCACCATGCCCGCCATGAAGATCGAGTGCCGCATCACCGGCA<br>CCCTGAACGGCGTGGAGTTCGAGCTGGTGGGCGGCGGAGAGGGC<br>ACCCCCGAGCAGGGCCGCATGACCAACAAGATGAAGAGCACCAA<br>AGGCGCCCTGACCTTCAGCCCCTACCTGCTGAGCCACGTGATGGG<br>CTACGGCTTCTACCACTTCGGCACCTACCCCAGCGGCTACGAGAA<br>CCCCCTTCCTGCACGCCATCAACAACGGCGGCTACACCAACACCCG<br>CATCGAGAAGTACGAGGACGGCGGCGTGCTGCACGTGAGCTTCAG<br>CTACCGCTACGAGGCCGGCCGCGTGATCGGCGACTTCAAGGTGGT<br>GGGCACCGGCTTCCCCGAGGACAGCGTGATCTTCACCGACAAGAT<br>CATCCGCAGCAACGCCACCGTGGAGCACCTGCACCCCATGGGCGA<br>TAACGTGCTGGTGGGCAGCTTCGCCCGCACCTTCAGCCTGCGCGA<br>CGGCGGCTACTACAGCTTCGTGGTGGACAGCCACATGCACTTCAA<br>GAGCGCCATCCACCCCAGCATCCTGCAGAACGGGGGCCCCATGTT<br>CGCCTTCCGCCGCGTGGAGGAGCTGCACAGCAACACCGAGCTGGG<br>CATCGTGGAGTACCAGCACGCCTTCAAGACCCCCATCGCCTTCGCC<br>AGATCTCGAGCTCGATGAGTTTGGACAAACCACAACTAGAATGCA<br>GTGAAAAAAATGCTTTATTTGTGAAATTTGTGATGCTATTGCTTTA<br>TTTGTGGGCCCGCCCCAACTGGGGTAACCTTTGAGTTCTCTCAGTT<br>GGGGGTAATCAGCATCATGATGTGGTACCACATCATGATGCTGAT<br>TATAAGAATGCGGCCGCCACACTCTAGTGGATCTCGAGTTAATAA<br>TTCAGAAGAACTCGTCAAGAAGGCGATAGAAGGCGATGCGCTGCG<br>AATCGGGAGCGGCGATACCGTAAAGCACGAGGAAGCGGTCAGCC<br>CATTCGCCGCCAAGCTCTTCAGCAATATCACGGGTAGCCAACGCT<br>ATGTCCTGATAGCGGTCCGCCACACCCAGCCGGCCACAGTCGATG<br>AATCCAGAAAAGCGGCCATTTTCCACCATGATATTCGGCAAGCAG<br>GCATCGCCATGGGTCACGACGAGATCCTCGCCGTCGGGCATGCTC<br>GCCTTGAGCCTGGCGAACAGTTCGGCTGGCGCGAGCCCCTGATGC<br>TCTTCGTCCAGATCATCCTGATCGACAAGACCGGCTTCCATCCGAG<br>TACGTGCTCGCTCGATGCGATGTTTCGCTTGGTGGTCGAATGGGCA<br>GGTAGCCGGATCAAGCGTATGCAGCCGCCGCATTGCATCAGCCAT<br>GATGGATACTTTCTCGGCAGGAGCAAGGTGTAGATGACATGGAGA<br>TCCTGCCCCGGCACTTCGCCCAATAGCAGCCAGTCCCTTCCCGCTT<br>CAGTGACAACGTCGAGCACAGCTGCGCAAGGAACGCCCGTCGTGG<br>CCAGCCACGATAGCCGCGCTGCCTCGTCTTGCAGTTCATTCAGGGC<br>ACCGGACAGGTCGGTCTTGACAAAAAGAACCGGGCGCCCCTGCGC<br>TGACAGCCGGAACACGGCGGCATCAGAGCAGCCGATTGTCTGTTG<br>TGCCCAGTCATAGCCGAATAGCCTCTCCACCCAAGCGGCCGGAGA<br>ACCTGCGTGCAATCCATCTTGTTCAATCATGCGAAACGATCCTCAT<br>CCTGTCTCTTGATCAGAGCT |
| SEQ ID NO: 77<br>Gaussia Luciferase<br>minicircle template<br>(Artificial Sequence) | TGATCCCCTGCGCCATCAGATCCTTGGCGGCGAGAAAGCCATCCA<br>GTTTACTTTGCAGGGCTTCCCAACCTTACCAGAGGGCGCCCCAGCT<br>GGCAATTCCGGTTCGCTTGCTGTCCATAAAACCGCCCAGTCTAGCT<br>ATCGCCATGTAAGCCCACTGCAAGCTACCTGCTTTCTCTTTGCGCT<br>TGCGTTTTCCCTTGTCCAGATAGCCCAGTAGCTGACATTCATCCGG<br>GGTCAGCACCGTTTCTGCGGACTGGCTTTCTACGTGCTCGAGGGGG<br>GCCAAACGGTCTCCAGCTTGGCTGTTTTGGCGGATGAGAGAAGAT<br>TTTCAGCCTGATACAGATTAAATCAGAACGCAGAAGCGGTCTGAT<br>AAAACAGAATTTGCCTGGCGGCAGTAGCGCGGTGGTCCCACCTGA<br>CCCCATGCCGAACTCAGAAGTGAAACGCCGTAGCGCCGATGGTAG<br>TGTGGGGTCTCCCCATGCGAGAGTAGGGAACTGCCAGGCATCAAA<br>TAAAACGAAAGGCTCAGTCGAAAGACTGGGCCTTTCGTTTTATCT<br>GTTGTTTGTCGGTGAACGCTCTCCTGAGTAGGACAAATCCGCCGG<br>GAGCGGATTTGAACGTTGCGAAGCAACGGCCCGGAGGGTGGCGG<br>GCAGGACGCCCGCCATAAACTGCCAGGCATCAAATTAAGCAGAAG<br>GCCATCCTGACGGATGGCCTTTTTGCGTTTCTACAAACTCTTTTGTT<br>TATTTTTCTAAATACATTCAAATATGTATCCGCTCATGACCAAAAT<br>CCCTTAACGTGAGTTTTCGTTCCACTGAGCGTCAGACCCCGTAGAA<br>AAGATCAAAGGATCTTCTTGAGATCCTTTTTTTCTGCGCGTAATCT<br>GCTGCTTGCAAACAAAAAAACCACCGCTACCAGCGGTGGTTTGTT<br>TGCCGGATCAAGAGCTACCAACTCTTTTTCCGAAGGTAACTGGCTT<br>CAGCAGAGCGCAGATACCAAATACTGTCCTTCTAGTGTAGCCGTA<br>GTTAGGCCACCACTTCAAGAACTCTGTAGCACCGCCTACATACCTC<br>GCTCTGCTAATCCTGTTACCAGTGGCTGCTGCCAGTGGCGATAAGT<br>CGTGTCTTACCGGGTTGGACTCAAGACGATAGTTACCGGATAAGG |

TABLE 4-continued

| SEQ ID NO/DESCRIPTION/SOURCE | SEQUENCE |
|---|---|
| | CGCAGCGGTCGGGCTGAACGGGGGGTTCGTGCACACAGCCCAGCT |
| | TGGAGCGAACGACCTACACCGAACTGAGATACCTACAGCGTGAGC |
| | TATGAGAAAGCGCCACGCTTCCCGAAGGGAGAAAGGCGGACAGG |
| | TATCCGGTAAGCGGCAGGGTCGGAACAGGAGAGCGCACGAGGGA |
| | GCTTCCAGGGGGAAACGCCTGGTATCTTTATAGTCCTGTCGGGTTT |
| | CGCCACCTCTGACTTGAGCGTCGATTTTTGTGATGCTCGTCAGGGG |
| | GGCGGAGCCTATGGAAAAACGCCAGCAACGCGGCCTTTTTACGGT |
| | TCCTGGCCTTTTGCTGGCCTTTTGCTCACATGTTCTTTCCTGCGTTA |
| | TCCCCTGATTCTGTGGATAACCGTATTACCGCCTTTGAGTGAGCTG |
| | ATACCGCTCGCCGCAGCCGAACGACCGAGCGCAGCGAGTCAGTGA |
| | GCGAGGAAGCGGAAGAGCGCCTGATGCGGTATTTTCTCCTTACGC |
| | ATCTGTGCGGTATTTCACACCGCATATGGTGCACTCTCAGTACAAT |
| | CTGCTCTGATGCCGCATAGTTAAGCCAGTATACACTCCGCTATCGC |
| | TACGTGACTGGGTCATGGCTGCGCCCCGACACCCGCCAACACCCG |
| | CTGACGCGCCCTGACGGGCTTGTCTGCTCCCGGCATCCGCTTACAG |
| | ACAAGCTGTGACCGTCTCCGGGAGCTGCATGTGTCAGAGGTTTTC |
| | ACCGTCATCACCGAAACGCGCGAGGCAGCAGATCAATTCGCGCGC |
| | GAAGGCGAAGCGGCATGCATAATGTGCCTGTCAAATGGACGAAGC |
| | AGGGATTCTGCAAACCCTATGCTACTCCGTCAAGCCGTCAATTGTC |
| | TGATTCGTTACCAATTATGACAACTTGACGGCTACATCATTCACTT |
| | TTTCTTCACAACCGGCACGGAACTCGCTCGGGCTGGCCCCGGTGC |
| | ATTTTTTAAATACCCGCGAGAAATAGAGTTGATCGTCAAAACCAA |
| | CATTGCGACCGACGGTGGCGATAGGCATCCGGGTGGTGCTCAAAA |
| | GCAGCTTCGCCTGGCTGATACGTTGGTCCTCGCGCCAGCTTAAGAC |
| | GCTAATCCCTAACTGCTGGCGGAAAAGATGTGACAGACGCGACGG |
| | CGACAAGCAAACATGCTGTGCGACGCTGGCGATACATTACCCTGT |
| | TATCCCTAGATGACATTACCCTGTTATCCCAGATGACATTACCCTG |
| | TTATCCCTAGATGACATTACCCTGTTATCCCTAGATGACATTTACC |
| | CTGTTATCCCTAGATGACATTACCCTGTTATCCCAGATGACATTAC |
| | CCTGTTATCCCTAGATACATTACCCTGTTATCCCAGATGACATACC |
| | CTGTTATCCCTAGATGACATTACCCTGTTATCCCAGATGACATTAC |
| | CCTGTTATCCCTAGATACATTACCCTGTTATCCCAGATGACATACC |
| | CTGTTATCCCTAGATGACATTACCCTGTTATCCCAGATGACATTAC |
| | CCTGTTATCCCTAGATACATTACCCTGTTATCCCAGATGACATACC |
| | CTGTTATCCCTAGATGACATTACCCTGTTATCCCAGATGACATTAC |
| | CCTGTTATCCCTAGATACATTACCCTGTTATCCCAGATGACATACC |
| | CTGTTATCCCTAGATGACATTACCCTGTTATCCCAGATGACATTAC |
| | CCTGTTATCCCTAGATACATTACCCTGTTATCCCAGATGACATACC |
| | CTGTTATCCCTAGATGACATTACCCTGTATCCCAGATAAACTCAA |
| | TGATGATGATGATGATGGTCGAGACTCAGCGGCCGCGGTGCCAGG |
| | GCGTGCCCTTGGGCTCCCCGGGCGCGACTATAAGCTGCGAGCAAC |
| | TTCACTTGGGTATGCCGGCGGTAGCGCTTACCGTTCGTATAATGTA |
| | TGCTATACGAAGTTATCCGAAGCCGCTAGCGGTGGTTTGTCTGGTC |
| | AACCACCGCGGTCTCAGTGGTGTACGGTACAAACCCACTACCGGT |
| | CGCCACCATGGGAGTCAAAGTTCTGTTTGCCCTGATCTGCATCGCT |
| | GTGGCCGAGGCCAAGCCCACCGAGAACAACGAAGACTTCAACATC |
| | GTGGCCGTGGCCAGCAACTTCGCGACCACGGATCTCGATGCTGAC |
| | CGCGGGAAGTTGCCCGGCAAGAAGCTGCCGCTGGAGGTGCTCAAA |
| | GAGATGGAAGCCAATGCCCGGAAAGCTGGCTGCACCAGGGGCTGT |
| | CTGATCTGCCTGTCCCACATCAAGTGCACGCCCAAGATGAAGAAG |
| | TTCATCCCAGGACGCTGCCACACCTACGAAGGCGACAAAGAGTCC |
| | GCACAGGGCGGCATAGGCGAGGCGATCGTCGACATTCCTGAGATT |
| | CCTGGGTTCAAGGACTTGGAGCCCATGGAGCAGTTCATCGCACAG |
| | GTCGATCTGTGTGTGGACTGCACAACTGGCTGCCTCAAAGGGCTT |
| | GCCAACGTGCAGTGTTCTGACCTGCTCAAGAAGTGGCTGCCGCAA |
| | CGCTGTGCGACCTTTGCCAGCAAGATCCAGGGCCAGGTGGACAAG |
| | ATCAAGGGGGCCGGTGGTGACTAAGCGGAGCTCGATGAGTTTGGA |
| | CAAACCACAACTAGAATGCAGTGAAAAAAATGCTTTATTTGTGAA |
| | ATTTGTGATGCTATTGCTTTATTTGTGGGCCCGCCCCAACTGGGGT |
| | AACCTTTGAGTTCTCTCAGTTGGGGGTAATCAGCATCATGATGTGG |
| | TACCACATCATGATGCTGATTATAAGAATGCGGCCGCCACACTCT |
| | AGTGGATCTCGAGTTAATAATTCAGAAGAACTCGTCAAGAAGGCG |
| | ATAGAAGGCGATGCGCTGCGAATCGGGAGCGGCGATACCGTAAA |
| | GCACGAGGAAGCGGTCAGCCCATTCGCCGCCAAGCTCTTCAGCAA |
| | TATCACGGGTAGCCAACGCTATGTCCTGATAGCGGTCCGCCACAC |
| | CCAGCCGGCCACAGTCGATGAATCCAGAAAAGCGGCCATTTTCCA |
| | CCATGATATTCGGCAAGCAGGCATCGCCATGGGTCACGACGAGAT |
| | CCTCGCCGTCGGGCATGCTCGCCTTGAGCCTGGCGAACAGTTCGG |
| | CTGGCGCGAGCCCCTGATGCTCTTCGTCCAGATCATCCTGATCGAC |
| | AAGACCGGCTTCCATCCGAGTACGTGCTCGCTCGATGCGATGTTTC |
| | GCTTGGTGGTCGAATGGGCAGGTAGCCGGATCAAGCGTATGCAGC |
| | CGCCGCATTGCATCAGCCATGATGGATACTTTCTCGGCAGGAGCA |
| | AGGTGTAGATGACATGGAGATCCTGCCCCGGCACTTCGCCCAATA |
| | GCAGCCAGTCCCTTCCCGCTTCAGTGACAACGTCGAGCACAGCTG |

TABLE 4-continued

| SEQ ID NO/<br>DESCRIPTION/<br>SOURCE | SEQUENCE |
|---|---|
| | CGCAAGGAACGCCCGTCGTGGCCAGCCACGATAGCCGCGCTGCCT<br>CGTCTTGCAGTTCATTCAGGGCACCGGACAGGTCGGTCTTGACAA<br>AAAGAACCGGGCGCCCCTGCGCTGACAGCCGGAACACGGCGGCA<br>TCAGAGCAGCCGATTGTCTGTTGTGCCCAGTCATAGCCGAATAGC<br>CTCTCCACCCAAGCGGCCGGAGAACCTGCGTGCAATCCATCTTGTT<br>CAATCATGCGAAACGATCCTCATCCTGTCTCTTGATCAGAGCT |
| SEQ ID NO: 78<br>pseudo attP site<br>(Artificial sequence) | CCCCAACTGGGGTAACCTTTGAGTTCTCTCAGTTGGGG |
| SEQ ID NO: 79<br>Albumin-pegRNA-<br>SERPIN<br>(Artificial Sequence) | GACTGAAACTTCACAGAATAGTTTTAGAGCTAGAAATAGCAAGTT<br>AAAATAAGGCTAGTCCGTTATCAACTTGAAAAAGTGGCACCGAGT<br>CGGTGCTTGGGATAGTTATGAATTCAATCTTCAACCCTATCCGGAT<br>GATCCTGACGACGGAGACCGCCGTCGTCGACAAGCCGGCCTCTGT<br>GAAGTTTCAGTCA |
| SEQ ID NO: 80<br>Albumin-pegRNA-<br>CPS1<br>(Artificial Sequence) | GACTGAAACTTCACAGAATAGTTTTAGAGCTAGAAATAGCAAGTT<br>AAAATAAGGCTAGTCCGTTATCAACTTGAAAAAGTGGCACCGAGT<br>CGGTGCTTGGGATAGTTATGAATTCAATCTTCAACCCTATCCGGAT<br>GATCCTGACGACGGAGACCGCCGTCGTCGACAAGCCGGCCTCTGT<br>GAAGTTTC |
| SEQ ID NO: 81<br>34 bp lox71 pegRNA<br>(Artificial Sequence) | GGCCCAGACTGAGCACGTGAGTTTTAGAGCTAGAAATAGCAAGTT<br>AAAATAAGGCTAGTCCGTTATCAACTTGAAAAAGTGGCACCGAGT<br>CGGTGCTGGAGGAAGCAGGGCTTCCTTTCCTCTGCCATCATACCGT<br>TCGTATAGCATACATTATACGAAGTTATCGTGCTCAGTCTG |
| SEQ ID NO: 82<br>34 bp lox66 pegRNA<br>(Artificial Sequence) | GGCCCAGACTGAGCACGTGAGTTTTAGAGCTAGAAATAGCAAGTT<br>AAAATAAGGCTAGTCCGTTATCAACTTGAAAAAGTGGCACCGAGT<br>CGGTGCTGGAGGAAGCAGGGCTTCCTTTCCTCTGCCATCAATAACT<br>TCGTATAGCATACATTATACGAACGGTACGTGCTCAGTCTG |
| SEQ ID NO: 83<br>gRNA<br>(Artificial Sequence) | GGCCCAGACTGAGCACGTGA |
| SEQ ID NO: 84<br>ACTB N-term PBS<br>13 RT 29 attB 46<br>(original length)<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGCCGGATGATCC<br>TGACGACGGAGACCGCCGTCGTCGACAAGCCGGCCTGAGCTGCGA<br>GAA |
| SEQ ID NO: 85<br>ACTB N-term<br>PBS_13_RT_29_with<br>TP901-1 minimal<br>attB f pegRNA<br>(Artificial Sequence) | GCTATTCTCGCAGCTCACCAGTTTTAGAGCTAGAAATAGCAAGTT<br>AAAATAAGGCTAGTCCGTTATCAACTTGAAAAAGTGGCACCGAG<br>TCGGTGCGAGTCGGTGCGACGAGCGCGGCGATATCATCATCCAT<br>GGCACAATTAACATCTCAATCAAGGTAAATGCTTGAGCTGCGAG<br>AA |
| SEQ ID NO: 86<br>ACTB N-term<br>PBS_13_RT_29_with<br>TP901-1 minimal<br>attB rc pegRNA<br>(Artificial Sequence) | GCTATTCTCGCAGCTCACCAGTTTTAGAGCTAGAAATAGCAAGTT<br>AAAATAAGGCTAGTCCGTTATCAACTTGAAAAAGTGGCACCGAG<br>TCGGTGCGAGTCGGTGCGACGAGCGCGGCGATATCATCATCCAT<br>GGAGCATTTACCTTGATTGAGATGTTAATTGTGTGAGCTGCGAGA<br>A |
| SEQ ID NO: 87<br>ACTB N-term<br>PBS_13_RT_29_with<br>PhiBT1 minimal<br>attB f pegRNA<br>(Artificial Sequence) | GCTATTCTCGCAGCTCACCAGTTTTAGAGCTAGAAATAGCAAGTT<br>AAAATAAGGCTAGTCCGTTATCAACTTGAAAAAGTGGCACCGAG<br>TCGGTGCGAGTCGGTGCGACGAGCGCGGCGATATCATCATCCAT<br>GGCAGGTTTTTGACGAAAGTGATCCAGATGATCCAGTGAGCTGC<br>GAGAA |
| SEQ ID NO: 88<br>ACTB N-term<br>PBS 13 RT 29_with<br>PhiBT1 minimal<br>attB rc pegRNA<br>(Artificial Sequence) | GCTATTCTCGCAGCTCACCAGTTTTAGAGCTAGAAATAGCAAGTT<br>AAAATAAGGCTAGTCCGTTATCAACTTGAAAAAGTGGCACCGAG<br>TCGGTGCGAGTCGGTGCGACGAGCGCGGCGATATCATCATCCAT<br>GGCTGGATCATCTGGATCACTTTCGTCAAAAACCTGTGAGCTGCG<br>AGAA |

TABLE 4-continued

| SEQ ID NO/ DESCRIPTION/ SOURCE | SEQUENCE |
|---|---|
| SEQ ID NO: 89<br>ACTB N-term<br>Nicking guide 1 +48<br>guide<br>(Artificial Sequence) | GAAGCCGGCCTTGCACATGCGTTTTAGAGCTAGAAATAGCAAGT<br>TAAAATAAGGCTAGTCCGTTATCAACTTGAAAAAGTGGCACCGA<br>GTCGGTGC |
| SEQ ID NO: 90<br>ACTB N-term<br>PBS_18_RT_16_with_<br>Lox71_Cre<br>pegRNA<br>(Artificial Sequence) | GAAGCCGGCCTTGCACATGCGTTTTAGAGCTAGAAATAGCAAGT<br>TAAAATAAGGCTAGTCCGTTATCAACTTGAAAAAGTGGCACCGA<br>GTCGGTGCATATCATCATCCATGGTACCGTTCGTATAGCATACAT<br>TATACGAAGTTATTGAGCTGCGAGAATAGCC |
| SEQ ID NO: 91<br>ACTB N-term<br>PBS_13_RT_29_with_<br>Lox71_Cre<br>pegRNA<br>(Artificial Sequence) | GAAGCCGGCCTTGCACATGCGTTTTAGAGCTAGAAATAGCAAGT<br>TAAAATAAGGCTAGTCCGTTATCAACTTGAAAAAGTGGCACCGA<br>GTCGGTGCGACGAGCGCGGCGATATCATCATCCATGGTACCGTT<br>CGTATAGCATACATTATACGAAGTTATTGAGCTGCGAGAA |
| SEQ ID NO: 92<br>ACTB N-term PBS<br>13 RT 34 pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCTCGACGACGAGCGCGGCGATATCATCATCCATGGCCGGAT<br>GATCCTGACGACGGAGACCGCCGTCGTCGACAAGCCGGCCTGAGC<br>TGCGAGAA |
| SEQ ID NO: 93<br>ACTB N-term PBS<br>13 RT 26 pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGAGCGCGGCGATATCATCATCCATGGCCGGATGATCCTGA<br>CGACGGAGACCGCCGTCGTCGACAAGCCGGCCTGAGCTGCGAGAA |
| SEQ ID NO: 94<br>ACTB N-term PBS<br>13 RT 23 pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCCGCGGCGATATCATCATCCATGGCCGGATGATCCTGACGAC<br>GGAGACCGCCGTCGTCGACAAGCCGGCCTGAGCTGCGAGAA |
| SEQ ID NO: 95<br>ACTB N-term PBS<br>13 RT 20 pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGGCGATATCATCATCCATGGCCGGATGATCCTGACGACGG<br>AGACCGCCGTCGTCGACAAGCCGGCCTGAGCTGCGAGAA |
| SEQ ID NO: 96<br>ACTB N-term PBS<br>13 RT 16 pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCATATCATCATCCATGGCCGGATGATCCTGACGACGGAGAC<br>CGCCGTCGTCGACAAGCCGGCCTGAGCTGCGAGAA |
| SEQ ID NO: 97<br>ACTB N-term PBS<br>18 RT 34 pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCTCGACGACGAGCGCGGCGATATCATCATCCATGGCCGGAT<br>GATCCTGACGACGGAGACCGCCGTCGTCGACAAGCCGGCCTGAGC<br>TGCGAGAATAGCC |
| SEQ ID NO: 98<br>ACTB N-term PBS<br>18 RT 29 pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGCCGGATGATCC<br>TGACGACGGAGACCGCCGTCGTCGACAAGCCGGCCTGAGCTGCGA<br>GAATAGCC |
| SEQ ID NO: 99<br>ACTB N-term PBS<br>18 RT 16 pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCATATCATCATCCATGGCCGGATGATCCTGACGACGGAGAC<br>CGCCGTCGTCGACAAGCCGGCCTGAGCTGCGAGAATAGCC |
| SEQ ID NO: 100<br>LMNB1 N-term PBS<br>13 RT 39 pegRNA<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAG<br>TCGGTGCCTGCCCATCCGCGGCGGCACGGGGGTCGCAGTCGCCA<br>TGCCGGATGATCCTGACGACGGAGACCGCCGTCGTCGACAAGCC<br>GGCCCGGGCGGCGGAGA |
| SEQ ID NO: 101<br>LMNB1 N-term PBS<br>13 RT 34 pegRNA<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAG<br>TCGGTGCCATCCGCGGCGGCACGGGGGTCGCAGTCGCCATGCCG<br>GATGATCCTGACGACGGAGACCGCCGTCGTCGACAAGCCGGCCC<br>GGGCGGCGGAGA |

TABLE 4-continued

| SEQ ID NO/<br>DESCRIPTION/<br>SOURCE | SEQUENCE |
| --- | --- |
| SEQ ID NO: 102<br>LMNB1 N-term PBS<br>13 RT 29 pegRNA<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAG<br>TCGGTGCGCGGCGGCACGGGGGTCGCAGTCGCCATGCCGGATGA<br>TCCTGACGACGGAGACCGCCGTCGTCGACAAGCCGGCCCGGGCG<br>GCGGAGA |
| SEQ ID NO: 103<br>LMNB1 N-term PBS<br>13 RT 24 pegRNA<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAG<br>TCGGTGCGGCACGGGGGTCGCAGTCGCCATGCCGGATGATCCTG<br>ACGACGGAGACCGCCGTCGTCGACAAGCCGGCCCGGGCGGCGGA<br>GA |
| SEQ ID NO: 104<br>LMNB1 N-term PBS<br>13 RT 19 pegRNA<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAG<br>TCGGTGCGGGGGTCGCAGTCGCCATGCCGGATGATCCTGACGAC<br>GGAGACCGCCGTCGTCGACAAGCCGGCCCGGGCGGCGGAGA |
| SEQ ID NO: 105<br>LMNB1 N-term PBS<br>18 RT 39 pegRNA<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAG<br>TCGGTGCCTGCCCATCCGCGGCGGCACGGGGGTCGCAGTCGCCA<br>TGCCGGATGATCCTGACGACGGAGACCGCCGTCGTCGACAAGCC<br>GGCCCGGGCGGCGGAGACAGCG |
| SEQ ID NO: 106<br>LMNB1 N-term PBS<br>18 RT 34 pegRNA<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAG<br>TCGGTGCCATCCGCGGCGGCACGGGGGTCGCAGTCGCCATGCCG<br>GATGATCCTGACGACGGAGACCGCCGTCGTCGACAAGCCGGCCC<br>GGGCGGCGGAGACAGCG |
| SEQ ID NO: 107<br>LMNB1 N-term PBS<br>18 RT 29 pegRNA<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAGT<br>CGGTGCGCGGCGGCACGGGGGTCGCAGTCGCCATGCCGGATGATC<br>CTGACGACGGAGACCGCCGTCGTCGACAAGCCGGCCCGGGCGGCG<br>GAGACAGCG |
| SEQ ID NO: 108<br>LMNB1 N-term PBS<br>18 RT 24 pegRNA<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAG<br>TCGGTGCGGCACGGGGGTCGCAGTCGCCATGCCGGATGATCCTG<br>ACGACGGAGACCGCCGTCGTCGACAAGCCGGCCCGGGCGGCGGA<br>GACAGCG |
| SEQ ID NO: 109<br>LMNB1 N-term PBS<br>18 RT 19 pegRNA<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAG<br>TCGGTGCGGGGGTCGCAGTCGCCATGCCGGATGATCCTGACGAC<br>GGAGACCGCCGTCGTCGACAAGCCGGCCCGGGCGGCGGAGACAG<br>CG |
| SEQ ID NO: 110<br>LMNB1 N-term<br>Nicking guide 1 +46<br>(Artificial Sequence) | GCGTGGTGGGGCCGCCAGCGGTTTTAGAGCTAGAAATAGCAAGT<br>TAAAATAAGGCTAGTCCGTTATCAACTTGAAAAAGTGGCACCGA<br>GTCGGTGC |
| SEQ ID NO: 111<br>ACTB N-term PBS<br>13 RT 29 attB 42<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGGGATGATCCTG<br>ACGACGGAGACCGCCGTCGTCGACAAGCCGGTGAGCTGCGAGAA |
| SEQ ID NO: 112<br>ACTB N-term PBS<br>13 RT 29 attB 40<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGGATGATCCTGA<br>CGACGGAGACCGCCGTCGTCGACAAGCCGTGAGCTGCGAGAA |
| SEQ ID NO: 113<br>ACTB N-term PBS<br>13 RT 29 attB 38<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGATGATCCTGAC<br>GACGGAGACCGCCGTCGTCGACAAGCCTGAGCTGCGAGAA |
| SEQ ID NO: 114<br>ACTB N-term PBS<br>13 RT 29 attB 36<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGTGATCCTGACG<br>ACGGAGACCGCCGTCGTCGACAAGCTGAGCTGCGAGAA |

TABLE 4-continued

| SEQ ID NO/ DESCRIPTION/ SOURCE | SEQUENCE |
|---|---|
| SEQ ID NO: 115 LMNB1 N-term PBS 13 RT 29 attB 44 pegRNA v2 (Artificial Sequence) | GCTGTCTCCGCCGCCCGCCAGTTTTAGAGCTAGAAATAGCAAGTTAAAATAAGGCTAGTCCGTTATCAACTTGAAAAAGTGGCACCGAGTCGGTGCGCGGCGGCACGGGGGTCGCAGTCGCCATGCGGATGATCCTGACGACGGAGACCGCCGTCGTCGACAAGCCGGCCGGGCGGCGGAGA |
| SEQ ID NO: 116 LMNB1 N-term PBS 13 RT 29 attB 42 pegRNA v2 (Artificial Sequence) | GCTGTCTCCGCCGCCCGCCAGTTTTAGAGCTAGAAATAGCAAGTTAAAATAAGGCTAGTCCGTTATCAACTTGAAAAAGTGGCACCGAGTCGGTGCGCGGCGGCACGGGGGTCGCAGTCGCCATGGGATGATCCTGACGACGGAGACCGCCGTCGTCGACAAGCCGGCGGGCGGCGGAGA |
| SEQ ID NO: 117 LMNB1 N-term PBS 13 RT 29 attB 40 pegRNA v2 (Artificial Sequence) | GCTGTCTCCGCCGCCCGCCAGTTTTAGAGCTAGAAATAGCAAGTTAAAATAAGGCTAGTCCGTTATCAACTTGAAAAAGTGGCACCGAGTCGGTGCGCGGCGGCACGGGGGTCGCAGTCGCCATGGATGATCCTGACGACGGAGACCGCCGTCGTCGACAAGCCGCGGGCGGCGGAGA |
| SEQ ID NO: 118 LMNB1 N-term PBS 13 RT 29 attB 38 pegRNA v2 (Artificial Sequence) | GCTGTCTCCGCCGCCCGCCAGTTTTAGAGCTAGAAATAGCAAGTTAAAATAAGGCTAGTCCGTTATCAACTTGAAAAAGTGGCACCGAGTCGGTGCGCGGCGGCACGGGGGTCGCAGTCGCCATGATGATCCTGACGACGGAGACCGCCGTCGTCGACAAGCCCGGGCGGCGGAGA |
| SEQ ID NO: 119 NOLC1 N-term PBS 18 RT 29 attB 46 pegRNA (Artificial Sequence) | GCGTATTGCCTGGAGGATGGGTTTTAGAGCTAGAAATAGCAAGTTAAAATAAGGCTAGTCCGTTATCAACTTGAAAAAGTGGCACCGAGTCGGTGCGAACCACGCGGCGAATGCCGGCGTCCGCCCCGGATGATCCTGACGACGGAGACCGCCGTCGTCGACAAGCCGGCCTCCTCCAGGCAATACGCG |
| SEQ ID NO: 120 NOLC1 N-term PBS 13 RT 29 attB 46 pegRNA (Artificial Sequence) | GCGTATTGCCTGGAGGATGGGTTTTAGAGCTAGAAATAGCAAGTTAAAATAAGGCTAGTCCGTTATCAACTTGAAAAAGTGGCACCGAGTCGGTGCGAACCACGCGGCGAATGCCGGCGTCCGCCCCGGATGATCTGACGACGGAGACCGCCGTCGTCGACAAGCCGGCCTCCTCCAGGCAAT |
| SEQ ID NO: 121 NOLC1 N-term PBS 13 RT 29 attB 44 pegRNA (Artificial Sequence) | GCGTATTGCCTGGAGGATGGGTTTTAGAGCTAGAAATAGCAAGTTAAAATAAGGCTAGTCCGTTATCAACTTGAAAAAGTGGCACCGAGTCGGTGCGAACCACGCGGCGAATGCCGGCGTCCGCCCGGATGATCCTGACGACGGAGACCGCCGTCGTCGACAAGCCGGCTCCTCCAGGCAAT |
| SEQ ID NO: 122 NOLC1 N-term PBS 13 RT 29 attB 42 pegRNA (Artificial Sequence) | GCGTATTGCCTGGAGGATGGGTTTTAGAGCTAGAAATAGCAAGTTAAAATAAGGCTAGTCCGTTATCAACTTGAAAAAGTGGCACCGAGTCGGTGCGAACCACGCGGCGAATGCCGGCGTCCGCCGGATGATCCTGACGACGGAGACCGCCGTCGTCGACAAGCCGGTCCTCCAGGCAAT |
| SEQ ID NO: 123 NOLC1 N-term PBS 13 RT 29 attB 40 pegRNA (Artificial Sequence) | GCGTATTGCCTGGAGGATGGGTTTTAGAGCTAGAAATAGCAAGTTAAAATAAGGCTAGTCCGTTATCAACTTGAAAAAGTGGCACCGAGTCGGTGCGAACCACGCGGCGAATGCCGGCGTCCGCCGATGATCCTGACGACGGAGACCGCCGTCGTCGACAAGCCGTCCTCCAGGCAAT |
| SEQ ID NO: 124 NOLC1 N-term PBS 13 RT 29 attB 38 pegRNA (Artificial Sequence) | GCGTATTGCCTGGAGGATGGGTTTTAGAGCTAGAAATAGCAAGTTAAAATAAGGCTAGTCCGTTATCAACTTGAAAAAGTGGCACCGAGTCGGTGCGAACCACGCGGCGAATGCCGGCGTCCGCCATGATCCTGACGACGGAGACCGCCGTCGTCGACAAGCCTCCTCCAGGCAAT |
| SEQ ID NO: 125 NOLC1 nicking guide-43 (Artificial Sequence) | GAGCCGAGCACGAGGGGATACGTTTTAGAGCTAGAAATAGCAAGTTAAAATAAGGCTAGTCCGTTATCAACTTGAAAAAGTGGCACCGAGTCGGTGC |
| SEQ ID NO: 126 ACTB N-term PBS 13 RT 20 attB 38 pegRNA (Artificial Sequence) | GCTATTCTCGCAGCTCACCAGTTTTAGAGCTAGAAATAGCAAGTTAAAATAAGGCTAGTCCGTTATCAACTTGAAAAAGTGGCACCGAGTCGGTGCGGCGATATCATCATCCATGGATGATCCTGACGACGGAGACCGCCGTCGTCGACAAGCCTGAGCTGCGAGAA |
| SEQ ID NO: 127 ACTB N-term PBS 13 RT 15 attB 38 pegRNA (Artificial Sequence) | GCTATTCTCGCAGCTCACCAGTTTTAGAGCTAGAAATAGCAAGTTAAAATAAGGCTAGTCCGTTATCAACTTGAAAAAGTGGCACCGAGTCGGTGCTATCATCATCCATGGATGATCCTGACGACGGAGACCGCCGTCGTCGACAAGCCTGAGCTGCGAGAA |

TABLE 4-continued

| SEQ ID NO/ DESCRIPTION/ SOURCE | SEQUENCE |
|---|---|
| SEQ ID NO: 128 ACTB N-term PBS 13 RT 10 attB 38 pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCTCATCCATGGATGATCCTGACGACGGAGACCGCCGTCGTC GACAAGCCTGAGCTGCGAGAA |
| SEQ ID NO: 129 ACTB N-term PBS 9 RT 20 attB 38 pegRNA (Artificial Sequence) | GCTATTCTCGCAGCTCACCAGTTTTAGAGCTAGAAATAGCAAGTT AAAATAAGGCTAGTCCGTTATCAACTTGAAAAAGTGGCACCGAG TCGGTGCGGCGATATCATCATCCATGGATGATCCTGACGACGGAG ACCGCCGTCGTCGACAAGCCTGAGCTGCG |
| SEQ ID NO: 130 ACTB N-term PBS 9 RT 15 attB 38 pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCTATCATCATCCATGGATGATCCTGACGACGGAGACCGCCG TCGTCGACAAGCCTGAGCTGCG |
| SEQ ID NO: 131 ACTB N-term PBS 9 RT 10 attB 38 pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCTCATCCATGGATGATCCTGACGACGGAGACCGCCGTCGTC GACAAGCCTGAGCTGCG |
| SEQ ID NO: 132 LMNB1 N-term PBS 13 RT 20 attB 38 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAG TCGGTGCCGGGGGTCGCAGTCGCCATGATGATCCTGACGACGGA GACCGCCGTCGTCGACAAGCCCGGGCGGCGGAGA |
| SEQ ID NO: 133 LMNB1 N-term PBS 13 RT 15 attB 38 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAG TCGGTGCGTCGCAGTCGCCATGATGATCCTGACGACGGAGACCG CCGTCGTCGACAAGCCCGGGCGGCGGAGA |
| SEQ ID NO: 134 LMNB1 N-term PBS 13 RT 10 attB 38 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAG TCGGTGCAGTCGCCATGATGATCCTGACGACGGAGACCGCCGTC GTCGACAAGCCCGGGCGGCGGAGA |
| SEQ ID NO: 135 LMNB1 N-term PBS 9 RT 20 attB 38 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAGT CGGTGCCGGGGGTCGCAGTCGCCATGATGATCCTGACGACGGAGA CCGCCGTCGTCGACAAGCCCGGGCGGC |
| SEQ ID NO: 136 LMNB1 N-term PBS 9 RT 15 attB 38 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAG TCGGTGCGTCGCAGTCGCCATGATGATCCTGACGACGGAGACCG CCGTCGTCGACAAGCCCGGGCGGCG |
| SEQ ID NO: 137 LMNB1 N-term PBS 9 RT 10 attB 38 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAGT CGGTGCAGTCGCCATGATGATCCTGACGACGGAGACCGCCGTCGT CGACAAGCCCGGGCGGCG |
| SEQ ID NO: 138 SUPT16H N-term PBS 13 RT 24 Bxb1-GT_Initial length (Artificial Sequence) | GAGAAGCGGCGTCCGGGGCTAGTTTTAGAGCTAGAAATAGCAAGT TAAAATAAGGCTAGTCCGTTATCAACTTGAAAAAGTGGCACCGAG TCGGTGCTCTTTGTCCAGAGTCACAGCCATACCGGATGATCCTGAC GACGGAGACCGCCGTCGTCGACAAGCCGGCCCCCCGGACGCCGC |
| SEQ ID NO: 139 SRRM2 N-term PBS 13 RT 24 Bxb1 Initial length (Artificial Sequence) | GGGCACGGGGCCATGTACAAGTTTTAGAGCTAGAAATAGCAAGT TAAAATAAGGCTAGTCCGTTATCAACTTGAAAAAGTGGCACCGA GTCGGTGCGGCGTCGGCAGCCCGATCCCGTTGCCGGATGATCCT GACGACGGAGACCGCCGTCGTCGACAAGCCGGCCTACATGGCCC CGT |
| SEQ ID NO: 140 DEPDC4 N-term PBS 18 RT 24 Bxb1 | GTGTCAGGTGGGCGGGGCTAGTTTTAGAGCTAGAAATAGCAAG TTAAAATAAGGCTAGTCCGTTATCAACTTGAAAAAGTGGCACCG AGTCGGTGCGCTGGCTCCTCCCCTGGCACCATACCGGATGATCCT |

TABLE 4-continued

| SEQ ID NO/<br>DESCRIPTION/<br>SOURCE | SEQUENCE |
|---|---|
| Initial length<br>(Artificial Sequence) | GACGACGGAGACCGCCGTCGTCGACAAGCCGGCCCCCCGCCCCA<br>CCTGACAC |
| SEQ ID NO: 141<br>NES N-term PBS 13<br>RT 29 Bxb1 Initial<br>length<br>(Artificial Sequence) | GAGTGGGTCAGACGAGCAGGAGTTTTAGAGCTAGAAATAGCAAGT<br>TAAAATAAGGCTAGTCCGTTATCAACTTGAAAAAGTGGCACCGAG<br>TCGGTGCGATGGAGGGCTGCATGGGGGAGGAGTCGCCGGATGATC<br>CTGACGACGGAGACCGCCGTCGTCGACAAGCCGGCCTGCTCGTCT<br>GACC |
| SEQ ID NO: 142<br>SUPT16H nicking<br>guide-53<br>(Artificial Sequence) | GCAGCCACCCGCTCTCGGCCCGTTTTAGAGCTAGAAATAGCAAG<br>TTAAAATAAGGCTAGTCCGTTATCAACTTGAAAAAGTGGCACCG<br>AGTCGGTGC |
| SEQ ID NO: 143<br>SRRM2 N-term<br>nicking guide 1 +87<br>(Artificial Sequence) | GTGTAGTCAGGCCGCTCACCCGTTTTAGAGCTAGAAATAGCAAG<br>TTAAAATAAGGCTAGTCCGTTATCAACTTGAAAAAGTGGCACCG<br>AGTCGGTGC |
| SEQ ID NO: 144<br>DEPDC4 N-term<br>Nicking guide 1 +59<br>(Artificial Sequence) | GCTGACAAGTCTACGGAACCTGTTTTAGAGCTAGAAATAGCAAG<br>TTAAAATAAGGCTAGTCCGTTATCAACTTGAAAAAGTGGCACCG<br>AGTCGGTGC |
| SEQ ID NO: 145<br>NES N-term Nicking<br>guide 2 + 9<br>(Artificial Sequence) | GCTCCTCCAGCGCCTTGACCGTTTTAGAGCTAGAAATAGCAAGTTA<br>AAATAAGGCTAGTCCGTTATCAACTTGAAAAAGTGGCACCGAGTC<br>GGTGC |
| SEQ ID NO: 146<br>HITI_ACTB_guide<br>(Artificial Sequence) | GCTATTCTCGCAGCTCACCA |
| SEQ ID NO: 147<br>HITI_SUPTH16_guide<br>(Artificial Sequence) | AGAAGCGGCGTCCGGGGCTA |
| SEQ ID NO: 148<br>HITI_SRRM2_guide<br>(Artificial Sequence) | GGGCACGGGGCCATGTACAA |
| SEQ ID NO: 149<br>HITI_NOLC1_guide<br>(Artificial Sequence) | GCGTATTGCCTGGAGGATGG |
| SEQ ID NO: 150<br>HITI_DEPDC4_guide<br>(Artificial Sequence) | TGTCAGGTGGGGCGGGGCTA |
| SEQ ID NO: 151<br>HITI_NES_guide<br>(Artificial Sequence) | AGTGGGTCAGACGAGCAGGA |
| SEQ ID NO: 152<br>HITI_LMNB1_guide<br>(Artificial Sequence) | GCTGTCTCCGCCGCCCGCCA |
| SEQ ID NO: 153<br>HDR Cas9 ACTB<br>guide<br>(Artificial Sequence) | GCTATTCTCGCAGCTCACCAGTTTTAGAGCTAGAAATAGCAAGTT<br>AAAATAAGGCTAGTCCGTTATCAACTTGAAAAAGTGGCACCGAG<br>TCGGTGC |
| SEQ ID NO: 154<br>ACTB N-term PBS<br>13 RT 29 attB<br>original length<br>pegRNAs for<br>dinucleotides<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGCCGGATGATCC<br>TGACGACGGAGXXCGCCGTCGTCGACAAGCCGGCCTGAGCTGCGA<br>GAA<br>XX: CG, GC, AT, TA, GG, TT, GA, AG, CC, TC, CT, AA, TG, GT, CA, or<br>AC |
| SEQ ID NO: 155<br>ACTB N-term PBS<br>13 RT 29 pegRNA<br>with attB 46 GT for<br>fusion<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGCCGGATGATCCT<br>GACGACGGAGACCGCCGTCGTCGACAAGCCGGCCTGAGCTGCGAG<br>AA |

TABLE 4-continued

| SEQ ID NO/<br>DESCRIPTION/<br>SOURCE | SEQUENCE |
| --- | --- |
| SEQ ID NO: 156<br>ACTB N-term PBS<br>13 RT 29 pegRNA<br>with attB 46 CT for<br>multiplexing<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGCCGGATGATCCT<br>GACGACGGAGAGCGCCGTCGTCGACAAGCCGGCCTGAGCTGCGA<br>GAA |
| SEQ ID NO: 157<br>NOLC1 N-term PBS<br>18 RT 29 pegRNA<br>with attB 46 GA for<br>multiplexing<br>(Artificial Sequence) | GCGTATTGCCTGGAGGATGGGTTTTAGAGCTAGAAATAGCAAGTT<br>AAAATAAGGCTAGTCCGTTATCAACTTGAAAAAGTGGCACCGAGT<br>CGGTGCGAACCACGCGGCGAATGCCGGCGTCCGCCCCGGATGATC<br>CTGACGACGGAGTCCGCCGTCGTCGACAAGCCGGCCTCCTCCAGG<br>CAATACGCG |
| SEQ ID NO: 158<br>LMNB1 N-term PBS<br>18 RT 29 pegRNA<br>with attB 46 AG for<br>multiplexing<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAGT<br>CGGTGCGCGGCGGCACGGGGGTCGCAGTCGCCATGCCGGATGATC<br>CTGACGACGGAGCTCGCCGTCGTCGACAAGCCGGCCCGGGCGGCG<br>GAGACAGCG |
| SEQ ID NO: 159<br>EMX1 Cas9 guide 1<br>(Artificial Sequence) | GTCACCTCCAATGACTAGGG |
| SEQ ID NO: 160<br>EMX1 Cas9 guide 2<br>(Artificial Sequence) | GGGCAACCACAAACCCACGA |
| SEQ ID NO: 161<br>ACTB N-term PBS<br>13 RT 29 attB 56 GA<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGCTATGCCGGAT<br>GATCCTGACGACGGAGTCCGCCGTCGTCGACAAGCCGGCCCTAGC<br>TGAGCTGCGAGAA |
| SEQ ID NO: 162<br>ACTB N-term PBS<br>13 RT 29 attB 51 GA<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGTGCCGGATGAT<br>CCTGACGACGGAGTCCGCCGTCGTCGACAAGCCGGCCCTATGAGC<br>TGCGAGAA |
| SEQ ID NO: 163<br>ACTB N-term PBS<br>13 RT 29 attB 46 GA<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGCCGGATGATCC<br>TGACGACGGAGTCCGCCGTCGTCGACAAGCCGGCCTGAGCTGCGA<br>GAA |
| SEQ ID NO: 164<br>ACTB N-term PBS<br>13 RT 29 attB 41 GA<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGGGATGATCCTG<br>ACGACGGAGTCCGCCGTCGTCGACAAGCCGTGAGCTGCGAGAA |
| SEQ ID NO: 165<br>ACTB N-term PBS<br>13 RT 29 attB 36 GA<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGTGATCCTGACG<br>ACGGAGTCCGCCGTCGTCGACAAGCTGAGCTGCGAGAA |
| SEQ ID NO: 166<br>ACTB N-term PBS<br>13 RT 29 attB 31 GA<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGATCCTGACGAC<br>GGAGTCCGCCGTCGTCGACATGAGCTGCGAGAA |
| SEQ ID NO: 167<br>ACTB N-term PBS<br>13 RT 29 attB 26 GA<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGCCTGACGACGG<br>AGTCCGCCGTCGTCGTGAGCTGCGAGAA |

TABLE 4-continued

| SEQ ID NO/ DESCRIPTION/ SOURCE | SEQUENCE |
|---|---|
| SEQ ID NO: 168 ACTB N-term PBS 13 RT 29 attB 21 GA pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGTGACGACGGAG TCCGCCGTCGTGAGCTGCGAGAA |
| SEQ ID NO: 169 ACTB N-term PBS 13 RT 29 attB 16 GA pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGACGACGGAGTC CGCCGTGAGCTGCGAGAA |
| SEQ ID NO: 170 ACTB N-term PBS 13 RT 29 attB 11 GA pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGGACGGAGTCCG TGAGCTGCGAGAA |
| SEQ ID NO: 171 ACTB N-term PBS 13 RT 29 attB 6 GA pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGCGGAGTTGAGC TGCGAGAA |
| SEQ ID NO: 172 ACTB N-term PBS_18_RT_34_with_ Lox71_Cre pegRNA (Artificial Sequence) | GAAGCCGGCCTTGCACATGCGTTTTAGAGCTAGAAATAGCAAGTT AAAATAAGGCTAGTCCGTTATCAACTTGAAAAAGTGGCACCGAGT CGGTGCTCGACGACGAGCGCGGCGATATCATCATCCATGGTACCG TTCGTATAGCATACATTATACGAAGTTATTGAGCTGCGAGAATAG CC |
| SEQ ID NO: 173 ACTB N-term PBS_18_RT_29_with_ Lox71_Cre pegRNA (Artificial Sequence) | GAAGCCGGCCTTGCACATGCGTTTTAGAGCTAGAAATAGCAAGTT AAAATAAGGCTAGTCCGTTATCAACTTGAAAAAGTGGCACCGAGT CGGTGCGACGAGCGCGGCGATATCATCATCCATGGTACCGTTCGT ATAGCATACATTATACGAAGTTATTGAGCTGCGAGAATAGCC |
| SEQ ID NO: 174 ACTB N-term PBS_13_RT_34_with_ Lox71_Cre pegRNA (Artificial Sequence) | GAAGCCGGCCTTGCACATGCGTTTTAGAGCTAGAAATAGCAAGTT AAAATAAGGCTAGTCCGTTATCAACTTGAAAAAGTGGCACCGAGT CGGTGCTCGACGACGAGCGCGGCGATATCATCATCCATGGTACCG TTCGTATAGCATACATTATACGAAGTTATTGAGCTGCGAGAA |
| SEQ ID NO: 175 ACTB N-term PBS_13_RT_16_with_ Lox71_Cre pegRNA (Artificial Sequence) | GAAGCCGGCCTTGCACATGCGTTTTAGAGCTAGAAATAGCAAGTT AAAATAAGGCTAGTCCGTTATCAACTTGAAAAAGTGGCACCGAGT CGGTGCATATCATCATCCATGGTACCGTTCGTATAGCATACATTAT ACGAAGTTATTGAGCTGCGAGAA |
| SEQ ID NO: 176 ACTB N-term Nicking guide 2 +93 guide (Artificial Sequence) | CCCCACGATGGAGGGGAAGAGTTTTAGAGCTAGAAATAGCAAGTT AAAATAAGGCTAGTCCGTTATCAACTTGAAAAAGTGGCACCGAGT CGGTGC |
| SEQ ID NO: 177 LMNB1 N-term Nicking guide 2 +87 guide (Artificial Sequence) | CCTTCTCCTGGAGCCGCGACGTTTTAGAGCTAGAAATAGCAAGTT AAAATAAGGCTAGTCCGTTATCAACTTGAAAAAGTGGCACCGAGT CGGTGC |

Sequences of insertion sites can be found in Table 4 below.

TABLE 4

| DESCRIPTION/ SOURCE | FORWARD SEQUENCE (5'-3') | | REVERSE SEQUENCE (5'-3') | |
| --- | --- | --- | --- | --- |
| | SEQ ID NO | Sequence | SEQ ID NO | Sequence |
| Bxb1_attP_GT_ original_site (Artificial Sequence) | 178 | GTGGTTTGTCTGGTC AACCACCGCGGTCT CAGTGGTGTACGGT ACAAACCCA | 179 | TGGGTTTGTACCGTA CACCACTGAGACCG CGGTGGTTGACCAG ACAAACCAC |
| Bxb1_attP_CG_ site (Artificial Sequence) | 180 | GTGGTTTGTCTGGTC AACCACCGCGCGCT CAGTGGTGTACGGT ACAAACCCA | 181 | TGGGTTTGTACCGTA CACCACTGAGCGCG CGGTGGTTGACCAG ACAAACCAC |
| Bxb1_attP_GC_ site (Artificial Sequence) | 182 | GTGGTTTGTCTGGTC AACCACCGCGGCCT CAGTGGTGTACGGT ACAAACCCA | 183 | TGGGTTTGTACCGTA CACCACTGAGGCCG CGGTGGTTGACCAG ACAAACCAC |
| Bxb1_attP_AT_ site (Artificial Sequence) | 184 | GTGGTTTGTCTGGTC AACCACCGCGATCT CAGTGGTGTACGGT ACAAACCCA | 185 | TGGGTTTGTACCGTA CACCACTGAGATCG CGGTGGTTGACCAG ACAAACCAC |
| Bxb1_attP_TA_ site (Artificial Sequence) | 186 | GTGGTTTGTCTGGTC AACCACCGCGTACT CAGTGGTGTACGGT ACAAACCCA | 187 | TGGGTTTGTACCGTA CACCACTGAGTACG CGGTGGTTGACCAG ACAAACCAC |
| Bxb1_attP_GG_ site (Artificial Sequence) | 188 | GTGGTTTGTCTGGTC AACCACCGCGGGCT CAGTGGTGTACGGT ACAAACCCA | 189 | TGGGTTTGTACCGTA CACCACTGAGCCCG CGGTGGTTGACCAG ACAAACCAC |
| Bxb1_attP_TT_ site (Artificial Sequence) | 190 | GTGGTTTGTCTGGTC AACCACCGCGTTCTC AGTGGTGTACGGTA CAAACCCA | 191 | TGGGTTTGTACCGTA CACCACTGAGAACG CGGTGGTTGACCAG ACAAACCAC |
| Bxb1_attP_GA_ site (Artificial Sequence) | 192 | GTGGTTTGTCTGGTC AACCACCGCGGACT CAGTGGTGTACGGT ACAAACCCA | 193 | TGGGTTTGTACCGTA CACCACTGAGTCCG CGGTGGTTGACCAG ACAAACCAC |
| Bxb1_attP_AG_ site (Artificial Sequence) | 194 | GTGGTTTGTCTGGTC AACCACCGCGAGCT CAGTGGTGTACGGT ACAAACCCA | 195 | TGGGTTTGTACCGTA CACCACTGAGCTCG CGGTGGTTGACCAG ACAAACCAC |
| Bxb1_attP_CC_ site (Artificial Sequence) | 196 | GTGGTTTGTCTGGTC AACCACCGCGCCCT CAGTGGTGTACGGT ACAAACCCA | 197 | TGGGTTTGTACCGTA CACCACTGAGGGCG CGGTGGTTGACCAG ACAAACCAC |
| Bxb1_attP_TC_ site (Artificial Sequence) | 198 | GTGGTTTGTCTGGTC AACCACCGCGTCCTC AGTGGTGTACGGTA CAAACCCA | 199 | TGGGTTTGTACCGTA CACCACTGAGGACG CGGTGGTTGACCAG ACAAACCAC |
| Bxb1_attP_CT_ site (Artificial Sequence) | 200 | GTGGTTTGTCTGGTC AACCACCGCGCTCTC AGTGGTGTACGGTA CAAACCCA | 201 | TGGGTTTGTACCGTA CACCACTGAGAGCG CGGTGGTTGACCAG ACAAACCAC |
| Bxb1_attP_AA_ site (Artificial Sequence) | 202 | GTGGTTTGTCTGGTC AACCACCGCGAACT CAGTGGTGTACGGT ACAAACCCA | 203 | TGGGTTTGTACCGTA CACCACTGAGTTCGC GGTGGTTGACCAGA CAAACCAC |
| Bxb1_attP_CA_site (Artificial Sequence) | 204 | GTGGTTTGTCTGGTC AACCACCGCGCACT CAGTGGTGTACGGT ACAAACCCA | 205 | TGGGTTTGTACCGTA CACCACTGAGTGCG CGGTGGTTGACCAG ACAAACCAC |
| Bxb1_attP_AC_ site | 206 | GTGGTTTGTCTGGTC AACCACCGCGACCT | 207 | TGGGTTTGTACCGTA CACCACTGAGGTCG |

TABLE 4-continued

| DESCRIPTION/ SOURCE | FORWARD SEQUENCE (5'-3') | | REVERSE SEQUENCE (5'-3') | |
|---|---|---|---|---|
| | SEQ ID NO | Sequence | SEQ ID NO | Sequence |
| (Artificial Sequence) | | CAGTGGTGTACGGT ACAAACCCA | | CGGTGGTTGACCAG ACAAACCAC |
| Bxb1_attP_TG_ site (Artificial Sequence) | 208 | GTGGTTTGTCTGGTC AACCACCGCGTGCT CAGTGGTGTACGGT ACAAACCCA | 209 | TGGGTTTGTACCGTA CACCACTGAGCACG CGGTGGTTGACCAG ACAAACCAC |
| Bxb1_attB_46_ GT_original_ site (Artificial Sequence) | 210 | GGCCGGCTTGTCGA CGACGGCGGTCTCC GTCGTCAGGATCATC CGG | 211 | CCGGATGATCCTGA CGACGGAGACCGCC GTCGTCGACAAGCC GGCC |
| Bxb1_attB_46_ AA_site (Artificial Sequence) | 212 | GGCCGGCTTGTCGA CGACGGCGAACTCC GTCGTCAGGATCATC CGG | 213 | CCGGATGATCCTGA CGACGGAGTTCGCC GTCGTCGACAAGCC GGCC |
| Bxb1_attB_46_ GA_site (Artificial Sequence) | 214 | GGCCGGCTTGTCGA CGACGGCGGACTCC GTCGTCAGGATCATC CGG | 215 | CCGGATGATCCTGA CGACGGAGTCCGCC GTCGTCGACAAGCC GGCC |
| Bxb1_attB_46_ CA_site (Artificial Sequence) | 216 | GGCCGGCTTGTCGA CGACGGCGCACTCC GTCGTCAGGATCATC CGG | 217 | CCGGATGATCCTGA CGACGGAGTGCGCC GTCGTCGACAAGCC GGCC |
| Bxb1_attB_46_ TA_site (Artificial Sequence) | 218 | GGCCGGCTTGTCGA CGACGGCGTACTCC GTCGTCAGGATCATC CGG | 219 | CCGGATGATCCTGA CGACGGAGTACGCC GTCGTCGACAAGCC GGCC |
| Bxb1_attB_46_ AG_site (Artificial Sequence) | 220 | GGCCGGCTTGTCGA CGACGGCGAGCTCC GTCGTCAGGATCATC CGG | 221 | CCGGATGATCCTGA CGACGGAGCTCGCC GTCGTCGACAAGCC GGCC |
| Bxb1_attB_46_ GG_site (Artificial Sequence) | 222 | GGCCGGCTTGTCGA CGACGGCGGGCTCC GTCGTCAGGATCATC CGG | 223 | CCGGATGATCCTGA CGACGGAGCCCGCC GTCGTCGACAAGCC GGCC |
| Bxb1_attB_46_ CG_site (Artificial Sequence) | 224 | GGCCGGCTTGTCGA CGACGGCGCGCTCC GTCGTCAGGATCATC CGG | 225 | CCGGATGATCCTGA CGACGGAGCGCGCC GTCGTCGACAAGCC GGCC |
| Bxb1_attB_46_ TG_site (Artificial Sequence) | 226 | GGCCGGCTTGTCGA CGACGGCGTGCTCC GTCGTCAGGATCATC CGG | 227 | CCGGATGATCCTGA CGACGGAGCACGCC GTCGTCGACAAGCC GGCC |
| Bxb1_attB_46_ AC_site (Artificial Sequence) | 228 | GGCCGGCTTGTCGA CGACGGCGACCTCC GTCGTCAGGATCATC CGG | 229 | CCGGATGATCCTGA CGACGGAGGTCGCC GTCGTCGACAAGCC GGCC |
| Bxb1_attB_46_ GC_site (Artificial Sequence) | 230 | GGCCGGCTTGTCGA CGACGGCGGCCTCC GTCGTCAGGATCATC CGG | 231 | CCGGATGATCCTGA CGACGGAGGCCGCC GTCGTCGACAAGCC GGCC |
| Bxb1_attB_46_ CC_site (Artificial Sequence) | 232 | GGCCGGCTTGTCGA CGACGGCGCCCTCC GTCGTCAGGATCATC CGG | 233 | CCGGATGATCCTGA CGACGGAGGGCGCC GTCGTCGACAAGCC GGCC |
| Bxb1_attB_46_ TC_site (Artificial Sequence) | 234 | GGCCGGCTTGTCGA CGACGGCGTCCTCC GTCGTCAGGATCATC CGG | 235 | CCGGATGATCCTGA CGACGGAGGACGCC GTCGTCGACAAGCC GGCC |

TABLE 4-continued

| DESCRIPTION/ SOURCE | FORWARD SEQUENCE (5'-3') | | REVERSE SEQUENCE (5'-3') | |
|---|---|---|---|---|
| | SEQ ID NO | Sequence | SEQ ID NO | Sequence |
| Bxb1_attB_46_AT_site (Artificial Sequence) | 236 | GGCCGGCTTGTCGACGACGGCGATCTCCGTCGTCAGGATCATCCGG | 237 | CCGGATGATCCTGACGACGGAGATCGCCGTCGTCGACAAGCCGGCC |
| Bxb1_attB_46_CT_site (Artificial Sequence) | 238 | GGCCGGCTTGTCGACGACGGCGCTCTCCGTCGTCAGGATCATCCGG | 239 | CCGGATGATCCTGACGACGGAGAGCGCCGTCGTCGACAAGCCGGCC |
| Bxb1_attB_46_TT_site (Artificial Sequence) | 240 | GGCCGGCTTGTCGACGACGGCGTTCTCCGTCGTCAGGATCATCCGG | 241 | CCGGATGATCCTGACGACGGAGAACGCCGTCGTCGACAAGCCGGCC |
| Bxb1_attB_38_GT_site (Artificial Sequence) | 242 | GGCTTGTCGACGACGGCGGTCTCCGTCGTCAGGATCAT | 243 | ATGATCCTGACGACGGAGACCGCCGTCGTCGACAAGCC |
| Bxb1_attB_38_AA_site (Artificial Sequence) | 244 | GGCTTGTCGACGACGGCGAACTCCGTCGTCAGGATCAT | 245 | ATGATCCTGACGACGGAGTTCGCCGTCGTCGACAAGCC |
| Bxb1_attB_38_GA_site (Artificial Sequence) | 246 | GGCTTGTCGACGACGGCGGACTCCGTCGTCAGGATCAT | 247 | ATGATCCTGACGACGGAGTCCGCCGTCGTCGACAAGCC |
| Bxb1_attB_38_CA_site (Artificial Sequence) | 248 | GGCTTGTCGACGACGGCGCACTCCGTCGTCAGGATCAT | 249 | ATGATCCTGACGACGGAGTGCGCCGTCGTCGACAAGCC |
| Bxb1_attB_38_TA_site (Artificial Sequence) | 250 | GGCTTGTCGACGACGGCGTACTCCGTCGTCAGGATCAT | 251 | ATGATCCTGACGACGGAGTACGCCGTCGTCGACAAGCC |
| Bxb1_attB_38_AG_site (Artificial Sequence) | 252 | GGCTTGTCGACGACGGCGAGCTCCGTCGTCAGGATCAT | 253 | ATGATCCTGACGACGGAGCTCGCCGTCGTCGACAAGCC |
| Bxb1_attB_38_GG_site (Artificial Sequence) | 254 | GGCTTGTCGACGACGGCGGGCTCCGTCGTCAGGATCAT | 255 | ATGATCCTGACGACGGAGCCCGCCGTCGTCGACAAGCC |
| Bxb1_attB_38_CG_site (Artificial Sequence) | 256 | GGCTTGTCGACGACGGCGCGCTCCGTCGTCAGGATCAT | 257 | ATGATCCTGACGACGGAGCGCGCCGTCGTCGACAAGCC |
| Bxb1_attB_38_TG_site (Artificial Sequence) | 258 | GGCTTGTCGACGACGGCGTGCTCCGTCGTCAGGATCAT | 259 | ATGATCCTGACGACGGAGCACGCCGTCGTCGACAAGCC |
| Bxb1_attB_38_AC_site (Artificial Sequence) | 260 | GGCTTGTCGACGACGGCGACCTCCGTCGTCAGGATCAT | 261 | ATGATCCTGACGACGGAGGTCGCCGTCGTCGACAAGCC |
| Bxb1_attB_38_GC_site (Artificial Sequence) | 262 | GGCTTGTCGACGACGGCGGCCTCCGTCGTCAGGATCAT | 263 | ATGATCCTGACGACGGAGGCCGCCGTCGTCGACAAGCC |
| Bxb1_attB_38_CC_site (Artificial Sequence) | 264 | GGCTTGTCGACGACGGCGCCCTCCGTCGTCAGGATCAT | 265 | ATGATCCTGACGACGGAGGGCGCCGTCGTCGACAAGCC |

TABLE 4-continued

| DESCRIPTION/ SOURCE | FORWARD SEQUENCE (5'-3') SEQ ID NO | Sequence | REVERSE SEQUENCE (5'-3') SEQ ID NO | Sequence |
|---|---|---|---|---|
| Bxb1_attB_38_ TC_site (Artificial Sequence) | 266 | GGCTTGTCGACGAC GGCGTCCTCCGTCGT CAGGATCAT | 267 | ATGATCCTGACGAC GGAGGACGCCGTCG TCGACAAGCC |
| Bxb1_attB_38_ AT_site (Artificial Sequence) | 268 | GGCTTGTCGACGAC GGCGATCTCCGTCGT CAGGATCAT | 269 | ATGATCCTGACGAC GGAGATCGCCGTCG TCGACAAGCC |
| Bxb1_attB_38_ CT_site (Artificial Sequence) | 270 | GGCTTGTCGACGAC GGCGCTCTCCGTCGT CAGGATCAT | 271 | ATGATCCTGACGAC GGAGAGCGCCGTCG TCGACAAGCC |
| Bxb1_attB_38_ TT_site (Artificial Sequence) | 272 | GGCTTGTCGACGAC GGCGTTCTCCGTCGT CAGGATCAT | 273 | ATGATCCTGACGAC GGAGAACGCCGTCG TCGACAAGCC |
| Cre Lox 66 site (Artificial Sequence) | 274 | TACCGTTCGTATAAT GTATGCTATACGAA GTTAT | 275 | ATAACTTCGTATAGC ATACATTATACGAA CGGTA |
| Cre Lox 71 site (Artificial Sequence) | 276 | ATAACTTCGTATAAT GTATGCTATACGAA CGGTA | 277 | TACCGTTCGTATAGC ATACATTATACGAA GTTAT |
| TP901-1 minimal attB site (Artificial Sequence) | 278 | TTTACCTTGATTGAG ATGTTAATTGTG | 279 | CACAATTAACATCTC AATCAAGGTAAA |
| TP901-1 minimal attP site (Artificial Sequence) | 280 | GCGAGTTTTTATTTC GTTTATTTCAATTAA GGTAACTAAAAAAC TCCTTT | 281 | AAAGGAGTTTTTTAG TTACCTTAATTGAAA TAAACGAAATAAAA ACTCGC |
| PhiBT1 minimal attB site (Artificial Sequence) | 282 | CTGGATCATCTGGAT CACTTTCGTCAAAAA CCTG | 283 | CAGGTTTTTGACGAA AGTGATCCAGATGA TCCAG |
| PhiBT1 minimal attP site (Artificial Sequence) | 284 | TTCGGGTGCTGGGTT GTTGTCTCTGGACAG TGATCCATGGGAAA CTACTCAGCACCA | 285 | TGGTGCTGAGTAGTT TCCCATGGATCACTG TCCAGAGACAACAA CCCAGCACCCGAA |

Sequences of Bxb1 and RT mutants can be found in Table 6 below.

TABLE 6

| SEQ ID NO/ DESCRIPTION/ SOURCE | FORWARD SEQUENCE (5'-3') |
|---|---|
| SEQ ID NO: 286 Bxb1_mut_V368A (Artificial Sequence) | AAAAGTGTGGGCTGCAGGATCTGA |
| SEQ ID NO: 287 Bxb1_mut_E379A (Artificial Sequence) | GGAGCTGGCAGCTGTCAATGCC |

TABLE 6-continued

| SEQ ID NO/<br>DESCRIPTION/<br>SOURCE | FORWARD SEQUENCE (5'-3') |
|---|---|
| SEQ ID NO: 288<br>Bxb1_mut_E383A<br>(Artificial Sequence) | AGTCAATGCCGCTCTCGTGGA |
| SEQ ID NO: 403<br>RT_mut_L139P<br>(Artificial Sequence) | TTGAGCGGGCCCCCACCGT |
| SEQ ID NO: 289<br>RT_mut_E562Q<br>(Artificial Sequence) | CAGCGGGCTCAGCTGATAGCA |
| SEQ ID NO: 290<br>RT_mut_D653N<br>(Artificial Sequence) | CGGATGGCTAACCAAGCGGCC |
| SEQ ID NO: 404<br>RT(1-478)_Sto7d<br>fusion | atgactcactatcaggccttgcttaggacacggaccgggtccagttcggaccggtggtagccctgaaccc<br>ggctacgctgctcccactgcctgaggaagggctgcaacacaactgccttgatGGGACAGGTGG<br>CGGTGGTGTCACCGTCAAGTTCAAGTACAAGGGTGAGGAACTT<br>GAAGTTGATATTAGCAAAATCAAGAAGGTTTGGCGCGTTGGTA<br>AAATGATATCTTTTACTTATGACGACAACGGCAAGACAGGTAG<br>AGGGGCAGTGTCTGAGAAAGACGCCCCCAAGGAGCTGTTGCAA<br>ATGTTGGAAAAGTCTGGGAAAAAGtctggcggctcaaaaagaaccgccgacgg<br>cagcgaattcgagcccaagaagaagaggaaagtc |

Sequences of primers, probes and restriction enzymes used in ddPCR readout can be found in Table 7 below.

TABLE 7

| Locus | Cargo | SEQ ID NO: | Forward Primer | SEQ ID NO: | Reverse Primer | Probe | SEQ ID NO: | Restriction Enzymes |
|---|---|---|---|---|---|---|---|---|
| ACTB | GFP (pDY0186) | 291 | CCCG GCTTC CTTTG TCC | 292 | GAAC TCCAC GCCG TTCA | /56-FAM/C GGC TTG T/ZEN/ C GAC GAC GGC G/3IAB kFQ/ | 405 | Eco91I, HindIII |
| ACTB | TP90-1 GFP (pDY0333) | 293 | CCCG GCTTC CTTTG TCC | 294 | AACC ACAA CTAG AATG CAGT GA | /56-FAM/T G CTA TTG C/ZEN/ T TTA TTT GTG GGC CCG /3IABk FQ/ | 406 | None |
| ACTB | TP90-1 rc GFP (pDY0334) | 295 | CCCG GCTTC CTTTG TCC | 296 | GAAC TCCAC GCCG TTCA | /56-FAM/ CC ATG AAG A/ZEN/ T CGA GTG CCG CAT CA/3I ABkF Q/ | 407 | None |

TABLE 7-continued

| Locus | Cargo | SEQ ID NO: | Forward Primer | SEQ ID NO: | Reverse Primer | Probe | SEQ ID NO: | Restriction Enzymes |
|---|---|---|---|---|---|---|---|---|
| ACTB | PhiBT1 GFP (pDY0367) | 297 | CCCGGCTTCCTTTGTCC | 298 | AACCACAACTAGAATGCAGTGA | /56-FAM/TG CTA TTG C/ZEN/T TTA TTT GTG GGC CCG /3IABkFQ/ | 406 | None |
| ACTB | PhiBT1 rc GFP (pDY0368) | 299 | CCCGGCTTCCTTTGTCC | 300 | GAACTCCACGCCGTTCA | /56-FAM/CC ATG AAG A/ZEN/T CGA GTG CCG CAT CA/3IABkFQ/ | 407 | None |
| LMNB1 | GFP (pDY0186) | 301 | TCCTTATCACGGTCCCGCTCG | 302 | GAACTCCACGCCGTTCA | /56-FAM/CC ATG AAG A/ZEN/T CGA GTG CCG CAT CA/3IABkFQ/ | 407 | Eco91I, HindIII |
| NOLC1 | GFP (pDY0186) | 303 | CGTCGACAACGGTAGTG | 304 | GAACTCCACGCCGTTCA | /56-FAM/CC ATG AAG A/ZEN/T CGA GTG CCG CAT CA/3IABkFQ/ | 407 | Eco91I, HindIII |
| SUPT16H | GFP pDY0186) | 305 | TCGCGTGATTCTCGGAAC | 306 | GAACTCCACGCCGTTCA | /56-FAM/CC ATG AAG A/ZEN/T CGA GTG CCG CAT CA/3IABkFQ/ | 407 | Eco91I, HindIII |
| SRRM2 | GFP (pDY0186) | 307 | GGGCGGTAAGTGGTTAGTTT | 308 | GAACTCCACGCCGTTCA | /56-FAM/CC ATG AAG A/ZEN/ | 407 | Eco91I, HindIII |

TABLE 7-continued

| Locus | Cargo | SEQ ID NO: | Forward Primer | SEQ ID NO: | Reverse Primer | Probe | SEQ ID NO: | Restriction Enzymes |
|---|---|---|---|---|---|---|---|---|
| | | | | | | T CGA GTG CCG CAT CA/3IABkFQ/ | | |
| DEPDC4 | GFP (pDY0186) | 309 | AAGAGGCGGAGCCAGTA | 310 | GAACTCCACGCCGTTCA | /56-FAM/CC ATG AAG A/ZEN/T CGA GTG CCG CAT CA/3IABkFQ/ | 407 | Eco91I, HindIII |
| NES | GFP (pDY0186) | 311 | CTCCCTTCTCCCGGTGCCC | 312 | GAACTCCACGCCGTTCA | /56-FAM/CC GGC TTG T/ZEN/C GAC GAC GGC G/3IABkFQ/ | 405 | Eco91I, HindIII |
| ACTB | ACTB HITI template GFP (pDY0219) | 313 | CCCGGCTTCCTTTGTCC | 314 | GAACTCCACGCCGTTCA | /56-FAM/CC ATG AAG A/ZEN/T CGA GTG CCG CAT CA/3IABkFQ/ | 407 | Eco91I |
| SRRM2 | SRRM2 HITI template GFP (aRY0182_A2) | 315 | GGGCGGTAAGTGGTTAGTTT | 316 | GAACTCCACGCCGTTCA | /56-FAM/CC ATG AAG A/ZEN/T CGA GTG CCG CAT CA/3IABkFQ/ | 407 | Eco91I |
| NOLC1 | NOLC1 HITI template GFP (aRY0182_A3) | 317 | CGTCGACAACGGTAGTG | 318 | GAACTCCACGCCGTTCA | /56-FAM/CC ATG AAG A/ZEN/T CGA GTG CCG CAT | 407 | Eco91I |

TABLE 7-continued

| Locus | Cargo | SEQ ID NO: | Forward Primer | SEQ ID NO: | Reverse Primer | Probe | SEQ ID NO: | Restriction Enzymes |
|---|---|---|---|---|---|---|---|---|
| | | | | | | CA/3I ABkFQ/ | | |
| DEPDC4 | DEPDC4 HITI template GFP (aRY0182_A5) | 319 | AAGAGGCGGAGCCAGTA | 320 | GAACTCCACGCCGTTCA | /56-FAM/CCATGAAGA/ZEN/TCGAGTGCCGCATCA/3IABkFQ/ | 407 | Eco91I |
| NES | NES HITI template GFP (aRY0182_A7) | 321 | CTCCCTTCTCCCGGTGCCC | 322 | GAACTCCACGCCGTTCA | /56-FAM/CCATGAAGA/ZEN/TCGAGTGCCGCATCA/3IABkFQ/ | 407 | Eco91I |
| LMNB1 | LMNB1 HITI template GFP (aRY0182_A4) | 323 | TCCTTATCACGGTCCCGCTCG | 324 | GAACTCCACGCCGTTCA | /56-FAM/CCATGAAGA/ZEN/TCGAGTGCCGCATCA/3IABkFQ/ | 407 | Eco91I |
| ACTB | SERPINA (pDY0298) | 325 | CCCGGCTTCCTTTGTCC | 326 | GGCCTGCCAGCAGGAGGA | /56-FAM/CCGGCTTGT/ZEN/CGACGACGGCG/3IABkFQ/ | 405 | EcoRI, XhoI, HindIII |
| ACTB | CPS1 (pDY299) | 327 | CCCGGCTTCCTTTGTCC | 328 | GGTGTGCAGTCACATTGGTAAAGCC | /56-FAM/ACAGCTTTC/ZEN/AAAGTGGTGAGGACACT/3IA | 408 | XhoI, HindIII |

TABLE 7-continued

| Locus | Cargo | SEQ ID NO: | Forward Primer | SEQ ID NO: | Reverse Primer | Probe | SEQ ID NO: | Restriction Enzymes |
|---|---|---|---|---|---|---|---|---|
| | | | | | | BkFQ/ | | |
| ACTB | CFTR (pDY0373) | 329 | CCCG GCTTC CTTTG TCC | 330 | GATG GGTCT AGTC CAGC TAAA G | /56-FAM/ TAC GGT ACA/ ZEN/ AAC CC ACC CGA GAG A/3I ABkF Q/ | 409 | Eco91I, HindIII |
| ACTB | NYESO TRAC (pDY0318) | 331 | CCCG GCTTC CTTTG TCC | 332 | GAGA GACA AGGC TGCA CA | /56-FAM/ TAC GGT ACA/ ZEN/ AAC CC ACC CGA GAG A/3I ABkF Q/ | 409 | Eco47III, HindIII |
| NC_000003 | GFP (pDY0186) | 333 | CCAG GTGA GAGT CAGG GTAG TGTTC A | 334 | GAAC TCCAC GCCG TTCA | /56-FAM/ CC GGC TTG T/ZEN/ C GAC GAC GGC G/3I ABkF Q/ | 405 | Eco91I, HindIII |
| NC_000002 | GFP (pDY0186) | 335 | AGGG ACCTT TGCCT GTGT GAGT C | 336 | GAAC TCCAC GCCG TTCA | /56-FAM/ CC GGC TTG T/ZEN/ C GAC GAC GGC G/3I ABkF Q/ | 405 | Eco91I, HindIII |
| NC_000009 | GFP (pDY0186) | 337 | TCAG CTCTG TGCTG AGGC GAA | 338 | GAAC TCCAC GCCG TTCA | /56-FAM/ CC GGC TTG T/ZEN/ C GAC GAC GGC G/3I ABkF Q/ | 405 | Eco91I, HindIII |

TABLE 7-continued

| Locus | Cargo | SEQ ID NO: | Forward Primer | SEQ ID NO: | Reverse Primer | Probe | SEQ ID NO: | Restriction Enzymes |
|---|---|---|---|---|---|---|---|---|
| chr6: 149045959 | GFP (pDY0186) | 339 | AAGCCATCTCCCAGAATATCTGCTTAGAAATG | 340 | GAACTCCACGCCGTTCA | /56-FAM/CCGGCTTGT/ZEN/CGACGACGGCG/3IABkFQ/ | 405 | Eco91I, HindIII |
| chr16: 18607730 | GFP (pDY0186) | 341 | GAGAGGAGCAACAGTGAGCATGATG | 342 | GAACTCCACGCCGTTCA | /56-FAM/CCGGCTTGT/ZEN/CGACGACGGCG/3IABkFQ/ | 405 | Eco91I, HindIII |
| chr6: 149045959 | ACTB HITI template GFP (pDY0219) | 343 | AAGCCATCTCCCAGAATATCTGCTTAGAAATG | 344 | GAACTCCACGCCGTTCA | /56-FAM/CCGGCTTGT/ZEN/CGACGACGGCG/3IABkFQ/ | 405 | Eco91I |
| chr16: 18607730 | ACTB HITI template GFP (pDY0219) | 345 | GAGAGGAGCAACAGTGAGCATGATG | 346 | GAACTCCACGCCGTTCA | /56-FAM/CCGGCTTGT/ZEN/CGACGACGGCG/3IABkFQ/ | 405 | Eco91I |
| ACTB | CAG_Kozak_bGH_therapeutic_genes generic minicircle | 347 | CCCGGCTTCCTTTGTCC | 348 | GGCTATGAACTAATGACCCCGT | /56-FAM/CCGGCTTGT/ZEN/CGACGACGGCG/3IABkFQ/ | 405 | Eco91I, HindIII |
| ACTB | Hibit-SERPINA (pDY045) | 349 | CCCGGCTTCCTTTGTCC | 350 | GGCCTGCCAGCAGGAGGA | /56-FAM/CCGGCTTG | 405 | EcoRI, XhoI, HindIII |

TABLE 7-continued

| Locus | Cargo | SEQ ID NO: | Forward Primer | SEQ ID NO: | Reverse Primer | Probe | SEQ ID NO: | Restriction Enzymes |
|---|---|---|---|---|---|---|---|---|
| | | | | | | T/ZEN/C GACGAC GGCG/3IABkFQ/ | | |
| ACTB | Hibit-CPS1 (pDY406) | 351 | CCCG GCTTC CTTTG TCC | 352 | GGTG TGCA GTCA CATTG GTAA AGCC | /56-FAM/AC AGC TTT C/ZEN/A AAG TGG TGA GGA CAC T/3IA BkFQ/ | 408 | XhoI, HindIII |

Sequences of primers used for NGS readout can be found in Table 8 below.

TABLE 8

| SEQ ID NO/DESCRIPTION/SOURCE | ID | SEQUENCE (5'-3') |
|---|---|---|
| SEQ ID NO: 353 N-term ACTB Tn5 readout F 1 (Artificial Sequence) | PD0966 | ACACTCTTTCCCTACACGACGCTCTTCCGATCTCCGAC CTCGGC TCACAGCG |
| SEQ ID NO: 354 N-term ACTB Tn5 readout F 2 (Artificial Sequence) | PD0967 | ACACTCTTTCCCTACACGACGCTCTTCCGATCTACCGA CCTCGG CTCACAGCG |
| SEQ ID NO: 355 N-term ACTB Tn5 readout F 3 (Artificial Sequence) | PD0968 | ACACTCTTTCCCTACACGACGCTCTTCCGATCTGACCG ACCTCG GCTCACAGCG |
| SEQ ID NO: 356 N-term ACTB Tn5 readout F 4 (Artificial Sequence) | PD0969 | ACACTCTTTCCCTACACGACGCTCTTCCGATCTTGACC GACCTC GGCTCACAGCG |
| SEQ ID NO: 357 N-term ACTB Tn5 readout F 5 (Artificial Sequence) | PD0970 | ACACTCTTTCCCTACACGACGCTCTTCCGATCTCTGAC CGACCT CGGCTCACAGCG |
| SEQ ID NO: 358 N-term ACTB Tn5 readout F 6 (Artificial Sequence) | PD0971 | ACACTCTTTCCCTACACGACGCTCTTCCGATCTACTGA CCGACC TCGGCTCACAGCG |
| SEQ ID NO: 359 N-term ACTB Tn5 readout F 7 (Artificial Sequence) | PD0972 | ACACTCTTTCCCTACACGACGCTCTTCCGATCTTACTG ACCGAC CTCGGCTCACAGCG |
| SEQ ID NO: 360 N-term ACTB Tn5 readout F 8 (Artificial Sequence) | PD0973 | ACACTCTTTCCCTACACGACGCTCTTCCGATCTGTACT GACCGA CCTCGGCTCACAGCG |

TABLE 8-continued

| SEQ ID NO/DESCRIPTION/SOURCE | ID | SEQUENCE (5'-3') |
|---|---|---|
| SEQ ID NO: 361<br>ACTB N-term NGS<br>R for Cas14 indels<br>(Artificial Sequence) | FP0952 | GTGACTGGAGTTCAGACGTGTGCTCTTCCGATCTCCAC CCAGCC AGCTCCC |
| SEQ ID NO: 362<br>NGS EMX1<br>Forward 1<br>(Artificial Sequence) | PD0313 | ACACTCTTTCCCTACACGACGCTCTTCCGATCTCCGGT GGCGCAT TGCCAC |
| SEQ ID NO: 363<br>NGS EMX1<br>Forward 2<br>(Artificial Sequence) | PD0314 | ACACTCTTTCCCTACACGACGCTCTTCCGATCTACCGG TGGCGCA TTGCCAC |
| SEQ ID NO: 364<br>NGS EMX1<br>Forward 3<br>(Artificial Sequence) | PD0315 | ACACTCTTTCCCTACACGACGCTCTTCCGATCTGACCG GTGGCGC ATTGCCAC |
| SEQ ID NO: 365<br>NGS EMX1<br>Forward 4<br>(Artificial Sequence) | PD0316 | ACACTCTTTCCCTACACGACGCTCTTCCGATCTTGACC GGTGGCG CATTGCCAC |
| SEQ ID NO: 366<br>NGS EMX1<br>Forward 5<br>(Artificial Sequence) | PD0317 | ACACTCTTTCCCTACACGACGCTCTTCCGATCTCTGAC CGGTGGC GCATTGCCAC |
| SEQ ID NO: 367<br>NGS EMX1<br>Forward 6<br>(Artificial Sequence) | PD0318 | ACACTCTTTCCCTACACGACGCTCTTCCGATCTACTGA CCGGTGG CGCATTGCCAC |
| SEQ ID NO: 368<br>NGS EMX1<br>Forward 7<br>(Artificial Sequence) | PD0319 | ACACTCTTTCCCTACACGACGCTCTTCCGATCTTACTG ACCGGTG GCGCATTGCCAC |
| SEQ ID NO: 369<br>NGS EMX1<br>Forward 8<br>(Artificial Sequence) | PD0320 | ACACTCTTTCCCTACACGACGCTCTTCCGATCTGTACT GACCGG GGCGCATTGCCAC |
| SEQ ID NO: 370<br>NGS EMX1 Reverse<br>(Artificial Sequence) | PD0321 | GTGACTGGAGTTCAGACGTGTGCTCTTCCGATCTCAGA GTCCAGC TTGGGCCCA |

Sequences of off-target sites can be found in Table 9 below.

TABLE 9

| SEQ ID NO/DESCRIPTION/SOURCE | SEQUENCE (5'-3') |
|---|---|
| SEQ ID NO: 371<br>Cas9_chr6:149045959<br>(Artificial Sequence) | GATATTTTCCCAGCTCACCA |
| SEQ ID NO: 372<br>Cas9_chr16:18607730<br>(Artificial Sequence) | TCTATTCTCCCAGCTCCCCA |
| SEQ ID NO: 373<br>Bxb1_NC_000002<br>(Artificial Sequence) | AGCGGCTTCTGTCTCTGTGAGTGAGCTGGCGGTCTCCGTC |

TABLE 9-continued

| SEQ ID NO/DESCRIPTION/SOURCE | SEQUENCE (5'-3') |
|---|---|
| SEQ ID NO: 374 Bxb1_NC_000003 (Artificial Sequence) | GACTAGCCCACGCTCCGGTTCTGAGCCGCGACGGCGGTCTCCG |
| SEQ ID NO: 375 Bxb1_NC_000009 (Artificial Sequence) | CCCAGGGTCCCATGCGCTCCCCGGCCCTGACGGCGGTCTCC |

Linker sequences in Table 10 below.

TABLE 10

| Description | Sequence (5'-3') | Amino acid sequence |
|---|---|---|
| A-P2A | GGAAGCGGAGCTACTAACTTCAGCCTGCTGAAGCAGGCTGGCGACGTGGAGGAGAACCCTGGACCT (SEQ ID NO: 410) | GSGATNFSLLKQAGDVEENPGP (SEQ ID NO: 418) |
| B-(GGGS)3 | GGGGGAGGAGGTTCTGGAGGCGGAGGCTCCGGAGGCGGAGGGTCA (SEQ ID NO: 411) | GGGGSGGGGSGGGGS (SEQ ID NO: 419) |
| C-GGGGS | GGAGGTGGCGGGAGC (SEQ ID NO: 412) | GGGGS (SEQ ID NO: 420) |
| D-PAPAP | CCCGCACCAGCGCCT (SEQ ID NO: 413) | PAPAP (SEQ ID NO: 421) |
| E-(EAAAK)3 | GAGGCAGCTGCCAAGGAAGCCGCTGCCAAGGAGGCGGCCGCAAAG (SEQ ID NO: 414) | EAAAKEAAAKEAAAK (SEQ ID NO: 422) |
| F-XTEN | AGTGGGAGCGAGACCCCTGGGACTAGCGAGTCAGCTACACCCGAAAGC (SEQ ID NO: 415) | SGSETPGTSESATPES (SEQ ID NO: 423) |
| G-(GGS)6 | GGGGGGTCAGGTGGATCCGGCGGAAGTGGCGGATCCGGTGGATCTGGCGGCAGT (SEQ ID NO: 416) | GGSGGSGGSGGSGGSGGS (SEQ ID NO 424) |
| H-EAAAK | GAAGCTGCTGCTAAG (SEQ ID NO: 417) | EAAAK (SEQ ID NO: 425) |

Exemplary fusion sequences in Table 11 below.

| Description | Sequence |
|---|---|
| SpCas9-XTEN-RT(1-478)-Sto7d-GGGGS-BxbINT Amino acid SEQ ID NO: 376 | MKRTADGSEFESPKKKRKVDKKYSIGLDIGTNSVGWAVITDEYKVPS KKFKVLGNTDRHSIKKNLIGALLFDSGETAEATRLKRTARRRYTRR KNRICYLQEIFSNEMAKVDDSFFHRLEESFLVEEDKKHERHPIFGNI VDEVAYHEKYPTIYHLRKKLVDSTDKADLRLIYLALAHMIKFRGHF LIEGDLNPDNSDVDKLFIQLVQTYNQLFEENPINASGVDAKAILSAR LSKSRRLENLIAQLPGEKKNGLFGNLIALSLGLTPNFKSNFDLAEDA KLQLSKDTYDDDLDNLLAQIGDQYADLFLAAKNLSDAILLSDILRVN TEITKAPLSASMIKRYDEHHQDLTLLKALVRQQLPEKYKEIFFDQS KNGYAGYIDGGASQEEFYKFIKPILEKMDGTEELLVKLNREDLLRK QRTFDNGSIPHQIHLGELHAILRRQEDFYPFLKDNREKIEKILTFRIP YYVGPLARGNSRFAWMTRKSEETITPWNFEEVVDKGASAQSFIER MTNFDKNLPNEKVLPKIISLLYEYFTVYNELTKVKYVTEGMRKPAF LSGEQKKAIVDLLFKTNRKVTVKQLKEDYFKKIECFDSVEISGVED RFNASLGTYHDLLKIIKDKDFLDNEENEDILEDIVLTLTLFEDREMIE ERLKTYAHLFDDKVMKQLICRRRYTGWGRLSRKLINGIRDKQSGK TILDFLKSDGFANRNFMQLIHDDSLTFKEDIQKAQVSGQGDSLHEHI ANLAGSPAIKKGILQTVKVVDELVKVMGRHKPENIVIEMARENQTT QKGQKNSRERMKRIEEGIKELGSQILKEHPVENTQLQNEKLYLYYL QNGRDMYVDQELDINRLSDYDVDAIVPQSFLKDDSIDNKVLTRSDK NRGKSDNVPSEEVVKKMKNYWRQLLNAKLITQRKFDNLTKAERG |

| Description | Sequence |
|---|---|
| | GLSELDKAGFIKRQLVETRQITKHVAQILDSRMNTKYDENDKLIRE |
| | VKVITLKSKLVSDFRKDFQFYKVREINNYHHAHDAYLNAVVGTALI |
| | KKYPKLESEFVYGDYKVYDVRKMIAKSEQEIGKATAKYFFYSNIMN |
| | FFKTEITLANGEIRKRPLIETNGETGEIVWDKGRDFATVRKVLSMP |
| | QVNIVKKTEVQTGGFSKESILPKRNSDKLIARKKDWDPKKYGGFDS |
| | PTVAYSVLVVAKVEKGKSKKLKSVKELLGITIMERSSFEKNPIDFLE |
| | AKGYKEVKKDLIIKLPKYSLFELENGRKRMLASAGELQKGNELAL |
| | PSKYVNFLYLASHYEKLKGSPEDNEQKQLFVEQHKHYLDEHEQISE |
| | FSKRVILADANLDKVLSAYNKHRDKPIREQAENIIHLFTLTNLGAPA |
| | AFKYFDTTIDRKRYTSTKEVLDATLIHQSITGLYETRIDLSQLGGDS |
| | GGSSGGSSGSETPGTSESATPESSGSETPGTSESATPESSGSETPGTSESAT |
| | PESSGGSSGGSSTLNIEDEYRLHETSKEPDVSLGSTWLSDFPQAWAET |
| | GGMGLAVRQAPLIIPLKATSTPVSIKQVPMSQEARLGIKPHIQRLLD |
| | QGILVPCQSPWNTPLLPVKKPGTNDYRPVQDLREVNKRVEDIHPTV |
| | PNPYNLLSGPPPSHQWYTVLDLKDAFFCLRLHPTSQPLFAFEWRDP |
| | EMGISGQLTWTRLPQGFKNSPTLFNEALHRDLADFRIQHPDLILLQ |
| | YVDDLLLAATSELDCQQGTRALLQTLGNLGYRASAKKAQKQKQV |
| | KYLGYLLKEGQRWLTEARKETVMGQPTPKTPRQLREFLGKAGFC |
| | RLFIPGFAEMAAPLYPLTKPGTLFNWGPDQQKAYQEIKQALLTAPA |
| | LGLPDLTKPFELFVDEKQGYAKGVLTQKLGPWRRPVAYLSKKLDP |
| | VAAGWPPCLRMVAAIAVLTKDAGKLTMGQPLVILAPHAVEALVK |
| | QPPDRWLSNARNITHYQALLLDTDRVQFGPVVALNPATLLPLPEEG |
| | LQIINCLDGTGGGGVTVKFKYKGEELEVDISKIKKVWRVGKNIISFT |
| | YDDNGKTGRGAVSEKDAPKELLQMLEKSGKKSGGSKRTADGSEFE |
| | PKKKRKVGGGGSPKKKRKVYPYDVPDYAGSRALVVIRLSRVTDATTS |
| | PERQLESCQQLCAQRGWDVVGVAEDLDVSGAVDPFDRKRRPNLAR |
| | WLAFEEQPFDVIVAYRVDRLTRSIRHLQQLVHWAEDHKKLVVSAT |
| | EAHFDTTTPFAAVVIALMGTVAQMELEAIKERNRSAAHFNIRAGKY |
| | RGSLPPWGYLPTRVDGEWRLVPDPVQRERILEVYHRVVDNHEPLH |
| | LVAHDLNRRGVLSPKDYFAQLQGREPQGREWSATALKRSMISEAM |
| | LGYATLNGKTVRDDDGAPLVRAEPILTREQLEALRAELVKTSRAKP |
| | AVSTPSLLLRVLFCAVCGEPAYKFAGGGRKHPRYRCRSMGFPKHC |
| | GNGTVAMAEWDAFCEEQVLDLLGDAERLEKVWVAGSDSAVELAE |
| | VNAELVDLTSLIGSPAYRAGSPQREALDARIAALAARQEELEGLEAR |
| | PSGWEWRETGQRFGDWWREQDTAAKNTWLRSMNVRLTFDVRGG |
| | LTRTIDFGDLQEYEQHLRLGSVVERLHTGMS |
| SpCas9-XTEN-RT(1-478)-Sto7d-GGGGS-BxbINT Nucleic acid SEQ ID NO: 377 | ATGAAACGGACAGCCGACGGAAGCGAGTTCGAGTCACCAAAGAAG |
| | AAGCGGAAAGTCGACAAGAAGTACAGCATCGGCCTGGACATCGGCA |
| | CCAACTCTGTGGGCTGGGCCGTGATCACCGACGAGTACAAGGTGCC |
| | CAGCAAGAAATTCAAGGTGCTGGGCAACACCGACCGGCACGATC |
| | AAGAAGAACCTGATCGGAGCCCTGCTGTTCGACAGCGGCGAAACAG |
| | CCGAGGCCACCCGGCTGAAGAGAACCGCCAGAAGAAGATACACCA |
| | GACGGAAGAACCGGATCTGCTATCTGCAAGAGATCTTCAGCAACGA |
| | GATGGCCAAGGTGGACGACAGCTTCTTCCACAGACTGGAAGAGTCC |
| | TTCCTGGTGGAAGAGGATAAGAAGCACGAGCGGCACCCCATCTTCG |
| | GCAACATCGTGGACGAGGTGGCCTACCACGAGAAGTACCCCACCAT |
| | CTACCACCTGAGAAAGAAACTGGTGGACAGCACCGACAAGGCCGAC |
| | CTGCGGCTGATCTATCTGGCCCTGGCCCACATGATCAAGTTCCGGGG |
| | CCACTTCCTGATCGAGGGCGACCTGAACCCCGACAACAGCGACGTG |
| | GACAAGCTGTTCATCCAGCTGGTGCAGACCTACAACCAGCTGTTCGA |
| | GGAAAACCCCATCAACGCCAGCGGCGTGGACGCCAAGGCCATCCTG |
| | TCTGCCAGACTGAGCAAGAGCAGACGGCTGGAAAATCTGATCGCCC |
| | AGCTGCCCGGCGAGAAGAAGAATGGCCTGTTCGGAAACCTGATTGC |
| | CCTGAGCCTGGGCCTGACCCCCAACTTCAAGAGCAACTTCGACCTGG |
| | CCGAGGATGCCAAACTGCAGCTGAGCAAGGACACCTACGACGACGA |
| | CCTGGACAACCTGCTGGCCCAGATCGGCGACCAGTACGCCGACCTG |
| | TTTCTGGCCGCCAAGAACCTGTCCGACGCCATCCTGCTGAGCGACAT |
| | CCTGAGAGTGAACACCGAGATCACCAAGGCCCCCCTGAGCGCCTCT |
| | ATGATCAAGAGATACGACGAGCACCACCAGGACCTGACCCTGCTGA |
| | AAGCTCTCGTGCGGCAGCAGCTGCCTGAGAAGTACAAAGAGATTTT |
| | CTTCGACCAGAGCAAGAACGGCTACGCCGGCTACATTGACGGCGGA |
| | GCCAGCCAGGAAGAGTTCTACAAGTTCATCAAGCCCATCCTGGAAA |
| | AGATGGACGGCACCGAGGAACTGCTCGTGAAGCTGAACAGAGAGG |
| | ACCTGCTGCGGAAGCAGCGGACCTTCGACAACGGCAGCATCCCCCA |
| | CCAGATCCACCTGGGAGAGCTGCACGCCATTCTGCGGCGGCAGGAA |
| | GATTTTTACCCATTCCTGAAGGACAACCGGGAAAAGATCGAGAAGA |
| | TCCTGACCTTCCGCATCCCCTACTACGTGGGCCCTCTGGCCAGGGGA |
| | AACAGCAGATTCGCCTGGATGACCAGAAAGAGCGAGGAAACCATCA |
| | CCCCCTGGAACTTCGAGGAAGTGGTGGACAAGGGCGCTTCCGCCCA |
| | GAGCTTCATCGAGCGGATGACCAACTTCGATAAGAACCTGCCCAAC |
| | GAGAAGGTGCTGCCCAAGCACAGCCTGCTGTACGAGTACTTCACCG |
| | TGTATAACGAGCTGACCAAAGTGAAATACGTGACCGAGGGAATGAG |
| | AAAGCCCGCCTTCCTGAGCGGCGAGCAGAAAAAGGCCATCGTGGAC |
| | CTGCTGTTCAAGACCAACCGGAAAGTGACCGTGAAGCAGCTGAAAG |
| | AGGACTACTTCAAGAAAATCGAGTGCTTCGACTCCGTGGAAATCTCC |
| | GGCGTGGAAGATCGGTTCAACGCCTCCCTGGGCACATACCACGATC |

| Description | Sequence |
|---|---|
| | TGCTGAAAATTATCAAGGACAAGGACTTCCTGGACAATGAGGAAAA |
| | CGAGGACATTCTGGAAGATATCGTGCTGACCCTGACACTGTTTGAGG |
| | ACAGAGAGATGATCGAGGAACGGCTGAAAACCTATGCCCACCTGTT |
| | CGACGACAAAGTGATGAAGCAGCTGAAGCGGCGGAGATACACCGG |
| | CTGGGGCAGGCTGAGCCGGAAGCTGATCAACGGCATCCGGGACAAG |
| | CAGTCCGGCAAGACAATCCTGGATTTCCTGAAGTCCGACGGCTTCGC |
| | CAACAGAAACTTCATGCAGCTGATCCACGACGACAGCCTGACCTTT |
| | AAAGAGGACATCCAGAAAGCCCAGGTGTCCGGCCAGGGCGATAGCC |
| | TGCACGAGCACATTGCCAATCTGGCCGGCAGCCCCGCCATTAAGAA |
| | GGGCATCCTGCAGACAGTGAAGGTGGTGGACGAGCTCGTGAAAGTG |
| | ATGGGCCGGCACAAGCCCGAGAACATCGTGATCGAAATGGCCAGAG |
| | AGAACCAGACCACCCAGAAGGGACAGAAGAACAGCCGCGAGAGAA |
| | TGAAGCGGATCGAAGAGGGCATCAAAGAGCTGGGCAGCCAGATCCT |
| | GAAAGAACACCCCGTGGAAAACACCCAGCTGCAGAACGAGAAGCT |
| | GTACCTGTACTACCTGCAGAATGGGCGGGATATGTACGTGGACCAG |
| | GAACTGGACATCAACCGGCTGTCCGACTACGATGTGGACGCTATCG |
| | TGCCTCAGAGCTTTCTGAAGGACGACTCCATCGACAACAAGGTGCT |
| | GACCAGAAGCGACAAGAACCGGGGCAAGAGCGACAACGTGCCCTC |
| | CGAAGAGGTCGTGAAGAAGATGAAGAACTACTGGCGGCAGCTGCTG |
| | AACGCCAAGCTGATTACCCAGAGAAAGTTCGACAATCTGACCAAGG |
| | CCGAGAGAGGCGGCCTGAGCGAACTGGATAAGGCCGGCTTCATCAA |
| | GAGACAGCTGGTGGAAACCCGGCAGATCACAAAGCACGTGGCACA |
| | GATCCTGGACTCCCGGATGAACACTAAGTACGACGAGAATGACAAG |
| | CTGATCCGGGAAGTGAAAGTGATCACCCTGAAGTCCAAGCTGGTGT |
| | CCGATTTCCGGAAGGATTTCCAGTTTTACAAAGTGCGCGAGATCAAC |
| | AACTACCACCACGCCCACGACGCCTACCTGAACGCCGTCGTGGGAA |
| | CCGCCCTGATCAAAAAGTACCCTAAGCTGGAAAGCGAGTTCGTGTA |
| | CGGCGACTACAAGGTGTACGACGTGCGGAAGATGATCGCCAAGAGC |
| | GAGCAGGAAATCGGCAAGGCTACCGCCAAGTACTTCTTCTACAGCA |
| | ACATCATGAACTTTTTCAAGACCGAGATTACCCTGGCCAACGGCGA |
| | GATCCGGAAGCGGCCTCTGATCGAGACAAACGGCGAAACCGGGGA |
| | GATCGTGTGGGATAAGGGCCGGGATTTTGCCACCGTGCGGAAAGTG |
| | CTGAGCATGCCCCAAGTGAATATCGTGAAAAAGACCGAGGTGCAGA |
| | CAGGCGGCTTCAGCAAAGAGTCTATCCTGCCCAAGAGGAACAGCGA |
| | TAAGCTGATCGCCAGAAAGAAGGACTGGGACCCTAAGAAGTACGGC |
| | GGCTTCGACAGCCCCACCGTGGCCTATTCTGTGCTGGTGGTGGCCAA |
| | AGTGGAAAAGGGCAAGTCCAAGAAACTGAAGAGTGTGAAAGAGCT |
| | GCTGGGGATCACCATCATGGAAAGAAGCAGCTTCGAGAAGAATCCC |
| | ATCGACTTTCTGGAAGCCAAGGGCTACAAAGAAGTGAAAAAGGACC |
| | TGATCATCAAGCTGCCTAAGTACTCCCTGTTCGAGCTGGAAAACGGC |
| | CGGAAGAGAATGCTGGCCTCTGCCGGCGAACTGCAGAAGGGAAACG |
| | AACTGGCCCTGCCCTCCAAATATGTGAACTTCCTGTACCTGGCCAGC |
| | CACTATGAGAAGCTGAAGGGCTCCCCCGAGGATAATGAGCAGAAAC |
| | AGCTGTTTGTGGAACAGCACAAGCACTACCTGGACGAGATCATCGA |
| | GCAGATCAGCGAGTTCTCCAAGAGAGTGATCCTGGCCGACGCTAAT |
| | CTGGACAAAGTGCTGTCCGCCTACAACAAGCACCGGGATAAGCCCA |
| | TCAGAGAGCAGGCCGAGAATATCATCCACCTGTTTACCCTGACCAAT |
| | CTGGGAGCCCCTGCCGCCTTCAAGTACTTTGACACCACCATCGACCG |
| | GAAGAGGTACACCAGCACCAAAGAGGTGCTGGACGCCACCCTGATC |
| | CACCAGAGCATCACCGGCCTGTACGAGACACGGATCGACCTGTCTC |
| | AGCTGGGAGGTGACTCTGGAGGATCTAGCGGAGGATCCTCTGGCAG |
| | CGAGACACCAGGAACAAGCGAGTCAGCAACACCAGAGAGCTCTGGT |
| | AGCGAGACACCCGGTACCAGTGAAAGCGCCACGCCAGAAAGCAGT |
| | GGGAGTGAGACTCCGGGTACATCTGAATCAGCGACACCGGAATCAA |
| | GTGGCGGCAGCAGCGGCGGCAGCAGCACCCTAAATATAGAAGATGA |
| | GTATCGGCTACATGAGACCTCAAAAGAGCCAGATGTTTCTCTAGGGT |
| | CCACATGGCTGTCTGATTTTCCTCAGGCCTGGGCGGAAACCGGGGGC |
| | ATGGGACTGGCAGTTCGCCAAGCTCCTCTGATCATACCTCTGAAAGC |
| | AACCTCTACCCCCGTGTCCATAAAACAATACCCCATGTCACAAGAA |
| | GCCAGACTGGGGATCAAGCCCCACATACAGAGACTGTTGGACCAGG |
| | GAATACTGGTACCCTGCCAGTCCCCCTGGAACACGCCCCTGCTACCC |
| | GTTAAGAAACCAGGGACTAATGATTATAGGCCTGTCCAGGATCTGA |
| | GAGAAGTCAACAAGCGGGTGGAAGACATCCACCCCACCGTGCCCAA |
| | CCCTTACAACCTCTTGAGCGGGCCCCACCGTCCCACCAGTGGTACA |
| | CTGTGCTTGATTTAAAGGATGCCTTTTTCTGCCTGAGACTCCACCCC |
| | ACCAGTCAGCCTCTCTTCGCCTTTGAGTGGAGAGATCAGAGATGGG |
| | AATCTCAGGACAATTGACCTGGACCAGACTCCCACAGGGTTTCAAA |
| | AACAGTCCCACCCTGTTTAATGAGGCACTGCACAGAGACCTAGCAG |
| | ACTTCCGGATCCAGCACCCAGACTTGATCCTGCTACAGTACGTGGAT |
| | GACTTACTGCTGGCCGCCACTTCTGAGCTAGACTGCCAACAAGGTAC |
| | TCGGGCCCTGTTACAAACCCTAGGGAACCTCGGGTATCGGGCCTCG |
| | GCCAAGAAAGCCCAAATTTGCCAGAAACAGGTCAAGTATCTGGGGT |
| | ATCTTCTAAAAGAGGGTCAGAGATGGCTGACTGAGGCCAGAAAAGA |
| | GACTGTGATGGGGCAGCCTACTCCGAAGACCCCTCGACAACTAAGG |
| | GAGTTCCTAGGGAAGGCAGGCTTCGTCGCCTCTTCATCCCTGGGTT |
| | TGCAGAAATGGCAGCCCCCTGTACCCTCTCACCAAACCGGGGACT |
| | CTGTTTAATTGGGGCCCAGACCAACAAAAGGCCTATCAAGAAATCA |

| Description | Sequence |
|---|---|
| | AGCAAGCTCTTCTAACTGCCCCAGCCCTGGGGTTGCCAGATTTGACT |
| | AAGCCCTTTGAACTCTTTGTCGACGAGAAGCAGGGCTACGCCAAAG |
| | GTGTCCTAACGCAAAAACTGGGACCTTGGCGTCGGCCGGTGGCCTA |
| | CCTGTCCAAAAGCTAGACCCAGTAGCAGCTGGGTGCCCCCTTGC |
| | CTACGGATGGTAGCAGCCATTGCCGTACTGACAAAGGATGCAGGCA |
| | AGCTAACCATGGGACAGCCACTAGTCATTCTGGCCCCCCATGCAGTA |
| | GAGGCACTAGTCAAACAACCCCCCGACCGCTGGCTTTCCAACGCCC |
| | GGATGACTCACTATCAGGCCTTGCTTTTGGACACGGACCGGGTCCAG |
| | TTCGGACCGGTGGTAGCCCTGAACCCGGCTACGCTGCTCCCACTGCC |
| | TGAGGAAGGGCTGCAACACAACTGCCTTGATGGGACAGGTGGCGGT |
| | GGTGTCACCGTCAAGTTCAAGTACAAGGGTGAGGAACTTGAAGTTG |
| | ATATTAGCAAAATCAAGAAGGTTTGGCGCGTTGGTAAAATGATATC |
| | TTTTACTTATGACGACAACGGCAAGACAGGTAGAGGGGCAGTGTCT |
| | GAGAAAGACGCCCCCAAGGAGCTGTTGCAAATGTTGGAAAAGTCTG |
| | GGAAAAAGTCTGGCGGCTCAAAAAGAACCGCCGACGGCAGCGAATT |
| | CGAGCCCAAGAAGAAGAGGAAAGTCGGAGGTGGCGGGAGCCCAAA |
| | AAAGAAAAGAAAAGTGTATCCCTATGATGTCCCCGATTATGCCGGT |
| | TCAAGAGCCCTGGTCGTGATTAGACTGAGCCGAGTGACAGACGCCA |
| | CCACAAGTCCCGAGAGACAGCTGGAATCATGCCAGCAGCTCTGTGC |
| | TCAGCGGGGTTGGGATGTGGTCGGCGGTGGCAGAGGATCTGGACGTG |
| | AGCGGGGCCGTCGATCCATTGACAGAAAGAGGAGGCCCAACCTGG |
| | CAAGATGGCTCGCTTTCGAGGAACAGCCCTTTGATGTGATCGTCGCC |
| | TACAGAGTGGACCGGCTGACCCGCTCAATTCGACATCTCCAGCAGCT |
| | GGTGCATTGGGCTGAGGACCACAAGAAACTGGTGGTCAGCGCAACA |
| | GAAGCCCACTTCGATACTACCACACCTTTTGCCGCTGTGGTCATCGC |
| | ACTGATGGGCACTGTGGCCCAGATGGAGCTCGAAGCTATCAAGGAG |
| | CGAAACAGGAGCGCAGCCCATTTCAATATTAGGGCCGGTAAATACA |
| | GAGGCTCCCTGCCCCCTTGGGGATATCTCCCTACCAGGGTGGATGGG |
| | GAGTGGAGACTGGTGCCAGACCCCGTCCAGAGAGAGCGGATTCTGG |
| | AAGTGTACCACAGAGTGGTCGATAACCACGAACCACTCCATCTGGT |
| | GGCACACGACCTGAATAGACGCGGCGTGCTCTCTCCAAAGGATTAT |
| | TTTGCTCAGCTGCAGGGAAGAGAGCCACAGGGAAGAGAATGGAGTG |
| | CTACTGCACTGAAGAGATCTATGATCAGTGAGGCTATGCTGGGTTAC |
| | GCAACACTCAATGGCAAAACTGTCCGGGACGATGACGGAGCCCCTC |
| | TGGTGAGGGCTGAGCCTATTCTCACCAGAGAGCAGCTCGAAGCTCT |
| | GCGGGCAGAACTGGTCAAGACTAGTCGCGCCAAACCTGCCGTGAGC |
| | ACCCCAAGCCTGCTCCTGAGGGTGCTGTTCTGCGCCGTCTGTGGAGA |
| | GCCAGCATACAAGTTTGCCGGCGGAGGGCGCAAACATCCCCGCTAT |
| | CGATGCAGGAGCATGGGGTTCCCTAAGCACTGTGGAAACGGGACAG |
| | TGGCCATGGCTGAGTGGGACGCCTTTTGCGAGGAACAGGTGCTGGA |
| | TCTCCTGGGTGACGCTGAGCGGCTGGAAAAAGTGTGGGTGGCAGGA |
| | TCTGACTCCGCTGTGGAGCTGGCAGAAGTCAATGCCGAGCTCGTGG |
| | ATCTGACTTCCCTCATCGGATCTCCTGCATATAGAGCTGGGTCCCCA |
| | CAGAGAGAAGCTCTGGACGCACGAATTGCTGCACTCGCTGCTAGAC |
| | AGGAGGAACTGGAGGGCCTGGAGGCCAGGCCCTCTGGATGGGAGTG |
| | GCGAGAAACCGGACAGAGGTTTGGGGATTGGTGGAGGGAGCAGGA |
| | CACCGCAGCCAAGAACACATGGCTGAGATCCATGAATGTCCGGCTC |
| | ACATTCGACGTGCGCGGTGGCCTGACTCGAACCATCGATTTTGGCGA |
| | CCTGCAGGAGTATGAACAGCACCTGAGACTGGGGTCCGTGGTCGAA |
| | AGATGCACACTGGGATGTCC |
| SpCas9<br>Amino acid<br>SEQ ID NO: 378 | DKKYSIGLDIGTNSVGWAVITDEYKVPSKKFKVLGNTDRHSIKKNLIGA<br>LLFDSGETAEATRLKRTARRRYTRRKNRICYLQEIFSNEMAKVDDSFFH<br>RLEESFLVEEDKKHERHPIFGNIVDEVAYHEKYPTIYHLRKKLVDSTDK<br>ADLRLIYLALAHMIKFRGHFLIEGDLNPDNSDVDKLFIQLVQTYNQLFE<br>ENPINASGVDAKAILSARLSKSRRLENLIAQLPGEKKNGLFGNLIALSLG<br>LTPNFKSNFDLAEDAKLQLSKDTYDDDLDNLLAQIGDQYADLFLAAKN<br>LSDAILLSDILRVNTEITKAPLSASMIKRYDEHHQDLTLLKALVRQQLPE<br>KYKEIFFDQSKNGYAGYIDGGASQEEFYKFIKPILEKMDGTEELLVKLN<br>REDLLRKQRTFDNGSIPHQIHLGELHAILRRQEDFYPFLKDNREKIEKILT<br>FRIPYYVGPLARGNSRFAWMTRKSEETITPWNFEEVVDKGASAQSFIER<br>MTNFDKNLPNEKVLPKHSLLYEYFTVYNELTKVKYVTEGMRKPAFLSG<br>EQKKAIVDLLFKTNRKVTVKQLKEDYFKKIECFDSVEISGVEDRFNASL<br>GTYHDLLKIIKDKDFLDNEENEDILEDIVLTLTLFEDREMIEERLKTYAH<br>LFDDKVMKQLKRRRYTGWGRLSRKLINGIRDKQSGKTILDFLKSDGFA<br>NRNFMQLIHDDSLTFKEDIQKAQVSGQGDSLHEHIANLAGSPAIKKGIL<br>QTVKVVDELVKVMGRHKPENIVIEMARENQTTQKGQKNSRERMKRIE<br>EGIKELGSQILKEHPVENTQLQNEKLYLYYLQNGRDMYVDQELDINRL<br>SDYDVDAIVPQSFLKDDSIDNKVLTRSDKNRGKSDNVPSEEVVKKMKN<br>YWRQLLNAKLITQRKFDNLTKAERGGLSELDKAGFIKRQLVETRQITK<br>HVAQILDSRMNTKYDENDKLIREVKVITLKSKLVSDFRKDFQFYKVREI<br>NNYHHAHDAYLNAVVGTALIKKYPKLESEFVYGDYKVYDVRKMIAKS<br>EQEIGKATAKYFFYSNIMNFFKTEITLANGEIRKRPLIETNGETGEIVWD<br>KGRDFATVRKVLSMPQVNIVKKTEVQTGGFSKESILPKRNSDKLIARKK<br>DWDPKKYGGFDSPTVAYSVLVVAKVEKGKSKKLKSVKELLGITIMERS<br>SFEKNPIDFLEAKGYKEVKKDLIIKLPKYSLFELENGRKRMLASAGELQ<br>KGNELALPSKYVNFLYLASHYEKLKGSPEDNEQKQLFVEQHKHYLDEII |

-continued

| Description | Sequence |
|---|---|
| | EQISEFSKRVILADANLDKVLSAYNKHRDKPIREQAENIIHLFTLTNLGA<br>PAAFKYFDTTIDRKRYTSTKEVLDATLIHQSITGLYETRIDLSQLGGD |
| RT(1-478)-Sto7d<br>Amino acid<br>SEQ ID NO: 379 | LNIEDEYRLHETSKEPDVSLGSTWLSDFPQAWAETGGMGLAVRQAPLII<br>PLKATSTPVSIKQYPMSQEARLGIKPHIQRLLDQGILVPCQSPWNTPLLP<br>VKKPGTNDYRPVQDLREVNKRVEDIHPTVPNPYNLLSGPPPSHQWYTV<br>LDLKDAFFCLRLHPTSQPLFAFEWRDPEMGISGQLTWTRLPQGFKNSPT<br>LFNEALHRDLADFRIQHPDLILLQYVDDLLLAATSELDCQQGTRALLQT<br>LGNLGYRASAKKAQICQKQVKYLGYLLKEGQRWLTEARKETVMGQPT<br>PKTPRQLREFLGKAGFCRLFIPGFAEMAAPLYPLTKPGTLFNWGPDQQK<br>AYQEIKQALLTAPALGLPDLTKPFELFVDEKQGYAKGVLTQKLGPWRR<br>PVAYLSKKLDPVAAGWPPCLRMVAAIAVLTKDAGKLTMGQPLVILAP<br>HAVEALVKQPPDRWLSNARMTHYQALLLDTDRVQFGPVVALNPATLL<br>PLPEEGLQHNCLDGTGGGGVTVKFKYKGEELEVDISKIKKVWRVGKMI<br>SFTYDDNGKTGRGAVSEKDAPKELLQMLEKSGKKSGGSKRTADGS |
| BxbINT<br>Amino acid<br>SEQ ID NO: 380 | SRALVVIRLSRVTDATTSPERQLESCQQLCAQRGWDVVGVAEDLDVSG<br>AVDPFDRKRRPNLARWLAFEEQPFDVIVAYRVDRLTRSIRHLQQLVHW<br>AEDHKKLVVSATEAHFDTTTPFAAVVIALMGTVAQMELEAIKERNRSA<br>AHFNIRAGKYRGSLPPWGYLPTRVDGEWRLVPDPVQRERILEVYHRVV<br>DNHEPLHLVAHDLNRRGVLSPKDYFAQLQGREPQGREWSATALKRSM<br>ISEAMLGYATLNGKTVRDDDGAPLVRAEPILTREQLEALRAELVKTSRA<br>KPAVSTPSLLLRVLFCAVCGEPAYKFAGGGRKHPRYRCRSMGFPKHCG<br>NGTVAMAEWDAFCEEQVLDLLGDAERLEKVWVAGSDSAVELAEVNA<br>ELVDLTSLIGSPAYRAGSPQREALDARIAALAARQEELEGLEARPSGWE<br>WRETGQRFGDWWREQDTAAKNTWLRSMNVRLTFDVRGGLTRTIDFG<br>DLQEYEQHLRLGSVVERLHTGMS |

EXAMPLES

While several experimental Examples are contemplated, these Examples are intended to be non-limiting.

Example 1

CRE Integration Efficiency

Figure 3:
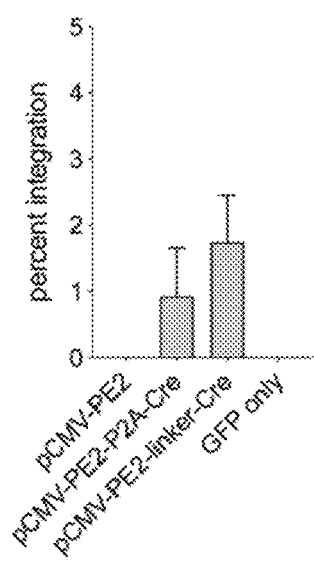
FIG. 3 shows the percent integration of green fluorescent protein (GFP) in the lentiviral integrated lox71 site in HEK293FT cell line in the presence of various plasmids according to embodiments of the present teachings.

The efficiency of the CRE integration was tested. In order to test the efficacy of PASTE with GFP using lox71/lox66/Cre recombinase system, a clonal HEK293FT cell line with lox71 sequence (SEQ ID NO: 1) integrated into the genome using lentivirus was developed. The integration of GFP was tested by transfection of modified HEK293FT cell line with: (1) plus/minus SEQ ID NO: 71 comprising a Cre recombinase expression plasmid, and (2) SEQ ID NO: 72 comprising a GFP template and a lox 66 Cre site of SEQ ID NO: 2. After 72 hours, the percent integration of GFP into the lox71 site was probed. FIG. 3 shows the percent integration of GFP in the lentiviral integrated lox71 site in HEK293FT cell line in the presence of various plasmids. It was observed that pCMV PE2 P2A Cre (SEQ ID NO: 73), a mammalian expression vector with prime editing complex and Cre recombinase linked to PE2 via a cleavable linker or a non-cleavable linker, shows integration of GFP.

Example 2

Figure 4:
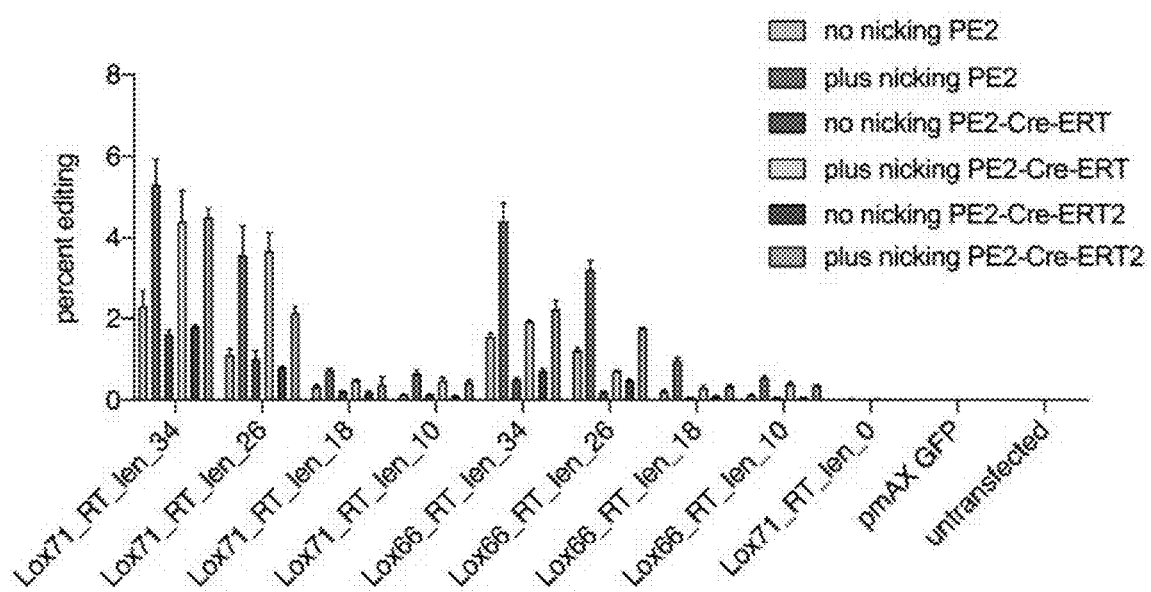
FIG. 4 shows the percent editing of the HEK293FT genome for incorporation of various lengths of lox71 or lox66 according to embodiments of the present teachings.

Programmable Addition Via Site-Specific Targeting Elements (PASTE) with Cre Recombinase—Addition of Lox Site The lox71 (SEQ ID NO: 1) or lox66 (SEQ ID NO: 2) sequence was inserted into the HEK293FT cell genome using prime editing to test integration of GFP into the HEK293FT genome. In order to insert lox71 or lox66 sequence into HEK293FT cell genome, a pegRNA with PBS length of 13 base pairs operably linked to RT region of varying lengths was used. The following plasmids were used in the transfection of HEK293FT cells. The cells were transfected with (1) prime editing construct (PE2) or PE2 with conditional Cre expression, (2) Lox71 or Lox66 pegRNA targeting the HEK3 locus, and (3) plus/minus +90 HEK3 nicking second guide RNA targeting the HEK3 locus (+90 ngRNA). After 72 hours, the percent editing of the HEK293FT genome at the HEK3 locus was probed for incorporation of various lengths of lox71 or lox66 (see FIG. 4). It was observed that 34 base pair lox71 (HEK3 locus guide, SEQ ID NO: 83; and Lox71 pegRNA with RT 34 and PBS 13, SEQ ID NO: 81) with +90 ngRNA (SEQ ID NO: 75) and 34 base pair lox66 (HEK3 locus guide, SEQ ID NO: 83; and Lox66 pegRNA with RT 34 and PBS 13, SEQ ID NO: 82) with +90 ngRNA (SEQ ID NO: 75) had the highest percent editing.

Example 3

PASTE with Cre Recombinase—Integration of Gene

Figure 5A:
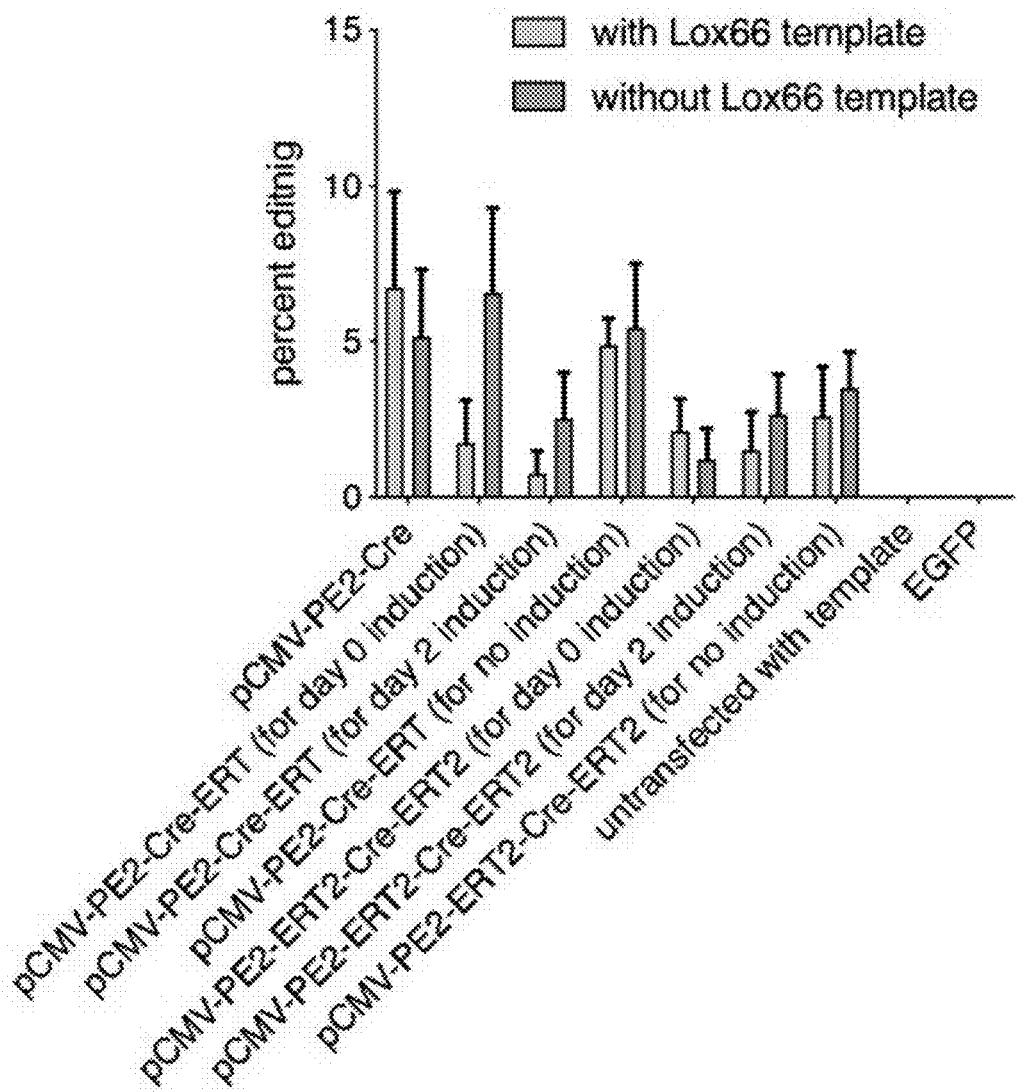
FIG. 5A shows the percent editing of lox71 site with different PE/Cre vectors according to embodiments of the present teachings.
Figure 5B:
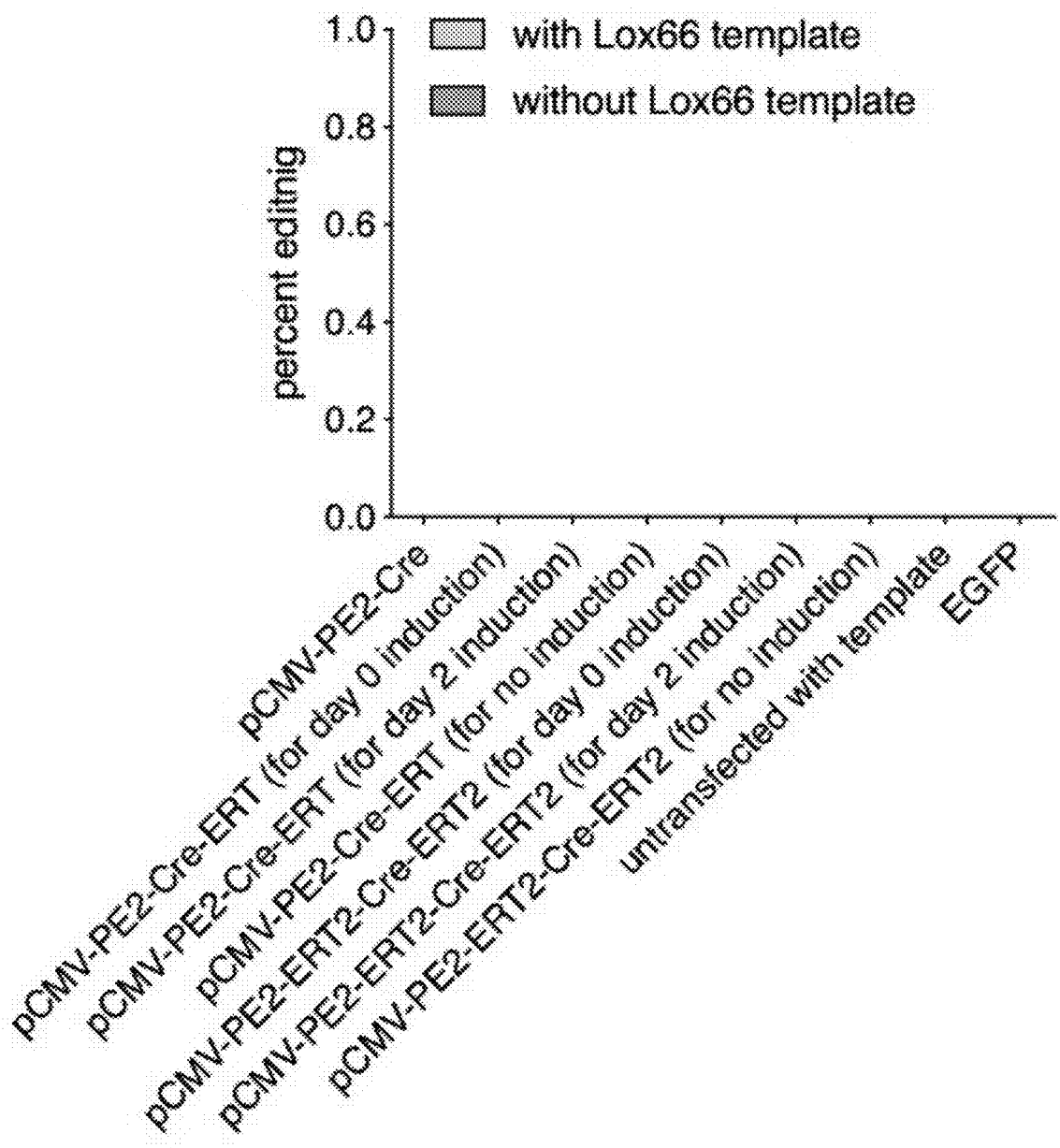
FIG. 5B shows the percent integration of GFP at the lox71 site in HEK293FT cell genome according to embodiments of the present teachings.

The lox71 or lox66 pegRNAs having PBS length of 13 base pairs and insert length of 34 base pairs were used to probe integration of GFP in the HEK293F genome. The PE and Cre were delivered in an inducible expression vectors and induced at day 2. The HEK293FT cells were transfected with the following plasmids: (1) prime editing construct (PE2 or PE2 with conditional Cre expression); (2) Lox71 pegRNA; (3) plus/minus +90 HEK3 nicking guide RNA; and (4) EGFP template with Lox66 site. After 72 hours, the percent editing of lox71 site and percent integration of GFP was probed with or without lox66 site in the presence of various PE/Cre constructs. FIG. 5A summarizes the percent editing of lox71 site with different PE/Cre vectors. FIG. 5B summarizes the percent integration of GFP at the lox71 site in HEK293FT cell genome. It was observed that although the lox71 site was edited in the presence of inducible or non-inducible PE/Cre expression system, there was no GFP integration.

Example 4

Bxb1 Integration Data Lenti Reporter

Figure 6:
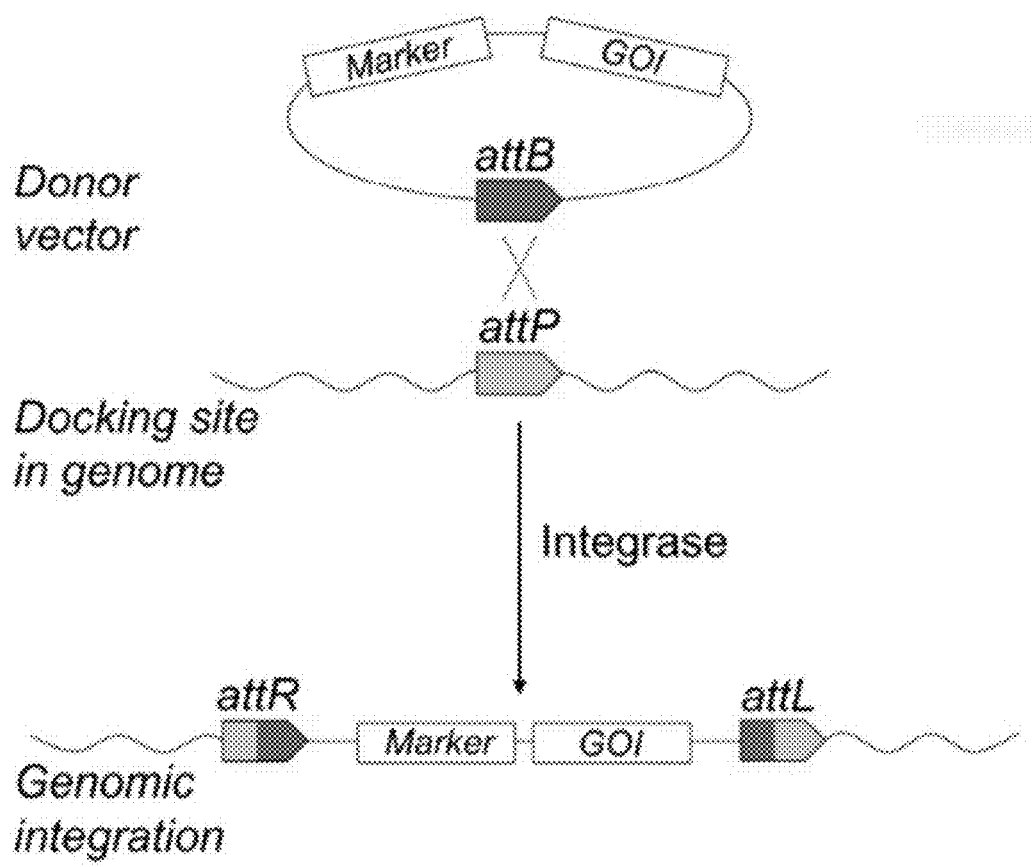
FIG. 6 shows a schematic representation of using Bxb1 to integrate a nucleic acid into the genome according to embodiments of the present teachings.

The integration system was switched to an integrase system that could result in an integration of target genes into a genome with higher efficiency. Serine integrase Bxb1 has been shown to be more active than Cre recombinase and highly efficient in bacteria and mammalian cells for irreversible integration of target genes. FIG. 6 shows a schematic of PASTE methodology using Bxb1 (Merrick, C. A. et al., *ACS Synth. Biol.* 2018, 7, 299-310).

Figure 7:
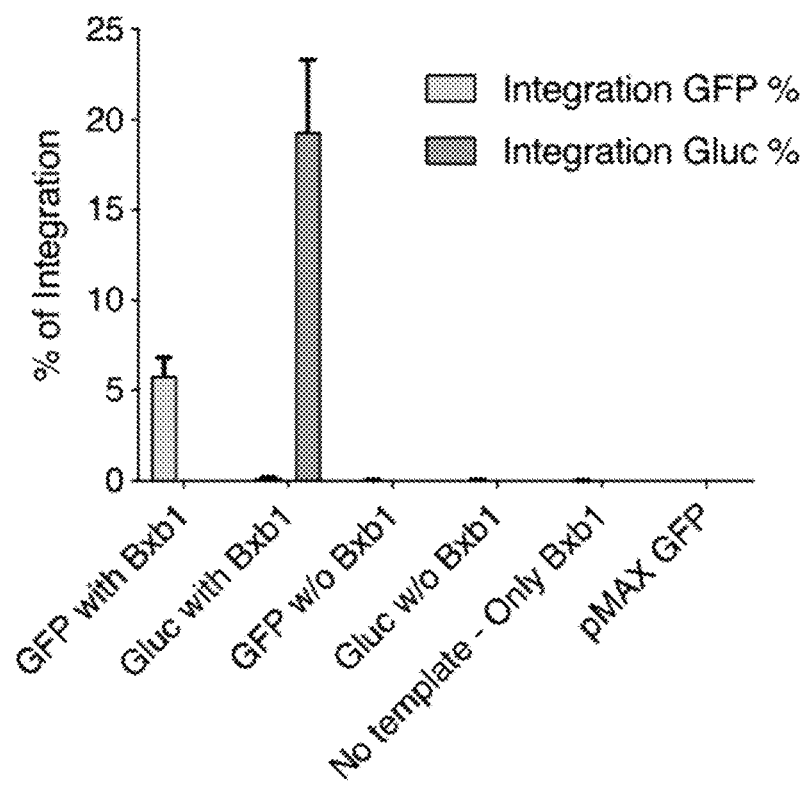
FIG. 7 shows the percent integration of GFP or Gluc into the attB locus using Bxb1 Programmable Addition via Site-Specific Targeting Elements (PASTE) according to embodiments of the present teachings.

To probe the efficiency of the Bxb1 integration system, a clonal HEK293FT cell line with attB Bxb1 site (SEQ ID NO: 3) integrated using lentivirus was developed. The modified HEK293FT cell line was then transferred with the following plasmids: (1) plus/minus Bxb1 expression plasmid and (2) plus/minus GFP (SEQ ID NO: 76) or G-Luc (SEQ ID NO: 77) minicircle template with attP Bxb1 site. After 72 hours, the integration of GFP or Gluc into the attB site in the HEK293FT genome was probed. The percent integrations of GFP or Gluc into the attB locus are shown in FIG. 7. It was observed that GFP and Gluc showed efficient integration into the attB site in HEK293FT cells.

Example 5

Addition of Bxb1 Site to Human Genome Using PRIME

Figure 8:
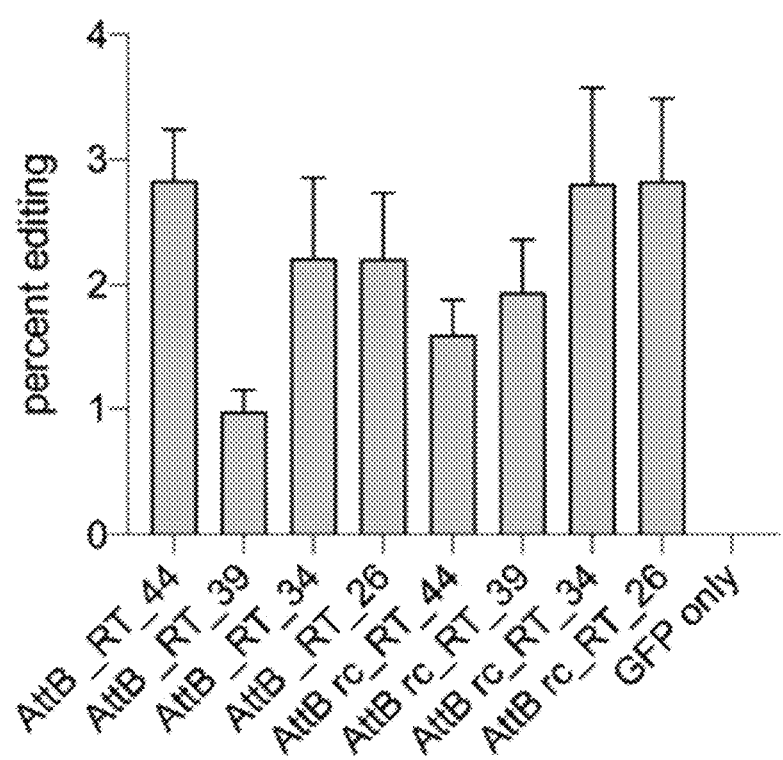
FIG. 8 shows the percent editing of various HEK3 targeting pegRNA Programmable Addition via Site-Specific Targeting Elements (PASTE) according to embodiments of the present teachings.
Figure 9A:
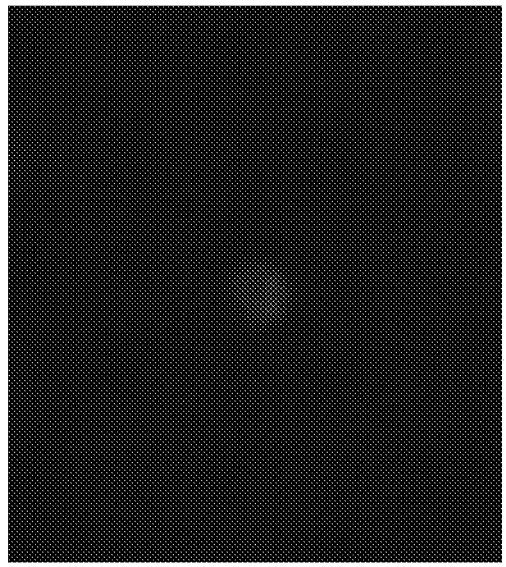
FIG. 9A shows a fluorescent image of cells wherein the SUPT16H marker is tagged with EGFP using PASTE according to embodiments of the present teachings.
Figure 9B:
FIG. 9B shows a fluorescent image of cells wherein the SRRM2 marker is tagged with EGFP using Programmable Addition via Site-Specific Targeting Elements (PASTE) according to embodiments of the present teachings.
Figure 9C:
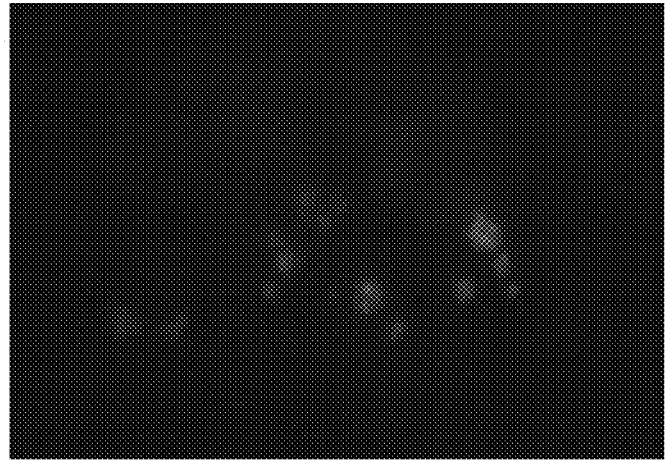
FIG. 9C shows a fluorescent image of cells wherein the LAMNB1 marker is tagged with EGFP using Programmable Addition via Site-Specific Targeting Elements (PASTE) according to embodiments of the present teachings.
Figure 9D:
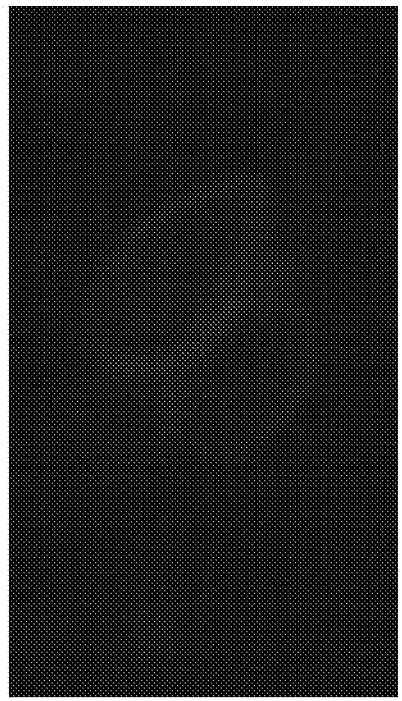
FIG. 9D shows a fluorescent image of cells wherein the NOLC1 marker is tagged with EGFP using Programmable Addition via Site-Specific Targeting Elements (PASTE) according to embodiments of the present teachings.
Figure 9E:
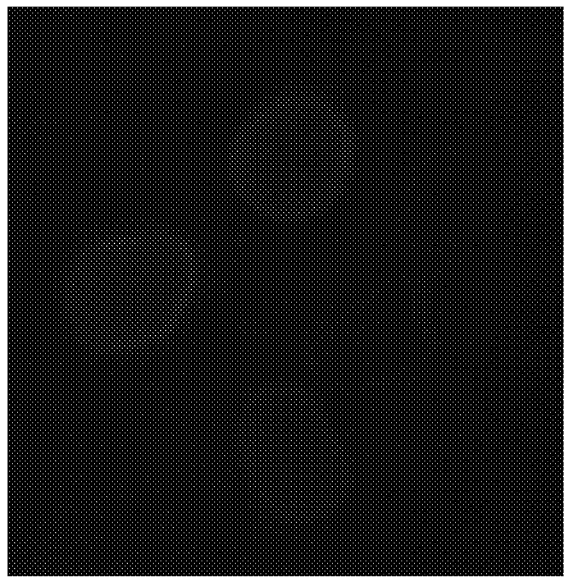
FIG. 9E shows a fluorescent image of cells wherein the NOLC1 marker is tagged with EGFP using Programmable Addition via Site-Specific Targeting Elements (PASTE) according to embodiments of the present teachings.
Figure 9F:
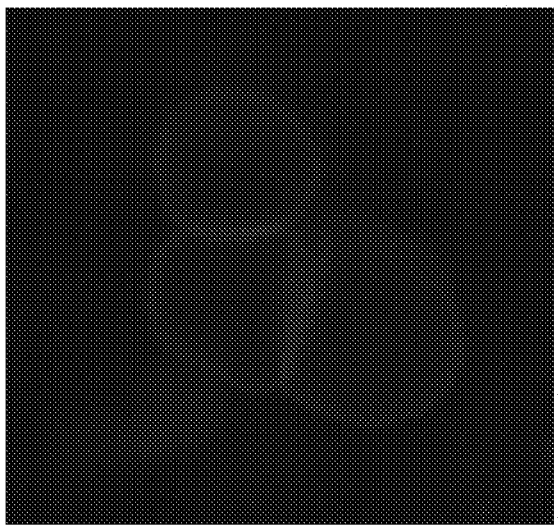
FIG. 9F shows a fluorescent image of cells wherein the NOLC1 marker is tagged with EGFP using Programmable Addition via Site-Specific Targeting Elements (PASTE) according to embodiments of the present teachings.
Figure 9G:
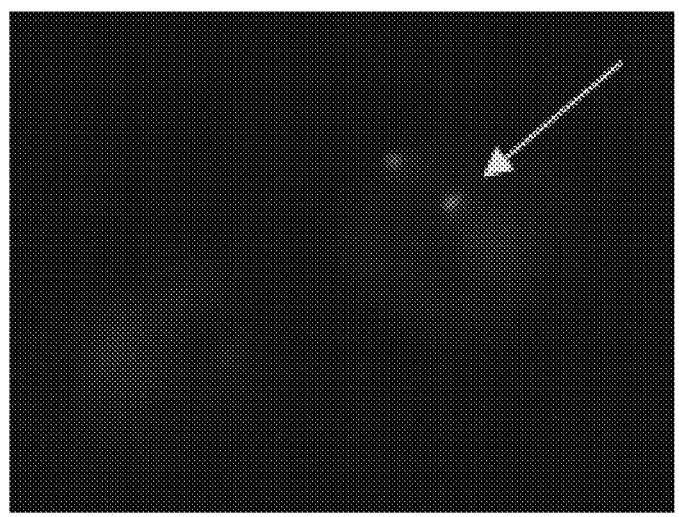
FIG. 9G shows a fluorescent image of cells wherein the DEPDC4 marker is tagged with EGFP using Programmable Addition via Site-Specific Targeting Elements (PASTE) according to embodiments of the present teachings.

The maximum length of attB that can be integrated into a HEK293FT cell line with the best efficiency was probed. To probe the best length of attB (SEQ ID NO: 3) or its reverse complement attP (SEQ ID NO: 4) for prime editing, pegRNAs having PBS length of 13 nt with varying RT homology length were used. The following plasmids were transfected in HEK293FT: (1) prime expression plasmid; (2) HEK3 targeting pegRNA design; and (3) HEK3+90 nicking guide. After 72 hours, the percent integration of each of the attB construct was probed. FIG. 8 shows the percent editing in each HEK3 targeting pegRNA. It was observed that attB with 44, 34 and 26 base pairs and attB reverse complement with 34 and 26 base pairs showed the highest percent editing.

Integration PASTE was then tested with tagging cell-organelle marker proteins with GFP in HEK29FT cells. PASTE was used to tag SUPT16H, SRRM2, LAMNB1, NOLC1 and DEPDC4 with GFP in different cell-culture wells and to test the usefulness of PASTE in tracking protein localization within the cells using microscopy. FIGS. 9A-9G shows the fluorescent microscopy results for each of the organelles. SUPT16H-GFP was observed to be enriched in the nucleus, SRRM2-GFP was observed to be enriched in the nuclear speckles, LAMNB1-GFP was observed to be enriched in the nuclear membrane, NOLC1-GFP was observed to be enriched in the fibrillar center, and DEPDC4-GFP was observed to be enriched in the aggresome.

Figure 10A:
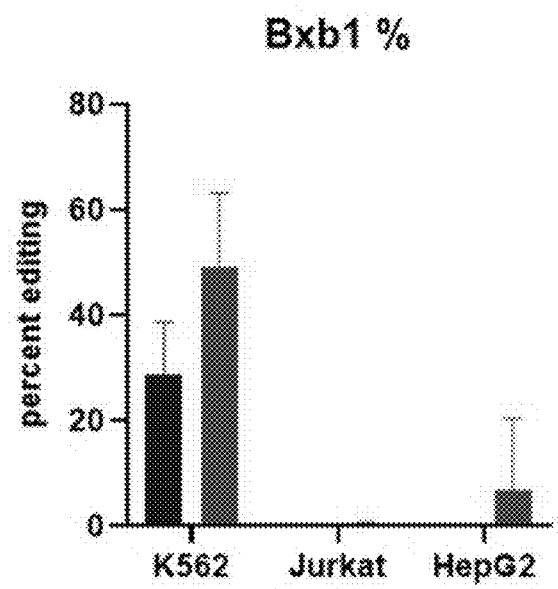
FIG. 10A shows comparisons of lipofectamine aided transfection in blue with electroporation aided transfection in red for the addition of the Bxb1 attB site at the ACTB N-terminal site in the genome using PASTE according to embodiments of the present teachings.
Figure 10B:
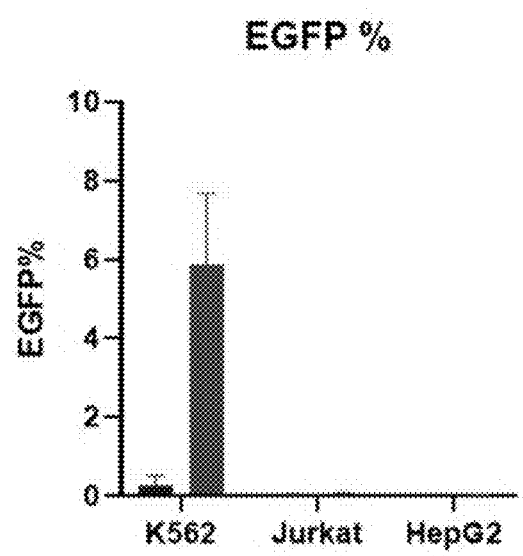
FIG. 10B shows comparisons of lipofectamine aided transfection in blue with electroporation aided transfection in red for EGFP integration at the ACTB N-terminal site in the genome using PASTE according to embodiments of the present teachings.

The transfection of the plasmids can be achieved using electroporation as illustrated in FIGS. 10A-10B.

Example 6

Programmable Integration of Genes with PASTE

The efficiency of gene integration of Gluc or EGFP with PASTE was tested. To enable gene integration with PASTE, the following HEK3 targeting pegRNAs were used: (1) 44 pegRNA: PBS of 13 nt and RT homology of 44nt; (2) 34 pegRNA: PBS of 13 nt and RT homology of 34 nt; and (3) 26 pegRNA: PBS of 13 nt and RT homology of 26 nt.

Figure 11:
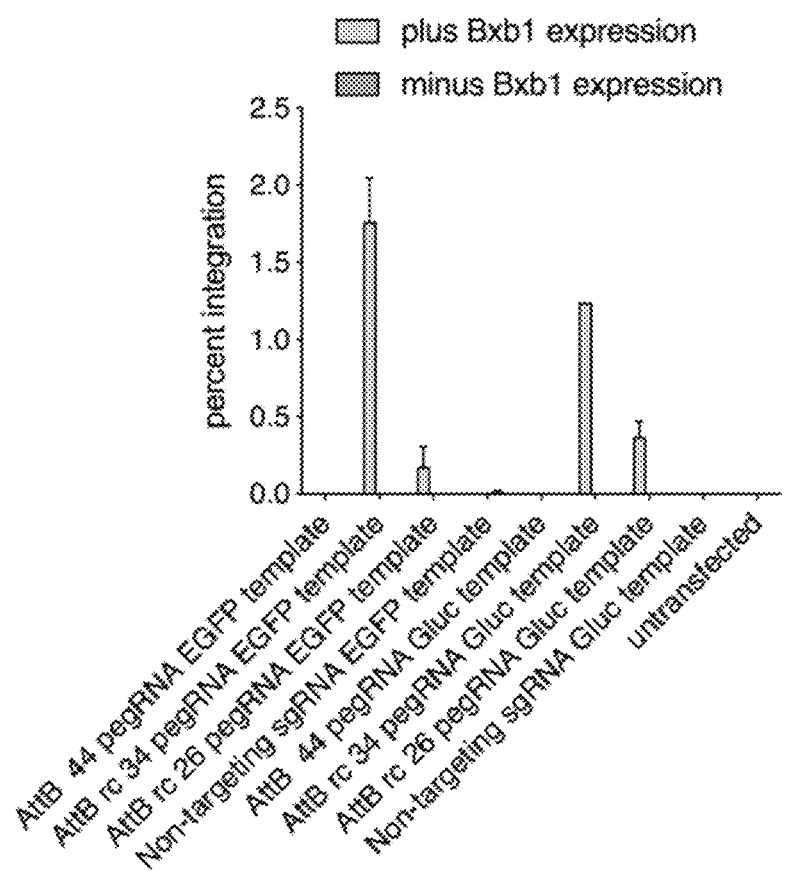
FIG. 11 shows a diagram of the integration of EGFP and Gluc with various HEK3 targeting pegRNAs according to embodiments of the present teachings.

A HEK293 cell line was transfected with following plasmids HEK293FT: (1) Prime expression plasmid; (2) Bxb1 expression plasmid; (3) HEK3 targeting pegRNA design; (4) HEK3+90 nicking guide; and (5) EGFP or Gluc minicircle. After 72 hours, the percent integration of Gluc or EGFP was observed. FIG. 11 shows integration of EGFP and Gluc with each of the tested HEK3 targeting pegRNAs. It was observed that EGFP and Gluc were efficiently integrated using PASTE.

Example 7

PASTE for Integration of Multiple Genes

The PASTE technique for site-specific integration of multiple genes into a cell is facilitated with the use of orthogonal attB and attP sites. Central dinucleotide can be changed to GA from GT, and only GA containing attB/attP sites can interact and do not cross react with GT containing sequences. A screen of dinucleotide combinations to find orthogonal attB/attP pairs for multiplexed PASTE editing can be performed. It has been shown that many orthogonal dinucleotide combinations can be found using a Bxb1 reporter system.

Figure 14A:
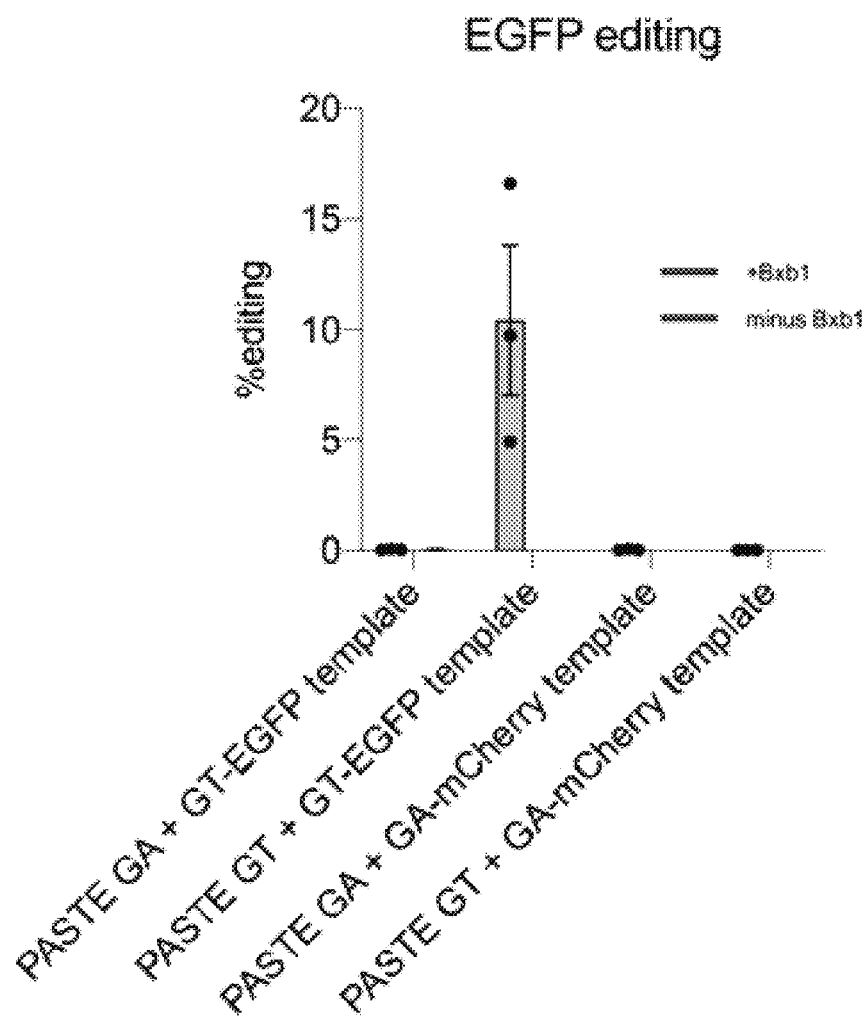
FIG. 14A shows a diagram of the orthogonal editing with the right GT-EGFP according to embodiments of the present teachings.
Figure 14B:
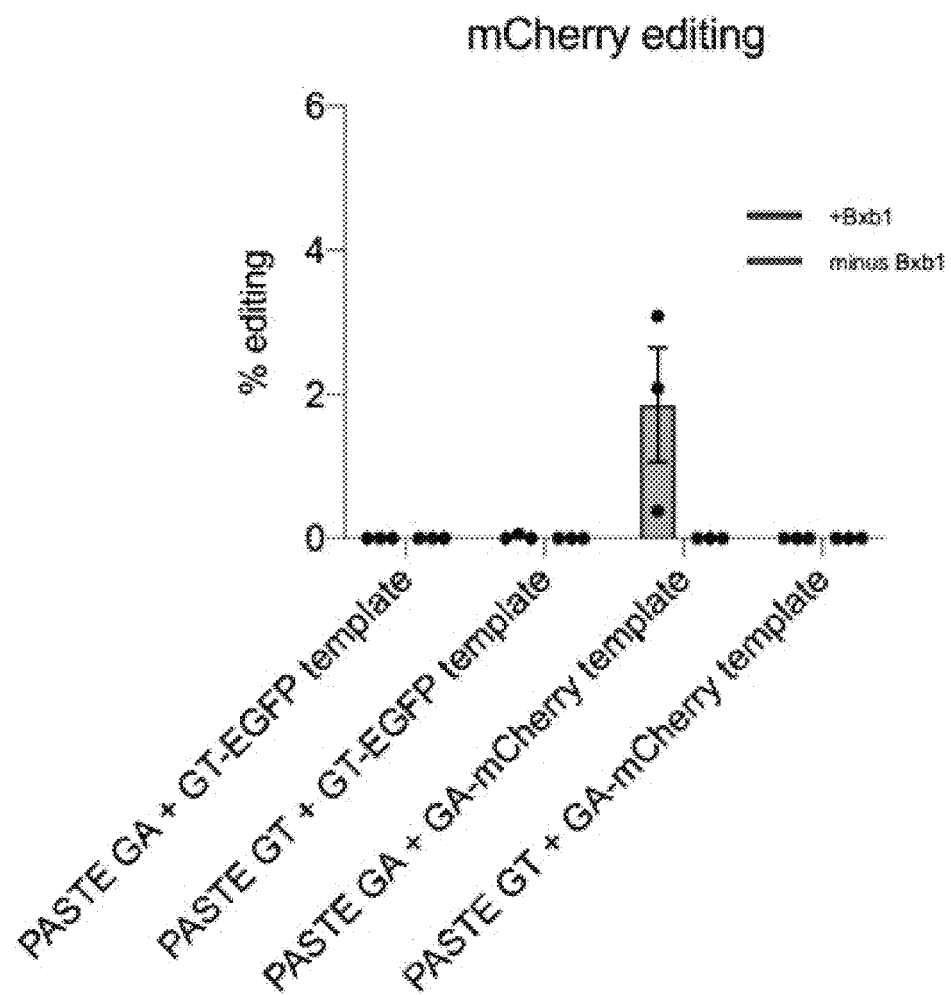
FIG. 14B shows a diagram of the orthogonal editing with the right GA-mCherry according to embodiments of the present teachings.

To test this, attB$^{GT}$ and attB$^{GA}$ dinucleotides for Bxb1 was added at a ACTB site by prime editing. A EGFP-attP$^{GT}$ DNA minicircle and a mCherry-attP$^{GA}$ DNA minicircle was introduced to test the percent EGFP and mCherry editing in the presence or absence of Bxb1. The results of EGFP and mCherry editing are shown in FIGS. 14A-14B.

Orthogonal editing with the right GT-EGFP and GA-mCherry pairs was achieved demonstrating the ability for multiplexed PASTE editing in cells.

Figure 15A:
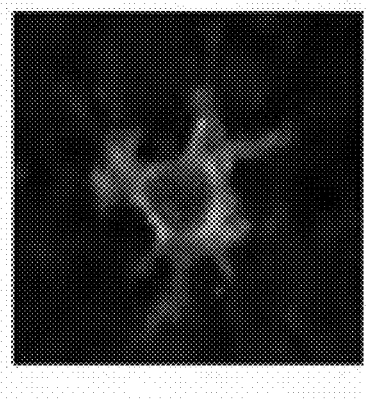
FIG. 15A shows a fluorescent image of a multiplexing of ACTB-EGFP and NOLC1-mCherry according to embodiments of the present teachings
Figure 15B:
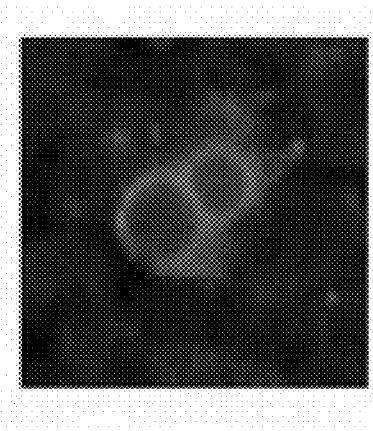
FIG. 15B shows a fluorescent image of a multiplexing of ACTB-EGFP and LAMNB1-mCherry according to embodiments of the present teachings.

Two genes were introduced in the same cell using multiplexed PASTE to tag two different genes in a single reaction. EGFP and mCherry were tagged into the loci of ACTB and NOLC1 in a x cell line, in a single reaction. Further, EGFP and mCherry were tagged into the loci of ACTB and LAMNB1. The cells were visualized using fluorescence microscopy. FIGS. 15A-15B show the results of fluorescent microscopy for multiplexed PASTE.

Figure 16A:
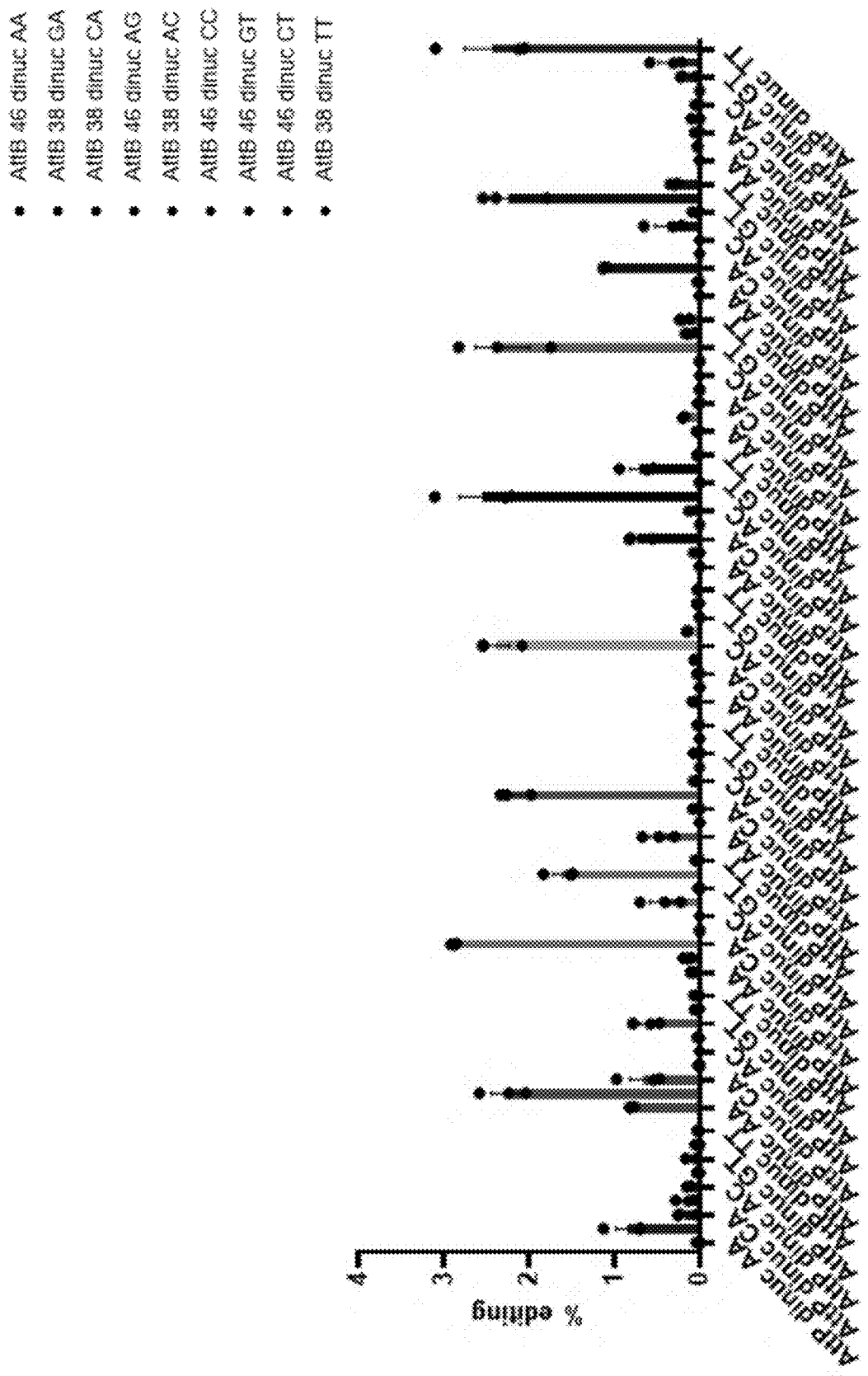
FIG. 16A shows next generation sequencing results of 9×9 attP and attB central dinucleotide variants and their edit percentage wherein the orthogonality of attB/attP combinations for potential multiplexing applications is shown according to embodiments of the present teachings.
Figure 16B:
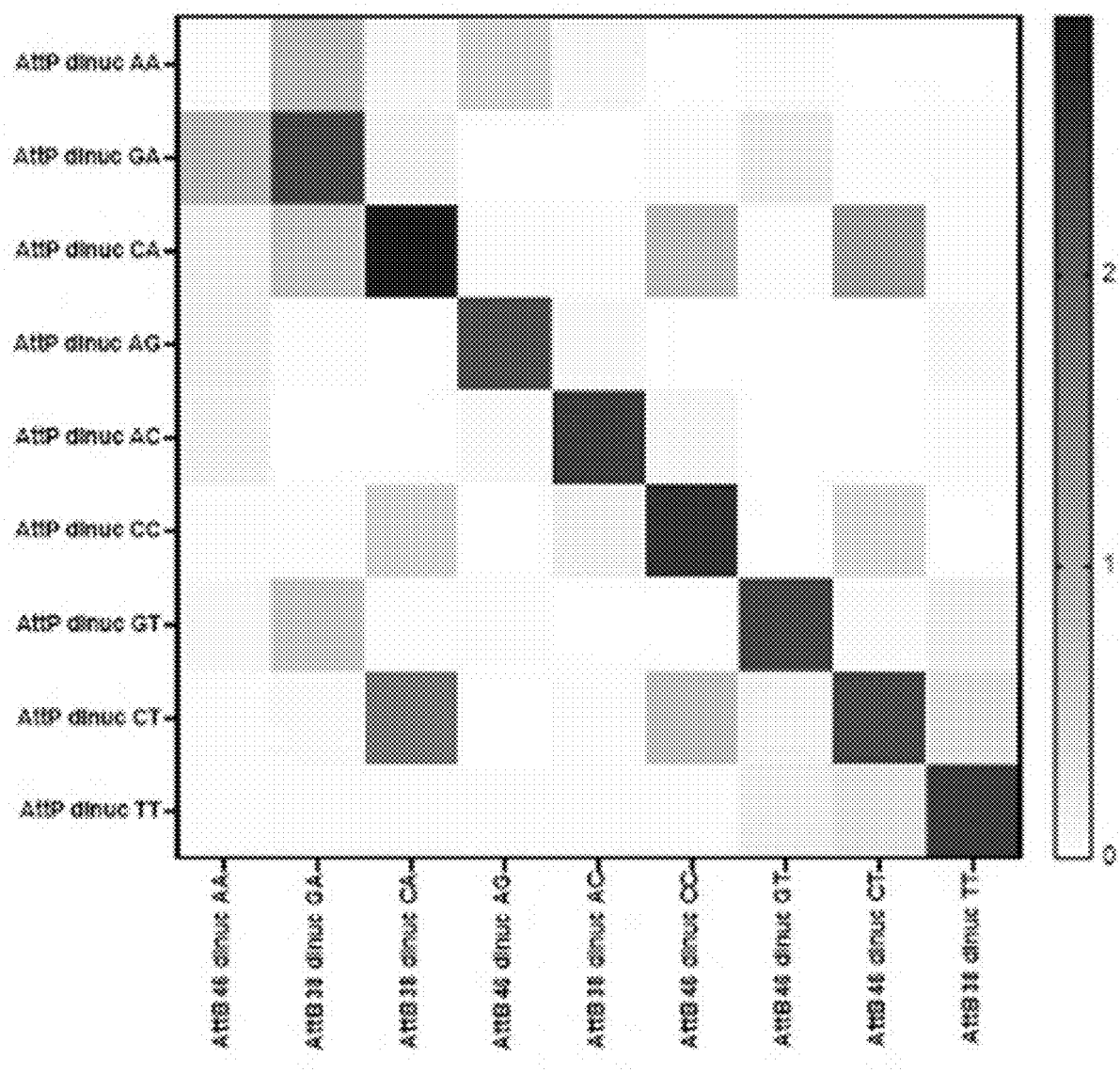
FIG. 16B shows an heatmap of 9×9 attP and attB central dinucleotide variants and their edit percentage according to embodiments of the present teachings.

The ability of multiplexing with 9-different attB and attP central dinucleotides—AA, GA, CA, AG, AC, CC, GT, CT and TT (SEQ ID NOs: 7, 8, 23, 24, 19, 20, 25, 26, 27, 28, 9, 10, 15, 16, 17, 18, 5 and 6)—in a 9×9 cross of attB and attP was tested. The edits were probed using next-generation sequencing. The results of the 9×9 cross of attB and attP central dinucleotides—AA, GA, CA, AG, AC, CC, GT, CT and TT—are shown in FIG. 16A. Only orthogonal pairs of attB and attP show the highest edit percentage. This result is also shown in the heat-map of FIG. 16B.

Example 8

Figure 17:
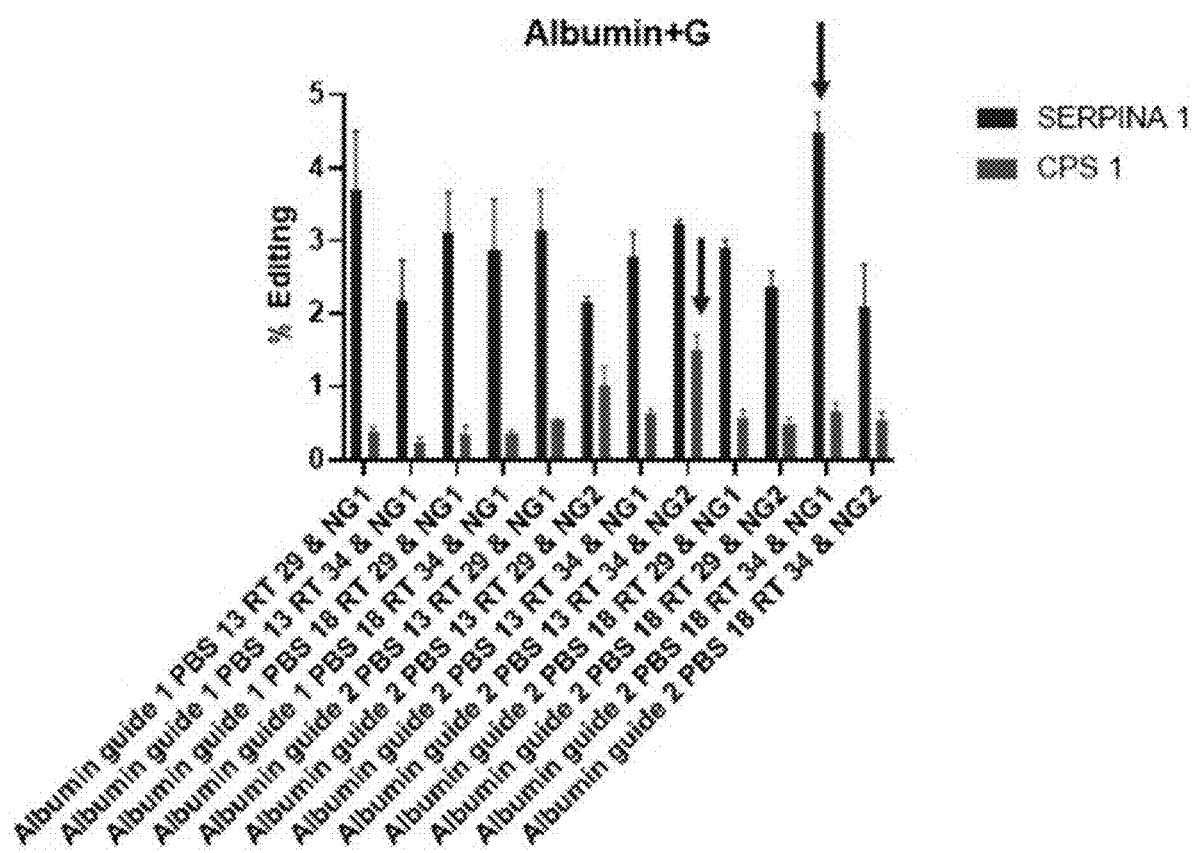
FIG. 17 shows integration of SERPINA and CPS1 into Albumin loci using Albumin guide-pegRNA in HEK293FT cells according to embodiments of the present teachings.

Integration of Albumin and CPS1 into Albumin Locus 12 pegRNAs with albumin guide were linked to PBS and reverse transcriptase sequence of variable length, and different nicking guide RNAs were used to transfect HEK293FT cells. The percent editing in the albumin was probed using next-generation sequencing. The results of prime editing at the albumin locus are shown in FIG. 17. It was observed that SEQ ID NO: 79 showed the highest percent edits with SERPINA1 and SEQ ID NO: 80 showed the highest percent edits with CPS1.

Example 9

Engineering T-Cells

Figure 18:
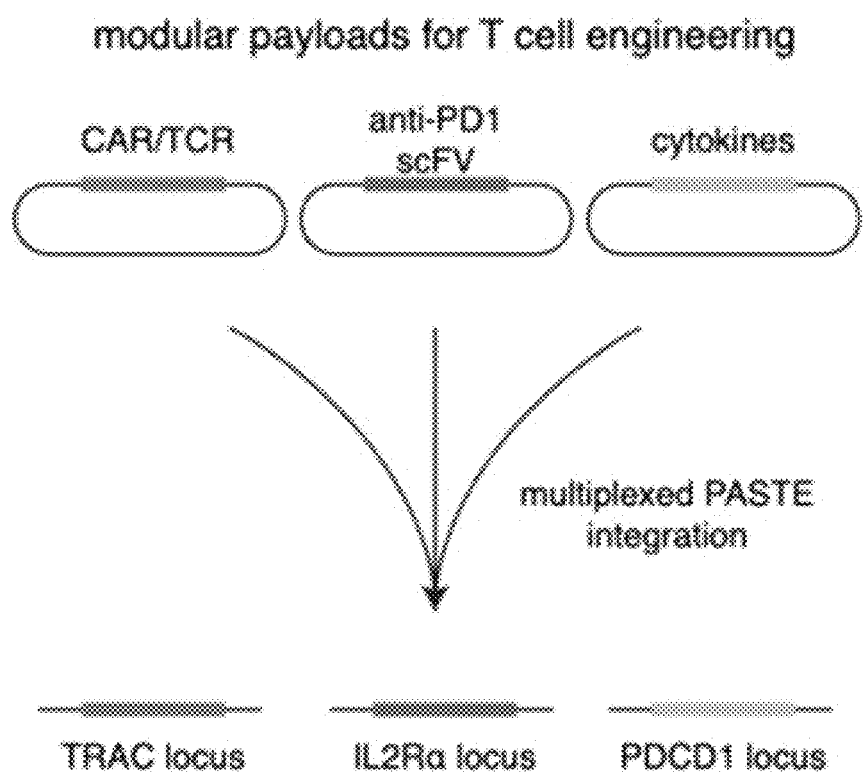
FIG. 18 shows schematics for different nucleic acids for engineering T-cells according to embodiments of the present teachings.

In order to engineer CD8+ T-cells, the efficiency of PASTE delivery and editing in T-cells can be evaluated (FIG. 18). ACTB targeting pegRNA can be used to insert an integration site with an EGFP insertion template. To deliver the PASTE components to CD8+ T-cells, electroporation can be used along with an optimized electroporation protocol for unstimulated T-cells. As multiple plasmids may reduce the efficiency of electroporation, the consolidated PASTE components that use fewer vectors can be applied.

Figure 19:
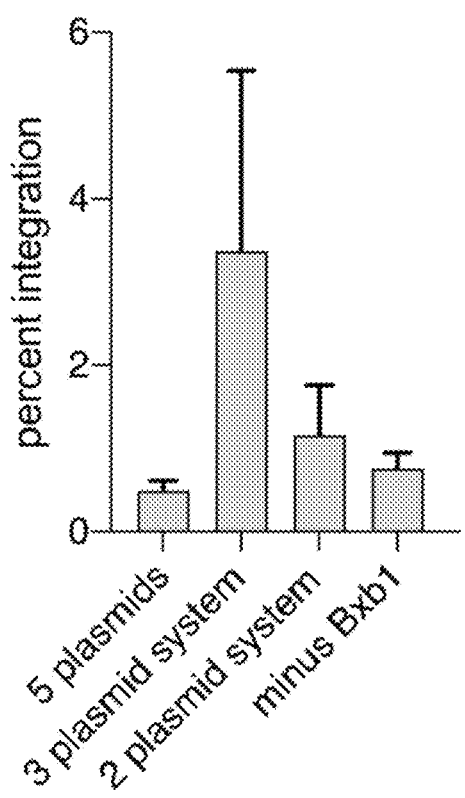
FIG. 19 shows the editing efficiency for EGFP integration at the ACTB locus in primary T-cells according to embodiments of the present teachings.
Figure 20:
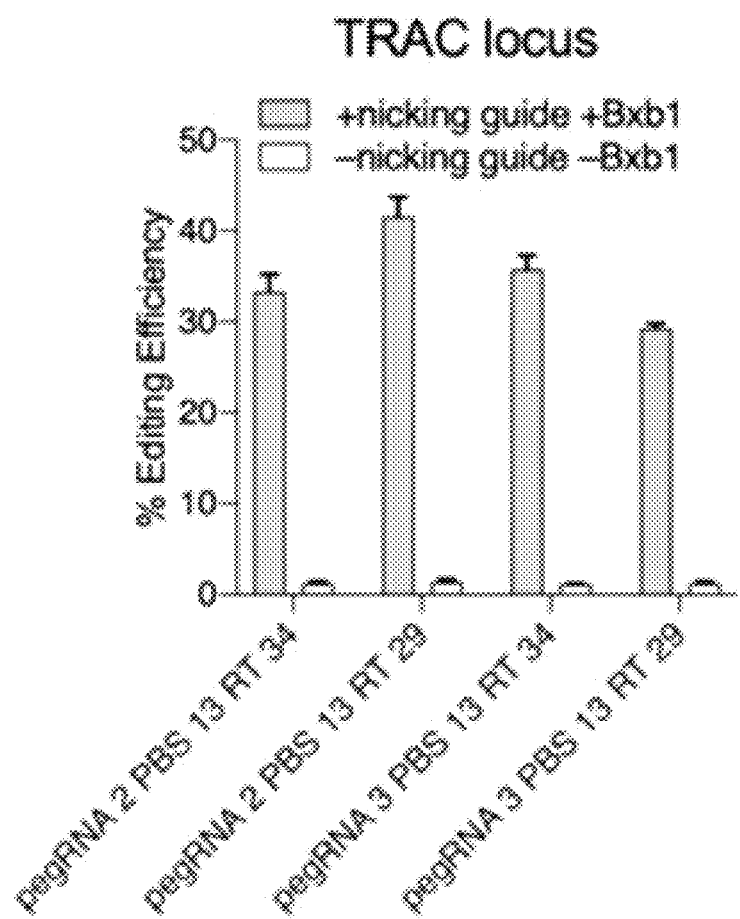
FIG. 20 shows editing in TRAC locus in HEK293FT with different pegRNA according to embodiments of the present teachings.

Five vectors, three vectors, and two vectors PASTE systems show that robust T-cell editing can be achieved with maximal editing using the three-vector approach (FIG. 19). Further, expanded sets of electroporation conditions, including the overall plasmid amounts, cell numbers, and voltage/amperage protocol can be tested. In addition, stimulation of T-cells may influence the efficiency of transduction and PASTE efficiency. Further, CD4+/CD8+ T cell mixtures stimulated with T-Activator CD3/CD28 ligands can have higher PASTE editing efficiency versus unstimulated cells. In order to separate efficiency of PASTE from the overall delivery rate, an mCherry expression cassette on PASTE vectors can be evaluated in order to sort successfully transfected T cells. Once optimized parameters are achieved, a panel of 10 insertion sites with PASTE in T cells, including the TRAC, IL2Rα, and PDCD1 loci, can be evaluated, using different insertions (e.g. EGFP, BFP, and YFP), both in single and multiplexed editing contexts. A tested subset of relevant sites in HEK293FT achieved greater than 40% editing for EGFP insertion (FIG. 20). The PASTE efficiency at TRAC locus with different TCR and CAR constructs can be evaluated. The T-cells can successfully be transfected to achieve insertion of CARs or TCRs.

Example 10

PASTE for CFTR

PASTE for the CFTR locus can be tested in HEK293FT cells to identify top performing pegRNA and nicking designs for human cells. Neuro-2A cells can also be tested to identify top performing pegRNA and nicking designs for mouse cells. The best constructs can be applied for testing in mouse air lung interface (ALI) organoids in vitro or for delivery in pre-clinical models of cystic fibrosis in mice. Table 12 shows the pegRNA, nicking guide and minicircle DNA characteristics for the CFTR gene modulation.

TABLE 12

| Variables | Characteristics |
|---|---|
| pegRNA | 38 bp shortened minimal attB and normal 46 bp attB sequence with:<br>a. PBS of 17, 13, and 9 nt length, and<br>b. RT of 20, 15, and 10 nt in length |
| Nicking guides | Nicking guide 1 +64 bp Nicking guide 2 +23 bp<br>Nicking guide 3 −60 bp Nicking guide 4 −78 bp<br>(distance is calculated from cut site of pegRNA) |
| Minicircle template | A. CFTR coding sequence alone (~4,454 pb in size)<br>B. CFTR coding sequence plus 5' and 3' UTRs (~6,011 bp in size) |

TABLE 12-continued

| Variables | Characteristics |
|---|---|
| | (Both minicircles have attP site on them for integration by Bxb1 and a bGH poly A signal) |

Example 11

AttB and EGPF Integration Using PASTE

Figure 21A:
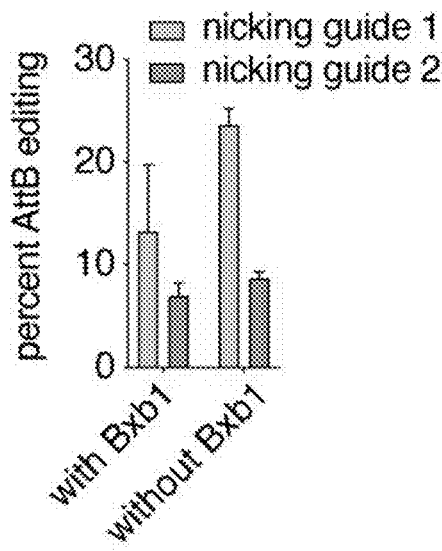
FIG. 21A shows the attB integration at the ACTB locus using nicking guides 1 and 2 according to embodiments of the present teachings.
Figure 21B:
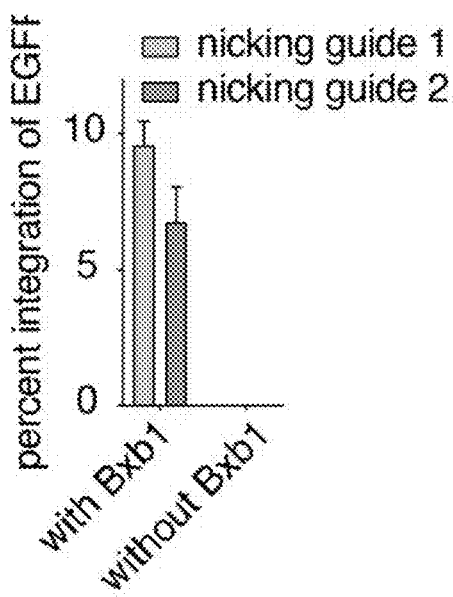
FIG. 21B shows the EGFP integration at the ACTB locus using nicking guides 1 and 2 according to embodiments of the present teachings.
Figure 21C:
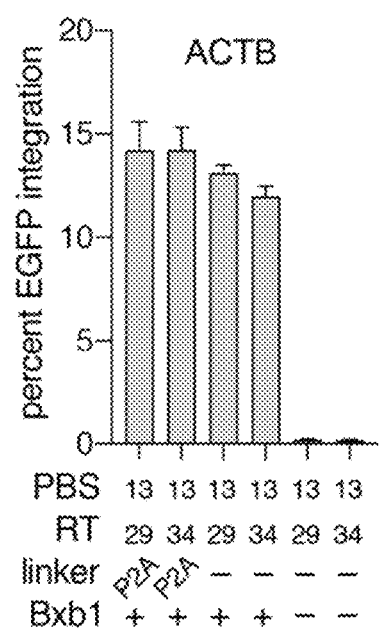
FIG. 21C shows the EGFP integration at an ACTB site according to embodiments of the present teachings.

The efficiency of the integration of attB and EGPF at the ACTB locus was evaluated (FIGS. 21A-21C). To investigate whether Bxb1 can add an EGFP template into this site, a delivery approach using a 5 plasmid system expressing each of the following component was deployed: 1) pegRNA expression, 2) nicking guide expression, 3) Prime expression (Cas9-RT), 4) Bxb1 expression and 5) the insertion template (in this case EGFP). This approach was found to yield editing efficiency of the attB site up to 24% and integration of EGFP ~10% in HEK293FT cells as measured by sequencing (FIGS. 21A-21B). Optimal activity is achieved in 3-4 days and can be performed as a single step transfection or electroporation of all components. Because the EGFP plasmid is designed as a minicircle, allowing removal of all undesired bacterial components, only the desired gene is inserted along with minimal scars from the Bxb1 recombined sites.

To make the tool simpler to use, the Bxb1 can be linked to Prime via a P2A linker to the Cas9-RT fusion, allowing for only a single plasmid to be used for PASTE protein expression rather than two. This optimization can maintain the same level of editing, making it easier to use the tool and deliver it (FIG. 21C).

Example 12

Programmable EGFP Integrations in Different Cell Types

Figure 22A:
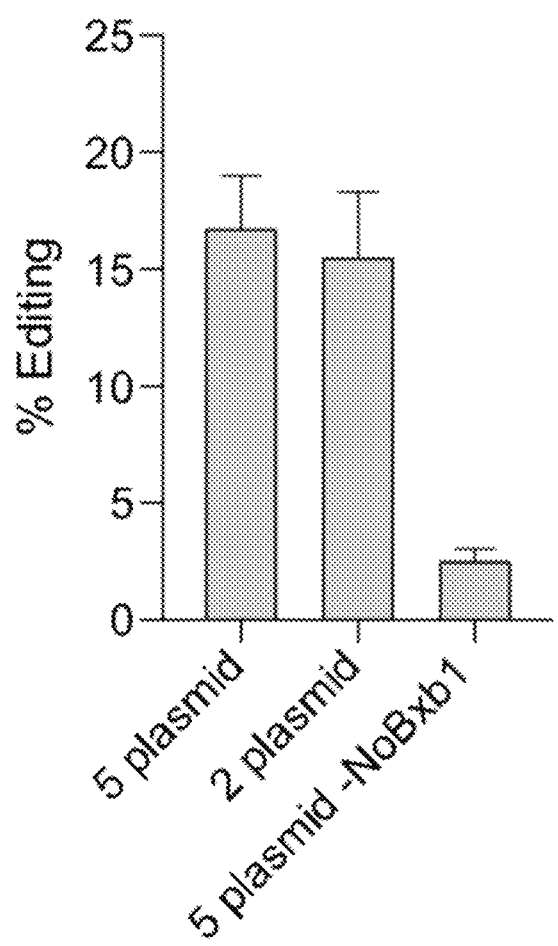
FIG. 22A shows PASTE editing in liver hepatocellular carcinoma cell line HEPG2 according to embodiments of the present teachings.
Figure 22B:
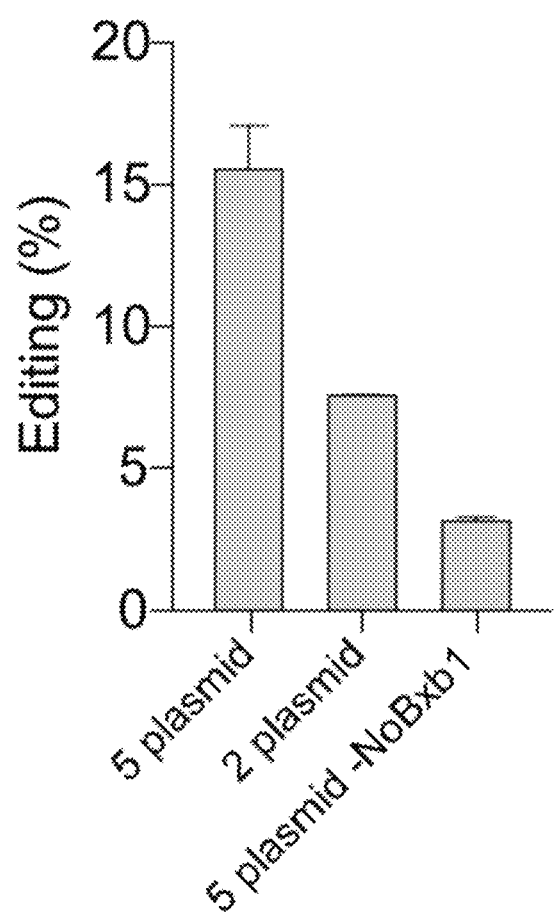
FIG. 22B shows PASTE editing of chronic myelogenous leukemia cell line K562 according to embodiments of the present teachings.

The programmable EGFP integration in liver hepatocellular carcinoma cell line HEPG2 (FIG. 22A) and chronic myelogenous leukemia cell line K562 (FIG. 22B) was evaluated. EGFP integration at the ACTB locus in K562 and HEPG2 cells of about 15% was observed, demonstrating robustness of the platform across cell types.

Example 13

Mutagenesis of Bxb1 for Enhanced PASTE Activity

Figure 23A:
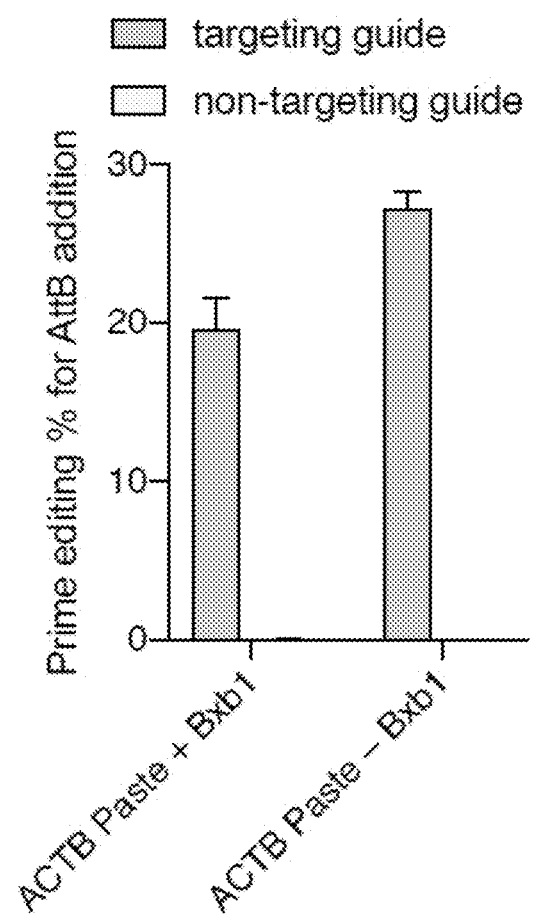
FIG. 23A shows the attB addition with targeting and non-targeting guides according to embodiments of the present teachings.
Figure 23B:
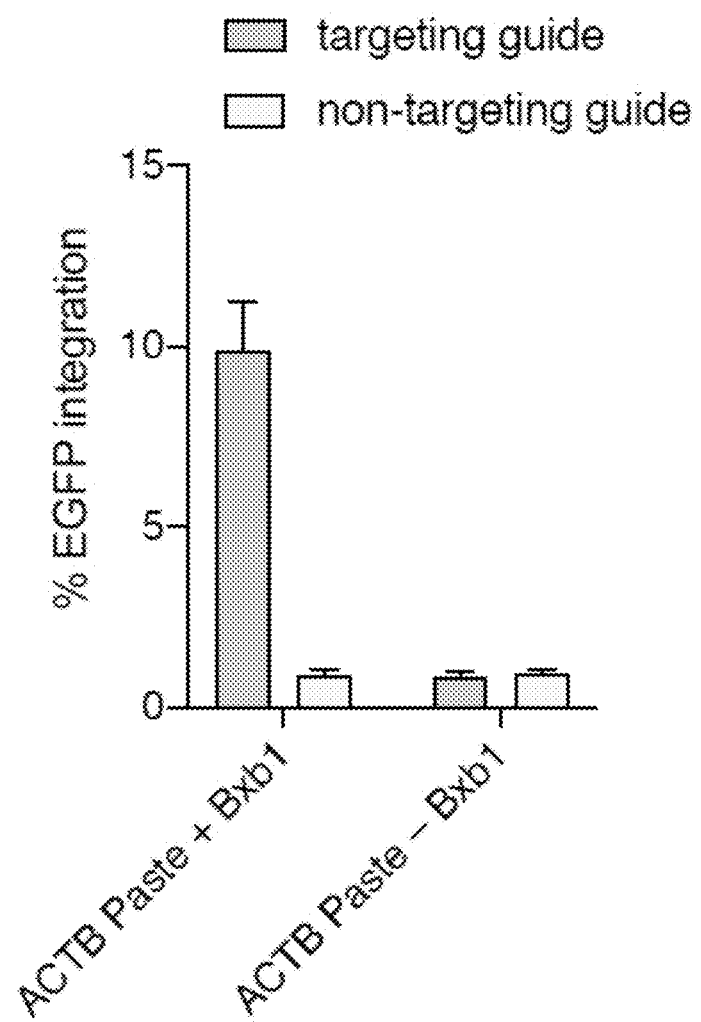
FIG. 23B shows the EGFP integration with targeting and non-targeting guides according to embodiments of the present teachings.
Figure 23C:
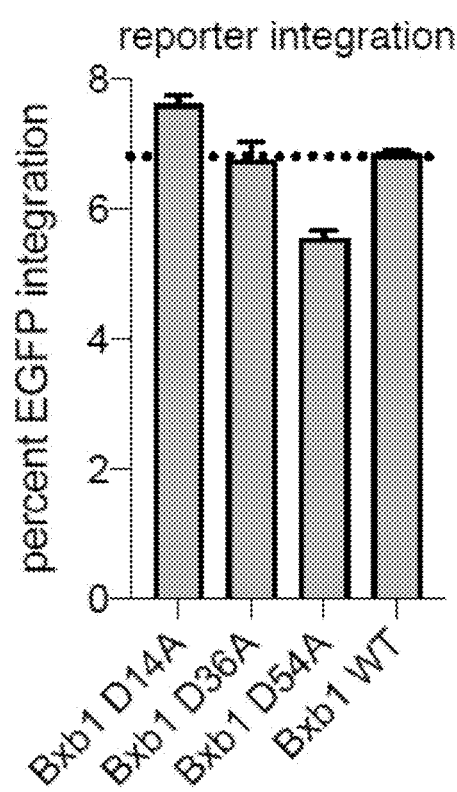
FIG. 23C shows the EGFP integration for mutagenized Bxb1 according to embodiments of the present teachings.

The mutagenesis of Bxb1 for enhanced PASTE activity was evaluated (FIGS. 23A-23C). Two levers for optimizing PASTE activity exist: 1) improving the activity of the integrase and 2) enhancing the Prime addition of the integration sequence. As illustrated in FIGS. 23A-23B, Bxb1 activity can be improved as only about 30% of Bxb1 attB sites that are added by PASTE are integrated into by Bxb1. This illustrates that if the Bxb1 efficiency can be improved, the PASTE can be improved. Furthermore, catalytic residues in the Bxb1 integrase were identified via conservation and structural analyses and Bxb1 mutants were generated to test as part of PASTE. As illustrated in FIG. 23B, the mutations can improve integration by about 20-30%.

Example 14

Figure 25A:
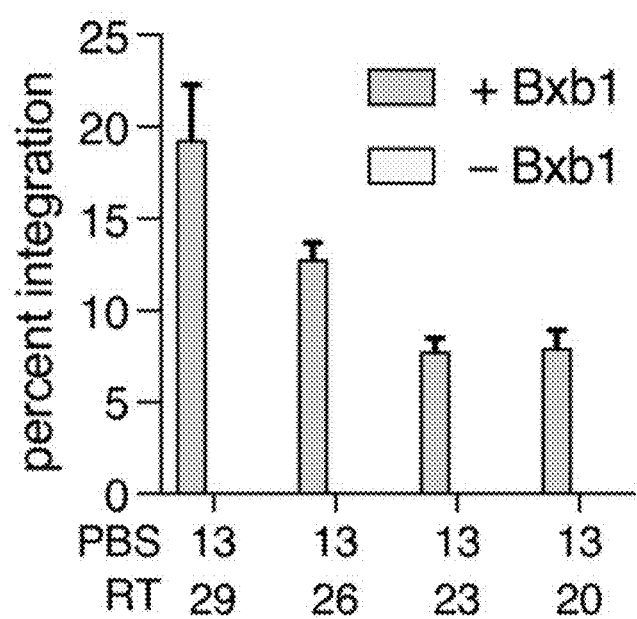
FIG. 25A shows the integration of EGFP at the ACTD locus with different PBS and RT lengths according to embodiments of the present teachings.
Figure 25B:
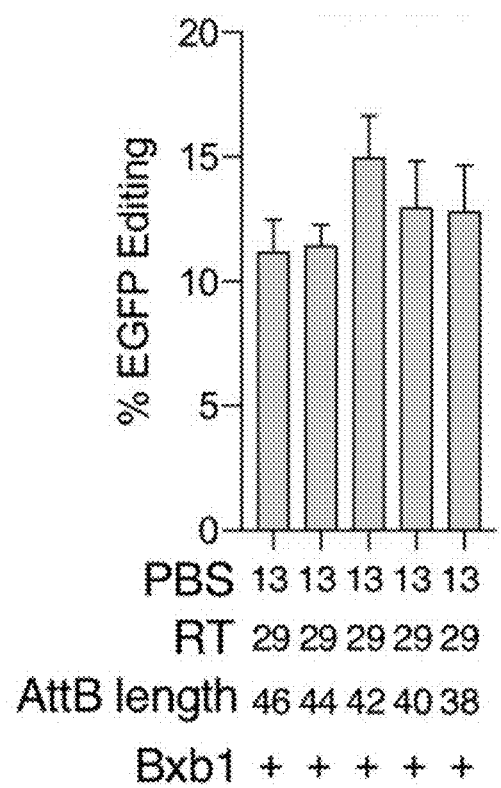
FIG. 25B shows the integration of EGFP at the LMNB1 loci with different PBS and RT lengths according to embodiments of the present teachings.
Figure 25C:
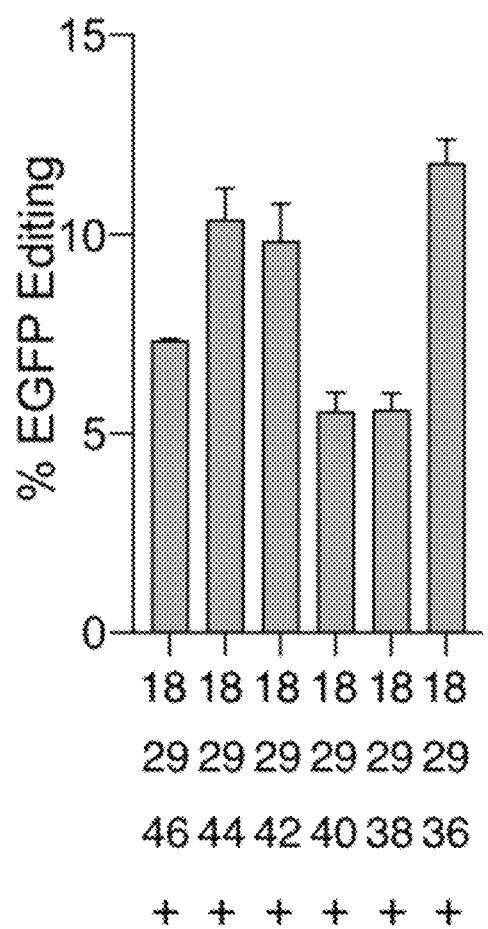
FIG. 25C shows the integration of EGFP at the NOLC1 loci with different PBS and RT lengths according to embodiments of the present teachings.
Figure 25D:
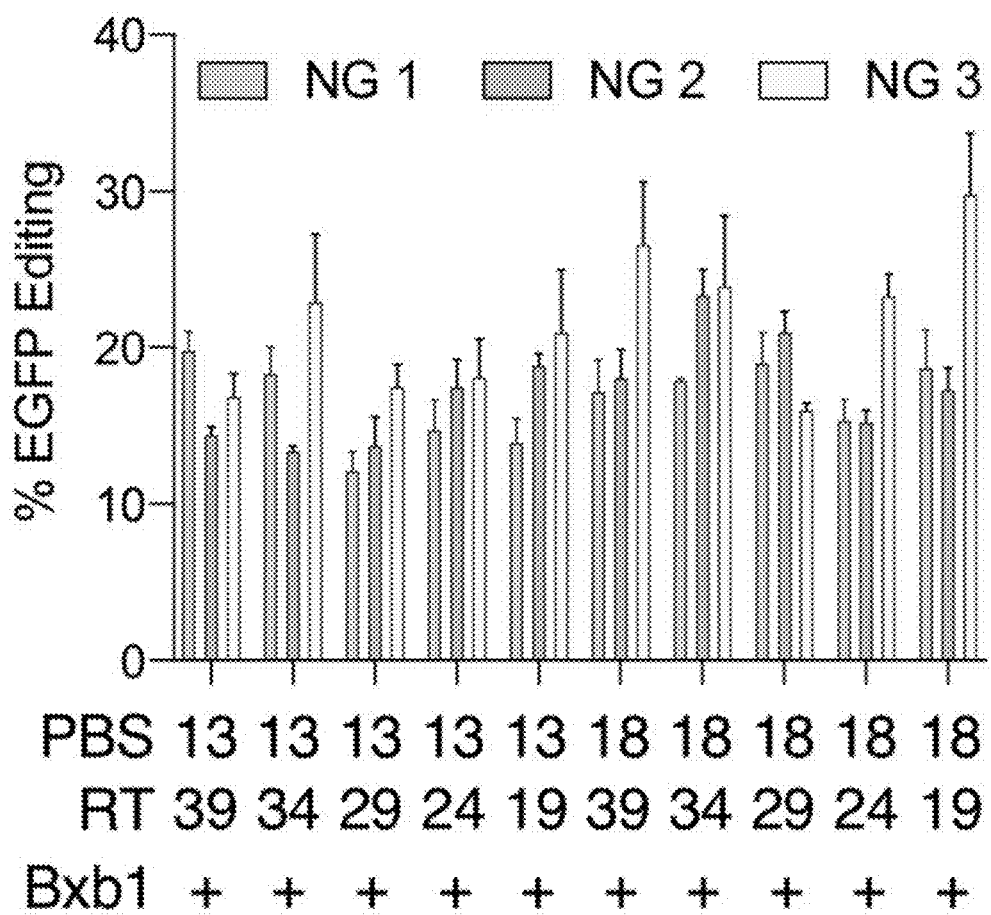
FIG. 25D shows the integration of EGFP at the GRSF1 locus with different PBS and RT lengths and different nicking guides according to embodiments of the present teachings.
Figure 25E:
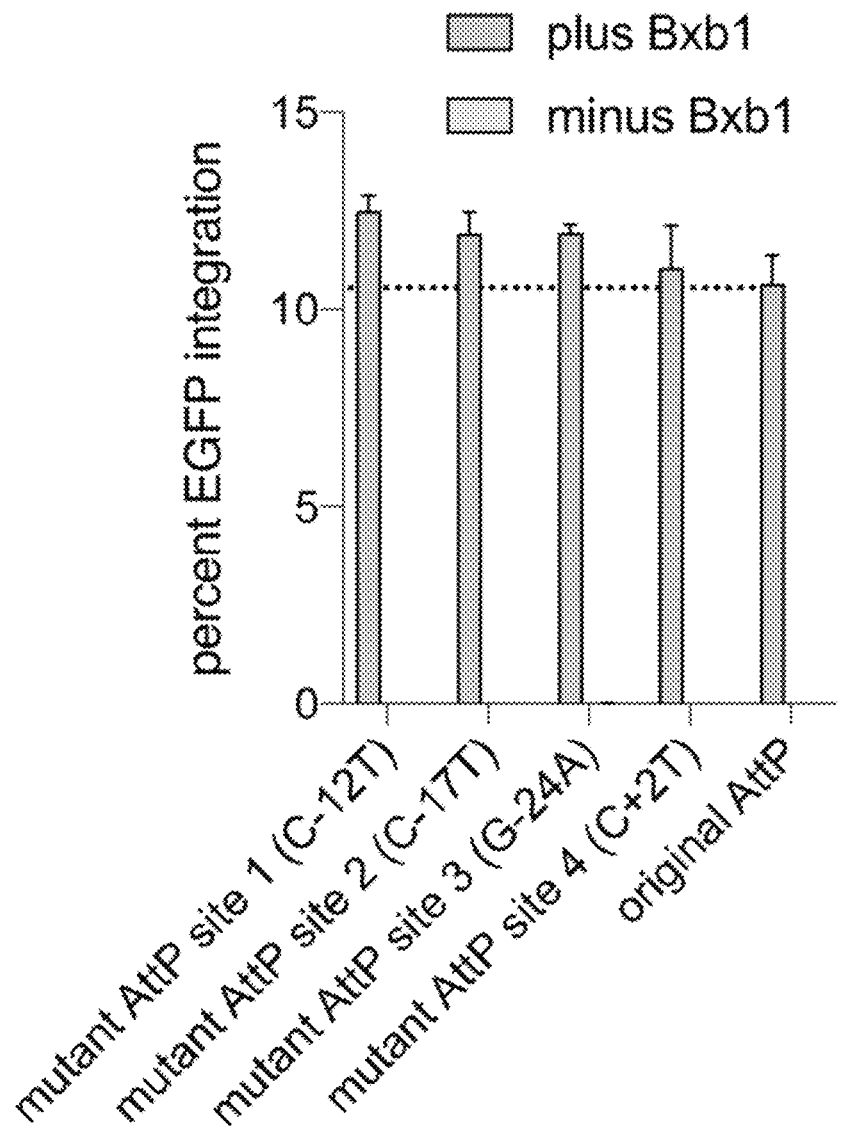
FIG. 25E shows EGFP integration with mutant attP sites according to embodiments of the present teachings.
Figure 25F:
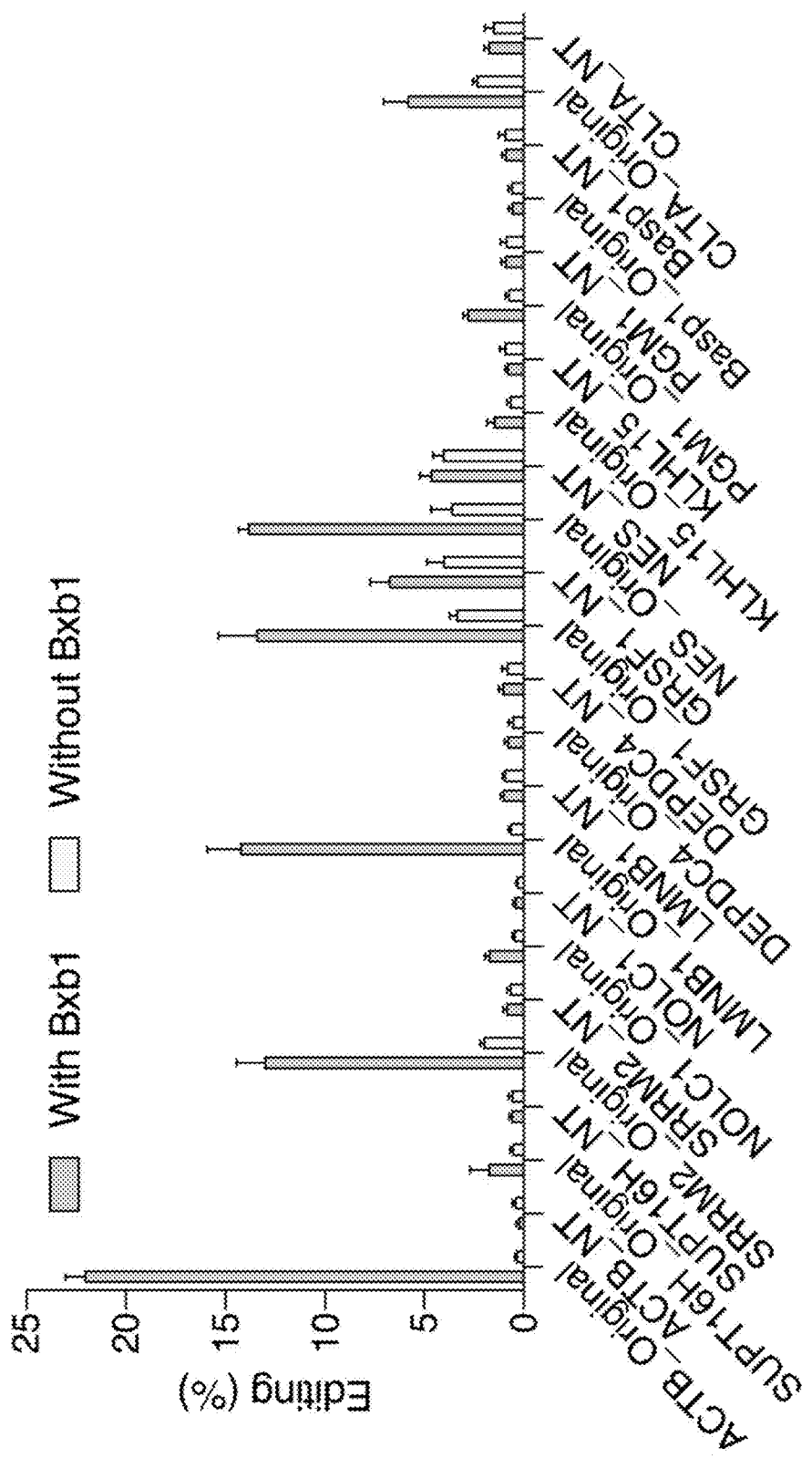
FIG. 25F shows the PASTE editing of an expanded panel of genes according to embodiments of the present teachings.

Effect of the pegRNA PBS and RT Lengths on the Prime Editing Integration Efficiency The effect of the pegRNA PBS and RT lengths on the prime editing integration efficiency was evaluated (FIGS. 25A-25F). It was found that PASTE can be optimized by tuning the PBS and RT lengths at the ACTB locus to achieve editing rates up to about 20% (FIG. 25A). It was found that shortening the attB site can help improve PASTE function as Prime is better at inserting shorter sequences. Further optimization of PBS, RT, and attB lengths showed that optimal designs can be found for insertion upstream of the LMNB1, NOLC1, and GRSF1 loci (FIGS. 25B, 25C, and 25D). Lengths as short as 36 nt for attB were found to be still functional for integration into a reporter plasmid (FIGS. 25B and 25C). It was found that the reverse complemented version of the attB sequence was better integrated via Prime editing, suggesting that the sequence of what Prime is inserting matters. EGFP integrations with attP site mutants showed that certain mutants can improve integration efficiency significantly (FIG. 25E). PASTE was also performed with a large panel of genes, inserting EGFP at the N-terminus of ACTB, LMNB1, SUPT16H, SRRM2, NOLC1, KLHL15, GRSF1, DEPDC4, NES, PGM1, CLTA, BASP1, and DNAJC18 (FIG. 25F). Editing rates that are about 5%-40% were found using digital droplet PCR (ddPCR).

Example 15

Comparison of PASTE and HITI On-Target and Off-Target Activities

Figure 26A:
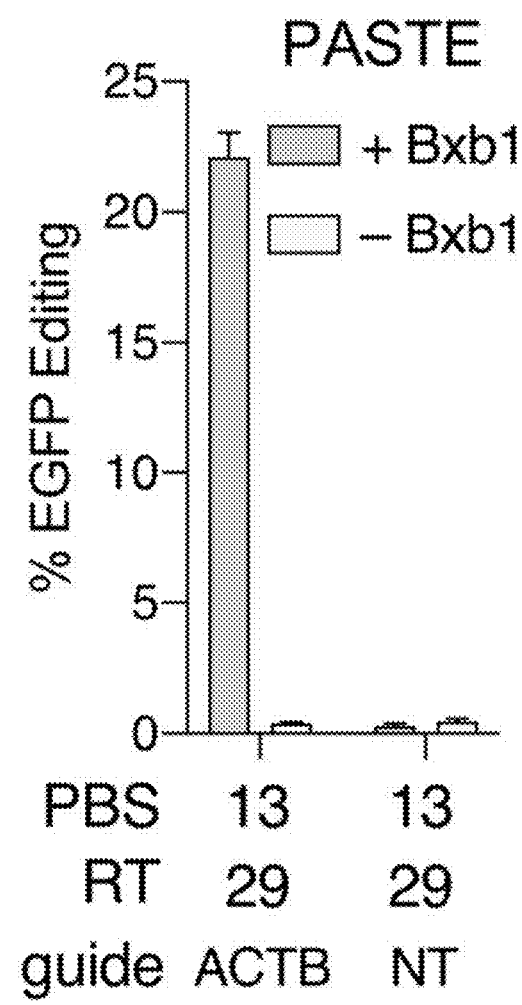
FIG. 26A shows the PASTE EGPF editing at the ACTB locus according to embodiments of the present teachings.
Figure 26B:
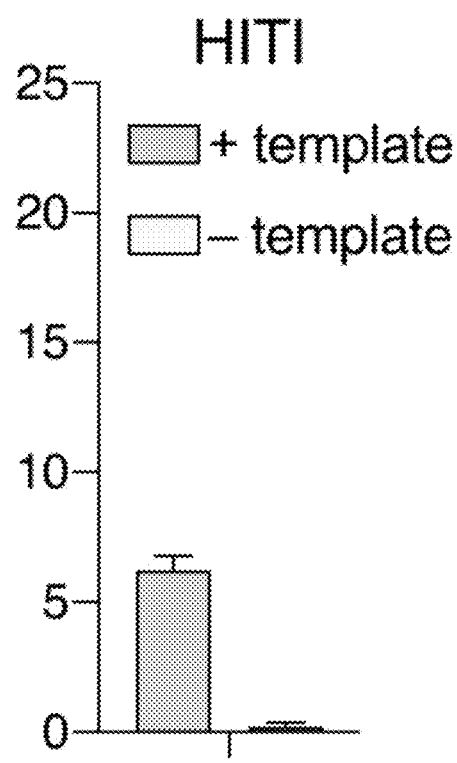
FIG. 26B shows the HITI EGPF editing at the ACTB locus according to embodiments of the present teachings.
Figure 26C:
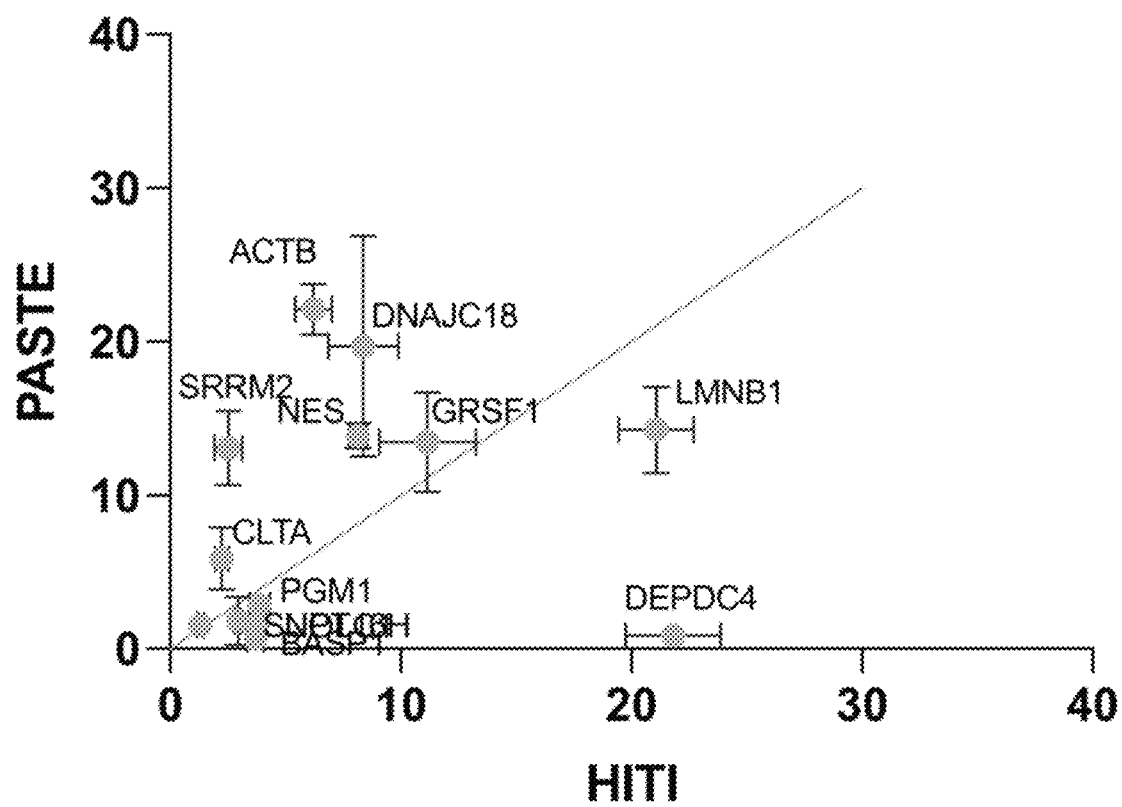
FIG. 26C shows the comparison between the PASTE and HITI editing a panel of 14 genes according to embodiments of the present teachings.
Figure 26D:
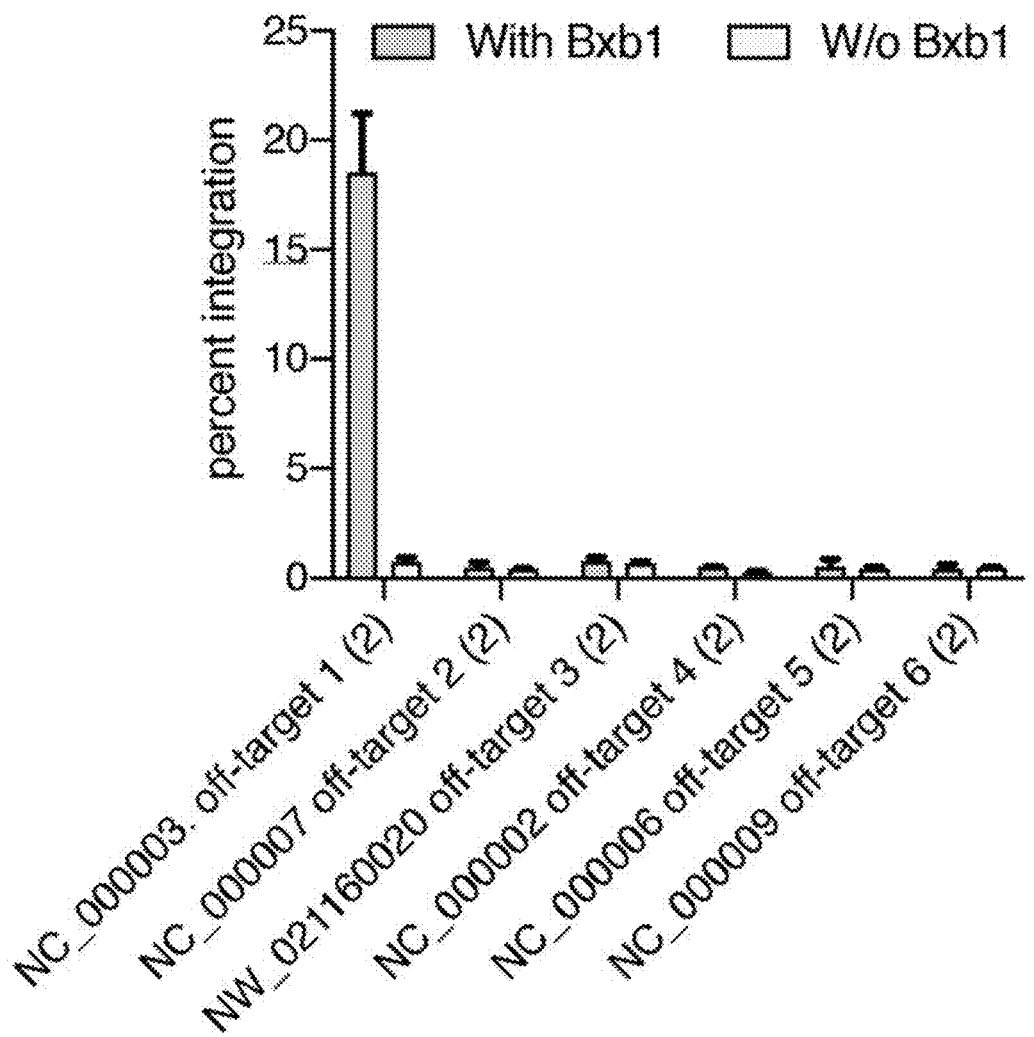
FIG. 26D shows PASTE Bxb1 off-target integrations according to embodiments of the present teachings.
Figure 26E:
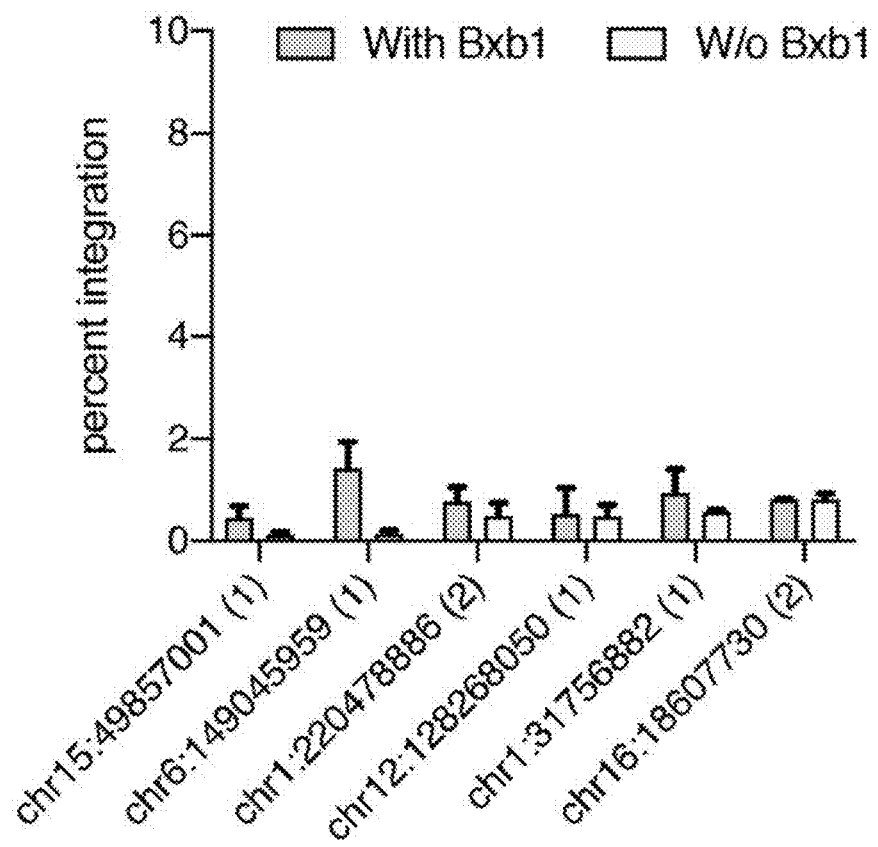
FIG. 26E shows PASTE Cas9 off-target integrations according to embodiments of the present teachings.
Figure 26F:
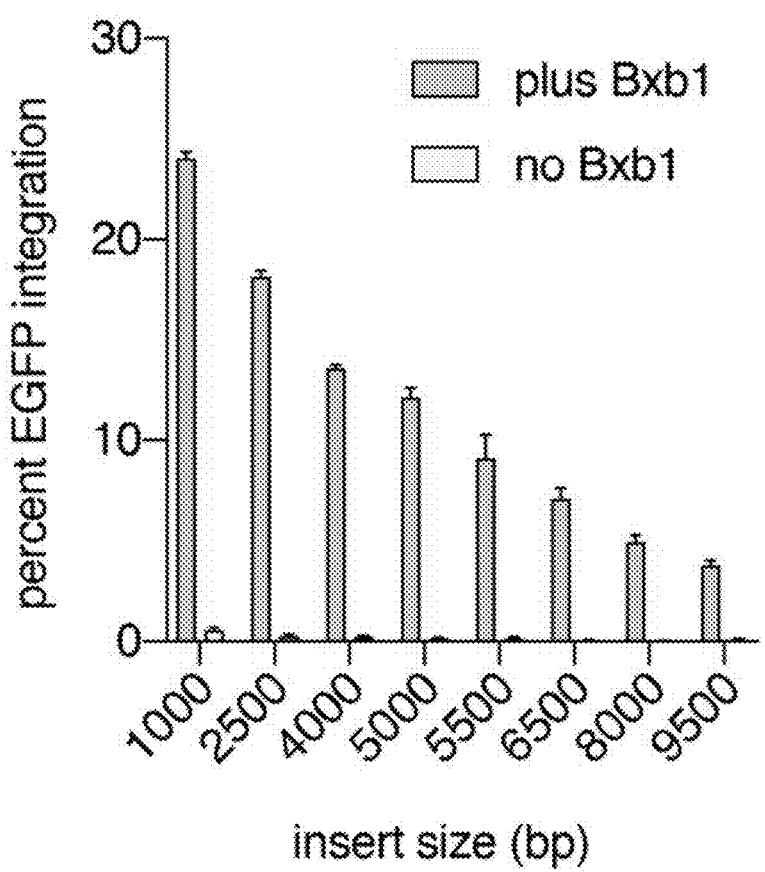
FIG. 26F shows the EGFP integration for gene inserts of different sizes according to embodiments of the present teachings.
Figure 27A:
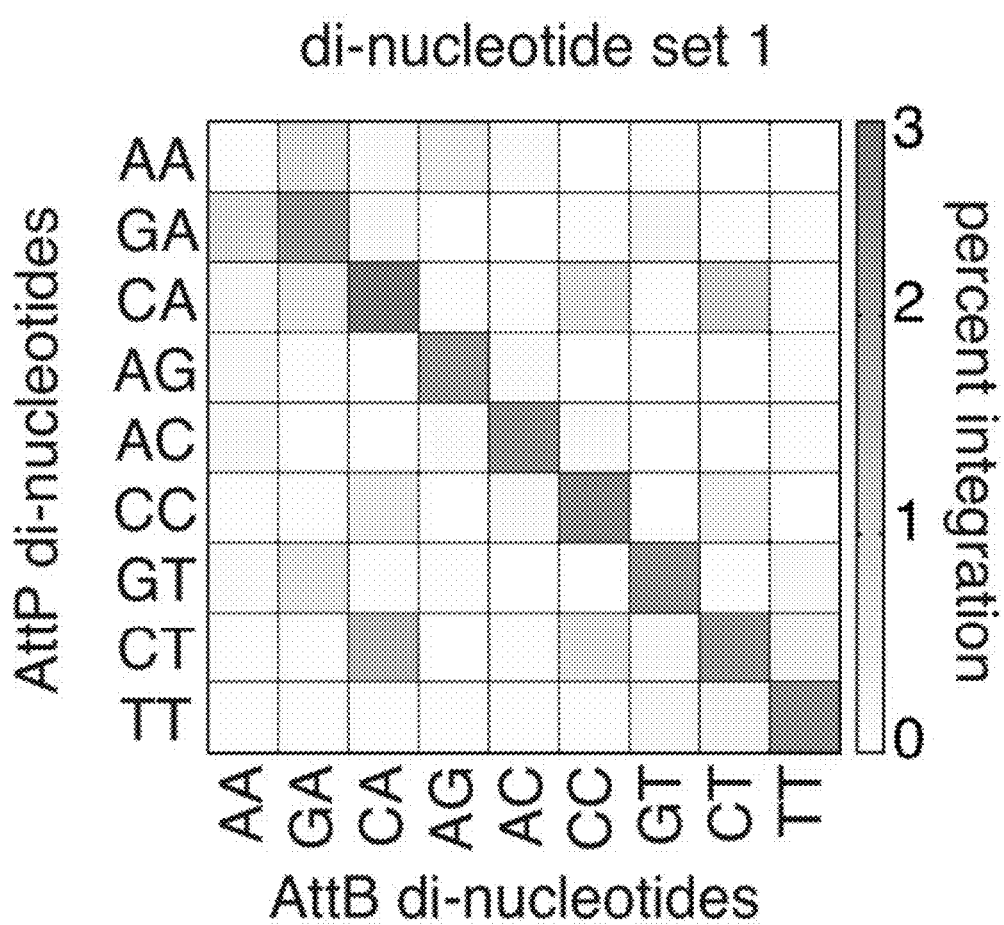
FIG. 27A shows the orthogonality between selected sets of attB and attP sites according to embodiments of the present teachings.
Figure 27B:
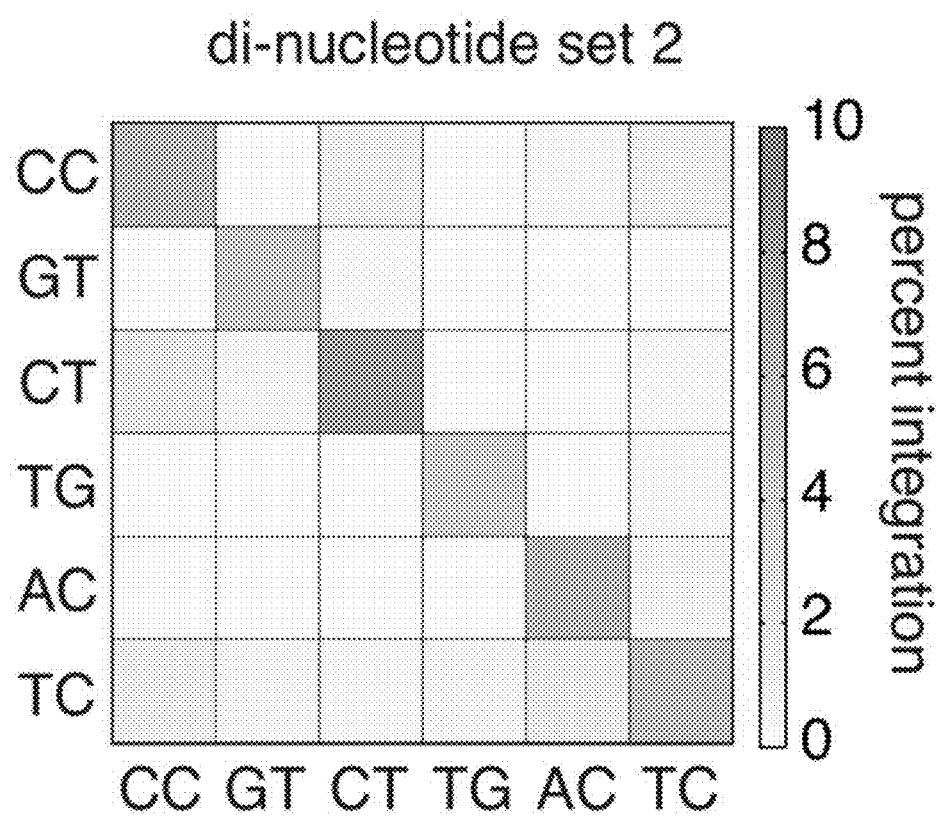
FIG. 27B shows the orthogonality between selected sets of attB and attP sites according to embodiments of the present teachings.
Figure 27C:
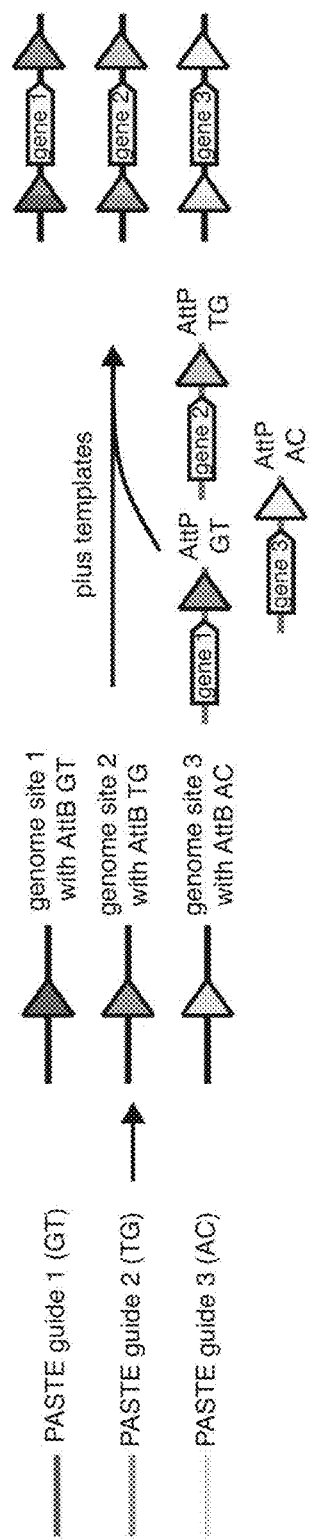
FIG. 27C shows a schematic for the orthogonal PASTE editing using engineered di-nucleotide combinations according to embodiments of the present teachings.

The PASTE and HITI on-target and off-target activities were compared (FIGS. 26A-26F). PASTE and HITI were found to have about 22% and 5% integration efficiencies respectively when using the same guide sequence (FIGS. 26A and 26B). PASTE was found to outperform HITI at most sites when analyzing the editing of 14 genes (FIG. 26C). Using a ddPCR based approach, it was found that PASTE was very specific with minimal off-target activity for Bxb1 off-targets integrations (FIG. 26D) and Cas9 off-targets integrations (FIG. 26E). The analysis of inserts of different sizes showed that PASTE can reliably insert sequences 1 kb-10 kb in size (FIG. 26F), revealing the wide range of sequence sizes PASTE is capable of working with. A decrease in insertion efficiency at larger sizes was also observed, which was likely due to the reduction in plasmid delivery to HEK293FT cells at larger plasmid sizes.

Example 16

Multiplexing with PASTE and Orthogonal Di-Nucleotide attB and attP Sites

Figure 28A:
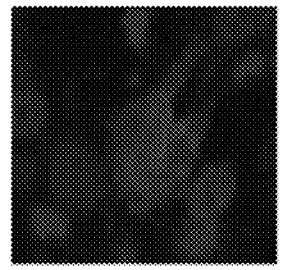
FIG. 28A shows fluorescent images of the GFP tagging of ACTB and SUPT16H genes with PASTE according to embodiments of the present teachings.
Figure 28A:
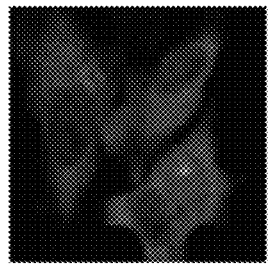
Figure 28A:
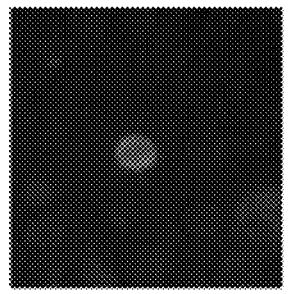
Figure 28A:
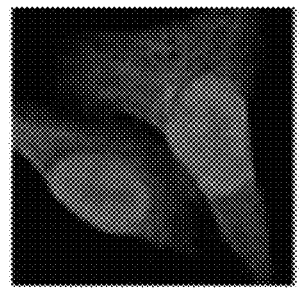
Figure 28B:
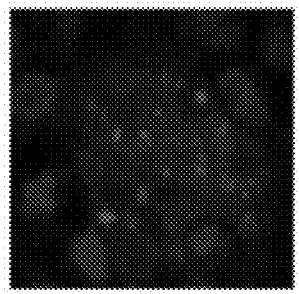
FIG. 28B shows fluorescent images of the GFP tagging of NOLC1 and SRRM2 genes with PASTE according to embodiments of the present teachings.
Figure 28B:
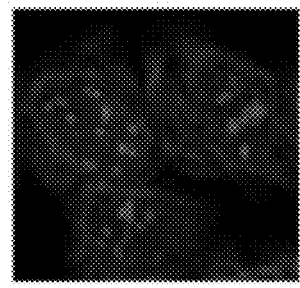
Figure 28B:
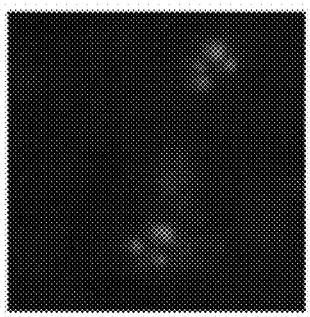
Figure 28B:
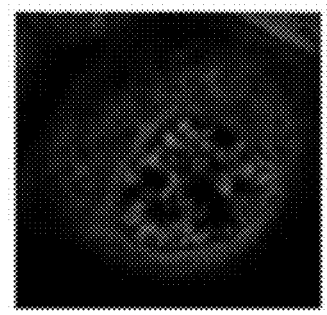
Figure 28C:
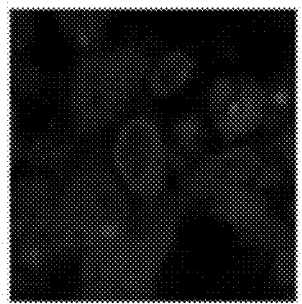
FIG. 28C shows fluorescent images of the GFP tagging of LMNB1 and DEPDC4 genes with PASTE according to embodiments of the present teachings.
Figure 28C:
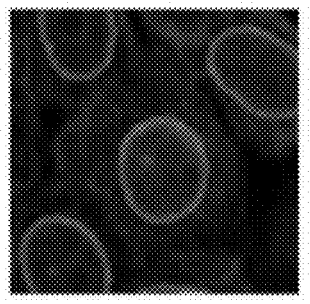
Figure 28C:
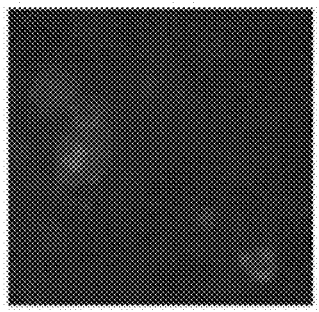
Figure 28C:
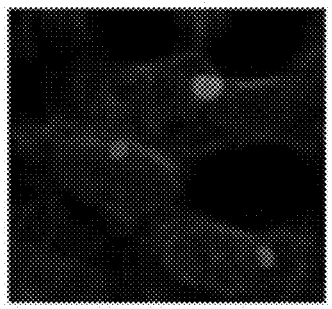

Multiplexing with PASTE and orthogonal di-nucleotide attB and attP sites was evaluated (FIGS. 28A-28C). Multiple orthogonal combinations were found for mutants of the central di-nucleotide motif (FIGS. 28A and 28B). As illustrated in FIG. 28C, programmable multiplexed gene insertion can be achieved by using these orthogonal combinations with PASTE only delivering different pegRNAs and gene inserts while keeping the protein components the same (FIG. 8C).

Example 17

PASTE Multiplexed Integrations at Endogenous Sites

Figure 28D:
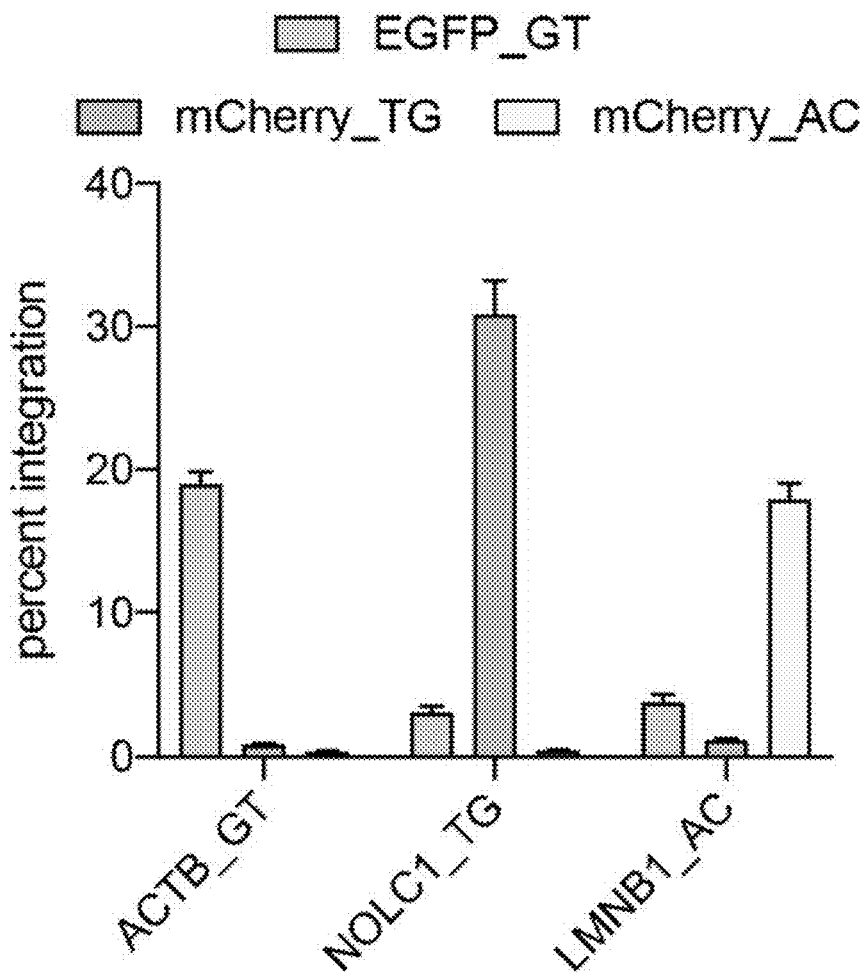
FIG. 28D shows the orthogonal gene integration at three endogenous sites with PASTE according to embodiments of the present teachings.
Figure 28E:
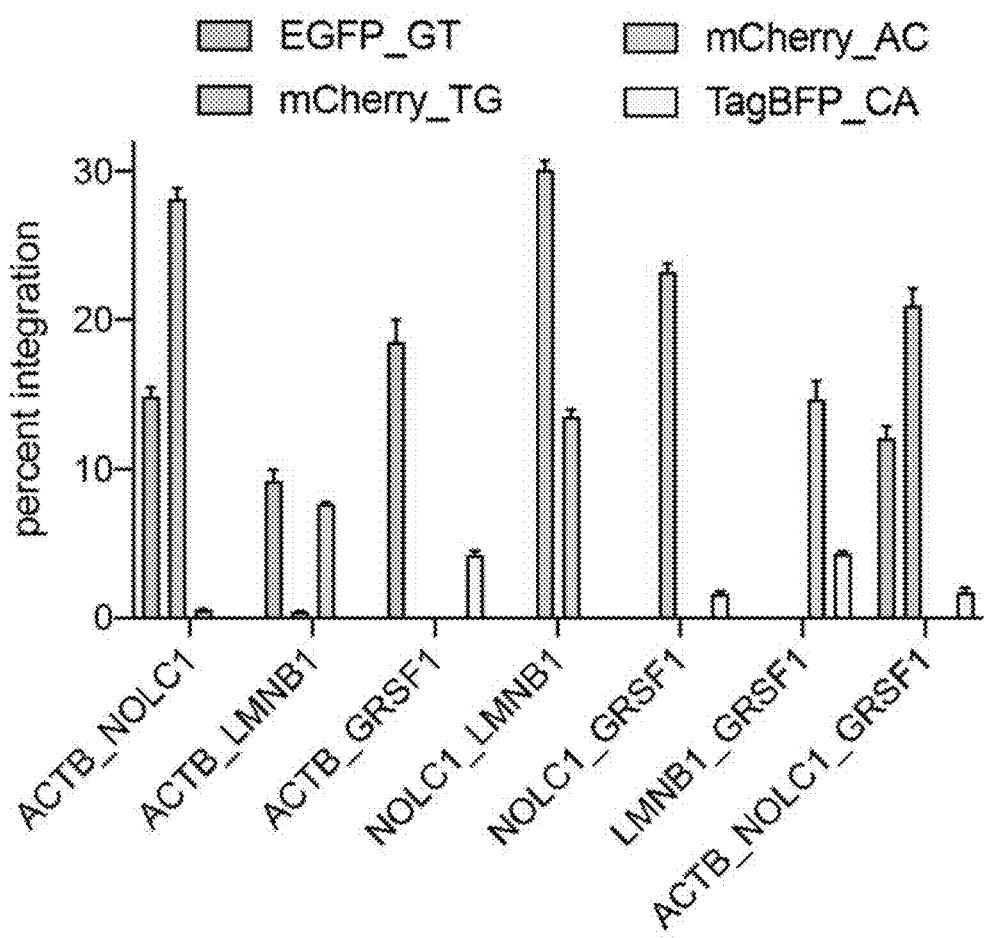
FIG. 28E shows the multiplexed insertion via one-plex, two-plex, and three-plex gene insertion at three endogenous sites via PASTE according to embodiments of the present teachings.
Figure 28F:
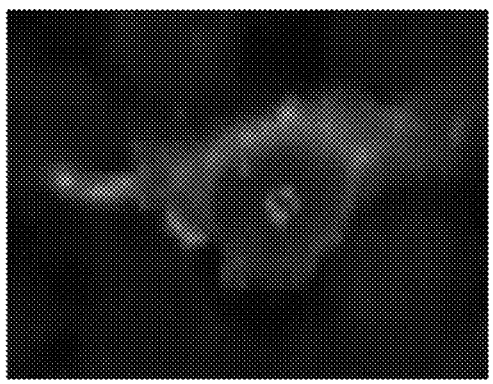
FIG. 28F shows fluorescent images of two single cells with multiplexed gene tagging of ACTB (EGFP) and NOLC1 (mCherry) using PASTE according to embodiments of the present teachings.
Figure 28F:
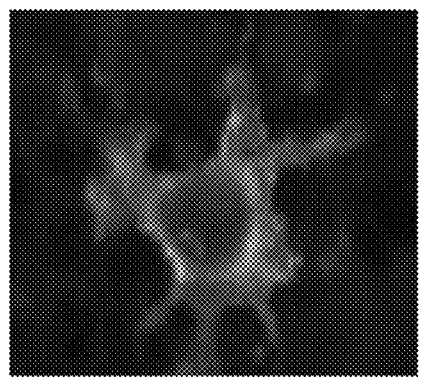
Figure 28G:
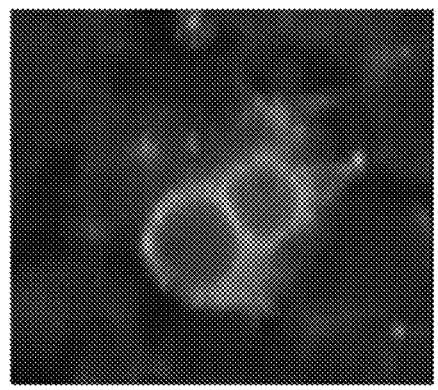
FIG. 28G shows fluorescent images two single cells with multiplexed gene tagging of ACTB (EGFP) and LMNB1 (mCherry) using PASTE according to embodiments of the present teachings.
Figure 28G:
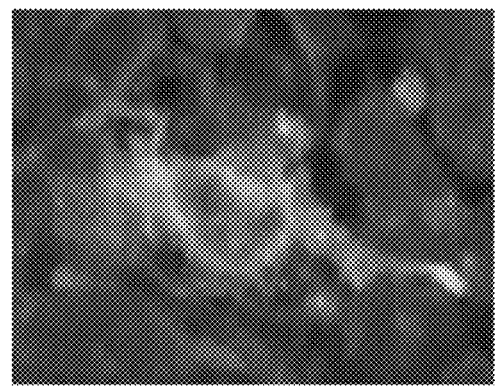

PASTE multiplexed integrations at endogenous sites were evaluated (FIGS. 28A-28G). A reading frame for the attR scar that is left post-integration by Bxb1 that is ideal for a protein linker due to the enrichment of glycines, serines, and prolines in the sequence (GLSGQPPRSPSSGSSG (SEQ ID NO: 426)) was identified. PegRNAs were designed using this linker frame for the resolution of the attR for tagging a number of genes at the N-terminus with EGFP (ACTB, NOLC1, LMNB1, SUPT16H, SRRM2, and DEPDC4). As these genes all have distinct protein localization appearances, microscopy can be used for ascertaining proper gene tagging. PASTE was found to be capable of high-efficiency gene tagging with protein localizations that match the reference images and expected localization of the proteins in the cells (FIGS. 28A-28C). Genes were also tagged in multiplexed fashion to demonstrate the orthogonality of the engineered integration sites. ACTB, LMNB1, NOLC1, and GRSF were targeted with orthogonal pegRNAs carrying GT, TG, AC, and CA, respectively in HEK293FT in groups of single, dual-plexing, and triple-plexing (FIGS. 28D-28E). These dinucleotides were paired with templates carrying EGFP, BFP, and mCherry to allow for multicolor imaging of these labeled genes. The efficiencies of integration for these multiplexing experiments were found to range from about 5%-32%, revealing efficient multiplex integration with PASTE. Using confocal microscopy of these multiplexed integration experiments, cells were found with simultaneous labeling of these different proteins (FIGS. 28F-28G).

Example 18

Combination of CRISPR-Based Genome Editing and Site-Specific Integration

The combination of CRISPR-based genome editing and site-specific integration was evaluated.

Figure 29A:
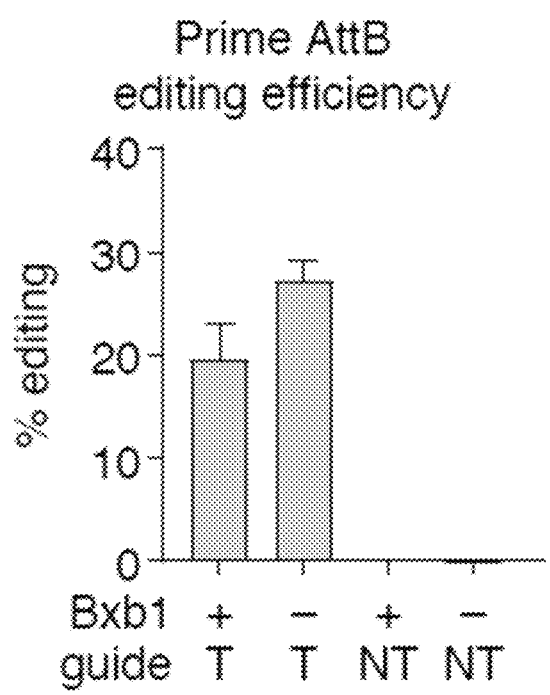
FIG. 29A shows the prime editing efficiency of Bxb1 attB site insertion at the ACTB locus according to embodiments of the present teachings.
Figure 29B:
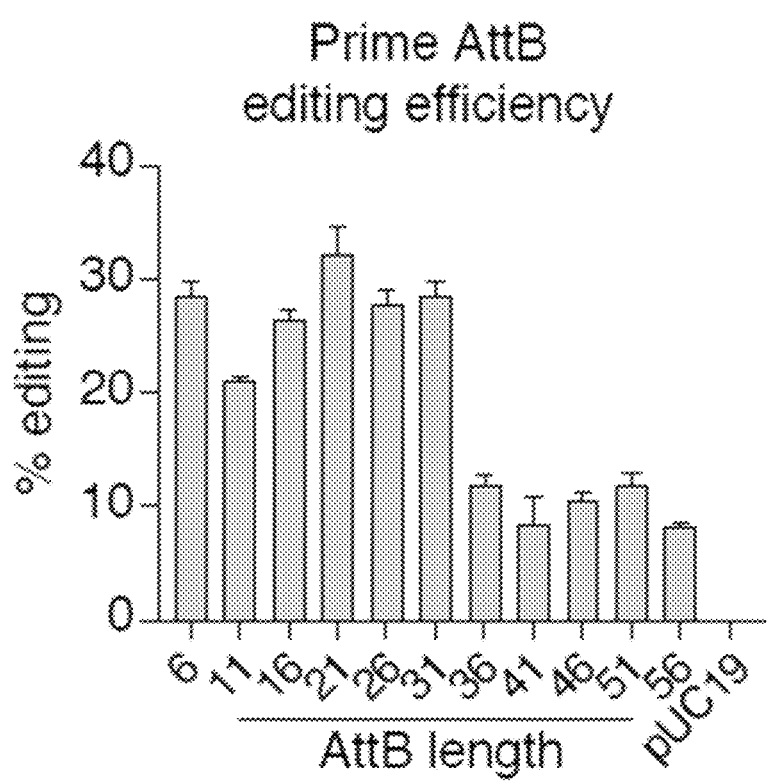
FIG. 29B shows the prime editing efficiency at inserting Bxb1 attB sites of different lengths at the ACTB locus according to embodiments of the present teachings.
Figure 29C:
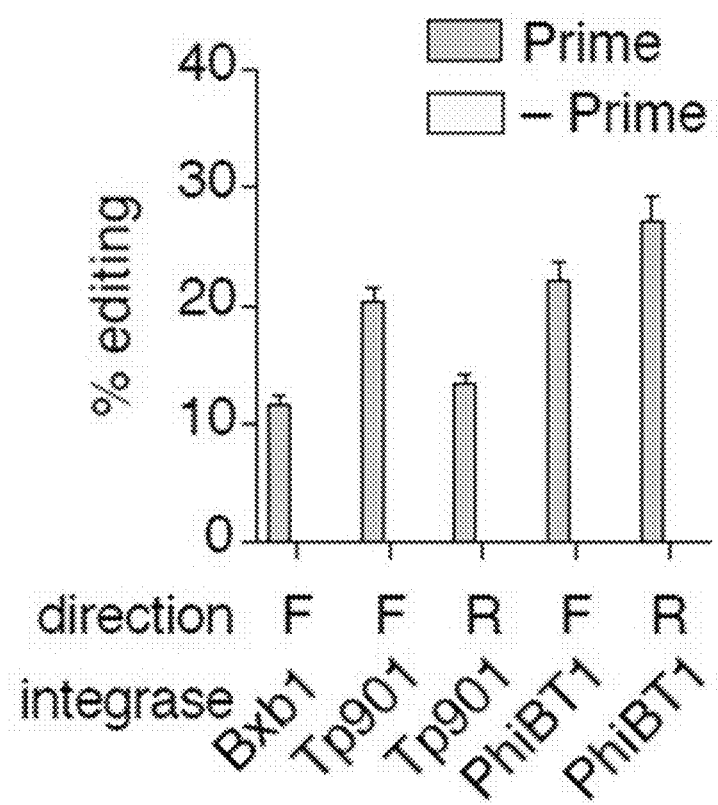
FIG. 29C shows the prime editing efficiency of inserting attB sequences from different integrases, wherein both orientations of landing sites are profiled (F, forward; and R, reverse) according to embodiments of the present teachings.
Figure 29D:
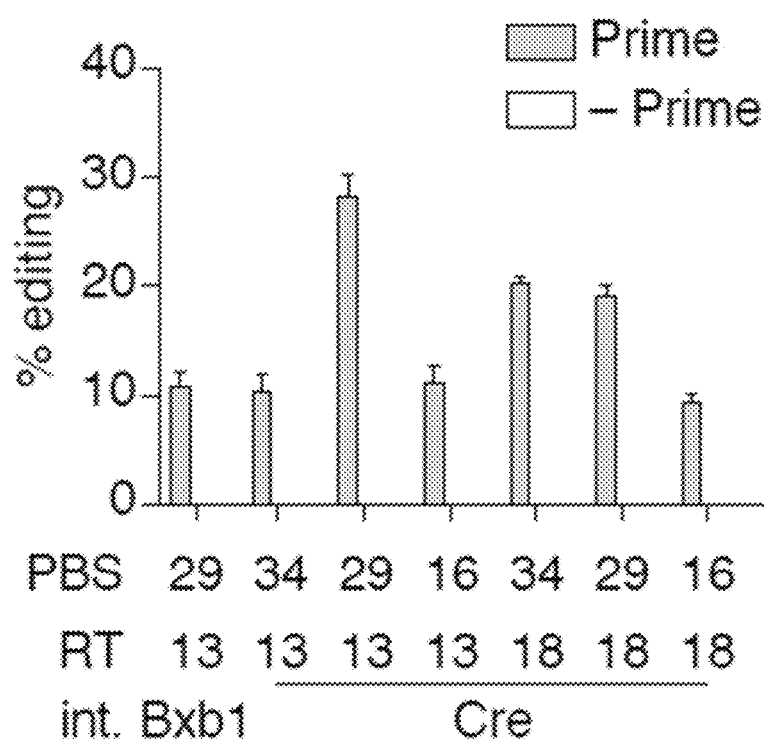
FIG. 29D shows the prime editing efficiency of inserting attB sequences from Bxb1 integrase and Cre recombinase, wherein both orientations of landing sites are profiled (F, forward; and R, reverse) according to embodiments of the present teachings.
Figure 29E:
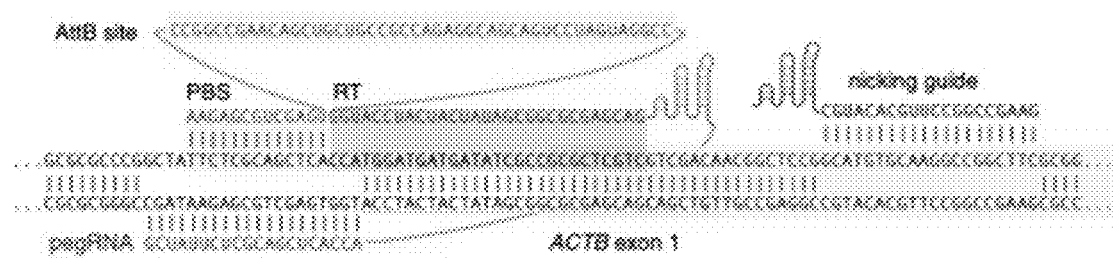
FIG. 29E shows a schematic of PASTE insertion at the ACTB locus showing guide and target sequences according to embodiments of the present teachings.
Figure 29F:
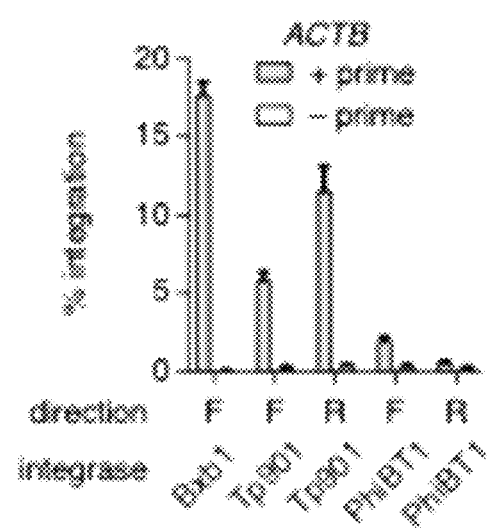
FIG. 29F shows a comparison of PASTE integration efficiency of GFP with a panel of integrases targeting the 5' end of the ACTB locus, wherein both orientations of landing sites are profiled (F, forward; and R, reverse) according to embodiments of the present teachings.
Figure 29G:
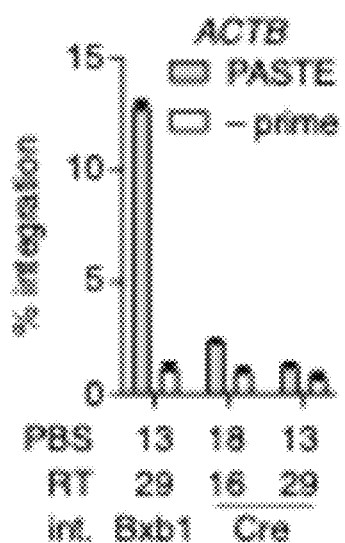
FIG. 29G shows a comparison of GFP cargo integration efficiency between Bxb1 integrases and Cre recombinase according to embodiments of the present teachings.
Figure 29H:
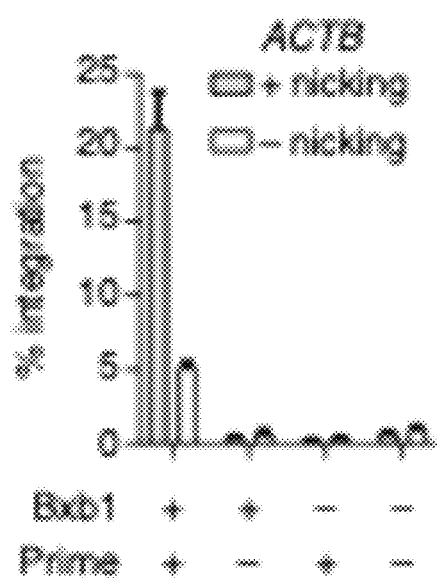
FIG. 29H shows the dependence of PASTE editing activity on different prime and integrase components according to embodiments of the present teachings.
Figure 29I:
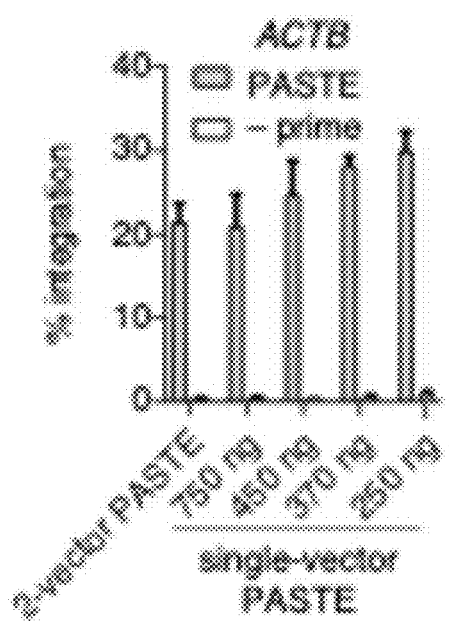
FIG. 29I shows a titration of a single vector PASTE system (SpCas9-RT-P2A-Bxb1) on integrase efficiency according to embodiments of the present teachings.
Figure 29J:
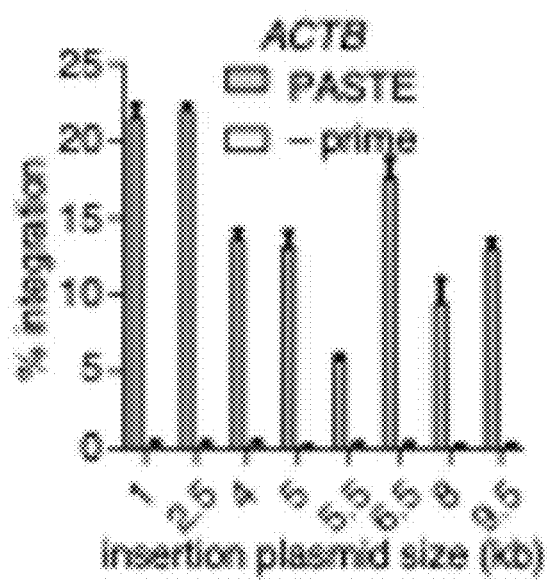
FIG. 29J shows the effect of cargo size on PASTE insertion efficiency at the endogenous ACTB target according to embodiments of the present teachings.
Figure 29K:
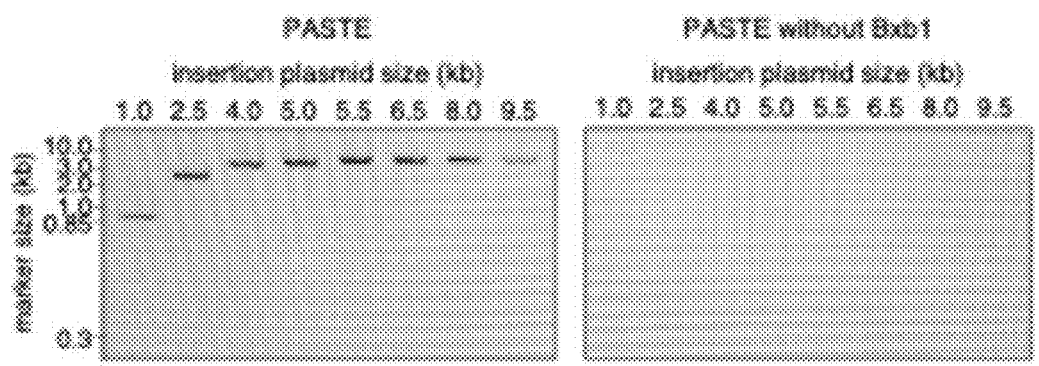
FIG. 29K shows a gel electrophoresis showing complete insertion by PASTE for multiple cargo sizes according to embodiments of the present teachings.
Figure 30A:
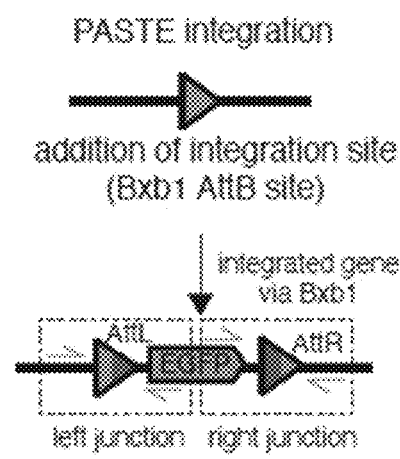
FIG. 30A shows a schematic of PASTE integration, including resulting attR and attL sites that are generated and PCR primers for assaying the integration junctions according to embodiments of the present teachings.
Figure 30B:
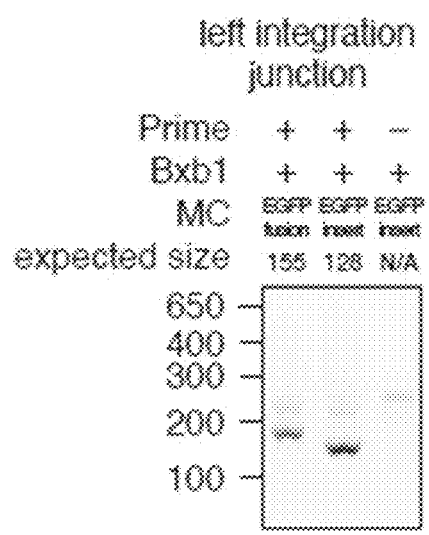
FIG. 30B shows a PCR and gel electrophoresis readout of left integration junction from PASTE insertion of GFP at the ACTB locus, wherein the insertion is analyzed for in-frame and out-of-frame GFP integration experiments as well as for a no prime control and expected sizes of the PCR fragments are shown using the primers shown in the schematic in subpanel FIG. 30A according to embodiments of the present teachings.
Figure 30C:
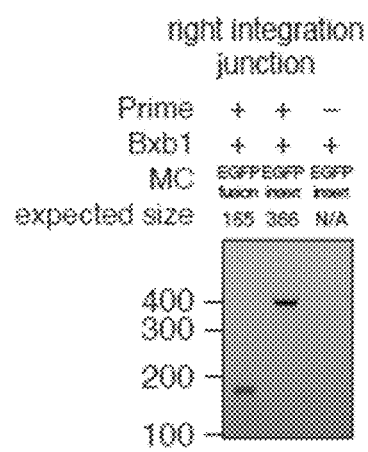
FIG. 30C shows a PCR and gel electrophoresis readout of right integration junction from PASTE insertion of GFP at the ACTB locus, wherein the insertion is analyzed for in-frame and out-of-frame GFP integration experiments as well as for a no prime control and the expected sizes of the PCR fragments are shown using the primers shown in the schematic in subpanel FIG. 30A according to embodiments of the present teachings.
Figure 30D:
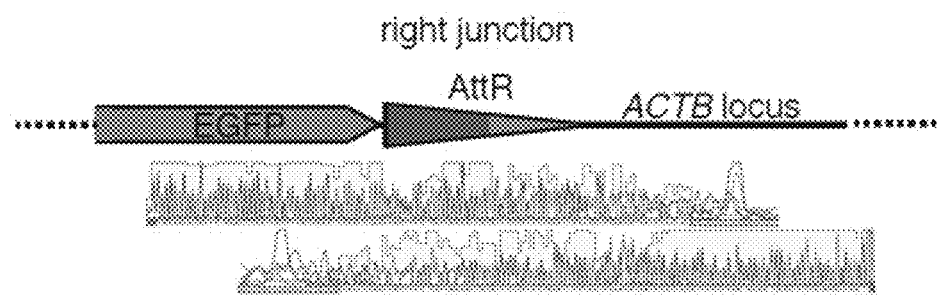
FIG. 30D shows a Sanger sequencing shown for the right integration junction for an in-frame fusion of GFP via PASTE to the N-terminus of ACTB according to embodiments of the present teachings.
Figure 30E:
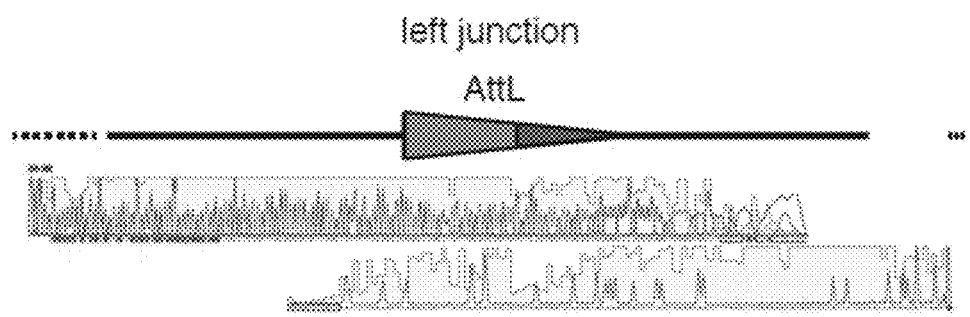
FIG. 30E shows a Sanger sequencing shown for the left integration junction for an in-frame fusion of GFP via PASTE to the N-terminus of ACTB according to embodiments of the present teachings.

PegRNAs containing different attB length truncations were assessed (FIG. 29A). Prime editing was found to be capable of inserting sequences up to 56 bp at the beta-actin (ACTB) gene locus, with higher efficiency at lengths below 31 bp (FIGS. 29A-B) The integration of cognate landing sites was tested for multiple insertion enzymes: Bxb1, TP901, and phiBT1 phage serine integrases and Cre recombinase. Prime editing successfully inserted all landing sites tested, with efficiencies between 10-30% (FIGS. 29C-D). To test the complete system, all components were combined and delivered in a single transfection: the prime editing vector, the landing site containing pegRNA, a nicking guide for stimulating prime editing, a mammalian expression vector for the corresponding integrase or recombinase and a 969 bp minicircle DNA cargo encoding green fluorescent protein (GFP) (FIG. 29E). GFP integration rates among the four integrases and recombinases were compared and Bxb1 integrase was found to have the highest integration rate (~20%) at the targeted ACTB locus and require the prime editing nicking guide for optimal performance (FIGS. 29F-H). Finally, to reduce the number of transfected components, Bxb1 was co-expressed with the SpCas9-M-MLV reverse transcriptase (PE2) fusion protein via a P2A protein cleavage site. This combination maintained high GFP insertion efficiency, up to 30% (FIG. 29E). The complete system, PASTE, achieved precise integration of templates as large as 9,500 bp with greater than 10% integration efficiency (FIGS. 29J-K and 26E), with complete integration of the full-length cargo confirmed by Sanger sequencing (FIG. 30A-E).

Example 19

Impact of Prime Editing and Integrase Parameters on PRIME Editing

The impact of prime editing and integrase parameters on the integration efficiency of PRIME editing was assessed.

Figure 31A:
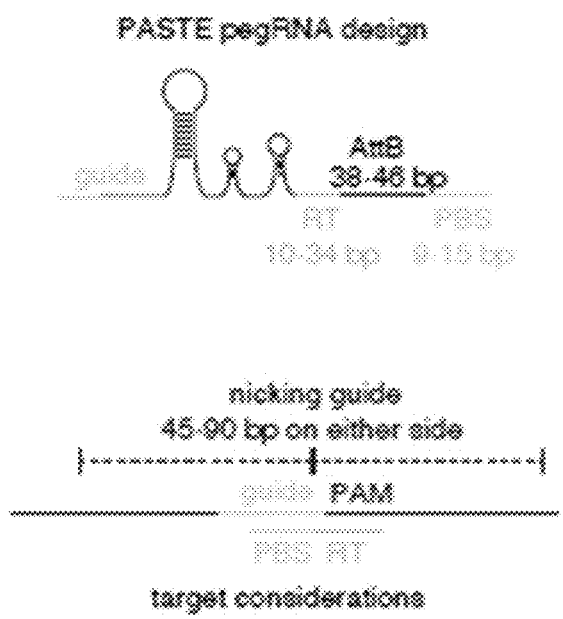
FIG. 31A shows a schematic of various parameters that affect PASTE integration of ~1 kb GFP insert, wherein on the pegRNA, the PBS, RT, and attB lengths can alter the efficiency of attB insertion, and nicking guide selection also affects overall gene integration efficiency according to embodiments of the present teachings.
Figure 31B:
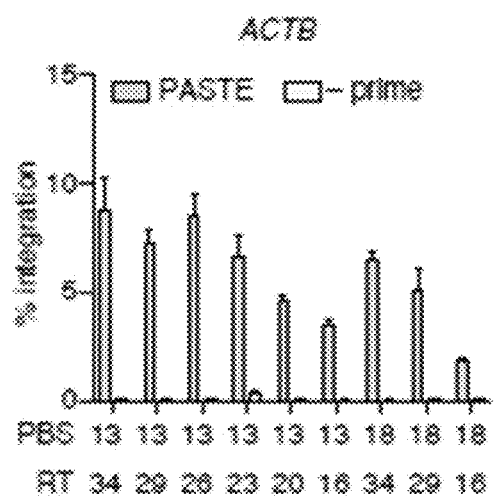
FIG. 31B shows the impact of PBS and RT length on PASTE integration of GFP at the ACTB locus according to embodiments of the present teachings.
Figure 31C:
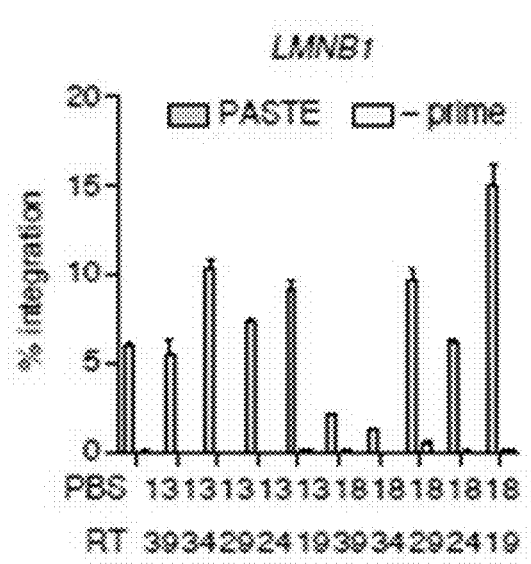
FIG. 31C shows the impact of PBS and RT length on PASTE integration of GFP at the LMNB1 locus according to embodiments of the present teachings.
Figure 31D:
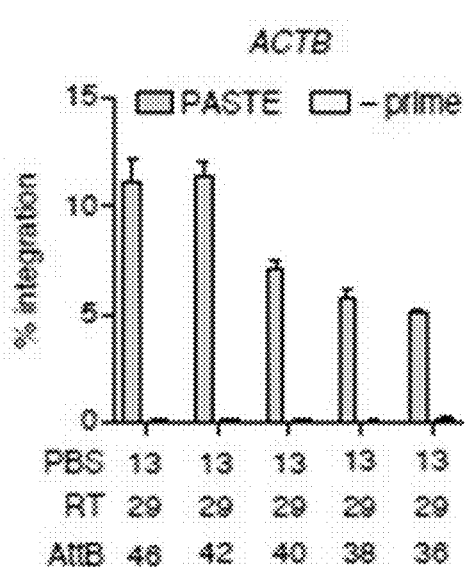
FIG. 31D shows the impact of attB length on PASTE integration of GFP at the ACTB locus according to embodiments of the present teachings.
Figure 31E:
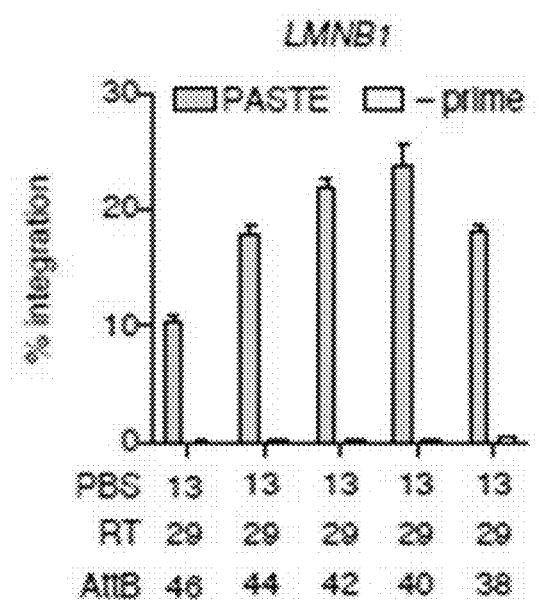
FIG. 31E shows the impact of attB length on PASTE integration of GFP at the LMNB1 locus according to embodiments of the present teachings.
Figure 31F:
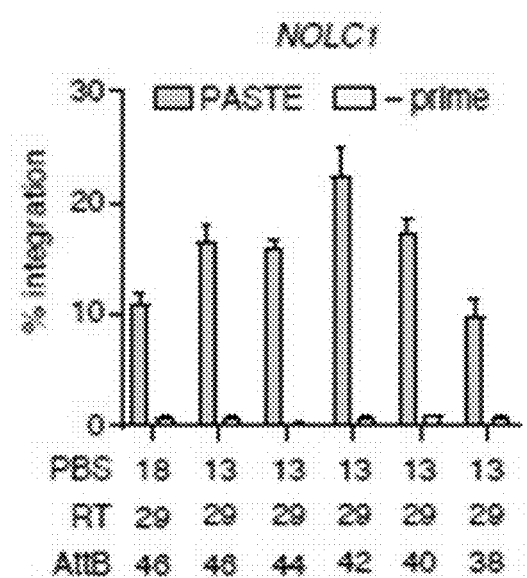
FIG. 31F shows the impact of attB length on PASTE integration of GFP at the NOLC1 locus according to embodiments of the present teachings.
Figure 31G:
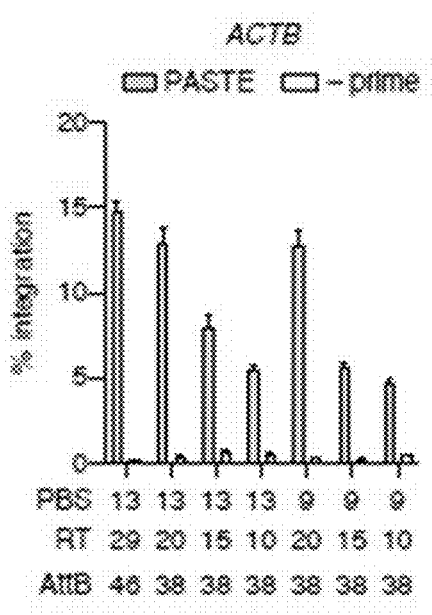
FIG. 31G shows the impact of minimal PBS, RT, and attB lengths on PASTE integration efficiency of GFP at the ACTB locus according to embodiments of the present teachings.
Figure 31H:
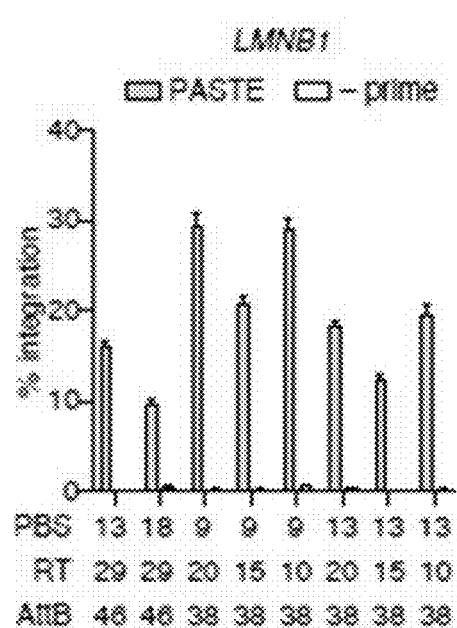
FIG. 31H shows the impact of minimal PBS, RT, and attB lengths on PASTE integration efficiency of GFP at the LMNB1 locus according to embodiments of the present teachings.

Relevant pegRNA parameters for PASTE include the primer binding site (PBS), reverse transcription template (RT), and attB site lengths, as well as the relative locations and efficacy of the pegRNA spacer and nicking guide (FIG. 31A). A range of PBS and RT lengths were tested at two loci, ACTB and lamin B1 (LMNB1), and rules governing efficiency were found to vary between loci, with shorter PBS lengths and longer RT designs having higher editing at the ACTB locus (FIG. 31B) and longer PBS and shorter RT designs performing better at LMNB1 (FIG. 31C).

The length of the attB landing site must balance two conflicting factors: the higher efficiency of prime editing for smaller inserts and reduced efficiency of Bxb1 integration at shorter attB lengths. AttB lengths were evaluated at ACTB, LMNB1, and nucleolar phosphoprotein p130 (NOLC1), and the optimal attB length was found to be locus dependent. At the ACTB locus, long attB lengths could be inserted by prime editing (FIG. 29B) and overall PASTE efficiencies for the insertion of GFP were highest for long attB lengths (FIG. 31$d$). In contrast, intermediate attB lengths had higher overall integration efficiencies (>20%) at LMNB1 (FIG. 31E) and NOLC1 (FIG. 31F), indicating that the increased efficiency of installing shorter attB sequences overcame the reduction of Bxb1 integration at these sites.

Figure 32A:
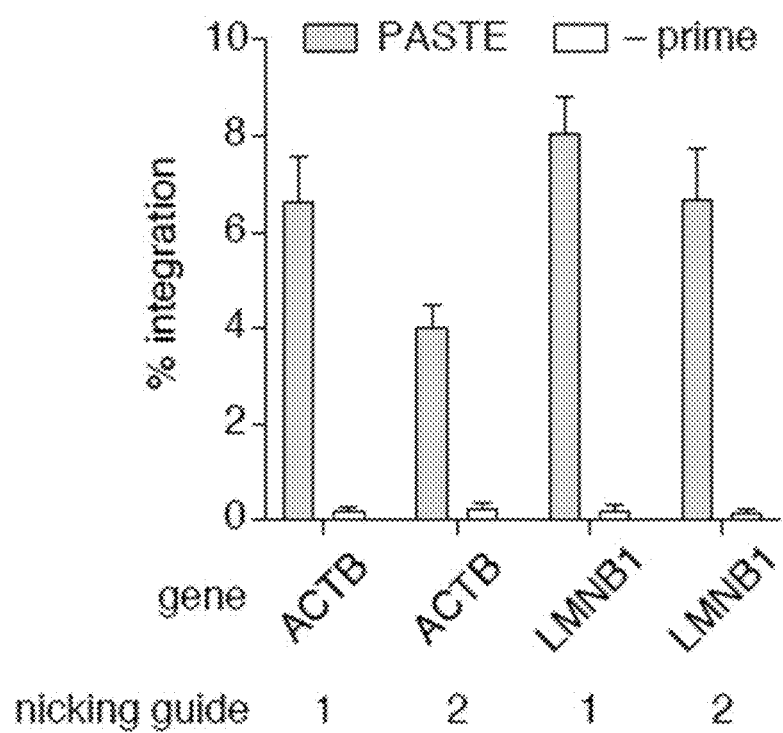
FIG. 32A shows the PASTE insertion efficiency at ACTB and LMNB1 loci with two different nicking guide designs according to embodiments of the present teachings.
Figure 32B:
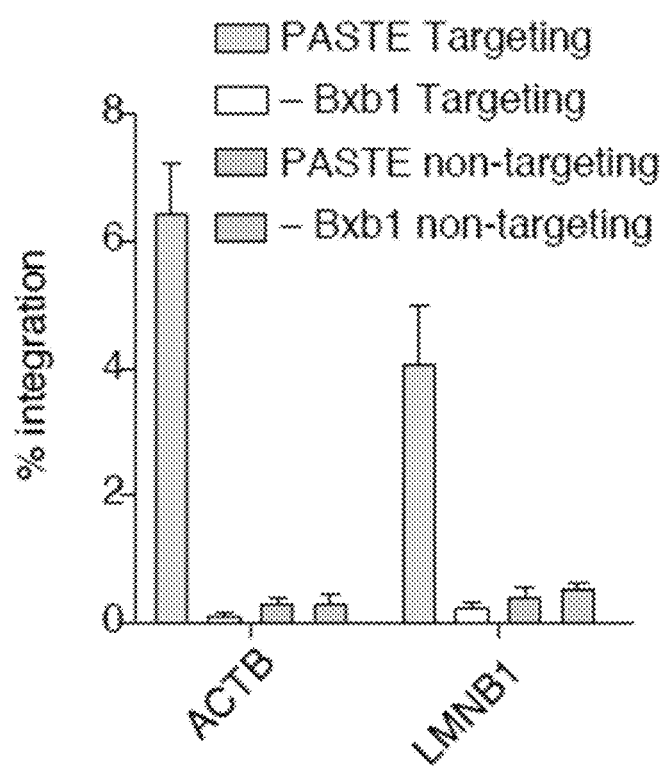
FIG. 32B shows the PASTE editing efficiency at ACTB and LMNB1 with target and non-targeting spacers and matched pegRNAs with and without Bxb1 expression according to embodiments of the present teachings.

The PE3 version of prime editing combines PE2 and an additional nicking guide to bias resolution of the flap intermediate towards insertion. To test the importance of nicking guide selection on PASTE editing, editing at ACTB and LMNB1 loci was tested with two nicking guide positions. Suboptimal nicking guide positions were found to reduce the PASTE efficiency up to 30% (FIG. 32A) in agreement with the 75% reduction of PASTE efficiency in the absence of nicking guide (FIG. 29G). The pegRNA spacer sequence was found to be necessary for PASTE editing, and substitution of the spacer sequence with a non-targeting guide was found to eliminate editing (FIG. 32B).

Figure 33A:
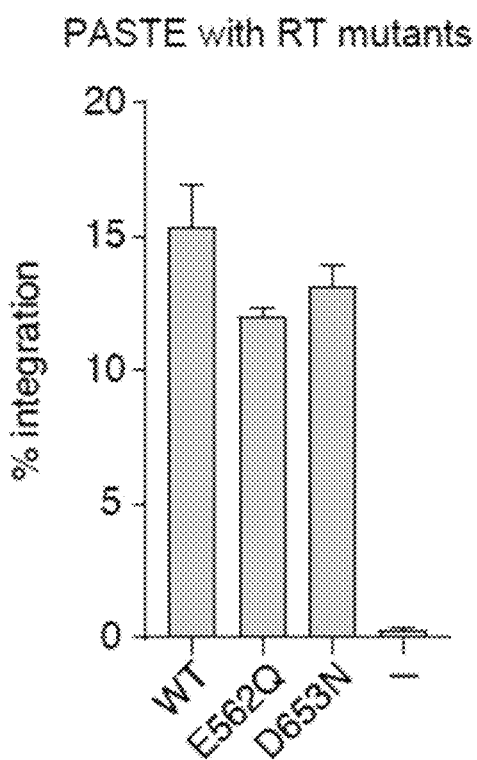
FIG. 33A shows the PASTE integration of GFP at the ACTB locus with different Bxb1 catalytic mutants according to embodiments of the present teachings.
Figure 33B:
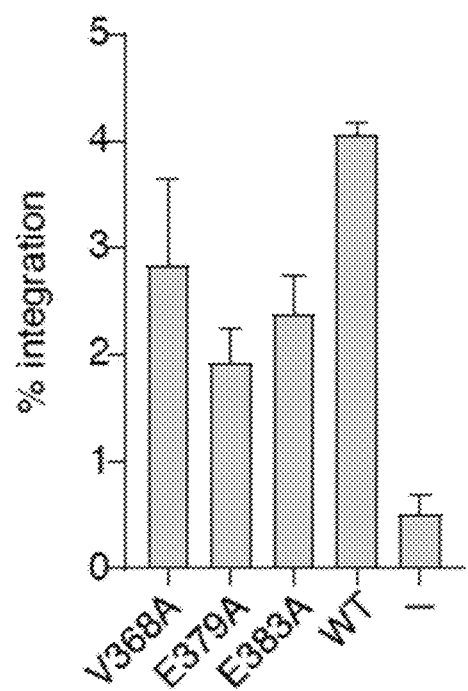
FIG. 33B shows the PASTE integration of GFP at the ACTB locus with different RT catalytic mutants according to embodiments of the present teachings.

Rational mutations were also introduced in both the Bxb1 integrase and reverse transcriptase domain of the PE2 construct to optimize PASTE further. While some of these mutations were well tolerated by PASTE (FIGS. 33A-B), none of them improved PASTE editing efficiency.

Figure 31I:
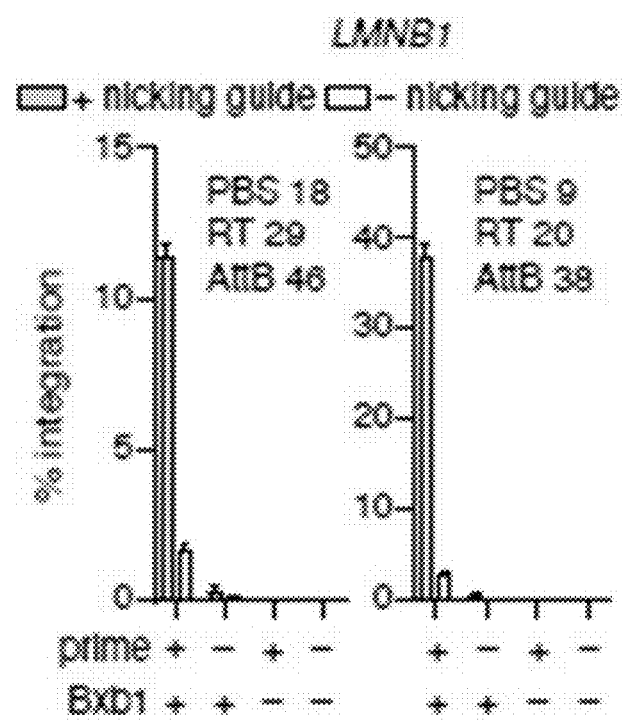
FIG. 31I shows the PASTE integration of GFP at the LMNB1 locus in the presence and absence of nicking guide, prime, and Bxb1 with a minimally compact pegRNA containing a 38 bp attB compared to a longer pegRNA design according to embodiments of the present teachings.

Short RT and PBS lengths can offer additional improvements for editing. A panel of shorter RT and PBS guides were tested at ACTB and LMNB1 loci and while shorter RT and PBS sequences did not increase editing at ACTB (FIG. 31G), it was found that they had improved editing at LMNB1 (FIG. 31H) with best performing guides reaching GFP insertion rates of ~40% (FIG. 31I).

Example 20

PASTE Tagging at Multiple Endogenous Genes

Figure 34A:
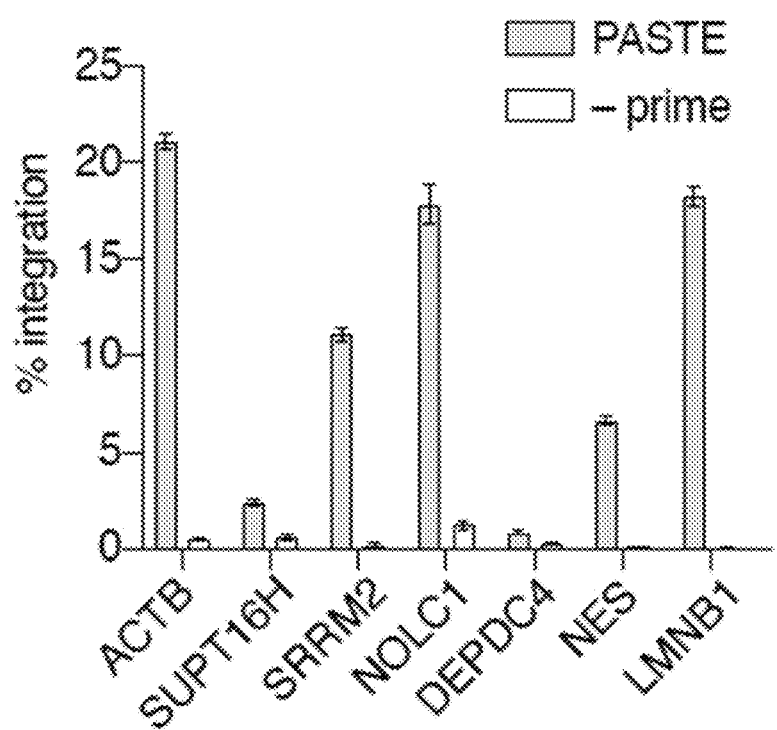
FIG. 34A shows the GFP integration by PASTE at a panel of endogenous genomic loci according to embodiments of the present teachings.
Figure 34B:
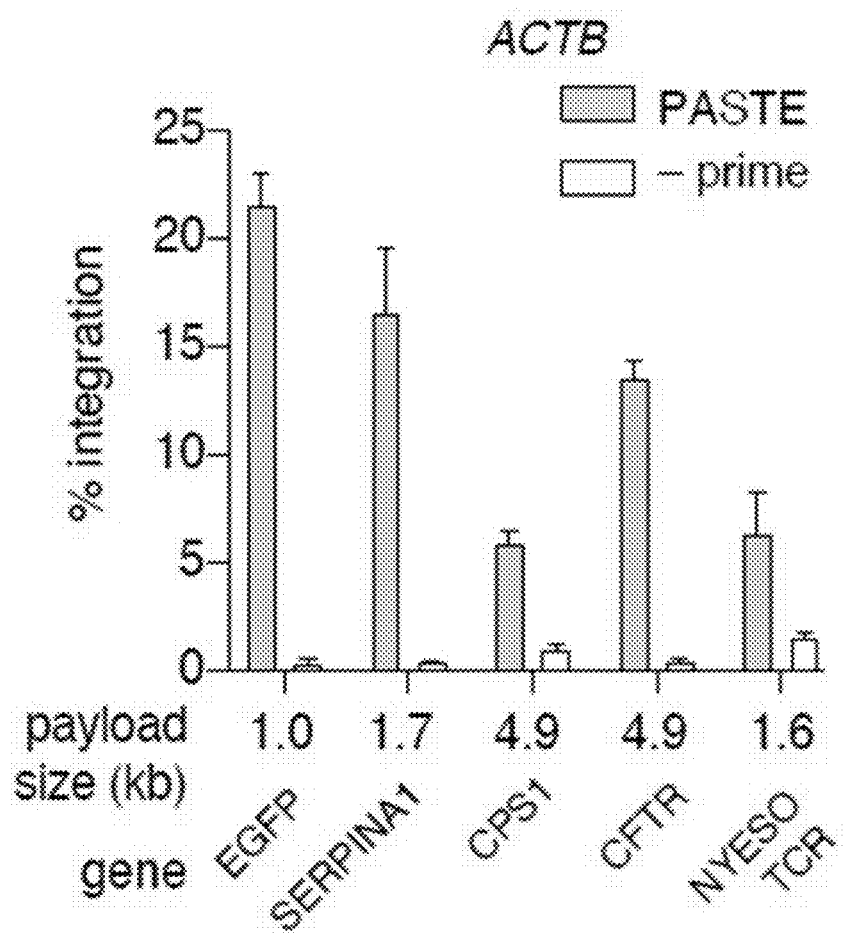
FIG. 34B shows the integration of a panel of different gene cargo at ACTB locus via PASTE according to embodiments of the present teachings.
Figure 34C:
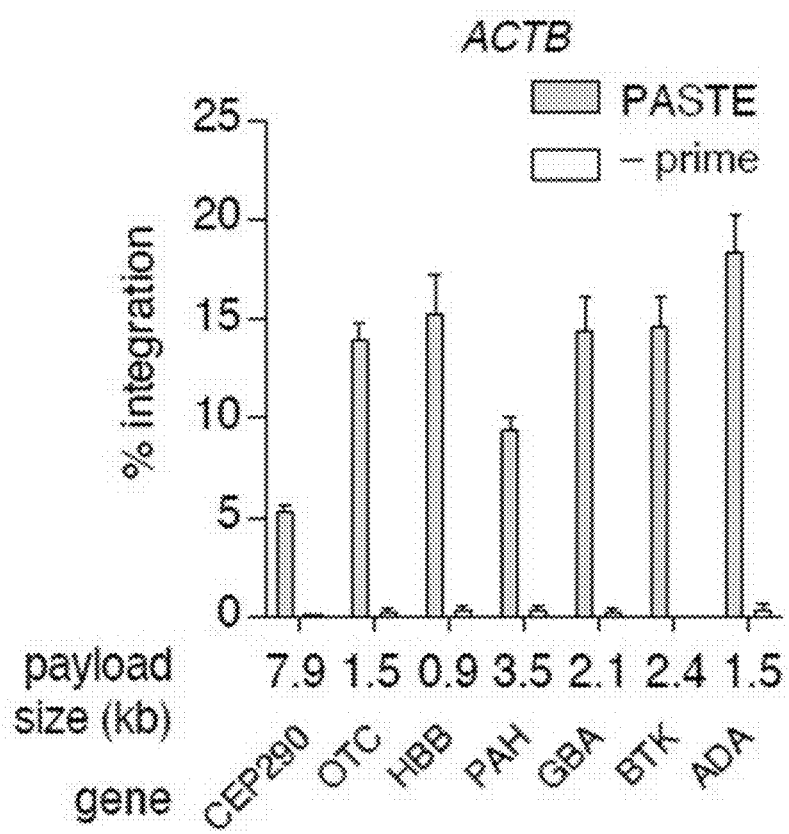
FIG. 34C shows the integration efficiency of therapeutically relevant genes at the ACTB locus according to embodiments of the present teachings.
Figure 35:
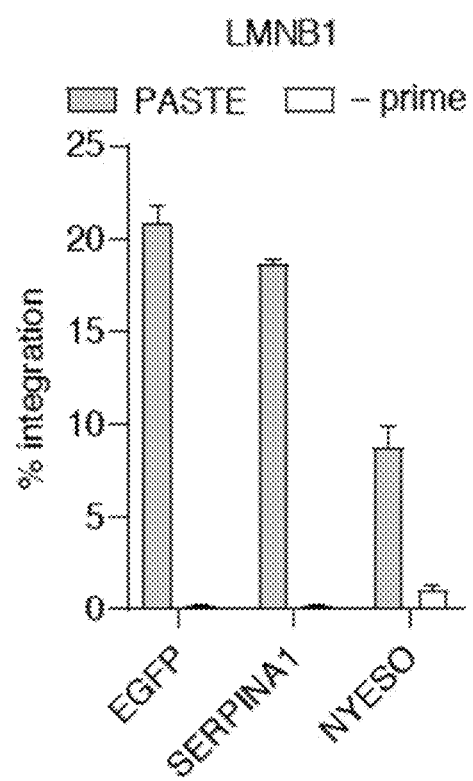
FIG. 35 shows the integration of a panel of different gene cargo at LMNB1 locus via PASTE according to embodiments of the present teachings.

GFP insertion efficiency was measured at seven different gene loci—ACTB, SUP T16H, SRM2, NOLC1, DEPDC4, NES, and LMNB1—to test the versatility of the PASTE programming. A range of integration rates up to 22% was found (FIG. 34A). Because PASTE does not require homology or sequence similarity on cargo plasmids, integration of diverse cargo sequences is modular and easily scaled across different loci. Six different gene cargos, varying in size from 969 bp to 4906 bp, were tested for insertion at ACTB and LMNB1 loci with PASTE. Integration frequencies between 5% and 22% depending on the gene and insertion locus were found (FIGS. 34B and 35). Additionally, a panel of seven common therapeutic genes, CEP290, OTC, HBB, PAH, GBA, BTK, and ADA was evaluated for insertion at the ACTB locus, and the efficient integration of these cargos were found between 5%-20% (FIG. 34C).

Figure 34D:
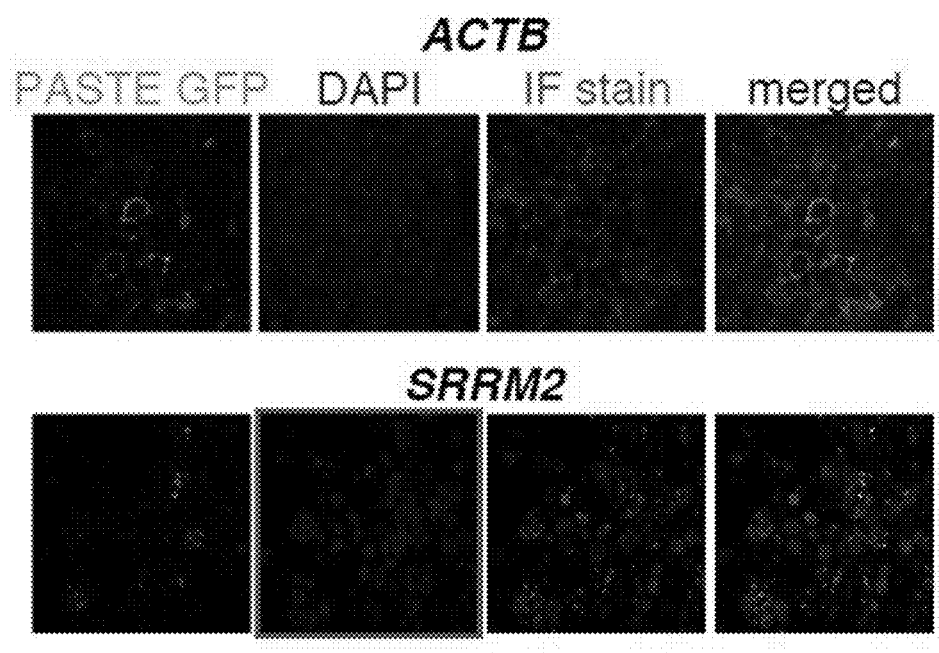
FIG. 34D shows the endogenous protein tagging with GFP via PASTE by in-frame endogenous gene tagging at the ACTB loci and SRRM2 loci according to embodiments of the present teachings.
Figure 34E:
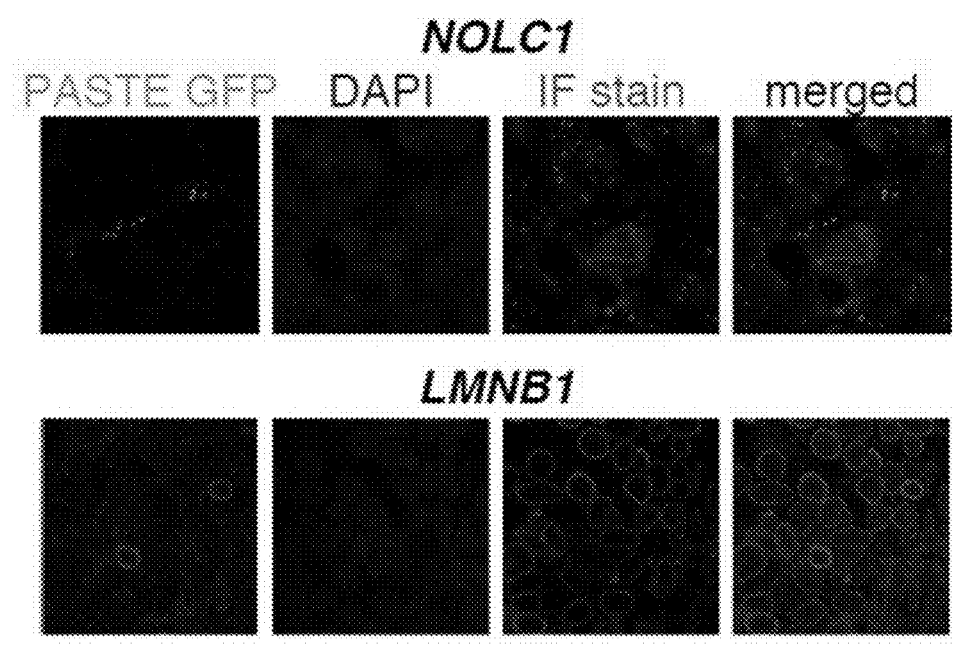
FIG. 34E shows the endogenous protein tagging with GFP via PASTE by in-frame endogenous gene tagging at the NOLC1 loci and LMNB1 loci according to embodiments of the present teachings.

The precise insertions of PASTE for in-frame protein tagging or expressing cargo without disruption of endogenous gene expression was assessed. As Bxb1 leaves residual sequences in the genome (termed attL and attR) after cargo integration, these genomic scars can serve as protein linkers. The frame of the attR sequence was positioned through strategic placement of the attP on the minicircle cargo, achieving a suitable protein linker, GGLSGQP-PRSPSSGSSG (SEQ ID NO: 427). Using this linker, four genes (ACTB, SRRM2, NOLC1, and LMNB1) were tagged with GFP using PASTE. To assess correct gene tagging, the subcellular location of GFP was compared with the tagged gene product by immunofluorescence. For all four targeted loci, GFP co-localized with the tagged gene product, indicating successful tagging (FIGS. 34D-E).

Example 21

Orthogonal Sequence Preferences for Bxb1 Integration

Figure 36A:
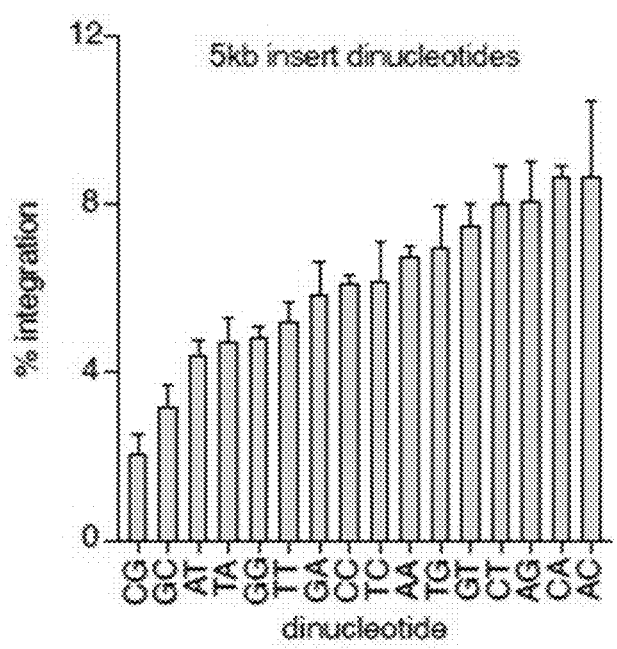
FIG. 36A shows the PASTE integration efficiency for all 16 central dinucleotide attB/attP sequence pairs with a 5 kb GFP template at the ACTB locus according to embodiments of the present teachings.

The central dinucleotide of Bxb1 is involved in the association of attB and attP sites for integration, and changing the matched central dinucleotide sequences can modify integrase activity and provide orthogonality for insertion of two genes. Expanding the set of attB/attP dinucleotides can enable multiplexed gene insertion with PASTE. The efficiency of GFP integration at the ACTB locus with PASTE across all 16 dinucleotide attB/attP sequence pairs was profiled to find optimal attB/attP dinucleotides for PASTE insertion. Several dinucleotides with integration efficiencies greater than the wild-type GT sequence were found (FIG. 36A). A majority of dinucleotides had 75% editing efficiency or greater compared to wild-type attB/attP efficiency, implying that these dinucleotides can be orthogonal channels for multiplexed gene insertion with PASTE.

Figure 36B:
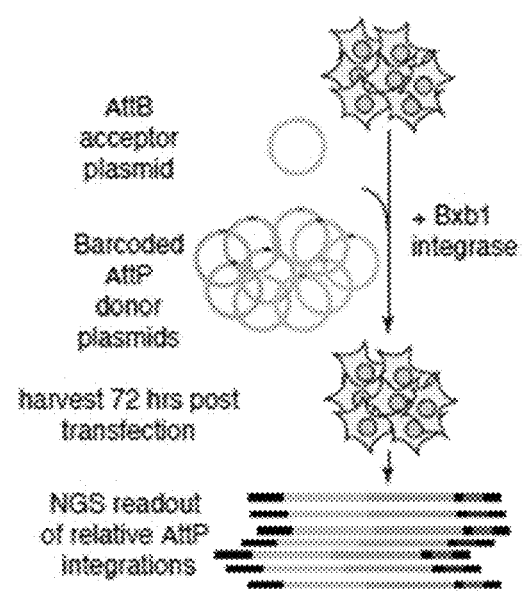
FIG. 36B shows a schematic of the pooled attB/attP dinucleotide orthogonality assay, wherein each attB dinucleotide sequence is co-transfected with a barcoded pool of all 16 attP dinucleotide sequences and Bxb1 integrase, relative integration efficiencies are determined by next generation sequencing of barcodes, and all 16 attB dinucleotides are profiled in an arrayed format with attP pools according to embodiments of the present teachings.
Figure 36C:
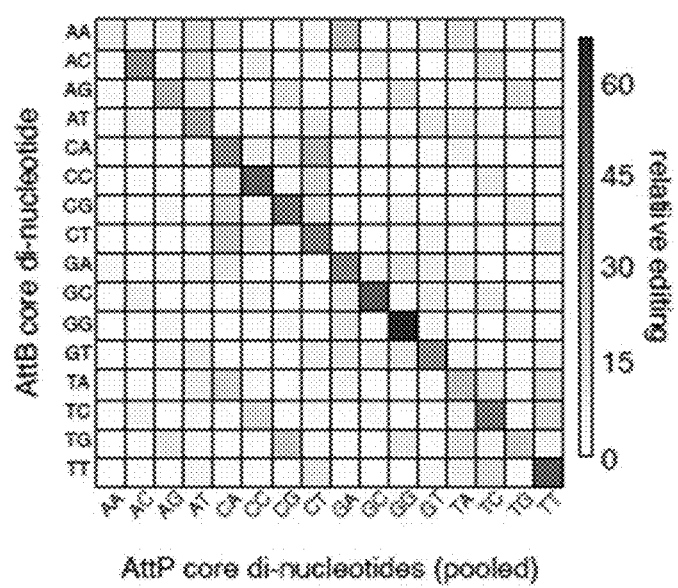
FIG. 36C shows the relative insertion preferences for all possible attB/attP dinucleotide pairs determined by the pooled orthogonality assay according to embodiments of the present teachings.
Figure 37:
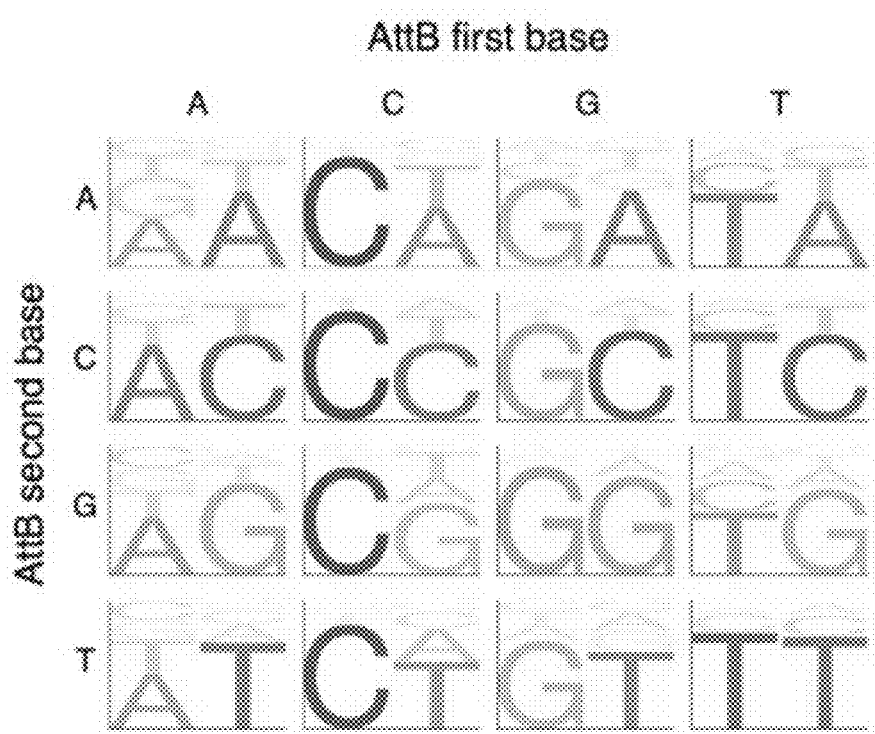
FIG. 37 shows the orthogonality of Bxb1 dinucleotides as measured by a pooled reporter assay, wherein each web logo motif shows the relative integration of different attP sequences in a pool at a denoted attB sequence with the listed dinucleotide according to embodiments of the present teachings.

The specificity of matched and unmatched attB/attP dinucleotide interactions was then assessed. The interactions between all dinucleotide combinations in a scalable fashion using a pooled assay to compare attB/attP integration were profiled (FIG. 36B). By barcoding 16 attP dinucleotide plasmids with unique identifiers, co-transfecting this attP pool with the Bxb1 integrase expression vector and a single attB dinucleotide acceptor plasmid, and sequencing the resulting integration products, the relative integration efficiencies of all possible attB/attP pairs were measured (FIG. 36C). Dinucleotide specificity was found to vary, with some dinucleotides (GG) exhibiting strong self-interaction with negligible crosstalk, and others (AA) showing minimal self-preference. Sequence logos of attP preferences (FIG. 37) revealed that dinucleotides with C or G in the first position have stronger preferences for attB dinucleotide sequences with shared first bases, while other attP dinucleotides, especially those with an A in the first position, have reduced specificity for the first attB base.

Figure 36D:
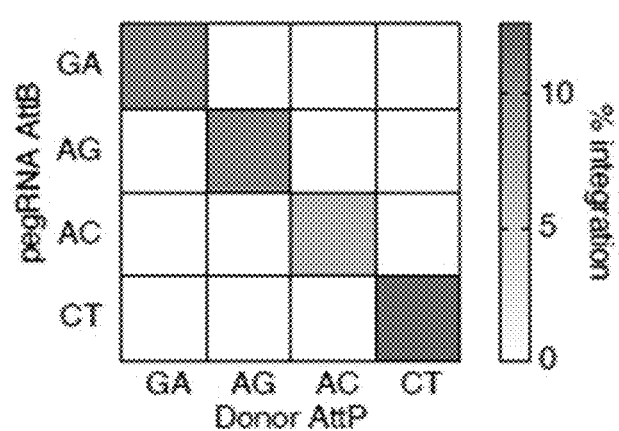
FIG. 36D shows the orthogonality of top 4 attB/attP dinucleotide pairs evaluated for GFP integration with PASTE at the ACTB locus according to embodiments of the present teachings.

GA, AG, AC, and CT dinucleotide pegRNAs were then tested for GFP integration at ACTB, either paired with their corresponding attP cargo or mispaired with the other three dinucleotide attP sequences. All four of the tested dinucleotides efficiently were found to integrate cargo only when paired with the corresponding attB/attP pair, with no detectable integration across mispaired combinations (FIG. 36D).

Example 22

Multiplex Gene Integration with PASTE

Figure 38A:
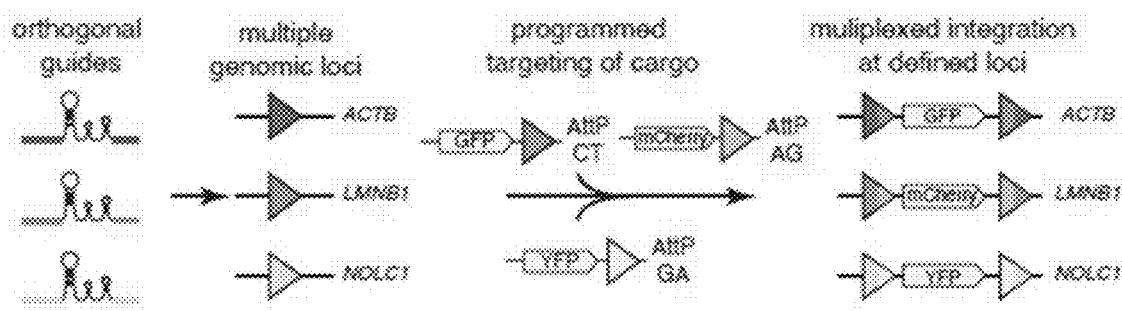
FIG. 38A shows a schematic of multiplexed integration of different cargo sets at specific genomic loci, wherein three fluorescent cargos (GFP, mCherry, and YFP) are inserted orthogonally at three different loci (ACTB, LMNB1, NOLC1) for in-frame gene tagging according to embodiments of the present teachings.
Figure 38B:
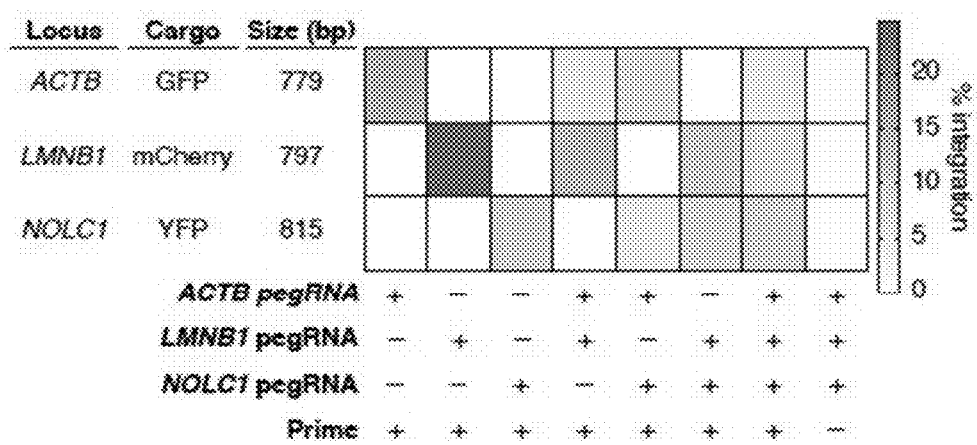
FIG. 38B shows the efficiency of multiplexed PASTE insertion of combinations of fluorophores at ACTB, LMNB1, and NOLC1 loci according to embodiments of the present teachings.

Multiplexing in cells by using orthogonal pegRNAs that direct a matched attP cargo to a specific site in the genome was assessed (FIG. 38A). Selecting the three top dinucleotide attachment site pairs (CT, AG, and GA), pegRNAs that target ACTB (CT), LMNB1 (AG), and NOLC1 (GA) and corresponding minicircle cargo containing GFP (CT), mCherry (AG), and YFP (GA) were designed. Upon co-delivering these reagents to cells, single-plex, dual-plex, and trip-plex editing of all possible combinations of these pegRNAs and cargo in the range of 5%-25% integration was found to be achieved (FIG. 38B).

An application for multiplexed gene integration is for labeling different proteins to visualize intracellular localization and interactions within the same cell. PASTE was used to simultaneously tag ACTB (GFP) and NOLC1 (mCherry) or ACTB (GFP) and LMNB1 (mCherry) in the same cell. No overlap of GFP and mCherry fluorescence was observed and tagged genes were confirmed to be visible in their appropriate cellular compartments, based on the known subcellular localizations of the ACTB, NOLC1 and LMNB1 protein products (FIGS. 15A-B).

Example 23

PASTE Efficiencies Compared With DSB-based Insertion Methods

PASTE efficiencies were found to exceed comparable DSB-based insertion methods.

Figure 39A:
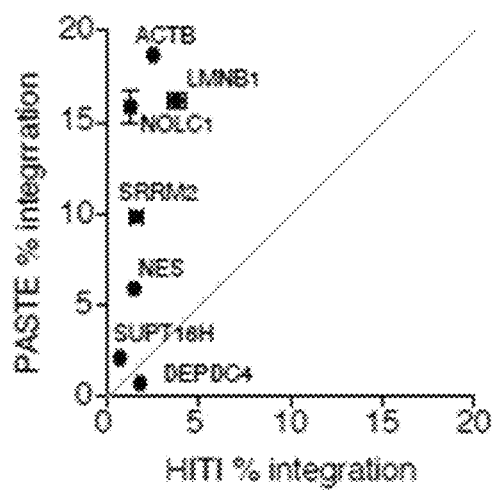
FIG. 39A shows the GFP integration efficiency at a panel of genomic loci by PASTE compared to insertion rates by homology-independent targeted integration (HITI) according to embodiments of the present teachings.
Figure 39B:
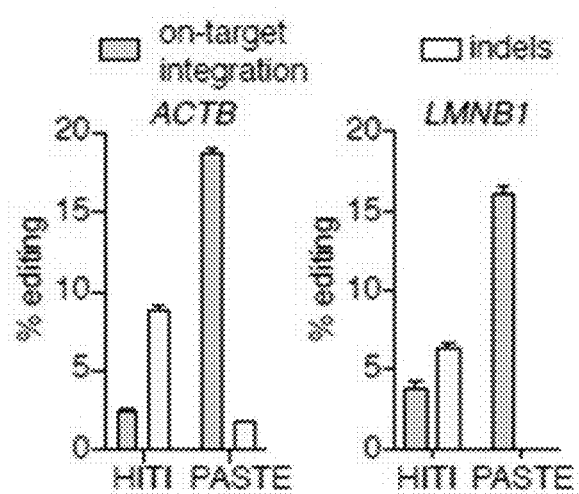
FIG. 39B shows a comparison of unintended indel generation by PASTE and HITI at the ACTB and LMNB1 target sites, wherein the on-target EGFP integration rate observed compared to unintended indels is shown according to embodiments of the present teachings.
Figure 39C:
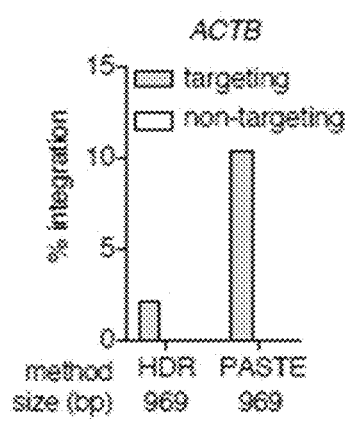
FIG. 39C shows the integration of a GFP template by PASTE at the ACTB locus compared to homology-directed repair (HDR) at the same target, wherein the quantification is by single-cell clone counting, wherein targeting and non-targeting guides were used for HDR insertion, and wherein for PASTE targeting and non-targeting refers to the presence or absence of the SpCas9-RT protein respectively according to embodiments of the present teachings.
Figure 39D:
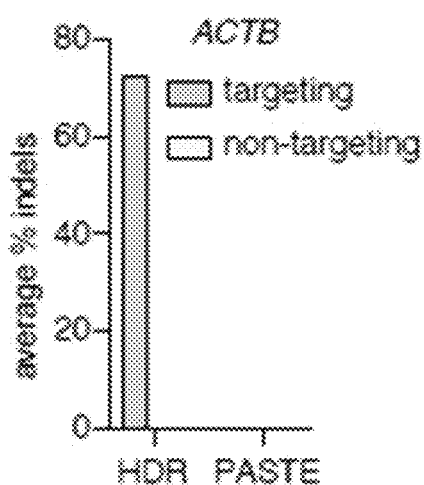
FIG. 39D shows the comparison of unintended indel generation by PASTE and HDR based EGFP insertion at the ACTB target site, wherein the average indel rate measured across all single-cell clones generated is showed according to embodiments of the present teachings.
Figure 40A:
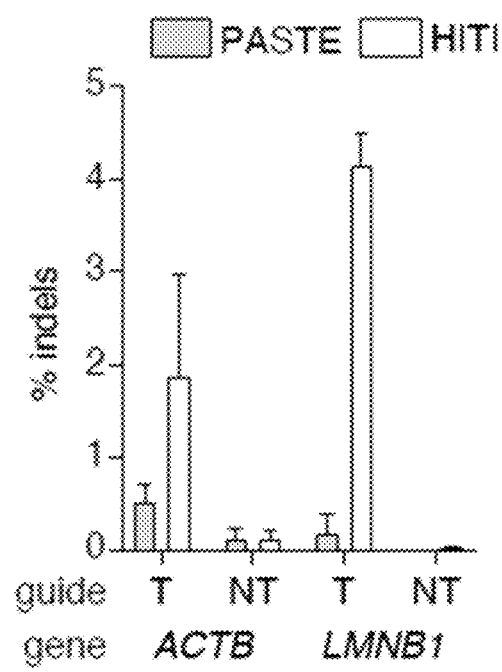
FIG. 40A shows a comparison of indel rates generated by PASTE and HITI mediated insertion of EGFP at the ACTB and LMNB1 loci in HepG2 cells according to embodiments of the present teachings.
Figure 40B:
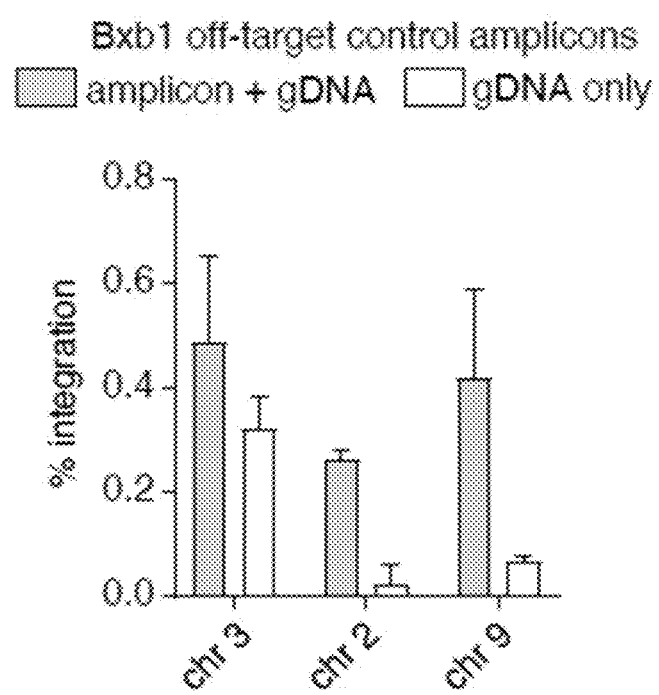
FIG. 40B shows the validation of ddPCR assays for detecting editing at predicted Bxb1 offtarget sites using synthetic amplicons according to embodiments of the present teachings.
Figure 40C:
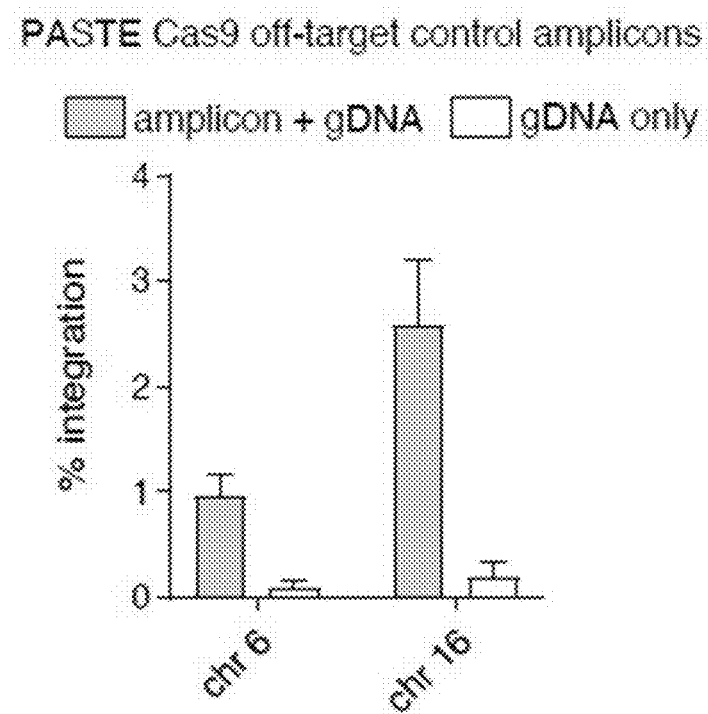
Figure 40D:
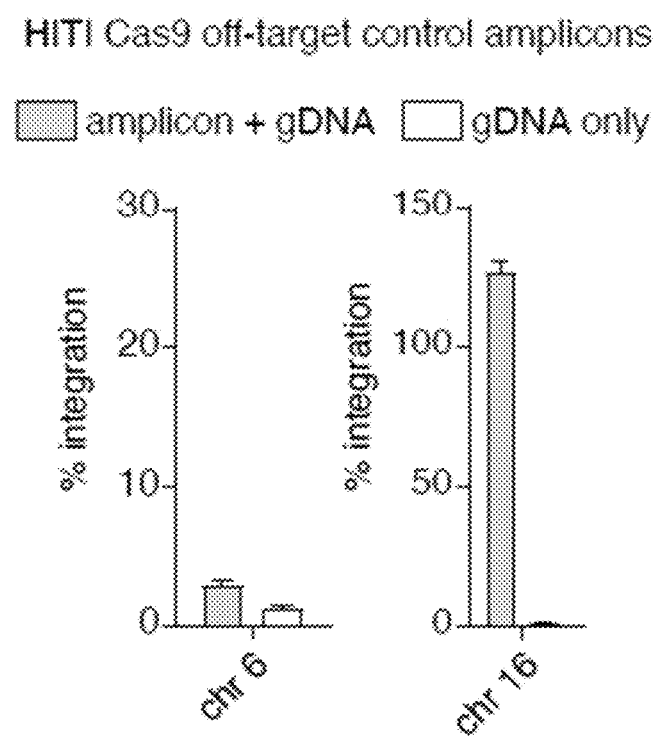

PASTE editing was assessed alongside DSB-dependent gene integration using either NHEJ (i.e., homology-independent targeted integration, HITI) or HDR pathways. PASTE had equivalent or better gene insertion efficiencies than either HITI (FIGS. 39A-B) or HDR (FIGS. 39C-D). On a panel of 7 different endogenous targets, PASTE exceeded HITI editing at 6 out of 7 genes, with similar efficiency for the 7th gene (FIG. 39A). As DSB generation can lead to insertions or deletions (indels) as an alternative and undesired editing outcome, the indel frequency of all three methods was assessed by next-generation sequencing, finding significantly fewer indels generated with PASTE than either HDR or HITI in both HEK293FT and HepG2 cells (FIGS. 39B, 39D and 40A), showcasing the high purity of gene integration outcomes with PASTE.

Example 24

Off-Target Characterization of PASTE and HITI Gene Integration

Figure 39E:
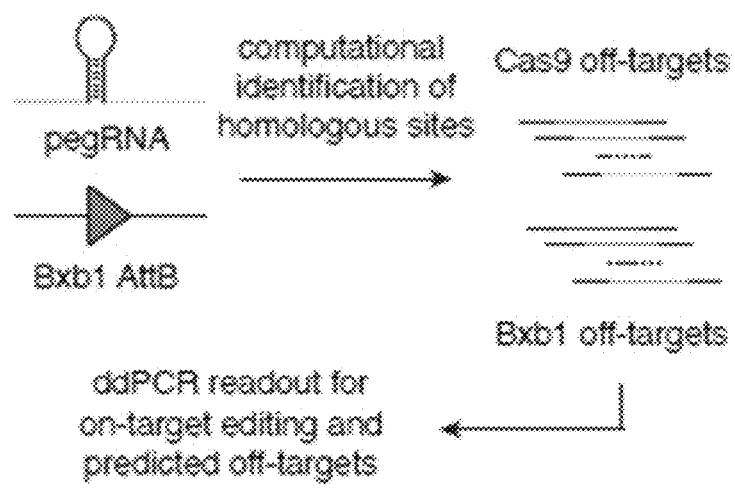
FIG. 39E shows a schematic for Bxb1 and Cas9 off-target identification and a detection assay according to embodiments of the present teachings.
Figure 39F:
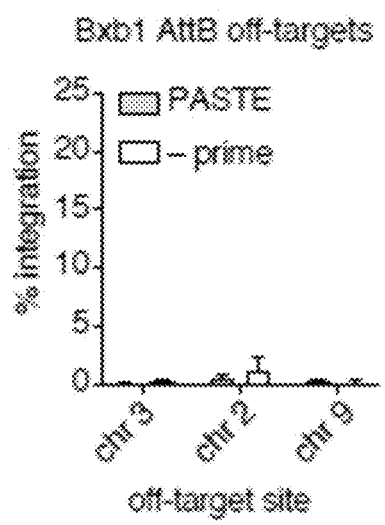
FIG. 39F shows the GFP integration activity at predicted Bxb1 off-target sites in the human genome according to embodiments of the present teachings.
Figure 39G:
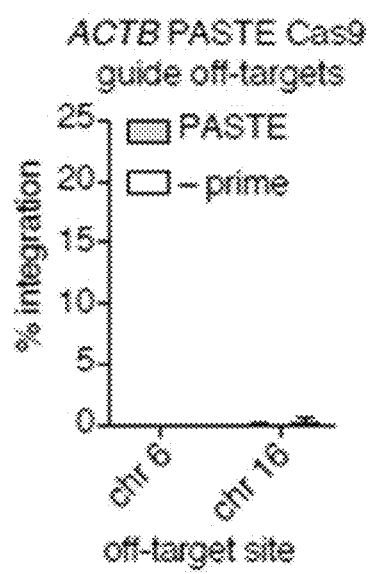
FIG. 39G shows the GFP integrations activity at predicted PASTE ACTB Cas9 guide off target sites according to embodiments of the present teachings.
Figure 39H:
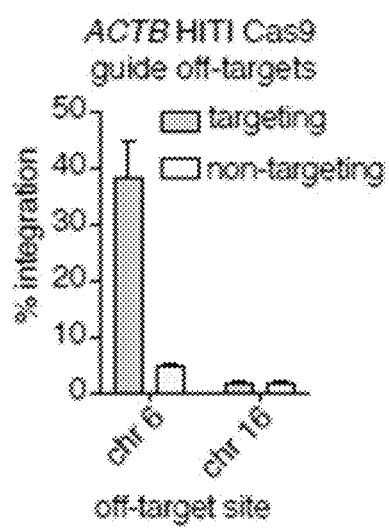
FIG. 39H shows the GFP integration activity at predicted HITI ACTB Cas9 guide off-target sites according to embodiments of the present teachings.

Off-target editing can be used in genome editing technologies. The specificity of PASTE at specific sites was assessed based on off-targets generated by Bxb1 integration into pseudo-attB sites in the human genome and off-targets generated via guide- and Cas9-dependent editing in the human genome (FIG. 39E). While Bxb1 lacks documented integration into the human genome at pseudo-attachment sites, potential sites with partial similarity to the natural Bxb1 attB core sequence were computationally identified. Bxb1 integration by ddPCR across these sites was tested and no off-target activity was found (FIGS. 39F and 40B-D). To assay Cas9 off-targets for the ACTB pegRNA, two potential off-target sites were identified via computational prediction and no off-target integration for PASTE was found (FIGS. 39G and 40A-D), but substantial off-target activity by HITI at one of the sites was found (FIGS. 39H and 40A-D).

Figure 39I:
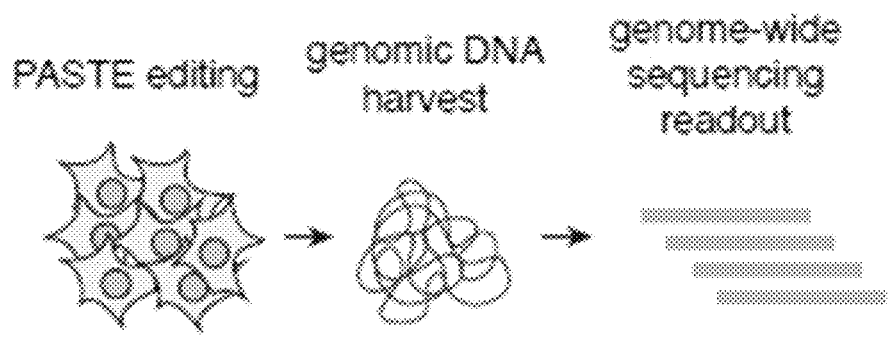
FIG. 39I shows a schematic of next-generation sequencing method to assay genome-wide off-target integration sites by PASTE according to embodiments of the present teachings.
Figure 39J:
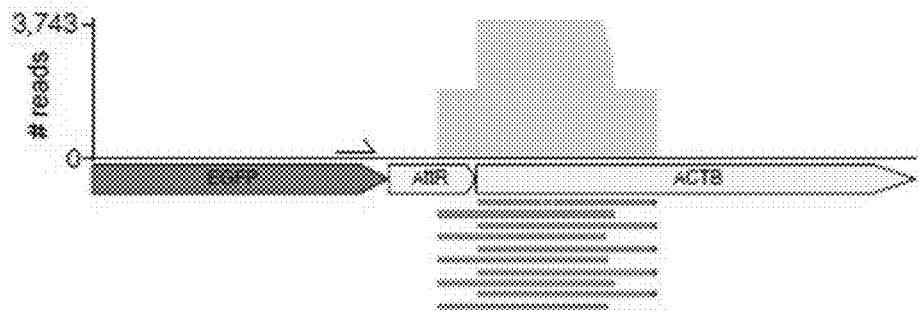
FIG. 39J shows the alignment of reads at the on-target ACTB site using a genome-wide integration assay, wherein expected on-target integration outcomes are shown according to embodiments of the present teachings.
Figure 39K:
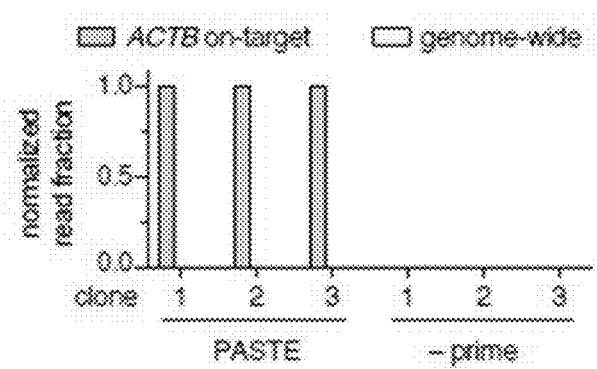
FIG. 39K shows the analysis of on-target and off-target integration events across 3 single-cell clones for PASTE and 3 single-cell clones for no prime condition according to embodiments of the present teachings.
Figure 39L:
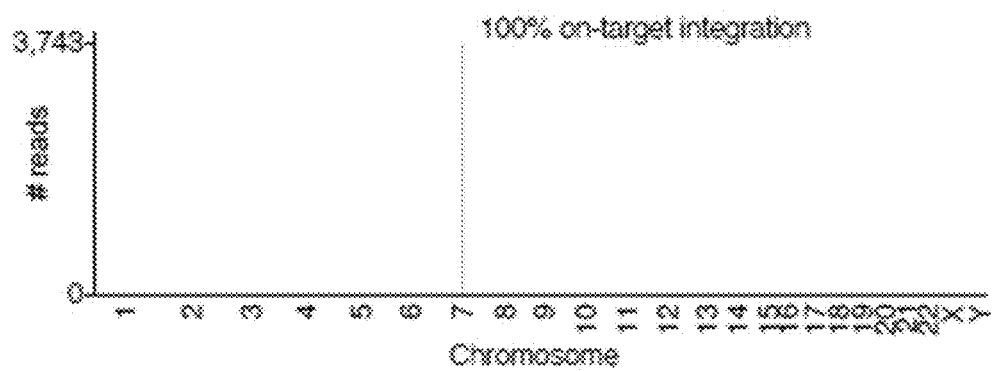
FIG. 39L shows a Manhattan plot of integration events for a representative single-cell clone with PASTE editing, wherein the on-target site is at the ACTB gene on chromosome 7 according to embodiments of the present teachings.

Genome-wide off-targets due to either Cas9 or Bxb1 through tagging and PCR amplification of insert-genomic junctions were additionally assessed (FIG. 39I). Single cell clones were isolated for conditions with PASTE editing and negative controls missing PE2, and deep sequencing of insert genomic junctions from these clones showed all reads aligning to the on-target ACTB site, confirming no off-target genomic insertions (FIGS. 39J-L).

Expression of reverse transcriptases and integrases involved in PASTE can have detrimental effects on cellular health. The complete PASTE system, the corresponding guides and cargo with only PE2, and the corresponding guides and cargo with only Bxb1 were transfected and compared to both GFP control transfections and guides without protein expression via transcriptome-wide RNA sequencing to determine the extent of these effects. While Bxb1 expression in the absence of Prime editing was found to have several significant off targets, the complete PASTE system had only one differentially regulated gene with more than a 1.5-fold change (FIGS. 41A-B). Genes upregulated by Bxb1 overexpression included stress response genes, such as TENT5C and DDIT3, but these changes were not seen in the expression of the PASTE system (FIG. 41C), potentially due to the decreased expression of Bxb1 from the P2A linker on the PASTE construct.

Example 25

PASTE Efficiency in Non-Dividing Cell

PASTE activity in non-dividing cells was assessed. Cas9 and HDR templates or PASTE were transfected into HEK293FT cells and cell division was arrested via aphidicolin treatment (FIG. 42A). In this model of blocked cell division, PASTE was found to maintain a GFP gene integration activity greater than 20% at the ACTB locus whereas HDR-mediated integration was abolished (FIGS. 42B and 43A).

Example 26

Production and Secretion of Therapeutic Transgene

PASTE with larger transgenes and in additional cell lines were assessed.

To evaluate the size limits for therapeutic transgenes, insertion of cargos up to 13.3 kb in length in both dividing and aphidicolin treated cells was assessed. Insertion efficiency greater than 10% was found (FIG. 42C), enabling insertion of ~99.7% of all full-length human cDNA transgenes. To overcome reduction of large insert delivery to cells because of delivery inefficiencies, delivering larger DNA amounts of insert was found to significantly improve gene integration efficiency (FIG. 43B). PASTE editing to additional cell types such as PASTE in the K562 lymphoblast line and in primary human T cells were also assessed. Both PE2-P2A-Bxb1 (PASTE) and separate delivery of PE2 and Bxb1 were found to result in efficient editing in both cell types (FIGS. 42D-E). Lastly, as therapeutic delivery of PASTE in vivo might require viral delivery of the DNA cargo, whether AAV could deliver an attP containing payload that could be integrated into the genome via Bxb1 was evaluated. Targeting the ACTB locus, AAV was found to be capable of delivering the appropriate template for integrase mediated insertion with rates up to 4% in a dose dependent fashion (FIGS. 42F and 43C).

To improve the efficiency of PASTE, PE2* NLS was incorporated for prime editing and improved PASTE integration at multiple loci was found (FIG. 44A). Furthermore, PE2* resulted in more robust integration at lower titrations of cargo plasmid, demonstrating integration at amounts as low as 8 ng of plasmid (FIG. 44B). To combat reductions in PASTE efficiency due to incomplete plasmid delivery, a puromycin resistance gene was co-delivered and found to increase the PASTE efficiency in the presence of drug selection (FIG. 45).

Programmable gene integration provides a modality for expression of therapeutic protein products, and protein production was assessed for therapeutically relevant proteins Alpha-1 antitrypsin (encoded by SERPINA1) and Carbamoyl phosphate synthetase I (encoded by CPS1), involved in the diseases Alpha-1 antitrypsin deficiency and CPS1 deficiency, respectively. By tagging gene products with the luminescent protein subunit HiBiT, the transgene production and secretion were assessed independently in response to PASTE treatment (FIG. 42G). PASTE was transfected with SERPINA1 or CPS1 cargo in HEK293FT cells and a human hepatocellular carcinoma cell line (HepG2) and efficient integration at the ACTB locus was found (FIG. 42H-I). This integration resulted in robust protein expression, intracellular accumulation of transgene products (FIGS. 42J and 46A-B), and secretion of proteins into the media (FIG. 42K).

Example 27

Optimized PASTE Constructs

To optimize complex activity, a panel of protein modifications were screened, including alternative reverse transcriptase fusions and mutations, various linkers between the reverse transcriptase domain and integrase and between the Cas9 and reverse transcriptase domain, and reverse transcriptase and BxbINT domain mutants (FIG. 47A and FIG. 49C-FIG. 49F). A number of protein modifications, including a 48 residue XTEN linker between the Cas9 and reverse transcriptase and the fusion of MMuLV to the Sto7d DNA binding domain (Oscorbin et al. FEBS Lett. 594. 4338-4356. 2020) improved editing efficiency (FIG. 47A and FIG. 49C-FIG. 49D). When these top modifications were combined with a GGGGS linker (SEQ ID NO: 420) between the reverse transcriptase-Sto7d domain and the BxbINT, they produced ~55% gene integration, highlighting the importance of directly recruiting the integrase to the target site (FIG. 47A). This optimized construct was referred to as SpCas9-(XTEN-48)-RT-Sto7d-(GGGGS)-BxbINT. The optimized contruct achieved precise integration of templates as large as ~36,000 bp with ~20% integration efficiency (FIG. 47A), with complete integration of the full-length cargo confirmed by Sanger sequencing.

Additionally, pegRNAs containing different AttB length truncations were tested and found that prime editing was capable of inserting sequences up to 56 bp at the beta-actin (ACTB) gene locus, with higher efficiency at lengths below 31 bp (FIG. 48A-FIG. 48B). A panel of multiple enzymes was evaluated, including Bxb1 (i.e., BxbINT), TP901 (i.e., Tp9INT), and phiBT1 (i.e., Bt1INT) phage serine integrases. Prime editing successfully inserted all landing sites tested, with efficiencies between 10-30% (FIG. 48C-FIG. 48D)

Example 28

Viral Delivery & In Vivo Editing

In order to package the complete PASTE system in viral vectors, an AdV vector was utilized (FIG. 50B). Adenovirus was evaluated for if it could deliver a suitable template for BxbINT-mediated insertion along with plasmids for SpCas9-RT-BxbINT and guide expression, or AdV delivery of guides and BxbINT with plasmid delivery of SpCas9-RT, finding that 10-20% integration of the ~36 kb adenovirus genome carrying EGFP in HEK293FT and HepG2 cells was achieved (FIG. 50C). Upon packaging and delivering the cargo and PASTE system components across 3 AdV vectors, the complete PASTE system (Cas9-reverse transcriptase, integrase and guide RNAs, or cargo) could be substituted by adenoviral delivery, with integration of up to ~50-60% with viral-only delivery in HEK293FT and HepG2 cells (FIG. 50D).

To further demonstrate PASTE would be amenable for in vivo delivery, an mRNA version of the PASTE protein components was developed as well as chemically-modified synthetic atgRNA and nicking guide against the LMNB1 target (FIG. 50E). Electroporation of the mRNA and guides along with delivery of the template via adenovirus or plasmid yielded high efficiency integration up to ~23% (FIG. 50E-FIG. 50F). More sustained BxbINT expression could allow for integration into newly placed AttB sites in the genome, so circular mRNA expression was tested and found to boost the efficiency of integration to ~30% (FIG. 50G-FIG. 50I).

Example 29

Simultaneous Deletion & Insertion with PASTE

The PASTE system was used to simultaneously delete one sequence and insert another. 130 bp and 385 bp deletions of first exon of LMNB1 with combined insertion of AttB nucleic acid sequence was performed (FIG. 51A). This data shows that it is possible to replace DNA sequence using the PASTE system.

A130 bp deletion of the first exon of LMNB1 with combined insertion of a 967 bp cargo using the PASTE system was also performed.

One of two attP sequences were inserted using the mini circle template that has mutated AttP, as described above. This AttP mutants shows better integration kinetics and efficiency, especially for the shorter AttBs (38-44 bp). The LMNB1 AttB used in this experiment is 38 bp (FIG. 51B).

What is claimed is:

1. A system capable of site-specifically integrating an exogenous nucleic acid into a mammalian cell genome at a desired target site, wherein the system comprises, in a single composition:
   (a) a nucleic acid encoding a DNA binding nickase domain linked to a reverse transcriptase domain;
   (b) a nucleic acid encoding a guide RNA (gRNA) comprising, from 3' to 5',
      i. a primer binding sequence,
      ii. a sequence complementary to one strand of an integration recognition sequence, and
      iii. a target binding sequence,
      wherein the gRNA is capable of guiding the linked nickase-reverse transcriptase domains to the genomic target site;
   (c) a nucleic acid encoding an integration enzyme; and
   (d) an exogenous nucleic acid linked to a sequence that is an integration cognate of the integration recognition sequence.

2. The system of claim 1, wherein the DNA binding nickase domain is linked to the reverse transcriptase domain by in-frame fusion.

3. The system of claim 1, wherein the DNA binding nickase domain is linked to the reverse transcriptase domain by a linker.

4. The system of claim 3, wherein the linker is a peptide fused in-frame between the nickase and reverse transcriptase domains.

5. The system of claim 1, wherein the linked DNA binding nickase-reverse transcriptase domains are further linked to the integration enzyme.

6. The system of claim 1, wherein the DNA binding nickase domain is selected from Cas9-DI0A, Cas9-H840A, and Cas12a/b nickase.

7. The system of claim 1, wherein the reverse transcriptase domain is selected from the group consisting of Moloney Murine Leukemia Virus (M-MLV) reverse transcriptase domain, transcription xenopolymerase (RTX), avian myeloblastosis virus reverse transcriptase (AMV-RT), and *Eubacterium* rectale maturase RT.

8. The system of claim 7, wherein the reverse transcriptase domain is a M-MLV reverse transcriptase domain.

9. The system of claim 7, wherein the M-MLV reverse transcriptase domain comprises one or more mutations selected from the group consisting of D200N, T306K, W313F, T330P, and L603W.

10. The system of claim 1, wherein the exogenous nucleic acid is a minicircle, a plasmid, a mRNA, or a linear DNA.

11. The system of claim 9, wherein exogenous nucleic acid is a minicircle.

12. The system of claim 11, wherein the minicircle does not comprise a sequence of a bacterial origin.

13. The system of claim 1, wherein the integration enzyme is selected from the group consisting of Dre, Vika, Bxb1, φC31, RDF, FLP, φBT1, RI, R2, R3, R4, RS, TP901-1, A118, φFC1, φC1, MR11, TG1, φ370.1, Wβ, BL3, SPBc, K38, Peaches, Veracruz, Rebeuca, Theia, Benedict, KSSJEB, PattyP, Doom, Scowl, Lockley, Switzer, Bob3, Troube, Abrogate, Anglerfish, Sarfire, SkiPole, ConceptII, Museum, Severus, Airmid, Benedict, Hinder, ICleared, Sheen, Mundrea, BxZ2, φRV, retrotransposases encoded by R2, LI, Tol2 Tel, Tc3, Mariner Rimar 1, Mariner mos-I, and Minos.

14. The system of claim 13, wherein the integration enzyme is Bxb1.

15. The system of claim 13, wherein the integration recognition sequence is an attB sequence, an attP sequence, a Vox sequence, or a FRT sequence.

16. The system of claim 15, wherein the integration recognition sequence is an attB sequence and the integration cognate is an attP sequence.

17. The system of claim 15, wherein the exogenous nucleic acid encodes:
   a reporter gene;
   a degradation tag for programmable knockdown of proteins in the presence of small molecules;
   a T-cell receptor (TCR), a chimeric antigen receptor (CAR), an interleukin, a cytokine, or an immune checkpoint gene and the mammalian cell is a T-cell or natural killer (NK) cell;
   a beta hemoglobin (HBB) gene and the mammalian cell is a hematopoietic stem cell (HSC);
   a metabolic gene; or
   a gene involved in an inherited disease or syndrome.

18. The system of claim 1, wherein the exogenous nucleic acid is between 1000 bp and 36,000 bp in length.

19. The system of claim 1, wherein the exogenous nucleic acid is more than 36,000 bp in length.

20. The system of claim 1, wherein the exogenous nucleic acid is less than 1000 bp in length.

21. The system of claim 17, wherein the inherited disease is cystic fibrosis, familial hypercholesterolemia, adenosine deaminase (ADA) deficiency, X-linked SCID (X-SCID), Wiskott-Aldrich syndrome (WAS), hemochromatosis, Tay-Sachs, fragile X syndrome, Huntington's disease, Marfan syndrome, phenylketonuria, or muscular dystrophy.

22. The system of claim 1, further comprising a nicking gRNA.

23. The system of claim 1, wherein the nucleic acids are incorporated into one or more adenoviral vector genomes.

* * * * *

UNITED STATES PATENT AND TRADEMARK OFFICE
CERTIFICATE OF CORRECTION

PATENT NO. : 11,827,881 B2
APPLICATION NO. : 18/066223
DATED : November 28, 2023
INVENTOR(S) : Abudayyeh et al.

It is certified that error appears in the above-identified patent and that said Letters Patent is hereby corrected as shown below:

In the Specification

In Column 1, Line 17, after paragraph "CROSS REFERENCES TO RELATED APPLICATIONS" insert heading & paragraph:

--GOVERNMENT SUPPORT
This invention was made with government support under EB031957 awarded by the National Institutes of Health. The government has certain rights in the invention.--

Signed and Sealed this
Eleventh Day of November, 2025

John A. Squires
*Director of the United States Patent and Trademark Office*